US010362788B2

(12) United States Patent
Arrizubieta et al.

(10) Patent No.: US 10,362,788 B2
(45) Date of Patent: Jul. 30, 2019

(54) ***HELICOVERPA ARMIGERA* SINGLE NUCLEOPOLYHEDROVIRUS (HEARSNPV) GENOTYPES, METHOD OF PRODUCING SAME AND USE AS A BIOLOGICAL CONTROL AGENT**

(71) Applicants: UNIVERSIDAD PÚBLICA DE NAVARRA, Pamplona (ES); CONSEJO SUPERIOR DE INVESTIGACIONES CIENTÍFICAS (CSIC), Madrid (ES); INSTITUTO DE ECOLOGÍA, A.C., El Haya Xalapa, Veracruz (MX)

(72) Inventors: Maite Arrizubieta, Mutilva (ES); Oihane Simón, Mutilva (ES); Primitivo Caballero Murillo, Mutilva (ES); Trevor Williams, El Haya Xalapa (MX)

(73) Assignees: UNIVERSIDAD PÚBLICA DE NAVARRA, Pamplona (ES); CONSEJO SUPERIOR DE INVESTIGACIONES CIENTÍFICAS (CSIC), Madrid (ES); INSTITUTO DE ECOLOGÍA, A.C., Veracruz (MX)

( * ) Notice: Subject to any disclaimer, the term of this patent is extended or adjusted under 35 U.S.C. 154(b) by 0 days.

(21) Appl. No.: 15/321,898

(22) PCT Filed: Jun. 24, 2015

(86) PCT No.: PCT/ES2015/070490
§ 371 (c)(1),
(2) Date: Mar. 23, 2017

(87) PCT Pub. No.: WO2015/197900
PCT Pub. Date: Dec. 30, 2015

(65) Prior Publication Data

US 2017/0196224 A1 Jul. 13, 2017

(30) Foreign Application Priority Data

Jun. 24, 2014 (ES) .................................. 201430956

(51) Int. Cl.

| | |
|---|---|
| ***A01N 63/00*** | (2006.01) |
| ***C12N 7/00*** | (2006.01) |
| ***C12Q 1/70*** | (2006.01) |
| ***C12R 1/91*** | (2006.01) |

(52) U.S. Cl.
CPC ............... *A01N 63/00* (2013.01); *C12N 7/00* (2013.01); *C12Q 1/701* (2013.01); *C12R 1/91* (2013.01); *C12N 2710/14031* (2013.01); *C12N 2710/14121* (2013.01); *C12N 2710/14131* (2013.01); *C12N 2710/14151* (2013.01); *C12Q 2600/158* (2013.01)

(58) Field of Classification Search
None
See application file for complete search history.

(56) References Cited

FOREIGN PATENT DOCUMENTS

EP 0908099 A1 4/1999

OTHER PUBLICATIONS

Arrizubieta et al., "Selection of a nucleopolyhedrovirus isolate from Helicoverpa armigera as the basis for a biological insecticide," Pest Management Science, vol. 70, Iss. 6, Jun. 2014, pp. 967-976 (Abstract only provided).
Christian et al., "A rapid method for the identification and differentiation of Helicoverpa nucleopolyhedroviruses (NPV Baculoviridae) isolated from the environment," Journal of Virological Methods, vol. 96, 2001, pp. 51-65.
European Nuceotide Archive, "Sequence: AP010907.1," Oct. 11, 2008, 2 pages.
Figueiredo et al., "Diversity of Iberian nucleopolyhedrovirus wild-type isolates infecting Helicoverpa armigera (Lepidoptera: Noctuidae)," Biological Control, vol. 50, 2009 (available online Feb. 12, 2009), pp. 43-49.
Guo et al., "Biological comparison of two genotypes of Helicoverpa armigera single-nucleocapsid nucleopolyhedrovirus," BioControl, 2006, 11 pages.
International Search Report (Form PCT/ISA/210), dated Oct. 2, 2015, for International Application No. PCT/ES2015/070490, together with a partial English translation thereof.
Rowley et al., "Genetic variation and virulence of nucleopolyhedroviruses isolated worldwide from the heliothine pests Helicoverpa armigera, Helicoverpa zea, and Heliothis virescens," Journal of Invertebrate Pathology, vol. 107, 2011 (available online Mar. 23, 2011), pp. 112-126.

*Primary Examiner* — Nicole Kinsey White
(74) *Attorney, Agent, or Firm* — Birch, Stewart, Kolasch & Birch, LLP

(57) ABSTRACT

Two new *Helicoverpa armigera* single nucleopolyhedrovirus genotypes, HearSNPV, HearSNPV-SP1B and HearSNPV-LB6, each originating from mixtures of genotypes obtained from different locations and crops, are described. Each exhibits specific insecticidal activity against *H. armigera* larvae comparable to that of commonly used commercial insecticides. Further, mixing the two genotypes, especially in the ratio of 1:1, within co-occluded virions of the mixed genotypes, is capable of controlling *H. armigera* infestations of tomato crops and is as efficacious as commonly used chemical and biological insecticides. Their use as bioinsecticides is safe for vertebrates, in that they specifically target arthropods. In addition, they are easy to produce and good yields can be obtained by orally inoculating *H. armigera* larvae with HearSNPV occlusion bodies.

17 Claims, 38 Drawing Sheets

Specification includes a Sequence Listing.

Fig. 7
A)
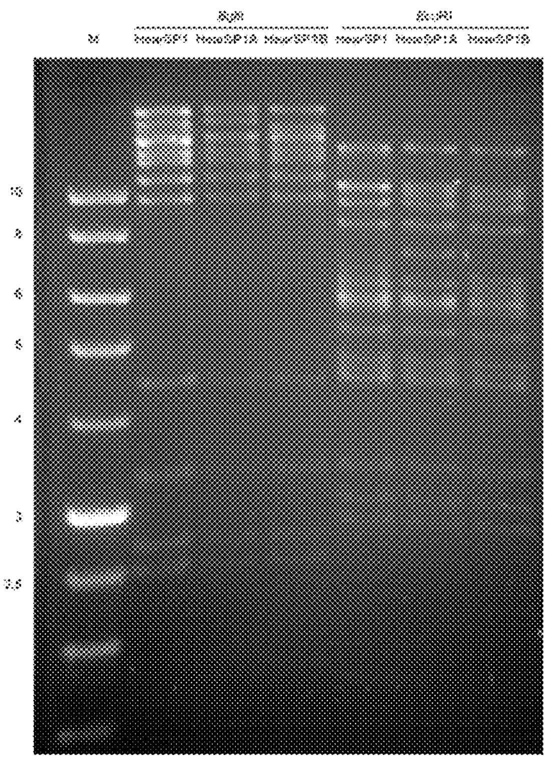
B)
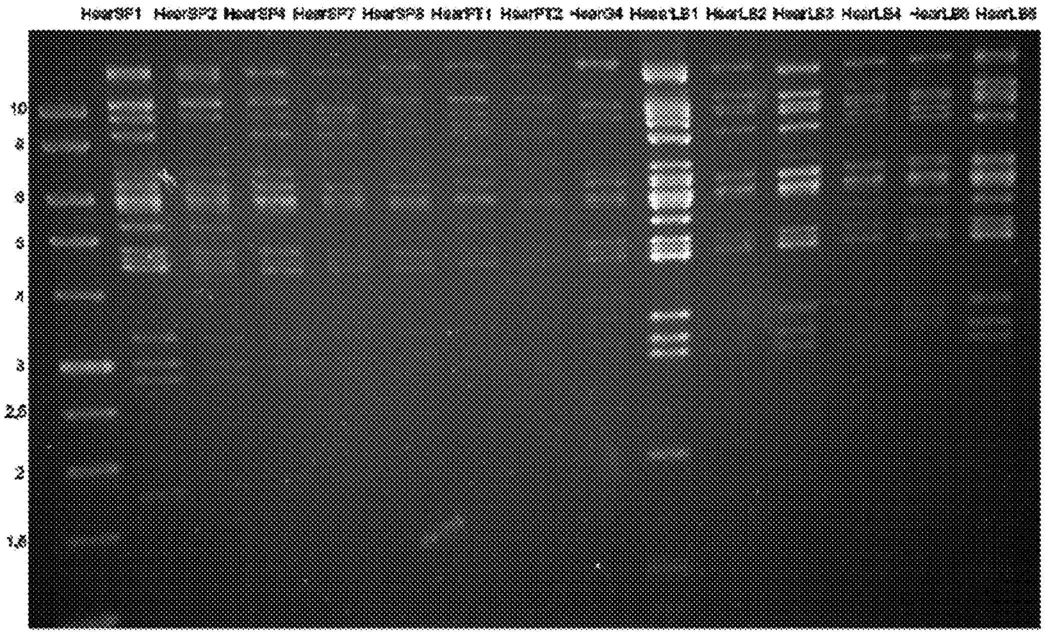

C)

Fig. 8
A)
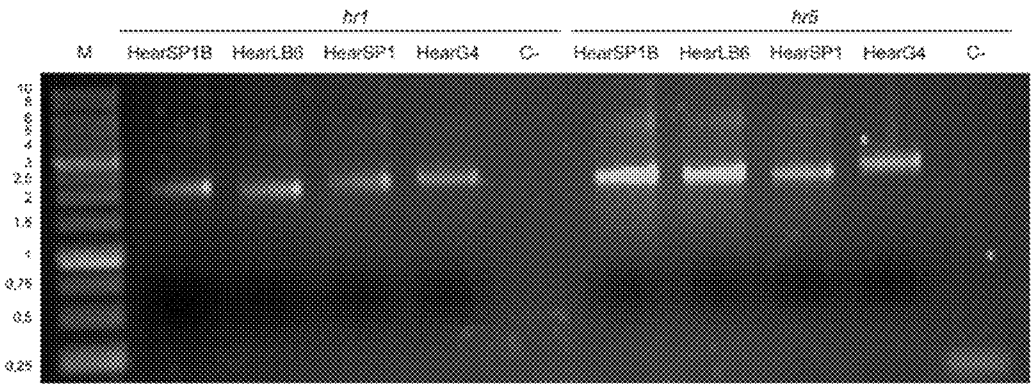
B)
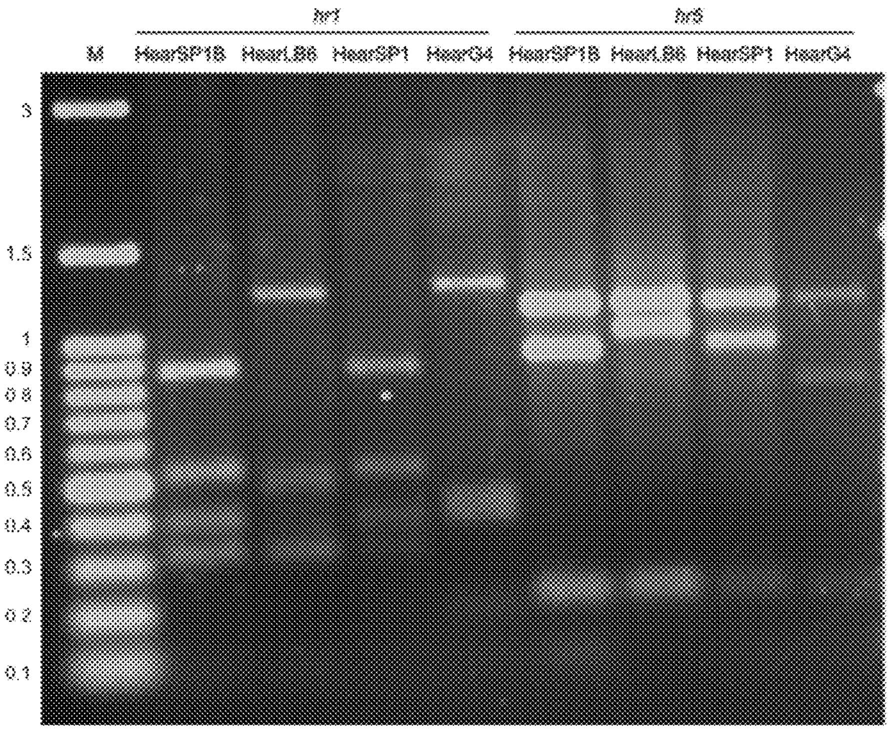

Fig. 9A

```
HearSP1B      1 CGAAATCGACAACACCATGCACATTACTACTTTACCCGTAGCCACTGATTACTCAGAACA
HearLB6       1 CGAAATCGACAACACCATGCACATTACTACTTTACCCGTAGCCACGGATTACTCAGAACA
HearG4        1 CGAAATCGACAACACCATGCACATTACTACTTTACCCGTAGCGACTGATTACGCAGAACA
HearC1        1 CGAAATCGACAACACCATGCACATTACTACTTTACCCGTAGCGACTGATTACGCAGAACA
HearNNg1      1 CGAAATCGACAACACCATGCACATTACTACTTTACCCGTAGCCACGGATTACTCAGAACA
HearAus       1 CGAAATCGACAACACCATGCACATTACTACTTTACCCGTAGCGACTGATTACGCAGAACA
                ****************************************** ** ****** *******

HearSP1B     61 AAACAAACTTGATCAGGCCGCCGTCGTTGTAGACGACCAATACAATTCGCCATTAGTGTT
HearLB6      61 AAACAAACTTGATCAGGCCGCCGTCGTTGTAGACGACCAATACAATTCGCCATTAGTGTT
HearG4       61 AAACAAACTTGATCAGGCCGCCGTCGTTGTAGACGACCAGTACAATTCGCCATTAGTGTT
HearC1       61 AAACAAACTTGATCAGGCCGCCGTCGTTGTAGACGACCAGTACAATTCGCCATTAGTGTT
HearNNg1     61 AAACAAACTTGATCAGGCCGCCGTCGTTGTAGACGATCAATACAATTCGCCATTAGTGTT
HearAus      61 AAACAAACTTGATCAGGCCGCCGTCGTTGTAGACGACCAGTACAATTCGCCATTAGTGTT
                ************************************ ** ********************

HearSP1B    121 TCATGACAATTCCACACTCAACAACTCTTCCGAACTATGGAATATTCCATCAACAAACAA
HearLB6     121 TCATGACAATTCCACACTCAACAACTCTTCTGAACTATGGAATATTCCATCAACAAACAA
HearG4      121 TCATGACAATTCCACACTCAATAACTCTTCTGAATTATGGAATATTCCAACAACAAACAA
HearC1      121 TCATGACAATTCCACACTCAATAACTCTTCTGAATTATGGAATATTCCAACAACAAACAA
HearNNg1    121 TCATGACAATTCCACACTCAACAACTCTTCTGAACTATGGAATATTCCATCAACAAACAA
HearAus     121 TCATGACAATTCCACACTCAATAACTCTTCTGAATTATGGAATATTCCAACAACAAACAA
                ********************* ******** *** ************** **********

HearSP1B    181 ATGACATCATCGTTCGAAATCTGCTGTAGGCAACGAATTATCACACACGAGATTATATTG
HearLB6     181 ATGACATCATCGTTCGAAATCTGCTGTAGGCAACGAATTATCACACACGAGATTATATTG
HearG4      181 ATGACATCATCGTTCGAAATCTGCTGTAGGCACCGAATTATCACACACGAGATTATATTG
HearC1      181 ATGACATCATCGTTCGAAATCTGCTGTAGGCACCGAATTATCACACACGAGATTATATTG
HearNNg1    181 ATGACATCATCGTTCGAAATCTGCTGTAGGCAACGAATTATCACACACGAGATTATATTG
HearAus     181 ATGACATCATCGTTCGAAATCTGCTGTAGGCACCGAATTATCACACACGAGATTATATTG
                ******************************* ****************************

HearSP1B    241 AAAAAATTA-CGTCATCCGTTTAAAATATTGCATCATCTTTAAATTCGAAACCCGCCCGC
HearLB6     241 AAAAAAATGTCATCATCGTTTTAAAATATTGCATCATCTTTAGATTCGAAACTAGCCCGC
HearG4      241 AAAAAATAA-CATCATC-GTTTTAAAAATTGCATCATCTTTAAATTCGAAACTAGCCCGC
HearC1      241 AAAAAATAA-CATCATC-GTTTTAAAAATTGCATCATCTTTAAATTCGAAACTAGCCCGC
HearNNg1    241 AAAAAAATGTCATCATCGTTTTAAAATATTGCATCATCTTTAAATTCGAAACTTGCCCGC
HearAus     241 AAAAAATAA-CATCATC-GTTTTAAAAATTGCATCATCTTTAAATTCGAAACTAGCCCGC
                ******    * *****  *** *** *************** *********  ******

HearSP1B    300 GCTTTCATATGAAACCGTCGGCAAAGATCGATAAAATTTATTCTAGAACATTCCACGGCT
HearLB6     301 GCTTTCATATGAAACCGTCGGCAAAGATCGATAAAATTTATTCTAGAACATTCCACGGTT
HearG4      299 GCTTTCATACGAAACTGTCGGCAAAAATCGATAAAATTTGTTCTAGAACGTTCCACGGCT
HearC1      299 GCTTTCATACGAAACTGTCGGCAAAAATCGATAAAATTTGTTCTAGAACGTTCCACGGCT
HearNNg1    301 GCTTTCATATAAAACCGCCGGCAAAAATCGATAAAATTTGTTCTAGAACGTTCCACGACT
HearAus     299 GCTTTCATACGAAACTGTCGGCAAAAATCGATAAAATTTGTTCTAGAACGTTCCACGGCT
                *********  **** * ******* ************* ********* *******  *

HearSP1B    360 TGACCCAAAAAAACAAATGACGTCATATGGCGTGATCTAGAAATGGTCCAATCACAAACG
HearLB6     361 TGACCCAAAAAAACAAATGACGTCATATGGCGTGATCTAGAAATGGTCCAATCACAAACG
HearG4      359 TGTCCCAAAAAAACAAATGACGTCATATGGCGATA-----------TCCAATCACAAACA
HearC1      359 TGTCCCAAAAAAACAAATGACGTCATATGGCGATA-----------TCCAATCACAAACA
HearNNg1    361 TGACCCAAAAAAACAAATGACGTCATATGGCGTGATCTAGAAATGGTCCAATCACAAACG
HearAus     359 TGTCCCAAAAAAACAAATGACGTCATATGGCGATA-----------TCCAATCACAAACA
                ** *****************************  *           *************
```

Fig 9A Continuation

```
HearSP1B        420 TATTCCACGAATCACGCCACGCCCAAAGAT--AACGTACTTTT-----------G-----
HearLB6         421 TATTCCACGAATCACGCCACGCCCAAAGAT--AACGTATTTTTAAACTGGCCTTG-----
HearG4          408 AATTCCACGAATCACGCCACGCCCAAACATTTAAACCGGTCTT-----------G-----
HearC1          408 AATTCCACGAATCACGCCACGCCCAAACATTTAAACCGGTCTT-----------G-----
HearNNg1        421 TATTCCACGAATCACGCCACGCCCAAAGAT--AACGTATTTTT-----------AAACTG
HearAus         408 AATTCCACGAATCACGCCACGCCCAAACATTTAAACCGGTCTT-----------G-----
                     ************************** **  **     * **

HearSP1B        462 ------GTTATTTTCGTTCGAAACGGGCCGTGATCTTTTGCTTCGA--------------
HearLB6         474 ------GATCATTACGTTCGAAACGGGCCGTGATCTTTTGTTTTGA--------------
HearG4          452 ------GATCTTTTCGTTTGAAACGGGCCGTGATCTTTTGTTTCGACTCATGACCCAAAA
HearC1          452 ------GATCTTTTCGTTTGAAACGGGCCGTGATCTTTTGTTTCGACTCATGACCCAAAA
HearNNg1        468 GCCTTAGATCATTACGTTCGAAACGGGCCGTGATCTTTTGTTTTGA--------------
HearAus         452 ------GATCTTTTCGTTTGAAACGGGCCGTGATCTTTTGTTTCGACTCATGACCCAAAA
                          * *  ** **** ********************* ** **

HearSP1B            ------------------------------------------------------------
HearLB6             ------------------------------------------------------------
HearG4          506 AAACAAATTACGTCATTAGTTTAAAATATTGCATCATCTTTAAATTCGAAACTAGCCCGC
HearC1          506 AAACAAATTACGTCATTAGTTTAAAATATTGCATCATCTTTAAATTCGAAACTAGCCCGC
HearNNg1            ------------------------------------------------------------
HearAus         506 AAACAAATTACGTCATTAGTTTAAAATATTGCATCATCTTTAAATTCGAAACTAGCCCGC

HearSP1B        502 ------------AACCGACGGCAAAGATTGATAAAATTTGTTCTAGAACGTTCCACGGCT
HearLB6         514 --------------------------CTCGTGATATTTTG-----------CACACGGCA
HearG4          566 GCTTTCATATGAAACCGTCGGCGAAGATCGATTATAAATGTTCTAGAACATTCGATGGTT
HearC1          566 GCTTTCATATGAAACCGTCGGCGAAGATCGATTATAAATGTTCTAGAACATTCGATGGTT
HearNNg1        514 --------------------------CTCGTGATATTTTG-----------CACACGGC-
HearAus         566 GCTTTCATATGAAACCGTCGGCGAAGATCGATTATAAATGTTCTAGAACATTCGATGGTT
                                               * *        **              * **

HearSP1B        550 TGACCCAAAAAAACAAATGACGTCATATAGCGTGATCTAGAAAAAGT--C----------
HearLB6         537 CTATTCCAACAA---ATTTTCCGCGCATGTTAAAATCAATTTAA-----C----------
HearG4          626 TGACCCAAAAAAACAAATGACGTCATATAGCGTGATCTAGAAATCGT--CCAATCACAAA
HearC1          626 TGACCCAAAAAAACAAATGACGTCATATAGCGTGATCTAGAAATCGT--CCAATCACAAA
HearNNg1        536 ---ACTATTCCAACAAATTTCCGC-----GCATGTTCAAATCAATTTAAC----------
HearAus         626 TGACCCAAAAAAACAAATGACGTCATATAGCGTGATCTAGAAATCGT--CCAATCACAAA
                               *   * *  *  *           ** *   *      *

HearSP1B        598 ----------GAATCACGAGACGCCCAAAAATAACGTACTTTTAAACTGGTCTTGGATCA
HearLB6         579 ----------AAATCACGCCACGCCCAAAGATAACGTATTTTTAAACTGGTCTTGGATGT
HearG4          684 CGTATTCCACGAATCACGCCACGCCCAAACATAACGTACTTTTGAACCGGTCTTGGATCA
HearC1          684 CGTATTCCACGAATCACGCCACGCCCAAACATAACGTACTTTTGAACCGGTCTTGGATCA
HearNNg1        579 ----------AAATCACGCCACGCCCAAAGATAACGTATTTTTAAACTGGTCTTGGATGT
HearAus         684 CGTATTCCACGAATCACGCCACGCCCAAACATAACGTACTTTTGAACCGGTCTTGGATCA
                               *******  ********* ******** **** *** **********

HearSP1B        648 TTTCGTTCGAAACGGGCCGTGATCTTTTGCTTCTATTCATGA------------------
HearLB6         629 GTTCGTTCGAAACGGGCCGTGATCTT---------TTCATGA------------------
HearG4          744 TTTCGTTCGAAACGGACCGTGATTTTGTGTTTTGACTCGTGACCCCCAAAATTAAAACAT
HearC1          744 TTTCGTTCGAAACGGACCGTGATTTTGTGTTTTGACTCGTGACCCCCAAAATTAAAACAT
HearNNg1        628 GTTCGTTCGAAACGGGCCGTGATCTTTTGCTTCTATTCATGA------------------
HearAus         744 TTTCGTTCGAAACGGACCGTGATTTTGTGTTTTGACTCGTGACCCCCAAAATTAAAACAT
                     ************** ******* **          ** ***
```

Fig 9A Continuation

```
HearSP1B        ------------------------------------------------------------
HearLB6         ------------------------------------------------------------
HearG4      804 TATTTTGCACACGGCACTATTCCAACAAATTTTCCGCGCATGTTAAAATCAGTCGCCACG
HearC1      804 TATTTTGCACACGGCACTATTCCAACAAATTTTCCGCGCATGTTAAAATCAGTCGCCACG
HearNNg1        ------------------------------------------------------------
HearAus     804 TATTTTGCACACGGCACTATTCCAACAAATTTTCCGCGCATGTTAAAATCAGTCGCCACG

HearSP1B    690 ------------------TT-AAGGA----------------------------------
HearLB6     662 ------------------CCCAAAAA----------------------------------
HearG4      864 CCCAAAGATAACGTATTTTT-ATGGATGTGTTCGTTCGAAACGGGCCGTGATATTTTCAT
HearC1      864 CCCAAAGATAACGTATTTTT-ATGGATGTGTTCGTTCGAAACGGGCCGTGATATTTTCAT
HearNNg1    670 ------------------TT-GAGGA----------------------------------
HearAus     864 CCCAAAGATAACGTATTTTT-ATGGATGTGTTCGTTCGAAACGGGCCGTGATATTTTCAT
                                         *

HearSP1B    697 ------AAAAACAAATTACGTCATCCGTTTAGGATATTGCATCATCTTTAAATTCAAAAC
HearLB6     670 ------AAAAACAAATTACGTCATCCGTTTAGGATATTGCATCATCTTTAAATTCGAAAC
HearG4      923 GACCCAAAAAACAAATTACGTCATCCGTTTAGGATATTGCATCATCTTTAAATTCAAAAC
HearC1      923 GACCCAAAAAACAAATTACGTCATCCGTTTAGGATATTGCATCATCTTTAAATTCAAAAC
HearNNg1    677 ------AAAAACAAATTACGTCATCCGTTTAGGATATTGCATCATCTTTAAATTCGAAAC
HearAus     923 GACCCAAAAAACAAATTACGTCATCCGTTTAGGATATTGCATCATCTTTAAATTCAAAAC
                      ************************************************* ****

HearSP1B    751 TAGCCCGCGCTTTCATATGAAACCGTCGGCAAAGATTGATAAAATTTGTTCTAGAACGTT
HearLB6     724 TAGCCCGCGCTTTTATATGAAACCGTCGGCAAAGATTGATAAAATTTGTTCTAGAACGTT
HearG4      983 TAGCCCGCGCTTTCATATGAAACCGTCGGCAAAGATTGATAAAATTTGTTCTAGAACGTT
HearC1      983 TAGCCCGCGCTTTCATATGAAACCGTCGGCAAAGATTGATAAAATTTGTTCTAGAACGTT
HearNNg1    731 TAGCCCGCGCTTTCATATGAAACCGTCGGCAAAGATTGATAAAATTTGTTCTAGAACGTT
HearAus     983 TAGCCCGCGCTTTCATATGAAACCGTCGGCAAAGATTGATAAAATTTGTTCTAGAACGTT
                ************* **********************************************

HearSP1B    811 CCACGGCTTGACCCAAAAAA-CAAATGACGTCATATAACGTGATCTAGAAAAAGTCGAAT
HearLB6     784 CCACGGTTTGACCCAAAAAAACAAATGACGTCATATAGCGTGATCTAGAAAAAGTCGAAT
HearG4     1043 CCACGGCT----------------------------------------------------
HearC1     1043 CCACGGCT----------------------------------------------------
HearNNg1    791 CCACGGCTTGAACCAAAAAAACAAATGACGTCATATAGCGTGATCTAGAAAAAGTCGAAT
HearAus    1043 CCACGGCT----------------------------------------------------
                ****** *

HearSP1B    870 CACGAGACGCCCAAAGATAACGTACTTTTAAACTGGTCTTGGTTATTTTCGTTCGAAACG
HearLB6     844 CACGAGACGCCCAAAAATAACGTACTTTTAAACCGGTCTTATATCTTTTCGTTCGAAACG
HearG4          ------------------------------------------------------------
HearC1          ------------------------------------------------------------
HearNNg1    851 CACGAGCCGCCCAAAAATAACGTACTTTTAAACTGGTCTTGGATCTGTTCGTTCGAAACG
HearAus         ------------------------------------------------------------

HearSP1B    930 GGCCGTGATCTTTTGCTTCGATTCATGACCCAAAAAAACAAATGACATCATTTACCAAAG
HearLB6     904 GGCCGTGATTTTTTGCTTCGATTCATGACCCAAAAAAACAAATGACATCATCTACCAAAG
HearG4     1051 -------------------------TGACCCAAAAAAACAAATGACATCATCTACCAAAG
HearC1     1051 -------------------------TGACCCAAAAAAACAAATGACATCATCTACCAAAG
HearNNg1    911 GGCCGTGATCTTTTGTTTCGACTCGTGACCCAAAAAAACAAATGATATCATCTACCAAAG
HearAus    1051 -------------------------TGACCCAAAAAAACAAATGACATCATCTACCAAAG
                                         ******************** ***** ********
```

Fig 9A Continuation

```
HearSP18    990 ATAATGTTTCCCGCGCACGTTTAAACTAGTCTTAGATCTTTTCGTTCGAAACGGGCTGTG
HearLB6     964 ATAATGTTTCCCGCGCACGTTTAAACTAGTCTTGGATCTTTTCGTTCGAAACGGGCTGTG
HearG4     1086 ATAATGTTTCCCGCGCACGTTTAAACTAGTCTTGGATCTTTTCGTTCGAAACGGGCCGTG
HearC1     1086 ATAATGTTTCCCGCGCACGTTTAAACTAGTCTTGGATCTTTTCGTTCGAAACGGGCCGTG
HearNNg1    971 ATAATGTTTCCCGCGCACGTTTAAACTAGTCTTGGATCTTTTCGTTCGAAACGGGCTGTG
HearAus    1086 ATAATGTTTCCCGCGCACGTTTAAACTAGTCTTGGATCTTTTCGTTCGAAACGGGCCGTG
                ********************************* ********************** ***

HearSP18   1050 ATCTTTTTGCTTCGAGTCATGACCAGAAAAAAAAACCGATTAAGTCATTTTGCACACGGCT
HearLB6    1024 ATCTTTTTGCTTCGAGTCATGACCAGAAAAAAAAACCGATTAAGTCATTTTGCACACGGCT
HearG4     1146 ATCT-TTTGCTTCGATTCATGACCAG--AAAAAACCGATTAAGTCATTTTGCACACGGCT
HearC1     1146 ATCT-TTTGCTTCGATTCATGACCAG--AAAAAACCGATTAAGTCATTTTGCACACGGCT
HearNNg1   1031 ATCTTTTTGCTTCGAGTCATGACCAGAAAAAAAAACCGATTAAGTCATTTTGCACACGGCT
HearAus    1146 ATCT-TTTGCTTCGATTCATGACCAG--AAAAAACCGATTAAGTCATTTTGCACACGGCT
                **** ********** **********   ******************************

HearSP18   1110 CTCTTTGAAAAACAAATTACGTCATAAAACGTGATTATAGAATCGTCCAATCAAAAACGA
HearLB6    1084 CTCTTTGAAAAACAAATTACGTCATAAAACGTGATTATAGAATCGTCCAATCAAAAACGA
HearG4     1203 CTCTTTGAAAAACAAATTACGTCATAAAACGTGATTATAGAATTGTCCAATCAAAAACGA
HearC1     1203 CTCTTTGAAAAACAAATTACGTCATAAAACGTGATTATAGAATTGTCCAATCAAAAACGA
HearNNg1   1091 CTCTTTGAAAAACAAATTACGTCATAAAACGTGATTATAGAATCGTCCAATCAAAAACGA
HearAus    1203 CTCTTTGAAAAACAAATTACGTCATAAAACGTGATTATAGAATTGTCCAATCAAAAACGA
                ******************************************* ****************

HearSP18   1170 ACACGAATCGCGTCACGCGCACGAAATTTACTATTCGACTTGACCTAAAA----------
HearLB6    1144 ACACGAATCGCGTCACGCGCACGAAATTTACTATTCGACTTGACCTAAAA----------
HearG4     1263 ACACGAATTGCGTCACGCACACGAAATTTACTATTCGACTTGACCTATACGTTACGCCAC
HearC1     1263 ACACGAATTGCGTCACGCACACGAAATTTACTATTCGACTTGACCT--------------
HearNNg1   1151 ACACGAATCGCGTCACGCGCACGAAATTTACTATTCGACTTGACCTAAAA----------
HearAus    1263 ACACGAATTGCGTCACGCACACGAAATTTACTATTCGACTTGACCT--------------
                ******** ********* ***************************

HearSP18   1220 ----AAACAAAGAACGTA-----TTCC---------------------------------
HearLB6    1194 ----AAACAAAGAACGTA-----TTCC---------------------------------
HearG4     1323 ATTTAAAAATTGAACATAAAAATTTACCGCGCTTTTTTAAACTGGTCTTGGATCTTATCG
HearC1     1309 -----------ATACGTTA-----CGCC--------------------------------
HearNNg1   1201 ----AAACAAAGAACGTA-----TTCC---------------------------------
HearAus    1309 -----------ATACGTTA-----CGCC--------------------------------
                             *    **          *

HearSP18   1238 -------------------------------------------------ACG---AATCAC
HearLB6    1212 -------------------------------------------------ACG---AATCAC
HearG4     1383 TTCGAAACGAGCCGTGATCTTTTGCTTCTATTCATGATTGAGGAAAAAAACA---AATGAC
HearC1     1321 -------------------------------------------------ACATTTAAAAAT
HearNNg1   1219 -------------------------------------------------ACG---AATCAC
HearAus    1321 -------------------------------------------------ACATTTAAAAAT
                                                                  **     **   *

HearSP18   1247 GCCA-CGCCCAAACATAAC---GTACTTTT--AAACTGGTCTTGGATCATTTCGTTCGAA
HearLB6    1221 GCCA-CGCCCAAACATAAC---GTACTTTT--AAACTGGTCTTGGATTATTTCGTTCGAA
HearG4     1440 ATCATCGACCAAAAATTCCCGCGCATATTT--AAACTG-TCTTGGATCTTTTTGTTTGAA
HearC1     1333 TGAA-CATAAAAATTTACC---GCGCTTTTTTAAACTGGTCTTGGATCTTATCGTTCGAA
HearNNg1   1228 GCCA-CGCCCAAACATAAC---GTACTTTT--AAACTGGTCTTGGATCATTTCGTTCGAA
HearAus    1333 TGAA-CATAAAAATTTACC---GCGCTTTTTTAAACTGGTCTTGGATCTTATCGTTCGAA
                  * *    ***  *   *    *    ***  ****** ********  * * *** ***
```

Fig 9A Continuation

```
HearSP1B   1301 ACGGGCCGTGATCTTTTGTTTCGCTTCGTGACCCAA-AAAAAACAAATGACATCATCGCC
HearLB6    1275 ACGGGCCGTGATCTTTTGTTTCGCTTCGTGA-CTTA-AAAAAACAAATGACATCATCGCC
HearG4     1497 ACGGGCCGTGATCTTTTGTTTCGACTCGTGACCCA--AAAAAACAAATGACATCATCGAC
HearC1     1389 ACGAGCCGTGATCTTTTGCTTCTATTCATGATTGAGGAAAAAACAAATGACATCATCGAC
HearNNg1   1282 ACGGGCCGTGATCTTTTGTTTCGCTTTGTGACCCA--AAAAAACAAATGACATCATCGCC
HearAus    1389 ACGAGCCGTGATCTTTTGCTTCTATTCATGATTGAGGAAAAAACAAATGACATCATCGAC
                *** ************** ***   *  ***      ********************* *

HearSP1B   1360 CAAACATAAC---GTACTTTTAAACTAGTCTTGGATATTTTCGTTCGAAACGGGCCGTGA
HearLB6    1333 CAAAAATAAC---GTACTTTTAAACTGGTCTTGGATCATTTCGTTCGAAACGGGCCGTGA
HearG4     1555 CAAAAATTCCCGCGCATGTTTAAACTAGTCTTGGATCTTTTTGTTTGAAACGGGCCGTAA
HearC1     1449 CAAAAATTCCCGCGCATATTTAAACT-GTCTTGGATCTTTTTGTTTGAAACGGGCCGTGA
HearNNg1   1340 CAAACATAAC---GTACTTTTAAACTGGTCTTGGATCTTTTCGTTCGAAACGGGCCGTGA
HearAus    1449 CAAAAATTCCCGCGCATATTTAAACT-GTCTTGGATCTTTTTGTTTGAAACGGGCCGTGA
                **** **  *   * *  ******** *********  *** *** ************ *

HearSP1B   1417 TCTTTTGTTTCGCTTCGTGACCCAAAAAAACAAATTACGTCATCGACCAAAG-TA-----
HearLB6    1390 TCTTTTGTTTCGCTTCGTGACCCAAAAAAACAAATTACGTCATCGACCAAAG-CA-----
HearG4     1615 TCTTTTGT-TCGACTCGTGACCCAAAAAAACAAATGACATCATCGACC------A-----
HearC1     1508 TCTTTTGTTTCGACTCGTGACCCAAAAAAACAAATGACATCATCGACC------A-----
HearNNg1   1397 TCTTTTGCTTCGATTCATGACCCAAAAAAACAAATGACATCATCTACCAAAGATA-----
HearAus    1508 TCTTTTGTTTCGACTCGTGACCCAAAAAAACAAATGACATCATCGACAAAAT-CCGCGCA
                *******  ***  ** ****************** ** ***** **

HearSP1B        ------------------------------------------------------------
HearLB6         ------------------------------------------------------------
HearG4          ------------------------------------------------------------
HearC1          ------------------------------------------------------------
HearNNg1        ------------------------------------------------------------
HearAus    1567 TATTAACTGTCTGATCTTTGTTGAAACGGGCCGTGATCTTGTTCGACTCGTGACCAAAAA

HearSP1B   1471 -------------------AAAATTCTTGCGCATGTTTAAACTAGTCTTGGATATTTTCG
HearLB6    1444 -------------------AAAATTCTTGCGCATGTTTAAACTAGTCTTGGATATTTTCG
HearG4     1663 -------------------AAAATTCCCGCGCATGTTTAAACTAGTCTTGGATCTTTTTG
HearC1     1557 -------------------AAAATTCCCGCGCATGTTTAAACTAGTCTTGGATCTTTTTG
HearNNg1   1452 -------------------ATGTTTCCCGCGCATGTTTAAACTGGTCTTGGATCATTTCG
HearAus    1627 ACAAATGACATCATCGACCAAAAATCCCGCGCATGTTTAAACTAGTCTTGGATC-TTTCG
                                   *    **  *************** *********  *** *

HearSP1B   1512 TTCGAAACGGGCCGTGATCTTTTGTTTCGCTTCGTGACCCAAAAAAACAAAT--------
HearLB6    1485 TTCGAAACGGGCCGTGATCTTTTGTTTCGCTTCGTGACCCAAAAAAACAAAT--------
HearG4     1704 TTCAAAACATGACGTAATCTTTCG-TTCTACTCGTGACCCAAAAAAACAAAT--------
HearC1     1598 TTCAAAACATGACGTAATCTTTCG-TTCTACTCGTGACCCAAAAAAACAAAT--------
HearNNg1   1493 TTCGAAACGGGCCGTGATCTTTTGTTTCGCTTTGTGACCCAAAAAAACAAATGACATCAT
HearAus    1686 TTCAAAACATGACGTAATCTTTCG-TTCTACTCGTGACCCAAAAAAACAAAT--------
                *** ****  * *** ****** * ***   * *******************

HearSP1B        ------------------------------------------------------------
HearLB6         ------------------------------------------------------------
HearG4          ------------------------------------------------------------
HearC1          ------------------------------------------------------------
HearNNg1   1553 CGACCAAAGATAATGTTTCCCGCGCATGTTTAAACTAGTCTTGGATCTTTTCGTTCGAAA
HearAus         ------------------------------------------------------------
```

Fig 9A Continuation

```
HearSP1B  1564  -------------------------------------TACGTCATTCGTTTAAAATATTG
HearLB6   1537  -------------------------------------TACGTCATTCGTTTAAAATATTG
HearG4    1755  -------------------------------------TACGTCATTTGTTTAAATTATTG
HearC1    1649  -------------------------------------TACGTCATTTGTTTAAATTATTG
HearNNg1  1613  CGGGCCGTGATCTTTTCATGACCCAAAAAAAACAAATTACGTCATCCGTTTAGGATATTG
HearAus   1737  -------------------------------------TACGTCATTTGTTTAAATTATTG
                                                     ********  *****   *****
HearSP1B  1587  CATCATCTTTAAATTCGAAACCCGCCCGCGCTTTCATATGAAACCGTCGGCGAAGATCGA
HearLB6   1560  CATCATCTTTAAATTCGAAACCCGCCCGCGCTTTCATATGAAACCGTCGGCAAAGATCGA
HearG4    1778  CATCATCTTTAAATTCAAAACTCGCCCGGGCTTTCATATAAAACCGTCGGCGAAGATCGA
HearC1    1672  CATCATCTTTAAATTCAAAACTCGCCCGCGCTTTCATATAAAACCGTCGGCGAAGATCGA
HearNNg1  1673  CATCATCTTTAAATTTGAAACTAGCCCGCGCTTTCATATGAAACCGTCGGCGAAGATTGA
HearAus   1760  CATCATCTTTAAATTCAAAACTCGCCCGCGCTTTCATATAAAACCGTCGGCGAAGATCGA
                ***************  ****  ***** ********** *********** ***** **

HearSP1B  1647  TAAAATTTGTTCTAGAACATTCGATGGTTTGACCCAAAAAAACAAATGACGTCATATAGC
HearLB6   1620  TAAAATTTGTTCTAGAACATTCGATGGTTTGACCCAAAAAAACAAATGACGTCATATAGC
HearG4    1838  TAAAATTTGTTTTAGAACATTCCACGGCTTGACCCAAAAAAACAAATGACGTCATATAGC
HearC1    1732  TAAAATTTGTTTTAGAACATTCCACGGCTTGACCCAAAAAAACAAATGACGTCATATAGC
HearNNg1  1733  TAAAATTTGTTCTAGAACATTCGATGGCCCGACCT--AAAAACAAATTACGTCATATAGC
HearAus   1820  TAAAATTTGTTTTAGAACATTCCACGGCTTGACCCAAAAAAACAAATGACGTCATATAGC
                *********** ********** * **   ****   ********** ************

HearSP1B  1707  GTG----------CGTCCAATCACAACACGAATCACGCCTTGTCTAAAGATAACATTTCC
HearLB6   1680  GTG----------CGTCCAATCACAACACGAATCACGCCTTGTCTAAAGATAACATTTCC
HearG4    1898  GTGATTTGGAAATCGTCCAATCACAACACGAATCACGCCTTGTCTAAAGATAACATTTCC
HearC1    1792  GTGATTTGGAAATCGTCCAATCACAACACGAATCACGCCTTGTCTAAAGATAACATTTCC
HearNNg1  1791  GTG----------CGTCCAATCACAACACGAATCACGCCTTGTCTAAAGATAACATTTCC
HearAus   1880  GTGATTTGAAAATCGTCCAATCACAACACGAATCACGCCTTGTCTAAAGATAACATTTCC
                ***          ***********************************************

HearSP1B  1757  CGCGCATGTTTAAACTAATCTTGGATCTTTTCGTTCGAAACGGGCCGTGGTCTTTTGTTT
HearLB6   1730  CGCGC-----------------------------------CGGGCCGTGATCTTTTGTTT
HearG4    1958  CGCGCATGTTTAAAATAGTCTTGGATCTTTTCGTTCGAAACGGGCCGTGATCTTTTGTTT
HearC1    1852  CGCGCATGTTTAAAATAGTCTTGGATCTTTTCGTTCGAAACGGGCCGTGATCTTTTGTTT
HearNNg1  1841  CGCGCATGTTAAAACTAATCTTGGATCTTTTCGTTCGAAACGGGCCGTGATCTTTTGTTT
HearAus   1940  CGCGCATGTTTAAAATAGTCTTGGATCTTTTCGTTCGAAACGGGCCGTGATCTTTTGTTT
                *****                                   ********* **********
HearSP1B  1817  CAATTCATGATTTAGAAAAAAA--CGAACATAAAATTTTACCGCGCATTTTTAAACTAGT
HearLB6   1755  CAGTTCATGATTTAGAAAAAAAAACGAACATAAAATTTTACCGCGCATTTTTAAACTAGT
HearG4    2018  CGACTTATGATTTAGAAAAAAA--CGAACATAAAATTTTACCGCGCATTTTTAAACTAGT
HearC1    1912  CGACTTATGATTTAGAAAAAAA--CGAACATAAAATTTTACCGCGCATTTTTAAACTAGT
HearNNg1  1901  CAATTCATGATTTAGAAAAAAA--CGAACATAAAATTTTACCGCGCATTTTTAAACTAGT
HearAus   2000  CGACTTATGATTTAGAAAAAAA--CGAACATAAAATTTTACCGCGCATTTTTAAACTAGT
                *   * ****************  ************************************

HearSP1B  1875  CTAGGATCTTTTTGTTCAAAACGTGCCGTGATCTTTTCGTTCGAAACGGGCCGTGATCTT
HearLB6   1815  GTTGGATTTTTTTGTTTGAAACGAGCCGTGATCTTTTCGTTCGAAACGGGCCGTGATCTT
HearG4    2076  CTAGGATCTTTTCGTTCAAAACGGGCCGTAATCTTTT-GTTCAAAACGGGCCGTAATCTT
HearC1    1970  CTAGGATCTTTTCGTTCAAAACGGGCCGTAATCTTTT-GTTCAAAACGGGCCGTAATCTT
HearNNg1  1959  GTTGGATTTTTTTGTTTGAAACGAGCCGTGATCTTTTCGTTCGAAACGGGCCGTGATCTT
HearAus   2058  CTAGGATCTTTTCGTTCAAAACGGGCCGTAATCTTTT-GTTCAAAACGGGCCGTAATCTT
                 * **** **** ***  ***** ***** ******* **** *********** *****

HearSP1B  1935  TTCGTTCGAAACGGGCCGTGATCTTTTGTTTCGCTGACTCGTGACCCAAAAAAACAAATT
HearLB6   1875  TTCGTTCGAAACGGGCCGTGATCTTTTGTTTCGCTGACTCGTGACCCAAAAAAACAAATC
HearG4    2135  TTCGTTCGAAACGGGCCGTGATCTTTTGTT---CT-ACTCATGACCCAAAAAAACAAATT
```

Fig 9A (Continuation)

```
HearC1     2029 TTCGTTCGAAACGGGCCGTGATCTTTTGTT---CT-ACTCATGACCCAAAAAAACAAATT
HearNNg1   2019 TTCGTTCGAAACGGGCCGTGATTTTTTGTTTCGCTGACTCGTGACCCAAAAAAACAAATT
HearAus    2117 TTCGTTCGAAACGGGCCGTGATCTTTTGTTTCGCTGACTCGTGACCCAAAAAAACAAATC
                ********************** *******   ** **** ******************

HearSP1B   1995 ACGTCATTCGTTTAAAATATTGCATCATCTTTAAATTCGAAACTCGCCCGCGCTTTCATA
HearLB6    1935 ACGTCATTCGTTTAGAATATTGCATCATCTTTAAATTCGAAACTCGCCCGCGCTTTCATA
HearG4     2191 ACGTCATCCGTTTAGGATATTGCATCATCTTTAAATTCAAAACTAGCCCGCGCTTTCATA
HearC1     2085 ACGTCATCCGTTTAGGATATTGCATCATCTTTAAATTCAAAACTAGCCCGCGCTTTCATA
HearNNg1   2079 ACGTCATTCGTTTAAAATATTGCATCAT-TTTTAATTCGAAACTCGCCCGCGCTTTCATA
HearAus    2177 ACGTCATCCGTTTAGGATATTGCATCATCTTTAAATTCAAAACCCGCCCGCGCTTTCATA
                ******* ******  ************ *** ***** ****  ***************
HearSP1B   2055 CGAAACCGCCGGCAAAGATCGGTAAAATTTGTTCTAGAACGTTCCACGGCTTGACCCAAA
HearLB6    1995 CGAAACCGTCGGCAAAGATCGATAAAATTTGTTCTAGAACGTTCCACGGCTTGACCCAAA
HearG4     2251 TGAAACCGTCGGCAAAGATCGGTAAAATTTGTTCTAGAACGTTCCACGGCTTGACCC-AA
HearC1     2145 TGAAACCGTCGGCAAAGATCGGTAAAATTTGTTCTAGAACGTTCCACGGCTTGACCC-AA
HearNNg1   2138 CAAAACCGTCGGCGAAGATCGGTAAAATTTGTTCTAGAACGTTCCACGGCTTGACCCAAA
HearAus    2237 TGAAACCGTCGGCAAAGATCGGTAAAATTTGTTCTAGAACGTTCCACGGCTTGACCC-AA
                  ****** **** ******* *********************************** **

HearSP1B   2115 AAAACAAATGACGTCATATGGCGTGATTTTAAATCTATTTAATCGTCTCTGGCGTACAAA
HearLB6    2055 AAAACAAATGACGTCATATGGCGTGATTTTAAATCTATTTAATCGTCTCTGGCGTACAAA
HearG4     2310 AAAACAAATGACGTCATATGGCG--------------TTTAATCGTCTCTGGCGTACAAA
HearC1     2204 AAAACAAATGACGTCATATGGCG--------------TTTAATCGTCTCTGGCGTACAAA
HearNNg1   2198 AAAACAAATGACGTCATATGGCGTGATTTTAAATCTATTTAATCGTCTCTGGCGTACAAA
HearAus    2296 AAAACAAATGACGTCATATGGCG-----TTTAATCAA--------TCTTTGGCGTACAAA
                ***********************                      *** ***********

HearSP1B   2175 AGT
HearLB6    2115 AGT
HearG4     2356 AGT
HearC1     2250 AGT
HearNNg1   2258 AGT
HearAus    2343 AGT
                ***
```

Fig 9B

```
HearSP1B     1 CTAGCCGGTCCGTTTCTGTTGACGCTGAACGCTGTATGTTTGATGCGGTACCGTTCTTTG
HearLB6      1 CTAGCCGGTCCGTTTCTGTTGACGCTGAACGCTGTATGTTTGATGCGGTAGCGTTCTTTG
HearG4       1 CTAGCCGGTCCGTTTCTGTTGACGCTGAACGCTGTATGTTTGATGCGGTAGCGTTCTTTG
HearC1       1 CTAGCCGGTCCGTTTCTGTTGACGCTGAACGCTGTATGTTTGATGCGGTAGCGTTCTTTG
HearNNg1     1 CTAGCCGGTCCGTTTCTGTTGACGCTGAACGCTGTATGTTTGATGCGGTAGCGTTCTTTG
HearAus      1 CTAGCCGGTCCGTTTCTGTTGACGCTGAACGCTGTATGTTTGATGCGGTAACGTTCTTTG
               ************************************************** *********

HearSP1B    61 CGAGCGTTCATTGCACGTCGGACTTCGTCTACAGTCGTGTCGCGATATGTATGCGGCCAT
HearLB6     61 CGAGCGTTCATTGCACGTCGGACTTCGTCTACAGTCGTGTCGCGATATGTATGCGGCCAT
HearG4      61 CGAGCGTTCATTGCACGTCGGACTTCGTCGACAGTCGTGTCGCGATATGTATGCGGACAT
HearC1      61 CGAGCGTTCATTGCACGTCGGACTTCGTCTACAGTCGTGTCGCGATATGTATGCGGACAT
HearNNg1    61 CGAGCGTTCATTGCACGTCGGACTTCGTCTACAGTCGTGTCGCGATATGTATGCGGCCAT
HearAus     61 CGAGCGTTCATTGCACGTCGGACTTCGTCTACAGTCGTGTCGCGATATGTATGCGGACAT
               ***************************** *************************** ***

HearSP1B   121 TTTATTTCCATAGGCACAATCGTGTCGTCGTCTAGAATAAAGTAGGCGTCCGGCGATGCG
HearLB6    121 TTTATTTCCATAGGCACAATCGTGTCGTCGTCTAGAATAAAGTAGGCGTCCGGCGATGCG
HearG4     121 TTTATTTCCATGGGCACAATCGTGTCGTCGTCTAGAATAAAGTAGGCGTCCGGCGATGCG
HearC1     121 TTTATTTCCATGGGCACAATCGTGTCGTCGTCTAGAATAAAGTAGGCGTCCGGCGATGCG
HearNNg1   121 TTTATTTCCATAGGCACAATCGTGTCGTCGTCTAGAATAAAGTAGGCGTCCGGCGATGCG
HearAus    121 TTTATTTCCATGGGCACAATCGTGTCGTCGTCTAGAATAAAGTAGGCGTCTGGCGATGCG
               *********** ************************************** *********

HearSP1B   181 GAATGTAATCCGTATTTGCTAAAGAACATACCGCAATCGAGAACAGTCTCTGTAATTTTT
HearLB6    181 GAATGTAATCCGTATTTGCTAAAGAACATACCGCAATCGAGAACAGTCTCTGTAATTTTT
HearG4     181 GAATGTAATCCGTATTTGCTAAAGAACATACCGCAATCGAGAACAGTCTCTGTAATTTTT
HearC1     181 GAATGTAATCCGTATTTGCTAAAGAACATACCGCAATCGAGAACAGTCTCTGTAATTTTT
HearNNg1   181 GAATGTAATCCGTATTTGCTAAAGAACATACCGCAATCGAGAACAGTCTCTGTAATTGTT
HearAus    181 GAATGTAATCCGTATTTGCTAAAGAACATACCGCAATCGAGAACAGTCTCTGTAATTTTT
               ********************************************************* **

HearSP1B   241 TTATTAGTTTCGCGTTCGACACATTCACGAACCAGATTCAAAAGCGATTCATTGTTTTTC
HearLB6    241 TTATTAGTTTCGCGTTCGACACATTCACGAACCAGATTCAAAAGCGATTCATTGTTTTTC
HearG4     241 TTATTAGTTTCGCGTTCGACACATTCACGAACCAGATTCAGAAGCGATTCATTGTTTTTC
HearC1     241 TTATTAGTTTCGCGTTCGACACATTCACGAACCAGATTCAGAAGCGATTCATTGTTTTTC
HearNNg1   241 TTATTAGTTTCGCGTTCGACACATTCACGAACCAGATTCAGAAGCGATTCATTGTTTTTC
HearAus    241 TTATTAGTTTCGCGTTCGACACATTCACGAACCAGATTCAGAAGCGATTCATTGTTTTTC
               **************************************** *******************

HearSP1B   301 ACGCAAGTTTCCTGTTCCAATCCGTAGGTGAGCGCCGGAATCGGTCGCAGACCAATGCCG
HearLB6    301 ACGCAAGTTTCCTGTTCCAATCCGTAGGTGAGCGCCGGAATCGGTCGCAGACCAATGCCG
HearG4     301 ACGCAAGTTTCCTGTTCCAATCCGTAGGTGAGCGCCGGAATCGGTCGCAGACCAATGCCG
HearC1     301 ACGCAAGTTTCCTGTTCCAATCCGTAGGTGAGCGCCGGAATCGGTCGCAGACCAATGCCG
HearNNg1   301 ACGCAAGTTTCCTGTTCCAATCCGTAGGTGAGCGCCGGAATCGGTCGCAGACCAATGCCG
HearAus    301 ACGCAAGTTTCCTGTTCCAATCCGTAGGTGAGCGCCGGAATCGGTCGCAGACCAATGCCG
               ************************************************************

HearSP1B   361 CTGCTGCTGTTCGTATTAGATCCCGAAGCAGTTTGTCGATCGAGCCGCAACAAAAACCAT
HearLB6    361 CTACTGCTGTTCGTATTAGATCCCGAAGCAGTTTGTCGATCGAGCCGCAACAAAAACCAT
HearG4     361 CTGCTGCTGTTCGTATTAGATCCCGAAGCAGTTTGTCGATCGAGCCGCAACAAAAACCAT
HearC1     361 CTGCTGCTGTTCGTATTAGATCCCGAAGCAGTTTGTCGATCGAGCCGCAACAAAAACCAT
HearNNg1   361 CTGCTGCTGTTCGTATTAGATCCCGAAGCAGTTTGTCGATCGAGCCGCAACAAAAACCAT
HearAus    361 CTGCTGCTGTTCGTATTAGATCCCGAAGCAGTTTGTCGATCGAGCCGCAACAAAAACCAT
               ** *********************************************************
```

Fig 9B Continuation

```
HearSP1B     421 AGCGGGTTCGTCGATTGTCCACGTGTTGCTTTTTCGATTTCCATGATTTCATGCCGTGAC
HearLB6      421 AGCGGGTTCGTCGATTGTCCACGTGTTGCTTTTTCGATTTTCATGATTTCATGCCGTGAC
HearG4       421 AGCGGGTTCGTCGATTGTCCACGTGTTGCTTTTTCGATTTTCATGATTTCATGCCGTGAC
HearC1       421 AGCGGGTTCGTCGATTGTCCACGTGTTGCTTTTTCGATTTTCATGATTTCATGCCGTGAC
HearNNg1     421 AGCGGGTTCGTCGATTGTCCACGTGTTGCTTTTTCGATTTTCATGATTTCATGCCGTGAC
HearAus      421 AGCGGGTTCGTCGATTGTCCACGTGTTGCTTTTTCGATTTTCATGATTTCATGCCGTGAC
                 **************************************** *******************

HearSP1B     481 AATAATTGTGTTATGCTTTTCAGTTGACTCACATAATTGGTAAAACAGTATTTGTCAAAT
HearLB6      481 AATAATTGTGTTATGCTTTTCAGTTGACTCACATAATTGGTAAAACAGTATTTGTCAAAT
HearG4       481 AATAATTGTGTTATGCTTTTCAGTTGACTCACATAATTGGTAAAACAGTATTTGTCAAAT
HearC1       481 AATAATTGTGTTATGCTTTTCAGTTGACTCACATAATTGGTAAAACAGTATTTGTCAAAT
HearNNg1     481 AATAATTGTGTTATGCTTTTCAGTTGACTCACATAATTGGTAAAACAGTATTTGTCAAAT
HearAus      481 AATAATTGTGTTATGCTTTTCAGTTGACTCACATAATTGGTAAAACAGTATTTGTCAAAT
                 ************************************************************

HearSP1B     541 ATGTTCTGCTGTTCGGCGGTGAGCAAATCGCACGGCGACACTAATGATTTGGTCATTTTT
HearLB6      541 ATGTTCTGCTGTTCGGCGGTGAGCAAATCGCACGGAGACACTAATGATTTGGTCATTTTT
HearG4       541 ATGTTCTGCTGTTCGGCGGTGAGCAAATCGCACGGAGACACTAATGATTTGGTCATTTTT
HearC1       541 ATGTTCTGCTGTTCGGCGGTGAGCAAATCGCACGGAGACACTAATGATTTGGTCATTTTT
HearNNg1     541 ATGTTCTGCTGTTCGGCGGTGAGCAAATCGCACGGAGACACTAATGATTTGGTCATTTTT
HearAus      541 ATGTTCTGCTGTTCGGCGGTGAGCAAATCGCACGGAGACACTAATGATTTGGTCATTTTT
                 *********************************** ************************

HearSP1B     601 GTGGTCGACATGGTCACGCGCAATAATATATTATAAATTATATTTCGTGAGAAGCCAATC
HearLB6      601 GTGGTCGACATGGTCACGCGCAATAATATATTATAAATTATATTTCGTGAGAAGCCAATC
HearG4       601 GTGGTCGACATGGTCACGCGCAATAATATATTATAAATTATATTTCGTGAGAAGCCAATC
HearC1       601 GTGGTCGACATGGTCACGCGCAATAATATATTATAAATTATATTTCGTGAGAAGCCAATC
HearNNg1     601 GTGGTCGACATGGTCACGCGCAATAATATATTATAAATTATATTTCGTGAGAAGCCAATC
HearAus      601 GTGGTCGACATGGTCACGCGCAATAATATATTATAAATTATATTTCGTGAGAAGCCAATC
                 ************************************************************

HearSP1B     661 GAGAAGTTTTACGTACACGGCCGACTGTAGCGTGTTATCGGATTCACTGTATTTAACTAG
HearLB6      661 GAGAAGTTTTACGTACACGGCCGACTGTAGCGTGTTATCGGATTCACTGTATTTAACTAG
HearG4       661 GAGAAGTTTTACGTACACGGCCGACTGTAGCGTGTTATCGGATTCACTGTATTTAACTAG
HearC1       661 GAGAAGTTTTACGTACACGGCCGACTGTAGCGTGTTATCGGATTCACTGTATTTAACTAG
HearNNg1     661 GAGAAGTTTTACGTACACGGCCGACTGTAGCGTGTTATCGGATTCACTGTATTTAACTAG
HearAus      661 GAGAAGTTTTACGTACACGGCCGACTGTAGCGTGTTATCGGATTCACTGTATTTAACTAG
                 ************************************************************
HearSP1B     721 AAATTGCACTAAAATATTTAAAATTCTGCTCTGATTGAACATCAATCGTTCCGTTTCAAT
HearLB6      721 AAATTGCACTAAAATATTTAAAATTCTGCTCTGATTGAACATCAATCGTTCCGTTTCAAT
HearG4       721 AAATTGCACTAAAATATTTAAAATTCTGCTCTGATTGAACATCAATCGTTCCGTTTCAAT
HearC1       721 AAATTGCACTAAAATATTTAAAATTCTGCTCTGATTGAACATCAATCGTTCCGTTTCAAT
HearNNg1     721 AAATTGCACTAAAATATTTAAAATTCTGCTCTGATTGAACATCAATCGTTCCGTTTCAAT
HearAus      721 AAATTGCACTAAAATATTTAAAATTCTGCTCTGATTGAACATCAATCGTTCCGTTTCAAT
                 ************************************************************

HearSP1B     781 AGCCATGTCCATGAACGATTGAACGGTGATCATCATACCATGTTGTTGAAAATTAATTTT
HearLB6      781 AGCCATGTCCATGAACGATTGAACGGTGATCATCATACCATGTTGTTGAAAATTAATTTT
HearG4       781 AGCCATGTCCATGAACGATTGAACGGTGATCATCATACCATGTTGTTGAAAATTAATTTT
HearC1       781 AGCCATGTCCATGAACGATTGAACGGTGATCATCATACCATGTTGTTGAATATTAATTTT
HearNNg1     781 AGCCATGTCCATGAACGATTGAACGGTGATCATCATACCATGTTGTTGAAAATTAATTTT
HearAus      781 AGCCATGTCCATGAACGATTGAACGGTGATCATCATACCATGTTGTTGAAAATTAATTTT
                 ************************************************** *********

HearSP1B     841 GCCCAATACGTTTTCAACTATACTGATGAATACCGTGTAAAATGTTTTTCGAGCAATATT
HearLB6      841 GCCCAATACGTTTTCAACTATACTGATGAATACCGTGTAAAATGTTTTTCGAGCAATATT
```

Fig 9B (Continuation)

```
HearG4      841 GCCCAATACGTTTTCAACTATACTGATGAATACCGTGTAAAATGTTTTTCGAGCAATATT
HearC1      841 GCCCAATACGTTTTCAACTATACTGATAAATACCGTGTAAAATGTTTTTCGAGCAATATT
HearNNg1    841 GCCCAATACGTTTTCAACTATACTGATGAATACCGTGTAAAATGTTTTTCGAGCAATATT
HearAus     841 GCCCAATACGTTTTCAACTATACTGATGAATACCGTGTAAAATGTTTTTCGAGCAATATT
                *************************** ********************************

HearSP1B    901 CTGATTACAATTGAACGGATCGACGACCGTGTCGCGTAGAAAGTCTATGACAGATCTAAG
HearLB6     901 CTGATTACAATTGAACGGATCGACGACCGTGTCGCGTAGAAAGTCTATGACAGATCTAAG
HearG4      901 CTGATTACAATTGAACGGATCGACGACCGTGTCGCGTAGAAAGTCTATGACAGATCTAAG
HearC1      901 CTGATTACAATTGAACGGATCGACGACCGTGTCGCGTAGAAAGTCTATGACAGATCTAAG
HearNNg1    901 CTGATTACAATTGAACGGATCGACGACCGTGTCGCGTAGAAAGTCTATGACAGATCTAAG
HearAus     901 CTGATTACAATTGAACGGATCGACGACCGTGTCGCGTAGAAAGTCTATGACAGATCTAAG
                ************************************************************

HearSP1B    961 TTTAATCGATTTGTCACGTATTCGATCGTTGCGTTGCAATCTTTTCACGTAAGGTTTCAT
HearLB6     961 TTTAATCGATTTGTCACGTATTCGATCGTTGCGTTGCAATCTTTTCACGTAAGGTTTCAT
HearG4      961 TTTAATCGATTTGTCACGTATTCGATCGTTGCGTTGCAATCTTTTCACGTAAGGTTTCAT
HearC1      961 TTTAATCGATTTGTCACATATTCGATCGTTGCGTTGCAATCTTTTCACGTAAGGTTTCAT
HearNNg1    961 TTTAATCGATTTGTCACGTATTCGATCGTTGCGTTGCAATCTTTTCACGTAAGGTTTCAT
HearAus     961 TTTAATCGATTTGTCACGTATTCGATCGTTGCGTTGCAATCTTTTCACGTAAGGTTTCAT
                ***************** ******************************************

HearSP1B   1021 CGCAAAATTACAATCGTGTTGGAAAAGTTATTCCGTCACAAAAAAAGTCCCTTAAATTAA
HearLB6    1021 CGCAAAATTACAATCGTGTTGGAAAAGTTATTCCGTCACAAAAAAAGTCCCTTAAATTAA
HearG4     1021 CGCAAAATTACAATCGTGTTGGAAAAGTTATTCCGTCACAAAAAAAGTCCCTTAAATTAA
HearC1     1021 CGCAAAATTACAATCGTGTTGGAAAAGTTATTCCGTCAC-AAAAAAGTCCCTTAAATTAA
HearNNg1   1021 CGCAAAATTACAATCGTGTTGGAAAAGTTATTCCGTCAC-AAAAAAGTCCCTTAAATTAA
HearAus    1021 CGCAAAATTACAATCGTGTTGGAAAAGTTATTCCGTCACAAAAAAAGTCCCTTAAATTAA
                *************************************** ********************

HearSP1B   1081 AAAATTTCTACCGTGTAATCGATCTTCGCCGACGGTTTCATATGAAAGCGCGGGCGGGTT
HearLB6    1081 AAAATTTCTACCGTGTAATCGATCCTCGCCGACGGTTTCATATGAAAGCGCGGGCGGGTT
HearG4     1081 AAAATTTCTACCGTGTAATCGATCTTTGCCAACGGTTTCATATGAAAGCGCGGGCGAGTT
HearC1     1080 AAAAATTCGACCGTGTAATCGATCTTTGCCGACGGTTTCATATGAAAGCGCGGGCGGGTT
HearNNg1   1080 AAAATTTCTACCGTGTAATCGATCCTCGCCGACGGTTTCATATGAAAGCGCGGGCTAGTT
HearAus    1081 AAAATTTCTACCGTGTAATCGATCTTTGCCAACGGTTTCATATGAAAGCGCGGGCGAGTT
                **** *** *************** * *** ************************  ***

HearSP1B   1141 TTGAATTTAAAGATGATGCAATATCTTAAATGGATGACGTAATTTGTTTTTT--CCTCAA
HearLB6    1141 TCGAATTTAAAAATGATGCAATATCTTAAACGGATGACGTAATTTGTTTTTT--CCTCAA
HearG4     1141 TCGAA-TTAAAAATGATGCAATATTCTAAACGGATGACGTAATTTGTTTTTT--CCTCAA
HearC1     1140 TCGAATTTAAAGATGATGCAATATCCTAAACGGATGACGTAATTTGTTTTTT--CCTCAA
HearNNg1   1140 TCGAATTTAAAGATGATGCAATATCCTAAACGGATGATGTAATTTGTTTTTTTTCCTCAA
HearAus    1141 TCGAA-TTAAAAATGATGCAATATTCTAAACGGATGACGTAATTTGTTTTTT--CCTCAA
                * *** ***** ************  **** ****** **************  ******

HearSP1B   1199 TCATGAATAGAAGCAAAAGATCACGGCCCGTTTCGAACGAAAAGATCCAAGACCGGTTTA
HearLB6    1199 TCATGAATAGAAGCAAAAGATCACGGCCCGTTTCGAACGAAAAGATCCAAGACCGGTTTA
HearG4     1198 TCATGAATAAAAGCAAAAGATCACGGCCCGTTTCGAACGAAAAGATCCAAGACCGGTTTA
HearC1     1198 TCATGAATAAAAGCAAAAGATCACGGCCCGTTTCGAACGAAAAGATCCAAGACCGGTTTA
HearNNg1   1200 TCATGAATAGAAGCAAAAGATCACGGCCCGTTTCGAACGAAAAGATCCAAGACCGGTTTA
HearAus    1198 TCATGAATAGAAGCAAAAGATCACGACCCGTTTCGAACGAAAAGATCCAAGACCGGTTTA
                ********* *************** **********************************
HearSP1B   1259 AAAGTACGTTATCTTTGGGAGTGGCGTGATTCGTGGAATACGTTTATGATTGGACAACTT
HearLB6    1259 AAAGTACGTTATTTTTGGGCGTGGCGTGATTCGTAGAATACGTTTGTGATTGGACAACTT
HearG4     1258 AAAGTACGTTATCTTTGGGCGTGGCGTGATTCGTGGAATACGTTTATGATTGGACAATTT
HearC1     1258 AAAGTACGTTATCTTTGGGCGTGGCGTGATTCGTGGAATACGTTTATGATTGGACAATTT
HearNNg1   1260 AAAGTACGTTATTTTTGGGCGTGGCGTGATTCGTGGAATACGTTTATGATTGGACAACTT
HearAus    1258 AAAGTACGTTATCTTTGGGCGTGGCGTGATTCGTGGAATACGTTTATGATTGGACAATTT
                ************ ****** ************** ********** *********** **
```

Fig 9B Continuation

```
HearSP1B   1319  TTAAA-TCACGCCATATGACGTCATTTGTTTTTTT-AGGTCGAGCCATCGAACGTTCTAG
HearL86    1319  TAAAAATCACGCCATATGATGTCATTTGTTTTTTTTAAATCGAGCCATCGAACGTTCTAG
HearG4     1318  CTAGA-TCACGCCATATGACGTCATTTGTTTTTTT-AGGTCGAGCCATCGAATGTTCTAG
HearC1     1318  CTAGA-TCACGCCATATGACGTCATTTGTTTTTTT-GGGTCAAGCCGTGGAATGTTCTAG
HearNNg1   1320  TTAAA-TCACGCCATATGACGTCATTTGTTTTTTT-GGGTCAAGCCGTGGAATGTTCTAG
HearAus    1318  CTAGA-TCACGCCATATGACGTCATTTGTTTTTTT-AGGTCGAGCCATCGAATGTTCTAG
                  *  * ************ **************   ** **** * *** *******

HearSP1B   1377  AACAAATTTTATCGATCTTTGCCGACGGTTTCATATGAAAGCGCGGGCGAGTTTCGAATT
HearL86    1378  AACAAATTTTATCGATCTTTGCCGACGGTTTCGTATGAAAGCGCGGGCGAGTTTCGAATT
HearG4     1376  AACAAATTTTATCGATCTTTGCCAACGGTTTCATATGAAAGCGCGGGCGGGTTTCGAATT
HearC1     1376  AACAAATTTTATCGATCTTTGCCAACGGTTTCATATGAAAGCGCGGGCGGGTTTCGAATT
HearNNg1   1378  AACAAATTTTATCGATCTTCGCCGACGGTTTCATATGAAAGCGCGGGCGAGTTTCGAATT
HearAus    1376  AACAAATTTTATCGATCTTTGCCAACGGTTTCATATGAAAGCGCGGGCGGGTTTCGAATT
                 ******************* *** *** ******** ****************** ***********

HearSP1B   1437  TAAAGATGATGCAATAATTTAAACGAATGACGTAATTTGTTTTTT---------------
HearL86    1439  TAAAGATGATGCAATATTTTAAACGACGTAATTTGTTTTT---------------
HearG4     1436  TAAAGATGATGCAATATCCTAAACGGATGACGTAATTTGTTTTTTCCTCAATCATGAATA
HearC1     1436  TAAAGATGATGCAATAATTTAAACGAATGACGTAATTTGTTTTTT---------------
HearNNg1   1438  TAAAAATGATGCAATAATTTAAACGAATGACGTAATTTGTTTTTTT---------------
HearAus    1436  TAAAGATGATGCAATATCCTAAACGGATGACGTAATTTGTTTTTTCCTCAATCATGAATA
                 **** ***********  *****  ****************

HearSP1B         ------------------------------------------------------------
HearL86          ------------------------------------------------------------
HearG4     1496  AAAGCAAAAGATCACGGCCCGTTTCGAACGAAAAGATCCAAGACCGGTTAAAAGTACGT
HearC1           ------------------------------------------------------------
HearNNg1         ------------------------------------------------------------
HearAus    1496  AAAGCAAAAGATCACGGCCCGTTTCGAACGAAAAGATCCAAGACCGGTTAAAAGTACGT

HearSP1B         ------------------------------------------------------------
HearL86          ------------------------------------------------------------
HearG4     1556  TATCTTTGGGCGTGGCGTGATTCGTGGAATACGTTTATGATTGGACAATTCTAGATCAC
HearC1           ------------------------------------------------------------
HearNNg1         ------------------------------------------------------------
HearAus    1556  TATCTTTGGGCGTGGCGTGATTCGTGGAATACGTTTATGATTGGACAATTCTAGATCAC

HearSP1B   1492  ---------------------TGGGTCACG------------------------------
HearL86    1484  ---------------------TGGGTCACG------------------------------
HearG4     1615  GCCATATGACGTCATTTGTTTTTTGGGTCAAGCCGTGGAATGTTCTAGAACAAATTTTA
HearC1     1491  ---------------------TGGGTCATG------------------------------
HearNNg1   1493  ---------------------TGGGTCATG------------------------------
HearAus    1616  GCCATATGACGTCATTTGTTTTTTGGGTCAAGCCGTGGAATGTTCTAGAACAAATTTTA
                                      *******  *

HearSP1B   1491  ----------------------AAGCG--------------------------------
HearL86    1493  ----------------------AAGCG--------------------------------
HearG4     1676  TCGATCTTTGCCAACGGTTTCATATGAAAGCGCGGGCGGGTTTCGAATTTAAAGATGATG
HearC1     1490  ----------------------AATAA--------------------------------
HearNNg1   1492  ----------------------AGTGT--------------------------------
HearAus    1676  TCGATCTTTGCCAACGGTTTCATATGAAAGCGCGGGCGGGTTTCGAATTTAAAGATGATG
```

Fig 9B Continuation

```
HearSP1B   1496 --------------------------------------------------AAACAAAAGA
HearLB6    1498 --------------------------------------------------AAACAAAAGA
HearG4     1736 CAATATCCTAAACGGATGACGTAATTTGTTTTTTCCTCAATCATGAATAAAAGCAAAAGA
HearC1     1495 --------------------------------------------------AAGCAAAATA
HearNNg1   1497 --------------------------------------------------AAGCAAAAGA
HearAus    1736 CAATATCCTAAACGGATGACGTAATTTGTTTTTTCCTCAATCATGAATAAAAGCAAAAGA
                                                                  ** ***** *

HearSP1B   1506 TCACGGCCCGTTTCGAACA----AAAAAATCCAAGACTAGTTTGAACATGCGCGAAAATT
HearLB6    1508 TCACGGCCCGTTTCGAACATAAAAAAAAAATCCAAGACTAGTTTGAACATGCGCGAGAATT
HearG4     1796 TCACGGCCCGTTTCGAACA----AAAAAATCCAAGACTAGTTTGAACATGCGCGAGAATT
HearC1     1505 TCACGGCCCGTTTCGAACA----AAAAAATCCAAGACTAGTTTGAACATGCGCGAGAATT
HearNNg1   1507 TCACGGCCCGTTTCGAACA----AAAAAATCCAAGACTAGTTTGAACATGCGCGAGAATT
HearAus    1796 TCACGGCCCGTTTCGAACA----AAAAAATCCAAGACTAGTTTGAACATGCGCGAGAATT
                *******************    ******************************** ****

HearSP1B   1562 TTTATTTTGGTAGATGATGTCATTTGTTTTTTTT--GGGTCACGACAAAAAATCACGGCC
HearLB6    1568 TTTATTTTGATAGATGATGTCATTTGTTTTTTTTTTGGGTCACGACAAAAAATCACGGCC
HearG4     1852 TTTACTTTGGTAGATGATGTCATTTG--TTTTTT--GGGTCACGACAAAAAATCACGGCC
HearC1     1561 TTTACTTTGGTAGATGATGTCATTTG--TTTTTT--GGGTCACGACAAAAAATCACGGCC
HearNNg1   1563 TTTATTTTGGTAGATGATGTCATTTGTTTTTTTTTTGGGTCACGACAAAAAATCACGGCC
HearAus    1852 TTTACTTTGGTAGATGATGTCATTTG--TTTTTT--GGGTCACGACAAAAAATCACGGCC
                **** **** ****************  ******  ************************

HearSP1B   1620 CGTTTCAAACGAAAAGATCCGAGATCAGTTTAAACATTCGCGGGAATTTTTACTTTGGGC
HearLB6    1628 CGTTTCAAACGAAAAGATCCGAGATCAGTTTAAACATTCGCGGGAATTTTTACTTTGGTC
HearG4     1908 CGTTTCAAACAAAAAGATCCGAGATCAGTTTAAACATTCGCGGGAATTTTTACTTTGGTC
HearC1     1617 CGTTTCAAACAAAAAGATCCGAGATCAGTTTAAACATTCGCGGGAATTTTTACTTTGGTC
HearNNg1   1623 CGTTTCAAACGAAAAGATCCGAGATCAGTTTAAACATTCGCGGGAATTTTTACTTTGGTC
HearAus    1908 CGTTTCAAACAAAAAGATCCGAGATCAGTTTAAACATTCGCGGGAATTTTTACTTTGGTC
                ********** *********************************************** *

HearSP1B   1680 GATGATGTCATTTGTTTTTTTGGGTCATAAATCGAAACAAAAGATCACGGTCCGTTTCGA
HearLB6    1688 GATGATATCATTTGTTTTTTTGGGTCACGAGTCGAAACAAAAAATCACGGCCCGTTTCGA
HearG4     1968 GATGATGTCATTTGTTTTTTTGGGTCATAAATCGAAACAAAAGATCACGGCCCGTTTCGA
HearC1     1677 GATGATATCATTTGTTTTTTTGGGTCATAAATCGAAACAAAAGATCACGGCCCGTTTCGA
HearNNg1   1683 GATGATATCATTCGTTTTTTTGGGTCACGAGTCGAAACAAAAAATCACGGCCCGTTTCGA
HearAus    1968 GATGATGTCATTTGTTTTTTTGGGTCATAAATCGAAACAAAAGATCACGGCCCGTTTCGA
                ****** ***** **************  * *********** ******* *********

HearSP1B   1740 ACGAAAAGATCCAAGACTAGTTTAAACGTGCGCGGGAAACATTATCTTTGGTAGATGATG
HearLB6    1748 ACGAAAAGATCCAAGACTAGTTTAAACGTGCGCGGGAAACATTATCTTTGGTAGATGATG
HearG4     2028 ACGAAAAAATCCAAGACTAGTTTAAACGTGCGCGGGA-ACATTATCTTTGGTAGATGATG
HearC1     1737 ACGAAAAAATCCAAGACTAGTTTAAACGTGCGCGGGATACATTATCTTTGGTAGATGATG
HearNNg1   1743 ACGAAAAGATCCAAGACTAGTTTAAACGTGCGCGGGAAACATTATCTTTGGTAGATGATG
HearAus    2028 ACGAAAAAATCCAAGACTAGTTTAAACGTGCGCGGGA-ACATTATCTTTGGTAGATGATG
                ******* ***************************** **********************

HearSP1B   1800 TCATTTGTTTTTTTGGGTCATGAATCGAAGCAAAAGATCACGGCCCGTTTCGAACGAACA
HearLB6    1808 TCATTTGTTTTTTTGGGTCATGAATCGAAGCAAAAGATCACGGCCCGTTTCGAACGAACA
HearG4     2087 TCATTTGTTTTTTTGGGTCATGAATCGAAGCAAAAGATCACGGCCCGTTTCGAACGAACA
HearC1     1797 TCATTTGTTTTTTTGGGTCATTAGTCGAAGTGAACGATCACGATCCGTTTC---------
HearNNg1   1803 TCATTTGTTTTTTTGGGTCATGAATCGAAGCAAAAGATTACGGCCCGTTTCGAACGAACA
HearAus    2087 TCATTTGTTTTTTTGGGTCATGAATCGAAGCAAAAGATCACGGCCCGTTTCGAACGAACA
                ********************* * ******   ** *** ***   *******
```

Fig 9B Continuation

```
HearSP1B    1860 GATCCAAGACCAGTTTAAATTTGCGCGGGAAATGTTATCTGTTGTTGATGACGTAATTTG
HearLB6     1868 GATCCAAGACCAGTTTAAACTTGCGCGGGAAATGTTATCTGTTGTTGATGACGTAAATTG
HearG4      2147 GATCCAAGACCAGTTTAAACTTGCGCGGGAAATGTTATCTGTTGTTAATGACGTAAATTG
HearC1           ------------------------------------------------------------
HearNNg1    1863 GATCCAAGACCAGTTTAAACTTGCGCGGGAAATGTTATCTGTTGTTGATGACGTAAATTG
HearAus     2147 GATCCAAGACCAGTTTAAACTTGCGCGGGAAATGTTATCTGTTGTTAATGACGTAAATTG

HearSP1B    1920 TTTTTCGAATAGTGTCGTGTGCAAATTTTGGGTCATGAAACAAAAGATCGCGGCCCGTTT
HearLB6     1928 TTTTTCGAATAGTGTCGTGTGCAAATTTTGGGTCATGAAACAAAAGATCGCGGCCCGTTT
HearG4      2207 TTTTTCGAATAGTGTCGTGTGCAAATTTTGGGTCATGAAACAAAAGATCGCGGCCCGTTT
HearC1      1848 -------------------------------------AAACAAAA---------------
HearNNg1    1923 TTTTTCGAATAGTGTCGTGTGCAAATTTTGGGTCATGAAACAAAAGATCGCGGCCCGTTT
HearAus     2207 TTTTTCGAATAGTGTCGTGTGCAAATTTTGGGTCATGAAACAAAAGATCGCGGCCCGTTT
                                                      ********

HearSP1B    1980 CAAACGAAAAGATCCGAGATCAGTTTAAAAATGCGATGCGCGGGAATTTTTTT-AATTTG
HearLB6     1988 CAAACGAAAAGATCCGAGATCAGTTTAAAAATGCGATGCGCGGGAATTTTTTTTAATTTG
HearG4      2267 CAAACGAAAAGATCCGAGATCAGTTTAAAAATGCGA------------------------
HearC1           ------------------------------------------------------------
HearNNg1    1983 CAAACGAAAAGATCCGAGATCAGTTTAAAAATGCGATGCGCGGGAATTTTTTT-AATTTG
HearAus     2267 CAAACGAAAAGATCCGAGATCAGTTTAAAAATGCGA------------------------

HearSP1B    2039 GTCAATGACGTA-TTTGTTTTTCGAGTAGTGCCGTGTGCAAAATGCTTTGAGTCATAAAT
HearLB6     2048 GTCGATGACGTAATTTGTTTTTCGATTAGTGCCGTGTGCAAAATGCTTTGAGTCATGAAT
HearG4           ------------------------------------------------------------
HearC1           ------------------------------------------------------------
HearNNg1    2042 GTCAATGACGTAATTTGTTTTTCGAGTAGTGCCGTGTGCAAAATGCTTTGAGTCATAAAT
HearAus          ------------------------------------------------------------

HearSP1B    2098 CAAAGCAAAAGATCGCGGCCCGTTTCAAACGAAAAGGTTCAAGATCAGTTTAAACCTGCG
HearLB6     2108 CAAAGCAAAAGATCGCGGCCCGTTTCAAACGAAAAGGTCCAAGATTAGTTTAAACATGCG
HearG4      2303 --------------------------------------------------------TGCG
HearC1           ------------------------------------------------------------
HearNNg1    2102 CAAAGCAAAAGATCGCGGCCCGTTTCAAACGAAAAGGTTCAAGATCAGTTTAAACCTGCG
HearAus     2303 --------------------------------------------------------TGCG

HearSP1B    2158 CGGGAAATGTTATCTGTTGTTGATGACGTAATTTGTTTTTCGAGTAGTGCCGAGTGCAAA
HearLB6     2168 CGGGAAATGTTATCTGTTGTTGATGACATAATTTGTTTTTCGAGTAGTGCCGAGTGCAAA
HearG4      2307 CGGGAAATGTTATCTGTTGTTGATGACGTAATTTGTTTTTCGAGTAGTGCCGAGTGCAAA
HearC1      1856 ----------------------------TAATT---------------------------
HearNNg1    2162 CGGGAAATGTTATCTGTTGTTGATGACGTAATTTGTTTTTCGAGTAGTGCCGAGTGCAAA
HearAus     2307 CGGGAAATGTTATCTGTTGTTGATGACGTAATTTGTTTTTCGAGTAGTGCCGAGTGCAAA
                                             *****

HearSP1B    2218 ATGACTTAATCTGTTTTTCTAAATCACGAATCGAAGCAAGAGATCACGGTCCGTTTCGAA
HearLB6     2228 ATGACTTAATCTGTTT------ATCACGAATCGAAGCAAAAGATCACGGTCCGTTTCGAA
HearG4      2367 ATGACGAAATCTGTTTTTCTAAATCACGAATCGAAGCAAGAGATCACGGTCCGTTTCGAA
HearC1      1861 -----------------------------ATCGA--------------------------
HearNNg1    2222 ATGACTTAATCTGTTTTTCTAAATCACGAATCGAAGCAAGAGATCACGGTCCGTTTCGAA
HearAus     2367 ATGACGAAATCTGTTTTTCTAAATCACGAATCGAAGCAAGAGATCACGGTCCGTTTCGAA
                                              *****
```

Fig 9B Continuation

```
HearSP1B   2276  CGAAAAGATCCAAGACTAGTTTAAAAATACGTTATGTTTTGGGTGGGGC
HearLB6    2282  CGAAAAGATCCAAGACTAGTTTAAAAATACGTTATGTTTTGGGTGGGGC
HearG4     2427  CGAAAAGATCCAAGACTAGTTTAAAAATACGTTATGTTTTGGGTGGGGC
HearC1     1866  --------------------------------------GCGTGGC--
HearNNg1   2282  CGAAAAGATCCAAGACTAGTTTAAAAATACGTTATGTTTTGGGTGGGGC
HearAus    2427  CGAAAAGATCCAAGACTAGTTTAAAAATACGTTATGTTTTGGGTGGGGC
                                                         *  ****
```

Fig. 15
A)
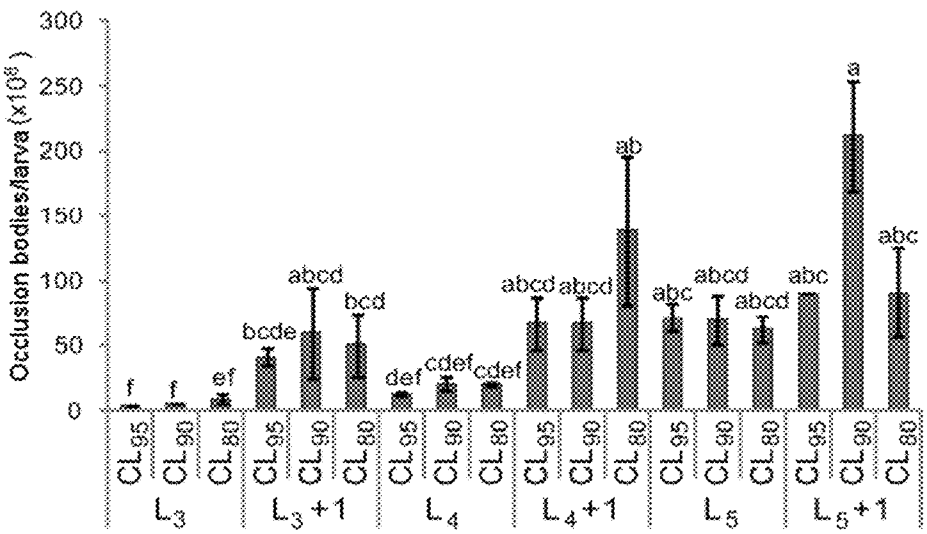
B)
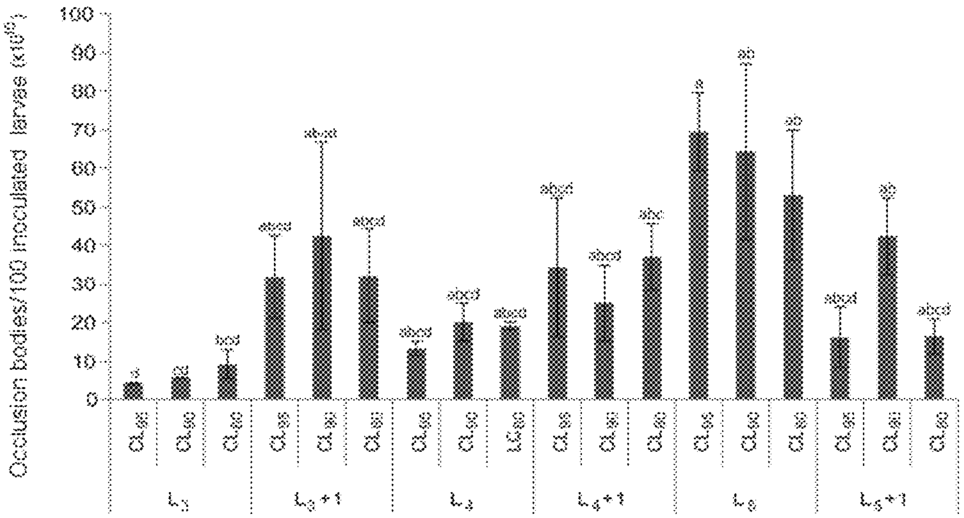

Fig. 16
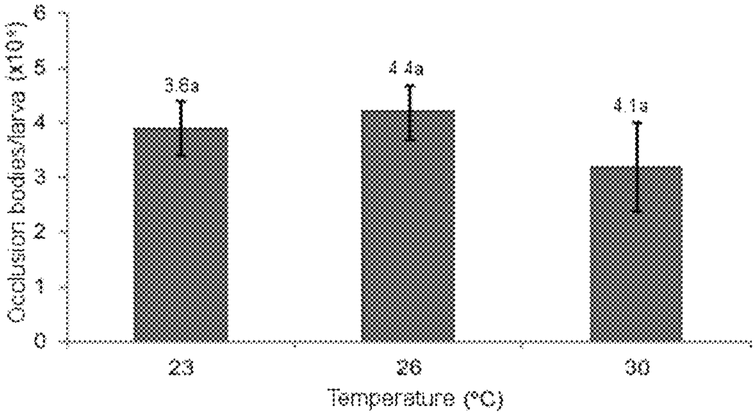
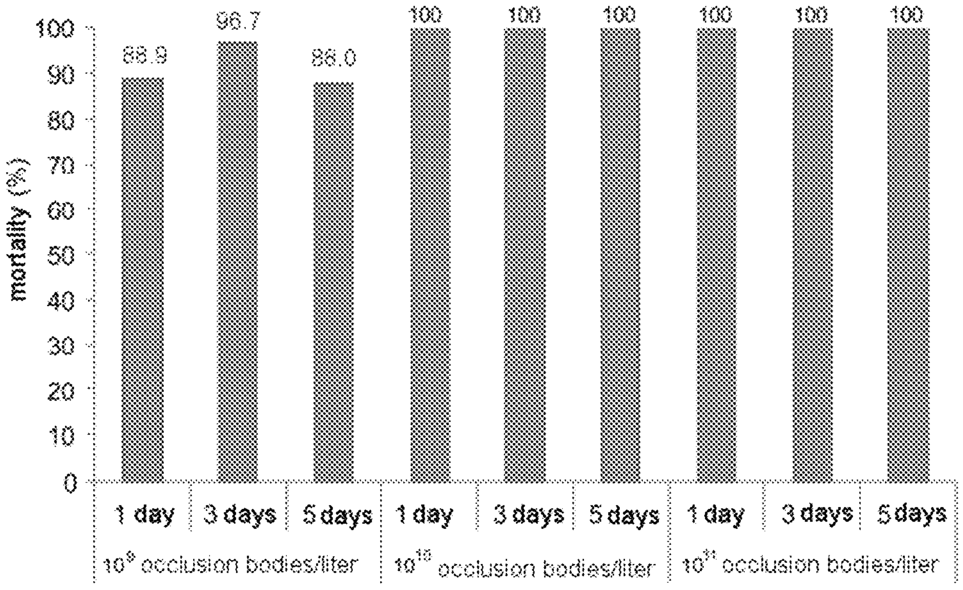
Fig. 17

Fig. 22
A)
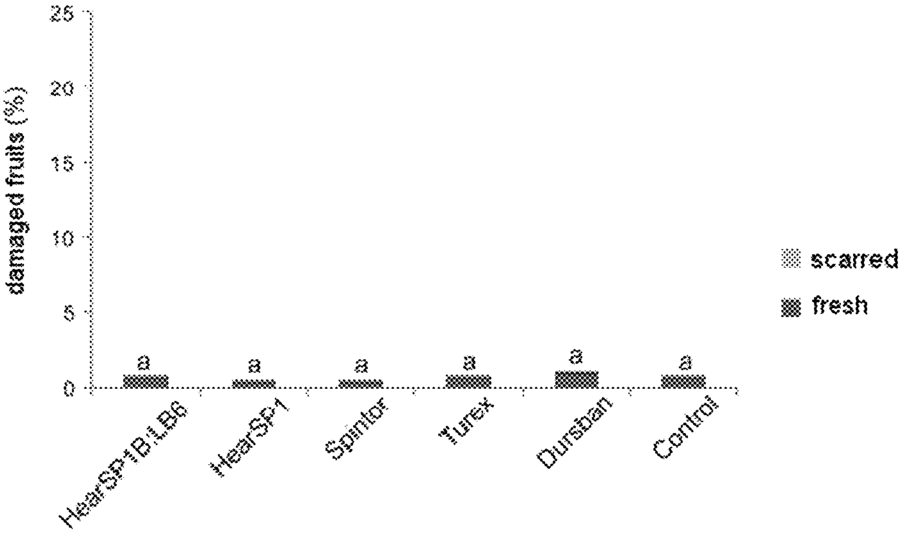
B)
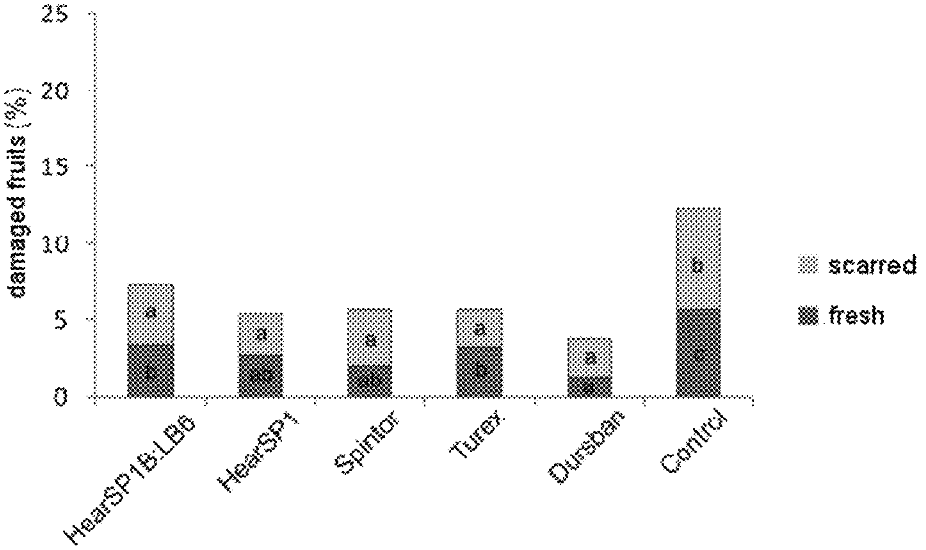

Fig. 22
C)
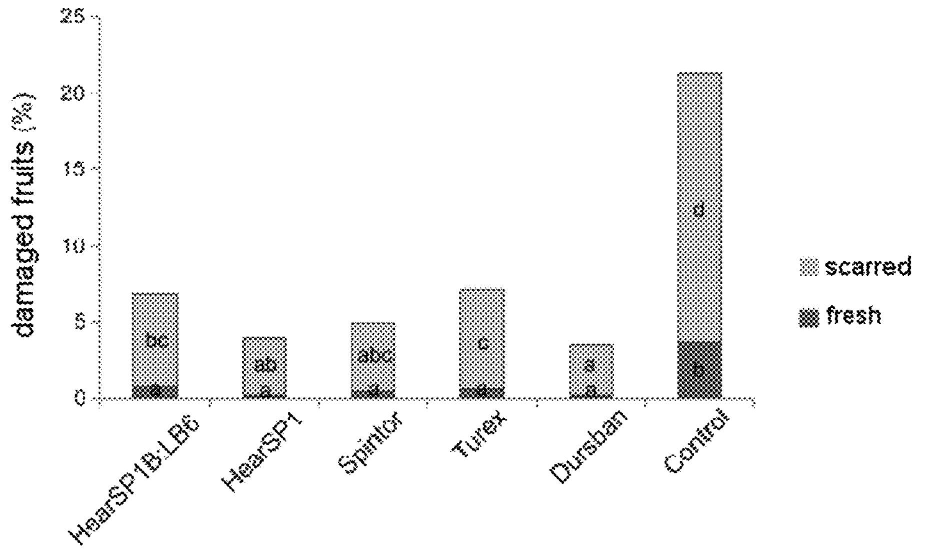
D)
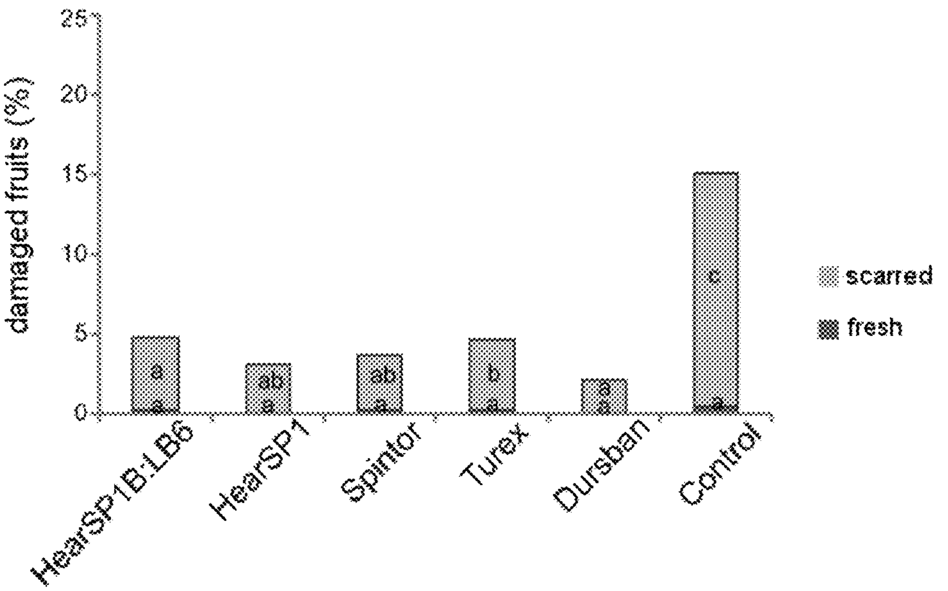

Fig. 26
D)
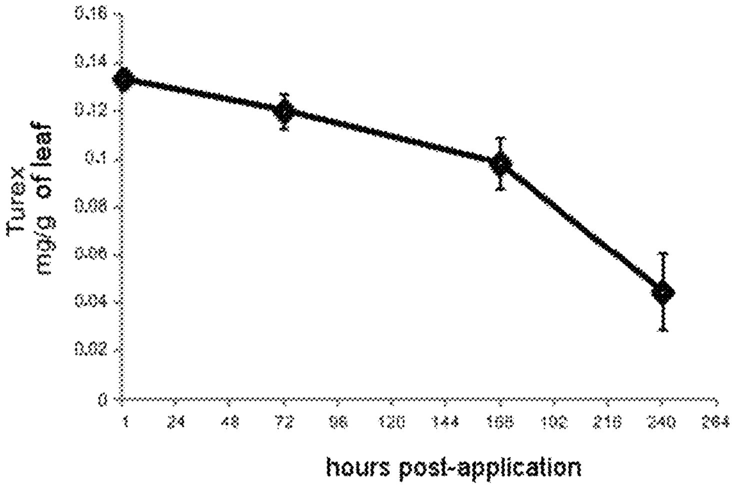
E)
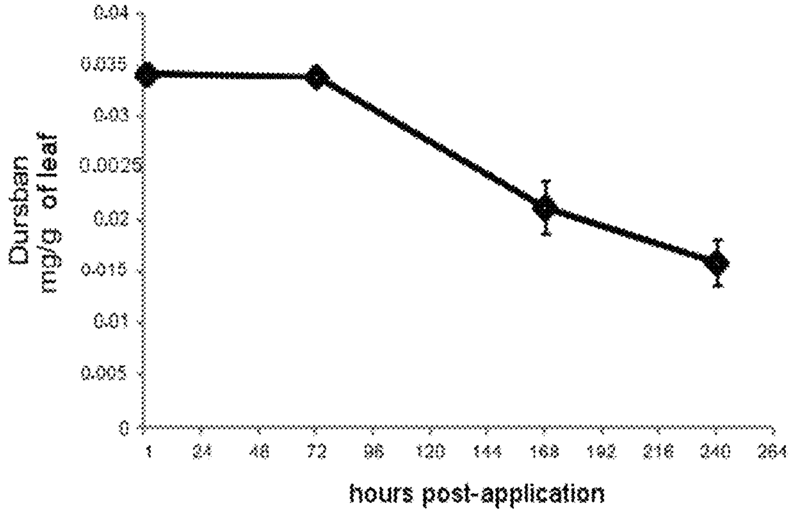

HELICOVERPA ARMIGERA SINGLE NUCLEOPOLYHEDROVIRUS (HEARSNPV) GENOTYPES, METHOD OF PRODUCING SAME AND USE AS A BIOLOGICAL CONTROL AGENT

REFERENCE TO SEQUENCE LISTING SUBMITTED VIA EFS-WEB

This application includes an electronically submitted substitute sequence listing in .txt format. The .txt file contains a sequence listing entitled "2017-03-22_5293-0122PUS1_ST25.txt" created on Mar. 22, 2017 and is 368,000 bytes in size. The sequence listing contained in this .txt file is part of the specification and is hereby incorporated by reference herein in its entirety.

FIELD OF THE INVENTION

The invention relates to the technical sector of biological pesticides for controlling insect pests. Specifically, the invention relates to two new genotypes of a nucleopolyhedrovirus capable of infecting the larvae of *Helicoverpa armigera* (Hübner, 1809), to compositions comprising one or more of the new genotypes, to a method of producing same and to their use in pest control for the said insect.

BACKGROUND OF THE INVENTION

The tomato crop in Spain covers 59,300 hectares and production comes to more than 4.3 million metric tonnes per year and Spain is the fourth leading tomato-producing country, only after the United States (California), China and Italy (www.magrama.gob.es/estadistica/pags/anuario/2011/AE_2011_13_06_27_01.pdf). Most of the tomato crop is grown in. Extremadura (73%), Andalusia (13%) and the Ebro Valley (10%) (www.navarraagraria.com/n184/artoma11.pdf). Tomatoes are also a major crop in Portugal, with 15,300 hectares planted and a production of over 1.1 million tonnes (www.ine.pt/ine_novidades/Estatisticas_Agricolas_2011/index.html#). One of the most important pests of tomato is the tomato fruit borer, *Helicoverpa armigera* (Lepidoptera: Noctuidae) (Torres-Vila et al., 2003). Worldwide, few pests cause as many economic losses as the noctuid *H armigera* (Cunningham et al., 1999; Reed and Pawar, 1982). In Spain *H. armigera* has been a key pest on crops such as cotton and corn and, for over a decade, this pest has been gaining importance in the greenhouses in Southeastern Spain, from there spreading to the rest of the regions of Spain and to Portugal (Torres-Vila et al., 2003). It is currently regarded as the most serious phytophagous species in a large portion of field-grown tomato crops in the Mediterranean region (Torres-Vila et al., 2003). The larvae can attack crops in all stages of growth, although the flowering stage is preferred by females for laying their eggs. They prefer the parts of plants with high nitrogen concentrations, such as the reproductive structures (flower and fruit) and the growing tips, so infestation has a direct effect on harvests. Furthermore, the species is highly polyphagous, highly mobile, highly fecund and multivoltine, so population levels can change rapidly both in space and in time. Damage thresholds used by tomato canning company quality controls are between 2 and 5% of harvested tomatoes. If larvae are present, the threshold drops to 0-2% (Torres-Vila et al., 2003). These quality thresholds make plain the need for an efficacious pest control method against *H armigera*.

*H. armigera* control ordinarily takes the form of applying chemical insecticides (Torres-Vila et al., 2003). However, indiscriminate use of synthetic insecticides has given rise to a variety of problems, such as increased production costs, the development of resistance to the various active ingredients, destruction of useful fauna, lower quality owing to higher chemical residues on fruits and fruit products (Torres-Vila et al., 2000). This has spurred the search for other control methods, including virus and other entomopathogenic microorganisms (Moscardi, 1999).

The Family Baculoviridae (baculoviruses) is the most widely studied of all those infecting insects, and is useful to man in that these viruses possess highly desirable traits as bioinsecticides, namely high pathogenicity, compatibility with pests' natural enemies, high specificity (they specifically target arthropods) (Gröner, 1986), long-lasting persistence where protected from ultraviolet light, high horizontal transmission and hence the ability to cause epizootic outbreaks (Caballero et al., 1992; Gelernter and Federici, 1986). In addition, they can be formulated just like synthetic chemical insecticides, are fully compatible with chemical insecticides and can be applied using conventional equipment (Cherry and Williams, 2001). Baculovirus isolates have been collected from around the world and characterized biologically and biochemically (Gelernter and Federici, 1986; Caballero et al., 1992; Hara et al., 1995). Some have already been registered as insecticides in different parts of the world and are being used for pest control (Moscardi, 1999).

Baculoviruses were previously classified into two genera on the bases of viral occlusion body (OB) morphology: Nucleopolyhedrovirus, in which the occlusion bodies are formed from polyhedrin in the shape of irregular polyhedrons and *Granulovirus* (GV), in which the occlusion bodies are formed from granulin and are granular in shape (Theilmann et al., 2005). However, a more recent, phylogenetically based (genome homology) classification divides the Family Baculoviridae into four genera: *Alphabaculovirus* (lepidopteran-specific nucleopolyhedroviruses [NPVs]), *Betabaculovirus* (lepidopteran-specific GVs), *Deltabaculovirus* (dipteran-specific NPVs) and *Gammabaculovirus* (hymenopteran-specific NPVs) (Jehle et al., 2006).

Baculoviruses have a double-stranded circular DNA genome enclosed within a protein capsid to form the nucleocapsid, which in its turn is surrounded by a trilaminar envelope composed of a protein layer between two lipid layers acquired during replication of the virus, forming the virion (Caballero et al., 2001). This lipoprotein membrane can be acquired in one of two ways, therefore giving rise to two types of virion. If the nucleocapsids remain in the same cell in which they were formed, they acquire a membrane synthesized de novo, giving rise to occlusion-derived virions (ODV), which are subsequently embedded in a matrix mainly formed by a single protein, giving rise to an occlusion body (OB). However, after synthesis, other nucleocapsids migrate and leave the host cell, acquiring a membrane from the host cell's cytoplasmic membrane as it crosses the cell membrane at specific points where a virus-encoded glycoprotein has been inserted (GP64 or F-protein, depending on the virus). These virions are budded virus (BVs) that move freely in the host's hemocoele and are responsible for spreading the infection to cells in various other tissues. In this stage all baculoviruses synthesize large quantities of polyhedrin (in the case of nucleopolyhedrovirus or NPV) or granulin (in the case of granulovirus or GV), which crystallize to form a matrix or occlusion body (OB) in the form of irregular polyhedrons (polyhedrin) or granules (granulin). For this reason, OBs made of polyhedrin are also known as polyhedra, while those made of granulin are also known as granules. In the final stages of infection, after three to six days, larvae die with large numbers of occlusion bodies that are readily observable under the optical microscope. The infection results in degradation of the larval tegument, releasing millions of occlusion bodies, which contaminate the leaves of the plants and serve as inocula for new infections in other susceptible hosts (Caballero et al., 2001).

Therefore, baculoviruses have two types of morphologically and functionally different virions, or infectious viral particles. ODVs are present in all known baculoviruses and are the infectious particles responsible for primary infection of the epithelial cells of the midgut (alimentary canal) and hence are responsible for horizontal transmission of the virus between susceptible individuals. BVs, in their turn, always contain a single nucleocapsid and are morphologically identical in all cases (FIG. 1A). The BVs are infectious particles responsible for producing the secondary infection, spreading the infection to susceptible organs and tissues of the hemocoele of the host and in in vitro cell cultures (Caballero et al., 2001). The occlusion bodies of NPVs contain several ODVs, whereas granules or GVs contain only one. Morphologically, there are two different types of nucleopolyhedrovirus ODVs, one type gives rise to single nucleopolyhedrovirus (SNPV), having a single nucleocapsid per virion, the other to multiple nucleopolyhedrovirus (MNPV), having from one to several nucleocapsids per virion (FIG. 1B).

Occlusion bodies, both polyhedrons and granules, protect the virions, keeping the virus infectious outside the host. The OBs are capable of surviving in the environment for long periods in places protected from ultraviolet light, are water insoluble, are resistant to putrefaction and to disintegration by chemical agents and are also resistant to such physical treatments as freezing, desiccation and lyophilization. In contrast, occlusion bodies are soluble in alkaline solutions like those found in the digestive tract of certain insects (pH 9-11), thereby releasing the ODVs to initiate an infection (Caballero et al., 2001).

Baculoviruses have been isolated from more than 500 insect species, mainly in the Order Lepidoptera, including many of the most important agricultural pests. Besides considerable interspecific diversity, baculoviruses also exhibit high intraspecific diversity, as has been demonstrated by characterization of different geographical isolates of the same virus and of single isolates, with wild isolates often comprising different genotypic variants. Viral DNA analysis with restriction enzymes is commonly used to differentiate and characterize both isolates and the genotypes present in a single isolate, as this procedure results in characteristic profiles for each isolate or genotype (Erlandson et al., 2007; Figueiredo et al., 1999; Harrison and Bonning, 1999).

Genome variation between different isolates and genotypes of the same virus can give rise to significant differences in their insecticidal characteristics, such as pathogenicity, defined as the amount of inoculum needed to kill a percentage of the population, virulence or the speed with which it kills the insects and viral productivity. Host range, occlusion body size and larval liquefaction are other phenotypic traits that may be affected (Cory et al., 2005; Harrison et al., 2012). Knowing the intrapopulation diversity of baculoviruses therefore has special importance when it comes to designing bioinsecticides, the active ingredients of which should include the strains or genotypes that have the greatest insecticidal potential. Furthermore, local insect populations are known to be more susceptible to native isolates of the virus (Barrera et al., 2011; Bernal et al., 2013a), making it appropriate to select a virus isolate having the same geographical origin as the populations to be controlled.

*H. armigera* larvae are naturally infected by a nucleopolyhedrovirus known by the abbreviated name of HearSNPV (*Helicoverpa armigera* single nucleopolyhedrovirus, genus *Alphabaculovirus*). This is a single nucleopolyhedrovirus (SNPV) that also infects the larvae of other members of the genera *Helicoverpa* spp. and *Heliothis* spp., for instance, *Helicoverpa zea* larvae. Characterization has been performed on HearSNPV isolates from different regions around the world, such as China and Kenya (Chen et al., 2001; Ogembo et al., 2005). Isolates of this virus have also been obtained from Spain and Portugal (Figueiredo et al., 1999, 2009), where it causes natural epizootic outbreaks in *H. armigera* populations. Several isolates of this virus have been characterized to date, with most studies being carried out on:

Two pure genotypes from China, the genomes of which have been completely sequenced, HearSNPV-G4 (Chen et al., 2001) and HearSNPV-C1 (Zhang et al., 2005), which will be referred to in the rest of this specification using the abbreviations HearG4 and HearC1, respectively. Guo et al. (2006) compared the biological activity of these two genotypes. On the basis of the concentration-mortality relationship, HearC1 turned out to be 2.8 times more pathogenic than HearG4 against third-instar larvae of an *H. armigera* population from China. In addition, larvae infected with HearC1 died nine hours sooner than larvae infected with HearG4. Zhang et al.'s 2005 article compared the genomes of these two genotypes and found the nucleotide sequences to be 98.1% identical. Comparing the two genomes revealed four variable regions between the two genotypes, homologous regions 1, 4 and 5 (hr1, hr4 and hr5) and the bro-b region. Homologous regions (hrs) are intergenic regions present in many baculoviruses and located many times along the genome. They are characterized by the presence of multiple imperfect repeat sequences. The genome of HearSNPV contains five homologous regions. FIG. 1 in the article by Chen et al. (2000) shows the restriction profiles for the BamHI, Bg/II, EcoRI, HindIII, KpnI, PstI, SacI and XhoI restriction endonucleases (FIG. 2 in this application). Table 1 in that article sets out the estimated sizes of the restriction fragments generated by each of the said restriction endonucleases (REN) (Table 1). The complete genomes of HearG4 and HearC1 are available in the GenBank database under accession numbers AF271059 and AF303045, respectively. The HearG4 genotype is currently commercially available for controlling *H. armigera* on cotton crops in China (Zhang, 1994).

TABLE 1

Estimated sizes of HearG4 fragments generated by digestion with BamHI, BglII, EcoRI, HindIII, KpnI, PstI, SacI and XhoI and estimated total genome size (Chen et al., 2000).

| Fragment | BamHI | BglII | EcoRI | HindIII | KpnI | PstI | SacI | XhoI |
|---|---|---|---|---|---|---|---|---|
| A | 37.3 | 24.5 | 14.1 | 22.2 | 55.5 | 39.0 | 65.0 | 36.5 |
| B | 31.8 | 18.5 | 13.9 | 16.5 | 34.2 | 36.8 | 22.3 | 34.6 |
| C | 14.4 | 15.8 | 9.8 | 14.7 | 23.6 | 32.3 | 19.3 | 20.0 |
| D | 14.0 | 14.8 | 9.1 | 12.8 | 9.8 | 11.8 | 9.7 | 11.0 |
| E | 12.7 | 13.7 | 9.0 | 11.6 | 6.1 | 6.1 | 9.4 | 10.9 |
| F | 7.7 | 12.1 | 6.8 | 10.8 | 0.9 | 3.4 | 4.4 | 7.0 |
| G | 3.9 | 7.1 | 6.4 | 10.2 | | 0.6 | | 4.4 |
| H | 3.3 | 5.9 | 6.0 | 10.1 | | | | 3.5 |
| I | 1.9 | 4.9 | 6.0 | 7.3 | | | | 2.2 |
| J | 1.8 | 4.3 | 5.8 | 6.5 | | | | |
| K | 1.3 | 3.4 | 5.6 | 3.2 | | | | |
| L | | 2.6 | 4.7 | 2.7 | | | | |
| M | | 2.5 | 4.6 | 1.5 | | | | |
| N | | | 4.5 | | | | | |
| O | | | 4.4 | | | | | |
| P | | | 4.3 | | | | | |
| Q | | | 3.7 | | | | | |
| R | | | 3.3 | | | | | |
| S | | | 3.1 | | | | | |
| T | | | 1.7 | | | | | |
| U | | | 1.0 | | | | | |
| V | | | 0.8 | | | | | |
| W | | | 0.5 | | | | | |
| X | | | 0.5 | | | | | |
| Y | | | 0.5 | | | | | |
| Total | 130.1 | 130.1 | 130.1 | 130.1 | 130.1 | 130.1 | 130.1 | 130.1 |

An isolate from Kenya, HearSNPV-NNg1, referred to here as HearNNg1, the genome of which has also been sequenced completely (Ogembo et al., 2009). HearNNg1 was selected by Ogembo et al. (2007) as the isolate having the best attributes for development as a bioinsecticide against *H. armigera* larvae in Japan. Against third-instar larvae HearNNg1 was between 3.2 and 82.6 times more pathogenic than the other isolates studied and 311.5 times more pathogenic than the Chinese isolate HearG4. In addition, NNg1 killed third-instar *H. armigera* larvae between 0.4 and 1.8 days sooner than the other isolates and 4.3 days sooner than the HearG4 genotype. FIG. 1 in that article sets out the restriction profiles for the isolates characterized using Bg/II and XbaI endonucleases (FIG. 3 in this application). Table 2 in that same article sets out the estimated sizes of the restriction fragments generated for the different isolates digested by Bg/II, XbaI and HindII endonucleases (Table 2).

TABLE 2

Estimated sizes of fragments of HearNNg1 (NNg1) and other isolates from South Africa (NS2), Kenya (NMa1), Zimbabwe (NZ3), Thailand (NT1) and China (G4) generated by digestion with BglII, XbaI and HindIII and total estimated genome size (Ogembo et al., 2007).

| | BglII | | | | | | XbaI | | | | | | HindIII | | | | | |
|---|---|---|---|---|---|---|---|---|---|---|---|---|---|---|---|---|---|---|
| Fragment | NNg1 | NS2 | NMa1 | NZ3 | NT1 | G4 | NNg1 | NS2 | NMa1 | NZ3 | NT1 | G4 | NNg1 | NS2 | NMa1 | NZ3 | NT1 | G4 |
| A | 23.7 | 25.5 | 25.5 | 23.7 | 23.7 | 25.5 | 14.2 | 14.2 | 14.2 | 14.2 | 14.2 | 14.2 | 22.6 | 22.6 | 22.6 | 22.6 | 22.6 | 22.6 |
| B | 18.7 | 18.7 | 18.7 | 18.7 | 18.7 | 18.7 | 13.0 | 13.0 | 13.0 | 13.0 | 13.0 | 13.0 | 14.5 | 17.1 | 17.1 | 17.1 | 14.5 | 14.5 |
| C | 15.3 | 15.3 | 15.3 | 15.3 | 15.3 | 15.3 | 11.9 | 11.9 | 11.9 | 11.9 | 12.4 | 11.9 | 13 | 13.5 | 13.5 | 13.5 | 14.5 | 14.5 |
| D | 15.0 | 15.0 | 15.0 | 15.0 | 13.3 | 15.0 | 10.6 | 10.6 | 10.6 | 10.6 | 11.9 | 10.6 | 11 | 13 | 13 | 13 | 13 | 13 |
| E | 13.3 | 13.3 | 13.3 | 13.3 | 12.4 | 13.3 | 9.3 | 9.3 | 9.3 | 9.3 | 10.6 | 9.3 | 10.8 | 11 | 11 | 11 | 11 | 11 |
| F | 12.4 | 12.4 | 12.4 | 11.5 | 10.7 | 12.4 | 9.1 | 9.1 | 7.2 | 9.1 | 9.3 | 9.1 | 10.7 | 10.8 | 10.4 | 10.8 | 10.8 | 10.7 |
| G | 10.7 | 10.7 | 10.7 | 10.7 | 9.4 | 6.9 | 7.2 | 7.2 | 6.2 | 7.2 | 9.1 | 7.2 | 10.4 | 10.4 | 10 | 10.4 | 10.4 | 10.4 |
| H | 9.4 | 6.9 | 6.9 | 6.9 | 8.8 | 5.8 | 6.2 | 6.2 | 6.1 | 6.2 | 6.2 | 6.2 | 10 | 10 | 8.2 | 10 | 10 | 10 |
| I | 4.3 | 4.3 | 4.3 | 4.3 | 6.9 | 5.0 | 6.1 | 6.1 | 5.9 | 6.1 | 5.9 | 5.9 | 7.7 | 8.2 | 7.5 | 7.5 | 7.5 | 7.5 |
| J | 3.3 | 3.3 | 3.3 | 3.3 | 4.3 | 4.3 | 5.9 | 5.9 | 5.7 | 5.8 | 5.7 | 5.8 | 7.5 | 7.5 | 4 | 3.3 | 6.7 | 6.7 |
| K | 2.7 | 2.6 | 2.6 | 3.2 | 3.3 | 3.3 | 5.7 | 5.7 | 5.5 | 5.7 | 5.5 | 5.7 | 6.7 | 3.3 | 3.3 | 2.6 | 4 | 3.3 |
| L | 2.5 | 1.3 | 1.3 | 2.6 | 2.7 | 2.6 | 5.5 | 5.5 | 5.4 | 5.5 | 4.0 | 5.5 | 3.3 | 2.6 | 3 | 1.9 | 2.6 | 2.6 |
| M | — | — | — | 1.3 | 2.5 | 2.5 | 5.4 | 5.4 | 4.8 | 5.4 | 3.6 | 4.0 | 2.6 | 1.5 | 2.6 | 1.5 | 1.5 | 1.5 |
| N | | | | | | | 3.4 | 4.8 | 4.6 | 4.8 | 3.3 | 3.3 | 1.5 | | 1.5 | — | — | — |
| O | | | | | | | 3.2 | 4.6 | 3.6 | 3.4 | 3.2 | 3.2 | | | | | | |
| P | | | | | | | 3.1 | 4.4 | 3.2 | 3.2 | 2.1 | 2.5 | | | | | | |
| Q | | | | | | | 1.9 | 3.6 | 1.6 | 1.6 | 1.6 | 2.1 | | | | | | |
| R | | | | | | | 1.6 | 3.1 | 1.2 | 1.2 | 1.2 | 1.9 | | | | | | |
| S | | | | | | | 1.2 | 1.9 | 1.1 | 1.1 | 1.1 | 1.6 | | | | | | |
| T | | | | | | | 1.1 | 1.6 | 1.0 | 1.0 | 1.0 | 1.3 | | | | | | |
| U | | | | | | | 1.0 | 1.2 | — | — | — | 1.2 | | | | | | |

TABLE 2-continued

Estimated sizes of fragments of HearNNg1 (NNg1) and other isolates from South Africa (NS2), Kenya (NMa1), Zimbabwe (NZ3), Thailand (NT1) and China (G4) generated by digestion with BglII, XbaI and HindIII and total estimated genome size (Ogembo et al., 2007).

| | BglII | | | | | | XbaI | | | | | | HindIII | | | | | |
|---|---|---|---|---|---|---|---|---|---|---|---|---|---|---|---|---|---|---|
| Fragment | NNg1 | NS2 | NMa1 | NZ3 | NT1 | G4 | NNg1 | NS2 | NMa1 | NZ3 | NT1 | G4 | NNg1 | NS2 | NMa1 | NZ3 | NT1 | G4 |
| V | | | | | | | | 1.1 | — | — | — | 1.1 | | | | | | |
| W | | | | | | | | 1.0 | — | — | — | — | | | | | | |
| Total | 129.3 | 131.3 | 129.3 | 129.8 | 132 | 130.6 | 137.4 | 126.6 | 122.1 | 126.2 | 124.9 | 126.6 | 131.5 | 132.3 | 127.7 | 125.2 | 132.2 | 131.4 |

Furthermore, the article by Ogembo et al. (2009) compares the HearNNg1 genome with the genomes of the Chinese genotypes HearC1 and HearG4, and with the genome of *Helicoverpa zea* single nucleopolyhedrovirus (HzSNPV). The greatest differences of the NNg1 genotype with respect to the HearC1, HearG4 and HzSNPV genomes were in the homologous regions (hrs) and in the bro genes, as occurred in the comparison of the HearC1 and HearG4 genomes. The whole HearNNg1 genome is available in the GenBank database under accession number AP010907.

An Australian isolate, HearSNPV-Aus, which will be referred to in this specification by the abbreviation HearAus, the genome of which has been completely sequenced and is available in the GenBank database under accession number JN584482.

Seven isolates from the Iberian Peninsula: five from Spain, HearSP1, HearSP2, HearSP4, HearSP7 and HearSP8, and two from Portugal: HearPT1 and HearPT2 (Arrizubieta et al., 2014; Figueiredo et al., 1999, 2009). Figueiredo et al. (1999) selected the HearSP1 isolate as the one having the best insecticidal properties, in that it was two times more pathogenic than HearSP2 against second-instar larvae from a Portuguese population. Subsequently, a new study by Figueiredo et al. (2009) found that the HearSP7, HearPT1 and HearPT2 isolates exhibited the best bio-insecticidal attributes, though the study did not include the HearSP1 isolate. A recent study performed at our laboratory comparing all these Iberian Peninsula isolates selected HearSP1 as having the best insecticidal attributes against *H. armigera*, as it had the same pathogenicity as the other isolates considered, but it was more virulent and was also one of the most productive in terms of the number of occlusion bodies produced in each infected insect (Arrizubieta et al., 2014). FIG. 1B in the article by Figueiredo et al. (2009) presents the Bg/II restriction profiles for the Spanish isolates HearSP1, HearSP2, HearSP3, HearSP4, HearSP7 and HearSP8 and Portuguese isolates HearPT1 and HearPT2 (FIG. 4A in this application). FIG. 1 in the article by Arrizubieta et al. (2014) presents the EcoRI profiles for the HearSP1, HearSP2, HearSP4, HearSP7, HearSP8, HearPT1, HearPT2 and HearG4 isolates (FIG. 4B in this application) and Table 1 in that article listed the restriction fragment sizes (Table 3).

TABLE 3

Estimated fragment sizes for HearSP1, HearSP2, HearSP4, HearSP7, HearSP8, HearPT1, HearPT2 and HearG4 and actual fragment sizes for HearG4 generated in silico (G4*) from a sequence (AF271059) generated by digestion using EcoRI and total estimated genome sizes (Arrizubieta et al., 2014).

| | HearSNPV isolate | | | | | | | | |
|---|---|---|---|---|---|---|---|---|---|
| Fragment | SP1 | SP2 | SP4 | SP7 | SP8 | PT1 | PT2 | G4 | G4* |
| A | 13.4 | 13.4 | 13.4 | 13.2 | 13.4 | 13.4 | 13.4 | 14.3 | 14.13 |
| B | 10.7 | 13.2 | 10.7 | 10.0 | 10.7 | 10.7 | 10.7 | 13.4 | 13.45 |
| C | 9.3 | 10.7 | 9.3 | 9.3 | 9.0 | 9.3 | 9.3 | 10.1 | 10.15 |
| D | 9.2 | 9.3 | 9.2 | 9.0 | 8.2 | 9.0 | 9.2 | 9.0 | 9.05 |
| E | 8.2 | 9.2 | 8.2 | 8.2 | 7.5 | 8.2 | 8.2 | 6.6 | 6.64 |
| F | 7.1 | 7.1 | 7.1 | 7.1 | 6.3 | 7.5 | 7.5 | 6.4 | 6.36 |
| G | 6.3 | 6.3 | 6.3 | 6.3 | 6.0 | 6.3 | 6.3 | 6.3 | 6.29 |
| H | 6.0 | 6.0 | 6.0 | 6.0 | 5.9 | 6.0 | 6.0 | 6.0 | 5.99 |
| I | 5.9 | 5.9 | 5.9 | 5.9 | 5.8 | 5.9 | 5.9 | 5.8 | 5.84 |
| J | 5.8 | 5.8 | 5.8 | 5.8 | 5.8 | 5.8 | 5.8 | 5.8 | 5.84 |
| K | 5.8 | 5.7 | 5.8 | 5.8 | 5.7 | 5.8 | 5.8 | 5.7 | 5.67 |
| L | 5.7 | 5.3 | 5.7 | 5.7 | 4.9 | 5.3 | 5.7 | 4.8 | 4.75 |
| M | 5.3 | 4.9 | 4.9 | 4.9 | 4.6 | 4.9 | 5.3 | 4.6 | 4.58 |
| N | 4.9 | 4.6 | 4.6 | 4.6 | 4.4 | 4.6 | 4.9 | 4.4 | 4.42 |
| O | 4.6 | 4.4 | 4.4 | 4.4 | 4.4 | 4.4 | 4.6 | 4.4 | 4.40 |
| P | 4.4 | 4.4 | 4.4 | 4.4 | 3.3 | 4.4 | 4.4 | 4.1 | 4.14 |
| Q | 4.4 | 3.3 | 3.3 | 3.3 | 3.0 | 3.3 | 4.4 | 3.7 | 3.68 |
| R | 3.3 | 3.0 | 3.0 | 3.0 | 2.8 | 3.0 | 3.3 | 3.4 | 3.36 |
| S | 3.0 | 2.8 | 2.8 | 2.8 | 1.7 | 2.8 | 3.0 | 3.0 | 3.0 |
| T | 2.8 | 1.7 | 1.7 | 1.7 | 1.0 | 1.7 | 2.8 | 2.8 | 2.83 |
| U | 1.7 | 1.0 | 1.0 | 1.0 | 1.0 | 1.0 | 1.7 | 1.7 | 1.74 |
| V | 1.0 | 1.0 | 1.0 | 1.0 | 0.8 | 1.0 | 1.0 | 1.5 | 1.48 |
| X | 1.0 | 0.8 | 0.8 | 0.8 | | 0.8 | 1.0 | 1.0 | 1.00 |
| Y | 0.8 | | | | | | 0.8 | 0.8 | 0.78 |

TABLE 3-continued

Estimated fragment sizes for HearSP1, HearSP2, HearSP4, HearSP7, HearSP8, HearPT1, HearPT2 and HearG4 and actual fragment sizes for HearG4 generated in silico (G4*) from a sequence (AF271059) generated by digestion using EcoRI and total estimated genome sizes (Arrizubieta et al., 2014).

| | HearSNPV isolate | | | | | | | | |
|---|---|---|---|---|---|---|---|---|---|
| Fragment | SP1 | SP2 | SP4 | SP7 | SP8 | PT1 | PT2 | G4 | G4* |
| Z | 0.5 | | | | | | | | 0.48 |
| a | 0.4 | — | — | — | — | — | — | — | 0.45 |
| b | 0.4 | — | — | — | — | — | — | — | 0.41 |
| c | 0.3 | — | — | — | — | — | — | — | 0.31 |
| d | 0.18 | — | — | — | — | — | — | — | 0.18 |
| e | 0.02 | — | — | — | — | — | — | — | 0.02 |
| Total | 132.4 | 129.8 | 125.3 | 124.2 | 116.2 | 125.1 | 131.0 | 129.6 | 131.4 |

The difference in the number of different genotype fragments with the number generated in silico for the HearG4 genotype is attributable to the fact that its genome has been completely sequenced, making it possible to detect small fragments not visible on the REN profiles and hence impossible to detect by banding pattern analysis. In the case of HearSP1, small fragments were detected by PCR amplification and sequencing the amplified fragments using designed primers on the ends of the cloned fragments (Arrizubieta et al., 2014).

After selecting appropriate active material and before a bioinsecticide is marketed, field trials have to be performed to verify that it is efficacious in the conditions in which it will be applied, given that its efficacy in the field may vary from that recorded under controlled conditions in the laboratory. However, to be able to treat large areas of crop in order to carry out the field trials, large amounts of occlusion bodies are required, making it necessary to develop a system for mass producing the virus. The method currently employed for mass production of most baculoviruses is in vivo production in permissive hosts (Kalia et al., 2001; Lasa et al., 2007). This method consists of feeding susceptible larvae an artificial diet contaminated with a suspension of occlusion bodies on the surface. Certain essential aspects of this method, such as the artificial diet for the insect or mass breeding methods have to be developed specifically for each host-pathogen system (Lasa et al., 2007). Furthermore, a HearSNPV production system involving both in vivo and in vitro production has been developed in the United States (U.S. Pat. No. 7,521,219 B2). This method consists of first multiplying the virus in *H. armigera* larvae and then performing a limited number of serial passages in cells to obtain large amounts of occlusion bodies.

Since *H. armigera* larvae are developing resistance to synthetic chemical insecticides with ever greater frequency, the amount that has to be applied for these insecticides to achieve the sought-after effect is gradually increasing. Owing to the large land area given over to growing tomatoes in the Iberian Peninsula, this is turning into a problem with huge negative impacts for growers, consumers and the environment.

Contamination of soils, aquifers and other natural areas; their effects on other living organisms; and higher production costs of agricultural products coupled with lower product quality represent serious threats to various strategic sectors in the Iberian Peninsula. In view of the resistance to synthetic chemical insecticides developed by *H. armigera* larvae, there is interest in fostering the availability of an alternative that combines good insecticidal attributes with a very narrow host range to avoid targeting natural enemies and other beneficial organisms, for example, a biological control agent. One especially desirable agent of this kind would be an efficient control method sufficiently potent to counter the threats and predicaments posed by *H. armigera* in the Iberian Peninsula. In addition to being highly efficacious against pests in the Iberian Peninsula, there is also a need for an efficient production method, so that production costs and the amounts of insecticide to be applied do not make it uncompetitive by raising costs.

This invention provides an effective solution to these problems.

SUMMARY OF THE INVENTION

This invention is based on obtaining new genotypes of *Helicoverpa armigera* single nucleopolyhedrovirus isolated by means of in vitro purification. Two of these genotypes were purified from the HearSNPV-SP1 (HearSP1) isolate (Figueiredo et al., 1999), designated HearSNPV-SP1A and HearSNPV-SP1B (abbreviated here as HearSP1A and HearSP1B) and a further six genotypes were isolated from second-generation larvae from a population obtained from a cotton crop in Lebrija (Seville) killed during an epizootic outbreak that occurred in the laboratory, designated HearSNPV-LB1, HearSNPV-LB2, HearSNPV-LB3, HearSNPV-LB4, HearSNPV-LB5 and HearSNPV-LB6 (abbreviated here as HearLB1, HearLB2, HearLB3, HearLB4, HearLB5 and HearLB6). These genotypes were unlike any other isolate, or genotype, characterized to date.

Unexpectedly, the trials performed on these genotypes showed two of the new genotypes isolated, HearSNPV-SP1B (CNCM I-4806) and HearSNPV-LB6 (CNCM I-4807) and more particularly a mixture of the two HearSNPV-SP1B:LB6 in the ratio of 1:1, to be among the most active nucleopolyhedroviruses developed as bioinsecticides to date.

This product therefore affords a clean and safe technology, in that it leaves no toxic residues in the soil or on crops and is not toxic to humans or other animals, including the natural enemies of the pests, such as predators and parasitoids.

Furthermore, these nucleopolyhedroviruses have the added advantage of being easy to produce with good yields.

Therefore, to begin with, the object of this invention is an *H. armigera* single nucleopolyhedrovirus (HearSNPV) belonging to a genotype selected from a group of:

i) the HearSNPV genotypes on deposit at the Collection Nationale de Cultures de Microorganismes [National Collection of Microorganism Cultures] (CNCM) under deposit numbers CNCM I-4806 (HearSNPV-SP1B) and CNCM I-4807 (HearSNPV-LB6), or ii) the genotypes, the genome of which is represented by SEQ ID NO:13 (HearSNPV-SP1B) or SEQ ID NO:14 (HearSNPV-LB6).

These nucleopolyhedroviruses may take different forms, either that of a virus particle or virion, or that of an occlusion body, the form in which nucleopolyhedroviruses are found in nature and hence the form in which they are ingested by larvae. An occlusion body may contain virions of just one of the HearSNPV-SP1B (CNCM I-4806) or HearSNPV-LB6 (CNCM I-4807) genotypes or virions with more than one of the said genotypes co-occluded in a single occlusion body. The virions may be occlusion-derived virions (ODV) (the form embedded in the occlusion bodies used for propagation upon release in the larval gut when the polyhedrin dissolves) or budded virions (BVs) (the form used to propagate the infection among the different tissues in an infected insect, which may also be present in cell cultures).

Another object of this invention is an occlusion body containing several virions in which, at least, one virion belongs to an *H. armigera* single nucleopolyhedrovirus genotype selected from the group of HearSNPV-SP1B (CNCM I-4806) and HearSNPV-LB6 (CNCM I-4807). The occlusion body may contain various virions of a single genotype or virions of different genotypes co-occluded in the same occlusion body. When the virions are of the same genotype, the genotype may be either of the HearSNPV-SP1B or HearSNPV-LB6 genotypes. In the case of co-occluded virions, the genotype of the co-occluded virions may be either of HearSNPV-SP1B or HearSNPV-LB6, in varying proportions. Further, the mixture may include virions of other *H. armigera* single nucleopolyhedrovirus genotypes, or all the virions may belong to one of the genotypes in the group of HearSNPV-SP1B and HearSNPV-LB6. In either case the virions in the occlusion bodies will be occlusion-derived virions (ODV).

The HearSNPV-SP1B and HearSNPV-LB6 genotypes are distinguishable by the specific sequence of certain regions of their genomes, which are highly variable, such as the genome regions known as homologous regions (hrs) 1 and 5 (hr1 and hr5), as described in the Examples set out in this application. Accordingly, other possible embodiments of this aspect of the invention are occlusion bodies containing, at least, one ODV virion, the genome of which comprises a fragment of DNA having a sequence represented by:

i) SEQ ID NO:5 or SEQ ID NO:6 [the specific sequences of homologous region 1 (hr1) amplified by PCR using the F-hr1 and R-hr1 primers in the Examples set out in this application, respectively belonging to the HearSNPV-SP1B (CNCM I-4806) and HearSNPV-LB6 (CNCM I-4807) genotypes].

ii) SEQ ID NO:7 or SEQ ID NO:8 [the specific sequences of homologous region 5 (hr5) amplified by PCR using the F-hr5 and R-hr5 primers in the Examples set out in this application, respectively belonging to the HearSNPV-SP1B (CNCM I-4806) and HearSNPV-LB6 (CNCM I-4807) genotypes].

iii) SEQ ID NO:9 or SEQ ID NO:10 [the complete sequences of homologous region 1 (hr1), respectively belonging to the HearSNPV-SP1B (CNCM I-4806) and HearSNPV-LB6 (CNCM I-4807) genotypes].

iv) SEQ ID NO:11 or SEQ ID NO:12 [the complete sequences of homologous region 5 (hr5), respectively belonging to the HearSNPV-SP1B (CNCM I-4806) and HearSNPV-LB6 (CNCM I-4807) genotypes].

Yet another aspect of the invention is a composition containing nucleopolyhedrovirus of, at least, one of the genotypes HearSNPV-SP1B (CNCM I-4806) and HearSNPV-LB6 (CNCM I-4807) or combinations thereof. As in the previous case, the nucleopolyhedrovirus may take different forms, e.g., free virions, or preferably occlusion bodies, which may have a variable number of co-occluded virions [i.e., as already mentioned above, occlusion-derived virions (ODV)] In this case, the virions embedded in the occlusion body may be of a single genotype or of various genotypes, provided that, at least, one of the genotypes is HearSNPV-SP1B (CNCM I-4806) or HearSNPV-LB6 (CNCM I-4807). Therefore, this aspect of the invention relates to a composition containing a nucleopolyhedrovirus of the invention or an occlusion body of the invention. In particular, possible embodiments of the invention may comprise mixtures of virions of the different genotypes used to conduct the trials described in the Examples of this invention set out below, preferably compositions comprising a mixture of virions of the HearSNPV-SP1B (CNCM I-4806) and HearSNPV-LB6 (CNCM I-4807) genotypes.

The different genotypes may be present in any relative proportion, preferably in the ratio that provided the best results in the Examples described below, that is, where the HearSNPV-SP1B (CNCM I-4806) and HearSNPV-LB6 (CNCM I-4807) genotypes are present in the ratio of HearSNPV-SP1B to HearSNPV-LB6 of 1:1.

In addition, the compositions of the invention may comprise any suitable excipient or carrier for the agricultural sector, preferably those affording suitability for application by any of the methods conventionally used in agriculture, aerial or ground application, spraying in the form of a suspension or powder, or by means of irrigation systems of any kind. The composition may be in any form, such as aqueous or solid form. The composition may contain any other component, preferably components of particular interest in agriculture, e.g., *H. armigera* single nucleopolyhedrovirus may, for instance, be mixed with compost, fertilizer, a pesticide, or mixtures thereof. As an example of a specific case, where the composition of the invention further comprises an insecticide based on the bacterium *Bacillus thuringiensis* selected from endospores of that bacterium, Cry protein crystals, or mixtures thereof.

Furthermore, compositions comprising other agents to enhance the pathogenic effect of nucleopolyhedrovirus on the lepidopteran are other possible embodiments of the invention.

Yet another aspect of the invention is the use of, at least, one of the nucleopolyhedroviruses of this invention or of a composition containing, at least, one such virus as an insecticide. The insect to be controlled is preferably *H. armigera*, more specifically in the larval or caterpillar stage. The nucleopolyhedroviruses are preferably in the form of occlusion bodies, the form ordinarily ingested by larvae. The composition also preferably contains a mixture of two genotypes, HearSNPV-SP1B (CNCM I-4806) and HearSNPV-LB6 (CNCM I-4807) and preferably these genotypes are present in the ratio of HearSNPV-SP1B to HearSNPV-LB6 of 1:1.

Another aspect of the invention is a method of producing occlusion bodies that comprises a step in which *H. armigera* larvae are fed an artificial diet containing *H. armigera* nucleopolyhedrovirus occlusion bodies containing virions of either of the genotypes HearSNPV-SP1B (CNCM I-4806) or HearSNPV-LB6 (CNCM I-4807) or of a mixture of the two.

Yet another aspect of the invention is a method of identifying the presence of an *H. armigera* single nucleopolyhedrovirus genotype selected from HearSNPV-SP1B (CNCM I-4806) and HearSNPV-LB6 (CNCM I-4807) in a sample that comprises the steps of:

i) PCR amplification of DNA extracted from the said sample using a pair of primers that amplify homologous regions (hrs) 1 or 5, selected from those formed by:
   a. SEQ ID NO:1 (F-hr1) and SEQ ID NO:2 (R-hr1), or
   b. SEQ ID NO:3 (F-hr5) and SEQ ID NO:4 (R-hr5);
ii) analyzing the amplified fragment to determine its length or sequence;
iii) digesting the amplified fragment with NdeI endonuclease;
iv) analyzing the fragments generated by digestion to determine the number of fragments and the size of each one;
v) concluding that one of the genotypes HearSNPV-SP1B (CNCM I-4806) or HearSNPV-LB6 (CNCM I-4807) is present if:
   a. the fragment amplified by the pair of SEQ ID NO:1-SEQ ID NO:2 has:
      i. a length of 2,177 (HearSNPV-SP1B) or 2,177 (HearSNPV-LB6) nucleotides;
      ii. digestion of the said fragment with NdeI endonuclease generates six fragments of 857, 508, 381, 306, 78 and 47 nucleotides (HearSNPV-SP1B) or five fragments of 1,210, 475, 307, 78 and 47 nucleotides (HearSNPV-LB6);
      iii. the sequence represented by SEQ ID NO:5 (HearSNPV-SP1B) or SEQ ID NO:6 (HearSNPV-LB6);

or, alternatively, b) the fragment amplified by the primer pair of SEQ ID NO:3 and SEQ ID NO:4 has:
   i. a length of 2,326 (HearSNPV-SP1B) or 2,330 (HearSNPV-LB6) nucleotides;
   ii. digestion of the said fragment with NdeI endonuclease generates four fragments of 1,120, 917, 211 and 78 nucleotides (HearSNPV-SP1B) or three fragments of 1,120, 998 and 212 nucleotides (HearSNPV-LB6);

the sequence represented by SEQ ID NO:7 (HearSNPV-SP1B) or SEQ ID NO:8 (HearSNPV-LB6).

The invention is explained in greater detail with the aid of the Figures and Examples set out below.

DESCRIPTION OF THE FIGURES

FIG. 8. (A) Fragments from PCR amplification of the areas of variability of homologous regions hr1 (primers identified by SEQ ID NO:1 and SEQ ID NO:2) and hr5 (primers identified by SEQ ID NO:3 and SEQ ID NO:4) of the HearSP1B and HearLB6 genotypes in the HearSP1 isolate and the Chinese HearG4 genotype, where c− is the negative control without viral DNA. The 1 kb molecular weight marker (NIPPON Genetics, Europe GmbH) appears at left in the Figure with fragment sizes given in kilobases. (B) Fragments obtained on digesting the fragments resulting from PCR of the hr1 and hr5 areas of variability of the HearSP1B and HearLB6 genotypes of the HearSP1 isolate and the Chinese HearG4 genotype with NdeI endonuclease. The 100 bp molecular weight marker (NIPPON Genetics, Europe GmbH) appears at left in the Figure with fragment sizes given in base pairs.

FIG. 9. (A) Alignment of PCR amplified nucleotide fragments from homologous region 1 (hr1) for the HearSP1B and HearLB6 genotypes and the HearG4, HearC1, HearNNg1 and HearAus isolates. (B) Alignment of PCR amplified nucleotide fragments from homologous region 5 (hr5) for the HearSP1B and HearLB6 genotypes and the HearG4, HearC1, HearNNg1 and HearAus isolates.

FIG. 15. Mean occlusion body production (x$10^8$ occlusion bodies/larva) in newly molted third, fourth and fifth-instar ($L_3$, $L_4$ and $L_5$) *H. armigera* larvae and larvae one day after molting into those same stages ($L_3$+1, $L_4$+1 and $L_5$+1) inoculated with a 95% ($LC_{95}$), 90% ($LC_{90}$), or 80% ($LC_{80}$) lethal concentration of the co-occluded HearSP1B:LB6 mixture. (B) Mean occlusion body production (x$10^{10}$ occlusion bodies/100 larvae) in newly moulted $L_3$, $L_4$ and $L_5$ *H. armigera* larvae and larvae one day after molting into those same stages ($L_3$+1, $L_4$+1 and $L_5$+1) inoculated with $LC_{95}$, $LC_{90}$, or $LC_{80}$ of the co-occluded HearSP1B:LB6 mixture. Vertical bars indicate standard error. Different letters next to values indicate significant differences between treatments (P<0.05).

FIG. 16. Mean occlusion body production (x$10^9$ occlusion bodies/larva) in fifth-instar ($L_5$) *H. armigera* larvae inoculated with a 95% lethal concentration ($LC_{95}$) of the co-occluded HearSP1B:LB6 mixture and incubated at 23, 26 and 30° C. Vertical bars indicate standard error. The same letters next to values indicate no significant differences between treatments (P>0.05).

FIG. 17. Percentage mortality achieved in second-instar *H. armigera* larvae collected from tomato plants treated in laboratory conditions. Larvae were collected 1, 3 and 5 days after application of HearSNPV at three concentrations ($10^6$, $10^7$ and $10^8$ occlusion bodies/ml) of the co-occluded HearSP1B:LB6 mixture and reared separately on a semi-synthetic diet in cups in the laboratory until death or pupation.

FIG. 22. Percentage damaged fruit, scarred or fresh, in a field-grown tomato crop after applying HearSP1B:LB6, HearSP1, Spintor, Turex and Dursban during (A) the first, (B) the second, (C) the third and (D) the fourth two-week period. Different letters in the columns for each group indicate significant differences between the groups for the different treatments (P<0.05).

DETAILED DESCRIPTION OF THE INVENTION

Figure 5:
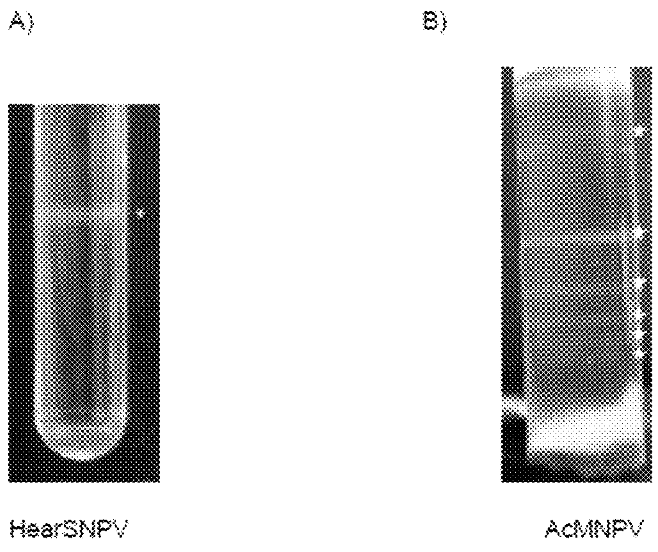
FIG. 5. Continuous sucrose gradient banding pattern after centrifuging the ODVs obtained from (A) HearSNPV and (B) AcMNPV. White asterisks indicate the bands representing ODVs. Only one band is visible in panel A, hence all the virions exhibited the same morphology, containing a single nucleocapsid. However, several bands are visible in panel B, each representing ODVs with a specific number of nucleocapsids; the bands have higher or lower weights depending on the number of nucleocapsids, therefore appearing at a higher or lower level.

The object of this invention relates to obtaining new genotypes of *Helicoverpa armigera* single nucleopolyhedrovirus (FIG. 5). The said genotypes were isolated by two different methods:

i) from the HearSNPV-SP1 (or HearSP1 in an abbreviated form), by means of an in vitro plaque assay in cell culture. The genotypes present in the isolate were different from all other isolates and genotypes that have been characterized to date and have been designated HearSNPV-SP1A and HearSNPV-SP1B (or HearSP1A and HearSP1B, respectively, in an abbreviated form).

ii) from larvae killed during an epizootic outbreak in the second generation of an *H. armigera* population from a cotton crop from Lebrija (Seville) that was reared in the laboratory. The genotypes obtained from these larvae were different from all other isolates and genotypes that have been characterized to date and have been designated HearSNPV-LB1, HearSNPV-LB2, HearSNPV-LB3, HearSNPV-LB4, HearSNPV-LB5 and HearSNPV-LB6 (or HearLB1, HearLB2, HearLB3, HearLB4, HearLB5 and HearLB6, respectively, in a more abbreviated form). Each of these genotypes came from an individual larva that died during the said epizootic. The absence of submolar bands in the restriction profiles suggests that these were pure genotypes, since submolar bands are caused by various genotypes present in different proportions. However, in order to be sure of their purity, in vitro cloning of the different isolates was carried out by an end-point dilution (EPD) assay. That cloning and subsequent analysis using restriction enzymes confirmed the purity of the genotypes, showing that each larva had died from infection by a single genotype.

Figure 3:
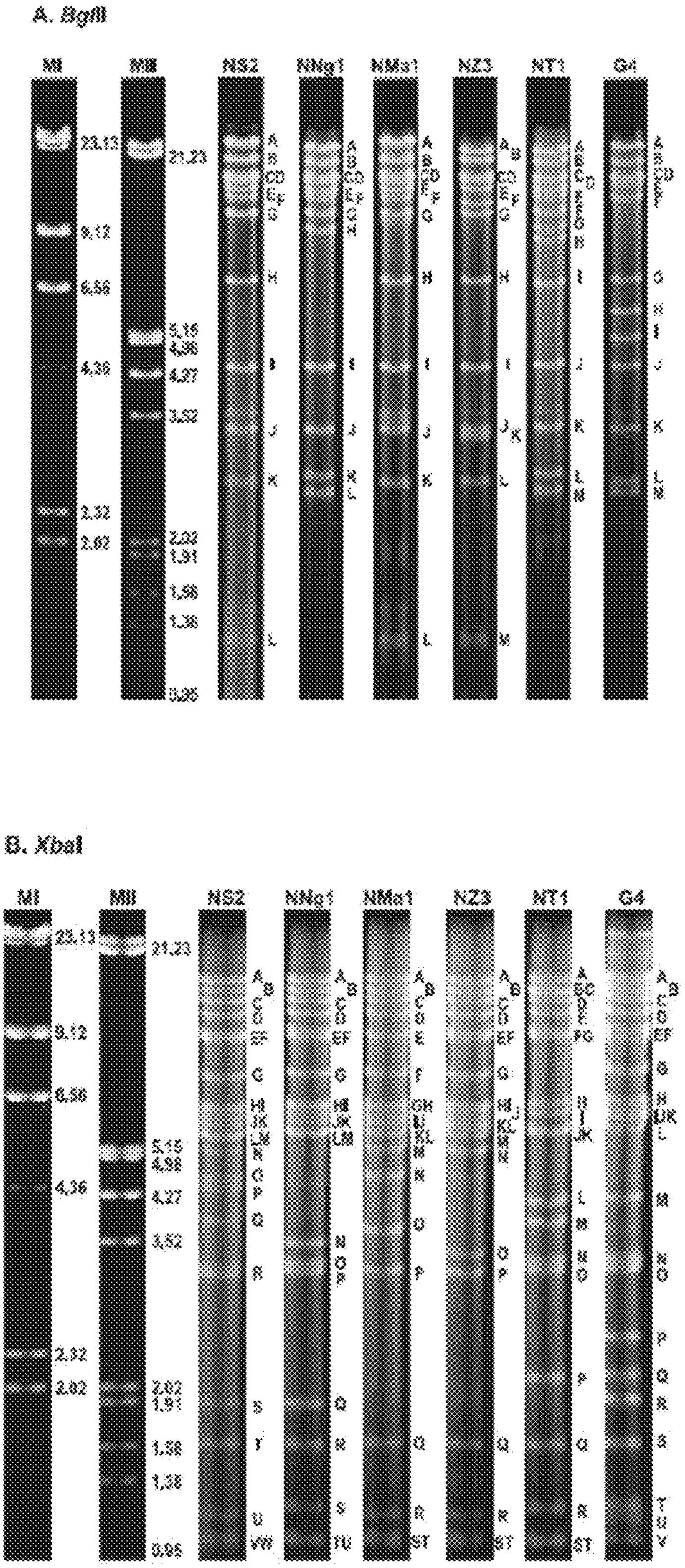
FIG. 3. Restriction profiles for different HearSNPV isolates: NNg1 (from Kenya), NS2 (South Africa), NMa1 (Kenya), NZ3 (Zimbabwe) and NT1 (Thailand) obtained on digestion of genomic DNA with Bg/II (A) and XbaI (B) endonuclease. The Lambda (λ) molecular weight marker digested with HindIII (MI) and with EcoRI-HindIII (MII) appears at left in the Figure with sizes given in kilobases (Ogembo et al., 2007).
Figure 4:
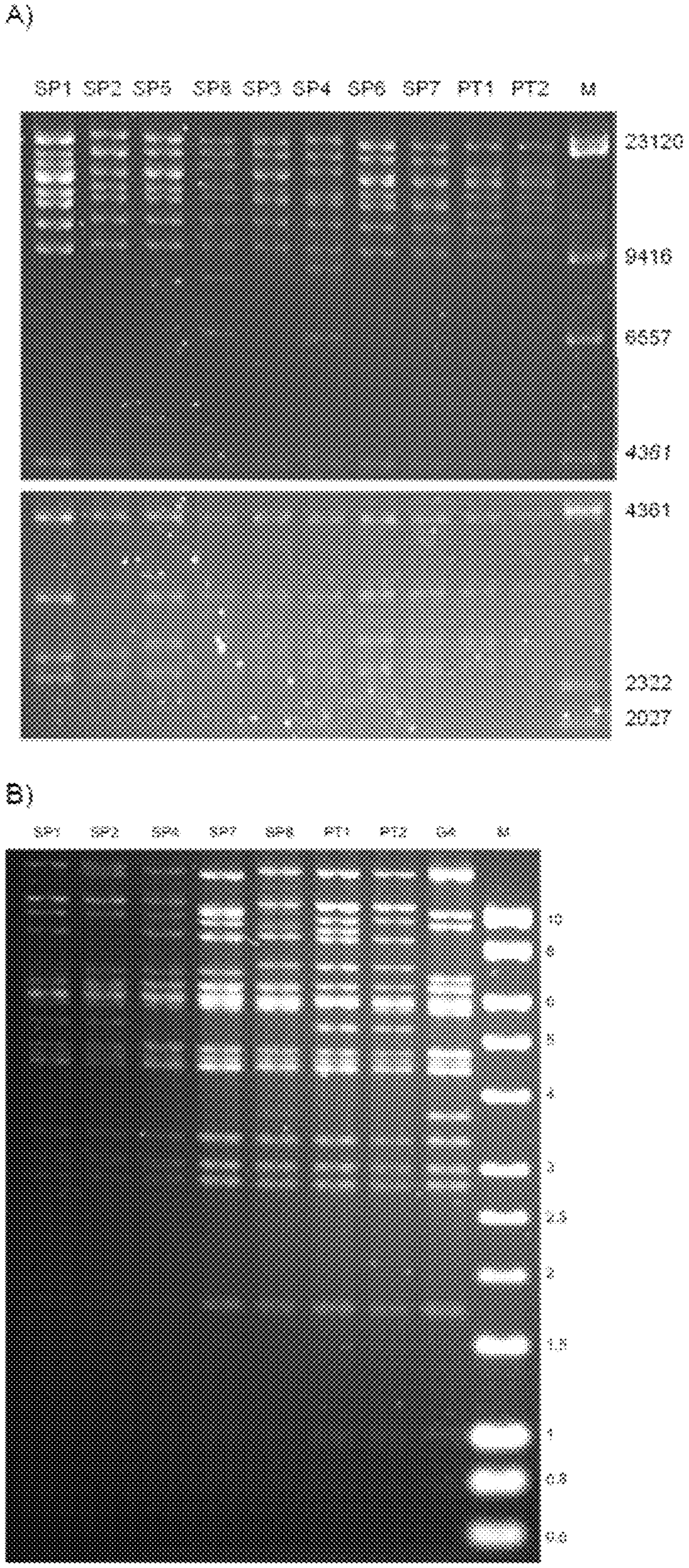
FIG. 4. (A) Restriction profiles for the HearSP1, HearSP2, HearSP3, HearSP4, HearSP5, HearSP6, HearSP7, HearSP8, HearPT1 and HearPT2 isolates after digestion of the genomic DNA with Bg/II endonuclease; the Lambda (A) molecular weight marker digested with HindIII appears at left in the Figure with sizes given in base pairs (Figueiredo et al., 2009). (B) Restriction profiles for the HearSP1, HearSP2, HearSP4, HearSP7, HearSP8, HearPT1, HearPT2 and HearG4 obtained with EcoRI endonuclease; the HyperLadder I molecular weight marker (Bioline) appears at left in the Figure with sizes given in kilobases (Arrizubieta et al., 2014).

Furthermore, the restriction profiles obtained by digestion of the genome of each of these genotypes with different restriction enzymes (endonucleases) confirmed that different genotypes were involved (HearSP1A, HearSP1B, HearLB1, HearLB2, HearLB3, HearLB4, HearLB5 and HearLB6) (FIG. 7) and also that they were different from other isolates and genotypes characterized to date (Table 4), such as the Chinese genotypes HearC1 and HearG4 (FIG. 2), the HearNNg1 isolate from Kenya (FIG. 3) and the HearSP1, HearSP2, HearSP4, HearSP7, HearSP8, HearPT1 and HearPT2 isolates from the Iberian Peninsula (FIG. 4).

Figure 1:
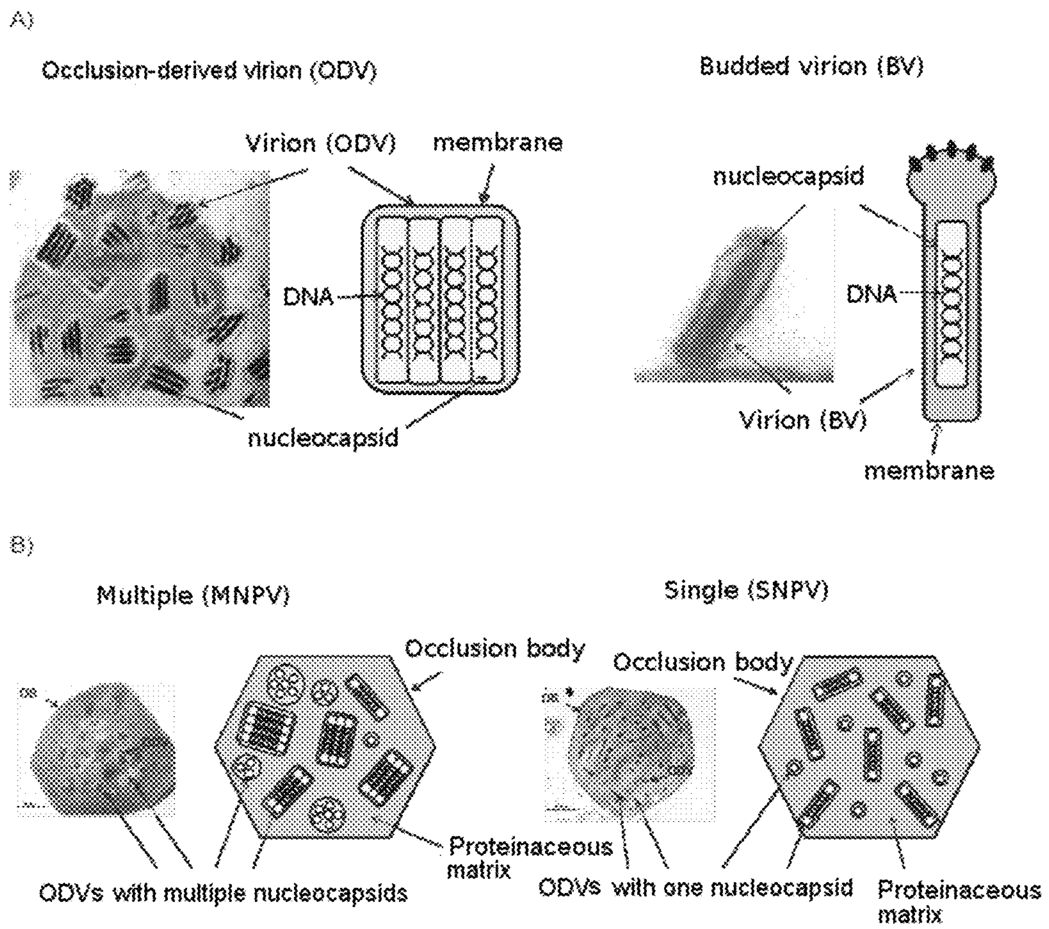
FIG. 1. (A) Transmission electron microscope photographs and schematic representation of occlusion-derived virions (ODV) and budded virions (BVs) and (B) of a multiple nucleopolyhedrovirus (MNPV) having virions with a variable number of nucleocapsids and of a single nucleopolyhedrovirus (SNPV) having virions with a single nucleocapsid.
Figure 2:
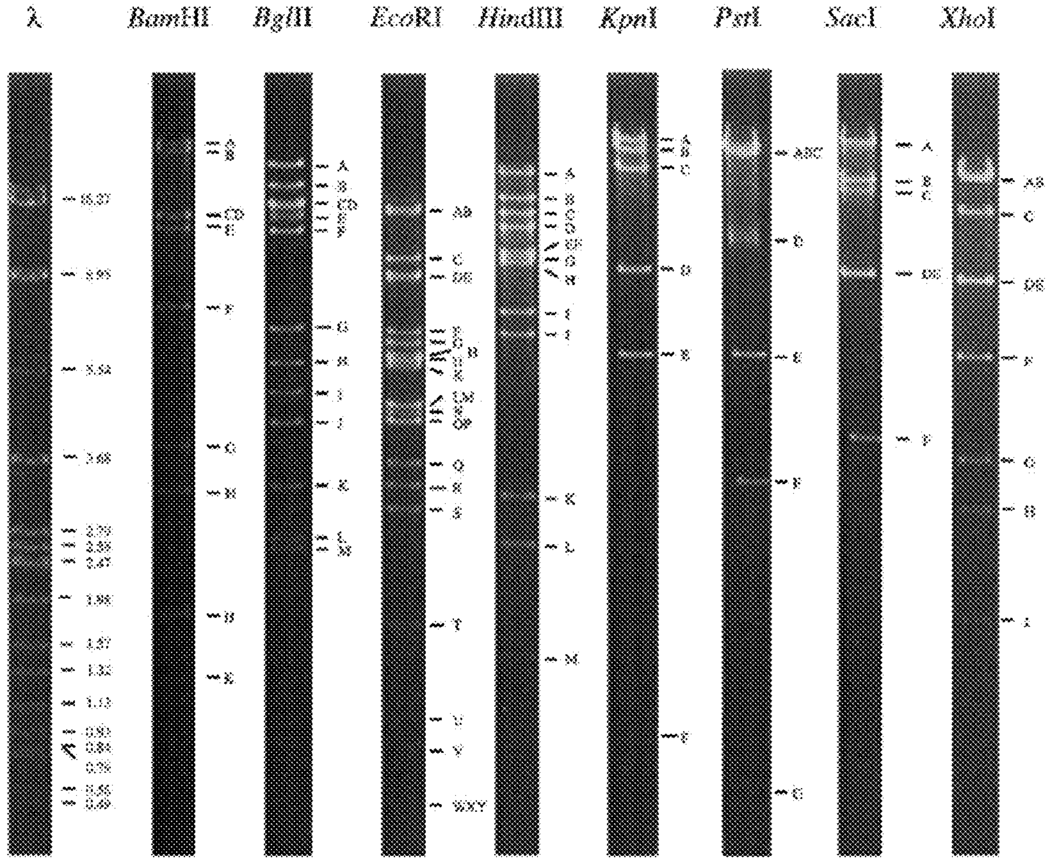
FIG. 2. Restriction profiles of the HearSNPV-G4 isolate after digestion of the genomic DNA with the BamHI, BglII, EcoRI, HindIII, KpnI, PstI, SacI and XhoI endonucleases. The Lambda (λ) molecular weight marker digested with BamHI-EcoRI-HindIII appears at left in the Figure with sizes given in kilobases (Chen et al., 2000).
Figure 7:
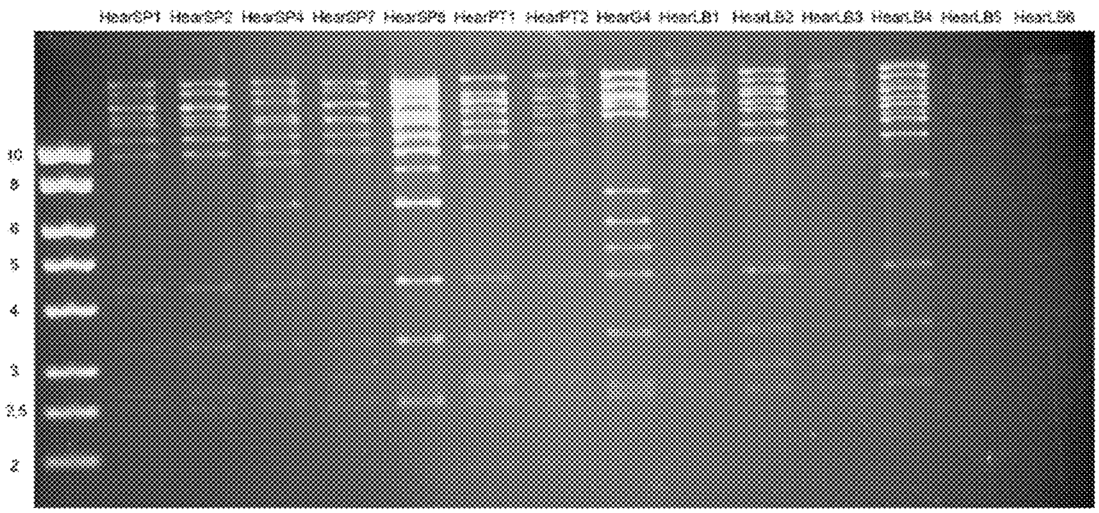
FIG. 7. (A) Electrophoresis of restriction fragments obtained by treating viral DNA from the HearSP1 isolate and the HearSP1A and HearSP1B genotype with BglII and EcoRI restriction endonuclease. (B) Electrophoresis of restriction fragments obtained by treating viral DNA from the HearSP1, HearSP2, HearSP4, HearSP7, HearSP8, HearPT1 and HearPT2 isolates and the HearG4, HearSP1A, HearSP1B, HearLB1, HearLB2, HearLB3, HearLB4, HearLB5 and HearLB6 genotypes with EcoRI restriction endonuclease. (C) Electrophoresis of restriction fragments obtained by treating viral DNA from the HearSP1, HearSP2, HearSP4, HearSP7, HearSP8, HearPT1 and HearPT2 isolates and the HearG4, HearSP1A, HearSP1B, HearLB1, HearLB2, HearLB3, HearLB4, HearLB5 and HearLB6 genotypes with Bg/II restriction endonuclease. The 1 kb molecular weight marker (NIPPON Genetics, Europe GmbH) appears at left in the Figures with fragment sizes given in kilobases.

Two of the different genotypes found, designated HearSP1B and HearLB6, which are readily distinguishable from each other and from the other HearSNPV isolates and genotypes by the profiles obtained by treating their genomes with restriction enzymes such as EcoRI and Bg/II. FIGS. 2, 3 and 4 depict the restriction profiles for the previously characterized HearSNPV isolates, whereas FIG. 7 shows the restriction profiles for the HearSP1A, HearSP1B, HearLB1, HearLB2, HearLB3, HearLB4, HearLB5 and HearLB6 genotypes and those for the Spanish isolates HearSP1, HearSP2, HearSP4, HearSP7 and HearSP8, the Portuguese isolates HearPT1 and HearPT2 and the Chinese genotype HearG4. Differentiation is based on the presence of characteristic polymorphic fragments in the restriction profile for each genotype or isolate. Submolar bands (bands containing fewer molecules than the other bands in the same DNA profile) are indicative of the presence of a mix of isolates, such as that observed for HearSP1 in FIG. 7A. Another example is the HearSP1B genotype, which, on being digested with NdeI, displayed a 9.73 kb band that was not observed in the profile for the HearSP1 isolate (FIG. 8B). In addition, the HearSP1B isolate exhibited various submolar bands at around 9.73 kb which were not observed in the profile for the HearSP1 isolate (FIG. 8B). Furthermore, the profiles obtained using Bg/II endonuclease displayed an 18.8 kb submolar band that was not observed in the profile for the HearSP1B genotype. The presence of these submolar bands plainly shows that the wild HearSP1 isolate was composed of a heterogeneous mix of genotypes.

In order to more clearly differentiate between the HearSP1B and HearLB6 and also differentiate them from other HearSNPV isolates, the genomes of which have been sequenced completely (HearG4, HearC1, HearNNg1 and HearAus), the values for the lengths of the restriction fragments generated by digestion of the said isolates and genotypes with EcoRI endonuclease are given in Table 4.

TABLE 4

Estimated length of DNA fragments generated by digestion of the genomic DNA of different isolates and genotypes with EcoRI endonuclease and total estimated genome size. The DNA fragments have been designated by letters, with A representing the longest fragment.

| | Size (kb) | | | | | |
|---|---|---|---|---|---|---|
| Fragment | HearSP1B | HearLB6 | HearG4 | HearC1 | HearNNg1 | HearAus |
| A | 13.54 | 13.55 | 14.13 | 14.13 | 13.51 | 13.44 |
| B | 10.18 | 10.50 | 13.45 | 12.84 | 10.20 | 10.15 |
| C | 9.73 | 9.74 | 10.15 | 9.75 | 9.73 | 9.48 |
| D | 9.20 | 9.38 | 9.05 | 9.05 | 9.20 | 9.06 |
| E | 8.21 | 8.26 | 6.64 | 6.91 | 8.23 | 8.23 |
| F | 6.52 | 6.45 | 6.36 | 6.54 | 6.60 | 6.68 |
| G | 6.30 | 6.29 | 6.29 | 6.30 | 6.30 | 6.28 |
| H | 6.15 | 5.98 | 5.99 | 6.00 | 6.23 | 6.00 |
| I | 5.98 | 5.93 | 5.84 | 5.84 | 6.00 | 5.94 |
| J | 5.93 | 5.85 | 5.84 | 5.84 | 6.00 | 5.84 |
| K | 5.84 | 5.84 | 5.67 | 5.67 | 5.80 | 5.84 |
| L | 5.69 | 5.68 | 4.75 | 4.74 | 5.80 | 5.70 |
| M | 5.25 | 5.25 | 4.58 | 4.65 | 5.70 | 4.83 |
| N | 4.73 | 4.73 | 4.42 | 4.57 | 4.75 | 4.75 |
| O | 4.57 | 4.57 | 4.40 | 4.41 | 4.57 | 4.57 |
| P | 4.42 | 4.42 | 4.14 | 4.40 | 4.41 | 4.41 |
| Q | 4.40 | 4.40 | 3.68 | 4.14 | 4.40 | 4.40 |
| R | 3.34 | 3.32 | 3.36 | 3.36 | 3.34 | 3.68 |
| S | 3.00 | 3.00 | 3.00 | 3.00 | 3.00 | 3.35 |
| T | 2.83 | 2.83 | 2.83 | 2.83 | 2.83 | 3.00 |
| U | 1.74 | 1.01 | 1.74 | 1.74 | 1.74 | 1.74 |
| V | 1.01 | 0.98 | 1.48 | 1.00 | 1.00 | 1.00 |
| X | 0.97 | 0.78 | 1.00 | 0.78 | 0.80 | 0.80 |

TABLE 4-continued

Estimated length of DNA fragments generated by digestion of the genomic DNA of different isolates and genotypes with EcoRI endonuclease and total estimated genome size. The DNA fragments have been designated by letters, with A representing the longest fragment.

| | Size (kb) | | | | | |
|---|---|---|---|---|---|---|
| Fragment | HearSP1B | HearLB6 | HearG4 | HearC1 | HearNNg1 | HearAus |
| Y | 0.78 | 0.48 | 0.78 | 0.48 | 0.48 | 0.48 |
| Z | 0.47 | 0.45 | 0.48 | 0.45 | 0.45 | 0.45 |
| a | 0.45 | 0.42 | 0.45 | 0.42 | 0.41 | 0.41 |
| b | 0.42 | 0.41 | 0.41 | 0.41 | 0.41 | 0.30 |
| c | 0.41 | 0.31 | 0.31 | 0.31 | 0.31 | 0.18 |
| d | 0.18 | 0.18 | 0.18 | 0.18 | 0.18 | 0.02 |
| e | 0.02 | 0.02 | 0.02 | 0.02 | 0.02 | |
| f | | | | | | |
| Total | 132.26 | 130.99 | 131.42 | 130.76 | 132.4 | 131.01 |

Comparing the data set out in Table 4 shows that there are differences in the number and sizes of the fragments, indicating that the HearSP1B and HearLB6 genotypes are different from the genotypes already known and hence that they are new. For example, the EcoRI-B fragment for the HearLB6 genotype (10.50 kb) is longer than the fragment for the HearSP1B genotype (10.18 kb). The EcoRI-F fragment for the HearLB6 genotype (6.45 kb) is not present in the HearSP1B profiles or in the profiles for the sequenced genotypes. On the other hand, the EcoRI-U (1.74) fragment for the HearSP1B genotype is not present in the profile for the HearLB6 genotype, though it is present in the sequenced genotypes. This can also be observed in FIG. 7.

The HearSP1B and HearLB6 genotypes are also differentiated from each other and from the other HearSNPV isolates and genotypes described in the literature by the specific nucleotide sequences each has in certain well-defined regions of the genome. For example, the region of the genome known as homologous region 1 (hr1) can be used, taking as reference the corresponding sequence in the genomes of the two Chinese isolates, HearG4 (Chen et al., 2001; GenBank accession number AF271059) and HearC1 (Zhang et al., 2005; GenBank accession number AF303045), of an isolate from Kenya, HearNNg1 (Ogembo et al., 2007; GenBank accession number AP010907) and of an isolate from Australia, HearAus (GenBank accession number JN584482). Homologous region 5 (hr5) is another useful region.

Rapid and precise differentiation of each of these two genotypes can therefore be obtained using PCR amplification followed by digestion of the amplified fragments with NdeI restriction enzyme, using specific primers to amplify, for instance, one of the following alternative regions:

i) Homologous region 1, hr1. The specific primers F-hr1 (5'-CGAAATCGACAACACCATGCA-3') and R-hr1 (5'-ACTTTTGTACGCCAGAGACGA-3') have been found to amplify a fragment having 2,177 and 2,177 nucleotides in this region of the HearSNPV genome for the HearSP1B and HearLB6 genotypes, respectively. Digestion of these amplified fragments with NdeI restriction endonuclease generates unique profiles for each genotype, yielding six fragments having 857, 508, 381, 306, 78 and 47 nucleotides for HearSP1B and five fragments having 1,210, 475, 307, 78 and 47 nucleotides for HearLB6. Similarly, these profiles differ from the profiles obtained for the sequenced genotypes (Table 6, FIG. 8B). Specifically, by way of example, FIG. 8B shows that the 508 and 381 nucleotide bands do not match up with any other band in the gels and that the bands for the HearSP1 isolate are located slightly higher up, indicating a larger size than the bands for HearSP1B.

ii) Homologous region 5, hr5. The specific primers F-hr5 (5'-CTAGCCGGTCCGTTTCTGTT-3') and R-hr5 (5'-GCCCCACCCAAAACATAACG-3') have been found to amplify a fragment having 2,326 and 2,330 nucleotides in this region of the HearSNPV genome for the HearSP1B and HearLB6 genotypes, respectively. Digestion of these amplified fragments with NdeI restriction endonuclease generates unique profiles for each genotype, yielding five fragments having 1,120, 917, 211 and 78 nucleotides for HearSP1B and three fragments having 1,120, 998 and 212 nucleotides for HearLB6. Similarly, these profiles differ from the profiles obtained for the sequenced genotypes (Table 6, FIG. 8B).

Panel A in FIG. 8 presents the photograph obtained following electrophoresis of the fragments amplified by PCR using the specific primers for the hr1 and hr5 regions. Panel B shows the photograph obtained after electrophoresis of the fragments obtained by digestion with NdeI of the fragments amplified by PCR using the specific primers for the hr1 and hr5 regions in the previous item. The photograph reveals that the fragments obtained for each genotype are different and distinguishable from each other. The fragments obtained for each genotype can also be seen to be different and distinguishable from each other. For example, in the case of hr1, the 1,120-bp fragment is characteristic for the HearLB6 genotype, whereas the HearSP1B genotype yields a characteristic 857-bp fragment. In the case of hr5, the HearSP1B genotype yields a characteristic 917-bp fragment, whereas the HearLB6 genotype yields a 998-bp fragment.

Therefore, the different genotypes can be distinguished from each other and from any other genotype of the virus described in the literature by a single PCR followed by digestion with NdeI (see Table 6 in Example 2 below).

In the case of natural isolates or artificial mixtures that may contain mixtures of genotypes, the proportion of the two genotypes HearSP1B and HearLB6 in the mixture may be determined by quantitative PCR using primers specific for each genotype, as mentioned below in the Materials and Methods sections of the Examples.

In addition, sequencing of the PCR-generated fragments also makes it possible to identify the different genotypes in the mixture. Therefore, the sequences represented by SEQ ID NO:5 and SEQ ID NO:6 match the amplified fragment sequences using primers F-hr1 and R-hr1 to amplify hr1 in the HearSP1B and HearLB6 genotypes, respectively, while SEQ ID NO:7 and SEQ ID NO:8 match the amplified fragment sequences for hr5 for those same genotypes.

As mentioned below, whole-genome sequences have been obtained for each of the two HearSP1B and HearLB6 genotypes, showing that SEQ ID NO:13 and SEQ ID NO:14, respectively, can be used to differentiate some genotypes from others. Specifically, on account of their variability, the complete sequences for the regions of variability in homologous region 1 (hr1) (SEQ ID NO:9 and SEQ ID NO:10 for the HearSP1B and HearLB6 genotypes, respectively) and for homologous region 5 (hr5) (SEQ ID NO:11 and SEQ ID NO:12 for the HearSP1B and HearLB6 genotypes, respectively) are set out individually below. For each of homologous region 1 (hr1) and homologous region 5 (hr5), the said sequences have been set out in the sense in which they appear in the whole-genome sequence. Since they are intergenic regions located between two open reading frames, there is no coding direction as in the case of reading frames. The latter may be transcribed in the sense direction (coding sequence) or in the antisense direction (the sequence complementary to the coding sequence).

In this invention complete sequences for each of the two genotypes, HearSP1B (SEQ ID NO:13) and HearLB6 (SEQ ID NO:14), have been obtained, a characteristic and defining trait for each one. Therefore, these genotypes are described in this application such that a person skilled in the art can reproduce the invention. Furthermore, the complete sequences for each of the genomes are supplemented with other data submitted in the application to the effect that the *Helicoverpa armigera* nucleopolyhedrovirus is a single nucleopolyhedrovirus (SNPV), that is, each whole virus particle or virion has a single nucleocapsid and hence a single copy of the nucleopolyhedrovirus genome. Additional data are also supplied to be able to identify each of the genotypes according to the profile obtained after digesting the genome with different restriction endonucleases as well as the size and sequence of the fragments obtained by PCR amplification of the regions of high variability in homologous regions 1 and 5 (hr1 and hr5) using the SEQ ID NO:1 and SEQ ID NO:2 or the SEQ ID NO:3 and SEQ ID NO:4 primers, respectively, along with the banding pattern obtained following digestion of these PCR fragments with NdeI. The Examples also contain data relating to the insecticidal activity of each genotype and of mixtures of the occlusion bodies containing co-occluded virions having different genotypes in a single occlusion body as well as how to obtain the different mixtures. Differences in pathogenicity, virulence and productivity between the genotypes and between the mixtures of genotypes of the invention were significant and the mixture of the two HearSP1B and HearLB6 genotypes in the ratio of 1:1 was more pathogenic than the rest of the genotypes and mixtures and as virulent as the fastest-killing genotypes.

The large number of possible combinations of genotypes and the differences between the relative potency of genotypes means that there was no way to predict in advance that the combination of this invention would yield better results than the others.

Of all the genotype mixtures formed, the HearSP1B:LB6 mixture in the ratio of 1:1 displayed the most desirable synergistic activity from a bioinsecticidal standpoint. However, this synergistic activity was not observed in many other mixtures of genotypes (in which the effect is merely additive or even antagonistic) and there is no way to predict which mixtures will result in synergistic activity. This result is neither obvious nor predictable, especially bearing in mind that the genotypes come from different geographical locations (Badajoz and Lebrija) and that up to now these two genotypes (HearSP1B and HearLB6) had not been obtained in a pure state from complex wild mixtures, such as field isolates.

In addition, data relating to the deposit of these two genotypes in accordance with the Budapest Treaty are submitted, making it possible to reference the genotypes by their deposit numbers, CNCM I-4806 (HearSP1B) and CNCM I-4807 (HearLB6).

Considering possible applications of the nucleopolyhedrovirus of this invention, each of the new HearSP1B and HearLB6 genotypes has been observed to have specific insecticidal activity against *H. armigera* larvae that can be regarded as comparable to that of chemical insecticides like Dursban and Spintor or to that of *Bacillus thuringiensis*-based biological insecticides like Turex commonly used against *H. armigera*. However, the two-genotype HearSP1B:LB6 mixture in the specific proportion of 1:1 in the form of occlusion bodies that include co-occluded ODVs, such that a single occlusion body may contain different HearSNPV genotypes, has further been found to possess enhanced insecticidal activity compared to each of the genotypes individually and any wild HearSNPV isolate currently known, exhibiting greater pathogenicity than the rest of the genotypes and mixtures while having the same mean time to death (MTD) as the fastest-killing genotypes. This represents a significant advantage, in that pathogenicity and speed of action are the main difficulties faced in developing baculoviruses as the active ingredients of bioinsecticides. Furthermore, this virus can be produced quickly, inasmuch as inoculating 100 newly moulted fifth-instar larvae ($L_5$) and incubating them with a diet at 30° C. yields in the order of $5\times10^{11}$ occlusion bodies in about five or six days.

What is more, trials on tomato plants, in the laboratory, in the greenhouse and in the field, have demonstrated that concentrations in the order of $10^{13}$ occlusion bodies of the nucleopolyhedrovirus of the invention/hectare are capable of effectively controlling infestations of larvae of this caterpillar with the same efficacy as the insecticides commonly used to combat this pest on tomato crops [Spintor, containing two spinosyn toxins (spinosad); Turex, based on *Bacillus thuringiensis* var. Aizawai; and Dursban, a chlorpyrifos-based chemical insecticide). The virus treatments result in a significant reduction in the number of damaged green and ripe fruit harvested compared to the control treatment while having no differences with respect to the other commonly used insecticides.

The fact that the host range of baculoviruses is restricted to invertebrates and the high specificity of HearSNPV in particular (which appears to infect only the larvae of a few moth species of the genus *Helicoverpa*, all of which are phylogenetically closely related), means that the technology of this product is clean and safe, since it leaves no toxic residues in soils or on crops and is not toxic to humans or other animals, including natural enemies such as parasitoids and predators.

Unexpectedly, the results set out in this patent application demonstrate that the co-occluded mixture of these two cloned genotypes (HearSP1B and HearLB6) in the ratio of 1:1 is among the most active nucleopolyhedrovirus of all those developed as bioinsecticides to date.

As HearNPV isolates native to the Iberian Peninsula, HearSP1B and HearLB6 are better adapted to the environmental conditions prevailing in southern Europe than isolates from other geographical origins. This is particularly significant bearing in mind the deleterious effects of UV radiation on bioinsecticide deposits after application, since to be able to exert their insecticidal effects, the NPVs have to remain active until they are ingested by *H. armigera*. In addition, a certain propensity for natural isolates from a given geographic region to be more pathogenic and virulent against larvae from the same region has been observed.

A further advantage of these nucleopolyhedroviruses is that they can be mass produced. Their occlusion bodies, in which their insecticidal activity resides, can be mass produced in vivo by inoculating *H. armigera* larvae with occlusion bodies previously obtained through the oral infection of larvae with mixtures of pure occlusion bodies of HearSP1B and HearLB6 in the ratio of 1:1. The occlusion bodies may contain virions of either one of genotypes HearSP1B or HearLB6, to obtain occlusion bodies with virions of a single genotype, or the two genotypes may be mixed, to obtain virions of both genotypes co-occluded in the same occlusion body. The specific method used to produce the new occlusion bodies may be any of the methods known to persons skilled in the art or the method used in the Examples set out below in this application. The Examples also describe an example of the composition of the artificial diet suitable for use with the method of producing occlusion bodies of the invention. The method of producing occlusion bodies may comprise the steps of:

i) feeding fifth-instar *H. armigera* larvae an artificial diet comprising *H. armigera* nucleopolyhedrovirus occlusion bodies containing virions of either one of the HearSP1B (CNCM I-4806) or HearLB6 (CNCM I-4807) genotypes or mixtures of both.

ii) holding the larvae separately at 30° C. until death occurs;

iii) purifying the occlusion bodies produced in the larvae by grinding the bodies of the larvae in water, filtering the resulting suspension, sedimenting the occlusion bodies, washing the sediment thus obtained and sedimenting again;

iv) resuspending the final pellet of sediment in water at neutral pH;

v) optionally storing the resulting suspension in one of the following conditions:

a) at room temperature b) under cooling or freezing c) lyophilizing the suspension and storing it at room temperature.

As used in this application, cooling conditions are defined as conditions in which the product is kept at between 0° C. and 8° C. and freezing conditions are defined as keeping the product at below 0° C. For purposes of this invention, cooling temperatures are preferably between 0° C. and 6° C. and freezing temperatures are preferably between −20° C. and −80° C.

The occlusion bodies may also be produced by feeding fifth-instar larvae an aqueous solution containing 10% sucrose and the selected co-occluded mixture at a 95% lethal concentration ($LC_{95}$). This method was described by Hughes and Wood in 1986 and consists of administering droplets of a suspension in which the occlusion bodies are suspended at the desired concentration together with a colorant, such as the Fluorella blue food coloring (Hilton-Davis, Cincinnati, Ohio, USA), to indicate whether the larvae have ingested the droplet. This method is less laborious than the former, because the artificial diet has to be thoroughly impregnated with the viral suspension and preparing the virus-impregnated diet cubes is more time-consuming.

The artificial diet used to feed and infect the larvae was administered in solid form using tablets containing, in addition to the *Helicoverpa armigera* nucleopolyhedrovirus occlusion bodies (when the purpose is to infect the larvae), 7.2% wheat germ, 2.5% soybean protein, 1.4% brewers yeast, 1.9% agar, 2.9% sugar, 1% mixed salts, 0.1% cholesterol, 0.4% ascorbic acid, 0.2% sorbic acid, 0.02% streptomycin, 0.04% tetracycline hydrochloride, 0.1% nipagin, 0.1% nipasol, 0.2% benzoic acid, 0.1% choline chloride, 0.01% vitamins, 15% agar and 80% distilled water. Larvae may be infected by administering the occlusion bodies within droplets of an aqueous suspension or as a solid artificial diet. A volume of several liters of diet is ordinarily prepared by mixing the above-mentioned ingredients that are subsequently autoclaved to sterilize the mixture and dissolve the agar. The antibiotics are added before it has completely cooled (at a temperature of 50° C.) and after thorough mixing, aliquots of the mixture are placed in square 120×120-mm Petri dishes. Next, the diet in the Petri dishes is cut into 5×5-mm cubes.

Example 4 in this application illustrates the mass production method implemented for the *H. armigera*-HearSNPV host-pathogen system described in this application. Many factors can influence final occlusion body production, such as larval stage, initial inoculum concentration, or even temperature. These factors can be changed so as to obtain different final production values. In the assays carried out at our laboratory certain conditions were preferred because they yielded the best results and hence the largest final production of occlusion bodies. The various factors that can be changed are indicated below together with the preferred conditions for each:

i) third ($L_3$), fourth ($L_4$) and fifth ($L_5$) instar *H. armigera* larvae, preferably fifth-instar larvae;

ii) differing concentrations of occlusion bodies supplied in the artificial diet, as demonstrated by assays using different concentrations in the range of $5.5\times10^6$ to $1.5\times10^8$ occlusion bodies/ml, preferably $L_5$ larvae and a concentration of $1.5\times10^8$ occlusion bodies/ml;

iii) larvae reared separately in plates with 12 wells to avoid cannibalism;

iv) larval incubation at 30° C. until death;

Studying the different larval stages and different viral doses showed that optimal occlusion body production was achieved by using newly molted fifth-instar larvae, inoculating the larvae with a concentration approaching the concentration resulting in death of 95% of the larvae in that stage ($LC_{95}$), in this case a concentration of $1.5\times10^8$ occlusion bodies/ml, followed by incubation of the larvae individually owing to the high level of cannibalism in larvae of this species, with the diet, at 30° C. until death. These conditions yield approximately $5\times10^9$ occlusion bodies/larva in five to six days. Therefore, infecting 100 larvae yields around $5\times10^{11}$ occlusion bodies.

The occlusion bodies produced in the *H. armigera* larvae can be purified, formulated in solid or liquid form and sprayed as aqueous suspensions that are highly effective at protecting tomato crops from infestation by *H. armigera* larvae both in greenhouses and in the field.

The nucleopolyhedrovirus may also be applied using other methods, such as aerial or ground application, spraying as a suspension, as a powder, or by irrigation. Furthermore, as previously explained, the occlusion bodies may be mixed with excipients and used with suitable carriers for the agricultural sector, in particular those best suited for preparation in a manner appropriate to the desired method of application. That same composition may also include, for example, compost, fertilizer, or a pesticide. Further, it may also contain an agent to enhance the pathogenic effect of the nucleopolyhedrovirus on *H. armigera*.

It is advisable to add agricultural wetting agents to products containing occlusion bodies, such as the commercially available product Agral® (Syngenta), used in the Examples in this application. The wetting agent used in this product is isotridecyl alcohol ethoxylate, which augments the biological action of insecticides, herbicides, fungicides and pesticides generally by achieving better coverage and penetration of the product on the crop to be treated. The website describing the properties of this product (in Spanish: www.syngenta.com/country/es/sp/productos/proteccion_cultivos/mojantes/Paginas/agral.as px) states that it is a non-ionic surfactant dispersing and wetting agent that is especially indicated for mixing with insecticides, fungicides and agrochemicals of all kinds.

Another special case of interest here is where the composition contains another pesticide, thereby increasing the range of action to other possible pests infesting the same crops, without being restricted solely to *H. armigera*. The pesticide may, for instance, be another biological insecticide, such as a *Bacillus thuringiensis* (Bt)-based pesticide like the previously mentioned Turex® product used in Example 6 in this application below, which is used on crops attacked by *H. armigera*. Combination with Bt-based insecticides is interesting, because cases of synergistic interactions between the insecticidal activities of such products and baculovirus against noctuids have been described (Granados et al., 2001).

The assays described in the Examples described below in this application show that each of the two genotypes concerned here has its own characteristic insecticidal activity against *H. armigera* larvae as a function of its pathogenicity, mean time to death (MTD) and ability to produce occlusion bodies in *H. armigera* larvae.

Work previously carried out by the inventors' research team has shown that mixtures of occlusion bodies or mixtures of virions co-occluded in a single occlusion body may sometimes exhibit enhanced insecticidal qualities compared with individual genotypes (Bernal et al., 2013b; López-Ferber et al., 2003; Simón et al., 2005) or even with the wild isolate (Muñoz et al., 1998). In addition, mixtures of virions having different genotypes co-occluded in a single occlusion body may display different activity from that of mixtures of occlusion bodies in which the virions of each occlusion body belong to the same genotype (López-Ferber et al., 2003), since some genotypes may be synergistic or antagonistic. Therefore, a study of insecticidal activity of the different mixtures of virions co-occluded in the same occlusion body has been carried out for this invention to ascertain whether the said mixtures exhibited different insecticidal properties from single-genotype occlusion bodies and whether the genotypes exhibited antagonistic or synergistic activity and to determine the variations that might arise among the different combinations and different types of mixtures.

Mixing the two HearSP1B:LB6 genotypes co-occluded in the same occlusion bodies in the ratio of 1:1 (that is, each occlusion body contains that proportion of both genotypes) was unexpectedly found to have greater insecticidal activity than that of the individual genotypes in terms of pathogenicity. At the same time, its virulence (MTD) is similar to that of the genotypes with the fastest larval kill times. For this reason, these genotypes were selected for application, co-occluded in the same occlusion bodies, contrasting with the form used for the other individual HearSNPV genotypes isolated.

Example 3 in this invention describes assays of insecticidal activity of the different genotypes and mixtures which unexpectedly showed the newly nucleopolyhedrovirus isolates to have some of the highest levels of activity against insect pests of any biological insecticide, especially the combination of the two. Their use as an insecticide is therefore proposed, particularly for controlling insects of the genera on which they are known to act, *Helicoverpa* and *Heliothis*, with particular preference for use in controlling *H. armigera*.

There has been no previous experience and/or prediction of any kind that might have suggested that the combination of the two genotypes selected from among the various combinations might exhibit appreciably better results in terms of relative potency than the rest of the isolates. The synergistic activity recorded in the case of HearSP1B:LB6 is not observed for many other combinations of genotypes, some of that even demonstrate a clearly antagonistic effect. This activity is surprising in that the synergistic activity of two different genotypes which are found in distant geographical areas in nature was unexpected.

The formulation may be applied to any plants subject to attack by this lepidopteran species where it is desired to protect them from the damage caused by this insect, whether they are grown in a greenhouse or in an open field, with emphasis on the tomato crop, especially in the Iberian Peninsula, where it has been proven to be efficacious on tomatoes grown both in a greenhouse and in an open field.

Having all these data in mind, it can be asserted that:
i) each of the new genotypes isolated, HearSP1B and HearLB6, is novel, in that each is different from the other genotypes and different from other known *H. armigera* nucleopolyhedrovirus, from which they are distinguishable both by the differences in their genome sequences (particularly in homologous regions 1 and 5, hr1 and hr5) and by the differences in the profiles generated by digestion of the said genomes by restriction enzymes, especially EcoRI and/or Bg/II.
ii) Inter alia, the two new genotypes isolated share the following technical characteristics:
a) individually, their insecticidal activity and productivity is greater than or equal to those of any other natural isolates previously known;
b) mixtures of the two genotypes, HearSP1B:LB6, particularly the mixture in which both are co-occluded in the ratio of 1:1, exhibit levels of pathogenicity and virulence against *H. armigera* larvae that are greater than or equal to those of wild isolates of this virus and comparable to those of insecticides commonly used against this pest, such as commercially available insecticides sold under the brand names Dursban® and Spintor® or the Bt-based biological insecticide Turex®, though without their drawbacks.
c) since the two genotypes have been isolated in relatively close geographical areas, it is to be anticipated that they might be especially active against the possible *H. armigera* variants occurring in that geographical region, specifically, the southern Iberian Peninsula or Andalusia and Extremadura.

EXAMPLES

The following materials and methods were used in carrying out the assays described in this application:

Insects

There are no officially recognized strains or varieties of *H. armigera*. The *H. armigera* larvae used for amplification of the different viruses for the laboratory bioassays and greenhouse assays were obtained from a laboratory culture at the Universidad Pública de Navarra (UPNA) from pupae received from the Centre for Ecology and Hydrology (NERC-CEH) in Oxford (United Kingdom). The population is kept at the UPNA's insectary at 25±1° C. at a relative humidity of 70±5% under a photoperiod of 16:8 (light: darkness). The larvae are fed an artificial diet previously described by Greene et al. (1976) and adults are fed 30-% diluted honey (weight:volume) ad libitum.

The *H. armigera* larvae used to carry out the field trials came from a natural infestation of a tomato crop in Guadajira (Badajoz).

Isolation and Amplification of the Occlusion Bodies

The occlusion bodies (OBs) were extracted from dead larvae by grinding the bodies in bidistilled sterile water with 0.1% sodium dodecyl sulfate (SDS) (weight:volume) and filtering the resulting suspension through muslin. The occlusion bodies were sedimented by centrifugation at 6,000×g for 10 min. Subsequently, the occlusion bodies were washed twice in water and sedimented in the same conditions as before. Finally, the purified occlusion bodies were resuspended in sterile double-distilled water and their concentration determined by counting samples in triplicate using an improved Neubauer counting chamber (Hawksley, Lancing, United Kingdom) under phase-contrast microscopy at 400×.

The occlusion bodies of the different isolates were multiplied by a single passage through fourth-instar *H. armigera* larvae. Groups of 24 larvae from the laboratory colony were held separately without food for approximately 12 hours. After that time, they were infected per os by the droplet method (Hughes and Wood, 1981) using a concentration of $10^6$ occlusion bodies/ml, 10% sucrose (weight:volume) and 0.001% Fluorella Blue (Hilton-Davis, Cincinnati, Ohio, USA) food coloring (weight:volume). The food coloring enables larvae that have ingested the occlusion body suspension to be differentiated from those that have not. Larvae with blue guts, that is, larvae that had drunk the suspension, were reared separately on the artificial diet until death. The advantage of the droplet method is that the viral dose or concentration is ingested in a short period of time, something that is particularly important for calculating certain parameters, such as mean time to death (MTD).

The purified occlusion bodies were stored at −20° C. for subsequent molecular and biological characterization.

Plaque Assay Genotype Purification

A plaque assay was used to purify the different genotypes present in the HearSP1 isolate (Muñoz et al., 2001). For this purpose, 25 fourth-instar *H. armigera* larvae were orally infected with a concentration of $10^6$ occlusion bodies/ml that caused 90% mortality ($LC_{90}$).

Next, 48 hours after infection a small incision was made in the last pair of pseudopods of the larvae to extract the hemolymph. At that point the hemolymph is full of budded virions (BVs) that have a single nucleocapsid and hence a single genotype. The hemolymph was filtered through a 0.45-μm filter to remove such possible contaminants as bacteria and was then serially diluted with EX-CELL 420 medium (Sigma) using a dilution factor of 5. Then, $2\times10^6$ HzAM1 cells were incubated in plates with six wells (35 mm in diameter) at 27° C. for three hours for cell deposition. After that time the medium was replaced by 100 μl of diluted hemolymph. One hour later the viral inoculum contained in the hemolymph dilutions was replaced with new EX-CELL 420 medium with 1% antibiotics (penicillin-streptomycin) (Lonza) and 2% agarose to prevent excessive spread of the infection. After five days the cells were stained with neutral red to differentiate healthy from infected cells, with the healthy cells being stained red while the infected cells produced an uncolored region called a plaque or bare spot, representing dead cells caused by infection by a single BV and hence by a single genotype. These regions of single infection (plaques) were extracted using a sterile Pasteur pipette and were individually diluted in 50 μl of EX-CELL 420 medium. Each suspension was then injected into fourth-instar *H. armigera* larvae for in vivo multiplication to obtain large quantities of occlusion bodies, which underwent molecular DNA analysis to determine the number of different genotypes present.

Genotype Purification by End-Point Dilution

To purify the genotypes obtained from the second generation larvae of an *H. armigera* population from a cotton crop in Lebrija killed in an epizootic episode that occurred in the laboratory, 25 fourth-instar *H. armigera* larvae were orally infected with $10^6$ occlusion bodies/ml. The hemolymph was extracted 48 hours after infection, filtered through a Lonza 0.45-μm filter and then serially diluted with EX-CELL 420 medium (Sigma) with 1% antibiotics (penicillin-streptomycin) (Lonza) using a dilution factor of 5. A volume of 100 μl of each dilution were mixed with 900 μl of a suspension of HzAM1 cells at a concentration of $2\times10^5$ cells/ml. Then 100 μl of the virus-cell suspension was added to the first 10 wells in a row on a 96-well plate, the last two wells holding a suspension containing only cells (no virus) as a negative control. Four replicates were performed in all. The plates were incubated at 28° C. for seven days. After that time, all the wells were observed under the microscope to determine the presence of infected cells. The nuclei of the infected cells were full of occlusion bodies. For those dilutions in which fewer than 10% of the wells were found to be infected, indicating that the infection in the well was caused by a single budded virion (and hence a single genotype), the supernatant in the wells was extracted using a sterile Pasteur pipette. The supernatant contained budded virions (BVs), which were injected into fourth-instar *H. armigera* larvae and allowed to multiply, which yielded sufficient occlusion bodies for molecular characterization and determination of the purity of each genotype or number of different genotypes present.

Determination of the Number of Nucleocapsids Per Virion

To determine whether the occlusion-derived virions (ODVs) from the Spanish isolates of *H. armigera* nucleopolyhedrovirus were single or multiple, the ODVs present in the occlusion bodies were released by incubating a suspension of $10^9$ occlusion bodies in an alkaline solution (1 volume of 0.1 M $Na_2CO_3$) for 30 min at 28° C. Polyhedrin and other components were sedimented by centrifugation at low speed (2 500×g) for five minutes. To separate the different bands (in the case of multiple bands) or the single band (in the case of just one), the supernatant containing the virions underwent equilibrium density-gradient centrifugation (90 000×g) for one hour in a 30-60% (weight/volume) continuous sucrose gradient. After this, visual inspection was performed and photographs taken, to be able to determine the nature of the virions.

DNA Extraction and Restriction Enzyme Analysis

To extract the DNA, 100 μl of a suspension of occlusion bodies at a concentration of $10^9$ occlusion bodies/ml was incubated with 100 μl of 0.5 M sodium carbonate ($Na_2CO_3$), 50 μl of 10-% SDS (weight/volume) and 250 μl of $H_2O$ at 60° C. for 10 minutes to dissolve the polyhedrin and release the virions. Undissolved occlusion bodies and other components were removed by low-speed centrifugation (3 800× g) for five minutes. The supernatant containing the virions was incubated with 500 μg of proteinase K at 50° C. for one hour. The viral DNA was extracted twice in a volume of saturated phenol and then once in chloroform and sedimented in 1/10 volume of 3 M sodium acetate (pH 5.2) and 2.5 volumes of cold absolute ethanol at 12 000×g for 10 minutes. It was then washed in cold 70% ethanol and centrifuged for five minutes. Lastly, the DNA was resuspended in 100 μl of 0.1× TE buffer (Tris-EDTA, pH 8) at 60° C. for 10 minutes. The concentration was estimated by reading the absorption at 260 nm in a spectrophotometer (Biophotometer Plus, Eppendorf, Freiberg, Germany).

For the restriction enzyme analysis, 2 μg of viral DNA or PCR amplified fragments were incubated with 10 U of one of the following enzymes: EcoRI or Bg/II (Takara Bio Inc., Japan) at 37° C. for 4 to 12 hours. For the PCR fragments, NdeI from the same supplier was used. The reactions were quenched by adding 4 μl of loading buffer [0.25-% bromophenol blue (weight/volume), 40% sucrose (weight/volume)]. Electrophoresis was performed on horizontal 1% agarose gels (weight/volume) in TAE buffer (0.04 M Tris-acetate, 0.001 M EDTA, pH 8.0) at 20 V for 12 to 16 hours. The DNA fragments were stained with ethidium bromide and viewed on an ultraviolet transilluminator (Chemi-Doc, BioRad, California, USA).

Whole-Genome Sequencing

To completely sequence the HearSP1B and HearLB6 genomes, the DNA was purified in cesium chloride (CsCl) (King and Possee, 1997). The ODVs were initially released and purified as set out in the section dealing with determination of the number of nucleocapsids per virion. To do this, 500 μl of occlusion body suspension ($10^9$ occlusion bodies/ml) were mixed with 500 μl of 0.1 M sodium carbonate ($Na_2CO_3$) and after centrifuging in a continuous sucrose gradient, a single band was obtained for each of the three genotypes. A 1-ml syringe and needle was inserted into the centrifuge tube containing the band and the entire band, comprising the single ODVs, was collected. These virions were diluted 1:3 in TE buffer (Tris-EDTA, pH 8), concentrated by sedimentation at 24 000 rpm for one hour and resuspended in 400 μl of TE. To extract the DNA, 400 μl of purified virion suspension was mixed with 100 μl of 20% sarkosyl (sodium lauroyl sarcosinate or N-lauroylsarcosine sodium salt, Sigma) (weight/volume) and incubated at 60° C. for 30 minutes. This resulted in lysis of the virions and rupture of the nucleocapsids, releasing the DNA into the medium. This lysate was immediately transferred to a 5-ml suspension of 50% cesium chloride in TE (weight/weight) that in turn contained 12.5 μl of ethidium bromide (10 mg/ml) to stain the DNA for viewing, followed by centrifugation at 35 000 rpm at 20° C. for, at least, 18 h. After centrifuging, the DNA was visible as two orange bands (thanks to the ethidium bromide). The two bands were supercoiled DNA (the lower band) and open circular DNA (the upper band). A 1-ml syringe and needle was inserted into the centrifuge tube and both bands were extracted. After extraction the ethidium bromide was removed by washing several times in butanol. For this, the same volume of butanol was added and mixed and the mixture was centrifuged, and the upper phase containing the butanol and ethidium bromide was removed. This step was repeated several times until the solution appeared clear. Finally, the sample was dialyzed in a beaker containing 500 ml of continuously-stirred TE buffer at 4° C., changing the TE two-three times at intervals of eight hours. After dialysis, the DNA was transferred to a tube, quantified in a spectrophotometer and stored at 4° C. Restriction analysis using the EcoRI and Bg/II endonucleases was also performed to verify the identity and quality of the DNA.

DNA sequencing of the two genotypes was carried out using PacBio technology by Lifesequencing S.L. (Paterna, Valencia). Between 5 and 10 μg of DNA purified by CsCl was used. Basically, a genomic library in a sequencing vector was constructed with the DNA from each genotype, with 10 kb inserts. A total of 24,627 and 3,731 readings were carried out for the HearSP1B and HearLB6 genomes, respectively. Finally, all the information was assembled using the HGAP v2.0.2 program. The complete sequences for each of the genotypes thereby obtained were compared to the existing sequences for other HearSNPV isolates (HearSNPV-G4, HearSNPV-C1, HearSNPV-NNg1 and HearSNPV-Aus) and to each other using the Clone Manager computer program (Scientific & Educational Software, 1994-2007).

Constructing Genotype Mixtures

Mixtures of the different genotypes were made up to find the genotype mixture with the best insecticidal properties for controlling *H. armigera*. For this, five genotypes were selected based on their insecticidal properties in order to optimize biological activity and therefore obtain a mixture having greater pathogenicity, virulence, and/or viral productivity. On the one hand, the two HearSP1A and HearSP1B genotypes, the only ones obtained from the HearSP1 isolate, were selected, since HearSP1 was the isolate having the best insecticidal properties against *H. armigera* larvae in Spain (Arrizubieta et al., 2014). On the other hand, the following three genotypes from the infected larvae collected in Lebrija were selected: HearLB1, one of the most virulent and one of the most productive in terms of the amount of occlusion bodies produced in infected insects; HearLB3, one of the fastest killing genotypes; and HearLB6, the most virulent genotype. Eight genotype mixtures were made up in all. Mixtures of HearSP1 genotypes only included HearSP1A:HearSP1B in the ratio of 1:1, referred to in this specification as HearSP1A:SP1B (1:1) and HearSP1A:HearSP1B in the ratio of 1:2, referred to here as HearSP1A:SP1B (1:2). In addition, a further four mixtures containing only Lebrija genotypes were made up, namely, HearLB1:HearLB3 in the ratio of 1:1, referred to here as HearLB1:LB3; HearLB3:HearLB6 also in the ratio of 1:1, referred to here as HearLB3:LB6; HearLB1:HearLB3:HearLB6 in a proportion of 1:1:1, referred to here as HearLB1:LB3:LB6; and finally another mixture of all six Lebrija genotypes in the proportions recorded in the population, referred to here as HearLBmix. Lastly, two mixtures that included one HearSP1 genotype and another Lebrija genotype were constructed, namely, HearSP1B:HearLB1 containing the HearSP1B and HearLB1 genotypes in the ratio of 1:1, referred to here as HearSP1B:LB1; and HearSP1B:HearLB6 containing the HearSP1B and HearLB6 genotypes, also in the ratio of 1:1, referred to here as HearSP1B:LB6.

Figure 6:
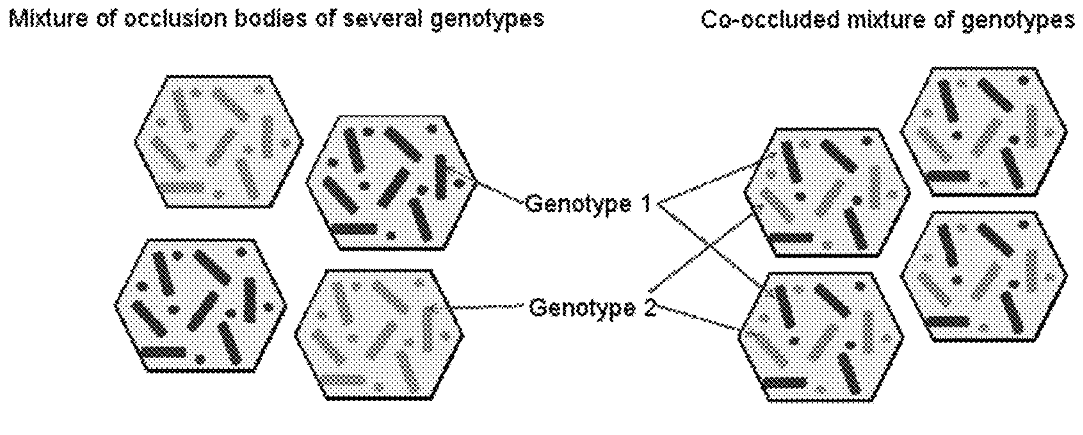
FIG. 6. Schematic representations of a mixture of occlusion bodies of different genotypes in which each occlusion body is formed by ODVs of a single genotype and of a mixture of co-occluded genotypes in the same occlusion body in which each occlusion body is formed by ODVs of different genotypes.

Furthermore, it is known that for co-occluded mixtures, since the genotypes are present in a proportion within an individual occlusion body, that same proportion is maintained when it enters the host (Bernal et al., 2013b; Clavijo et al., 2010). However, when occlusion bodies having the same genotype are mixed together, the proportion tends not to be maintained on entering the epithelial cells of the midgut. In addition, in other recent work carried out at our laboratory, co-occluded mixtures were found to be faster at killing the host than mixtures of occlusion bodies (Bernal et al., 2013b). Therefore, to make up co-occluded mixtures, concentrations of the different genotypes were initially homogenized by diluting them to the same concentration of $10^9$ occlusion bodies/ml and then mixing together the same volume of each, such that the ratio was 1:1, except in the case of the HearSP1A:SP1B (1:2) mixture, in which twice the volume of HearSP1B than HearSP1A was used. The occlusion bodies in these mixtures contained virions of the same genotype. Next, to co-occlude the different genotypes in the same occlusion bodies (co-occluded mixtures), fourth-instar *H. armigera* larvae were orally infected with the different mixtures of occlusion bodies at a concentration of $10^6$ occlusion bodies/ml [the previously produced occlusion body mixtures were diluted by a factor of one thousand ($10^3$) before infecting the larvae]. In this way, the mixture of occlusion bodies with ODVs of the same genotype entered the gut and after the virions were released, the virions of the different genotypes (from the different occlusion bodies) were mixed together. On entering the same cell and replicating, they were then co-occluded in the same occlusion bodies, forming co-occluded mixtures in which the virions of the different genotypes were co-occluded in the individual occlusion bodies, in the same proportion in which they were inoculated (Bernal et al., 2013b; López-Ferber et al., 2003) (FIG. 6).

In short, eight co-occluded mixtures were made up: HearSP1A:SP1B (1:1), HearSP1A:SP1B (1:2), HearLB1:LB3 (1:1), HearLB3:LB6 (1:1), HearLB1:LB3:LB6 (1:1:1), HearLBmix (six genotypes in their natural proportions, HearLB1-6), HearSP1B:LB1 (1:1) and HearSP1B:LB6 (1:1).

PCR Identification of Genotypes in the Mixtures and Restriction Analysis of the PCR Products To determine the nature of the different pure genotypes, in addition to whole-genome restriction analysis, PCR amplification was carried out on the viral DNA obtained from these genotypes using the F-hr1/R-hr1 and F-hr5-/R-hr5 primer pairs. For PCR, 20.5 μl $H_2O$, 2.5 μl polymerase buffer (10×), 0.75 μl magnesium chloride (50 mM $MgCl_2$), 0.25 μl dNTPs (nucleoside triphosphates), 0.25 μl of the respective primers (R-hr1/F-hr1 or F-hr5/R-hr5), 0.25 μl Taq polymerase and 0.25 μl extracted DNA were mixed. Reaction conditions were a denaturing period of 94° C. for two minutes, followed by 35 cycles consisting of denaturation at 94° C. for one minute, annealing at 60° C. for one minute and extension at 72° C. for three minutes, finally followed by 72° C. for 10 minutes for final elongation.

The PCR amplified fragments for hr1 and hr5 were then digested with NdeI endonuclease as previously described.

Bioassays on Insects

The insecticidal activity of the HearSNPV genotypes purified from the HearSP1 isolate (HearSP1A and HearSP1B) and those from Lebrija (Seville) (HearLB1, HearLB2, HearLB3, HearLB4, HearLB5 and HearLB6) and of the co-occluded HearSP1A:SP1B (1:1), HearSP1A:SP1B (1:2), HearLB1:LB3, HearLB3:LB6, HearLB1:LB3:LB6, HearLBmix, HearSP1B:LB1 and HearSP1B:LB6 mixtures was compared with that of the wild HearSP1 isolate, previously selected as the Iberian Peninsula isolate having the best insecticidal properties (Arrizubieta et al., 2014). The concentration-mortality curves (50% lethal concentration, $LC_{50}$), the mean time to death (MTD) and viral productivity (the number of occlusion bodies produced by a single larva, occlusion bodies/larva) were determined by per os (oral) assays carried out using the droplet feeding method previously described.

To determine the $LC_{50}$ values of the different genotypes, the genotype mixtures and the HearSP1 isolate, five viral concentrations were used: $5.7\times10^5$, $1.9\times10^5$, $6.3\times10^4$, $2.1\times10^4$ and $7.0\times10^3$ occlusion bodies/ml in second-instar larvae, which had previously been determined to kill between approximately 95% and 5% of experimental insects. Larvae that ingested the suspension within 10 minutes were transferred to individual wells on a 24-well culture plate containing an artificial diet cube as previously described. The bioassays of 24 larvae per viral concentration and 24 negative control larvae were carried out in triplicate. The larvae were reared at 25° C. and mortality data were recorded every 24 hours until the insects had died or pupated. The virus-induced mortality results underwent logit analysis using the POLO-PC program (Le Ora Software, 1987).

Mean time to death (MTD) for the individual genotypes, the different genotype mixtures and the HearSP1 isolate were determined by bioassay using second-instar *H. armigera* larvae. The larvae were inoculated by ingestion of the $LC_{90}$ dose (the concentration that kills approximately 90% of inoculated larvae) of each virus calculated from the pathogenicity assays previously described ($2.0\times10^5$, $1.8\times10^5$, $9.9\times10^4$, $1.5\times10^5$, $1.5\times10^5$, $2.5\times10^5$, $3.5\times10^5$, $1.5\times10^5$, $9.8\times10^4$, $1.0\times10^5$, $1.5\times10^5$, $1.2\times10^5$, $1.8\times10^5$, $9.3\times10^4$, $1.2\times10^5$, $5.8\times10^4$ and $5.1\times10^4$ occlusion bodies/ml for the wild HearSP1 isolate, the pure HearSP1A, HearSP1B, HearLB1, HearLB2, HearLB3, HearLB4, HearLB5 and HearLB6 genotypes and the co-occluded HearSP1A:SP1B (1:1), HearSP1A:SP1B (1:2), HearLB1:LB3, HearLB3:LB6, HearLB1:LB3:LB6, HearLBmix, HearSP1B:LB1 and HearSP1B:LB6 mixtures, respectively). A group of larvae treated with the same solution but without occlusion bodies served as the control. The larvae were reared separately with the diet at 25° C. and mortality was recorded every eight hours until all the larvae had died or pupated. Twenty-four larvae were infected per treatment and three separate replicates were carried out. Mortality data on time underwent Weibull survival analysis using the Generalized Linear Interactive Modelling (GLIM) program (Crawley, 1993). The mortality distribution over time for the different isolates was analyzed graphically. Microscopic observation of the dead larvae enabled the larvae that had died from nucleopolyhedrovirus disease to be identified and these were the ones that were included in the analyses.

Occlusion body production for the pure genotypes, the genotype mixtures and the HearSP1 isolate was determined in second-instar *H. armigera* larvae infected using the droplet method with occlusion body concentrations that resulted in 90% mortality (the same concentrations used in the mean time to death analysis). All the larvae that died from nucleopolyhedrovirus disease were collected and stored at −20° C. until required for occlusion body counting. For that purpose, each larva was homogenized in 100 μl of distilled water and the total occlusion body yield per larva was estimated by counting the samples in triplicate using an improved Neubauer counting chamber. The data were normalized by log transformation and analyzed by means of analysis of variance (ANOVA) using the SPSS 15.0 program.

Example 1: Isolation of New *H. armigera* Nucleopolyhedrovirus Genotypes 1.1. From the HearSNPV-SP1 Isolate The HearSNPV-SP1, HearSP1 in more abbreviated form, was selected in previous studies as the Iberian Peninsula isolate with the best insecticidal properties against *H. armigera* (Figueiredo et al., 1999; Arrizubieta et al., 2014). Further, the restriction profiles obtained using the different endonucleases in those studies revealed the presence of submolar bands, indicative of the presence of different genotypic variants in the wild isolate (FIGS. 4, 7 and 8).

An in vitro plaque analysis was performed as described in the Materials and Methods section to isolate the possible genotypes in the HearSP1 isolate. In this manner, 145 clones were obtained, each consisting of a unique genotype. Employing molecular methods based on using restriction endonucleases, two different genotypes were identified in the different clones isolated and these were designated HearSNPV-SP1A and HearSNPV-SP1B, or in an abbreviated form, HearSP1A and HearSP1B (FIG. 7A). The HearSP1A genotype was present in 69% of the clones and the HearSP1B genotype was present in 31% (FIG. 7A).

1.2. From the Cadavers of Insects that Died in an Epizootic Outbreak that Occurred in the Laboratory During an epizootic episode that occurred in the second generation of an *H. armigera* population reared at the laboratory from larvae collected from a cotton crop in Lebrija (Seville) in August 2009, 17 insect cadavers showing the typical signs of lethal nucleopolyhedrovirus disease were collected. The occlusion bodies from each individual insect were purified as previously described in the Materials and Methods section above. Sometimes the quantity of occlusion bodies obtained from a single larva was not enough for characterization, so that amplification of the isolates was necessary by inoculating healthy larvae from a laboratory colony using the droplet method. Therefore, sample amplification in larvae in laboratory conditions as previously mentioned in the occlusion body isolation and amplification section was performed. Only six different profiles could be identified in the 17 isolates amplified and these were designated HearSNPV-LB1, HearSNPV-LB2, HearSNPV-LB3, HearSNPV-LB4, HearSNPV-LB5 and HearSNPV-LB6, or, in a more abbreviated form, HearLB1, HearLB2, HearLB3, HearLB4, HearLB5 and HearLB6 (FIGS. 7B and 7C). These six genotypes were present in different proportions, HearLB3 being the most abundant, that was isolated from six different larvae and that accounted for 35.3% of the total genotypes; followed by HearLB1 and HearLB2, isolated from four larvae (accounting for 23.5%); and finally by HearLB4, HearLB5 and HearLB6, each isolated from just a single larva (accounting for 5.9%).

Subsequently, to determine the purity of the six isolates identified, an end-point dilution (EPD) assay was carried out as described in the Materials and Methods section. Following oral infection of *H. armigera* larvae with the various isolates, the hemolymph was extracted, serially diluted and used to infect cells. Next 20 wells in which occlusion bodies were present in the dilution that caused less than 10% viral infection (around 1/500 for all the isolates) were selected. The BVs obtained were multiplied in larvae by intrahemocoelic injection and the viral DNA of the occlusion bodies obtained was analyzed using the Bg/II and EcoRI endonucleases as described in the Materials and Methods section. All the clones/wells from a single isolate exhibited the same restriction profile as the original isolate from which the clones had been obtained and it was therefore concluded that each of the six isolates was composed of a single genotype.

Example 2: Molecular Characterization of the New HearSNPV Genotypes 2.1. Determination of the Number of Nucleocapsids Per Virion To determine whether the different genotypes were of the single or multiple type, the ODVs were released and centrifuged in a continuous sucrose gradient. All the genotypes displayed a single band, indicating that all the virions contained a single nucleocapsid (FIG. 5A). If the isolates had been multiple, several bands would have been observed and each would have contained ODVs with different numbers of nucleocapsids, since the weights of the virions would vary according to the number of nucleocapsids they contain (FIG. 5B). Based on this observation, it was concluded that all the HearNPV isolates were single type isolates with a single nucleocapsid per virion (ODV)

2.2. Restriction Profiles

Digestion of the viral DNA of the different genotypes with EcoRI restriction endonuclease yielded a unique, characteristic profile for each genotype (FIGS. 7A, 7B and 7C; Table 5) and some of the restriction fragments generated by the enzyme could be used as markers to differentiate them. For instance, the EcoRI-B fragment from the HearLB4 genotype (11.0 kb) is larger than those from the HearLB2, HearLB3 and HearLB6 genotypes (10.5 kb), the HearSP1A and HearSP1B genotypes (10.18 kb) and the HearLB1 genotype (10.15 kb) and was not present in the HearLB5 genotype. The HearLB1 (EcoRI-D), HearSP1A (EcoRI-D) and HearSP1B (EcoRI-E) genotypes exhibited a single fragment shared by the three genotypes (9.20 kb), whereas that fragment was 9.38 kb in the HearLB2 (EcoRI-D), HearLB3 (EcoRI-D), HearLB4 (EcoRI-D), HearLB5 (EcoRI-C) and HearLB6 (EcoRI-D) genotypes. The EcoRI-E fragment (9.01 kb) from the HearLB1 genotype was present only in that genotype, as was the EcoRI-E fragment (8.70 kb) from the HearLB4 genotype, which was only present in the HearLB5 genotype (EcoRI-D). In addition, the EcoRI-F fragment (7.16 kb) from the HearSP1A genotype was only located in the profile for the HearLB2 genotype (EcoRI-F), though it was smaller (7.10 kb), whereas the EcoRI-M fragment from the HearSP1A genotype (5.26 kb) was not present in the HearLB2 or HearLB3 genotypes. The HearLB5 genotype exhibited a single 3.10-kb fragment (EcoRI-S) and did not display the 2.83-kb fragment present in the other genotypes. No submolar bands were observed in the restriction profiles for these genotypes after passage through larvae and the profiles were the same for the various passages, indicative of genotype stability and purity.

The restriction profiles for these genotypes were also differentiated using other restriction enzymes, such as Bg/II (FIGS. 7A and 7C).

The presence of submolar bands in the profiles for the wild HearSP1 isolate obtained using both enzymes was clearly observed, demonstrating that the wild isolate was composed of a mixture of various different genotypes. Therefore, the profile for the HearSP1 isolate generated with EcoRI exhibited several submolar bands at around 6.5-7 kb that were not observed in the profile for the pure HearSP1B genotype. Similarly, the profile for the HearSP1 isolate obtained using Bg/II had an 18.8-kb submolar band that was not present in the profile of the HearSP1B genotype. In contrast, the absence of the said bands in the pure genotypes demonstrated the purity of those genotypes, with the HearSP1B genotype displaying a 9.73-kb band that was not observed in the profile of the HearSP1 isolate.

Table 5 sets out the estimated sizes of the restriction fragments generated by digestion of the viral DNA of the different genotypes with EcoRI. The reason for the difference in the number of fragments for the HearSP1A, HearSP1B, HearLB1, HearLB3, HearLB6, HearG4, HearC1, HearNNg1 and HearAus genotypes with respect to the HearLB2, HearLB4 and HearLB5 genotypes was that their genomes had been completely sequenced and hence it was possible to detect small fragments that were not visible in the restriction profiles and so could not be detected by banding pattern analysis (marked by an asterisk [*] in Table 5).

TABLE 5

Estimated sizes of the fragments of the HearSP1A, HearSP1B, HearLB1, HearLB2, HearLB3, HearLB4, HearLB5 and HearLB6 and the HearG4, HearC1, HearNNg1 and HearAus isolates obtained by digestion with EcoRI and total estimated genome size.

| | Size (kb) | | | | | | |
|---|---|---|---|---|---|---|---|
| Fragment | HearSP1A | HearSP1B | HearLB1 | HearLB2 | HearLB3 | HearLB4 | HearLB5 |
| A | 13.55 | 13.54 | 13.55 | 13.55 | 13.58 | 13.55 | 13.55 |
| B | 10.18 | 10.18 | 10.15 | 10.50 | 10.5 | 11.00 | 9.74 |
| C | 9.73 | 9.73 | 9.80 | 9.74 | 9.74 | 9.74 | 9.38 |
| D | 9.20 | 9.20 | 9.20 | 9.38 | 9.38 | 9.38 | 8.70 |
| E | 8.23 | 8.21 | 8.26 | 8.26 | 8.26 | 8.70 | 8.26 |
| F | 7.16 | 6.52 | 6.49 | 7.10 | 6.39 | 8.26 | 6.45 |
| G | 6.30 | 6.30 | 6.29 | 6.45 | 6.30 | 6.45 | 6.29 |
| H | 5.98 | 6.15 | 5.99 | 6.29 | 6.23 | 5.98 | 5.98 |
| I | 5.93 | 5.98 | 5.96 | 5.98 | 5.98 | 5.93 | 5.93 |
| J | 5.85 | 5.93 | 5.86 | 5.93 | 5.93 | 5.85 | 5.85 |
| K | 5.85 | 5.84 | 5.84 | 5.85 | 5.84 | 5.84 | 5.84 |
| L | 5.68 | 5.69 | 5.68 | 5.84 | 5.68 | 5.68 | 5.68 |
| M | 5.26 | 5.25 | 5.26 | 5.68 | 4.73 | 5.25 | 5.25 |
| N | 4.73 | 4.73 | 4.74 | 4.73 | 4.57 | 4.73 | 4.73 |
| O | 4.57 | 4.57 | 4.57 | 4.57 | 4.42 | 4.57 | 4.57 |
| P | 4.42 | 4.42 | 4.42 | 4.42 | 4.40 | 4.42 | 4.42 |
| Q | 4.40 | 4.40 | 4.40 | 4.40 | 3.32 | 4.40 | 4.40 |
| R | 3.34 | 3.34 | 3.34 | 3.32 | 3.00 | 3.32 | 3.32 |
| S | 3.00 | 3.00 | 3.00 | 3.00 | 2.82 | 3.00 | 3.10 |
| T | 2.83 | 2.83 | 2.83 | 2.83 | 1.01 | 2.83 | 3.00 |
| U | 1.74 | 1.74 | 1.74 | 1.70 | 0.78 | 1.70 | 1.70 |
| V | 1.01 | 1.01 | 1.01 | 1.01 | 0.48 | 1.01 | 1.01 |
| X | 0.99 | 0.97 | 0.98 | 0.98 | 0.45* | 0.98 | 0.98 |
| Y | 0.97 | 0.78 | 0.78 | 0.78 | 0.42* | 0.78 | 0.78 |
| Z | 0.78 | 0.47 | 0.48 | 0.48 | 0.41* | 0.48 | 0.48 |
| a | 0.48 | 0.45* | 0.45* | | 0.31* | | |
| b | 0.42* | 0.42* | 0.41* | | 0.18* | | |
| c | 0.41* | 0.41* | 0.31* | | 0.02* | | |
| d | 0.31* | 0.18* | 0.18* | | | | |
| e | 0.18* | 0.02* | 0.02* | | | | |
| | 0.02* | | | | | | |
| Total | 132.48 | 132.26 | 131.97 | 132.77 | 130.95 | 133.83 | 129.39 |

| | Size (kb) | | | | |
|---|---|---|---|---|---|
| Fragment | HearLB6 | HearG4 | HearC1 | HearNNg1 | HearAus |
| A | 13.55 | 14.13 | 14.13 | 13.51 | 13.44 |
| B | 10.50 | 13.45 | 12.84 | 10.20 | 10.15 |
| C | 9.74 | 10.15 | 9.75 | 9.73 | 9.48 |
| D | 9.38 | 9.05 | 9.05 | 9.20 | 9.06 |
| E | 8.26 | 6.64 | 6.91 | 8.23 | 8.23 |
| F | 6.45 | 6.36 | 6.54 | 6.60 | 6.68 |
| G | 6.29 | 6.29 | 6.30 | 6.30 | 6.28 |
| H | 5.98 | 5.99 | 6.00 | 6.23 | 6.00 |
| I | 5.93 | 5.84 | 5.84 | 6.00 | 5.94 |
| J | 5.85 | 5.84 | 5.84 | 6.00 | 5.84 |
| K | 5.84 | 5.67 | 5.67 | 5.80 | 5.84 |
| L | 5.68 | 4.75 | 4.74 | 5.80 | 5.70 |
| M | 5.25 | 4.58 | 4.65 | 5.70 | 4.83 |
| N | 4.73 | 4.42 | 4.57 | 4.75 | 4.75 |
| O | 4.57 | 4.40 | 4.41 | 4.57 | 4.57 |
| P | 4.42 | 4.14 | 4.40 | 4.41 | 4.41 |
| Q | 4.40 | 3.68 | 4.14 | 4.40 | 4.40 |
| R | 3.32 | 3.36 | 3.36 | 3.34 | 3.68 |
| S | 3.00 | 3.00 | 3.00 | 3.00 | 3.35 |
| T | 2.83 | 2.83 | 2.83 | 2.83 | 3.00 |
| U | 1.01 | 1.74 | 1.74 | 1.74 | 1.74 |
| V | 0.98 | 1.48 | 1.00 | 1.00 | 1.00 |
| X | 0.78 | 1.00 | 0.78 | 0.80 | 0.80 |

TABLE 5-continued

Estimated sizes of the fragments of the HearSP1A, HearSP1B, HearLB1, HearLB2, HearLB3, HearLB4, HearLB5 and HearLB6 and the HearG4, HearC1, HearNNg1 and HearAus isolates obtained by digestion with EcoRI and total estimated genome size.

| | | | | | |
|---|---|---|---|---|---|
| Y | 0.48 | 0.78 | 0.48 | 0.48 | 0.48 |
| Z | 0.45* | 0.48 | 0.45* | 0.45* | 0.45* |
| a | 0.42* | 0.45* | 0.42* | 0.41* | 0.41* |
| b | 0.41* | 0.41* | 0.41* | 0.41* | 0.30* |
| c | 0.31* | 0.31* | 0.31* | 0.31* | 0.18* |
| d | 0.18* | 0.18* | 0.18* | 0.18* | 0.02* |
| e | 0.02* | 0.02* | 0.02* | 0.02* | |
| Total | 130.99 | 131.42 | 130.76 | 132.40 | 131.01 |

*Small fragments detected by sequencing that were not visible in the restriction profiles.

2.2. Differentiation by PCR Amplification and Digestion of the Amplified Fragment More precise differentiation of each genotype was obtained by amplifying characteristic regions of the genome for each genotype using PCR (polymerase chain reaction) with specific primers designed for the variable regions, followed by digestion of the PCR amplified fragments with restriction enzymes.

Comparison of the HearSNPV genomes that have been completely sequenced to date has shown the variable regions mainly corresponded with the homologous regions (hr1, hr2, hr3, hr4 and hr5) and with the bro genes (Zhang et al., 2005; Ogembo et al., 2009). In this case specific primers were designed to amplify homologous regions hr1 and hr5.

Therefore, the following primers were designed:

For hr1:

```
forward F-hr1:
                                  (SEQ ID NO: 1)
5'-CGAAATCGACAACACCATGCA-3,

reverse R-hr1:
                                  (SEQ ID NO: 2)
5'-ACTTTTGTACGCCAGAGACGA-3'.
```

And for hr5:

```
forward: F-hr5:
                                  (SEQ ID NO: 3)
5'-CTAGCCGGTCCGTTTCTGTT-3',
```

-continued

```
reverse: R-hr5:
                                  (SEQ ID NO: 4)
5'-GCCCCACCCAAAACATAACG-3'.
```

Their usefulness in amplifying homologous regions 1 and 5 (hr1 and hr5), respectively, was demonstrated by PCR as discussed in the section dealing with the methods employed. The results obtained by electrophoresis of the amplified fragments is depicted in FIG. 8A. For hr1 amplified fragments of 2177 and 2117 nucleotides were obtained for HearSP1B and HearLB6, respectively and for hr5 fragments of 2326 and 2330 nucleotides were obtained for HearSP1B and HearLB6.

To be able to clearly differentiate the genotypes, the PCR amplified fragments for hr1 and hr5 were digested with NdeI. After digestion, the fragments underwent electrophoresis as previously described. The results obtained by electrophoresis of the digested fragments is shown in FIG. 8B and Table 6. For hr1, digestion with NdeI generated six fragments of 857, 508, 381, 306, 78 and 47 nucleotides for HearSP1B and five fragments of 1210, 475, 307, 78 and 47 nucleotides for HearLB6. For hr5, digestion with NdeI generated four fragments of 1120, 917, 211 and 78 nucleotides for HearSP1B and three fragments of 1120, 998 and 212 nucleotides for HearLB6.

The complete sequences for homologous region 1 (hr1) for each of the two genotypes HearSP1B and HearLB6 are represented by SEQ ID NO:9 and SEQ ID NO:10, respectively. By contrast, the complete sequences for homologous region 5 (hr5) for each of the two genotypes HearSP1B and HearLB6 are represented by SEQ ID NO:11 and SEQ ID NO:12, respectively. FIG. 9 depicts the alignment of the said sequences with those for the corresponding regions in the HearG4, HearC1, HearNNg1 and HearAus genomes.

TABLE 6

Specific primers designed for hr1 and hr5, nucleotide sequence, amplified fragment length for each genotype, number of fragments obtained by digesting the PCR amplified fragment with Ndel, digested fragment length and reference number of the sequence for the PCR amplified fragment.

| Primer (sequence) | Genotype | Amplicon length | No. of fragments generated by digestion with NdeI | Length of fragments generated by digestion with NdeI | SEQ ID NO: |
|---|---|---|---|---|---|
| | HearSP1B | 2 177 | 6 | 857, 508, 481, 306, 78, 47 | 5 |
| F-hr1 (SEQ ID NO: 1) | HearLB6 | 2 117 | 5 | 1, 210, 475, 307, 78, 47 | 6 |
| | HearG4 | 2 358 | 6 | 1, 251, 425, 383, 189, 77, 33 | |
| | | | | 1, 145, 425, 197, 189, | |

TABLE 6-continued

Specific primers designed for hr1 and hr5, nucleotide sequence, amplified fragment length for each genotype, number of fragments obtained by digesting the PCR amplified fragment with NdeI, digested fragment length and reference number of the sequence for the PCR amplified fragment.

| Primer (sequence) | Genotype | Amplicon length | No. of fragments generated by digestion with NdeI | Length of fragments generated by digestion with NdeI | SEQ ID NO: |
|---|---|---|---|---|---|
| R-hr1 (SEQ ID NO: 2) | HearC1 | 2 252 | 6 | 77, 33 | |
| | HearNNg1 | 2 260 | 5 | 963, 505, 385, 360, 47 | |
| | HearAus | 2 345 | 6 | 1, 237, 425, 383, 189, 77, 34 | |
| | HearSP1B | 2 326 | 4 | 1, 120, 917, 211, 78 | 7 |
| F-hr5 (SEQ ID NO: 3), | HearLB6 | 2 330 | 3 | 1, 120, 998, 212 | 8 |
| | HearG4 | 2 475 | 6 | 1, 120, 778, 211, 210, 78, 78 | |
| R-hr5 (SEQ ID NO: 4). | HearC1 | 1 872 | 4 | 1, 119, 464, 211, 78 | |
| | HearNNg1 | 2 330 | 4 | 1, 119, 920, 213, 78 | |
| | HearAus | 2 475 | 6 | 1, 120, 778, 211, 210, 78, 78 | |

Example 3: Insecticidal Activity of the Individual Genotypes and the Co-Occluded Genotype Mixtures The mixtures were made by employing different combinations of genotypes in various proportions as described in the previous section dealing with methods for "Constructing genotype mixtures". Briefly, to obtain the co-occluded mixtures, $L_4$ *H. armigera* larvae were orally inoculated with mixtures of occlusion bodies obtained by mixing the occlusion bodies of different genotypes in the desired proportions, which after infection yielded occlusion bodies containing virions of the different genotypes co-occluded in the same occlusion body in the desired proportions.

3.1. Insecticidal Activity of the Wild HearSP1 Isolate and the Pure HearSP1A and HearSP1B Genotypes To determine the biological activity of the purified individual genotypes derived from the HearSP1 isolate, the biological activities of the two genotypes and of the wild HearSP1 isolate were determined individually (Figueiredo et al., 1999; Arrizubieta et al., 2014). Table 7 gives the $LC_{50}$ and relative potency values for the individual HearSP1A and HearSP1B genotypes as compared to those for the wild HearSP1 isolate. Relative potency is the ratio between the $LC_{50}$ values for the different genotypes in relation to that for the wild HearSP1 isolate.

Pathogenicity bioassays showed that pathogenicity of the HearSP1B genotype was 2.8-fold higher than that of the wild HearSP1 isolate. However, the pathogenicity of the HearSP1A genotype was intermediate and therefore similar both to that of the wild HearSP1 isolate and that of the HearSP1B genotype (Table 7).

TABLE 7

Relative insecticidal activity of wild HearSP1 isolate and individual HearSP1A and HearSP1B genotype occlusion bodies.

| | Treatment | $LC_{50}$ (occlusion bodies/ml) | Relative potency | 95-% fiducial limits Lower | Upper | MTD (h) | 95-% fiducial limits Lower | Upper |
|---|---|---|---|---|---|---|---|---|
| Wild isolate | HearSP1 | $3.6 \times 10^4$ | 1 | — | — | 102.8 a* | 100.0 | 105.7 |
| Individual | HearSP1A | $2.4 \times 10^4$ | 1.5 | 0.8 | 2.7 | 99.6 a | 96.5 | 102.8 |
| genotypes | HearSP1B | $1.3 \times 10^4$ | 2.8 | 1.6 | 4.9 | 98.3 a | 95.3 | 101.4 |

*The same letters next to values indicate no significant differences between treatments (t-test, $P > 0.05$).

No significant differences in the mean time to death (MTD) values were observed between the pure genotypes and the wild isolate, as statistically HearSP1A and HearSP1B both killed second-instar *H. armigera* larvae just as fast as the wild isolate (Table 7).

Figure 10:
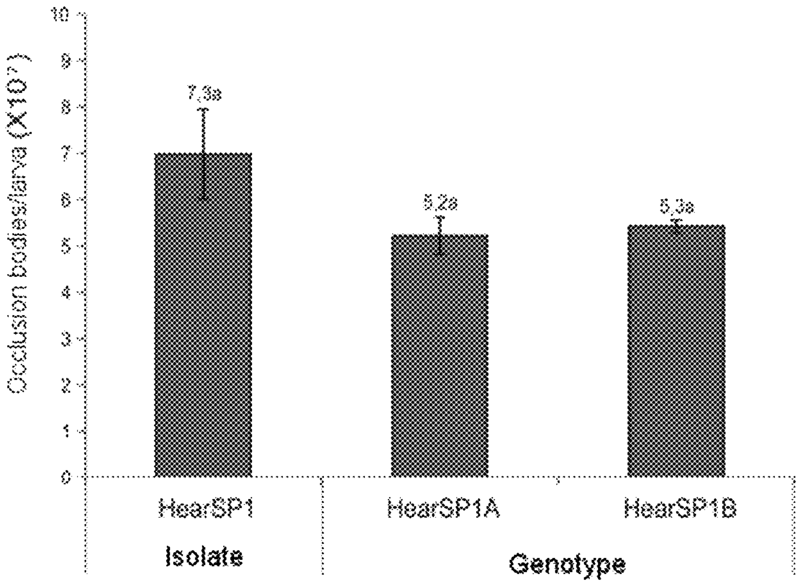
FIG. 10. Mean occlusion body production (x$10^7$ occlusion bodies/larva) in second-instar *H. armigera* larvae infected with the individual HearSP1A and HearSP1B genotypes and with the HearSP1 isolate. Vertical bars indicate standard error. The same letters next to values indicate that differences between treatments are not significant (P>0.05).

Additionally, the HearSP1A genotype ($5.2\times10^7$ occlusion bodies/larva) and HearSP1B genotype ($5.3\times10^7$ occlusion bodies/larva) were as productive as the wild HearSP1 isolate ($7.3\times10^7$ occlusion bodies/larva) in inoculated second-instar *H. armigera* larvae (FIG. 10).

We can therefore conclude that the pure HearSP1B genotype exhibited better insecticidal attributes, in that it had greater pathogenicity than the wild isolate and the pure HearSP1A genotype, while the virulence (MTD) and occlusion body production of this genotype were not lower than those of the other isolates/genotypes.

3.2. Insecticidal Activity of the Individual Lebrija (HearLB) Genotypes

Biological characterization of the individual genotypes from Lebrija was performed by determining the biological activity (pathogenicity, virulence and productivity) of the different genotypes individually and comparing these results with that of the HearSP1 isolate as described in section 3.1 (Figueiredo et al., 1999; Arrizubieta et al., 2014).

Table 8 presents the $LC_{50}$ and potency values for the HearSP1 isolate and the individual HearLB1, HearLB2, HearLB3, HearLB4, HearLB5 and HearLB6 genotypes. These values revealed that the 95% fiducial limits for relative potency calculated for $LC_{50}$ values overlapped broadly in all the treatments, indicating that pathogenicity was similar in the pure genotypes and the HearSP1 isolate.

TABLE 8

Relative insecticidal activity of the occlusion bodies of the wild HearSP1 isolate and individual HearLB1, HearLB2, HearLB3, HearLB4, HearLB5 and HearLB6 genotypes.

| | | $LC_{50}$ (occlusion | Relative | 95% fiducial limits | | | 95% fiducial limits | |
|---|---|---|---|---|---|---|---|---|
| | Treatment | bodies/ml) | potency | Lower | Upper | MTD (h) | Lower | Upper |
| Individual | HearLB1 | $1.2 \times 10^4$ | 1 | — | — | 109.8 a* | 108.1 | 111.5 |
| genotypes | HearLB2 | $1.6 \times 10^4$ | 0.8 | 0.4 | 1.4 | 108.0 a | 106.4 | 109.7 |
| | HearLB3 | $1.5 \times 10^4$ | 0.8 | 0.4 | 1.5 | 116.3 bc | 114.5 | 118.2 |
| | HearLB4 | $1.6 \times 10^4$ | 0.7 | 0.5 | 1.4 | 118.4 c | 116.9 | 119.9 |
| | HearLB5 | $1.4 \times 10^4$ | 0.8 | 0.5 | 1.5 | 109.1 a | 107.3 | 110.9 |
| | HearLB6 | $1.3 \times 10^4$ | 0.9 | 0.5 | 1.6 | 108.9 a | 107.4 | 110.6 |
| Isolate | HearSP1 | $1.6 \times 10^4$ | 0.8 | 0.4 | 1.4 | 114.5 b | 112.6 | 116.4 |

*Different letters next to values indicate significant differences between treatments (t-test, $P < 0.05$).

Furthermore, the HearLB1, HearLB2, HearLB5 and HearLB6 genotypes were significantly faster than the rest of the genotypes and the HearSP1 isolate at killing second-instar *H. armigera* larvae (Table 8).

Figure 11:
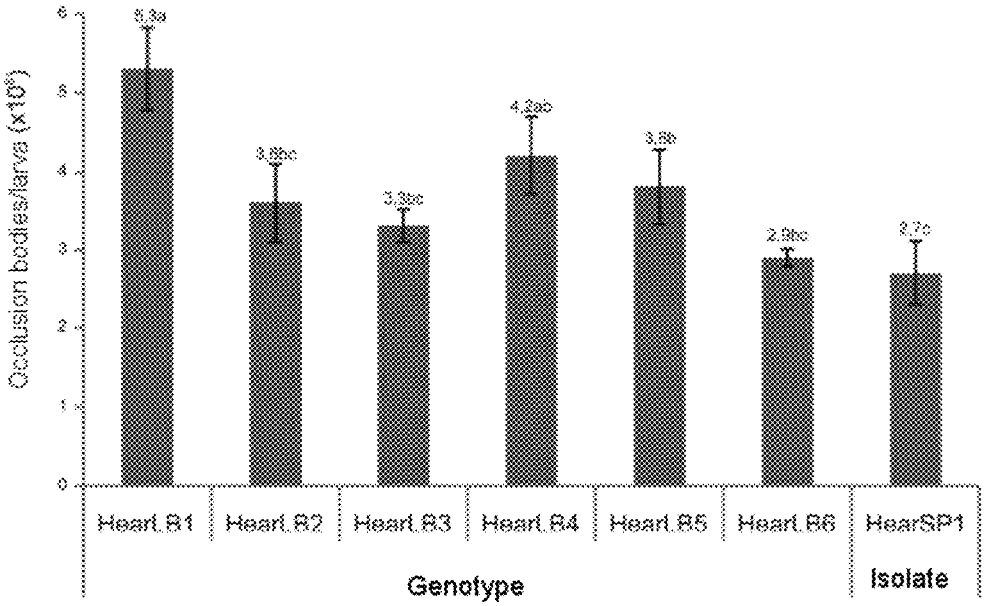
FIG. 11. Mean occlusion body production (x$10^8$ occlusion bodies/larva) in second-instar *H. armigera* larvae infected with the individual HearLB1, HearLB2, HearLB3, HearLB4, HearLB5 and HearLB6 genotypes and with the HearSP1 isolate. Vertical bars indicate standard error. Different letters next to values indicate significant differences between treatments (P<0.05).

The occlusion body production data were analyzed by ANOVA and Tukey's test using the SPSS 15.0 statistical program (FIG. 11). The HearLB1 genotype was the most productive ($5.3 \times 10^8$ occlusion bodies/larva) though not significantly different from the HearLB4 genotype ($4.2 \times 10^8$ occlusion bodies/larva). Also, the HearLB1, HearLB4 and HearLB5 genotypes were more productive than the HearSP1 isolate in second-instar *H. armigera* larvae.

3.3. Insecticidal Activity of the Co-Occluded Mixtures Obtained Using the Five Genotypes Selected in the Previous Sections (sections 3.2 and 3.3) and the HearLBmix Mixture In view of the minimal differences in insecticidal activity observed between the different genotypes, five genotypes from the preceding sections (sections 3.2 and 3.3) were selected and various mixtures were prepared to optimize biological activity and therefore obtain a mixture with enhanced insecticidal properties. To this end, eight co-occluded mixtures were produced, namely:

- HearSP1A:SP1B in the ratio of 1:1. The purpose of this mixture was to increase pathogenicity, since the HearSP1B genotype was more pathogenic than HearSP1 and was present in this mixture in a higher proportion than in the wild HearSP1 isolate (natural ratio of 2:1).
- HearSP1A:SP1B in the ratio of 1:2. The purpose of this mixture to was to increase pathogenicity, since the HearSP1B genotype was more pathogenic than HearSP1 and was present in this mixture in an even higher proportion than in the previous mixture.
- HearLB1:LB3 in the ratio of 1:1. The HearLB1 genotype was one of the fastest killing and also among the most productive genotypes. At the same time, the HearLB3 genotype was one of the most productive by being the slowest killing genotype. The purpose of this mixture was to maintain the virulence of the HearLB1 genotype while retaining the productivity of both genotypes.
- HearLB3:LB6 in the ratio of 1:1. The HearLB6 genotype was one of the fastest killing genotypes and the least productive, whereas the HearLB3 genotype was one of the most productive. In this case, the intent was to keep both the virulence of HearLB6 and the productivity of HearLB3.
- HearLB1:LB3:LB6 in the proportion of 1:1:1. This mixture was an attempt to maintain the virulence of the HearLB1 and HearLB6 genotypes and the productivity of the HearLB1 and HearLB6 genotypes.
- HearLBmix (HearLB1-6) in the proportion of 4:4:6:1:1:1. This mixture included the six genotypes from Lebrija in the proportions in which they were isolated. The fact that each of these genotypes was isolated in a proportion after an epizootic outbreak could have some biological significance.
- HearSP1B:LB1 in the ratio of 1:1. This mixture might maintain the pathogenicity of the HearSP1B genotype and the virulence of the HearLB1 genotype while increasing productivity, since HearLB1 was one of the most productive genotypes.
- HearSP1B:LB6 in the ratio of 1:1. This mixture was an attempt to maintain the pathogenicity of HearSP1B and the virulence of HearLB6.

The insecticidal activity of the different co-occluded mixtures was compared for pathogenicity, virulence and productivity as described in section 3.1. The individual HearSP1A, HearSP1B, HearLB1, HearLB3 and HearLB6 genotypes were included for reference purposes.

TABLE 9

Relative insecticidal activity of the HearSP1A:SP1B (1:1), HearSP1A:SP1B (1:2), HearLB1:LB3, HearLB3:LB6, HearLB1:LB3:LB6, HearLBmix, HearSP1B:LB1 and HearSP1B:LB6 occlusion body mixtures and of the individual HearSP1A, HearSP1B, HearLB1, HearLB3 and HearLB6 genotypes.

| | Treatment | $LC_{50}$ (occlusion bodies/ml) | Relative potency | 95-% fiducial limits Lower | Upper | MTD (h) | 95-% fiducial limits Lower | Upper |
|---|---|---|---|---|---|---|---|---|
| Individual genotypes | HearSP1A | $1.6 \times 10^4$ | 1 | — | — | 108.1 a* | 105.7 | 110.4 |
| | HearSP1B | $1.1 \times 10^4$ | 1.4 | 0.9 | 2.1 | 112.4 ab | 109.9 | 114.9 |
| | HearLB1 | $1.6 \times 10^4$ | 1.0 | 0.7 | 1.5 | 112.3 b | 110.8 | 113.8 |
| | HearLB3 | $1.5 \times 10^4$ | 1.1 | 0.8 | 1.8 | 113.5 b | 112.0 | 115.0 |
| | HearLB6 | $1.3 \times 10^4$ | 1.2 | 0.9 | 1.9 | 109.5 ab | 107.8 | 111.3 |
| Co-occluded mixtures | HearSP1A:SP1B (1:1) | $1.7 \times 10^4$ | 0.9 | 0.6 | 1.4 | 108.2 a | 106.0 | 110.5 |
| | HearSP1A:SP1B (1:2) | $1.2 \times 10^4$ | 1.3 | 0.8 | 2.0 | 110.9 ab | 108.6 | 113.2 |
| | HearLB1:LB3 | $1.6 \times 10^4$ | 1.0 | 0.7 | 1.5 | 115.8 b | 114.3 | 117.3 |
| | HearLB3:LB6 | $2.1 \times 10^4$ | 0.8 | 0.5 | 1.2 | 114.1 b | 112.8 | 115.5 |
| | HearLB1:LB3:LB6 | $1.1 \times 10^4$ | 1.5 | 0.9 | 2.3 | 108.7 ab | 107.3 | 110.1 |
| | HearLBmix | $1.4 \times 10^4$ | 1.1 | 0.7 | 1.8 | 115.3 b | 113.6 | 117.1 |
| | HearSP1B:LB1 | $9.8 \times 10^3$ | 1.6 | 1.1 | 2.4 | 112.8 b | 110.6 | 115.3 |
| | HearSP1B:LB6 | $5.7 \times 10^3$ | 2.8 | 1.8 | 4.3 | 108.8 ab | 106.5 | 111.1 |

*Different letters next to values indicate significant differences between treatments (t-test, $P > 0.05$).

Table 9 sets out the $LC_{50}$ and relative potency values for the co-occluded mixtures and the individual genotypes (in reference to the values for HearSP1A), together with the mean time to death values. Unexpectedly, the HearSP1B: HearLB6 genotype mixture ($5.7\times10^3$ occlusion bodies/ml) was the most pathogenic, between 1.7 and 3.7 times more pathogenic than the individual genotypes and the rest of the mixtures. In addition, this mixture, with a MTD of 108.8 hours, was as virulent as the fastest-killing genotypes such as HearSP1A, HearSP1B and HearLB6. Analyzing the data set out in Table 9, it can be concluded that there is no way of anticipating that one or another mixture will be more or less pathogenic, since there was no pattern or rule for predicting, a priori, which of the mixtures would be most potent.

Figure 12:
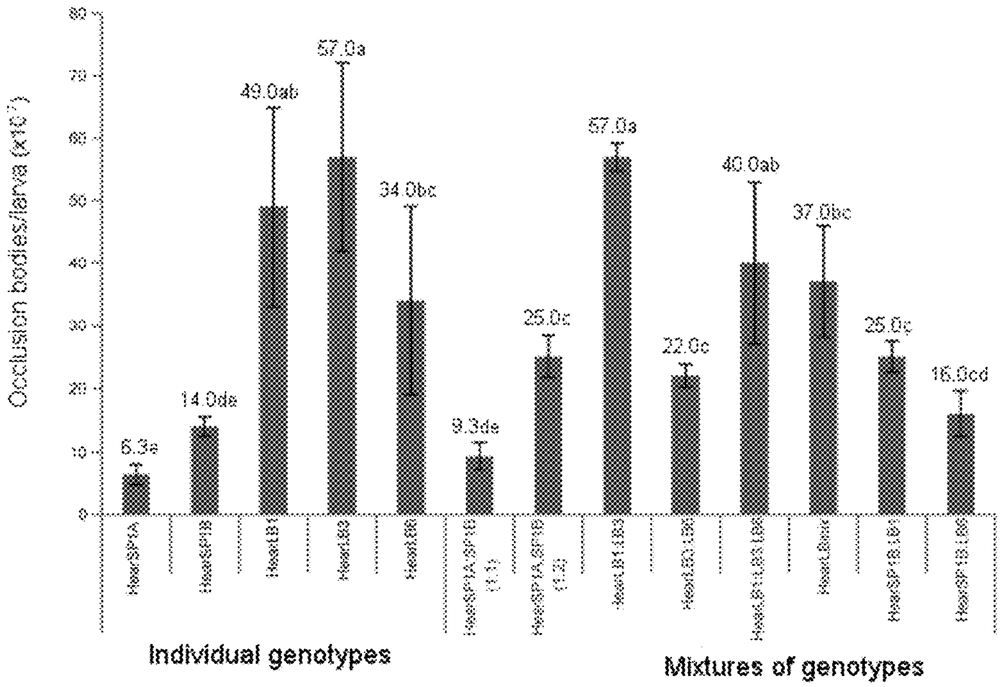
FIG. 12. Mean occlusion body production (x$10^7$ occlusion bodies/larva) in second-instar *H. armigera* larvae infected with the individual HearSP1A, HearSP1B, HearLB1, HearLB3 and HearLB6 genotypes and with the co-occluded mixtures of HearSP1A:SP1B (1:1), HearSP1A:SP1B (1:2), HearLB1:LB3, HearLB3:LB6, HearLB1:LB3:LB6, HearLBmix, HearSP1B:LB1 and HearSP1B:LB6. Vertical bars indicate standard error. Different letters next to values indicate significant differences between treatments (P<0.05).

The productivity bioassays showed the HearLB1 and HearLB3 genotypes and the co-occluded HearLB1:LB3 and HearLB1:LB3:LB6 mixtures to be the most productive ($4.9\times10^8$, $5.7\times10^8$, $5.7\times10^8$ and $4.0\times10^8$ occlusion bodies/ larva, respectively) (Tukey, $P<0.05$), followed by the HearLB6 genotype and the co-occluded HearSP1A:SP1B (1:2), HearLB3:LB6, HearLBmix, HearSP1B:LB1 and HearSP1B:LB6 mixtures ($3.4\times10^8$, $2.5\times10^8$, $3.7\times10^8$, $2.2\times10^8$, $2.5\times10^8$ and $1.6\times10^8$ occlusion bodies/larva, respectively). Finally, the HearSP1A and HearSP1B genotypes and the HearSP1A:SP1B (1:1) mixture were the least productive, with a viral productivity of $6.3\times10^7$, $1.4\times10^8$ and $9.3\times10^7$ occlusion bodies/larva, respectively (Tukey, $P<0.05$) (FIG. 12).

The co-occluded HearSP1B:LB6 genotype mixture was more pathogenic than the other pure genotypes and mixtures and furthermore was just as virulent as the fastest-killing genotypes. These attributes can be expected to allow rapid suppression of populations of pests in the field while employing minimal quantities of product, minimizing crop production costs. For these reasons, we selected the HearSP1B:LB6 mixture as the active ingredient for a new bioinsecticide to control *H. armigera*. Consequently, the mass production and efficacy assays described below were carried out using that mixture.

Example 4: Mass Production of HearSNPV

4.1. Study of *H. armigera* Cannibalism

The criterion used to determine the optimal conditions for mass production of HearSNPV was the number of occlusion bodies produced by the lethally infected larvae. Mass production of the co-occluded HearSP1B:LB6 mixture in *H. armigera* larvae can be carried out with larvae reared separately in plates with 12 wells or with a larger number of larvae in larger containers. However, this latter method may present difficulties depending on the degree of cannibalism exhibited by this species. Cannibalism ordinarily depends on, among other factors, larval density, even when food is not limiting (Polis, 1981). Cannibalism also typically increases with larval age (Chapman et al., 1999).

Here, cannibalism was studied in three larval stages of *H. armigera*, $L_3$, $L_4$ and $L_5$, in both healthy larvae and in larvae infected with a $LC_{90}$ concentration of inoculum, which was $6.1\times10^6$, $2.4\times10^6$ and $2.5\times10^7$ occlusion bodies/ml for instars $L_3$, $L_4$ and $L_5$, respectively. These concentrations were estimated in preliminary bioassays at three different densities: 5, 10 and 20 larvae per 0.5-liter plastic box. Five larvae, both healthy and infected, were reared separately for each stage as controls. The assay was replicated three times.

The percentages of cannibalism, mortality from nucleopolyhedrovirus and the larvae that achieved pupation were analyzed by ANOVA and Tukey's test using the SPSS 15.0 statistical program. Cannibalism in healthy and infected *H. armigera* instars $L_3$ and $L_4$ was observed to be similar (observing approximately 30% cannibalism) (Tukey, $P>0.05$). However, for instar $L_5$, a significantly higher percentage of cannibalism was observed in infected larvae (between 77 and 87%) than in healthy larvae (20-55%) (Tukey, $P<0.05$) (FIG. 12). In addition, cannibalism increased significantly with larval density (Tukey, $P<0.05$), being approximately 40% at a density of 5 larvae per box, increasing to 50-60% at a density of 10 larvae per box and finally reaching 80% in boxes containing 20 larvae. However, in infected $L_5$ larvae, the percentage of cannibalism was similar at between 77 and 87% at all densities (Tukey, $P>0.05$) (FIG. 13).

Figure 13:
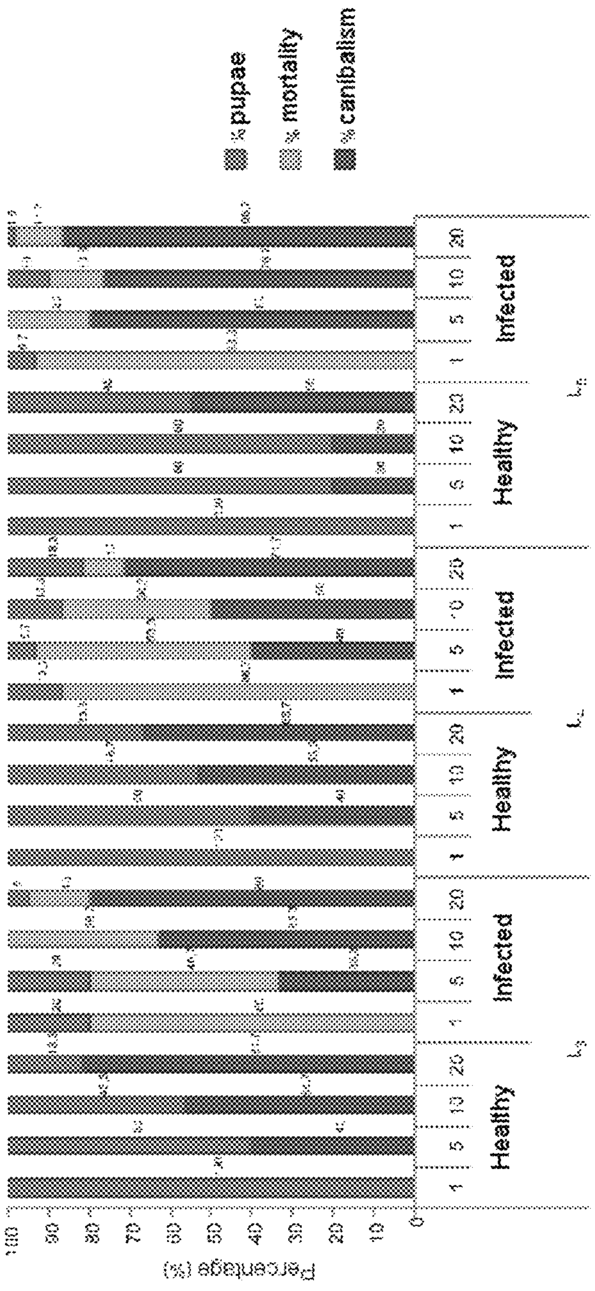
FIG. 13. Percentage infection-induced mortality, survival (reaching the pupal stage) and cannibalism in healthy third, fourth and fifth-instar ($L_3$, $L_4$ and $L_5$) larvae and the same larvae infected with a lethal concentration, 90% ($LC_{90}$) of the co-occluded mixture of HearSP1B:LB6 at different larval densities (1, 5, 10 and 20 larvae per box). Different letters next to values indicate significant differences between treatments (P<0.05).

Percentage of mortality caused by nucleopolyhedrovirus in the individually reared larvae was greater than 90%; however, in the higher-density containers, mortality did not reach 50%, because the diseased larvae were cannibalized before they died (FIG. 13).

Owing to the high percentage of cannibalism observed in the *H. armigera* larvae, resulting in reduced mortality and hence decreased production of occlusion bodies, HearSNPV mass production is much more efficient when carried out using larvae reared individually.

4.2. Effect of Larval Stage, Time of Inoculation and Viral Concentration on HearSNPV Production To achieve greater production of occlusion bodies per larva, it is necessary to select the larval age, inoculation time and viral concentration that allow the greatest larval growth and hence greatest viral production (Shieh, 1989; Gupta et al., 2007).

For the selection of stage and inoculation time, a study was carried out using the three larval stages, $L_3$, $L_4$ and $L_5$, infected at two different times, after molting (newly moulted) and one day after molting (molting+1 d). In addition, larvae are known to grow more slowly and therefore to produce fewer occlusion bodies when concentrations causing high percentages of mortality are employed. Therefore, it is advantageous to optimize the viral concentration that produces a high percentage of mortality with the greatest possible production of occlusion bodies/larva. For this, each stage was infected with three different concentrations of virus, corresponding to $LC_{80}$ ($1.5\times10^5$, $4.8\times10^5$ and $5.5\times10^6$ occlusion bodies/ml, for stages $L_3$, $L_4$ and $L_5$, respectively), $LC_{90}$ ($6.1\times10^5$, $2.4\times10^6$ and $2.5\times10^7$ occlusion bodies/ml for stages $L_3$, $L_4$ and $L_5$, respectively) and $LC_{95}$ ($1.9\times10^6$, $9.1\times10^6$ and $1.5\times10^6$ occlusion bodies/ml for stages $L_3$, $L_4$ and $L_5$, respectively); these concentrations had been determined previously in preliminary assays. The larvae were inoculated individually using the droplet method described by Hughes and Wood (1981) and were kept in individual cups to avoid cannibalism with an artificial diet until death due to the virus or pupation. The occlusion bodies produced by each dead larva were extracted, purified and titrated as previously described. A total of 24 larvae per treatment were inoculated and three replicates were performed. The data collected were analyzed by ANOVA and Tukey's test using the SPSS 15.0 statistical program.

Figure 14:
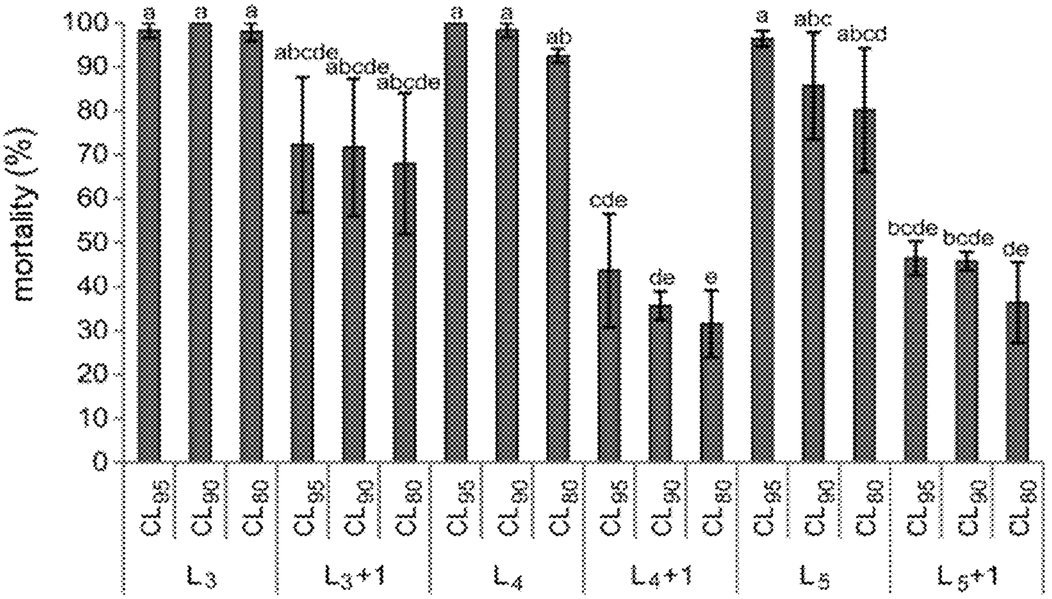
FIG. 14. Percentage larval mortality following inoculation of newly molted third, fourth and fifth-instar ($L_3$, $L_4$ and $L_5$) *H. armigera* larvae and inoculation of larvae one day after molting ($L_3$+1, $L_4$+1 and $L_5$+1) with a lethal concentration, 95% ($LC_{95}$), 90% ($LC_{90}$), or 80% ($LC_{80}$) of the co-occluded HearSP1B:LB6 mixture. Vertical bars indicate standard error. Different letters next to values indicate significant differences between treatments (P<0.05).

The percentage mortality values obtained in the infected larvae after molting were as expected (between 80 and 100%), but percentage mortality in the larvae inoculated one day after molting was significantly lower ($F_{17,36}=16.30$, $P<0.05$), at between 31 and 47% mortality in the case of fourth and fifth-instar larvae, respectively (FIG. 14). This may be due to the fact that these larvae are more resistant to infection owing to their larger size one day after molting and to the fact that the characteristics of the midgut change with the stage of intra-instar development (Washburn et al., 1998). The three doses employed yielded statistically similar percentage mortalities within each larval stage, though a slight increase in mortality was observed with increasing viral dose (Tukey, $P>0.05$) (FIG. 14).

The larvae produced significantly greater quantities of occlusion bodies as the age at inoculation increased ($F_{17,36}=14.25$; $P<0.05$) (FIG. 15A). Accordingly, the $L_4$ and $L_5$ larvae inoculated one day after molting and the newly moulted $L_5$ larvae produced more occlusion bodies than the other larvae (between 5.6 and $9.1\times10^9$ occlusion bodies/larva) (Tukey, $P<0.05$). However, as mentioned earlier, the $L_4$ and $L_5$ larvae inoculated one day after molting exhibited a much lower mortality rate than the newly moulted $L_5$ larvae, so final occlusion body production was lower (FIG. 15B). The newly moulted $L_5$ larvae inoculated with the $LC_{95}$ dose produced $6.9\times10^{11}$ occlusion bodies/100 larvae inoculated as opposed to $1.6\times10^{11}$-$4.2\times10^{11}$ occlusion bodies/100 larvae inoculated for the $L_5$ larvae inoculated one day after molting.

Therefore, the optimum stage for producing the HearSP1B:LB6 genotype mixture in *H. armigera* larvae was $L_5$ with inoculation with an $LC_{95}$ dose ($1.5\times10^8$ occlusion bodies/ml) when the larvae were newly moulted. This treatment produced nearly 100% mortality and achieved the highest productivity ($6.9\times10^{11}$ occlusion bodies/100 larvae inoculated).

4.3. Effect of Incubation Temperature on HearSNPV Production

Incubation temperature may influence larval growth and hence viral productivity (Subramanian et al., 2006). Therefore, a study was performed to determine the optimum temperature for HearSNPV production.

Newly moulted $L_5$ larvae were inoculated with the $LC_{95}$ concentration (the conditions selected in section 4.2) and incubated at 23, 26 and 30° C. Mortality was recorded every eight hours to determine the mortality time for the larvae at each temperature and the bodies were individually collected to determine occlusion body production. A total of 24 larvae per treatment were inoculated and five replicates were performed.

The production of occlusion bodies/larva and the MTD values were calculated as previously described. There were no significant differences in productivity among the larvae incubated at the different temperatures ($F_{212}=0.30$; $P>0.05$) (FIG. 16). However, at 30° C. the larvae died between 13 and 34 hours sooner than at 26° C. and 23° C., respectively (Table 10). Consequently, 30° C. was the optimum temperature for HearSNPV production, since the same quantity of occlusion bodies could be obtained faster than at the other incubation temperatures.

TABLE 10

Mean time to death (MTD) in hours after infection in $L_5$ *H. armigera* larvae infected with the $LC_{95}$ concentration and incubated at 23, 26 and 30° C.

| | | 95-% fiducial limits | |
|---|---|---|---|
| Temperature | MTD (h) | Lower | Upper |
| 23° C. | 163.4 c* | 167.0 | 159.8 |
| 26° C. | 142.2 b | 145.2 | 139.3 |
| 30° C. | 129.6 a | 132.4 | 126.1 |

*Different letters next to values indicate significant differences between treatments (t-test, P < 0.05).

Example 5: HearSNPV Efficacy Assays for Controlling *H. armigera* on Tomato Plants 5.1. Trials on a Tomato Crop Under Laboratory Conditions To determine the efficacy of the co-occluded HearSP1B:LB6 mixture in controlling *H. armigera*, an initial trial was carried out on tomato plants grown under laboratory conditions. The tomato plants were treated by spraying with an aqueous suspension containing different concentrations ($10^9$, $10^{10}$ and 10" occlusion bodies/liter) of the co-occluded HearSP1B:LB6 mixture together with 0.2% agricultural wetting agent (Agral®, Syngenta) (vol/vol). Plants treated with a solution containing water and 0.2% Agral® but no occlusion bodies were used as controls. After treatment, the plants were allowed to dry and were placed in 50-ml cups containing Hoagland solution in 10-liter glass containers and then infested with 150 second-instar ($L_2$) *H. armigera* larvae. The plants were kept at 25±1° C., 70±5% relative humidity and a photoperiod of 16:8 hours light:darkness.

Treatment efficacy was assessed by quantifying the percentage of mortality. For this purpose, 15 larvae were collected from each treatment on days 1, 3 and 5 following treatment. The larvae were placed individually in cups with artificial diet and mortality was recorded seven days after being collected from the plants.

The results obtained are represented in FIG. 16. No mortality was observed for the larvae collected from the control treatment, which indicates an absence of viral contamination in the plants used. The percentage of mortality in larvae collected on days 1, 3 and 5 from the plants treated with $10^9$ occlusion bodies/liter was 88.9, 96.7 and 88%, respectively. For the plants treated with $10^{10}$ and $10^{11}$ occlusion bodies/liter, by contrast, 100% mortality was recorded for the larvae collected on all collection days (FIG. 17).

The concentration of $1\times10^{10}$ occlusion bodies/liter was the minimum concentration producing 100% mortality on all collection days. Consequently, this concentration was taken as the optimum concentration for controlling *H. armigera* on tomato crops under laboratory conditions.

5.2. Trials on a Tomato Crop in a Greenhouse in Lisbon (Portugal)

To determine the efficacy of HearSP1B:LB6 in protecting tomato crops from *H armigera* under greenhouse conditions, trials were carried out in an experimental greenhouse at the Instituto Superior de Agronomia (Universidade Tecnica de Lisboa). Based on the results obtained in the laboratory trials, efficacy of the co-occluded HearSP1B:LB6 mixture was assessed at a concentration of $1\times10^{13}$ occlusion bodies/Ha (equivalent to $10^{10}$ occlusion bodies/liter in a volume of approximately 1,000 liters/Ha). In this study the efficacy of HearSP1B:LB6 was compared with that of:

- a biological insecticide made from the entomopathogenic bacterium *Bacillus thuringiensis aizawai* (Turex®, from Certis, Elche, Spain, containing 50% *B. thuringiensis* in the form of a wettable powder). This bioinsecticide is customarily used at a concentration of 1-2 kg/Ha and here 1.5 kg/Ha was employed (applied in a volume of 1,000 liters/Ha).
- a biological insecticide made from spinosad, a product composed of two spinosyn toxins obtained naturally from fermentation of the bacterium *Saccharopolyspora spinosa* (Spintor 480SC®, Dow AgroSciences, Madrid, Spain, containing 48% spinosad weight/volume). This insecticide is ordinarily used at a concentration of 250 ml/Ha (applied in a volume of 1,000 liters/Ha).

The control consisted of treatment with water. The application method was spraying with an aqueous suspension of the various treatments.

The experimental design consisted of two grids with four experimental plots each, for a total of eight replicates. A total of 28 tomato plants were included in each treatment, of which the 6 central plants were observed to determine the percentage of larval mortality, percentage of damaged fruit and persistence of the different treatments.

The trials were carried out by releasing insects, placing four $L_2$ *H. armigera* larvae on randomly selected fruits on each tomato plant. The different treatments were then applied the following day.

In the first place, the percentage of damaged fruit 10 days after application of the treatment was determined. Percentage of larval survival in each treatment was also determined. For this purpose, the number of larvae still alive on each plant 10 days after application of the treatment was counted. The data collected were analyzed by ANOVA and Tukey's test using the SPSS 15.0 statistical program.

Figure 18:
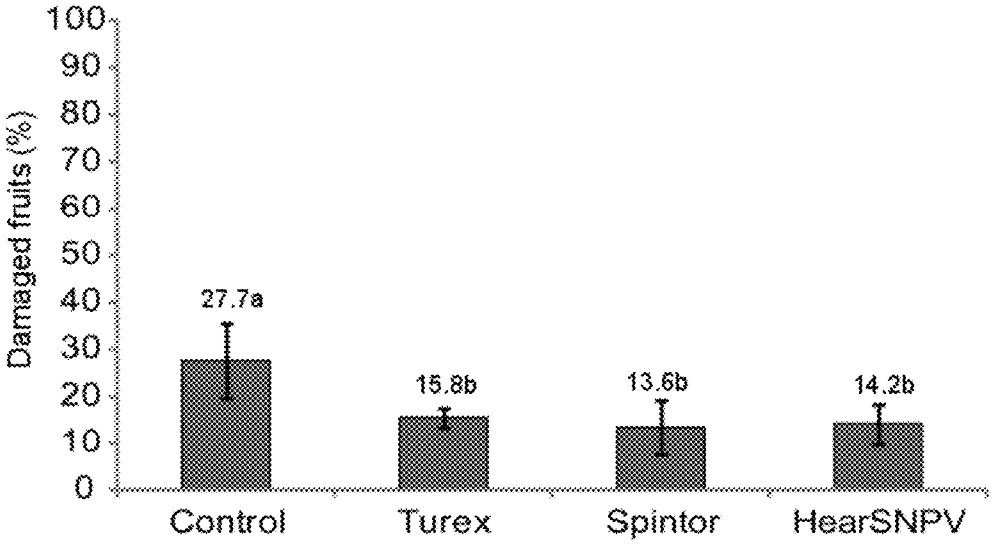
FIG. 18. Percentage damaged fruit in a greenhouse tomato crop 10 days after applying Turex, Spintor, or HearSNPV. Different letters next to values indicate significant differences between treatments (P<0.05).
Figure 19:
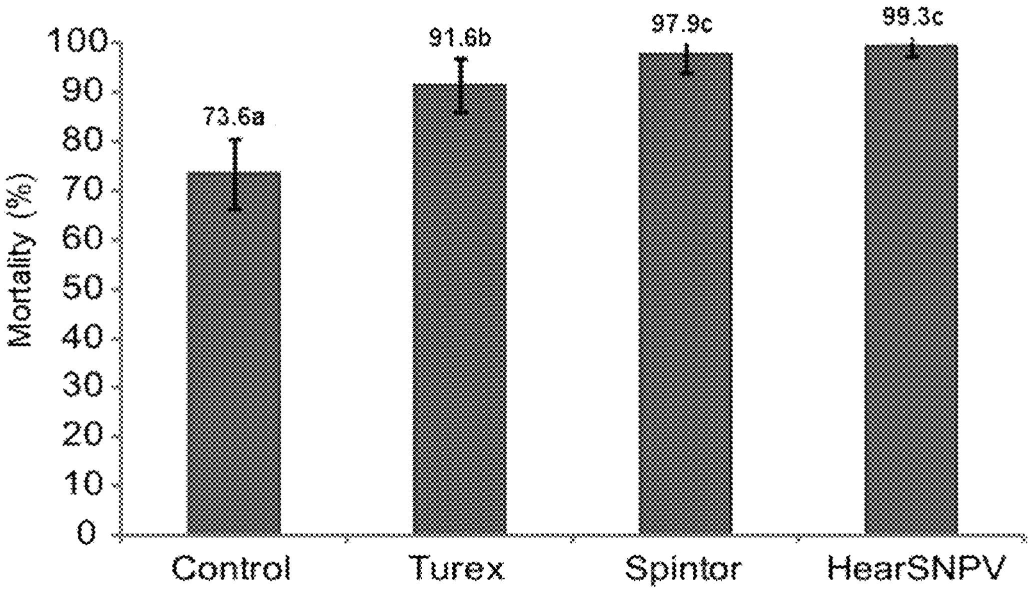
FIG. 19. Percentage larval mortality observed on a greenhouse tomato crop 10 days after applying Turex, Spintor, or HearSNPV. Different letters next to values indicate significant differences between treatments (P<0.05).

The three insecticides significantly reduced the percentage of damaged fruit with respect to the controls ($F_{3,20}$=9.79; P<0.05). However, there were no significant differences between the different insecticides (Tukey, P>0.05) (FIG. 18). Treatment with HearSP1B:LB6, Turex and Spintor significantly increased larval mortality with respect to the control treatment ($F_{3,20}$=37.70; P<0.05). Furthermore, HearSP1B:LB6 and Spintor caused significantly greater larval mortality than Turex (Tukey, P<0.05) (FIG. 19).

Finally, persistence of the different treatments on the tomato plant leaves was determined. For this, for each replicate 15 individual leaves per treatment were collected from the mid to upper portion of the plants at 1 hour after treatment and on days 3, 6 and 9 and were immediately frozen. The leaves were individually ground and mixed with artificial diet (in the ratio of 1:4, weight/weight). The mixture was distributed in five plastic cups and one $L_2$ larva was placed in each cup to avoid cannibalism. The percentage of mortality was recorded 7 days later. The ratio between mortality and the amount of viable insecticide was obtained by calibration bioassay. The calibration curves for the three insecticides were obtained by mixing leaves collected before treatment and hence not infected, with artificial diet and with five different known concentrations of the insecticides. A total of 50 larvae per concentration were used. The quantity of insecticide persisting on the leaves was estimated by comparing the percentage mortality obtained for the different treatments with the calibration curves. Data on the quantity of insecticide collected were analyzed by ANOVA and Tukey's test using the SPSS 15.0 statistical program. To be able to compare the persistence of the different treatments on the leaves of the greenhouse tomato plants, the percentage of residual insecticidal activity of each of the treatments was calculated compared to that observed one hour after application, when the applied insecticidal activity on the plant was deemed to be 100%.

Figure 20:
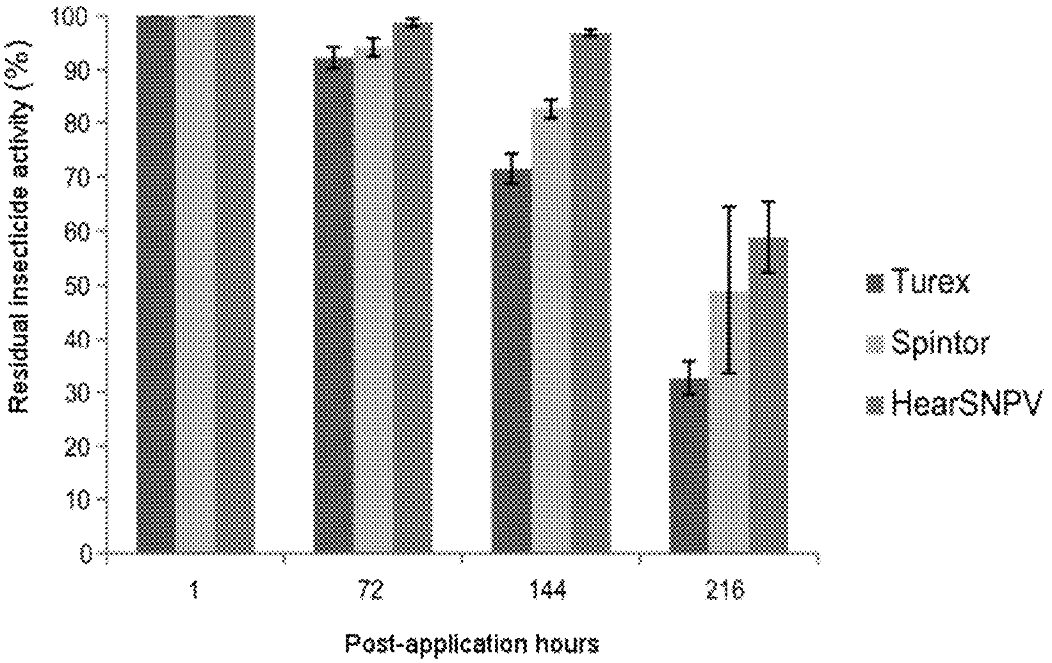
FIG. 20. Percentage residual insecticidal activity (Turex, Spintor and HearSNPV) on greenhouse tomato plant leaves over time on the amount of insecticide present on the tomato plant leaves one hour after treatment. Vertical bars indicate standard error.

Comparing the residual insecticidal activity of the different treatments at the different leaf collection times yielded significant differences in the persistence of HearSNPV and Turex on days 6 and 9 after application, the persistence of Turex being lower (Tukey, P<0.05) (FIG. 20). On the rest of the days a similar degree of residual insecticidal activity was observed for all treatments.

Figure 21:
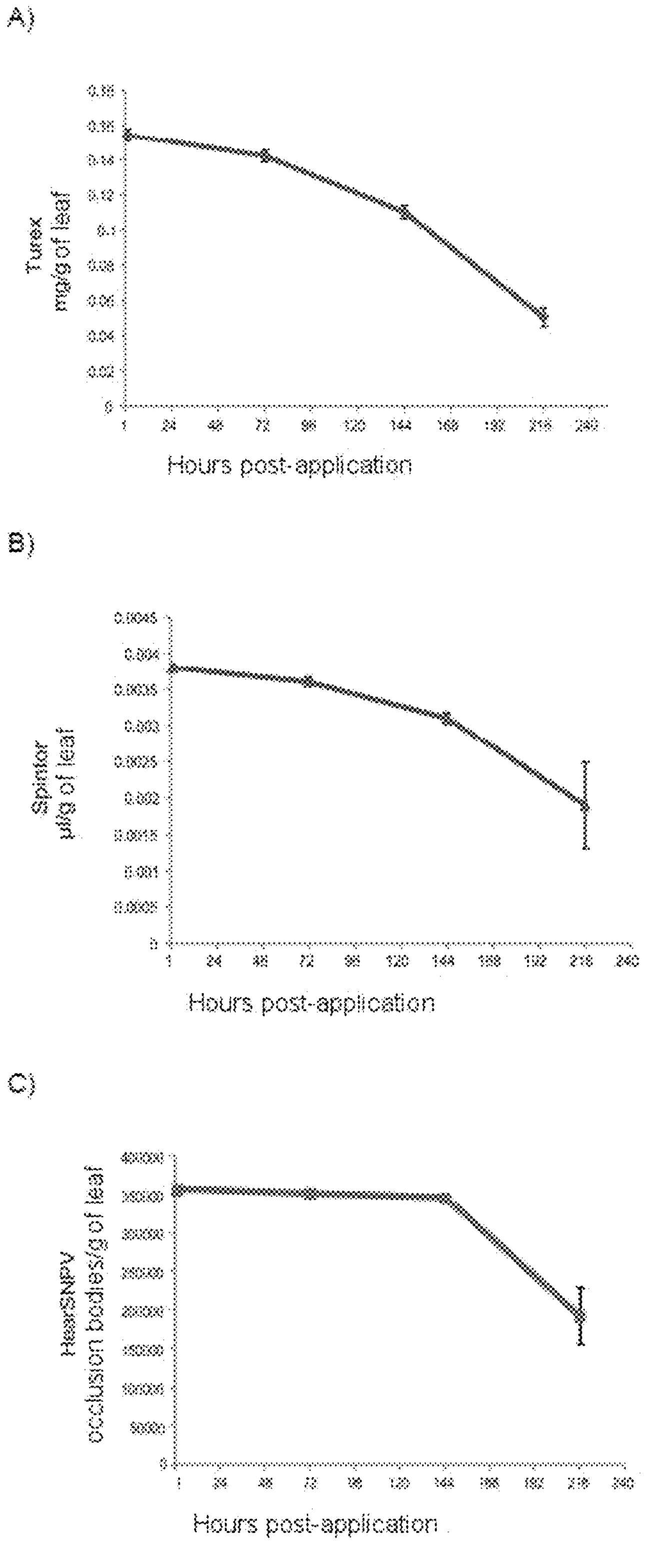
FIG. 21. Amount of residual insecticidal activity per gram of greenhouse tomato plant leaf at 1, 72, 144 and 216 hours (0, 3, 6 and 9 days) after treatment: A) Turex (mg), B) Spintor (μl) and C) HearSNPV (occlusion bodies). Vertical bars indicate standard error.

Residual insecticidal activity decreased significantly with the passage of time ($F_{15,48}$=88.25; P<0.05) in all cases (FIGS. 20 and 21). Persistence of HearSNPV and Spintor held steady until day 6 after application of the treatments, then decreased significantly on day 9 (Tukey, P<0.05), although 59% and 49%, respectively, of insecticidal activity still remained (FIGS. 21B and 21C). For Turex, residual insecticidal activity on day 6 after application of the treatments was significantly lower than insecticidal activity on the leaves one hour after treatment (Tukey, P<0.05) and by day 9 only 32% of insecticide remained (Tukey, P<0.05) (FIG. 21A).

5.3. Trials on a Field-Grown Tomato Crop in Badajoz (Spain)

To determine the efficacy of the co-occluded HearSP1B:LB6 mixture on a field-grown tomato crop, trials were carried out on a parcel at the La Orden experimental farm (Guadajira, Badajoz). The same dose of HearSP1B:LB6 as in the greenhouse trial was used in this trial, $10^{13}$ occlusion bodies/Ha (applied in a volume of 1,000 liters/Ha) and efficacy was compared with that of:

- the wild HearSP1 isolate from Badajoz (Figueiredo et al., 1999), where the trial was carried out, using the same dose as for HearSP1B:LB6, $10^{10}$ occlusion bodies/liter (equivalent to $10^{13}$ occlusion bodies/Ha, since the treatment volume applied was 1,000 liters/Ha).
- a biological insecticide made from the entomopathogenic bacterium *Bacillus thuringiensis aizawai* (Turex®, from Certis, Elche, Spain, containing 50% *B. thuringiensis* in the form of a wettable powder). This bioinsecticide is customarily used at a concentration of 1-2 kg/Ha and here 1.5 kg/Ha was employed (applied in a volume of 1,000 liters/Ha).
- a biological insecticide made from two spinosyn toxins obtained naturally from fermentation of a soil organism, the bacterium *Saccharopolyspora spinosa* (Spintor 480SC®, Dow AgroSciences, Madrid, Spain, containing 48% spinosad weight/volume). This insecticide is ordinarily used at a concentration of 250 ml/Ha (diluting 250 ml in 1,000 liters/Ha).
- a chlorpyrifos-based chemical insecticide (Dursban 75WG®, Dow AgroSciences, Madrid, Spain, containing 75% chlorpyrifos weight/weight). This is ordinarily used at a concentration of 1-1.25 kg/Ha and here 1.25 kg/Ha was used (again diluting it in 1,000 liters to give the same volume per Ha).

The control consisted of treatment with water and 0.2% Agral®. The application method was spraying with an aqueous suspension of the various treatments.

The trial consisted of 48 plots (1.5 m×4 m), each containing approximately 30 plants. The design consisted of random grids. Each grid consisted of two rows of six plots, with the different treatments being applied three times to half the parcels in each grid and five times to the other half, for a total of four replicates of the three and the five application treatments. All applications were performed 15 days apart. The central plants were observed to determine the percentage of damaged fruit, persistence of the different treatments and yield per plot.

In the first place, the percentage of damaged fruits was determined for both fresh damage and scarring every three or four days throughout the entire trial period. The data obtained were grouped to produce 15-day means and analyzed by ANOVA and Tukey's test using the SYSTAT statistical program (1990).

No significant differences in percentage of damaged fruits were observed for the plots with three and five applications of the different treatments ($F_{1,174}$=0.22; P>0.05), so the data for all the plots treated with each insecticide were grouped together, yielding a total of eight replicates.

FIG. 22 shows the percentage of freshly damaged and scarred fruit for each 15-day period for each treatment. For the first 15-day period there were no differences in the percentage of damage fruits obtained for the parcels treated with the different insecticides and values were similar to those for the control treatment ($F_{5,15}$=0.55; P>0.05) (FIG. 22A). However, for the second and third 15-day periods the percentage of freshly damaged and scarred fruit was greater for the control plots than for the plots treated with the different insecticides (Tukey, P<0.05) (FIGS. 22B and 22C). For the fourth 15-day period, a period in which attack by *H. armigera* larvae is not usually pronounced, the percentage of fruit damaged by scarring was also greater for the control plots (Tukey, P<0.05), but there were no differences for the percentage of freshly damaged fruit (P>0.05) (FIG. 22D).

These results show that HearSNPV significantly reduced the number of both freshly damaged and scarred fruits compared with the controls and furthermore it did so with an efficacy similar to that of the other insecticides customarily used to control *H. armigera* infestations.

Yield per plot was then determined. For this, fruit was harvested from the central meter of each plot and separated into green and ripe fruit. The green fruits were separated into healthy and infested and the ripe fruits into healthy, scarred and rotten. Each of the groups was then weighed. The data collected were analyzed by ANOVA and Tukey's test using the SYSTAT statistical program. Canning company quality controls reject batches of tomatoes in which less than 80% of the fruits are ripe and more than 5% of the ripe tomatoes are damaged. Green fruits are discarded before they reach the canning plant.

Figure 23:
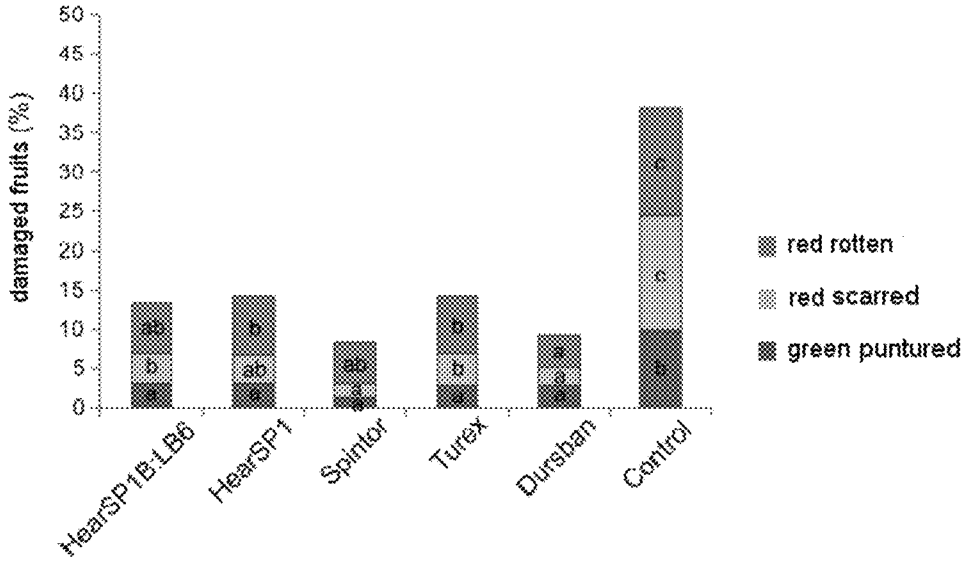
FIG. 23. Percentage damaged fruit harvested, i.e., rotten red, red with scarring, or infested green, in a field-grown tomato crop after treatment with HearSP1B:LB6, HearSP1, Spintor, Turex and Dursban. Different letters in the columns for each group indicate significant differences between the groups for the different treatments (P<0.05).

Here again there were no differences between the plots treated three times and those treated five times, that is, the number of applications and the data for all the parcels treated with each insecticide were therefore grouped together. FIG. 23 shows the damaged fruits harvested from each treatment. The percentage of damaged fruit, whether green and infested, red with scarring, or rotten red tomatoes, was greater for the control plots than for the plots treated with the different insecticides (Tukey, P<0.05). Additionally, the plots treated with Dursban and Spintor yielded a significantly lower percentage of red fruits with scarring than the plots treated with Turex and HearSP1B:LB6 (Tukey, P<0.05), whereas a greater percentage of rotten fruit was harvested from the plots treated with HearSP1 and Turex than from the parcels treated with Dursban (Tukey, P<0.05) (FIG. 23).

Figure 24:
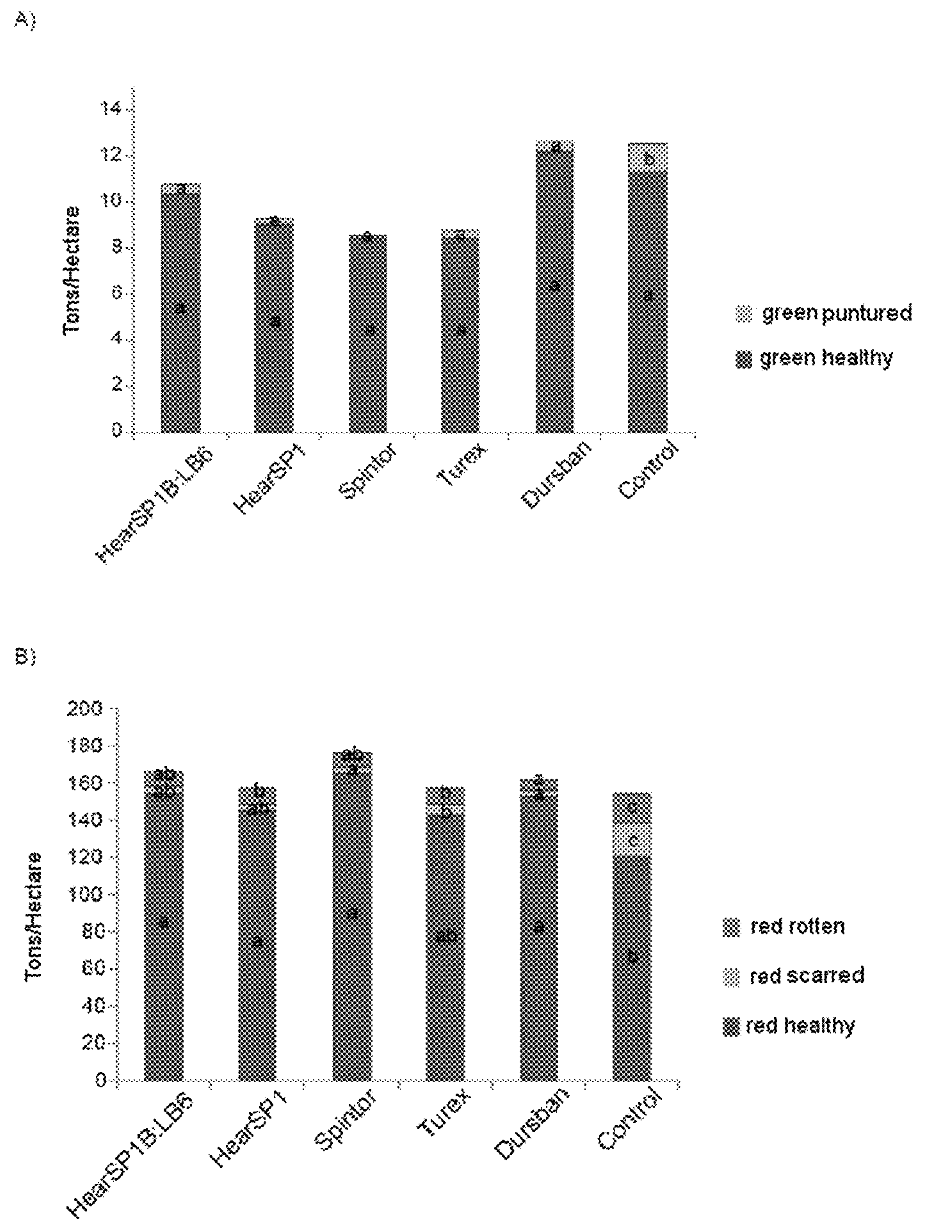
FIG. 24. Tonnes of field-grown A) green tomatoes, both healthy and infested and B) healthy, scarred, or rotten red tomatoes per hectare after treatment with HearSP1B:LB6, HearSP1, Spintor, Turex and Dursban. Different letters in the columns for each group indicate significant differences between the groups for the different treatments (P<0.05).

The number of tonnes of healthy green fruit per hectare (T/Ha) was similar for all the treatments ($F_{5,39}$=0.68; P>0.05) (FIG. 24A). However, the number of tonnes of green and infested fruit per hectare was significantly higher for the control plots than for the plots treated with the different insecticides ($F_{5,39}$=4.95; P<0.05) (FIG. 24A). The number of tonnes of healthy red fruit per hectare was significantly lower for the control plots than for the insecticide-treated plots except for Turex ($F_{5,39}$=2.78; P<0.05), though the differences for the other insecticides were not significant (Tukey, P>0.05) (FIG. 24B). For the damaged red fruit, whether scarred or rotten, yield in tonnes per hectare was higher for the control plots than for the plots treated with insecticide (Tukey, P<0.05). Additionally, there were no significant differences for tonnes of red fruit with scarring obtained from the plots treated with HearSP1B:LB6 and HearSP1 compared with the plots treated with the other insecticides (Tukey, P>0.05), though the plots treated with Dursban and Spintor yielded fewer tonnes of red fruit with scarring than the plots treated with Turex (Tukey, P<0.05) (FIG. 24B). Furthermore, the parcels treated with Dursban yielded fewer tonnes per hectare of rotten red fruit than those treated with HearSP1 and Turex (Tukey, P<0.05) (FIG. 24B), but there were no significant differences with respect to HearSP1B:LB6 (Tukey, P>0.05).

The plots treated with HearSP1B:LB6 or HearSP1 had yields similar to those of the plots treated with the other insecticides, since tonnes of healthy red, i.e., marketable, fruit was similar for all the treatments other than the control treatment. Also, percentage of damaged fruit was very low, similar to those of the other insecticide-treated plots. This is an extremely important detail with respect to marketing tomatoes, since Spanish canning companies do not accept batches with more than 5% damaged fruit.

Finally, persistence of the different treatments on the tomato plant leaves was determined. For this, leaves close to fruit were collected one hour after the first treatment and on days 3, 7 and 10. In all, 25 leaves were collected from each plot and immediately frozen. Groups of five leaves were ground, mixed with artificial diet (in the ratio of 1:4, weight/weight) and distributed in 10 individual cups with an $L_2$ larva in each to avoid cannibalism. The percentage of mortality was recorded on day 7. The ratio between mortality and the amount of viable insecticide was obtained by calibration bioassay. The calibration curves for the five insecticides were obtained by mixing the leaves collected before treatment with artificial diet and with five different known concentrations of the insecticides. A total of 50 larvae/concentration was used. The quantity of insecticide persisting on the leaves was estimated by comparing the percentage of mortality obtained for the different treatments with the calibration curves. The data on the quantity of insecticide obtained were analyzed by ANOVA and Tukey's test using the SPSS 15.0 statistical program. To be able to compare the persistence of the different treatments on the leaves of the field-grown tomato plants, the percentage of residual insecticidal activity of each of the treatments was calculated compared to that observed one hour after application.

Figure 25:
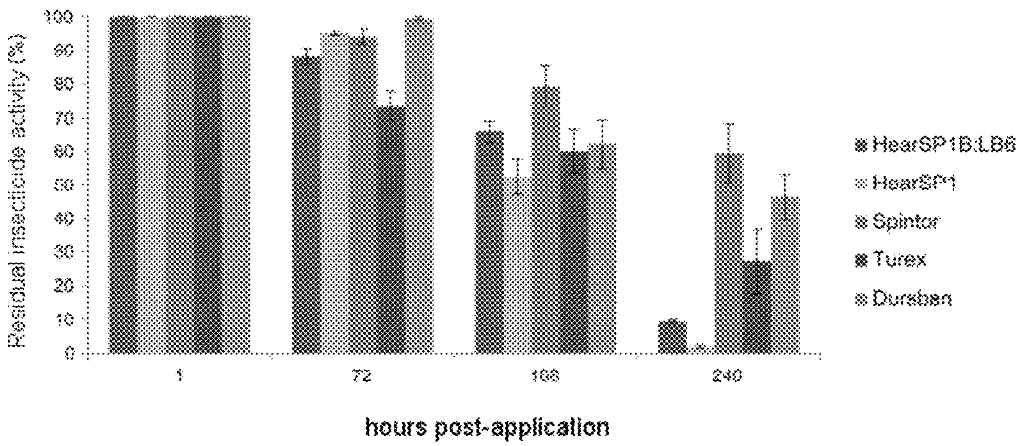
FIG. 25. Percentage residual insecticidal activity (HearSP1B:LB6, HearSP1, Spintor, Turex and Dursban) on field-grown tomato plant leaves over time with reference to the amount of insecticide present on tomato plant leaves one hour after treatment. Vertical bars indicate standard error.

Comparing the percentage of residual insecticidal activity of the different treatments at the different leaf collection times, there were only significant differences between the amount of HearSP1 and Spintor on day 7 after application, the persistence of HearSP1 being lower (Tukey, $P<0.05$) (FIG. 25) and between the amount of HearSP1B:LB6 and HearSP1 and Spintor and Dursban on day 10, the persistence of the baculovirus being lower (Tukey, $P<0.05$) (FIG. 25).

Figure 26:
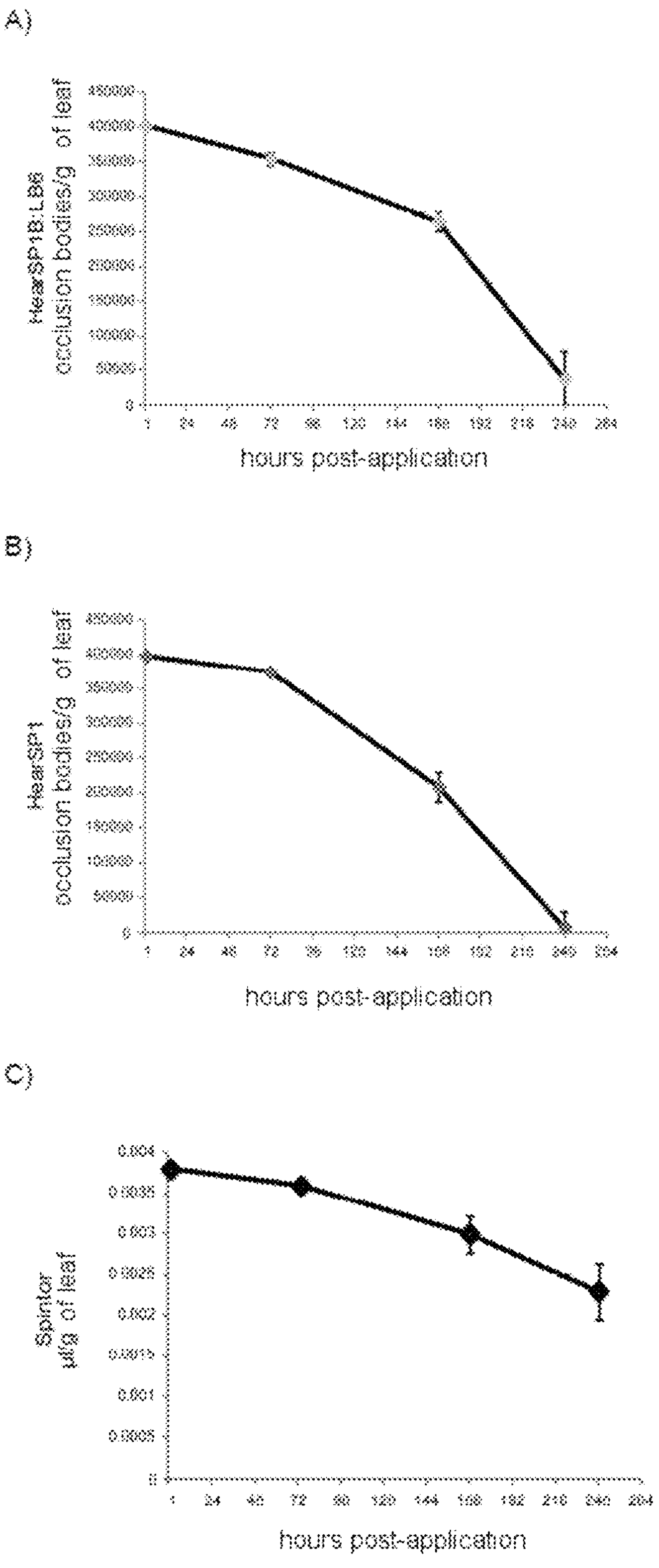
FIG. 26. Amount of residual insecticidal activity per gram of field-grown tomato plant leaf at 1, 72, 168 and 240 hours (0, 3, 7 and 10 days) after treatment: A) HearSP1B:LB6 (occlusion bodies), B) HearSP1 (occlusion bodies), C) Spintor (μl), D) Turex (mg) and E) Dursban (mg). Vertical bars indicate standard error.

Residual insecticidal activity on the field-grown tomato plants decreased significantly over time ($F_{19,140}=34.24$; $P<0.05$) in all cases (FIGS. 25 and 26). The amount of HearSNPV (both HearSP1B:LB6 and HearSP1) remained constant from day 1 to day 3 after application of the treatment, after which time it decreased significantly (Tukey, $P<0.05$). On day 7 after application, 66% and 52%, respectively, of the insecticidal activity of the HearSP1B:LB6 and HearSP1 occlusion bodies still persisted on the plants, whereas on day 10 only 9% and 2% of occlusion body activity persisted and while there were no significant differences between the two, it seems that the selected mixture might persist longer (FIGS. 26A and 26B). The activity of Dursban and Spintor remained constant on the plants until day 3 after application (Tukey, $P>0.05$), then decreased significantly on day 7 (Tukey, $P<0.05$) and exhibited the same level of insecticidal activity on day 10 (Tukey, $P>0.05$), when 59% of the original Spintor activity and 46% of Dursban activity still persisted on the plants (FIGS. 26C and 26E). In the case of Turex, insecticidal activity declined significantly on day 3 (Tukey, $P<0.05$) but then held steady until day 7 (Tukey, $P>0.05$), after which it again decreased significantly on day 10 (Tukey, $P<0.05$), with 27% of activity persisting (FIG. 26D).

For the HearSNPV isolates that are harmless to humans and other vertebrates, persistence of more than 50% of the insecticidal activity on day 7 after application of the treatment is positive, since larvae that eat the contaminated leaves may acquire the disease. For Dursban, which is toxic to humans, persistence of around 50% on day 10 is negative, since it lengthens the pre-harvest interval before the tomatoes may be harvested, not counting the environmental contamination it entails.

In view of these results, application of HearSNPV treatments at doses of $10^{13}$ occlusion bodies/Ha affords satisfactory protection for both greenhouse and field-grown tomato crops and is as effective as the chemical and biological treatments currently in use for this crop while avoiding their drawbacks.

DEPOSIT OF BIOLOGICAL MATERIAL

The new HearSP1B and HearLB6 genotypes have been deposited in the Collection Nationale de Cultures de Microorganismes [National Collection of Microorganism Cultures] (CNCM), Institut Pasteur, France pursuant to the provisions of the Budapest Treaty. The deposit numbers and deposit dates are:

| Genotype | Abbreviation | Deposit number | Date of deposit |
|---|---|---|---|
| HearSNPV-SP1B | HearSP1B | CNCM I-4806 | Madrid, 15 Oct. 2013 |
| HearSNPV-LB6 | HearLB6 | CNCM I-4807 | Madrid, 15 Oct. 2013 |

The two genotypes were deposited by one of the inventors, Dr. Primitivo Caballero (Instituto de Agrobiotecnologia y Recursos Naturales, Universidad PUblica de Navarra, Campus de Arrosadia, Mutilva Baja, E-31006, Pamplona, Navarre, Spain) as an employee of the first applicant for and on behalf of the three applicants (Universidad Pública de Navarra, Consejo Superior de Investigaciones Cientificas, Instituto de Ecologia A.C.).

BIBLIOGRAPHIC REFERENCES

Arrizubieta, M., Williams, T., Caballero, P., Simón, O., 2014. Selection of a nucleopolyhedrovirus isolate from *Helicoverpa armigera* as the basis for a biological insecticide. Pest Management Science 70, 967-976.

Barrera, G., Simón, O., Villamizar, L., Williams, T., Caballero, P., 2011. *Spodoptera frugiperda* multiple nucleopolyhedrovirus as a potential biological insecticide: genetic and phenotypic comparison of field isolates from Colombia. Biological Control 58, 113-120.

Bernal, A., Williams, T., Hernández-Suárez, E., Carnero, A., Caballero, P., Simón, O., 2013a. A native variant of *Chrysodeixis chalcites* nucleopolyhedrovirus: The basis for a promising bioinsecticide for control of *C. chalcites* on Canary Islands' banana crops. Biological Control 67, 101-110.

Bernal, A., Simón, O., Williams, T., Muñoz, D., Caballero, P., 2013b. A *Chrysodeixis chalcites* single nucleopolyhedrovirus population from the Canary Islands is genotypically structured to maximize survival. Applied and Environmental Microbiology 79, 7709-7718.

Caballero, P., Zuidema, D., Santiago-Alvarez, C., Vlak, J. M., 1992. Biochemical and biological characterization of four isolates of *Spodoptera exigua* nuclear polyhedrosis virus. Biocontrol Science and Technology 2, 145-157.

Caballero, P., Williams, T., López-Ferber, M., 2001. Estructura y clasificación de los baculovirus, pp. 15-46. En: Caballero, P., Williams, T., López-Ferber, M. (Eds.). Los baculovirus y sus aplicaciones como bioinsecticidas en el control biológico de plagas. Phytoma-España, Valencia, España.

Chapman, J. W., Williams, T., Escribano, A., Caballero, P., Cave, R. D., Goulson, D., 1999. Age-related cannibalism and horizontal transmission of a nuclear polyhedrosis virus in larval *Spodoptera frugiperda*. Ecological Entomology 24, 268-275.

Chen, X., Li, M., Sun, X., Arif, B. M., Hu, Z., Vlak, J. M., 2000. Genomic organization of *Helicoverpa armigera* single-nucleocapsid nucleopolyhedrovirus. Archives of Virology 145, 2539-2555.

Chen, X., IJkel, W. F. J., Tarchini, R., Sun, X., Sandbrink, H., Wang, H., Peters, S., Zuidema, D., Lankhorst, R. K., Vlak, J., Hu, Z., 2001. The sequence of the *Helicoverpa armigera* single nucleocapsid nucleopolyhedrovirus genome. Journal of General Virology 82, 241-257.

Cherry, A., Williams, T., 2001. Control de insectos plaga mediante baculovirus, pp. 389-450. En: Caballero, P., Williams, T., López-Ferber, M. (Eds.). Los baculovirus y sus aplicaciones como bioinsecticidas en el control biológico de plagas. Phytoma-España, Valencia, España.

Clavijo, G., Williams, T., Munoz, D., Caballero, P, López-Ferber, M., 2010. Mixed genotype transmission bodies and virions contribute to the maintenance of diversity in an insect virus. Proceedings of the Royal Society B 277, 943-951.

Cory, J. S., Green, B. M., Paul, R. K., Hunter-Fujita, F., 2005. Genotypic and phenotypic diversity of a baculovirus population within an individual insect host. Journal of Invertebrate Pathology 89, 101-111.

Crawley, 1993. GLIM for ecologists. Blackwell Scientific Publications, Oxford, UK.

Cunningham, J. P., Zalucki, M. P., West, S. A., 1999. Learning in *Helicoverpa armigera* (Lepidoptera: Noctuidae): a new look at the behaviour and control of a polyphagous pest. Bulletin of Entomological Research 89, 201-207.

Erlandson, M., Newhouse, S., Moore, K., Janmaat, A., Myers, J., Theilmann, D., 2007. Characterization of baculovirus isolates from *Trichoplusia ni* in populations from vegetable greenhouses. Biological Control 41, 256-263.

Figueiredo, E., Muñoz, D., Escribano, A., Mexia, A., Vlak, J. M., Caballero, P., 1999. Biochemical identification and comparative insecticidal activity of nucleopolyhedrovirus isolates pathogenic for *Heliothis armigera* (Lep. Noctuidae) larvae. Journal of Applied Entomology 123, 165-169.

Figueiredo, E., Muñoz, D., Murillo, R., Mexia, A., Caballero, P., 2009. Diversity of Iberian nucleopolyhedrovirus wild-type isolates infecting *Helicoverpa armigera* (Lepidoptera: Noctuidae). Biological Control 50, 43-49.

Gelernter, W. D., Federici, B. A., 1986. Isolation, identification and determination of virulence of a nuclear polyhedrosis virus from the beet armyworm, *Spodoptera exigua* (Lepidoptera: Noctuidae). Environmental Entomology 15, 240-245.

Granados, R., Fu, Y., Corsaro, B., Hughes, P., 2001. Enhancement of *Bacillus thuringiensis* toxicity to lepidopterous species with the enhancin from *Trichoplusia ni* granulovirus Biological Control 20, 153-159.

Greene, G. L., Leppla, N. C., Dickerson, W. A., 1976. Velvetbean caterpillar: a rearing procedure and artificial medium. Journal of Economic Entomology 69, 487-488.

Gröner, A., 1986. Specificity and safety of baculoviruses, pp. 177-202. En: Granados, R. R., Federici, B. A. (Eds.). The biology of baculoviruses: biological properties and molecular biology. CRC Press, Boca Ratón, Fla.

Guo, Z., Ge, J., Wang, D., Shao, Q., Zhang, C., 2006. Biological comparison of two genotypes of *Helicoverpa armigera* single-nucleocapsid nucleopolyhedrovirus. Biological Control 51, 809-820.

Gupta, R. K., Raina, J. C., Monobrullah, M. D., 2007. Optimization of in vivo production of nucleopolyhedrovirus in homologous host larvae of *Helicoverpa armigera*. Journal of Entomology 4, 279-288.

Hara, K., Funakoshi, M., Kawarabata, T., 1995. In vivo and in vitro characterization of several isolates of *Spodoptera exigua* nuclear polyhedrosis virus. Acta Virologica 39, 215-222.

Harrison, R. L., Bonning, B. C., 1999. The nucleopolyhedrovirus of *Rachoplusia ou* and *Anagrapha falcifera* are isolates of the same virus. Journal of General Virology 80, 2793-2798.

Harrison, R. L., Popham, H. J. R., Breitenbach, J. E., Rowley, D. L., 2012. Genetic variation and virulence of *Autographa californica* multiple nucleopolyhedrovirus and *Trichoplusia ni* single nucleopolyhedrovirus isolates. Journal of Invertebrate Pathology 110, 33-47.

Hughes, P. R., Wood, H. A., 1981. A synchronous peroral technique for the bioassay of insect viruses. Journal of Invertebrate Pathology 37, 154-159.

Jehle, J. A., Blissard, G. W., Bonning, B. C., Cory, J. S., Herniou, E. A., Rohrmann, G. F., Theilmann, D. A., Thiem, S. M., Vlak, J. M., 2006. On the classification and nomenclature of baculoviruses: a proposal for revision. Archives of Virology 151:1, 257-266.

Kalia, V., Chaudhari, S., Gujar, G., 2001. Optimization of production of nucleopolyhedrovirus of *Helicoverpa armigera* throughout larval stages. Phytoparasitica 29, 23-28.

King, L. A., Possee, R. D., 1992. The baculovirus expression system. A laboratory guide. Chapman & Hall, London, UK.

Lasa, R., Ruiz-Portero, C., Alcazar, M. D., Belda, J. E., Caballero, P., Williams, T., 2007. Efficacy of optical brightener formulations of *Spodoptera exigua* multiple nucleopolyhedrovirus (SeMNPV) as a biological insecticide in greenhouses in southern Spain. Biological Control 40, 89-96.

Le Ora Software, 1987. POLO-PC a user's guide to do probit or logit analysis. Berkeley, Calif., USA.

López-Ferber, M., Simón, O., Williams, T., Caballero, P., 2003. Defective or effective? Mutualistic interactions between virus genotypes. Proceedings of the Royal Society B 270, 2249-2255.

Moscardi, F., 1999. Assessment of the application of baculoviruses for control of Lepidoptera. Annual Review of Entomology 44, 257-289.

Muñoz, D., Castillejo, J. I., Caballero, P., 1998. Naturally occurring deletion mutants are parasitic genotypes in a wild-type nucleopolyhedrovirus population of *Spodoptera exigua*. Applied and Environmental Microbiology 64, 4372-4377.

Muñoz D., Martinez, A. M., Murillo, R., Ruiz de Escudero, I., Vilaplana, L. 2001. Técnicas básicas para la caracterización de baculovirus, pp. 479-518. En: Caballero, P., Williams, T., López-Ferber, M. (eds.) Los Baculovirus y sus Aplicaciones como Bioinsecticidas en el Control Biolôgico de Plagas. Phytoma-España, Valencia, España.

Ogembo, J. G., Kunjeku, E. C., Sithanantham, S., 2005. A preliminary study on the pathogenicity of two isolates of nucleopolyhedroviruses infecting the African bollworm, *Helicoverpa armigera* (Lepidoptera: Noctuidae). International Journal of Tropical Insect Science 25, 218-222.

Ogembo, J. G., Chaeychomsri, S., Kamiya, K., Ishikawa, H., Katou, Y., Ikeda, M., Kobayashi, M., 2007. Cloning and comparative characterization of nucleopolyhedroviruses isolated from African Bollworm, *Helicoverpa armigera*, (Lepidoptera: Noctuidae) in different geographic regions. Journal of Insect Biotechnology and Sericology 76, 39-49.

Ogembo, J. G., Caoili, B. L., Shikata, M., Chaeychomsri, S., Kobayashi, M., Ikeda, M., 2009. Comparative genomic sequence analysis of novel *Helicoverpa armigera* nucleopolyhedrovirus (NPV) isolated from Kenya and three other previously sequenced *Helicoverpa* spp. NPVs. Virus Genes 39, 261-272.

Polis, G. A., 1981. The evolution and dynamics of intraespecific predation. Annual Review of Ecology, Evolution and Systematics 12, 225-251.

Reed, W., Pawar, C. S., 1982. *Heliothis*: a global problem, pp. 9-14. En: Reed, W., Kumble, V. (Eds.). Proceedings of the International Workshop on *Heliothis* Management. ICRISAT, Pantanchera, India.

Shieh, T. R., 1989. Industrial production of viral pesticides. Advances in Virus Research 36, 315-343.

Simón, O., Williams, T., López-Ferber, M., Caballero, P., 2005. Functional importance of deletion mutant genotypes in an insect nucleopolyhedrovirus population. Applied and Environmental Microbiology 71, 4254-4262.

Subramanian, S., Santharam, G., Sathiah, N., Kennedy, J. S., Rabindra, R. J., 2006. Influence of incubation temperature on productivity and quality of *Spodoptera litura* nucleopolyhedrovirus. Biological Control 37, 367-374.

Systat, 1990. Systat: the system for statistics. Systat Incorporation, Evaston, Ill.

Theilmann, D. A., Blissard, G. W., Bonning, B., Jehle, J. A., O'Reilly, D. R., Rohrmann, G. F., Thiem, S., Vlak, J. M., 2005. Baculoviridae, pp. 177-185. En: Fauquet, C. M., Mayo, M. A., Maniloff, J., Desselberger, U., Ball, L. A. (Eds.). Eight Report of the International Committee on Taxonomy of Viruses. Academic Press, San Diego, Calif.

Torres-Vila, L. M., Rodriguez-Molina, M. C., Palo, E., Bielza, P., Lacasa, A., 2000. La resistencia a insecticides de *Helicoverpa armigera* Hubner en Espana: datos disponibles. Boletin de Sanidad Vegetal Plagas 26, 493-501.

Torres-Vila, L. M., Rodriguez-Molina, M. C., Lacasa-Plasencia, A., 2003. Impact of *Helicoverpa armigera* larval density and crop phenology on yield and quality losses in processing tomato: developing fruit count-based damage thresholds for IPM decision-making. Crop Protection 22, 521-532.

Washburn, J. O., Kirkpatrick, B. A., Haas-Stapleton, E., Volkman, L. E., 1998. Evidence that the stilbene-derived optical brightener M2R enhances *Autographa californica* M nucleopolyhedrovirus infection of *Trichoplusia ni* and *Heliothis virescens* by preventing sloughing of infected midgut epithelial cells. Biological Control 11, 58-69.

Zhang G., 1994. Research, development and application of *Heliothis* viral pesticide in China. Resource and Environment in the Yangtze Valley 3, 1-6.

Zhang, C. X., Ma, X. C., Guo, Z. J., 2005. Comparison of complete genome sequence between C1 and G4 isolates of the *Helicoverpa armigera* single nucleocapsid nucleopolyhedrovirus. Virology 333, 190-199.

The invention claimed is:

1. An occlusion body comprising occlusion-derived virions, wherein occlusion-derived virions of at least two different genotypes are co-occluded in the occlusion body, and wherein the genotypes are selected from the group of *Helicoverpa armigera* single nucleopolyhedrovirus genotypes consisting of HearSNPV-SP1B (CNCM I-4806) and HearSNPV-LB6 (CNCM I-4807).

2. A composition that comprises at least one occlusion body of claim 1.

3. The composition according to claim 2 in which genotypes HearSNPV-SP1B (CNCM I-4806) and HearSNPV-LB6 (CNCM I-4807) are present in the ratio HearSNPV-SP1B: HearSNPV-LB6 of 1:1.

4. The composition according to claim 3, in which virions are present in occlusion bodies containing co-occluded virions, and wherein the co-occluded virions of the same nucleopolyhedrovirus belong to the same genotype or different genotypes.

5. The composition according to claim 2, that further comprises an excipient or inert carrier appropriate to the agricultural sector.

6. The composition according to claim 2, in which any *Helicoverpa armigera* single nucleopolyhedroviruses are mixed with one or more of compost, fertilizer or pesticide.

7. A process for the production of the occlusion bodies of claim 1, comprising the steps:

i) feeding *Helicoverpa armigera* larvae an artificial diet comprising occlusion bodies of *H. armigera* single nucleopolyhedrovirus that contain virions of any one of the genotypes HearSNPV SP-B (CNCM I-4806) and HearSNPV-LB6 (CNCM I-4807) or mixtures thereof;

ii) maintaining the larvae at 23-30° C. until death occurs;

iii) purifying the occlusion bodies generated in larvae by grinding bodies of larvae in water, filtering the resulting suspension, sedimenting occlusion bodies, washing the sediment thus obtained and sedimenting again;

iv) resuspending the final pellet of sediment in water at neutral pH; and v) optionally, storing the resulting suspension in one of the following conditions:

a) at room temperature, b) cooling, or freezing, or c) lyophilizing the suspension and storing it at room temperature.

8. The process according to claim 7, wherein the *H. armigera* larvae are in the fifth instar.

9. The process according to claim 7, wherein the occlusion bodies that the larvae feed upon are present at a concentration in the range of $2.00 \times 10^7$ to $1.00 \times 10^9$ occlusion bodies/ml.

10. A method for identifying in a sample the presence of a genotype selected from HearSNPV-SP1 B (CNCM I-4806) and HearSNPV-LB8 (CNCM I-4807) of *H. armigera* single nucleopolyhedrovirus comprising the steps of:

i) PCR amplification of DNA extracted from said sample using a pair of primers selected from the group consisting of those formed by:

a) SEQ ID NO: 1 (F-hr1) and SEQ ID NO:2 (R-hr1), and b) SEQ ID NO:3 (F-hr5) and SEQ ID NO:4 (R-hr5);

ii) analyzing the amplified fragment to determine its size or sequence;

iii) digesting the amplified fragment using NdeI endonuclease;

iv) analyzing the fragments generated after digestion with NdeI to determine the number of fragments and the size of each of them;

v) concluding that one of the genotypes HearSNPV-SP1B (CNCM I-4806) or HearSNPV-LB6 (CNCM I-4807) is present if:

a) the fragment amplified by the pair of SEQ ID NO: 1 and SEQ ID NO: 2 has:

i) a length of 2177 (HearSNPV-SP1B) or 2117 (HearSNPV-LB6) nucleotides;

ii) digestion of said fragment with NdeI endonuclease generates six fragments of 857, 508, 381, 306, 78 and 47 nucleotides (HearSNPV-SP1B) or five fragments of 1210, 475, 307, 78 and 47 nucleotides (HearSNPV-LB6); or iii) the sequence represented by SEQ ID NO: 5 (HearSNPV-SP1B) or SEQ ID NO: 6 (HearSNPV-LB6);

or alternatively, b) the fragment amplified by the primer pair of SEQ ID NO: 3 and SEQ ID NO: 4 has:

i) a length of 2326 (HearSNPV SP1B) or 2330 (HearSNPV-LB6) nucleotides;

ii) digestion of the fragment with NdeI endonuclease generates four fragments of 1120, 917, 211 and 78 nucleotides (HearSNPV-SP1B) or three fragments of 1120, 998 and 212 nucleotides (HearSNPV-LB6); or iii) the sequence represented by SEQ ID NO: 7 (HearSNPV-SP1B) or SEQ ID NO: 8 (HearSNPV-LB6).

11. A method for controlling insect pests, comprising applying to plants a composition according to claim 2, wherein the pests are of the genera *Helicoverpa* or *Heliothis.*

12. The method according to claim 11, where the pests of the genera *Helicoverpa* are *Helicoverpa armigera* larvae.

13. A composition comprising:

i) HearSNPV deposited in the National Collection of Microorganism Cultures (CNCM) with the deposit numbers CNCM I-4806 (HearSNPV-SP1B) and CNCM I-4807 (HearSNPV-LB6), or ii) genotypes whose genome is represented by SEQ ID NO: 13 (HearSNPV-SP1B) and SEQ ID NO: 14 (HearSNPV-LB6).

14. A method for controlling insect pests, comprising applying to plants a composition according to claim 13, wherein the pests are of the genera *Helicoverpa* or *Heliothis.*

15. The method according to claim 14, where the pests of the genera *Helicoverpa* are *Helicoverpa armigera* larvae.

16. The composition according to claim 13, that further comprises an excipient or inert carrier appropriate to the agricultural sector.

17. The composition according to claim 13, in which any *Helicoverpa armigera* single nucleopolyhedroviruses are mixed with one or more of compost, fertilizer or pesticide.

* * * * *

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Primer PCR F- hr1

<400> SEQUENCE: 1

cgaaatcgac aacaccatgc a                                              21


<210> SEQ ID NO 2
<211> LENGTH: 21
<212> TYPE: DNA
<213> ORGANISM: Artificial Sequence
<220> FEATURE:
<223> OTHER INFORMATION: Primer PCR R-hr1

<400> SEQUENCE: 2

acttttgtac gccagagacg a                                              21


<210> SEQ ID NO 3
<211> LENGTH: 20
<212> TYPE: DNA
<213> ORGANISM: Artificial Sequence
<220> FEATURE:
<223> OTHER INFORMATION: Primer PCR F-hr5

<400> SEQUENCE: 3

ctagccggtc cgtttctgtt                                                20


<210> SEQ ID NO 4
<211> LENGTH: 20
```

<212> TYPE: DNA
<213> ORGANISM: Artificial Sequence
<220> FEATURE:
<223> OTHER INFORMATION: Primer PCR R-hr5

<400> SEQUENCE: 4
gccccaccca aaacataacg 20

<210> SEQ ID NO 5
<211> LENGTH: 2177
<212> TYPE: DNA
<213> ORGANISM: Helicoverpa armigera SNPV
<220> FEATURE:
<221> NAME/KEY: misc_feature
<223> OTHER INFORMATION: country=Spain, isolate=HearSNPV-SP1, Fragment
PCR hr1-HearSP1B, strain=HearSNPV-SP1B

<400> SEQUENCE: 5
cgaaatcgac aacaccatgc acattactac tttacccgta gccactgatt actcagaaca 60
aaacaaactt gatcaggccg ccgtcgttgt agacgaccaa tacaattcgc cattagtgtt 120
tcatgacaat tccacactca acaactcttc cgaactatgg aatattccat caacaaacaa 180
atgacatcat cgttcgaaat ctgctgtagg caacgaatta tcacacacga gattatattg 240
aaaaaattac gtcatccgtt taaaatattg catcatcttt aaattcgaaa cccgcccgcg 300
ctttcatatg aaaccgtcgg caaagatcga taaaatttat tctagaacat tccacggctt 360
gacccaaaaa aacaaatgac gtcatatggc gtgatctaga aatggtccaa tcacaaacgt 420
attccacgaa tcacgccacg cccaaagata acgtactttt ggttattttc gttcgaaacg 480
ggccgtgatc ttttgcttcg aaaccgacgg caaagattga taaaatttgt tctagaacgt 540
tccacggctt gacccaaaaa aacaaatgac gtcatatagc gtgatctaga aaaagtcgaa 600
tcacgagacg cccaaaaata acgtactttt aaactggtct tggatcattt cgttcgaaac 660
gggccgtgat cttttgcttc tattcatgat taaggaaaaa acaaattacg tcatccgttt 720
aggatattgc atcatcttta aattcaaaac tagcccgcgc tttcatatga aaccgtcggc 780
aaagattgat aaaatttgtt ctagaacgtt ccacggcttg acccaaaaaa caaatgacgt 840
catataacgt gatctagaaa aagtcgaatc acgagacgcc caaagataac gtacttttaa 900
actggtcttg gttattttcg ttcgaaacgg gccgtgatct tttgcttcga ttcatgaccc 960
aaaaaaacaa atgacatcat ttaccaaaga taatgtttcc cgcgcacgtt taaactagtc 1020
ttagatcttt tcgttcgaaa cggctgtga tctttttgct tcgagtcatg accagaaaaa 1080
aaaccgatta agtcattttg cacacggctc tctttgaaaa acaaattacg tcataaaacg 1140
tgattataga atcgtccaat caaaaacgaa cacgaatcgc gtcacgcgca cgaaatttac 1200
tattcgactt gacctaaaaa aacaaagaac gtattccacg aatcacgcca cgcccaaaca 1260
taacgtactt ttaaactggt cttggatcat ttcgttcgaa acgggccgtg atcttttgtt 1320
tcgcttcgtg acccaaaaaa aacaaatgac atcatcgccc aaacataacg tacttttaaa 1380
ctagtcttgg atattttcgt tcgaaacggg ccgtgatctt ttgtttcgct tcgtgaccca 1440
aaaaaacaaa ttacgtcatc gaccaaagta aaaattcttg cgcatgttta aactagtctt 1500
ggatattttc gttcgaaacg ggccgtgatc ttttgtttcg cttcgtgacc caaaaaaaca 1560
aattacgtca ttcgtttaaa atattgcatc atctttaaat tcgaaacccg cccgcgcttt 1620
catatgaaac cgtcggcgaa gatcgataaa atttgttcta gaacattcga tggtttgacc 1680
caaaaaaaca aatgacgtca tatagcgtgc gtccaatcac aacacgaatc acgccttgtc 1740

-continued

```
taaagataac atttcccgcg catgtttaaa ctaatcttgg atcttttcgt tcgaaacggg   1800

ccgtggtctt ttgtttcaat tcatgattta gaaaaaaacg aacataaaat tttaccgcgc   1860

atttttaaac tagtctagga tctttttgtt caaaacgtgc cgtgatcttt tcgttcgaaa   1920

cgggccgtga tcttttcgtt cgaaacgggc cgtgatcttt tgtttcgctg actcgtgacc   1980

caaaaaaaca aattacgtca ttcgtttaaa atattgcatc atctttaaat tcgaaactcg   2040

cccgcgcttt catacgaaac cgccggcaaa gatcggtaaa atttgttcta gaacgttcca   2100

cggcttgacc caaaaaaaca aatgacgtca tatggcgtga ttttaaatct atttaatcgt   2160

ctctggcgta caaaagt                                                  2177
```

```
<210> SEQ ID NO 6
<211> LENGTH: 2117
<212> TYPE: DNA
<213> ORGANISM: Helicoverpa armigera SNPV
<220> FEATURE:
<221> NAME/KEY: misc_feature
<223> OTHER INFORMATION: country=Spain, Fragment PCR hr1-HearLB6,
      strain=HearSNPV-LB6

<400> SEQUENCE: 6
```

```
cgaaatcgac aacaccatgc acattactac tttacccgta gccacggatt actcagaaca     60

aaacaaactt gatcaggccg ccgtcgttgt agacgaccaa tacaattcgc cattagtgtt    120

tcatgacaat tccacactca acaactcttc tgaactatgg aatattccat caacaaacaa    180

atgacatcat cgttcgaaat ctgctgtagg caacgaatta tcacacacga gattatattg    240

aaaaaaatgt catcatcgtt ttaaaatatt gcatcatctt tagattcgaa actagcccgc    300

gctttcatat gaaaccgtcg gcaaagatcg ataaaattta ttctagaaca ttccacggtt    360

tgacccaaaa aaacaaatga cgtcatatgg cgtgatctag aaatggtcca atcacaaacg    420

tattccacga atcacgccac gcccaaagat aacgtatttt taaactggcc ttggatcatt    480

acgttcgaaa cgggccgtga tcttttgttt tgactcgtga tattttgcac acggcactat    540

tccaacaaat tttccgcgca tgttaaaatc aatttaacaa atcacgccac gcccaaagat    600

aacgtatttt taaactggtc ttggatgtgt tcgttcgaaa cgggccgtga tcttttcatg    660

acccaaaaaa aaaacaaatt acgtcatccg tttaggatat tgcatcatct ttaaattcga    720

aactagcccg cgcttttata tgaaaccgtc ggcaaagatt gataaaattt gttctagaac    780

gttccacggt ttgacccaaa aaaacaaatg acgtcatata gcgtgatcta gaaaaagtcg    840

aatcacgaga cgcccaaaaa taacgtactt ttaaaccggt cttatatctt ttcgttcgaa    900

acgggccgtg attttttgct tcgattcatg acccaaaaaa acaaatgaca tcatctacca    960

aagataatgt ttcccgcgca cgtttaaact agtcttggat cttttcgttc gaaacgggct   1020

gtgatctttt tgcttcgagt catgaccaga aaaaaaaccg attaagtcat tttgcacacg   1080

gctctctttg aaaaacaaat tacgtcataa aacgtgatta tagaatcgtc caatcaaaaa   1140

cgaacacgaa tcgcgtcacg cgcacgaaat ttactattcg acttgaccta aaaaaacaaa   1200

gaacgtattc cacgaatcac gccacgccca aacataacgt acttttaaac tggtcttgga   1260

ttatttcgtt cgaaacgggc cgtgatcttt tgtttcgctt cgtgacttaa aaaaacaaat   1320

gacatcatcg cccaaaaata acgtactttt aaactggtct tggatcattt cgttcgaaac   1380

gggccgtgat cttttgtttc gcttcgtgac ccaaaaaaac aaattacgtc atcgaccaaa   1440

gcaaaaattc ttgcgcatgt ttaaactagt cttggatatt ttcgttcgaa acgggccgtg   1500

atcttttgtt tcgcttcgtg acccaaaaaa acaaattacg tcattcgttt aaaatattgc   1560
```

```
atcatcttta aattcgaaac ccgcccgcgc tttcatatga aaccgtcggc aaagatcgat   1620

aaaatttgtt ctagaacatt cgatggtttg acccaaaaaa acaaatgacg tcatatagcg   1680

tgcgtccaat cacaacacga atcacgcctt gtctaaagat aacatttccc gcgccgggcc   1740

gtgatctttt gtttcagttc atgatttaga aaaaaaaacg aacataaaat tttaccgcgc   1800

atttttaaac tagtgttgga ttttttttgtt tgaaacgagc cgtgatcttt tcgttcgaaa   1860

cgggccgtga tcttttcgtt cgaaacgggc cgtgatcttt tgtttcgctg actcgtgacc   1920

caaaaaaaca aatcacgtca ttcgtttaga atattgcatc atctttaaat tcgaaactcg   1980

cccgcgcttt catacgaaac cgtcggcaaa gatcgataaa atttgttcta gaacgttcca   2040

cggcttgacc caaaaaaaca aatgacgtca tatggcgtga ttttaaatct atttaatcgt   2100

ctctggcgta caaaagt                                                  2117


<210> SEQ ID NO 7
<211> LENGTH: 2326
<212> TYPE: DNA
<213> ORGANISM: Helicoverpa armigera SNPV
<220> FEATURE:
<221> NAME/KEY: misc_feature
<223> OTHER INFORMATION: country=Spain, isolate=HearSNPV-SP1, Fragment
      PCR hr5-HearSP1B, strain=HearSNPV-SP1B

<400> SEQUENCE: 7

ctagccggtc cgtttctgtt gacgctgaac gctgtatgtt tgatgcggta ccgttctttg     60

cgagcgttca ttgcacgtcg gacttcgtct acagtcgtgt cgcgatatgt atgcgggcat    120

tttatttcca taggcacaat cgtgtcgtcg tctagaataa agtaggcgtc cggcgatgcg    180

gaatgtaatc cgtatttgct aaagaacata ccgcaatcga gaacagtctc tgtaattttt    240

ttattagttt cgcgttcgac acattcacga accagattca aaagcgattc attgtttttc    300

acgcaagttt cctgttccaa tccgtaggtg agcgccggaa tcggtcgcag accaatgccg    360

ctgctgctgt tcgtattaga tcccgaagca gtttgtcgat cgagccgcaa caaaaaccat    420

agcgggttcg tcgattgtcc acgtgttgct ttttcgattt ccatgatttc atgccgtgac    480

aataattgtg ttatgctttt cagttgactc acataattgg taaaacagta tttgtcaaat    540

atgttctgct gttcggcggt gagcaaatcg cacggcgaca ctaatgattt ggtcattttt    600

gtggtcgaca tggtcacgcg caataatata ttataaatta tatttcgtga gaagccaatc    660

gagaagtttt acgtacacgg ccgactgtag cgtgttatcg gattcactgt atttaactag    720

aaattgcact aaaatattta aaattctgct ctgattgaac atcaatcgtt ccgtttcaat    780

agccatgtcc atgaacgatt gaacggtgat catcatacca tgttgttgaa aattaatttt    840

gcccaatacg ttttcaacta tactgatgaa taccgtgtaa aatgtttttc gagcaatatt    900

ctgattacaa ttgaacggat cgacgaccgt gtcgcgtaga aagtctatga cagatctaag    960

tttaatcgat ttgtcacgta ttcgatcgtt gcgttgcaat cttttcacgt aaggtttcat   1020

cgcaaaatta caatcgtgtt ggaaaagtta ttccgtcaca aaaaaagtcc cttaaattaa   1080

aaaatttcta ccgtgtaatc gatcttcgcc gacggtttca tatgaaagcg cgggcgggtt   1140

ttgaatttaa agatgatgca atatcttaaa tggatgacgt aatttgtttt ttcctcaatc   1200

atgaatagaa gcaaaagatc acggcccgtt tcgaacgaaa agatccaaga ccggtttaaa   1260

agtacgttat ctttgggagt ggcgtgattc gtggaatacg tttatgattg gacaactttt   1320

aaatcacgcc atatgacgtc atttgttttt ttaggtcgag ccatcgaacg ttctagaaca   1380
```

aattttatcg atctttgccg acggtttcat atgaaagcgc gggcgagttt cgaatttaaa 1440
gatgatgcaa taatttaaac gaatgacgta atttgttttt ttgggtcacg aagcgaaaca 1500
aaagatcacg gcccgtttcg aacaaaaaaa tccaagacta gtttgaacat gcgcgaaaat 1560
ttttattttg gtagatgatg tcatttgttt tttttgggtc acgacaaaaa atcacggccc 1620
gtttcaaacg aaaagatccg agatcagttt aaacattcgc gggaattttt actttgggcg 1680
atgatgtcat ttgttttttt gggtcataaa tcgaaacaaa agatcacggt ccgtttcgaa 1740
cgaaaagatc caagactagt ttaaacgtgc gcgggaaaca ttatctttgg tagatgatgt 1800
catttgtttt tttgggtcat gaatcgaagc aaaagatcac ggcccgtttc gaacgaacag 1860
atccaagacc agtttaaatt tgcgcgggaa atgttatctg ttgttgatga cgtaatttgt 1920
ttttcgaata gtgtcgtgtg caaattttgg gtcatgaaac aaaagatcgc ggcccgtttc 1980
aaacgaaaag atccgagatc agtttaaaaa tgcgatgcgc gggaattttt ttaatttggt 2040
caatgacgta tttgttttc gagtagtgcc gtgtgcaaaa tgctttgagt cataaatcaa 2100
agcaaaagat cgcggcccgt ttcaaacgaa aaggttcaag atcagtttaa acctgcgcgg 2160
gaaatgttat ctgttgttga tgacgtaatt tgtttttcga gtagtgccga gtgcaaaatg 2220
acttaatctg tttttctaaa tcacgaatcg aagcaagaga tcacggtccg tttcgaacga 2280
aaagatccaa gactagttta aaaatacgtt atgttttggg tggggc 2326

<210> SEQ ID NO 8
<211> LENGTH: 2330
<212> TYPE: DNA
<213> ORGANISM: Helicoverpa armigera SNPV
<220> FEATURE:
<221> NAME/KEY: misc_feature
<223> OTHER INFORMATION: country=Spain, Fragment PCR hr5-HearLB6,
strain=HearSNPV-LB6

<400> SEQUENCE: 8
ctagccggtc cgtttctgtt gacgctgaac gctgtatgtt tgatgcggta gcgttctttg 60
cgagcgttca ttgcacgtcg gacttcgtct acagtcgtgt cgcgatatgt atgcgggcat 120
tttatttcca taggcacaat cgtgtcgtcg tctagaataa agtaggcgtc cggcgatgcg 180
gaatgtaatc cgtatttgct aaagaacata ccgcaatcga gaacagtctc tgtaattttt 240
ttattagttt cgcgttcgac acattcacga accagattca aaagcgattc attgtttttc 300
acgcaagttt cctgttccaa tccgtaggtg agcgccggaa tcggtcgcag accaatgccg 360
ctactgctgt tcgtattaga tcccgaagca gtttgtcgat cgagccgcaa caaaaaccat 420
agcgggttcg tcgattgtcc acgtgttgct ttttcgattt tcatgatttc atgccgtgac 480
aataattgtg ttatgctttt cagttgactc acataattgg taaaacagta tttgtcaaat 540
atgttctgct gttcggcggt gagcaaatcg cacggagaca ctaatgattt ggtcattttt 600
gtggtcgaca tggtcacgcg caataatata ttataaatta tatttcgtga gaagccaatc 660
gagaagtttt acgtacacgg ccgactgtag cgtgttatcg gattcactgt atttaactag 720
aaattgcact aaaatattta aaattctgct ctgattgaac atcaatcgtt ccgtttcaat 780
agccatgtcc atgaacgatt gaacggtgat catcatacca tgttgttgaa aattaatttt 840
gcccaatacg ttttcaacta tactgatgaa taccgtgtaa aatgtttttc gagcaatatt 900
ctgattacaa ttgaacggat cgacgaccgt gtcgcgtaga aagtctatga cagatctaag 960
tttaatcgat ttgtcacgta ttcgatcgtt gcgttgcaat cttttcacgt aaggtttcat 1020
cgcaaaatta caatcgtgtt ggaaaagtta ttccgtcaca aaaaaagtcc cttaaattaa 1080

-continued aaaatttcta ccgtgtaatc gatcctcgcc gacggtttca tatgaaagcg cgggcgggtt 1140
tcgaatttaa aaatgatgca atatcttaaa cggatgacgt aatttgtttt ttcctcaatc 1200
atgaatagaa gcaaaagatc acggcccgtt tcgaacgaaa agatccaaga ccggtttaaa 1260
agtacgttat ttttgggcgt ggcgtgattc gtagaatacg tttgtgattg gacaacttta 1320
aaaatcacgc catatgatgt catttgtttt ttttaaatcg agccatcgaa cgttctagaa 1380
caaattttat caatctttgc cgacggtttc gtatgaaagc gcgggcgagt ttcgaattta 1440
aagatgatgc aatattttaa acaaatgacg taatttgttt ttttgggtca cgaagcgaaa 1500
caaaagatca cggcccgttt cgaacataaa aaaaaatcca agactagttt gaacatgcgc 1560
gagaattttt attttgatag atgatgtcat ttgttttttt tttgggtcac gacaaaaaat 1620
cacggcccgt ttcaaacgaa aagatccgag atcagtttaa acattcgcgg gaatttttac 1680
tttggtcgat gatatcattt gttttttttgg gtcacgagtc gaaacaaaaa atcacggccc 1740
gtttcgaacg aaaagatcca agactagttt aaacgtgcgc gggaaacatt atctttggta 1800
gatgatgtca tttgtttttt tgggtcatga atcgaagcaa aagatcacgg cccgtttcga 1860
acgaacagat ccaagaccag tttaaacttg cgcgggaaat gttatctgtt gttgatgacg 1920
taaattgttt ttcgaatagt gtcgtgtgca aatttttgggt catgaaacaa aagatcgcgg 1980
cccgtttcaa acgaaaagat ccgagatcag tttaaaaatg cgatgcgcgg gaattttttt 2040
taatttggtc gatgacgtaa tttgtttttc gattagtgcc gtgtgcaaaa tgctttgagt 2100
catgaatcaa agcaaaagat cgcggcccgt ttcaaacgaa aaggtccaag attagtttaa 2160
acatgcgcgg gaaatgttat ctgttgttga tgacataatt tgtttttcga gtagtgccga 2220
gtgcaaaatg acttaatctg tttatcacga atcgaagcaa aagatcacgg tccgtttcga 2280
acgaaaagat ccaagactag tttaaaaata cgttatgttt tgggtggggc 2330

<210> SEQ ID NO 9
<211> LENGTH: 1801
<212> TYPE: DNA
<213> ORGANISM: Helicoverpa armigera SNPV
<220> FEATURE:
<221> NAME/KEY: misc_feature
<223> OTHER INFORMATION: country=Spain, isolate=HearSNPV-SP1, Region hr1
HearSP1B, strain=HearSNPV-SP1B

<400> SEQUENCE: 9
aaattacgtc atccgtttaa aatattgcat catctttaaa ttcgaaaccc gcccgcgctt 60
tcatatgaaa ccgtcggcaa agatcgataa aatttattct agaacattcc acggcttgac 120
ccaaaaaaac aaatgacgtc atatggcgtg atctagaaat ggtccaatca caaacgtatt 180
ccacgaatca cgccacgccc aaagataacg tacttttggt tattttcgtt cgaaacgggc 240
cgtgatcttt tgcttcgaaa ccgacggcaa agattgataa aatttgttct agaacgttcc 300
acggcttgac ccaaaaaaac aaatgacgtc atatagcgtg atctagaaaa agtcgaatca 360
cgagacgccc aaaaataacg tacttttaaa ctggtcttgg atcatttcgt tcgaaacggg 420
ccgtgatctt ttgcttctat tcatgattaa ggaaaaaaca aattacgtca tccgtttagg 480
atattgcatc atctttaaat tcaaaactag cccgcgcttt catatgaaac cgtcggcaaa 540
gattgataaa atttgttcta gaacgttcca cggcttgacc caaaaaacaa atgacgtcat 600
ataacgtgat ctagaaaaag tcgaatcacg agacgcccaa agataacgta cttttaaact 660
ggtcttggtt attttcgttc gaaacgggcc gtgatctttt gcttcgattc atgacccaaa 720

-continued

```
aaaacaaatg acatcattta ccaaagataa tgtttcccgc gcacgtttaa actagtctta    780
gatcttttcg ttcgaaacgg gctgtgatct ttttgcttcg agtcatgacc agaaaaaaaa    840
ccgattaagt cattttgcac acggctctct ttgaaaaaca aattacgtca taaaacgtga    900
ttatagaatc gtccaatcaa aaacgaacac gaatcgcgtc acgcgcacga aatttactat    960
tcgacttgac ctaaaaaaac aaagaacgta ttccacgaat cacgccacgc ccaaacataa   1020
cgtactttta aactggtctt ggatcatttc gttcgaaacg ggccgtgatc ttttgtttcg   1080
cttcgtgacc caaaaaaaac aaatgacatc atcgcccaaa cataacgtac ttttaaacta   1140
gtcttggata ttttcgttcg aaacgggccg tgatcttttg tttcgcttcg tgacccaaaa   1200
aaacaaatta cgtcatcgac caaagtaaaa attcttgcgc atgtttaaac tagtcttgga   1260
tattttcgtt cgaaacgggc cgtgatcttt tgtttcgctt cgtgacccaa aaaaacaaat   1320
tacgtcattc gtttaaaata ttgcatcatc tttaaattcg aaacccgccc gcgctttcat   1380
atgaaaccgt cggcgaagat cgataaaatt tgttctagaa cattcgatgg tttgacccaa   1440
aaaaacaaat gacgtcatat agcgtgcgtc caatcacaac acgaatcacg ccttgtctaa   1500
agataacatt tcccgcgcat gtttaaacta atcttggatc ttttcgttcg aaacgggccg   1560
tggtcttttg tttcaattca tgatttagaa aaaaacgaac ataaaatttt accgcgcatt   1620
tttaaactag tctaggatct ttttgttcaa aacgtgccgt gatcttttcg ttcgaaacgg   1680
gccgtgatct tttcgttcga aacgggccgt gatcttttgt ttcgctgact cgtgacccaa   1740
aaaaacaaat tacgtcattc gtttaaaata ttgcatcatc tttaaattcg aaactcgccc   1800
g                                                                   1801
```

```
<210> SEQ ID NO 10
<211> LENGTH: 1732
<212> TYPE: DNA
<213> ORGANISM: Helicoverpa armigera SNPV
<220> FEATURE:
<221> NAME/KEY: misc_feature
<223> OTHER INFORMATION: country=Spain, Region hr1 HearLB6,
      strain=HearSNPV-LB6

<400> SEQUENCE: 10
```

```
tcatcgtttt aaaatattgc atcatcttta gattcgaaac tagcccgcgc tttcatatga     60
aaccgtcggc aaagatcgat aaaatttatt ctagaacatt ccacggtttg acccaaaaaa    120
acaaatgacg tcatatggcg tgatctagaa atggtccaat cacaaacgta ttccacgaat    180
cacgccacgc ccaaagataa cgtatttttta aactggcctt ggatcattac gttcgaaacg    240
ggccgtgatc ttttgttttg actcgtgata ttttgcacac ggcactattc caacaaattt    300
tccgcgcatg ttaaaatcaa tttaacaaat cacgccacgc ccaaagataa cgtattttta    360
aactggtctt ggatgtgttc gttcgaaacg ggccgtgatc ttttcatgac ccaaaaaaaa    420
aacaaattac gtcatccgtt taggatattg catcatcttt aaattcgaaa ctagcccgcg    480
cttttatatg aaaccgtcgg caaagattga taaaatttgt tctagaacgt tccacggttt    540
gacccaaaaa aacaaatgac gtcatatagc gtgatctaga aaaagtcgaa tcacgagacg    600
cccaaaaata acgtactttt aaaccggtct tatatctttt cgttcgaaac gggccgtgat    660
tttttgcttc gattcatgac ccaaaaaaac aaatgacatc atctaccaaa gataatgttt    720
cccgcgcacg tttaaactag tcttggatct tttcgttcga aacgggctgt gatctttttg    780
cttcgagtca tgaccagaaa aaaaaccgat taagtcattt tgcacacggc tctctttgaa    840
aaacaaatta cgtcataaaa cgtgattata gaatcgtcca atcaaaaacg aacacgaatc    900
```

gcgtcacgcg cacgaaattt actattcgac ttgacctaaa aaaacaaaga acgtattcca 960
cgaatcacgc cacgcccaaa cataacgtac ttttaaactg gtcttggatt atttcgttcg 1020
aaacgggccg tgatcttttg tttcgcttcg tgacttaaaa aaacaaatga catcatcgcc 1080
caaaaataac gtacttttaa actggtcttg gatcatttcg ttcgaaacgg gccgtgatct 1140
tttgtttcgc ttcgtgaccc aaaaaaacaa attacgtcat cgaccaaagc aaaaattctt 1200
gcgcatgttt aaactagtct tggatatttt cgttcgaaac gggccgtgat cttttgtttc 1260
gcttcgtgac ccaaaaaaac aaattacgtc attcgtttaa aatattgcat catctttaaa 1320
ttcgaaaccc gcccgcgctt tcatatgaaa ccgtcggcaa agatcgataa aatttgttct 1380
agaacattcg atggtttgac ccaaaaaaac aaatgacgtc atatagcgtg cgtccaatca 1440
caacacgaat cacgccttgt ctaaagataa catttcccgc gccgggccgt gatcttttgt 1500
ttcagttcat gatttagaaa aaaaaacgaa cataaaattt taccgcgcat ttttaaacta 1560
gtgttggatt tttttgtttg aaacgagccg tgatcttttc gttcgaaacg ggccgtgatc 1620
ttttcgttcg aaacgggccg tgatcttttg tttcgctgac tcgtgaccca aaaaaacaaa 1680
tcacgtcatt cgtttagaat attgcatcat ctttaaattc gaaactcgcc cg 1732

<210> SEQ ID NO 11
<211> LENGTH: 2205
<212> TYPE: DNA
<213> ORGANISM: Helicoverpa armigera SNPV
<220> FEATURE:
<221> NAME/KEY: misc_feature
<223> OTHER INFORMATION: country=Spain, isolate=HearSNPV-SP1, Region
hr5-HearSP1B, strain=HearSNPV-SP1B

<400> SEQUENCE: 11
cggtccgttt ctgttgacgc tgaacgctgt atgtttgatg cggtaccgtt ctttgcgagc 60
gttcattgca cgtcggactt cgtctacagt cgtgtcgcga tatgtatgcg ggcattttat 120
ttccataggc acaatcgtgt cgtcgtctag aataaagtag gcgtccggcg atgcggaatg 180
taatccgtat ttgctaaaga acataccgca atcgagaaca gtctctgtaa ttttttttatt 240 agtttcgcgt tcgacacatt cacgaaccag attcaaaagc gattcattgt ttttcacgca 300
agtttcctgt tccaatccgt aggtgagcgc cggaatcggt cgcagaccaa tgccgctgct 360
gctgttcgta ttagatcccg aagcagtttg tcgatcgagc cgcaacaaaa accatagcgg 420
gttcgtcgat tgtccacgtg ttgctttttc gatttccatg atttcatgcc gtgacaataa 480
ttgtgttatg cttttcagtt gactcacata attggtaaaa cagtatttgt caaatatgtt 540
ctgctgttcg gcggtgagca aatcgcacgg cgacactaat gatttggtca tttttgtggt 600
cgacatggtc acgcgcaata atatattata aattatattt cgtgagaagc caatcgagaa 660
gttttacgta cacggccgac tgtagcgtgt tatcggattc actgtattta actagaaatt 720
gcactaaaat atttaaaatt ctgctctgat tgaacatcaa tcgttccgtt tcaatagcca 780
tgtccatgaa cgattgaacg gtgatcatca taccatgttg ttgaaaatta attttgccca 840
atacgttttc aactatactg atgaataccg tgtaaaatgt tttcgagcca atattctgat 900
tacaattgaa cggatcgacg accgtgtcgc gtagaaagtc tatgacagat ctaagtttaa 960
tcgatttgtc acgtattcga tcgttgcgtt gcaatctttt cacgtaaggt ttcatcgcaa 1020
aattacaatc gtgttggaaa agttattccg tcacaaaaaa agtcccttaa attaaaaaat 1080
ttctaccgtg taatcgatct tcgccgacgg tttcatatga aagcgcgggc gggttttgaa 1140
tttaaagatg atgcaatatc ttaaatggat gacgtaattt gttttttcct caatcatgaa 1200
tagaagcaaa agatcacggc ccgtttcgaa cgaaaagatc caagaccggt ttaaaagtac 1260
gttatctttg ggagtggcgt gattcgtgga atacgtttat gattggacaa cttttaaatc 1320
acgccatatg acgtcatttg ttttttagg tcgagccatc gaacgttcta gaacaaattt 1380
tatcgatctt tgccgacggt ttcatatgaa agcgcgggcg agtttcgaat ttaaagatga 1440
tgcaataatt taaacgaatg acgtaatttg ttttttggg tcacgaagcg aaacaaaaga 1500
tcacggcccg tttcgaacaa aaaaatccaa gactagtttg aacatgcgcg aaaattttta 1560
ttttggtaga tgatgtcatt tgttttttt gggtcacgac aaaaaatcac ggcccgtttc 1620
aaacgaaaag atccgagatc agtttaaaca ttcgcgggaa tttttacttt gggcgatgat 1680
gtcatttgtt tttttgggtc ataaatcgaa acaaaagatc acggtccgtt tcgaacgaaa 1740
agatccaaga ctagtttaaa cgtgcgcggg aaacattatc tttggtagat gatgtcattt 1800
gtttttttgg gtcatgaatc gaagcaaaag atcacggccc gtttcgaacg aacagatcca 1860
agaccagttt aaatttgcgc gggaaatgtt atctgttgtt gatgacgtaa tttgtttttc 1920
gaatagtgtc gtgtgcaaat tttgggtcat gaaacaaaag atcgcggccc gtttcaaacg 1980
aaaagatccg agatcagttt aaaaatgcga tgcgcgggaa ttttttttaat ttggtcaatg 2040 acgtatttgt ttttcgagta gtgccgtgtg caaaatgctt tgagtcataa atcaaagcaa 2100
aagatcgcgg cccgtttcaa acgaaaaggt tcaagatcag tttaaacctg cgcgggaaat 2160
gttatctgtt gttgatgacg taatttgttt ttcgagtagt gccga 2205

<210> SEQ ID NO 12
<211> LENGTH: 2262
<212> TYPE: DNA
<213> ORGANISM: Helicoverpa armigera SNPV
<220> FEATURE:
<221> NAME/KEY: misc_feature
<223> OTHER INFORMATION: country=Spain, Region hr5-HearLB6,
strain=HearSNPV-LB6

<400> SEQUENCE: 12
cggtccgttt ctgttgacgc tgaacgctgt atgtttgatg cggtagcgtt ctttgcgagc 60
gttcattgca cgtcggactt cgtctacagt cgtgtcgcga tatgtatgcg ggcattttat 120
ttccataggc acaatcgtgt cgtcgtctag aataaagtag gcgtccggcg atgcggaatg 180
taatccgtat ttgctaaaga acataccgca atcgagaaca gtctctgtaa tttttttatt 240
agtttcgcgt tcgacacatt cacgaaccag attcaaaagc gattcattgt ttttcacgca 300
agtttcctgt tccaatccgt aggtgagcgc cggaatcggt cgcagaccaa tgccgctact 360
gctgttcgta ttagatcccg aagcagtttg tcgatcgagc cgcaacaaaa accatagcgg 420
gttcgtcgat tgtccacgtg ttgctttttc gattttcatg atttcatgcc gtgacaataa 480
ttgtgttatg cttttcagtt gactcacata attggtaaaa cagtatttgt caaatatgtt 540
ctgctgttcg gcggtgagca aatcgcacgg agacactaat gatttggtca tttttgtggt 600
cgacatggtc acgcgcaata atatattata aattatattt cgtgagaagc caatcgagaa 660
gttttacgta cacggccgac tgtagcgtgt tatcggattc actgtattta actagaaatt 720
gcactaaaat atttaaaatt ctgctctgat tgaacatcaa tcgttccgtt tcaatagcca 780
tgtccatgaa cgattgaacg gtgatcatca taccatgttg ttgaaaatta attttgccca 840
atacgttttc aactatactg atgaataccg tgtaaaatgt ttttcgagca atattctgat 900
tacaattgaa cggatcgacg accgtgtcgc gtagaaagtc tatgacagat ctaagtttaa 960

-continued tcgatttgtc acgtattcga tcgttgcgtt gcaatctttt cacgtaaggt ttcatcgcaa 1020
aattacaatc gtgttggaaa agttattccg tcacaaaaaa agtcccttaa attaaaaaat 1080
ttctaccgtg taatcgatcc tcgccgacgg tttcatatga aagcgcgggc gggtttcgaa 1140
tttaaaaatg atgcaatatc ttaaacggat gacgtaattt gtttttttcct caatcatgaa 1200 tagaagcaaa agatcacggc ccgtttcgaa cgaaaagatc caagaccggt ttaaaagtac 1260
gttatttttg ggcgtggcgt gattcgtaga atacgtttgt gattggacaa ctttaaaaat 1320
cacgccatat gatgtcattt gtttttttta aatcgagcca tcgaacgttc tagaacaaat 1380
tttatcaatc tttgccgacg gtttcgtatg aaagcgcggg cgagtttcga atttaaagat 1440
gatgcaatat tttaaacaaa tgacgtaatt tgtttttttg ggtcacgaag cgaaacaaaa 1500
gatcacggcc cgtttcgaac ataaaaaaaa atccaagact agtttgaaca tgcgcgagaa 1560
tttttatttt gatagatgat gtcatttgtt tttttttgg gtcacgacaa aaaatcacgg 1620
cccgtttcaa acgaaaagat ccgagatcag tttaaacatt cgcgggaatt tttactttgg 1680
tcgatgatat catttgtttt tttgggtcac gagtcgaaac aaaaaatcac ggcccgtttc 1740
gaacgaaaag atccaagact agtttaaacg tgcgcgggaa acattatctt tggtagatga 1800
tgtcatttgt ttttttgggt catgaatcga agcaaaagat cacggcccgt ttcgaacgaa 1860
cagatccaag accagtttaa acttgcgcgg gaaatgttat ctgttgttga tgacgtaaat 1920
tgtttttcga atagtgtcgt gtgcaaattt tgggtcatga aacaaaagat cgcggcccgt 1980
ttcaaacgaa aagatccgag atcagtttaa aaatgcgatg cgcgggaatt ttttttaatt 2040
tggtcgatga cgtaatttgt ttttcgatta gtgccgtgtg caaaatgctt tgagtcatga 2100
atcaaagcaa aagatcgcgg cccgtttcaa acgaaaaggt ccaagattag tttaaacatg 2160
cgcgggaaat gttatctgtt gttgatgaca taatttgttt ttcgagtagt gccgagtgca 2220
aaatgactta atctgtttat cacgaatcga agcaaaagat ca 2262

<210> SEQ ID NO 13
<211> LENGTH: 132265
<212> TYPE: DNA
<213> ORGANISM: Helicoverpa armigera SNPV
<220> FEATURE:
<221> NAME/KEY: misc_feature
<223> OTHER INFORMATION: country=Spain, isolate=HearSNPV-SP1, HearSP1B
Complete genome, strain=HearSNPV-SP1

<400> SEQUENCE: 13
atgtatactc gttacagtta cagccctact ttgggcaaaa cctatgtgta cgacaacaaa 60
tactttaaga atttaggtgc tgttattaaa aatgccaaac gcaagaagca tttagaggag 120
cacgaacatg aagaacgcaa cttggattcg ctcgacaaat acttggtggc ggaagatcct 180
tttttgggac ctggcaaaaa tcaaaaacta actttgttta aagaaattcg cagcgttaag 240
cccgacacaa tgaagcttgt agttaactgg agcggtcgtg aatttcttcg cgaaacttgg 300
actcgtttca tggaagacag ttttcccatt gtaaacgacc aagaaattat ggacgtgttt 360
ctgtctgtta atatgcgacc aaccaaaccg aaccgttgtt accgattctt agcgcaacac 420
gctctgcgtt gtgatcccga ctatattcct cacgaagtca ttcgtattgt agaaccttcc 480
tatgtaggca gtaacaacga gtacagaatt agtttagcca aaaaatacgg cggttgtccc 540
gttatgaact tgcacgctga atacactaat tcctttgaag acttcattac caacgtaatt 600
tgggagaact tctacaaacc aattgtttac gtaggcactg attctgccga agaagaggaa 660

-continued

```
atactcctag aggtttcttt gatatttaag atcaaagaat ttgcacctga cgctccgcta    720
tacactggtc ctgcatatta aacttgcgat tcagttgaca tcgtcaattt gtaactcata    780
attttatcta aattcgatcg caattcttgt aatttttgat tggtcggttt ggttcctaat    840
gccgacacca cattagctaa cgctttatcg tactgttttt tgaatgtcaa atcttccacc    900
gccataatga attgttgtaa atttttatcg gacaattgaa gttcgacatc atcggatttg    960
tccaaaggat tatcatacgt ttgttgtatc aagttatctt caataaatat ttgtagttta   1020
gcagaaactt gttgtgtttg tgcattcgaa agccgttgat ttaattgatt ttttattgat   1080
attaatgtgt cttgtgcttc agtagacaaa ggataatttt ttatccatga actgtccaat   1140
gttatattgt acaaagaacg tacatattgt ttcaattcgc tgctggctcg ctgctgttgt   1200
tcgtcgtcgg tccacccgtt ttccgattct gacgaaacta caggactcgg ttgaacggct   1260
atgcgtcgtt gtaaaatctt tgcagtagga ctggcggcgg cggtaacggt atttactatc   1320
gaaccgccat cggcgggttt tgatactttt tttaatttaa ttcctttctg tatttgttcc   1380
atcaattcgg tacgtggatc ttttaaaact tgccgagtcg acgttgtata atcgcgatct   1440
ttactggatg gtattactat atcttctatt aatggtaatg acggtggcgg aggaggcggc   1500
ggcggaggag gtatcgtcga agataagttt gtttgaggcg gcggcggtgg cggcggtatt   1560
ggtggtggta ttggtggcgg catatgtgtt tgcggcgagg aagattcaga atcgataatt   1620
attgttggcg aaattgtttt ttgcattata tccgatgtcg acacagttgt cggtttaggt   1680
attgttgttt taggtactgt tggtactgac attgtctgtg acaatgttgg tataataatt   1740
gatctatcac caatgtctat tagtacgtcg ttgttgtata tttcttgggc caatttcaat   1800
aactgaatac aatcgtacac gtttaattgt atccgatcag aattggactg agcgacagcg   1860
ctgaccgtac gtttcaaact gtgcggcgcc gagatcatgc gcagtagaaa gtcgacatta   1920
ttgatgtttg tgtagttttt ttcagccaaa tattgttgaa cactttgcag ttgaaccatt   1980
atcgcgaatc gcaatggacg accgtttcgt taaggaaata aaccaatttt tcgccgaaat   2040
aaaaatacaa aacaatgtgc gtttggtcga cggcaagttt ggcaaaatgt gtgttatcaa   2100
acacgagccc acgggcaaac tgttcgtaaa aaagagtgtc gcaattaaat atgtgaccga   2160
gatcgaacct atggtgcatc aactaatgaa ggacaaccga tatttcatca aattatatta   2220
ctcgttgaca acgttaaaat ctcaaatact catattagat tacgttgctg gaggcgattt   2280
gtttgatttt ttaaaaaaac acaaaaaagt atctgaagcg gaaacacgtt caatagtggg   2340
tcaattaacc gaagcactga acgcgcttca ctcttacaaa attatacata acgatctcaa   2400
actcgaaaac gtcctatacg tacgtcataa acaaatttat ttgtgtgatt atggactgtg   2460
taaaattgtc aacacgagtt cgtgtcgaga cggcacaaag gagtatatgt ctccggagaa   2520
gctcaaacga caaaactacg atgttcacgt cgattggtgg gctttgggca tcttgacgta   2580
tgaactttta attggacatc atccctacaa acatagcaac gacaacgatg aagatttcga   2640
tttggatgta ctacaacaga gacaacaaaa aaaacttcac aaatacaatt ttctaagtag   2700
tgacgctcaa aaatttttgg aagcaatgtt aatgtataac attaattaca ggttgtgtac   2760
atacgagact gtaataaaac acagtttttt atcataatat atatttatta aaaaaaaata   2820
atgttgtttc tttattacca ttacaactaa agtataaaat attacaaaag tgtatttaca   2880
atctattaca actaaaatat tatgatatta taaaagttac attaaatatt atctgctttg   2940
cgagcacgtg aagtgcgttg acgtttagct ggtggttctt cagtacgaag aactggtact   3000
ctaaccatac gaaaagtagc tatctgaggt ttcatgttat ctgcccattg cactatttca   3060
```

-continued

```
acctcatcgt cactatcgtc attgacgaac ctagcggggc ttaaaggtaa atttaaacat   3120
tcaacatcag acatatcgac aggttcttgt ttgggaacac attcttcatg atactcatta   3180
atataatcag gattttcaca ttcagtattg aaatcatctc caaacaattc ttttttttatt   3240
gcaatgtcaa atggtgcagc gtcattatta ttagtgttag catcctttga tgtttttttct   3300
gttttaacag tgatatgctc gaaatatttg ccatttttgt ctacattggt acttttagct   3360
aattctttat cgatactatc aagttcttca gtactcattg caactggtaa cactgtcgtt   3420
gatgatagtt ctttttcaag cagattgcgc acttcatttt caatttgact tatttcgttc   3480
aattgtgaca caattacttc tgaagctttc aattgctctg gactagtttt agacaatttt   3540
tgttttggtt gcaaagcaaa ttcattcata ttactattat tattactatt agaagaagga   3600
aacacgttat cggatgcgtt atcacaatga ttgtctataa cagtacgaga caaattagta   3660
atatttacaa taggaagaga taaattagaa atatcatcat catcgacgct gttcttgtca   3720
ttatcatttt ttgaattatt attaccttga ttactattga tattatcatg agaggtttga   3780
ctaacattat tactaacatt attactaaca ttattatcgt tatcaacagt atgttgaaca   3840
ttgtcattgg ctgctgaatt tgctacatca tcaacattag cattggtatc aacattagca   3900
ttagtatcaa cattagcatc aacattagta tcattatcat tagtagtatt gttaatttga   3960
ttatcactat taacattagt atttacatca ttaacatcat catcattaac atcatcatca   4020
tcaacatcat catcttgatc atcaacatca tcattatttt gatcatcaac atttgtattg   4080
ttattaacac tagcatcgtt gtcgacagta gtttcgatat cattatttac agtattagta   4140
ttcaattcgg cagtatcttc attatgaata gttgcatcgt cacaattact attattgtcg   4200
tcatcattat cattagtact attattgtcg tcgttgttat ttgtattatt aacatcaact   4260
acttcatcgt aaacctcgct atcactatta tcactattat caccatcact gttacggtct   4320
gaagttttac ttcgtttaca tgtcatacaa gtatttattt gtatcgatcg caatgaacat   4380
tcagtgcaca atctatgcat acattgcgga tataacgtat cagtggaatg tatattacaa   4440
taggaacatt tagttattac attgtcgagt ttgtgttgtt tcaaataatc agcatgttta   4500
gttttgtttt tttgtatttc gattctgaga cgatcatgtt cgttaacaaa agccggtcta   4560
caatattcgt ttaaaagaaa taattgatgt cgtatgtctt gcaaatttaa acttatcccg   4620
ttgtcgtcaa ctgaagcact gtcgcacgtt ttatacatgt tgagacattg aacgatagct   4680
tctttattgt tcatgtaacg cattttgtta ataaactttt gagtcgcact ataaatactg   4740
ttgtcgtccg acaaattagc atttagatag gcagtcaatt gtacagcgta atagttgatt   4800
ttttccatgg ccgctttttt tgtgagcaaa gtcacaaaat tctccaaact cttgcgataa   4860
ttgctgaaca ccgacatcgt tgatacgtga tcgtacaaat caaacaattt gttagagtaa   4920
acatgatgac acttggccgt aacaccactc atgcgaaaac gtttagtagt cttgcacaca   4980
taaccgagac gctttttatt ttgcgacaaa tgcaaataca catagatgcg ttgttcacta   5040
atgttctcac taatttcaag agttttgtga gtatttaatt gactaacagc cgtttcacta   5100
acagccgttt cactgctcga actcgagtca gagatgactc gccgcttgtt gtttgaaggc   5160
atagtgcttg ttccaaactg aattccagtt tggtttgcaa ctactatata taaatttgtt   5220
atcaggcgat aacatttatc attgaggtcg aactacattg gtgtcacgag acgcgagcgt   5280
gtgcaaaaca tttttatctc gaatcgaggt cgaggcgtac gtgaccacta cagcgtagct   5340
taccatgcag gcaaacgacg taatacagat aacgtatctt tttgttgtgc aaaaatgtac   5400
```

-continued

```
ctatttttgt agtatattgg gagcatatcg tacagtgtag actattctgg ttaaatagtc   5460
ttcgattcga aattttccac tgtatattga tgacgtcatt aacacgaatt tttttgtagt   5520
gcaaaaaaat tcaggtcgct tcgacaacac tttatcaatc atgtaaacca attggcagat   5580
tagataaaat gttcattata aattgaaact gtccgagcaa gaatcagttc aacagcagaa   5640
ttgtcctgtg caatacttga acatacagtt tgattttgtg tctcaccaca atgttgccat   5700
catatttctg gagaatgtct gctcatttta aaatgcattg tattgtcgcg ttaagatcgc   5760
gtccgaaaat aacgaccagg caacaatggc gtgataaaca gttatcggcc gttttgagat   5820
atcacaaaaa aatttatgtt ttgaaaaatt tgttatacaa actaaacaac aatgtcacgc   5880
caactataga agagtatcgt gaaaacggcg aaagcagtat ttgtaatacc gcgcacaaat   5940
tgctgcatgc cgtcaaacat cgtatccaat tgaagatcaa caagttacgc aaaaaagcag   6000
tcttgcataa acccattcaa aaaagatcta cattgacacg ttacgaacgt gatttggagt   6060
gtttgatgcc gcgtcgtcga tcggtgcgtt ctctggactc tgatcgcaag tataaagtgt   6120
tcgagaaaaa tgtgtatccg actgatgtgt cgcgtaaagt gttacccaaa aagttagatt   6180
tcaaaaccaa tcggtttttg ttcatggacc tcatgaatgt tcgaaaaaag cattttgacg   6240
acaacgatag tgatgaggaa aacgatgata atgagaacat cagcgaacaa gtgcgtgata   6300
ttttatctca tattcgttat attcgttttc agcaagccaa agaccaaatt acaagtgtaa   6360
ttaactttaa attagagaac aacaaaagtt ttttgttggc aatgatattg gagccattga   6420
ttgaccaata caatagtgat tttttgttta ttaagatatt gcaaaacagc aagtattata   6480
atcattttag tttagacgat atcgacgacg gctcatatag agatcgtctt gacgattatt   6540
ttatttaaaa ttatgttata acctatataa taattaaaca atgtacctat attataatca   6600
aaagtgtaac tatataatca ttacaaatgt ttacctatat aattaataaa aattgttaac   6660
tagtattatt gtaattagca attcattgtc tatgtatgtc tatgtgtgta caataaaaat   6720
attaaacaaa atatatgcaa ttttttatt taaacacaat tcaaacataa tttttttca   6780
tgtgtgcaaa tggcacatac atcctgtgac attgacgata tcctgccgaa tacactatat   6840
aagttgacaa attgataatg gaatttagtt ttgtcaatgg ttcacagcaa gctactagtg   6900
ttttaaaaaa tgtctggtac attgaaacgc atactgtacg acgatataag tgatgacagt   6960
gatcaagcca agttgttcag atataattct gaaatgcagc cgccggcgtc ccagcagatg   7020
aacactgctg tcgactacga aattgatgtt gaggtaataa aatgttttaa attaaaaaac   7080
atgtatagca gtgatgtaac tacgaatgct cgtgctcaat acaacgttaa attagcggct   7140
tttctaattg tactcgacga atacaaaaaa caatataaaa acaatttgga caaacagtca   7200
gtgttgtatt acaaagaaac atccgaatct gtaataacgc tcgacgaaga tcagtgtcat   7260
cacactttgt tgcctatcat tcaacgattg ttaaaaacca tatgctatct gatgaacttt   7320
tccgatgacg aagtgaacta tgtcaaacaa aagtttattt ttttaccta tttaaagtat   7380
ttaaataaaa tactcaaact gtttcaatac gacaagtgtt gtgccaaact cacaaaacaa   7440
cttcaagctc aattgaatac attgctaaca caatcggtag attcgtgcaa acacattcac   7500
gccataaata gacaaagtca agtgttaact gtgtttctgg agaatccttt gtacgaatgt   7560
aacatatgtc gcgacacgtt caacgacgaa cgacacataa aacccaacga atgttgcggt   7620
tacaaaatat gcaatttgtg ctatgccaat ctatggaaat atagcactgt atttccaacg   7680
tgtcccgttt gcaaaactag ttttaagtcg tcgtctgtgt catcgttcaa acaagtttac   7740
acggcggaca caacagacaa catttaagta agtccacaac aagatgaact tggacgaaaa   7800
```

-continued

```
caaagtcgct ttggagcgta acaattataa atatctgttt ttggcaagtt atttcaattt   7860
agcagacacc ggtttgcttt cgacatcatc aaaaccgttc attcgcgaat atttgtataa   7920
taatttcaat aacattgacg atgccagttt attgggttat ctcgactatc tcgatctcat   7980
tggtctaaac aatgtattac tcgatcgtga cgttaacatg ttcaaataca taaaaccgca   8040
atttcgattc gtctgtacaa aaaagaatgt ggaaatactg aaattcgacc agcgcgtata   8100
cataaaacca gacacaccgg tttacgcaac aaactttttc gtcaaaaatc caagcgaatt   8160
taaatttttg ctatacaacg tattttcgag tgtgatcgat aaacgtaatt ttgttaacaa   8220
tgacaaaaac tattgtctca tacagggcaa tacgggctat gtgtttgacc aagcctacgt   8280
cgattggtgt ggcgtacgaa tgtgcgaagt gcctaaaata gaacttgaat catcgccctt   8340
tccttatcgt ttgtatttag tgggcgatgc tatggcgcgt cattttgcta cgaacaatat   8400
cagttttgac agtggcaatt ttatattgaa aaatttttat aaaggcttac ccatgtttcg   8460
gaccaattac aaaattatca atagtaaaaa atttacaact aaaaaaccca atcatttgtt   8520
caacgaattc aaacaagaat ttgacacaaa atcagcttac gtaaagttta ttcagcgcga   8580
ttacatatat gatgcaaaag cctatcccga tgatttactc gatttgctaa acgaacacat   8640
gacatacacg tccgtatata aatttgtcac caaattcatg gaagacggcg aagaacctgg   8700
taattattat agcgaaatcg ttatcgatcg gtacgccgtg gacaaatatc aaaaattgag   8760
tataaaaatc gatgaaacaa ctatgtttcc cactttgcgt tacaacgacc cttcatatat   8820
ttttataaga cctgatttaa tacaaataaa aggtacactg aacgctttct acgtgcccaa   8880
acacaaactg tttgccatat tagccaacaa cagtttgttt ggatctacca ctttgttgga   8940
attcgatcga aaattgattc cttatcgtca gtatcaacca ccgtacaggc tgaacgacga   9000
aacttacgtt gtggataaaa aacaaaaatt gtatctaacc aagtacacat ttgccaacac   9060
aatccctgca tatcttttaa taagaggtga ttacgaaagt tcttcggaaa tcaaaacttt   9120
gcgcgatctc aaaccttggg ttcaaaacac tctgttgaaa ttactaatag cagcaccacc   9180
ttctaaataa tacatacaat atggacgatc tgcgcggaac aaccacaaca ggagctggtc   9240
gttttaaccc caacatgctc aacccgagca tgctaatgac catactcata gcattagtta   9300
ttataatttt gttaataatg cttttccaat ctagcagtcc gggcagcaaa ggagccgata   9360
caaatgcttt tgcgtttcaa aatccgttga atgcaaccat gcgcaacaat ccgtttgtta   9420
atacgcccca aagaactatg atgtaaaata agaggcagcc atgaaaaagt ttaagtgtca   9480
aagtaataaa attcgcactg tcaccgaaat cataaatgcc gacgaaaaac tgcacaagga   9540
ctatgatttg gccgacttta atgccaaaaa tttgaacagc ctcgagagct atgataattt   9600
acagatcaaa atgattctag ccaagtacat ggcaatgttg aacatgctcg aattgacgca   9660
gccccttcta gccacttttc gcgataaaaa cgctatcagg gaaattgtca gtatcgtttt   9720
tgcttcactg ggctttgttc acaaccgtgt caatccgatg atcaatcatt tcaattcaaa   9780
aatggaattt atcgtgaccg aaaatcgcaa tgccagtata cctggtgagc cgttgttttt   9840
ttgtcaacac gataatggtg atgttgtatg ctacattgat cgaccgtcca tattgcaaat   9900
gctcagcaaa gactttgatc tagacgtgga cgttaacaat atgcacaaag aacgcaataa   9960
atacatgata gcgaagactt ttcgatgtgc accgaaacgt cgacacagtc gtgaacgtga  10020
acctccaccg ctggaaatca atcttaccga aacggacgtt acacagtata tgacattgtt  10080
gtttattcac gaacatgcct atttgcatta ttatattttg aaaaactatg gcgtcgtcga  10140
```

-continued

```
ctacagtcga tcattgtccg atcatacttt gttttcgaac aagtcgcggc caactttaaa  10200
catgaagttt tcaaatttac ttttaagtaa atttaaattt tccattgaag attacgatag  10260
tattaacacg aaaaatacta acaaaaactt gggcatattg acttatactg attaaattat  10320
tggttttttt aaataaaata aacgacgtaa gattaaatat gtggctttta ttggcattat  10380
tcattattgt aaaattgtta gtataccata aaatgcaaaa tcttcaagtc gacatgcatc  10440
accataaact ttgccccgcc ggttacaatg gtttaaatgc ggatccattc gattgcaacg  10500
cctactatat gtgtcctgaa aaaattaaat tttactgtcc tcgcaactat caattcaatt  10560
tggacgcgca aggttgtcag cctgatagcc tcgaaactgg atgcatcggt tataattatc  10620
ggaatctact tctttagaat atttttttgg aaattttcca ttcttagtga gttataattg  10680
taacacgtga tgaattgatg ataacgtgcg gatgagtaat attgatcatg tcacaacttg  10740
ttgtcgcggc tttgttcaat gacgcaataa aagcggcggg tacgttgcct tttaaaatga  10800
cgtgttcttt tttagagtat atttcgttgc cggcgctgtc ggtcgtaaat agagcgtcga  10860
cgcgttcgta gcatttggcc atattagatc ggcgtctcac acttagcacg tgccaaattt  10920
ccgtgctatt gttatagtca actgccagta gtagcaccgg tctgctaaaa catttttcgt  10980
cttcgatcag tgaacgtgcc acaaaaggta atctgaacat agtaataata aaaacgtcgt  11040
ccctgataat gttttcaccc catgattctg tcgtgctcat gttcatgctc acgtttcggc  11100
ctgattcgtg tccgctgact aatttagtaa taacagtatt tggtccttcg ttctgatcga  11160
taacgttatc tttagcgttg aacatgtaaa ctgtgaccga aaaacgtgca tccactatcg  11220
taaacacaat taaattatcg atatgcgata acggttgata taaattgatg ttcatttttg  11280
tttcagaatt tattgaaatt gaactttacg gcaagtatgg cgaatcgaat taccacaccg  11340
ctgcgcgatc aagttggaaa tcaagtcaca attaattatc cgtttcaaag tcaagaatcg  11400
tgcaattata acaacgacag cgattcttac atgaaccgca acaatgatgt ggatgtgaaa  11460
aagttgttta aaacagtcga aaatgcttcg aacaaaacag tcgaaaatgc ttctgcattt  11520
ttcgccagtt atataccacc aacatcatcg aacaagccat cgccgaggcc gaatcattta  11580
cgttttggcg acgaaattgt gatgtcgcca attgcgatgt cgccacaaag aattacaccg  11640
agatccgaaa ggtcagaaaa cgttatcgaa tcattacccg aatcgttgtc gtcgctcaaa  11700
caagttaccg tatcgctgcg tcgcggtagc ggactttatg gtaaaaatat acaaaatttg  11760
aaggaaaact acgaaaaaac catggatccg tacgagtcgg atagtagcag tttggaatta  11820
acaccaaagc ctaaaaaacg tagcaatact gagaaaaaaa ttgccgggat gggcgaaaaa  11880
agaagtaaaa aagaaaagcc agcaacgcca ctcaacgaag tcggacctgt ggccaacatg  11940
aacaaacaat tattgatgga cgatgctccc aatcgtagat acaaacaagt acatctaaaa  12000
ccgcaacatc cgcagccacg agacccgtcc gaacaagtgt tggccaatcc gagtttgaac  12060
gaatacatgc gaacaaatgt aatgccgctc gtacagaaca tgcccacgtt tcgcgtcgac  12120
aaatcacgac ggtttgtaga ttttattcaa caaaagaatt atcacatgtt cattgttaag  12180
gaacaagaaa atgttaattc ttcatctata gaacatgtaa ttttgtacgc aaatacggtg  12240
gcgtcgatca attacgaata ttcttcatat tattacaatg tggacaaatt agtgcacgtg  12300
gtgacattca atcgttacag atttatgata tcgcatcgtc tcttgaccaa attgaacgtg  12360
cacataccgg aatctgaaca gtttccgatg cgtgtacacc aggatgcatc taccaagtgt  12420
cattttaatg aaatcaaaga ttatgtgttt atgaacgaat tgaatcacat gttcaattta  12480
gacatggtaa tggtgcaaac cgaattgtac tttttgatgt ccgccatagg acctgacaaa  12540
```

-continued

```
ggcaaagtgc tcataaaatc tgtaatggaa cacattaatg acgatcatct tttcgtgttg  12600
cctatcaatt tgtcgcgcca agagagcaaa cttgaagaca tacaaagaac ggtcgcctct  12660
gtgtcgttgt acgtgcaaaa catagtctct ctgagcaaag acgtgcaatt caaacaaacg  12720
gcggaaaatt tcatgaatcg tgacgatgtc ataaattacg tgactgtagc actcaaattt  12780
tggttgagat caaaaaatga aaaaaatgtt gtaaaagaac aatccgattt tttcacctac  12840
aaatacggca gtgtggttcg attgttattc aaagagagca ttcacacgaa tgcgttgttg  12900
aaaatcaaaa gagaaaccgg tcatgccggt ttgattgaca actatttgga agccaatcaa  12960
aacgatacga cgtcaaacag tttcattttg atcaatacaa aaatggacga acgcataacc  13020
ataattaaaa aaggtccaat atttttgtgg atcacgagca tcatcaaaga catcatagca  13080
atggatttga ttgaaaaata caaaaagcac acacaccatg ttttcaattt gtcgaacact  13140
aatcgcaaag aaatgaataa caaacataac ggcatgataa agttattgag tttttacact  13200
tcgaatttat taatgttgga cgaattaaaa gagtttgctg tgaataattt taattgtagt  13260
tatgattgta aacactatgc ttaaacttag aataaatttt tttattttta tattatctat  13320
gttgtttttt ttctttcatc tattatagtt aacaggcggc ggaggcggtt gcatcaacat  13380
acgtttaata acaatatatc ctataaaaat tatcaatagt acaattccca aaacaacaat  13440
aataggcaaa agtttctgaa aagatgtgct cgatttatcg ctagatttat tcaaaagtcc  13500
ctcctcgcct aatagaccgt ccagaccgag atcgccaatt aaatcaccaa aatcgtacgg  13560
ttcaatgcaa gatattgtat gaccggtagc caaaggcgat atgtccacgt attgtaacga  13620
caagggatcc gcattcggat cgcttcgacg acacactgtt cgttcgactt cggcgttata  13680
gccgtgacat acactttgta acgcattgag attgtctatc aatggatcgg acggacatac  13740
gttaacatcg ttcaaattgt tcacgtccag aacgcatgtt ctgtaacgta acaaacaaga  13800
ttcaacttgt tcgccgccat tcagtccaat gtgatagtag ctaccaccgg tacgacgcaa  13860
agcttcaaca atatcgccaa taactgttgc cgttcgtgct actaatacga cacctactcc  13920
tactagaccc acgtaacctg cttgtttagc tgtttctaaa tagcggctga gtcgcggctg  13980
ttggttgaga acattggaga cgccttcggc tgtacgggta tttgttgatg gaaaatttgt  14040
ttttacactt tggcgtcgca aattgtttgc atgcaaacgg gcgtcgggca cgttgtccat  14100
gcgtcgcaat gtggacaacg aatccaattg attagtgttc gcgttgggaa atacctgacg  14160
caatcggggc acatcattgt tgcgcatgaa actattcatt tggggtgtac tgacaaaacc  14220
ggccggtgtt tgatatccgc ccaatacggt attgttttga agcgattgac tactgggtgt  14280
ctgaaataca ttgttaaaac cggaaggtgc gttgttcacg acagatgtgt tagcggtcac  14340
gaatgatgcg tgattcggaa acggtctgtt gacattacgc agatttctaa aaaacgacat  14400
gatgtcagct acttactttc tactaacaat tctcatgata tttacgtcag cacccattgg  14460
actgactagt aaacgaacga atatagctta gttctgactg gtggtcaagt ataaataaga  14520
gcttactagt cacggcaaag atcagtaaca attcgacatc atggcgtcaa catcgacggc  14580
agcgtcgcta gttaaccaac atcgtcaaga tttacgacac aagttcttga gtgtggaaag  14640
taaaaatcta ctatgcggca tggcaaagtt tgcggacgaa tatgttcgcg gcatccataa  14700
tgtgactcaa gtcaatttgc ataattgtga aaatttaaag agtccacacg atctcgccgt  14760
gcgcacaatg tgcgacaaat gtcagacagt gtttcgagga ccgccgttta cacgctggtt  14820
gttttgcgct gtgaactttc gaatttcatt cgacaatacc aaacagaaac gtgaccaaaa  14880
```

-continued

```
gtttaagttg gtgtgcgaag attgcgctca aacttacata ttacatccag aatttcaagt  14940
ttacgaactc tatccgagga tacatttgaa acacgtcttg gagctatgtc gtcatggatt  15000
tattcgaaaa tattttctgc ccatcaatcc cgacctgtat tcggaacgtc gagtggacat  15060
tgttcgtaat gaaacttaca aagtcaacga catctacgct acgattcaag atattatatc  15120
caacaaaaat ccgcacgaac aaattactaa aatatcattt cgtaccattg gacgagtttt  15180
tttcgacgaa acattcgaag acatgtttgt agaaaagcgc ggcacgatct ccgttgtacc  15240
tggaccgagc aaaatgctcg aatttttgtc gaaacctttt gattttacac caaattttac  15300
ctattactat catgtacatg ttgcggtcgg aagggaaaaa caacgctatg taatgtattt  15360
ggagatacca tgtttgcgct attgtaaatt gtgcactttg gaaaaacaac ataaaggcta  15420
tccggtagtt tggtgttcgg tgtgcggcta cacagacacc atgtattatg atgaagaatt  15480
tttgcatttt caaaatatgg aatatgagtc ttttcgtttg cgacccatgt acaacaaaaa  15540
gaaaactgaa tgcatcatat actacaaact gccgtttatg ccgccttcat ttctaaaaaa  15600
taagacacaa tcaactctgt tgtctgtcac caaacaatag ctatgaacaa aactaaaaat  15660
atgtgtaata tttatgtcat gagacaaacg gcagcgttgc aaactgattg tattcgcaat  15720
aaaacaacag accaaagtca taatcaatca tcacgatcat catcgtcttc acatgtacaa  15780
caaaataata aagaatacaa aaaaatataa aaatgtgttt tattgtaata atatgtacaa  15840
atatttcaca aacatataga atttaattta ttttcaattt acatttttgt ttgtctatct  15900
tcttcaaagt gttggcacga aatatgtaaa aagtagtgcc attatgacga ttaggcacag  15960
tatcgacgac gcgatattta agtcgacgct tccgttcttc gttgccggtc ataatactat  16020
ctagatcgac acatttgtat gcatagttaa acgtagagtc ggcattaata gccactatgt  16080
acacgtacgg cgaatgtttg tcaaaaattt ttttgttcaa ataatacatg atgttcttgt  16140
ccattttgtt tgatttctga tcaaatgtcc atgtcgaata tcatttatat acataacggc  16200
tatctcgaag agataagata cactagaatg agtcaaccta ctgtacctac gccaacattt  16260
gaagacgcgc tgaacgccgg caaattcgca ttcaacatta gtcggctaaa attcataccg  16320
aaatggcggg cgagatttcc gcacattttt atcgattaca aaatatggcc ggctaacaat  16380
gaagattttt acgttcccgc cgccctgttc aatcgagcta ttggtgttcg cgtcacgttt  16440
agtcgcaaag gctgcgaaag catgagttgt tatccgtttc acgaaacagg tccgataact  16500
ccgtacacac agttcgggta tacacaaaca tcggaaacgg cagtggcgta cgctcaaccc  16560
gcatgctaca atttggacag ggcggcggcg gtgcgcgacg gtgccgaaaa tgaaatacaa  16620
acgcccgaat tgcgttacac tgacggggga aaatgtatta tagtggacac tttgacaaaa  16680
atgtatttga atactcccta tttgcgtacc gatgaccatt tgatacaggg cattgatgat  16740
gtgcccggat tcaatgtgac aaacgatacg gatcaacttt ttcccgaaag attcgaaggt  16800
tttttcaacg aagcctattg ccgtcgattc ggccgttcct tacaaccgaa cggcggttgt  16860
tcacttcaat ggtgggaaag tttaataggt ttcgttctag gcgatactgt acttgtcagt  16920
ttcaaattgt tagtgaacaa tatttttagt gaactgcgag gattcgatta tacgcgaccg  16980
tcgccggtgt tgccaccgaa accgatagtg acatcgcccg cgcttgtggt ccaagaatgg  17040
cgtagccaac gcgatcgtga agcgcccatt gatctagaat tgtcgttttt agattacgaa  17100
caatattcgg acattggatt gactgcgaac actgttctcg aatatgtagc cgaaaacgga  17160
tttcgagtga atccttatcg cggaacaacg gatagatggc aacgcaaaac tctatacaac  17220
gacgctaagg caacgacgat cgacgaacaa actctaaaag atataattac tcaatttttg  17280
```

```
gaggacaacg ctttagtggc tggtatagcg gcaagtttcg gtttcgattt tttgtttgat  17340
gtgctcaaag acatgttgaa acgtatcaat acacaattgt tgccgttact gagacgagtt  17400
cttatcagcg gcagtcgtca gttcacaact cgtttgttgg gcgaaactta caaagccgcc  17460
gtcatccatt cgatgaacaa gattgctatc aaaaccgtta cggcggtcgc caaagcgatg  17520
actaaaatag caattaaagc cgcttctgtc attgggatcg ttttaatcat attgaccatt  17580
agcgatttgg tattagcgtt gtgggatcca ttcggctaca gcaacatgtt tccccgcgaa  17640
tttccgcgtg atctgtcaaa ttcttttttg acagcctttt ttcagagcat gggcgaaaat  17700
agggacatga tggaattgtt gcccgaatat tatgacgatt tgttggcgca aaacgaaaac  17760
gacaccgacc aaactatggc caccttcgaa gacattctaa atattgccga atacctttcc  17820
gcgttgaccg tcaattccaa cggacaaatg ttggatttga acgccggcga acctattgac  17880
gattttgatg aaatgactct ggtaggtgcg gcgttagctt cgagcgccat gtatacgcat  17940
ttggaatttt tacaatacac cgaacggatg aacaaactgt tcaaacatag tcagccggaa  18000
tcgtttcgaa acgatacgct cttagccaaa ctgtttggtc ttagctcttt gatattgatg  18060
gcgttagtga tgattacaaa cgatcacaac gccgtatgtc tgttcgttat tgttctgttg  18120
attattctgt ttgttatatg tcgcagttcg ctgatgtttt atatgggttt gcgaaaacac  18180
gcgcaatacg cgacaatgcc atggtaccac aatttataca cataaaagta caaatttttt  18240
tgattaataa aattttattt aaaaaaacgt tgttacattc atttttttatt ggacactttt  18300
cgattgacgt tgggaacaac ttcatcggca ggaggtatcg taggattgag gatttctgtg  18360
atcgcttcta cggcgtcttg aagcgtttcc aacacggcac tttgaccgtc gatcttatca  18420
accagcaccg acacatcggg cagattactt ttgacgtcgg caacggcagc gctgagttca  18480
tcaagttgag ttttaacggc ggcaatatct tgccgtatga ccaatagaat gttttgtgac  18540
atgattattt cgtcgtacag aagggtgcaa tattcaagta cacgcaacta acaacttact  18600
ataatactaa attttgtatc tttattattt gtacaacaaa ggcccatcga atctgattct  18660
agaaatttcg aattcgcctt ccgacaaagt tataactatt tcatcatcat tatagaatat  18720
atgaacgttt cgtgtcaggt ttcgaaacgt ggcacgattc gcgacactag ttagggcaaa  18780
ctctttgatg ccaacagaac gttcgttcgg caggtacgac atttgacgac gaccgtacac  18840
cgatcgtccg gtgagcaatc gttccggtgt tacaccattg tttgaatcga attgaatttg  18900
accagaaact aaattgcgcg gacgtacacc cgtcaccggg aacattaccg cgtcgcgatc  18960
gcgatcgtcg tgacgatgcg tcactaccga cactagtttt ttgttacgaa aaattggagc  19020
ccctatgagt accatgtcgg cgactgttcg atcttctaga gcgaaagttg ccaattgact  19080
gtacacgagt cgatgtttgt gtacatgata attagtgtag acgaattctg gaaccactcg  19140
tgccatagca ccgtttttca aaagcacaaa caaagcacta gtcatgtcga tacgtggaaa  19200
cattacactc gtcgctacac cgggaaaatg atgtagacga tcgagcgtgt cgctgtcgtt  19260
gctctgatgc ccgattacat ttatggacac tgtacggtta tccactttgt gtataaaaat  19320
tctgtttaga tcattatcga tcgtatattc aacattgtat cgttgcaatg atttagcggc  19380
gattgccgaa gctaaaatcg caaaaaaacaa acacgtttgt cgcaacatta tatcgtaaac  19440
accttaatta tattcaaacg gataacctat gacttttaat tttgtatata tatatatgga  19500
tccgagattc atctcatatt cattaaatag aaattagtaa agatgtatac atctcacaag  19560
aaaaatttga atatagctca acaactttac gatataacgc aagctaaacg ccaattgacc  19620
```

-continued

```
ataaaacaaa ctcattatga gcgtttgaaa cggatcacca aggacgccag agaacttcaa  19680
gaaatagaac aacaattgca tcagatacga atggattttc tcaaatacag cacaaccatg  19740
ttttaagtct aatgaagaat gggaataaat aaaatttaat tttgttttgc attatattta  19800
ttattatcaa atacatattt attaatcttt gacactcata cgtttaattt tattatacaa  19860
agtgttatct tttgatcgtt cattattgcc gtatttgtcg tcgttgtcgt catttggatt  19920
caaaaggcgt tcttcgtcga cgtctcgaca ccagtctccg atttcagata tgcgatcggt  19980
acttttaaaa ctcacactac catcggagga tctacgacga tgacattttt gtttgcgtgt  20040
atagtcgctg tccgatgtta acggtggcag gggcggcggc gaaaacgaac gcttctgtag  20100
atattgttgg tgtttgtaat ggcggcgttt gcgtacaggc ggcgatgtca tttgacgagt  20160
cgaatacact cgacattcga atcgttcacc gcttggccaa aaaactcgtt gattcaattc  20220
ggcaaaacga tccgcagccc agcgcgaagt aaccaccaaa cgttttcgag aacattcgct  20280
ccaaatgacg caatcgcgaa tcgccggtcc gcacacgaac aaaataaatt cgcgcgaaaa  20340
tcgtttttcg atttgggctc cgttaatgta gacgacgtac gacatgttgg cagctcggtc  20400
actgatcgac tccttcgatg cgaaagaaca ccataggttt tattgataaa gaatatgatt  20460
tttcaaacaa tttcttgccc gtgacagttt caaattgtgt ttcgttcttg cttattttga  20520
ctccttctat gagcgctccc atcagcattt caacttcctc ggaaggtttt ggaggatcgg  20580
tgttggattc aaactgaaaa acgtcattaa acgtgtccac tgtaaacggt tcgcagcgga  20640
cgctcttcac taaatcgccg gtgctgaaca ctttttcgtt ttggctttgg gttatgttga  20700
agaacttgcg tacaaacatc attttattgg cgtagctcac attgtcctcg ggcaaattga  20760
ccaatacact attttgtagt tttaaatttt cctcttgcaa atgattcttc atgatgttgc  20820
cgaatatctt gttgtgaacg tgcatgttgg gccatgtgat catgaaaaat tcaccgtaaa  20880
cacttttgta acgtttcatt ttgaccatgt cgaaaaagta aaaatgaaac atacccccctt  20940
taacgagaac gccaatcttg tatgtgagtt taggcggttt caacggttcg atcaccacct  21000
tgtcgttgac ttgcggatac aatttgtcta tccaagactc caatgaaatg ctttcattca  21060
gaaagcccag cgactcgaac agtttgttaa aaggcgtatg acaccttagc accgtcaaat  21120
ttttcttttg cagattatgt gtaaatttgt ccacccatgt tatagatcgt gtttcggttt  21180
gcggtttaaa gatgcacaac attttgtcag attcgtcgta ctctacaatt tcgtcgctgt  21240
cgtcgttgtc gttttcattg cgatagacag ccaacgtcgt actcggaacg gaactgtcta  21300
gttttgcacg tttggactcg gtgtctccgt tgtcggcctc ctcgcagttt atagatcgtt  21360
tattattcat tatggtgacg ttagtattag cactccgact ctatcagcac ttgtgcaata  21420
cactacaatc gcactttgtg ttttatatta agtagcgtat caggcaacga ttattatcac  21480
taattttacc agacgatatc atccaactcg acgatggaat acaattgtaa caatctatta  21540
aaacacacgc cttattccaa caaactcaat ttgtcattca aaagatacat gatcacactg  21600
tctctggcca aaggtgtagt gccgtcgctg gccacgctcg aatccgttaa ggaattacaa  21660
aaattaaaat ttcaaatcga tcctgtaacc aattatatca gtaacgcgct cgattacgaa  21720
atgatagttc aaaacgatga tttatccgtt atacatgtcc tggaacgtga caccaagcgc  21780
tatgtaggcc aaattaagtt aacgttcgaa atcgacaaca ccatgcacat tactacttta  21840
cccgtagcca ctgattactc agaacaaaac aaacttgatc aggccgccgt cgttgtagac  21900
gaccaataca attcgccatt agtgtttcat gacaattcca cactcaacaa ctcttccgaa  21960
ctatggaata ttccatcaac aaacaaatga catcatcgtt cgaaatctgc tgtaggcaac  22020
```

```
gaattatcac acacgagatt atattgaaaa aattacgtca tccgtttaaa atattgcatc  22080
atctttaaat tcgaaacccg cccgcgcttt catatgaaac cgtcggcaaa gatcgataaa  22140
atttattcta gaacattcca cggcttgacc caaaaaaaca aatgacgtca tatggcgtga  22200
tctagaaatg gtccaatcac aaacgtattc cacgaatcac gccacgccca aagataacgt  22260
acttttggtt attttcgttc gaaacgggcc gtgatctttt gcttcgaaac cgacggcaaa  22320
gattgataaa atttgttcta gaacgttcca cggcttgacc caaaaaaaca aatgacgtca  22380
tatagcgtga tctagaaaaa gtcgaatcac gagacgccca aaaataacgt acttttaaac  22440
tggtcttgga tcatttcgtt cgaaacgggc cgtgatcttt tgcttctatt catgattaag  22500
gaaaaaacaa attacgtcat ccgtttagga tattgcatca tctttaaatt caaaactagc  22560
ccgcgctttc atatgaaacc gtcggcaaag attgataaaa tttgttctag aacgttccac  22620
ggcttgaccc aaaaaacaaa tgacgtcata taacgtgatc tagaaaaagt cgaatcacga  22680
gacgcccaaa gataacgtac ttttaaactg gtcttggtta ttttcgttcg aaacgggccg  22740
tgatcttttg cttcgattca tgacccaaaa aaacaaatga catcatttac caaagataat  22800
gtttcccgcg cacgtttaaa ctagtcttag atcttttcgt tcgaaacggg ctgtgatctt  22860
tttgcttcga gtcatgacca gaaaaaaaac cgattaagtc attttgcaca cggctctctt  22920
tgaaaaacaa attacgtcat aaaacgtgat tatagaatcg tccaatcaaa aacgaacacg  22980
aatcgcgtca cgcgcacgaa atttactatt cgacttgacc taaaaaaaca aagaacgtat  23040
tccacgaatc acgccacgcc caaacataac gtacttttaa actggtcttg gatcatttcg  23100
ttcgaaacgg gccgtgatct tttgtttcgc ttcgtgaccc aaaaaaaaca aatgacatca  23160
tcgcccaaac ataacgtact tttaaactag tcttggatat tttcgttcga aacgggccgt  23220
gatcttttgt ttcgcttcgt gacccaaaaa aacaaattac gtcatcgacc aaagtaaaaa  23280
ttcttgcgca tgtttaaact agtcttggat attttcgttc gaaacgggcc gtgatctttt  23340
gtttcgcttc gtgacccaaa aaaacaaatt acgtcattcg tttaaaatat tgcatcatct  23400
ttaaattcga aacccgcccg cgctttcata tgaaaccgtc ggcgaagatc gataaaattt  23460
gttctagaac attcgatggt ttgacccaaa aaaacaaatg acgtcatata gcgtgcgtcc  23520
aatcacaaca cgaatcacgc cttgtctaaa gataacattt cccgcgcatg tttaaactaa  23580
tcttggatct tttcgttcga aacgggccgt ggtcttttgt ttcaattcat gatttagaaa  23640
aaaacgaaca taaaatttta ccgcgcattt ttaaactagt ctaggatctt tttgttcaaa  23700
acgtgccgtg atcttttcgt tcgaaacggg ccgtgatctt ttcgttcgaa acgggccgtg  23760
atcttttgtt tcgctgactc gtgacccaaa aaaacaaatt acgtcattcg tttaaaatat  23820
tgcatcatct ttaaattcga aactcgcccg cgctttcata cgaaaccgcc ggcaaagatc  23880
ggtaaaattt gttctagaac gttccacggc ttgacccaaa aaaacaaatg acgtcatatg  23940
gcgtgatttt aaatctattt aatcgtctct ggcgtacaaa agtaaattac acacgaaacg  24000
tgccatgtta agtttgttta caatgaaact gattgtgtcg attttaatat ggacataaga  24060
tttttgcaaa aaattccatt aatcgaacga aagcgacaat aaacagttcg tttgttatac  24120
caaattttag tcgaatacgt ttgtatatta ttcacaatcc atcaattcaa aacatgcctc  24180
gtcgacgtcg ttcgcgcacg cataattata atgatcgaac aattgtttca atgaagtaaa  24240
accggttaaa tcacgcagca aaagtttagc agtcgtgttc caaaacggca cacacaaata  24300
cgagtaatac aattcaacga aactgataac gcccatttcg ctatttaaaa aagatacgta  24360
```

```
ttcgtctgga taggttttca tgtctttgtc gaatatgtat tttttgtgaa agtcacaacg  24420
aagattggca tttttgtgat aacacattcg acacgtatag aacttttcga tttgcaatgc  24480
gtttaaataa tcgcgagctt cgtccgatag ttcgttaatt tcgtttatag caaaatcgtt  24540
gtctttcttt tcgcgcaata acaatttgtt tcgtcccata tattggagca atgttcccaa  24600
gcaaggtttt tcgacaacgc caatgtttct ggcgacgatt tgttcgttaa gggttttagt  24660
caaatttttt agatctcgat gaaattcggc cgcgtccatc attattgacg acgacaacaa  24720
cttataagag tcttgcgtta caaaagttat catcatgcag atatttgtta aaaccttaac  24780
cggcaaaacg ataaccgtcg atgtcgaatc gagcgacagt gtagaaactg taaaggaaaa  24840
aattgctgca aaagaaggcg taccggttga ccagcaacgt ctaatatatg cgggcaaaca  24900
actggaagat tccatgacta tgaacgatta cagcatacag agagaggcca cgcttcattt  24960
agtgttacga ttgcgcggag gtcattcaat tcgaactggt ttctgataac ctaaatatga  25020
tagtataaat gtgtccatcc gcagaatatt tctgcagtct aagtttacaa tgtccgaaat  25080
atcgcaccat accatgtatc aagcgtattt gcaaagatcg tttttgtcac aaaaagattg  25140
gttgtatttc gatataccat cggaacaatt acaaaaggat tttagtctca atatgacgtc  25200
gaacgatatg actcgtatca tgcaaaacgc caaaacctac aatatggcac ggcgtatact  25260
tgatcgcctc ctgccagtcg aagccagatt ctatacaatg gaactcttgt ggaacagcat  25320
tcaaccatat gtaatttttt gtttcttatt cgcgctgtgt atacacatgg aagattggaa  25380
cagtcacgaa actgaccgtt tactggatga attgagcttg tttttacgtc aacccatcga  25440
tgaagattct cacagagaca aaatgtacgc cactagttat cgcgatatta aatttgaata  25500
tttacattgt ttcactgtag gtcaattaaa gaaattttca aaagcattca ataaaatcgt  25560
gatgagattc gaataaatgt acagcataag taaacatgtc gtattattca ttgtatcccc  25620
agttacctgc tcatgtggtg tatcgaattc tagcttatgt gccagttgac aaattactgg  25680
aattgcaatt gtctgagtac gactataaat gtattttaca gtgtaaaaat gtaacttgtt  25740
ttagtttgcc aaaaatatgt tacagtacaa gactactgtt gaacacattg attgatattc  25800
atggtatcga tcatgatttt agacattcgt gtttagttga tggtcacaaa ttttatttga  25860
tcaataacaa aacgttcgtt tcgtataccg gtttgagacg ttactttaca aaacatagta  25920
ttcgtaaatg ctaccaaagc aatgcaaacg tttccttcac ttgtttgttt gatattattg  25980
ctatacgatt tccggaacaa tttgaatggc acaaaaaatg ttgctttaca tcgtgcggcg  26040
gcggcggcgg cggcaaatta cgcaattttg cgtgtgtcag tataaatata gttgatcagc  26100
taaaaaacga aactgtttgt gaaccagctt ttttgttttt cgattatatg tatcatgtat  26160
tacgattaga ataattaaaa caagacattt ataaaatact ataacaattt attaaatatc  26220
aatgtacaaa attttaagca gacatttgac tatcgtcgca agtgtcgcta accattgcag  26280
gggacatggg atgtatttgt aacggctgct gctgctgctg ctgatgttga tattttgctt  26340
ttttcgatac tggcgctgaa gacgatacgg acggagcttg atgtcttttg ggctctttgc  26400
gtttgcgtaa acgtttgccc acttcttcgt ttttgtcatt gtcattggtt ttgtttgccg  26460
ctgtgggaac gacagattct ttagtggcaa ttgtaacatt gctcacgctc gtatttaatg  26520
cagtatgtag gaatttttta aattgcgata cagcattttc caagacgttt cgagtcaatt  26580
tcgaatcata aattatgctc gtagcgggcg ctttattgtt tgtgtacgta tatatgagaa  26640
tattattaaa ttccgtgtaa acttttgaac gtttctcgtt actctctttg atttcgtcca  26700
gatttaaatc gctttttta acgttcacag tgctcgtttt gttcgatttg gtgagaaggt  26760
```

-continued

```
cagtagtgtt gttgttggtg tcgtttgttg ttggcgtcgg tgatatttgt tgtttcttga  26820
tgattattgc ttttccgatc ttttccatgt aatcgaatat gtgtagaaaa gcatcgcttt  26880
ggttgtgcac tttgacgaga ttccacaagt gactgctgct cggccatccg gattgtttaa  26940
ttttcgatat gaatgtattg aacagaatgt atttgttgtt gctggtaatt ttcttgattt  27000
ttttcgataa ttttttgtcg tccgcaattg ttggcatcac gtgcacttga taaccaattt  27060
tttgtttctc aaacagattg atcacattga caagcgtttc gatgtgcgtc ttgttgtaca  27120
cgctattctc caatttaatg atcaacgact cggccgggat cgatgtcata tttgctgacc  27180
gcttgagcgt attcgtcttc tagggtagtt tttaaattaa ataaattcgt taaacgtttc  27240
gagtgatagc tcaacagtcg cttcttctct ggacaatcgc cgacaactag tgaggcggtg  27300
tcaagaatgc tgtttatata attttgctgc acagcaaagc cgggatcgga aacgtgatcg  27360
cacacacgat ccacttgcat atgatgtttg cgccaattga ttacttctcg cagcagtgcg  27420
tacacttcgc tacgcgtcaa acagtcaccg tgattagttt cgaactgatc gcaacgactg  27480
ttaattttag tattgccgct gcatatttcg ttgaccatgg cgctgctgta cgcgtaaaac  27540
tgccgtttta tcggcgccgt ggaagtgtac acgtttttca aaatcaaaaa ttgccggagt  27600
cctgatcgga acgttgcgta atgaaagagt aaaaaattta ttcaattgtc ccgaatcgta  27660
atcgatcttg acttgttcga cgaaatcgaa aaaatccaag tagttgctgg aatcgtacgt  27720
gaccagttgg ctttcgcgca tatattgaaa gtagtcttta atcggcacta tgtacaaatt  27780
gcgcggtatt tcgtgattgt gacggcgaac ttgtaaattg aactggtact cgttactgtc  27840
acggttgttg cgctgcaatt tgacgcaata cgtgttcggt tttcgactga cggtacgtaa  27900
tgggcctttc aaaatgccca cgtaaatggt gtaacggtaa actacgccgt gatcttgcca  27960
atgcaacaag aaaggtgacc ggtaaacgta agcgttttcg aaaaatgtac ccgtttcttc  28020
gatgaactcg cgcacggcgg tctcgtaatc gaaaatatct ctactgtccc atttgccgcg  28080
cggtatagaa atcttttcaa ggaaatgatt gccgttggcc acggacaagt tgtaggcgcg  28140
acgggcacac agcaacaccg ccctgtccgg ttccataata atcagaagac ccgagcaccg  28200
catgtcgcgc tacacagtgc tggttatcgc gtgtcgacca aactgaacgc gttgactaca  28260
agcgttagtg aggcagataa agctttgtgc gcaacagcta ataatagttt tatcatttta  28320
tcgtgatata ttgtacactg ttacttatta tctggtgcgg tgcgtatttg tagataacat  28380
tacagtataa aatatgcaac tgaaactgta aattatacag tggtgcttcg atcatggctt  28440
cgaaaacgac aaccgtattt ctcgtgatcg acgaactgtt cgaatacaaa tgttattaca  28500
aaattccaaa cactggcggc aacggttgtg ctcatgtcta cacatacaaa ccggtgcaac  28560
tggtaccggc catgttcgat accattacta cgcatatact aactagcaca gcggaatcat  28620
catcatcgcc tgaaaacatt aaaaaaccgt tgagtgtggt ttatcctaaa aatgaacatt  28680
tgttctcaaa ttggtttaaa tgtttaaaga acaatactgc gaaaataaca gaatcgacga  28740
cggagcaaag agtttatttg ttgtgctcat ttgctaaatt aaaatttgtt tatgattttg  28800
acatttacaa actggaacat tttggattcg gagccagcgg ttcgattgtg catttggcga  28860
gacattgtaa cgcccatcct acgtttggca aactgattct atcgtgcgtc atcatcgaat  28920
tgactgtgct gttgcgcatg ctggccaaac tcgaaaggat gccgacgata cgagattgca  28980
acgacagcaa tatggattgt ctggtggttc attcgtttgc ttcgtgcaaa gtgctcgctc  29040
aaatagcact aggtataact cacaatattc gcaagctcgc cgccgacgac aagatgatga  29100
```

-continued

```
cgagattgtc tcaatttttt gttcaaattt tggaagaacg tttctgtccc agtttggatg  29160
ctctcgaaag ctaccataac tatttcaaat tggccgtgca aatgatcaag ctcaattaca  29220
aaagttgtgc tcaacgccag tttagcgatt tcgttgtgcc gggcgtgttc gatctgatcc  29280
tcgccgatca cagagttttg aacaacatgt gtacgaattg tacaaacaaa aattccactg  29340
gctacgtgga cagcgtatat tacgactcta gttttgttcg tcacatgtat cagttgatag  29400
gactgagtaa tttgtacaaa gaaaacagtt gttttatgaa tattttggca atgttcagtc  29460
atgaacccat gcagactatg tgtttttctc gagtctatac atacaaaatg taaactaaat  29520
gtaatcacca aataatgtat tgaaataaaa ccaaatttat ataaagaaaa aaaacaattt  29580
ttatttgtat cattccaatt gtacaatgcg atgtccatag tgagttcctg tcttgatccg  29640
tttgccgtgt ataaaatcca ttttgatttc gctatcgttg tgcacgatgc gcgattgcac  29700
ggcggcgcgt ttcaacgagt tgagtctacg tgttgacaat tctaatggat tgtaaattag  29760
agatttttcc aaagtgaacg aattgagatg gcccttgttg caccattcta gactaatgat  29820
tagatttaat aaaaatatca tttcataatc acattcgtga aacacaaatt gattgcgcaa  29880
acagtaataa tataatttta acgaattgta caaatagaac atgtaatgtc cctcctttaa  29940
atagtattcg acgtcggtga cgaacagtac gttgatatat ttgttgacta gtaattgttg  30000
cagtttccta caatattgta aagaattttt gtcatcgtcc aattgcgtgg cgcacaaatt  30060
tggcaaatgg caattttcaa ttatacaaaa ctcggcggcc aacaggcgtt tgagctcgac  30120
actgtgatgc ggttccaatt cgaatacaat atatttagtt gaaaatcggt gccgtttaat  30180
aacgtccgat atagatgtaa aacttgccaa aaacttttcg aatgcaacgt cgttccagcc  30240
acgattgatt gcggtcgcag tggcgttttg ctgttggtgt ttaaaatcta agccgctttg  30300
gatcaatttt gtagtgatgc gtatgctcaa ttgttgccct agagtatagt ggttttcgta  30360
gccgcgttcc cataacacgt tacatgcaaa actaacgaga ttatccacgt ttggttgagt  30420
taacatcttt ttcatgcgaa catgatcgcc tttataccac cgatcgcgca ccaatagctt  30480
gaacaatcga atttgatgag cggtcaaatt agcgccccgc gtcaggttca cgtacatgtc  30540
caaatcgtcg ggcgtcgatt gtgccacagc gttgatatcg aacagaacgg tccgtttttt  30600
gagttgaacg aatccatggg cgtcaacgag gaacacttcg tcaacggtga acatgttggc  30660
gacatcgtcg acactcgctc ctttcagata taacaaatac atggtaattt cgtcggctag  30720
atatttgcaa cattgcggta acggttgaga ctgtacgtcg aaatagcgag caaacattgc  30780
ggtcgtatcg tttttcttca ctgatggtgt tgaagcggcg gttgtcataa tatattaatt  30840
attcgaaagt gttgcacgcg tgtatttgca cattattttt gatcaataac taaagtgaca  30900
atgtcgaaac cgagcacaac cattaatagc gccagtacta ttaccgtgct agataatgaa  30960
gagtactcga cgcgtttgaa aagtattaaa actatagtcg atatcgccaa ggaagccatc  31020
gaagacatgg ttaagtacaa tgaacttgaa cgtgacgacg ccgattcgct cagcgtggcc  31080
gatgctaccg ctgcatgggt ttgcggtcgt gtggctaaca ataactatgt aacgatgcga  31140
atccaatgta gcaaagctaa cttcgacggg catagcagag cgctcgatcg attacatttc  31200
gatcagtcgt acgaacaact gctattgtcc aacagcgaat ggcaatattt tatctacacc  31260
aagtatacga tacccatgtt gaatctaata gtggtcaaac gaacggatgt ctctttgttg  31320
ctttcaaacc cgtgcttgca attagcctat ttgatcaatg tacggactgg ccaaattgag  31380
actcgggatt gtgattgtct gcgcgtacca aacaatcgac atggctatgt ggaaatgaaa  31440
ttcgacgagg actacgtgtg cgacgagcgc gatcaacact gtcgatcttt gctgttacaa  31500
```

gaggatctga tcgaacagcc ttacgatcac ggtatagtca aagtggagtg tgaacacatt 31560
acacgattgt aatcaataaa actctcaatt gttagcactg tcttttattt gtatagcata 31620
acatacaaac tggcgttgtg gtaattaaga tataataatg ttcaaaaaga gtataccacg 31680
caacatatat gctacatgtt tcgtatgcga cgacaccata tatgtgtaca ggaaatgttc 31740
cgcgctgaaa aatgatgcgg cacgcgttgc tcaaaaattt ttctcctctc atcaaggcat 31800
caaaaagaac aacactttct tttgtcacaa gtgttataac gacatgaata tgaaacccat 31860
gcctaagcac aaacatagta ctcttttgca attctactag gacataattg tattattgca 31920
atgcatcaag ctagacatga cattgaattc gccactcgat tcgggcaagt ttgaacgtcc 31980
gcgaatacat tgcaaactct ccgcccagcg gttaccggcg aacgattgat taatcgtcca 32040
ttgatcgaga cgagtgcctt cgattttttc gtgacctgta tgatttattt taataaactc 32100
tttgaaaata ttatcgggag tgttattaaa gaacatgtat ggtatattaa atattggata 32160
gcgaggcgct tgtttattgc caaaatcacc gttacgaact acatacttgc gctcgatatt 32220
atcaaagtta gactgtcgtg ataaatacga aatgggcgac agacagattt gagcgcaagt 32280
accgtcttcg gccatccatt cggtgaggtc tttggcgtcg ttcatgacac ccttctggcc 32340
gtgtatgccg caaattttga cgcctctgaa atcgttggtg ctcgtaatta gcgataattt 32400
caagtatgca gtatcgttga aacacgtcag ggtcgcgtca attttctcca cgcgttgatt 32460
gttgatttgt ctaaagtaca cataaatttt gtatacgtaa aagtttttat tgcggcacgt 32520
ttcgattttg taacgtttgc catcgtacac ccaaccgatt ttgacattgg acactaccac 32580
gcctacgatg agaagcacgt tgccgccttc gacggtcacg taattgttgt cgttgctgtt 32640
gttgaatttc acaacgggcg tttcgttttt tgcgtacagc aatttgcctt tgagtttgtt 32700
gattttgttg ttgtacagtt tgataggtag ttttatgtcc ggtatgtagg gatcttcggc 32760
ggtctgtaat cgatcgtcac gtaccaacgt ccaaagtttg aacattttgt tgttgtgcaa 32820
aatgtgaggt gccaccacaa ccgaattgcc attgggcaac atattcaaaa aacgttcatt 32880
gtcatcgcac aaatcctgat aactcaaaac cggcatggcg tttttcaaat tggtcaatga 32940
cacgatcagt ttaggcaccg ggacggtgca gaacatttgc gtataccctt tataatagta 33000
ctgcaccaat ttggacatca aacaaacgac tgtgtccttt tcgattattg tggccacgtc 33060
gttgtgcgtg cgcaaaatcg aattggaatt atgatactcg tatgcggtga gcagcgctgt 33120
aatgtgcacg tcgcgtattt taagtttccg tttgatgcac accataccct cgtgatggtt 33180
gacaaacaaa atgttgttgg ctaatttcag ttctactgga cacatatttc gtttgaaata 33240
atagaaaatc gtttgtaaat cagttcgtcg acaattgaac actgtgggac gatcgttgaa 33300
tgcgatcaag agtaaatcgt cgttgttgtc gtcgtttgcg gatccaacat tgtttctgtt 33360
gtcgcttctg tcacgatggt ccaaatcgtt gctgcccaac cacgagcagt gaaatataaa 33420
tttcttgtcg atcaacatac gaaagcgttc ggcgaccatg atgtaatcga cgctcggcaa 33480
acggacgtcg cgacacaaaa aaaatttttt tccagccaca gtcatttcgc cgtgaaaaaa 33540
actatccaca aacttgacaa aatcagattg ttgcatgagc atatcttgac gcatagtgtc 33600
gttagttata cgcaccactt cgttgcctat gcgatatttg agcgtgggcg gattgatttc 33660
aatgttgttg ttgctggaat tgtcctggta attgacaaaa tttttctttt gtttgctgaa 33720
cgtcttcgat acgccataga tgagttttcc attgactata gtgtctacga tcttttttga 33780
ttctttgaaa tataatatag actgaatctt ttttcgtttg tttgcgccac cgttacaatt 33840
ggagttttca ttttcgtcta cggcagtttt tagcatgact tcgtaacatt tcaacacggg 33900
tttataaatc aggctcagca aatacacatg tttgtagata attttattgg acaaactgtc 33960
gatttgatag tttatttgtg tgcgcatagt ttgtttgata atgtccacta gttgaactac 34020
ttgtttggcg gtgtattcga ataggaaatt tagcggttcc catttgccgc tgcgactcaa 34080
atatatttcc aatatttgat tgagatcttc ggtgacgata tagtccttgg cgtatacgtc 34140
gcgcgcgaac agcacatcgt tctgatgatc gtacaccagt tgaattgcac gattgatctt 34200
cttctcctcg tccagattgc cgtacagaaa cattcgctta caacttttag agtagagttt 34260
gtcgtaaaaa ttatgtatca gtatattgtt gttcatcatg acattgggaa aactcaaatg 34320
gcgaccgtcc aacataaacg taccgttcaa atcgggtctc ggcgcgtcgt tgcatcgcaa 34380
ctgtttatcc agccacgtac cgaaaactac caggacgcac ttgtgtagaa cacatcgacc 34440
aacggtgtcg gcggcacagc aaaagtagga tttgcgctct tgcaaatatt ttagcgtaca 34500
ttcgttgacg gatctgtcgt tgcagtttaa ataaaaatcg agattatgtt ggttgcggat 34560
attgtcgtac attttgttga aatcggcaat cacgtccgtc attgttccaa atcgttgctt 34620
gactaatcat gtaagtgatt attattatcg tacgataatg tcggaaacag caacgacgcc 34680
cacaaacaga actgatttaa aaaacacatt aacgaaattg cgcgagcaat tgaaatgcga 34740
atcagacaga ttactcggtt ttgtcgatat tgtgtcgaac tttgaaacgg ccatcgaatc 34800
atcattgaac gcgtatgtcg aaaatttgat cagtacaaat ttggccaatc ggatcatgtt 34860
acggtacacc acgctgaatc gtttgcgcat ttggtggacc gtattgcccg atcagacaga 34920
aaccaacgcc ggcattactg aagaatattt gcgatcatat ttcgatcaat atggttacat 34980
tgttagttta atagtgtgtt ctcaaatgtt aggttgcgcc gtagttgaat acgaaactca 35040
acagagcgcc gaagaagcgt tcgaaaccga aaacgccaag aacaataaat tcaaactgac 35100
ctggtacagt gacactcaaa tgtatccccg tattcattac gtgcccaata ttaatcccga 35160
ccattatgat agagttcaaa atttaattcg aaaacataaa gctgctcgca tcagtagttt 35220
gtcgttgcga gcctgatact tgttggaatt aataaaaata cttttctgat gcaatcaaat 35280
gactatatta atcatctaaa ccaacgatta ttgccgacat tttgatatga aaacgtcggc 35340
aataatcgtt attacatttt aagactacta acaatcatgt atccaaattt aattgttgtt 35400
atcgaatata atacgacgcg aaaatttaaa aattattcca attacggtac gcgtcgacga 35460
cgttatatga aacgacattg gccaaaatca ctaacgaata cgaatacatt aaaaaaattt 35520
ttatactagt agtccattac aattcgttat gaatcaattt actgtttgta cctaggccgt 35580
tgcgatttgt tttcatcaag ccaacatgca tagcgttgag caaatcgccg ttgtccgcat 35640
cgatttccca tgcgaataat ccgccgagtc tacgcttaag cacgtattcg cctttggcca 35700
gtaccgatct ttcgctgtcg tacgatatta agtcgccaga ggcgcggtcg aatacgtacg 35760
cagccttggc cacgtcgtcg aatgcgtatt cgtaacgcga aatgttttta gcaatctgtc 35820
tgtagtcgac cacgccgttt tcccatgtac ccgtgatcgg tccgacggct acgccactga 35880
atggattgtc actgtcgtag ttgtggacgc ccgtccaacc gcggccgtac attgctacgc 35940
ccaacacgag ttttttgga ttcactcgtt gcgcgagcaa agcgtccacg gccacgttgg 36000
cggtgtacgg ttcgttaggt ttccacgcgg aaccgtacag tgccgtctga tgaccgagat 36060
cggtattaga ccaagctcct ttgaaatcat aactcatcac gaaaatttta tctaaatact 36120
gttgtgctcg gtcgtaatta atcgcggcga tcttgtctat gccagcgcta atcgctgtgg 36180
tgagttctaa agtacgattc gtttgtattt gaacttgatc gagcatggcg cgcaattcgc 36240

-continued ccaataaagc gatatacgtg ttattgtcgc gttccacgtc gccaacgttt ggattggcgc 36300
ctttgccgcc cggaaattcc caatcaatat cgatgccgtc gaaaaatttc catgtcaaca 36360
caaattcacg cacggattcg acaaaaattt gtcgcgttcg cgcatcgtgc atatgataga 36420
agggatcgga cagtgtccaa ccgccgattg atgccaacac ttttagattg ggattggcca 36480
attttgctgc cattaattga ccaaaattgc ctttgtaggg ttcgttccat gcgctaacgc 36540
ctgtttgtgg tttttggagc gccgcccacg gatcgtgtat ggaaacttta aaattgtccc 36600
tgccagcgca cgatctttgc aacgcttcaa aactccccgt gatagatttt aaactgtcgt 36660
ttataccgtc accgccgcaa atcggtataa atccgtataa aatgtgcgaa aggttcggcg 36720
tgggcacttt gtccacggga aaagatcgac cgtaaacgcc ccattcgaca aaataggccg 36780
ctacggtgtg atcagtgttg tacgtatacg gtttattgtt ttcttgccac gtgtattgta 36840
acggttttaa atgtttacca tcggtgtctg cgatcacgac ttctacggtt tgactagccg 36900
aacagccgtc ggcattgcac agttttacgt acatcgaata acgaccgctc gtattgtaat 36960
caaaagtagc aaaacgatct tgcgtcggac cggtccaaac gttgattact ttgctgtcta 37020
gtttattttc tagatacact tgagcgattt cgccttgttc gcccgaccat acgctccatg 37080
atactttgat agttacaaac ggttgagagt ttactaatga ttcgtaagcg gtggcttgat 37140
gatttatttg cactaaagcg taactgtgat cggcccagtc taatgtggga acgccgggtg 37200
gagcagcgta gctatgtaat attaaaatac taaaagcaaa caaatacaaa caataattat 37260
tcatatttat tttgtgtaat ttatagtact tattataaaa aaaaacatat taaaacacca 37320
aaataatcgt gtattattta attatttaaa agatataaca gtgaataatg gaaagaaaca 37380
tcgatcacaa aacaaattat agtcaaattg ataataagtt tcacctatat tgttacacga 37440
cacagaacat tgaacacatt tgtcggcaat cactttgtac aacagtttct ggttattatt 37500
tctaatttga ctagtaaatt ccccggtgct ccaagctaga cgtatccgtt cgcgccacac 37560
gcgttcgtct cctggatttt cccaatagca agcgcttagc aatgcgaaca ttctccaatc 37620
cgtttcgaac gaattcgaac agcaatacaa aggaaaaaaa cattgttcac aaaacagagc 37680
gttatgtgta gtgttgtgaa ggcaaaattg acaaatgttt atagattcgt tcttctctgc 37740
taaatcttcg caaatgattt gttcaacggc cagtgtttgt ccgttgacag cttgcagcca 37800
actgtcgaat acagcctgac gtgtatgctc gttgctgctg catcgatacg ctttagaata 37860
tttcacaaat atctctacaa attccattgt aatgtaggaa ttagtctgat ttgatgtgct 37920
cctataactg aatttttttt gatatcagtt tgccttttat aaggctatga tagagttata 37980
aattattgat aagaaacttc gacatgctga taactgtcgt ggcaaacgat aaagctcaac 38040
acatgtacaa gagtttcaaa caaatctggt ccgaatgtac agtcgaatgt caaatttgtt 38100
tcgatcgaat tcacgacgag ggcgtcgtcg ccgttaccca atgttgtacg ataaacattg 38160
aaaaaatgtt tcatgctgaa tgtttaaagc ggtggcatcg cgaaaacagc cgagatcctt 38220
tcaacagaaa cgtacgctat tggtatacgt ttccgcctcg ttcactggac gaatgtgctt 38280
cgttgctaga gaaaattaaa aactttatcg gtgaccagga ggcggacaaa aagtttcacg 38340
acgaatacaa tcgattgcaa aacgccaaat atttagatat agatttgaat tttgacagat 38400
tgttacgtta ttaagtatgt tcaatagcgc aaacgagttt cgactcgttg aactctcaat 38460
ggcacgtaaa cgatggcaaa ttccgctcgt tgcggtctaa cgcttcgatg aacgttgtca 38520
tcgttgtttt ctgtatattt atagaatgtt acattttgca aatctataat gcgactgtta 38580

-continued tatagattag ttaatcggcg ctgacgttcg tctaagagtt cgtacacgtc ccgtgtgtgt 38640
gtgcgagttt gtaacggctg actttgaagc aattgcaaca gtgtgctgat aacataatta 38700
gcgcacaaat ttataaaatg aattatcaat tccatgacat tggtttgatg ttctgtatat 38760
ttgacgttga ctgtaacatg tgttagggtc tcgactatat acgaatatga aacgtagtag 38820
ttgtacagca tgtccatgac gcgagtaaga ttttgcgtat taacattgta tttcataatc 38880
tcgcgtatca agtcgctgta gtcgatttta cactcctcgt ttgtatccaa tcgtaaaaaa 38940
gatgacaatg tatgagcagc gtttgacgga ttgttgaagg ctacttgcaa actttgtatg 39000
taagcttgta aacggtctat tgcttgttgt atgtacggca cgctgtcggg acgctgggga 39060
atttgattta ttgcgggcgg tataatatac attactcttt gggattgcgg gacgattgtc 39120
gtcgattcgg acacgttcat aggggaaggc ggtcgacgtg gcgttgttat aattgcattg 39180
gcgttgcttt cggcgacgtt agtcaccggt gtgggcactt gaaacgtttg cgctaacgtt 39240
tgcagttggg cttgcaattc ggaatctgga cgcgcagtta tatcggcaat gatatcttcc 39300
gccgaaggca atttatcggc gggattttgt gatggtttcg ctgacgtgat catttcgtct 39360
atggaagacg aaggcggtgg cgttgttgtc gaaatatttt ttttaccact accgctggcc 39420
atacctcccg acgttttact tgtcgtcgcc gtttgggttt tatcgacatt ttcgctggtt 39480
ttgcgtctgc tcattaaacc gagactcttg gacgataacg atttagatga ggctgattgt 39540
ttgctgggat tgctcatttt gttactaata caccagtaac aagtaattgt cgtaatcgct 39600
caaaactttt aattgccggg gaaacgattg ctccttattg gtatagcggt cgatgtaata 39660
atgttggccg tgactcgtat gcgaatacgt gtactgttgc aattgatggt attcgtcgta 39720
cctgagcaca cgcacgcgta ttacatcaaa aatgtccgag tcgttggaca aacctgacgt 39780
gctgtcgctc atactgaaag acaatttgac gatcgtgcaa gacacttata taattttaaa 39840
tgtcatcgac aaacacggtg cgcctaaatc aatgtgtatc ggtgaaatcg ataccctaca 39900
gaccgattcg atttcaaaag acacagtgtc cgattcatcc gttacgagcg aattgtcgag 39960
cgattgaaca tatgtgtgaa gacgaagatg acgacgacga cgacgaccag aacggctcgg 40020
aaacacgata taccgatcat gtaacatttt tggaatccac atatcaagat tggtgtagta 40080
ggccatattt tactttgttg ctcgatgcgc aacagcgaaa ttccgtaaaa cgacacaaat 40140
atttgaatgc taccgatatg gcgtgcacgg tcaaattgaa acgtgtcgca gacgatgaaa 40200
agtttttcac catcgatcaa gccggcgaac gtaacatgca caccatacgt attgtaataa 40260
aatctttgat ggactatttt caaaatgcgg acaaatattt cgttttaatg atcgacgaac 40320
aacacatcga tttgatatac acggagtatc gggcgttgtt gttgccccaa agattgctat 40380
gtctactgaa aagagattac aatccgcaaa caatgtctag taattttatt tatttcgacg 40440
tgccctgcac agccgaagcg ctagaatcgc aactgattta caaatcgttt ctattgtaca 40500
atactgtact caccatgata ctgaaacaaa cgaatccgtt taatagtgtc ggcggcaata 40560
aaaatatatc aattttattt cgcaacttgg gcaaatgtcc aaataacaaa gaacgtatta 40620
aatgttgcga tttacgttac ggtggcaatc ctcctggtca tatcatgtgt ccgccacgtg 40680
aaatggttaa gcgcgtgttt cattacgcca aatgggctcg tacaccaaac aattaccgtc 40740
gttatttcga attaattacg aaacccgttg tgcgtgaacg atattacaga atggaccgaa 40800
ccgtaacgac ccccgttaat ctcacttcgg acattgccct gctattgttg gattggtaca 40860
attttataga tgatttcaga acatattttc tttgataaaa caatgtagcc ttgacacaat 40920
tagtatttaa caatggtcgt cggggacaat attgcaatct caatcgcact ttggatgaga 40980

```
taacacatca gtgtgtatct tcctcacaac actcatggat agagttaatt ttaaattggg  41040
caacgttatc agtaacgctg tagattctaa catgaaatgt tacgaaaaaa aacagagtgt  41100
agcagaattc tacgctaaac ataaagaaga cactagcaaa gtcggacgta caaccacata  41160
caacgtgacc ggagagcgca attacaaatt gataagcgac gatcaacgtt acaaattcta  41220
aatggacgct gtcagtcgtc aatgttgtga aaatagtgtc gtacgaataa ttgatacgga  41280
gaattcggta gtgcggtgtg tgaagtgttt attcgtagct cctatgtcaa ttagttttga  41340
agagtttctc tatttacaca gaatatttaa ccaagcggtc aacacacgcg tcgctcatga  41400
tcagcggtca aagtaaataa agtatcatta gtttttgttt attctataga tttgtgaact  41460
aaataaatca gttttgtata tacaggttgt tttgatttct actcactttc ccgaagactg  41520
tcaaagtaga aagtaatttc atccaaattt gtttgtgttt gaagggtttc tgtgtgactt  41580
cacttaataa ttgtattggt aaatagatta ctacgcagcc agtaaagctt tgtataaaag  41640
agaaatcctt gatagaacag ctttagttta tcttgattgt gagccctagt aagtcatgca  41700
gagtgctcga tatattgagc gtgaccaatg cagcattgat atgcgacatg ttcgcgtatc  41760
ttgtgaccag aacaatcaat cgaacaatgc tgattatata atatttttaa tggtcaaacg  41820
agctttttat caaaatttc aattgaccac agatatgtcg atggaatcgc tgacgttgta  41880
tctgttcgat aatttgatat attgccgcaa cggacacgtt cgacaataca aacacgtcga  41940
ttttgtcgaa tacattttct ttaacgagca ggataagaac caatcgatga tcatcgaact  42000
cgaccacgat gcgcgtgtca tcgttgctaa acgattgcac gatcaagaaa cttatcatca  42060
gcgagtcagc ggttatatgg attttgaaaa aagacacaat acaacaacac cgatgcagat  42120
aataatgaac agcgcggaac gtgccgaatt tgatcgaaca atggaaatta cgttattaaa  42180
tgattaaaag tggtttttt tataaataac aataattgta ttgtaacaaa aatacatatc  42240
aatagttttg taaaactaat acatttaatt gctgtcatat tcatcgctaa cgttatcgcc  42300
agatgtattt tcttcatcat catcatcatc atcttcatta ttacggtaat ctatattatt  42360
attgttagtt ttatcgtagt tattgagttg tccacgtcgt ccattgtcgt ctttgactct  42420
gcgtgccgtt tggtctatga agcgttgttg attcatttcg tttttgttgt tgatgttatt  42480
gtcgtcgtcg tcgtcgtcat cgtcttcgtc gacgatatcg tgtcgtacaa tttcagcggc  42540
tgcggttttt ggtatccatc tgttgtttag tttaacataa tgacgtgtga ctgcttcata  42600
ggccgtttta agtgcggcat cttcgtcgcc agcgtgcaat ttgtgatact gatgaaatgt  42660
acgacgaaat aattgccgcg cttttgccgg catatattcg ttttcgatca ttttgtctag  42720
ataatacata ttatttcaaa tcactccgtt tcagattcgg tcgtgtccgt gttgtcggtt  42780
tcgtcgtcgt ctgttgtggt gtcgtgctcg ttggcatctg cgcgcgctac ccaacgtgta  42840
cccattttta catattttcg tttgaccgcg gaccaagcca cgcgaaatgc cgtcgattcg  42900
tcgcggtacg tttcgattgc gcggttaaaa acttttaaaa atattctttt accatgatag  42960
ggcaaatgtt gaacggtact cggtaaatct gatatactcg tatacatagt tataatcttg  43020
ctatattctt attttatagt aacgttttaa ttatattata atgtatggtg acctataacg  43080
tttacgataa taatacaatt tttagtaaag tacaattatt tattgagatt caactgaaca  43140
gttccaactt tattattaat cacaacctaa gtcatagtat cacaaccata tgacgggcaa  43200
gggagcggcg acggctagtc aaatgagtcg cgtattaacg aaatccactt catcgattcc  43260
gctgtcgata ccggcaattg ttgacttgtc gttttcatcg tcaaatttgg tatataattt  43320
```

-continued

```
gttaaccaat tcgtttatgt ccaattcatt tttcactatg aacactttgc tgcgatcgtt  43380
tcgtcgcacc attactccgc gtttgcacag cgacacgtac ttgtagaacg gtaatagggc  43440
gtcacgggtt tttttcaata attgtttgtg ttcagcagtg gccgcgacga aaattttcac  43500
aggtccatcg tagtctatgt ctagatcgta atttttaagt cgaacttcgc gcgatcgagt  43560
ttgccactct ttggccgtta cggcattgga cagtttcacg caaatgtgat ttttttcaaa  43620
atcagtttct gccacgagtc tgtagtcaag atcgaggagg gtacaaattt ttctaacata  43680
gttattacga atctttttgt tgtaaagttt tctatcgtga ataccgtaaa tttctaccgt  43740
gtcgtttaat ttgtcgtttt ctaatttttt gatcttgcct ttgattacgc tcatattgtc  43800
gttaacgcta cggtcaattt cgtgtttgat gagacttttc agtataggta cattaattag  43860
atcagtttcc atttttaaat tgtatttgtg tatatgtgtg cgtacgtgtg tgtacacaat  43920
actgctcaat atgtaaattg tatttattaa atcccctctt atttctttac atgcagtatt  43980
atagctgagc tagttgtata tctgacatct aacgtgttgc tactacacaa ttattgtata  44040
aaaatgaatg gcaaaaattc gtcaaacacg tggcgcacta tcactttgac cggtcaccaa  44100
atatggcctg tactcattga gtttatgcaa atgaccgaca acgaaaaaga ttgtatcaga  44160
ataaagaagc tcatccagtc gtatttgtta aacgaacgtc ctttaaaatt aacatattat  44220
gtaaaataat gttattgtat tgtacatact ttattgtcca catgtgtata tatgtctgtg  44280
tgtgtgtgtg tgtttttaaa tgaataaata ttgtaaaaat ttccatttag ttgtttcatt  44340
gtaatcatgt cggaaacacg tggctcgatt aaacgtaaat tgttatgtga tcatactgaa  44400
aaaacgtgca gcaaacgtgt gaaaagcaaa attcaatttg ttacaaaaga accggtacaa  44460
ttttcattgc tcaccgatcc caatcaaata aacaatgtcc tcttcataaa catacacaat  44520
ttcaaagtgt ttctcaagaa tttaattgcc gatttaaaaa aaataaaaat taatttttac  44580
aacagtttgt tggagcagct gatctctgtg tactcggact gcggtcatag aaacgagcac  44640
acaaacttgc tgagtcgaat cttggtagcc accagcgttg tcatcactga tctaccctcg  44700
aacgtttttt tgaaaaaact caaaactaac cgtttcaccg acaatataga ctacttgatt  44760
ttaccgaact ttgtgctatg ggatcacaat ttcattatat tcatgaacaa agcatttaat  44820
tcaaaacacg acaatggtct gatcgacata tcgggctcgc tgcaaaaaat caaattaacc  44880
cacggcgtaa ttaaagatca actacagagc aaaaacggct atgccggtca gtttttgtat  44940
tcgacattct tgaatacggc ctcgttctat gccaacgtgc aatgtttaaa cggagcaaac  45000
gaaattgtac caccgaaggc cagtctgcga cgctattatg gacgcgatgt gaaaaatgta  45060
cgcgcctgga caacgcgtca tccgaacata tctcaattaa gcacacagat atcaagcgtg  45120
cgcgaaccgg acaattacac cgattggaat gttaaagtcg gcttaggcac gtttactggc  45180
gctaatcgcg actgcgacgg tgataaagaa gttattactt ttttgcctca acccaattca  45240
ttgatagact tggaatgtct catgtacgga gatccgcgtt acaatttcat ttgtttcgac  45300
aagaaccgtt tatcgtttgt gtcgcagcaa atatattatt tgcacaaaaa caaaaaaacgt  45360
atcgaaaaac tattgcacag tatgcctatt ttatatacac tatggaagag ctacaaacgt  45420
tacagctcca tcaatttggc gacaaaaatt gattggttgt tacgcgattg tgctctatta  45480
ctcagctcca ataccagttt tctgctctac aacaaattgg ctacaattat agacaatgaa  45540
gaaatgactt gcggcgacga ggaaatattt aatttggcag gacaattcaa cgacgtcatc  45600
gaatgcggag ccaaaggcag cgccgatttg gtagcgagta ctaaaaaata tcgcaacact  45660
cattccgacg atatagatac aatcgccaag cgtgccatta ccggtttgaa cagccatatc  45720
```

```
acgtcacaca atcgagtgaa aatcggcggt ggtgatatct accacaatac gacagtattg  45780
caaaatgtct atctaaaaaa cgattacatt tgttataaaa atgacacgcg tcgtatttca  45840
agcgtgtgcg cgctgccatc gaaattccta tttcctgaac atttgctaga catgtttttg  45900
atatgaacaa ataacaaatg atgatgtgta tttaaaatgt attttattta ataaaattac  45960
atagtatcta actgtatggt gtatttttat tattgaatta ccgacgacgc gccgaattcg  46020
ttgagtaatc cgcaggcgtt gacgttgcgc cgcactcgca aaaagccgtt ttcgccccaa  46080
tcttctcccc atgaattttt tataatccaa tagggtacat tgttttcgat accccaaccg  46140
ataagcaaaa cggcatgatt caaatcataa atgtgacatt gattcaatat tcctctgcga  46200
taattaataa tgtccatggc gtcgactgct atcgccacag gtccagtagt gtacaccaat  46260
tctttcaatt tattctcgtc acgtatgtcg tatttaaagc aagagttcaa tttgacagct  46320
attttgcgat tatctaaagt gcacatttgt tcactgccct gatagggata atctgcttcc  46380
gtttcaacac cgcccatcag caatagttct tgaaacgcta aatgcatcaa accaccatta  46440
caacctaaat caacttcatc gcaatctaac agttgctgtt cggacagatc tattaatttg  46500
ttgtgccgta tggcatattg actttcaata ttgcctattg ctacgaaagc ccaacacgat  46560
ccgcaaactc cttgatcttt tatgggagtc actttattgg tgtcgcgcca atcataataa  46620
tcgggcaaac gtatgtcggg cgcgccttta actattctat tttcgcataa tgtgtagtgt  46680
tggctaagat ttaaaaaaaa accagtgttc gagtgtaaca cttcgtctgg ggtcttgtca  46740
ctaaatttgt tcacaccaaa ttgagccgat gtggaaagcg agtcgttatt gttcttgtta  46800
ttcaacagat tttctcgatt ttgagaattg attttgttca aattgtcttt gaacacattg  46860
taacggtatt ggtattcttt gggatcgtcg tagcttttgt tgtattgctg taggaaatgt  46920
ttgaaataaa tttcagattg atctaaatta taatacagga ctggcactgg cgaagacaat  46980
ggcggtggcg acgacgacgt atgcaaagaa atttcatcac acacgacaaa cgtccacaac  47040
aaggacacaa atgtaataat tttatgcatg atatttgaat ggtacttgcg cataaaacta  47100
aagtacctta attatgagca tgacaggcac gaatcaaccc aaaggtctaa gtatattaaa  47160
aatagtattt aatttactca aaagactatc gatattggtc tttgtgtctt tttgtaggga  47220
aactatttgc gctgatagat tttcgttaat ggcctgtatt tgagctgtcg tatcggtttt  47280
aatagtgttt aattgagtgg ccaatgtgtt gagttgtgtg tttaaagatt ttacgtcggc  47340
actgttgacg ctcattgttt tagttaccgc gtcaagtttg gtagttatat ctgaaacttg  47400
agattttacg ttatcaaaat tagctatcgc agcagtattc acgccagtga ccgctttttg  47460
aatttcatct gtttgcgttt taatattgtt ttcaaaccta tcagctgtcg tactaacatt  47520
ggtaacaata gattttacag tatcgtcaat agtgctgatt tgatttaaaa ttttatctat  47580
cggcatttga gtaattgtgt tgttcaatgt ttccatagac gacgtggacg cgttcgtgtc  47640
tgttttgacg gtttttaaac ggtcgtcgac atttttaatg tcctgacgaa ttatcagaaa  47700
aatattattg ggatccgcca ttatttcaaa tgcatacaaa aatacgacgc tataattttg  47760
aataccttat acaactagtg atgaatattt ttcatccgaa actattacgg cattgccaat  47820
tagactgttg cttagtaaaa cgatggtttg cggcgtgatc taatacgaaa tcatcaaata  47880
cgacatctgc acaattgtaa aaaccttcgc caacggcatc gtgacgttgc catcgcacat  47940
acaacatgaa ttgggtctgt cgaaaaggaa cgaccaccgg tataacataa atcatagagt  48000
ttgcgcatga cgaatcaatg tcgttgtttg caattagttt gctgccgttt cccccgatca  48060
```

-continued

```
gttccagatc gttccatgtc acttgattgt tatgtgacca cgcacgcttt gtaatgtaca  48120
cttcaaaata gcttggttcg tgcaccgttg tcgggcaaaa gtacaaattt gtggcgagtc  48180
cacgactata caacgaatca acgggccagt acaaagtgtc cggacgccaa tccggatacg  48240
gttcgtccat gcccgattta tcgccgaaat ttttcaaacg atcgttggcg ccggcagcgc  48300
atagattgtt tttaacaaca ttgtcgcgta cgtgttgtgc atcgttataa tttggacctg  48360
ccaatgccgc gtattcaaag tattgttgaa acatgtattg agctgcgttt gcggccacgc  48420
ccgatgattc accggcggcg cggtatttcg agtacacatg tttgtatgct cgacggcacg  48480
cagcgtcggg tatttgatcg ccattttcgg gccaccaaaa attattgtca cgaaaacatt  48540
tgtattgacg cgccgccggt tttgacagat aaccgtgtcc gtccgctgaa tatatgaaaa  48600
taaatgtaca taacacatat aatcgcagca ttgttctagc tataatatac tcttacataa  48660
tttacatatt aatctttgct tccactttga tatcaaaacg ccggcaagtt tcgaatgaat  48720
gatgtcattt catttaataa ttatgtggta tagatcacgc aatatgacgt aatttatttt  48780
ttaagacgaa caattcgcaa gcaaatacaa aaaagatgat gcaatatttt aacggataac  48840
gtaatttgtt tttttctaaa tcatgaatcg aaacaaaaga tcacggcccg tttcgaacaa  48900
aaaaatccaa gaccggttta aaagtacgtt atctttgggc gtggcgagaa tcgtggatta  48960
catttgtgat tggaccattt ctagatcacg ccatatgacg tcatttgttt ttttgggtcg  49020
agccatcgaa tgttctagaa caaattttat cgatctttgc cggcggtttt atatgaaagc  49080
gcgggctagt ttcgaattta aagatgatgc aatattttaa acggatgacg taattttttg  49140
ggcacgagtc gaagcaaaag atcacggccc gtttcgaaca aaaagatcta agactagttt  49200
aaaaatgcgc ggtaaaattg tgcaatacat ttgaatagtg ccgtgtgcaa aatgacgtaa  49260
tttgtttttt tttgggtcac gagtcgaaac aaaagatcac ggcccgtttc gaacgaaaat  49320
aaccaagacc agtttaaaag tacgttatct ttgagcgtgg cgtgattcgt agaatacgtt  49380
tgtgattgga ccatttctag atcacgccat atgacgtcat ttgttttttt gggtcaagcc  49440
gtggaatgtt ctagaacaaa ttttatcaat ctttgccgac ggtttcatat gaaagcgcgg  49500
gctagtttcg aatttaaaga tgatgcaata ttttaaacga atgacaaaat tagttttttg  49560
ggtcatgaat caaaacaaaa aattcacaac ccgtttcgaa cgaaaagatc caagaccggt  49620
ttaaacatgc gcgggaattt ttactttggt cgatgatatc atttgttttt ttggattacg  49680
agtcgaaaca aaagatcatg gcccgtttcg aacgaaatga tccaagacca gtttaaacat  49740
gcgcgggaaa cattatcttt ggtagatgat gtcatttgtt tttttgggtc acgagtcgaa  49800
acaaaagatc acggcccgtt tcgaacgaaa tgatccaaga ccagtttaaa agtacgttat  49860
gtttgggcgt ggcgtgattc gtggaatatg ccatcgaatg ttctagaaca tttataatcg  49920
atctttgccg acggtttcgt atgaaagcgc gggctagttt cgaatttaaa gatgatgcaa  49980
tattttaaac gaatgacgta atttgttttt ttttgggtca tgaatcaaaa caaaaagatc  50040
acggcccgtt tcaaaagaaa agattctaga ccagtttaaa tatgcgcggg aaatattatc  50100
tttggtcgat gatgtcattt ggtttttaaa tagtgccgtg tgcaaaatga tgtcatttgt  50160
tttttttggg tcaagaatcg aagcaaaaga tcacggcacg tttcgaatta aaagattcaa  50220
gactagttta aacttgcgcg gaaaacatta tttttagaga tgatgtaatt tgtttttggg  50280
tgatgaattg aagcataaga tcacggcttg tttcgaacga aaaaatttca gattagttta  50340
aacatggatt aaccacaagc catatgtagt tgatcatgcc aattcaggct cataataatt  50400
tcgggtcccg ttataatgaa atctatttgt attcagtaaa ataatttaga aaaaagggct  50460
```

ctgactaaat ctcaatttga cctcaaggaa attgagactt ataccacaaa ctatactggc 50520
caaaaatgga ttatggcaaa tccttttgct gaagcgttga attatagcaa gcctaataaa 50580
gctattttag aaaaggtatc ccaacaaaat actagaaatt tggaacaatt acgatcgtac 50640
cagattggta cgatcgatga ctcatcgctg tcgcttcatc cacgtacgaa gtttatcaac 50700
cgggcgggcg tgttcgagtt gatcaatgcg agcgacatgc cgggtgcgaa gcgtttccag 50760
gcgtggaaca acaacgactg ctgcccacac tgtgtcagga gggagagtac aaaatggcga 50820
gggacgcgcc cgccaacatc gcgcatggga tgaacgccgt gcacgtggcg accaacgagg 50880
gggtcgcggc tccgtggatg aaggatctgg accatctgaa gactgctatc gttgagaaag 50940
atcgcaagat tgacgatcta acgctggcac ttaagagctc gaacgatgaa ttggtcaagg 51000
cgaacgctca tttgtgcgac gcaaacaaag cgttggtatc ttttgcgacg gaaatgatat 51060
ctgcgcgtag agactgcgag tccgctcgta aggattgcga ggcggctaga aaagaaacgg 51120
cagagctcgc caaccgaatg gctgacatcg cgcaagacgt catagccaag cccagcgacc 51180
cgcagctgct acactcgttg gcagtgtgct cgatgggcga agaccagtac gctttcctta 51240
ggccgcaaaa acgcagcttg aaacgcagcc tcgatcgtct gtcggtcgac gagaaggaca 51300
tcgtgtacaa gagcgattat gtgcccaatt cgatgaacgt gctgaacaag gtgaaggagc 51360
gcctgccgaa agagaagtac aaagcgcgcc acaaccgcat cacgctacac gaagatttga 51420
cgcgcgaaga cctgttgcag gcgatagaat cgaccgtttc ttcgcgccaa gtcgcaataa 51480
ttgtgaacaa ggccactaac aacagcgtag ttggtaacaa gatgtaggtt ggcgagtcga 51540
agtatataaa ttttgtgact aataaaaacg tatcatttac atgattgatt tttatttctc 51600
aattttacat caaatgtatc attaggcact cgagagcgcc cgagtgcagt tatgttaaac 51660
aattaattct taaaatggcc gttaccacag ttcagtttgc caattctgaa ttagaagtga 51720
tcagtattaa ggacgatagt ggtcagctgt ggatgttggc taatcctttt gcaaggattt 51780
tggaatactc taatgcccca aatgcaattt ctacgtatgt cagagttgaa aatcaaaaat 51840
attttgaaga aatcaggtct gcccgatacg ggcagacttg tgtcatcatg cggttcaaac 51900
aaagtcaaag tttatcaatc gcgccggcct gttcgaactg attcaggcgt cgcgaataat 51960
agtgcaataa ataattctta atgttaattt gtctttcctt tattttctat ccatttacga 52020
cattgaagtg cccgagtgca gttgtgttaa acagttaatt cttaaaatgg ccgttattaa 52080
agttcagttc gcaactctga attagaagtg atcagtatta aggacgataa tggtgaattg 52140
tggatgcttg caaatccgtt tgcgagaatt ttagaatatt ccaacgccaa cagagccgta 52200
agagttcatg tgctagagaa aaccagtgta ttttagaaaa aatacgacca gaccactgcg 52260
gtctggatga cgtcacactc catccgctat caaagtttat caatcgcgcc ggcctgttcg 52320
aactgattca ggcgtcgcgc atgcccaagg cgcaggagtt ccgcgactgg atcaactcgg 52380
acctactacc taagctttgc gacgatggca agtacgacat ggcaacggac gctccggtgg 52440
gaatcgccgt gggtatgaac gccgtacact ccatcactaa cgaaggcgga agaggctcca 52500
tggatgaagg atttggcccg cttgaaaaat gccatcgtcg aaaaagatca aaaaatcgga 52560
acactgacag aggccctcac tcaatgtaac gagaaactag tgaactttgc cagtgctctt 52620
gttcaagcca acaatggcct cttggaagcc aatcgcaacg ccgagaccgc caggcaagac 52680
gctgaacgat cgaggaggga aacggccgag ctcgccaatc gcatggccga catcgcgcaa 52740
gacgtcatag ccaaaccgtc ggatccgcag ctgctgcact cgttggcggt gtgttcgatg 52800

```
ggcggcgatc agtacgcgtt ccttcgaccg caaaagcgta gtttgaagcg cagcctcgat  52860
cgcttgagtg tggacgaaaa ggacatcgta ttcaagagcg attacgtgcc caattcgatg  52920
aacgtgttga acaaagtgaa ggagcgcctg ccgaaagaga agttcaaagc gcgccacaac  52980
cgcatcacac tacacgaaga tttgacgcgc gaagacctgt tgcaggcgat agaatcgacg  53040
gtgtcgtcgc gccaagtcgc aataattgtg aacaaggcga cgagcaatat cactagtatt  53100
ggtaataaca ctacgaataa atagagtcgt cgtacatggt cgttttattt ttacgttcaa  53160
tttatccatt aagacccatt gtactctaca caggacatcg agtgtgagct atatcggtac  53220
ggtgtcgatg acgtcaattc gtaccgatac attattttta gtatgactca caactgctct  53280
cgtggccgaa cgacgcaatt tgtttttga gtagtgtcgt gtgcaaaatg tttttgaatc  53340
ataaattgaa gcaaaagatc ataggcagtt tcgaaccaaa aaattcaaaa caagttgcaa  53400
catgcgcgga aatttttac ttcaaacgtg gcgtaatatg acgtcatttg tttttgggt  53460
cgagccatcg aacgttctag aacaaaattt atcgatcttc gccgacggtt ttgtatgaaa  53520
gcgcgggcga gtttcgaatt aaaaatgatg caatattcta aacggatgac gtaatttgtt  53580
ttttttcaa ctaaacatgt taggttaatc ttgtttagga ttcggttcgg taatgtcatt  53640
acttgacgcg tgattatatg acgtaatttg tttgtaacta tttaaatatt gtgtaattat  53700
gttattttgt attgtcacga catcgattct atttatattc atgacataaa acacaaatgt  53760
gccattattg aaaagtttca tcatttattc gtactatagt ccagtggagt atatataaac  53820
agtgctgttt tattgaaaac atttacagtc atggagccta ccacactgta caagatcgat  53880
cgcggcagcc gagctatggg ttatgacata cgatcgagcg actatgatta tattgtgttt  53940
tccaaatgta ctcgtgaaga gtttttagac catgtgtttg ataggaaaaa gtttgtgaat  54000
aaacattgca aaatcaaaaa cgatgatgtc actctgtcca atttgtttgt cggattgaag  54060
gggatctaca atggcaacta cgcgcacttg gcaatatttt ctgaaccgcg acactttgga  54120
gttgacgatt attttttata caagtttgtg aaaaccgttg ccaaactcag aatgccgctt  54180
atactgaaaa ccatgctaaa atacaatcta aattctgaac atgtcacggc caaacaggct  54240
ctgcaactac tgtacaatgt gtcttatgcc gattatgtac tgaggcatgg tatgccagaa  54300
ggaatcgtta gaatgccagc ggttctgtgc agtactgttg ccaaaaatgc gtacgctact  54360
ttgatgtcgc agcgtttgga aaatgatacc gaaaacatac gatacaaact agaagatgaa  54420
gtaaaatttt tgatcaaata tcgtaacaac gtgctggaga gtgtcaatgt catgccgaat  54480
cctgaaaatc gtcccgacat cgaaacgagc atttgtaatt attttctgtg cgaaaatgta  54540
aatttaacga tacctcaata aaaatcaaat aaaaatgtta tatgttttat tttcaacatg  54600
agttacatct gacaaaaaaa attattacaa aacaccatta ctgtaaatac acttcgaatc  54660
gttcgactat ttttgctcga cacaaacagc atcgtttaca tcgtgctgcg caaattttgc  54720
aagtcattac atgacgacac ggcataaaac aaacctgtcg tgactggtcg aaacatattt  54780
tgcacaaact atcatcttcg ttggtgttgt ttttgttggt aacgacaaga tcatcacgat  54840
cgtttccgtc ttcttcgcta tagtttgatt tgtctatatc gatcagagta ggcgcggaag  54900
gaatcgattg gtcgtggtcg tttacaaaaa tacaatcaat tgaattgata cgatgaatat  54960
cggcaagatt gtcgttgaaa ttaaacttga cgattacaag caaacaatat gcacatctaa  55020
cttcggtttt gactccgtag taataaaatc cattttgtgc gagcaaatct aaagaatttt  55080
taaaatagga cttggccttt ttgtattgac gaaacgagtc gcgacgcaga tattcgcttt  55140
gtcgcagcaa atgtagactg cgtggacaca gagagaatga atgtgaccga atcgagcgca  55200
```

tatcaacttt taacatagta aatgtgcaaa aattacaaca atatgtgctt gttttgacat 55260
tgtaatatat tccagccttg gccagttttt ggcacaagtc acggcttaaa ttcacatgat 55320
aaaatgtaat aagacgattg tctagaaaat gatagggcgg cgccaagtct gctttgatga 55380
cacaatccat tgccctggcg gtgacagctg agtgtgtctt atataaatta caacacttta 55440
ttgagtattt tctgatttgt tcaattctct gagtagctta ttcaaagctc tgatttgttt 55500
tctagcgtat ttagttgttt ccaaatcgat gtgctgagtg tcatggtcga ttgttaacaa 55560
tcttggcgtg gccaatctat tcaaacacac cagatagcgt tcagcgttag ctggtctcga 55620
cgatactggc ttgaacacgt aaaattcact aaagttacta atgaaacttt ccagcacaac 55680
gaatgtgttg cgagcaaaag tgtcaaaaat tttcagcaca ctattaccac cgacgcgcaa 55740
acaatcaagt ataatctcgc actgtttcgc tattagcggt aacatgatca attcttgatc 55800
gttttctttg ccgtaaacgt ctataccgcc gtcggccacg acaagatcac atcgatgtcc 55860
gcacagcatg tttaatttgt tctgaatgtc ctcttcgaaa atatcaccag tgttggcgtc 55920
tccgtaaacg gcacagaagt tcggcacaaa cacattatag tcaagatggt tgcgtagagt 55980
gacgccgtac ccctgactgt ttaacgtact gttgttggaa atatagtttg caaattggcc 56040
cggtcctccg cacaaatcca catacaatcg tacatttcga cacagattga aacgttcgtc 56100
gatctctttc attttgtgcc aacagcgtcg gtgacgatgt gattttcgtt tgtccaatcg 56160
gtcgcgtgct actttaattt gactagttgt gaattcgtcg agttgcgatt tcagccggtc 56220
caatttaatt ttatatttcg atgtaatcgt cgaggacgtc attatctcgt aaactgttat 56280
cagatgggaa cacgaaagct actacgagcg cgagcaggac tgtgcaaata aaagccaaaa 56340
atatttgtac tgaagttata ttgagcgggg atagcacagc gcgcggtctg ttcagtgctc 56400
gattaaaaaa ctcactatta atcagcagag ttttatttgt gatttcgtat accaacggtc 56460
gattgtaatc aaagtttaat acgttggctt tatcgaaatt agttcggtaa ttgttgtcac 56520
gcggactcgt caacaacaaa tcgatcagca aatctttcca agcatattcg cgactttccg 56580
gcgatatttc tacgcgatcc gaattcaata tacgccaacg aattcttgac attgatattt 56640
aactgatcga tatgtcgaat atggatataa gccctgtcaa acaactcatt gatatcgaaa 56700
atgatgatgc aatgaatacg ccagagaaag gaatgaaacg ccctttgatg cgaactatgt 56760
cgagtgtgga agaaccccaa gccaaaatgg caaaactgcg tacgctcaat gtgaaaggac 56820
aattgcttac caaaaccaca atgagtatca acaatgaaga ttattactta tttaaatttt 56880
tggtcaacaa caagagtatc gactattacg gaacgcaaac tcaatttttc tcattgatta 56940
acaataaaac ttacgaattg gttttgcaat acagccgcaa aaagctactc attaaatcct 57000
atgagcaatg cgaagacgaa gacctgttga tgaccgtatg caaaagtgtg accctccaag 57060
agttctgtgc caacgagata aaatcgctgc tggcgaaatt cctatacggt tttaaagtct 57120
acggcagttc aaatgtttac aagttagttt ttgtgatttt gctcgaagac aacaatggta 57180
caatcaacgg tgttcaagta gaaatgatga gcgacttcaa acgtttaagc ggagccttca 57240
agaaccatgt cattgaaaat gaaaacgatt tgtttgagtg tatgtacaaa tctgaagaga 57300
aatatttcaa tttgtaccgt atcaaatgca atcacaacgc aaacaatttt aaaagtttgt 57360
cactgtcgtc gaacagtcaa ttggagcgtc tcgaaaccga cgacagtatg tttgaatatg 57420
aatttcaata cgattacact gtcaatatta gtcgttcgaa caagattata cagaaacacc 57480
gagttaccgg caattttact tcggagagaa atatctatca gaactccgat cgttttgtga 57540

-continued

```
tcagttacga cacggctaat gaaaaaatca agaccagcat ctacaatcgt atggaaaatg  57600
cagaatccaa aactgattac gacacatcga taacgttgaa agacgtaact ttgagtcaac  57660
tcaacagttt gattgaatcg aatctggtgc aagttgacgt gtaccttgtg actgatccaa  57720
ataatgttaa aaacaatgtt atcgccggca tcactaagat tgaaatcgac ggcacttacg  57780
aacctttgta aatcttttgt gaatatgttt gcataaatat atgtatatgt atcaataaat  57840
gttattaaac taatgtgtaa actttttttta ttacaaaaac cctttgaaat ttatttctta  57900
taattttttt gttatttctt cttgttcgat ggtttcaaac gaaggtaaag tattaagatt  57960
ttgagcgtat tgagcaaagt cgctatctat tattgcggtc atgtcaattg gaagaactcg  58020
gttgatatta tatttgtaat taattaaagt caaataatct ctcaatccaa tggcacgaac  58080
caatcgagtg taacctttttg gtggtaaagt tttaggagac gcctgtaatt ctatgagagc  58140
atcgtctaac gctcgttgtg caataatcgg atcgttaaat atatcgttga acaatggatt  58200
ttgcatccac tgttgcgaac gagtttctaa acctttttct aaacaagcac gtttactctc  58260
aacagcagca gtttcgtcag ccggttctac tgatcgttta ttgactgttc tattagcaat  58320
agttgtagca acaatactgg caggagccaa tgttgtaaca tcattaattt tttcggaatt  58380
attaacggtg cgcatgctaa ccgatcttaa cggcggtctg acgtttggtt ttattgttgg  58440
cggcgcggcc gacggtcttg aatacggact aggacgcgtc gttgtaatgg ttgacatttt  58500
acccgaaatt tccgcagaga gatttttgtc tagaatattt tcaattctag ttatttgcac  58560
tcttatcgat tcgatgttgt tcgttgcggt ttgtatatcg ttggttatgg cggtcagacg  58620
ctgttgttgt tctgcggcta cttggttttt gtattcggaa atttgtactc cgagagcttg  58680
acgcaaagcc gttatgatac tgttgtcgtc ggcttcttta tttttcaaat aactgatttg  58740
atcatttagc aaacgcactt cgtctacggc ggctacgctt ttttgcgtcg tactttcaag  58800
ccgttcgatt tcgcgccgca ttacgtttac ttcggtttct agttctttat attgttcttc  58860
gagcaaacgg ttttgatatg tgacggtttc gttagttgtt tccgttttga tataattgtc  58920
cgattcgatt ttgcatcggt tttctaattg cgtgtaattc gtttcgatag ttatcagacg  58980
ttgtttcaat tgatcacgtt cagttttgat ttgttcgtag tcttcaattt tagcgttggc  59040
ccgtagagtg tctatttcgt ttttttgttc gttgatttgt tcccgtaaat ctctcaatgc  59100
ggtctgttcg ttttttactg atagagtttt tcggtcgaca ttggacatta gatcgatcaa  59160
acgctcggtc agattagtga gaaacgtagg tgaaacgtcc acaattgtgc tataatttaa  59220
attttgtaat tgtgccgtat ttctgtcgcg agctatgatt gcgtcggcca attgattgta  59280
actcgatttg tacaattgca gcgcttcgac acgatcgttg accgacgtca atatgtattg  59340
taaattagtt tcgtcggcga gacccatgtc cgatgaattg gtttccattt gggctggtaa  59400
tttttctgtc ttcacattag ccaacaaccg atcgtgtatc aaacgaagat tgtcgtgcaa  59460
ttgcgatatc acattacaaa cctgagacat agacctaaaa gtgctgcccg ttctgccgtt  59520
gacgcaatcg agtaattcgt tgatgtcgtt tctttcaatg aatttttgat ctaaacaata  59580
caaacgacgc aaagcggcca cgaaattggg tgtcacgaca gaatcatcgc taaatgcccg  59640
cattactaca tcgatcaagg tcgatgtaaa tttgttcata ttttgcgatg taaaatctac  59700
acaaacgttt tcaattgctc ccgaaattaa tgacacgtca ttattagtga gtcgtgtcgg  59760
cggcgaagac ggcgtgagac ccgccgatgt tgtcgttgcc ggttgtgcgt tcggtggttg  59820
aactggatac tgattgatca cttgtacagg cggcggtggc ggcgcagatg gttgcgtcgg  59880
ctgcgccata ttgttttgga ccggtgttcc gaacgcgtca acactgttcg ctaacggaac  59940
```

gtttgaattg taatcgtatt tgtaattgta gttgtgtgta atctgactgt gcatcggttg 60000
gtcgtgatga cgaggcgaag ctagtgcttc tattatcaat tcgggcactt gtaaatcgtg 60060
tcgatcgata agatagggcc tgtaaaggac tataattgag cgtatgcgtt gcaaaatatc 60120
ttcagtagcg tccaagcttt tgcatcgttg actcatcgag tttattgttc gcaacaaact 60180
ctggaccgtg cctgaattta catcggtgtt tttatatttg gctgcgtacg acggaatacc 60240
tctgtttcga tacatgttag taacaacgac gacgacgacg acgacacaat ggatattgcc 60300
ttattgactt ggaatgattt gatcggtcaa ttgttgcggt tcggtaatcg acaacatcga 60360
accgtcattg agcctgaaga tgtgtttaga atcgtccgta tgacttatca cgacaattgc 60420
ttgctgatat tttttactgg ctacgtgtca tcggatccta cgaaaatttt tcaattttac 60480
atggagacca aatgcgattt gtattcgtat cgtcgctgct acaatgttca cactaacaac 60540
gagtgtagat acaaatgtaa aagttataaa acgttcgtta tgcccggttt gcgcggatcg 60600
tacaacgaac gtatcaacat agttcattac aagagaacac ccggtgaaca tgacagaaac 60660
aacaacaaaa attgtctcga ttcttttta aaagacatca acagagtaca tatgcaaacc 60720
gatctaatgg aaggcaatta cgtacaattc aaacagagac aatgcgtcac tgatcacaga 60780
ttgtgtttgc aaagtaacga taacactttc aaagacatat tcaccgtcat cgatccggac 60840
agtttgaaac gcgaaatagt tcctgtcatt gcgtgttacg acatagaaac gcattcggac 60900
ggacaacgat tttcatcggc tactgtggat aatatcattt cgatatctat tgtggttcgt 60960
cgtgatggtg tcgataaacg tatatgtcta tattatatgg acgacacggc caaagatgta 61020
aaatggaaca cagacaacga tgccataaac gcggccgaaa tttgggcggt acatttcaag 61080
aaagaaagtg atatgttgaa agcgtttttt tcgttgtttc cattgttgaa tatggatttt 61140
ttgctggatt ataatggtga cagattcgat ttaccattca tactggaacg cgtaaaacgt 61200
ttgaacagtg gtaaagaaat tgtgattaaa cgatacgatt tgagtccggt tgctataaaa 61260
actgaacaat tgtgtgataa atttcagaac aaaatcaata cacattattt tacatattat 61320
gtacacgtgg acttgtatca gtttctcagt tcggactcgg aacaaaacga tgtggaaaat 61380
tttcaattga acacggttgc caaacattat ttgaatatgc aaaaagttga tttaaaaatt 61440
acggacatgc tgcgtcggta caatgaaaaa ttgatgaaag acatcatcgt atataacgtt 61500
caagattgtg tgctacccat cgatttgttt ctgaaattgg aaattatgga ctttatgtat 61560
acacaatgta tgctattgta tttgtgtacc gacgatgtgt tacgcaatat ttctcataaa 61620
gtgaatgtgg ttctatttca caaggcattg atcaatacgc gctacgacga aaaacgcaat 61680
tgtaccgtac ccgaaccgta ttttttcaat aaacacgatt tgtcggtgac ctcgggtcgc 61740
aaacgtaacg ccgccggaga ttcggtggac gatcagcaaa tggtcgattt gagtctgtta 61800
cagcggcggc ccgtccccgt agatatgata ccttcgaatg ctgtaaaatt gtgcggtaaa 61860
agacaacgct gcgtgtacaa aggcggtaaa gtgctggaac ctcaacctgg tttcaagcaa 61920
tgggtggtca ccttggattt taattctttg tatttgagta taatgatgta tgaaggaata 61980
tgtttgtcta acgtttttgt cgcccaggac gacaatgttt atttgcacaa agatttggac 62040
gctgtcaatc ctaaattgtt acgagaattg ctcgatttgc gcgccaaata caagaatcgt 62100
cgcgacaaac acgaacccgg cacgtttcaa tacaatttga atgacaaaat acaaaatgcc 62160
gtcaaacgca ttgccaacag tatttacgga tattttggaa tttttttcaa accgctcgcc 62220
aattacatca ccaagatcgg tagagaaaaa ttgacggaag ctattgtacg catacaagca 62280

```
atgagtaatc gtgctgatat tttgaaagat tttaatttgt caagaatcaa ttttcgagtc  62340
atatatggcg atactgattc gtcgtttata caagtcgatt ttgaaaaaac ggacattccc  62400
attaaagatc aacacaacac tataaaaacc attgtcaacg attatgtact aaagacgttg  62460
aatgcctctt ggaacggtta taaaatggct ttggaaaatg taatgctgtc gttgattttg  62520
ttaaaaaaga aaaaatattg ctatttgaat agcgaacaac gtatcaaata taaaggatgg  62580
ctagtcaaaa aagacatgcc gttgtttatg cgaaaatcgt ttaggcaagt ggtggactcg  62640
tacttgcacg gacacagttt agcttgcgga ctcgcattgc tgacaaaatt gatgaccgaa  62700
tattatgaca attttggtgt caacaacaac tacaacgaat atggttttag tatgacatac  62760
aatgagaatt cgactagtgc caaaaaaaga aaaaccacca ccgtttcaac cagtacgcgt  62820
cccaacgttt tgaccattgc caaaaaatgt tacgaagacc tgaaagggag cggtactgat  62880
tttttaccca caaacggtga tcgtattccg tatgtgctca ttgatgttga gggcagcgtt  62940
acgcaaaagg cttttcctct taaactattc gattcgtcgt acaataccat caattggatc  63000
aaacacatgg gtattttgtg tacatttttt aacgagttga tcgaagtgtt tggcgattcg  63060
gaaatttttc aatattattt cgaccaaatt acgtctgttt ttatggccca acaacggtac  63120
gatgtaaaat atccagtttt ggtgacgata aacccaaaaa agttacaaac cgctgacgat  63180
agcgacgacg atagcgatga caaagaatca aatgtcgatg atgccaatca atgtaaaccc  63240
attcccaatc atactactaa atttgcattg cataaacgtc aaaaatctaa aatgactaaa  63300
tcgatgatta tcgacaatga atgctctgtt tgtaagagtg ctgtatgtta aattgtattc  63360
tatgtgtgta tgtgtgtatt tgtgttaatt gattaaataa aatataatta attgagtatc  63420
agttgtttta ttgtgtacag tttgtttcag tattttcctc gtcgactgta ttgctaacaa  63480
ctgtcagtag ttgttttaat agagtcttgt aatcattggt cacagatgta tcgttgtttt  63540
cgattaccac tttagattct ttatgtattt tgtcacgaat ttcttgcaat ctgtttacga  63600
ttaattgaca atcattcttc acatttgatt gttgcaaaga ccaaaaaatgt actttattac  63660
cgacaaaatc ttgtatgatg tagtctaata gttcaactac ggtatgaaca aactctttgt  63720
agtcatctgc agttacatta tcgtttgata cgaatgcaac aattagatta attaattttt  63780
ttatttgttg gtaatacgca atgtagttgg ttttgaggat ttgtgtgttg ttcgacattt  63840
gttcgtgttg tgtgcaactc tcgttggaac aattggttga agtcatgata aataataaca  63900
aggaaaattt ttatatagtc ttataataat atttttaatt acatcatcgt attagcgata  63960
tacaagagca ttattaaatt cttgcaccat aaattcagca atatcgtgta tttccggttc  64020
ggtcaaacgt tcgtgttcaa tatagttatt gactatactt aaaatgtagc cgttgtcgta  64080
tattctgcaa tacaaatatt caatttggtc ttgggacata ttgacgtcca cagcgttcat  64140
tatgttggcc atggcttcga cgggcacctg ttgttcgaca aacatttgga gcacagtgac  64200
gagtttgtaa cgcaacgtgt cgtcgcgttc caagtccttg agagcatgtt taatgtgtgt  64260
tgttgcaaag gccacttttg tgactactgg catcgaagtg gcaatttgag tgacaaaatt  64320
tttgatgaaa tccatgcttc tcaatcaata gaacttgtgt tcttatttat tattgcatcg  64380
aacgctcttt ccaattctcg tttctttttt atactcttag atttaccggt ttgtaagtcc  64440
gccggggtcg aatcgggttt gatataatac acgtgcagca tcattataaa aataaaaaac  64500
agcaacaaca agaaaaacat taacgtactg aacccttcgt tttgtcaaa gatgaacccg  64560
agagctatta aaaaaagaaa cgcaaaatat aattgcattt tgcttcaatt gttgtcgaaa  64620
cgtacttatt acaaatactt aattaaaaga taacaaatcg gcatcgtcgc cgctactgat  64680
```

attgttgtta aaatcgttgc cgctggtgtt attactactg ctgttgccgc tgctgctgtt 64740
gttaatatca taatttgaaa tatttgcgcc gcttgggttt tcatcaatga tacggtcgtc 64800
gttttcgtcg tcgtcgtcgt cgtcctcgtc attgtcgtcg ctttcgtcga caccaacatc 64860
gtatttgttc aaataatgtc gcgtgctggc cgatgattcg tggttcatga gacgcgcaac 64920
tttttgcagt ggcataccat tattgtacaa attactactc aaataatgac gtatcatgtt 64980
tgaacgtgga cggtccattt ctacattggc ttctttgagt aggcgcttaa agtctttgaa 65040
tggagtcgaa gtgttcttgg atatatttaa aatattggga ttttttatat agatttcgcg 65100
tgccaattcc aatggttttt gcttgatact atttagagaa ttgcttgtgc gatgtttttt 65160
ccttttcaag ccaatagtgc tgcgcagttt tccgcgtttg atgagtgtgt tgagatcgtc 65220
cacggacaaa tgacgggctt cgttgatacg catgcccgtg ccgagcatta tacaaaacac 65280
gatagctcct cgtatcagac cacgatcgtg gacaaattca ctgctcaaat gtttgatttt 65340
cttttctata caatccaata tggtgttgat gatttctcgc aaaactatat ttttttcgtt 65400
atttttata tttttaattt ctttatcgcg tggcaacatc acctgttttg gaattttata 65460
ttcgggcaaa ttcatcgtat tggtatagaa atttatagtt aactgtaaag tttctttggt 65520
tacagagcgc aattcaagca tgcgtctaca caattcttcc ggttttatca atggttgttg 65580
ctgaacgata gaattgaatt ctttgttcaa cgtgtgcgtg tcgtagttat tcaaatattc 65640
gtcatcgatt aggcaataaa ttagttttat gaaacgagac ttgtaactct tcaaagtggt 65700
gggtgcaaaa ggtttgcaaa acatgtattg cgaccacaag ctattgtttt ttacttcatc 65760
tggagtacat ctttgccggt ccgtggtcaa ttcgaaaatt tcatcgaatt tatcgtgatt 65820
ttgtattctt gatttccaat agttgaacga gctctcgttg cgtaatgtag cgggatgatt 65880
gttcataacg actcgatttt aaacgtaata gggttgtcga acaattgatt tccgtctttc 65940
tcttaatata acaaaataat acaatgcata caacagtacc atgacgcaaa acactgccag 66000
caaactaatc aacaatatat taccgatcca tgtggaatta ttgcgtttct gatagttgga 66060
tcgatacgat gtcaaatcgt tgtggccgag tatagatttt gtcgacgaat cgtcagtgtt 66120
gttacctaag tcggccgcat ctacgttaaa atcggatata gccaatttta gcggaatata 66180
gtccactttg tcgttaactc cgagacgatc gtagggtata tctaaattca tatttctgaa 66240
cagctatgcg tccaatgttt ttcaacaata aaaaccaatg tataatgcta aaattttttt 66300
taataatttt gtttgtagct taacttttga aaaatgtaac gacgtaacgc ttcgttttga 66360
aacgctaact ctgttaaact ctgctgacaa gaagtacgat tttgttctac attagaaccg 66420
ttgctagagg gagcgttgag gaacgtcgct ccttgaaaga ggctgggtct cttgccggcg 66480
cgtgtagcca aattggcaat atattgaaat atatccgtgg acgcagacaa tggcgctaaa 66540
aaccctatgt tctctttgag cgtaacgatg cgagcgcggt tcttttcatt gagtacataa 66600
taataatagt ttccatacac gcctgtgaac acgtcgtcaa tcacattgtt gattagatcg 66660
ttgatgatgt tcaatgttgg gtatttgcga ctggacacag cgtcttgcac gttgggcgga 66720
atgttagctc gttgcaacag caacgttata tacgtgttga cgagctgatg gcgaacaggc 66780
aatggaatcg gagtattact ggctacagct tcggctattt gatattgcaa agcttcgccc 66840
aattcatgcg ccgcttccga cacgctgtcg ccgctcacgt tttccgcgcc tttgttgtaa 66900
aatttttggg cataactcgg caacacatta tacacgaatg atggctgaaa tatattttcg 66960
gcaacttcac taccgcccaa ttctttgcgc aaacgtgaat aatgtttgat taaattttca 67020

-continued

```
tcgctatcga accgtttgac cacgttcacg ctaatcggat gcgattccac gcacaaatcg  67080
cgtatggtgt taatgagcat aatcatttgc ggtgtcaaat gcgacatatc gtttgtccta  67140
taaaatctaa tgatacgttc gacgtaatcg acacatttgt tggtccaagc gtccgaacta  67200
gattcctgca gctgtttttg atgctgctga tgctgtaacg ctgtagtgac ggcgtgaggc  67260
tgcgacatta taatttatca atttgtgtgg acagtaattt atcgtcggac tacttatcat  67320
ataattgttg ttcacataca ataatatcaa aatgaatata atgaaaaata tatagaacca  67380
agaaaattcg atcatattaa atatgagcac aactatagtc atagttatta ggacagtttg  67440
catgctacgt cttttgcaca atatagcttc acaattgtga aatgccaaat taaaaacgtt  67500
ttcgccttcg acgaaagagc gcaattcacg tttgcaacac tcgtcgcaca gtatacgtat  67560
gccgataaga tgaccgtccg aatggtcggt ttgaaacgtt ttcggctgac taccagggtg  67620
aaattcgaat gtatatccat tggaaatttg tattttagca taatagtgtg ccaacaaagt  67680
accacccgcc tttttactc gcactttaca cactttaatg atgttcaaat tttcgctatt  67740
attgagattg tcaaacaaat aatgtatcaa cagttcagag tcatatttga tgcgattaag  67800
agtggtcaaa tttttgtcgc ttagctgcag gttcttgaag ggtcgatgca acgtctgccg  67860
atccagtgtt gtcgtatccg tcaatggtgt tgtcgacgtc ggtatcatcg tcgtcgtcat  67920
catcgtttga atgaacttcg ctcgagccga tgtcggcaac aaatgtggat ctgaacaatt  67980
cgtcggattc gttagctata ttggtgtcgg tgtcgttcgc aaggttatta tcacacaaaa  68040
gtgtaggttc cgtgtcgttc gacatcttat tattcgttga aattaaatgt gttttgtcat  68100
cgttgtcatc gtaataggat attttaaaaa gacatgaacc ttttttgaga atagtaggtc  68160
ttgtgtttaa cagaatagcg tttatgccac cagtttcgtt ttgattgtaa gttaccacga  68220
aatatccaca ggcgattgtt gcacattgtt tattgtgcaa attggacagc aaacgagtgt  68280
ccaatatatt gacacaatac gcgccgacgg ccagtttttt taagtgatat tcatcttgaa  68340
caacaaaaga gagcgtgatt atattttttt caggctctct atcttgtaca acgtacgttg  68400
caatgtcaac ggtcccgtta ctgttgatcg ccattattgt gcttgtagtt tttacaataa  68460
tatacttatc catactcgac gaagcggcgg agaatgcatt cgaaaatcgt ttagccgtat  68520
atacagaata tttgcgtcgt accaatgcgg aagtgccgcc accaccgttt ttgggttacg  68580
tgtccgatgt gtacgacaat ttgttcaaag ttacgtattt cgataccgcc aatttggcag  68640
tgatcgacgc cagcgtgcac gacgacaact acgaaacgtt caatttcata aatcaaacat  68700
tcgaacagca aaaatatact aaaaaacgaac cgcgaatagc gccgcatagc acagatcctg  68760
ctaaatttat ggcacgcggc gacgacgacg actggatgga aatcgattgt cccgccgaca  68820
atcattttaa ttcgcaaact aatagatgcg agccggttcc accgtgctac aacaagcagc  68880
ccggtttgta tccgatagac gaaaaactgt tagatacttt agtgttaaat catcgagttc  68940
cgaaacaacg ggatgaaaat gtccccaaca aatatcatcc aacaatgtat ttgcaatgtc  69000
taatgggcgg ctcgcacgca gttcacgaat gtccaccaaa tcatttgttc aacattgatt  69060
ccgcagaatg tcaaattcgt aacgactgcg aaaatcgcgc cgacggtttc attattactc  69120
ccgtgccgga aaacctcaat ataaacgaat atctagaatg tcgcaacggt gacttgaacg  69180
tcgcttcgtg tccggccggt gaaattttcg acagacgatt gctaatgtgt gtcagaggac  69240
atccatgtac catgttcggc gacggataca cgtacatcac cgacgaaatt aacgacaatc  69300
aattctttag atgtacatca cattccgaat cacaattgat cacatgcatc cgccgcgtgt  69360
ttgccaacga tcaatacgaa tgtacgggcg acgatcggtg tttggtattc gaaaatggta  69420
```

```
gcggtataat gccgtatgta cacaatgacg gcatacttga atacgatacg ggctcattga  69480
tttgcgacaa ttacacaata attaatgacg tcatctgcga caattccaat ttactacaaa  69540
acaaactgta ttatgacaag tttgtcgcaa atatacattt gcctaaacaa atctacaata  69600
gcgcaaataa ttcttgtgta ccgttcgaaa ttgaccgtgt caaaattgta aatgatattt  69660
ttcccatcaa tatgatcgag aatgattaca aaattgacgc acaaactgct ctagtgggaa  69720
aaacaaaaaa tatttcgtct ctaatgaacg atactaatac attggccgat gttgtcgtct  69780
acgctcgcga ttctaactcg atcggattga atccggtcga cggtagttct atagaatgtt  69840
tcggcgatta tttgtatgat atcttcgacg gcaaacaaat aaatttctgc aacgatccga  69900
tgtcggccac tcctagttta cgtcaaacgc tcgatggaaa aaaatatttt caatccatcg  69960
ttgtcaaagt gggcagcgat tcagattatc aacagcaatg tgttcggtac ttggacgaga  70020
tcgatcaaaa tttcgtagaa ttagatcatt ttgcggcatc gtatattggc gatatactac  70080
acaatgacga atgttctaca cttttgacac aaattcatga ttcatatact acactttccc  70140
aaaaatatac tacactcgac tctaaatata cgtacgaaaa cgtaaaaaac gaaaaattcg  70200
tcgaacaata cgggacgaat atacacaaaa atgaacacta cgatttacaa aacgaaaaag  70260
atttgcaacc tctttttgat ccatttgtta aaatcgaaac tgttcgaccg ttatttaatc  70320
cgtttgacat ggattcgccg ccgatcattg atagtgaacc cgaaaacaat cctgaattta  70380
atcctaatcc cgtacccgaa cccgaacaag aagaattgat attgaaaaac aaaactgtaa  70440
attttgcatg tttctattct ttacctattt tcaaattgtc tgcgtgtcat ttaaacaatg  70500
aatcgttgat aattaacata tataatttac gaaaaaaagt ggacataagc gccgattgta  70560
tcaacgccgc cggtttagtt aacatcgtta attcctacgc ttatctgggc aacgatattg  70620
gttgtcgttg caagtactca acagaaaaag gcttgcatat tgaacgtgac gataatccga  70680
ttgtgtatac taatctcgac acacaatcaa atgacggaat aaaatataat atgtacatac  70740
atcgcaatgg aaacaatttt atagcatgtc caccagaatt gcttacggac acttttgagt  70800
gtaacgtcga aaacgacaga atgtatatta tgcacaacat tcaacctgaa tgaattcaat  70860
taacatgaaa ttttaatttt agagcagtta taattgaaac acaaaatttt ttaaaataat  70920
catttattat atacatataa tttttgttac atacaacatt tagaaataaa tatatatata  70980
tttatgattt atttcttttt gcctctggcg acacatcaat attgggcaac gccgatcgtt  71040
ttttattgac acttttctta gtctcttcta gtgtatcaat ttcacattgc agagtgttac  71100
gatagcgcaa cagttccatg ttcttacgtt gtatattgtt cttgtctctt ttcattttct  71160
cgtattctcg agtacattct gatttggcgt tcatcaaccg atcgacgtct gctcgatgat  71220
tgttaatctt cgtttccaat tcgttccatg tagattgtaa tttttctaat tttatttgtt  71280
gacgtgtcac attagtttcg atcgttttga gcaaatcgtt tttttcacac aacaatttag  71340
tttgtttgtc caaaagcgat tgtagagaag tggttttttc aatcaactct tcaatatgtt  71400
tattttgatc tgctataata ctgtcatagg cggtattatc gttcgtagta acgccactat  71460
cttctgacgt gacactactt ttgtaaatat ctttggccaa gctaactata tcgatagttt  71520
gtacagtatc atttgcagat gtcgaactaa tgttcggaca tttaacctct tcaatatcag  71580
tgctcgacat tgtactaaca acattcactg tattgccgct gatacagtaa tacgaatatt  71640
taatattgat cgatctgcac agagggcact tgacaattag tgattttcgc atacgcttca  71700
gacacatggt acacaacgca tgcagacatg attgcaatac aatcaaaggc aatactaaca  71760
```

-continued

```
attcttgttg atcgttattg taaatagtgg cgcggcctaa gcacacacaa caattcactg  71820
taatcgaatt cattgcagcc aaatagtaga ctgaatgtga actgtaaatg ttttggtatt  71880
tatagtgccg agccagtgtg ataaagtaga tcgtcacagt cttatcgtcc tgtgctgatt  71940
atctgtttgc ctaaaaacag cggaatatta atctgataaa gttcgtatcg tgataatttt  72000
tgttggagag cgttggcgtt gccttgaaac tgtaacacgt ttctgatttg cagacggttt  72060
tcgttgaccc catacaaata tttgggttgt actgaattgt acaaacgcac cgaggccaat  72120
aatccttcgc tggttatgcg acaagtgtta cagttacgca actgtaaatc ttccgtacca  72180
atggtgagac tttcaggagc tacgcattta cgtatcaggt tttgtatgaa cgtgggcagt  72240
acgttgaacg caagatcgtc ttcgacgctt agaccaaaac tgcgcgattc gttggtatta  72300
gtttgggcac agtaagcatc gggattggtg agagcgagca ctctcaaagt gctattatat  72360
aattcttcga ccacttcggg tctgaatctt tcgtacatgc gtagttgttg gcaaatttcg  72420
ttttgcttct ctttgttgtc gtaaatcatg tagaacacta accgttcggc gggaccgagc  72480
agcgacaaat tgagtaccgt ttcgtagttg ttctgactcg gtatcaaaat acgttcaatg  72540
ccttcggctt tgtcgtccac cagacttttg cctactgtac gatagtagtt gttgcccgta  72600
ccgtccggaa tggcgagagc gagtttttcc attttaaaga atcgcgacgc atgatattcg  72660
cacacgaacc atccgtcatc gacggtggcg tcggacgaac atggactcga atattgatcg  72720
caaaaatcca acggtttcac ggaactaaat acgcaaaagt tgcgcagtcg tgtagttgcc  72780
gtcggcacgg taacaagggc catggcgtta gaaaaagaaa tctcttatac aataaacttg  72840
agtcaagatc tattgtatat aattttcaat tcttatattg taaaacacat ggactaccga  72900
acacaatact gcgaccttat cgactgcaac gatgtacgaa cgcgattcga gagcggcact  72960
gttcagagtg ttctcaaaaa aaacgttgtc atgaaacgat tcgctcatta cgtcaacgac  73020
acggcaacaa ttgttggtct agtcgatcgc catagcatcg aagaagacat cggtgacgtg  73080
aacaaattag atcctcgatt gagaagaata gttcgatgtc aagtgtatcg cgatcgtcaa  73140
tgtccacaga tcgaaataaa attcgaacac atctatttga atcaacacat catggaccgg  73200
ttggattcgc tgttggccgt caagcagatg acacttctca atttgttaaa tcgtactaac  73260
gatagtgtta taaaaaattc tcaactcgga tccgatgaaa tccttgccaa tattcgactt  73320
gaatacgaat acgaaactga aattgccgat gtcgcggtga tcgatcgact gtgtgttttg  73380
gtccaagaaa tggacaaact ttcgcattat caaaacattc atccgttgtt agcgtacacg  73440
accatacaaa acaatatcat ttataggaaa tttattgacg aacgtttatt gtttgatagt  73500
aacggcgcca gtaacgaaat tgtcgatttg aatatttata aatgggcact aaaattggac  73560
ggcatacgtg gcagaggctt ctttactcaa caattagtgg tcatctttat ggacgacatg  73620
caactgtttg ccggacactt gtcgtctccg tttgcggtca acaatgttgt cgcgtttcaa  73680
tgcgaactgt tacccaacaa caggttgtat atcacagatt tgttgcacgt tttcaaatac  73740
gtatacaaca ataagaccca atacgaatgt tctttggacg cttacgatct cgatccatat  73800
agcgccgtgg catgtttaaa ccatatgcgt cacaatcgaa tcgaattatc gttcaatacg  73860
gacaataatg ttacgatgac gatttgcttt caacaattta acgagccccc gttgaatgtg  73920
gctggttatc atagcgtgcc cacggacggt tttgttgtgc tcgaccacga aggtcactac  73980
gtcaaataca aacatatcaa aactattgaa gtcgagtatg attctgttaa taatagattt  74040
gtcactctca acggtccggt tgaaaataaa aaaatcatta tgcaatcaaa actagaattg  74100
cttcatggtc agatatacga agcaaacatg gacgcagaca atttgttcat tatgaaaatt  74160
```

```
cgtaaagaca gattagttcc gaattgatct attgttaaaa ttgatgaata aaaatccaat  74220
gtacagtttt acaacaattt tattttaatt gtaatagatt tttgtatgta gtccaatcca  74280
tgcgctgggt gttctgctgt acgggcggct gaacgtttcg ctgtatccaa cgatagtcgt  74340
tgacgtgatt gtgaaacagc atgctagcgt aaagcatgcc gtggcgcatg agcacgtttt  74400
cggtagcgtc ggttgctcgc atctcgtcga ccataacgat tttttcaccg tatttttcgc  74460
gatacaatgc cacttcgata cgctcaactt gcattatgag atagcctttt atagtcaaat  74520
aatgattacg acacatggga caatttagtt taaaaaatac attataaaaa accggtttca  74580
ttaaacgtaa atgttgacga atcaattcgt tgtcgtattt ttcacgactc tccaccatgt  74640
cgtctatgag caaacacaaa aaatgaatcg aatcccatat ggttgtgaac gtgtacgcgt  74700
agttttttgg ttggggcgca cgtaaattga gttgttccat tttattggaa aattccgttt  74760
tcatttgttc taaagtcatg gtttgcggca acgacagtaa ccattcgcgc aactgatcaa  74820
tttcttgctc ctgaatatct ttgtacgtta ttagacacgc tatatgatat aaataagtca  74880
attccttgga caagatcagg gccagttcct tcgagggcga cgaacgtatc aagtccatat  74940
acctaaaagt gaacaaaaaa taactgtcgc gatatcgtga aaagagaggt gttaacggaa  75000
tcattatgac ctcgtcacag gagcaacaag acgaacgcac aatctatttg tatttgtgtg  75060
atccgcccga aaatgtgcaa aacaataagc aggacgacga tagcgttatt tatttcgaag  75120
gtatcataga atgtatgttg gacgagactt gtgacaagtt tagtttcttt tcggaactca  75180
aaaaggagga ggccttattt atgaaaaaga cctataacga tttgatagaa cacaacaatg  75240
gtacatattt taaatatcac gttctattgg acgcgctcat aatgtataag acattcgtgg  75300
aactggtcga cgactcggct ttcggtaaaa gtatattgac atattgcgaa caattcgtcg  75360
cgtacatatt taaattgttt cgtttgcaaa gtcgtattgt tgtcgtgctg ccgcccaacg  75420
tgaattggga agaggataat ttaagtgcgc ttttaaatca tttactgcaa ctgtctgtca  75480
tacaaattgt ttgagagtcg tcgcatatca accgtaatct tctacaatac caggacgtca  75540
tgatcggaac tatcgtattg atactgatag tgttagccgt actgtattgg ctgtacacga  75600
ataataaatt gaattttgat tcgttgaacg attcgtcagg ccaaagcagc gaatctattc  75660
gcgaaaacaa ccaaggacaa ttgactttaa aatttaacag tccgcgcata aaaactatgc  75720
gcattttgca cggcgacaat aaaatcagta aagtgtgcgt cgccgaacgt ccactgacgt  75780
acagtgaaat aatcgatgaa ggcaatcgta ccgtaggcgc aaattgcgtc tttatgggca  75840
ccataagcga accgtcgcaa acgtcaacat tgaatcagca acaacaacaa caacagcaat  75900
cggcgggctc atctttgcct accactgcaa atagggtcac agctaatttt gatattaaac  75960
aattcaaaaa cacatttatc gtgttcaaaa atgtcgaaat gataaagatt aaagagagcg  76020
ccaatatggt acggtatgaa tccgacggca tggtatattg cttgatcgat tcgcagtcta  76080
ccaccgtgcc cgacctaaga gaagtgtcat atcccatcgt agtgtacact accaatgcta  76140
atgtgcaatt gaaactcaag gaatggagct atgcccagat aaatgatgcc gggactatgt  76200
ttgtcaaaaa tgagacttca tttagaattc aataaataaa attgtattat ctttgaaatt  76260
gatgttttat tttataaatt tttcattatt attattgtca ttattacaca gacatttgtt  76320
atcgtttaat gtattgacac aatcgtctat ttctggatcg aaacaaaagg aatcagaaca  76380
tcgtaacatc attgctgtag gatgtaaaca caagataaac ttttgacaat catatttatg  76440
cggtaacctg ccccagtaat tatcgcattg tacggtacaa tcgcacgaag ttgaacactg  76500
```

ttgtgtttta ctgtcaaaac aagagggaca cacgtgcaac gtttttttcag ggcattgtac 76560 ataagtgtcg caataagcat atagatatct gcctgtgaat ccggtcggac acagattgtc 76620
gtcatcatcg ggcggtgtta ctggtggcgg tggtggttga ggcggtaagg gatctggtgt 76680
tataggtttg gacataaaat gagacaacat ggccacaatt aggtatacaa gaaaaaccaa 76740
aagtattgca tattgaggac tcatatttat tatttgttac acttagcact taaaactagg 76800
tacatttaaa ttaaaatcat ttttattaaa tgacatatct aaatttacaa atactttatc 76860
gtagggtcta tagtgttttt caaaagcttt acgaaattca gcacacaaag ttgtttcgta 76920
aaatttttga taatttcttt tgcgtaacaa tgcatgcaaa aacttatcca aaaatggaac 76980
agccaattcg atggctttat ctactttagt ttcgtcaatg ggtttggcgc ccggtcgcga 77040
ttttactttc aaaatataca cgatcgcttc caatggacta ttgttcaaat ccaaacattt 77100
tagattgtgt tcgtgtatcg aatccgattt taagatttcc ttgtagtaca cgtaaccgtc 77160
tttaggatta cgtttataca tgagaatgtg cgataaaaat aaacgaaccg gttttgtaag 77220
atcttcgaaa tacgcttttt cctgtgggta tttcttgttt ttggcatgaa agtatatcga 77280
accattgaat tgcatcgact ctaaaaattc atgatccgta tacactacac agaatctgtt 77340
gcgaacgccc ctgtcgtaat cgctaatgtg taatggtttg ttgttgacca ccaacaattt 77400
gtaattggct tcgtattttt gactaccctg atatttgcgg cagacactgt tgcttttgct 77460
cgaatcggcg gtgcttttga aaaaagaatc gttacattct ttgagttcgt taatgacgta 77520
caattgcgaa atcaatttgt tggcctccat ttcgtcagtt tctttttttgg acaaggtata 77580 tttgtccgcg tcgcgtttat gtactacaat aatggattct agcagatcga aaaagctaga 77640
tttgcccgag ccgggttcgc cgttcaaata tatacaacat ttttcgtagt cggtcggtat 77700
gcctaagcta gctccaaaat gcatcattaa caatgaattt tttacattaa aatttgtgaa 77760
caatctaaaa tacaaataac cacgtacaac ttgtttcaca aatagcggtg aatatgtttt 77820
gacatcgatg cgcgacatta ttacacgcat atagaaacga gtcaaccatt tggccaaatc 77880
gtccgacggt ctggctacaa ttaatttgtc ccaccacaca ctatatttgc gaagtatcac 77940
tattgtattg gcataatttt tgtaaaaatg atcaaaatac tgttcattac tattaccact 78000
aatataatca ctattgccat cgtcattgca attatttttt ggtgtctttg caaaatcatc 78060
atagtcataa ttgtcagcgg cggtgacgac gacattgcta tcgatggcag cgactgtact 78120
gtcttccatc gttagaattt ttaacaggat atttgcagac gaaaattcat atagtaacat 78180
gtcaatatcg atcgtgtcca atttgttgta caattgatcg attagctgta accgacgctc 78240
gtacacgata ggagcatatt tttcaattat aacgtcgttg gtttgagcgc ccaatatttt 78300
agtgtatgtt tcgggcgcat agtgcaaaca ccaaatcaat tctacaagtt gagcattgtc 78360
acaaaacaac tcaaagatta atgtcaattt gaaagctttt atgttgacat tcatttgagc 78420
gacgcacgaa caagaagtct gtgtcgtacc tgcttcttta cattcgacgc aacgtaaatt 78480
cttaatgagg tctgacattt tagtatcgtt caaataaata ccgtatatga ttaattcgtt 78540
tggtgaagag ttccagattt cgtgaaaata ctggttcaat ttagaatgtt ccgcgttttt 78600
gcattgacga caattgtcga acgaattaat tatcgacatg ttagttttga tgacttttat 78660
gtcgcgacac actttggcca cgtgataagt tttaaaaatt tccatttcat acttggcatt 78720
gttcagcatg taatcgatag tttccttggg taaaaattca ttttcatcga tatatctaaa 78780
cggattgact aagcaattgc caattatgaa cggacaacta ttgtgataat gattgatgaa 78840
cacattgaaa acaccctgtt cggcaaaaca caaatacttc caattattaa atttgattgt 78900

```
ggacaatttt acgcttggtc ctgtttcggt tactttgaac aattcatcgt ctttttttcac  78960
gggaacatag tgtttgccgt tgaacacgta aaagctgcct tgagactcga gtttttttcaa  79020
aaaacccaaa cacaacacat taggcggtaa tttacaagtc ataacccttt cgtatgtgta  79080
tgcccatcgt tcgttgaaac tcatgtcgtc attgagtgaa tttaaatata tacaatagtg  79140
tatggcataa taatagccga gtagcacgca aggattttcc attgaaaaaa aatgtaaact  79200
atcacaaaac ttcttgtaca ctcttgtcga caattgaaca tagggatcac atcgtgctct  79260
cactttcacc aatgattcgg catcgttctt gtagagcgct aaacataaca gttccaagta  79320
gagtttgatg tcggtctcac aaaactcgaa tcgttgtcga ctgaccattt tccagacaac  79380
aatgattaaa taatcaaaat tgaaatagtt actttcgctc aaataacgaa tcaaaacgtc  79440
accgtccaca ccttcttgat tttgcagccc ttcgatcatg cttgttttga ttttgtccaa  79500
actgatatcg atttcgtttt tgatgagttc atagttttca ctgctcgatg ttatgttttt  79560
gattatggtt ggtgagaatt tttgcacttt cacagtttca tagttactaa aagtcttgtc  79620
gtcaaacacg cgcatactac gcaaatcgat ctgaacgatg tcgctaaact ttggcgccgt  79680
aacacattct tgcagatgga tatcgtcacg aatatattca aacagatctt tgctcgaata  79740
caccagtttg ggtaggattt tgcatacacc cttgctgccg tccgacatgc gtatcgtgaa  79800
cagtgtatcg ttggaatcgt taaaaatcga atgtccgttg acaaagagcg tgtttcgatt  79860
gcacgtcatg cacaattcga cattcaaaaa atgttccgga taccaaacga atagattaac  79920
attgccgagg ctgcgattgt gcggcaacgg cacatactcg ccgatgtcga tgtcaaattt  79980
gagtttcaaa tacaaacgcc atccaaaata agaaatctca atattgggcc agtacacgta  80040
gtctcccgcc gattcagttt tgttggcata ttcttccgcg ttgctcatca caaattcact  80100
gaacgaaatc gagtcacgca cagcttcgta atatcgttgc aatataaacg gtctaatttt  80160
gatggcgaaa tagtttcctt gtacacacca atcgtgactg tctatacttt ttacatgatc  80220
tttcgaagac gacgcagccg ctccaccact atcggcatca acaacaccga atatttcgtt  80280
cacatgcacc aaattattgt tggcaatcgc gctattgttg ttgcatgatt tgtaattgca  80340
tcgcgtttgt ttagtagaaa ctgcgacaat aagtttttcc agaatttgat aggatttaat  80400
taaaaacttt tcctgcgtgg cactattttt gaacactata gtgtcaacac accccaaatt  80460
gacgacggtt tcattgtccg gttgttgaat acgattaaaa atgttctcaa atattgcgtc  80520
aacactaatt ggtgcggtgg ccattgtgtg tctattgatt tttttatcg tgctcgccct  80580
tttaaatcct tatcgtaata acgttaaaaa attaatcgag gaccacaaaa ggacgttgca  80640
attcggcgcg tatatagacg tgttcgattt gagcacatcg tccgcgcacg ttgaacgtct  80700
gtttttgata cgtcccgaaa atgttgtgtt atacaatttc gacggcgctc tatggtatta  80760
tttggaatcg ggtagcgtgc tatgtccgcg cgaattcgcc atcgttaggt ttacgtttaa  80820
cgacatcaaa actgtcaacg aaagcggtct gttcaatatt gtctgtacaa atgtgaatgc  80880
gttgacttta atagaacatt ttatgactct aaagaacgga ctcgccgacg agagaatcat  80940
tttgaacttg caaaacatta atttcagtat cattgatgtc atcaatctgc ttatacacaa  81000
aggatacgtt tatctagaat gattgtacgg aaaattttgg atgacatcat ttgttatcgc  81060
gttagtgaca atattatgtt ctagaaaaaa acatttttat tatctatatt gttgaacatg  81120
ctttcgtatt cgattacatt gttaacgata atatcgtgat acagttgcca gtcgttgatc  81180
ggttcagggc atttgtttac gtgaacaaaa tagtcgtagc catgattgtt gacggccaaa  81240
```

tcgtcgacca gtgttatgct cttgatataa ttgatacctt gtttacgcaa ataccacaag 81300
actattcgtg gcgacttcgg taaacgttta ccatccggca aatccaaaaa aaacggtttg 81360
tccacaaaca ctcgtttgta atgattatcg acgaggactc gactcgtcga cggtgatgat 81420
gattttttcg ttttatgacc gccgcatatg actacgtcga aataattttg tagattacat 81480
cgatccatgg aataggcgac atgatcccga tcaccgtacg accacagcat caatatgaaa 81540
cctttcgttt tcaattcggc tagactgtcg taaacgaatt cgtcgcgaat gtttacgttc 81600
gtttcgtctg tgatcaatgt gctgtccaaa tcgaaaacga tcacgtgagg catttccaac 81660
acgtaaattt ccatgccgag ctggtaaatt tccatatgac tttgaacata ccattcgttt 81720
aaacatgcgt acatgggaat tttttcattg acaacataca cgtgtcctaa agcagacgtt 81780
ttgtaggcgg ttttcaaatt caatctcaaa tctcgcatgt cgtcagcaca tcgaagcact 81840
tgcataaagt aacgtgacaa atcgattttc gtcgatgtaa tgtcatatcc gtcattgccg 81900
tggttatcaa tacgaaaaac gacgtactcg aacagttcgc gatgtttaaa accgaccata 81960
gccatgtctg cgtaactagt gaggaaaaga acgtgtcgtc gaatcagcgg atttcgcaat 82020
ctgagcgcga cccacaagca atgcattgct accagttgta tgtgattttt agtgagtttc 82080
gagagaagaa tcaacataaa caattaatcg atttcctcgt cgaacactat ccgtcgaatg 82140
ttaaaaacaa aacgtttaat tttcaaaata ctggccactt atttcattcg ctgtatgcgt 82200
atgtgcccag tgtgactaat gcagaacgtg aacgcaaaca gattcgacta tccacagaat 82260
gtatacacaa actgttcgtg aacactataa atgattttaa aatgtacggt gaaatattcg 82320
atttaattca caccacgccc gagtacaaaa ttaaatacgt gtgtccgtgc caaattatgc 82380
tcgacaaacg tgacgctatt caatcgtacg tggacaaaat taaaaccaaa aaatttgaca 82440
gtaaaccgcc caagttaaaa aaagagccca tcgacaatat tatgtacaag tactctttga 82500
attggaaaaa tttactcatg aaaaaaaaat accacaacaa ttccaatacg ttgcattcga 82560
acaatagtat cgctactagt tcgaattcga acgttacgtg tactcagaca tcgtcgtcga 82620
aaacaaccga tgtatattac cacaacagta tttacaagaa gaaaaggaga ctaaaaaaaa 82680
gaaatatatt aactgacgaa ttgattttat ttaaacctat taacagttca ttaaaataca 82740
aattatattc cataaacgga atgtcattac gcgcgtgtca acacagtttt gtgacagtgg 82800
aaaaacagac gcgcgcaggt gacgagattg tgtccttcat aaagtattgt caaatttgca 82860
aaattatcgc caccgcagat gatcaataat tgcgtcggct gtacgaatag gggttcgaag 82920
atcgtctgcg accaccgctc gaacgtctgc gaccaccgct cgaacgcctg cgacctccgc 82980
cgcctgatct tctacgtccg ccagaatttc ttcgtcgtct tccgccgcca ccaccaccag 83040
atctcctcct accgccgcct cgtctaccgc caccgctgga actgcgtcga cgaccgccgc 83100
tagaactgcg tcgaccgccc gaacgtctac ggccgccgcc gccgcctgag cgtcgccttc 83160
caccaccgct gccgctgctg ctttgagtgc ttgatctacg tcttcggtac attttggaaa 83220
taaattattt ctatggcgga gattgttgtt tttttcgtat acaccttata aaataattat 83280
attcttctac gtttcgacga tgtcgacgtt aattgtacat taagcgaatc gctacgcagt 83340
tgttgtgctg tcaccgttgc gtcgctatac tctcgaatat tgtccattga tttgaatata 83400
ttattgtagt cgtcgggagc aaatttacaa ttggccacag cgtaattttc catagttgtg 83460
tagaacagag aatttgctgc attgtagaac atgcgttgca acgaaaaatc gtccatcaac 83520
ctgactaatt cctcgatgaa atctgaatct tgacaatagg gtattttcga ttcttgaccg 83580
ttggtacatt gtggttccag tttggaaatg acatcggccc tttccattat gagttcttca 83640

```
attgtacacc gtttgtcgcg agttaatttc gaactttgca tgagcataat tttaggaaat  83700
ctactaattg gataattcat tactcgtccc aatgtaattt ttaacatttt tacatttgta  83760
aaatctataa ttgaagttgg taattctagt agattcttga gaagcgccac aatattctgc  83820
atatcgattg gcgacatggc aggcatacat tcgtaatctt cagacatggt tgtttctaat  83880
agttgaaaca acggtttgta ttgaggtgtt ttattcaaat atatcatgca agccactatg  83940
tcttttacgt aaaattcgtt ggatgtggtg ctgtttaatg tgtaatgctg caacaatcgt  84000
tgacaacacg agcgtaacat tgttagattg ctgctcacat ggctttgctg ctccggtaac  84060
gtggtgcgaa acaagttgag taaatttcct ctcgacggtt gtcgttgcgc agatacttcg  84120
accgttggcg acgtttgtgt attattagta ttcgaagggg gatacgtata ttgactcgca  84180
agtgcagcgt tgttgtcggt gcggtctatt tcggcaatac gcgccgttgt aaccaaaaaa  84240
tccactagct catctaatgt caaatccaag gtggcgttag catccaccag cagcggaaaa  84300
aacttaggcc aaatcgacat gttcatgcgt ctgtcaattt tgtttttcat gttttcaatt  84360
tccaaaaaaa gcataacccc actcattttg gcaacgttta cttactttga aattttcaaa  84420
gtcactgtag tttacgcggc attgcctaca aacttattgt caaaaatatc actaaataat  84480
cgcaaagttt ctatggcttg catagagccg ttcaatttga tcttgtcgtt accgttttcg  84540
ataacgtcca acaatcgttt ggctacggcc gattgtttag ccaaaatact caaaacgtta  84600
cgtttatgcg gcgtcggatc ttttagtatc gtactcgcca aagtgtcgag ttcgttcaac  84660
gattgtacaa actcggcaat gggcacttcg ctgacatttt cttccccaat cgatgaatgt  84720
ctacgacgat tttgacgtcg cgaagattgt tgtcgacgtt gacgcgcttc cactgaatcg  84780
atggtttcta tcaggtccat tattgtaaag ataaaccagt gctgttctgg ttgattagta  84840
cgcttatttc tttgtcaaga tcgtatttta cacacaaatt tcttatataa tgttcgggaa  84900
ctaggagatt ttccatcaaa gctacgcaca aatcgagttt tatcgttttt aatttctcaa  84960
taaattgttc gaactcgtta ttgttgtaac ctttgaatag catacggcac acgttgcgta  85020
tttcgagttc cgaagctgac aaagtcttgt tgggtgccgc gtccaaatag tgacgcatat  85080
aaaatccagt gaacaccacc gaggctactt tattgatctt tttcaattta gtctgatgac  85140
caatctcgtc catgaaacgt ttgaacgggg cgaacaattt tatatgatac gaactcatgt  85200
tgagcgaaca caagagcatt tccagttcgt tgtcgactag accgacggtg acgcggcgac  85260
attcgttaac gaacggttga cacattttat gattgacaaa attagacgtg gacttgtcgc  85320
acaacagatt gtacaagaat tgtgcaaacg aattggtgat taaatcgtca gcgttgaaca  85380
cgttgttttc gtcaaactcg gttcgcaaca atatattcaa aaataacggc aagccgaaca  85440
tgggtcgcaa gaatatgtcc caaccgtctt gtatgcccac atcgaacgcc gacaccgacg  85500
ccgacaaata cctacaacga cactcgaaac aaagcaatcg attgtcgccg cacgaagaac  85560
ataatgcgct cagttcgttg atgttaggcg ttagaacggg tctataatat ttgccaagat  85620
atttcataat aatctgaaaa ttaggcactt gtttcatgaa ctcatcgcgc aaaaacaaac  85680
taaatatacg ctttatttca ctggtgttct gtttactttc gaaattgttc tttatggttt  85740
cgacgcattg attgaactct gtaaaaaaag taagacctcg cactggtaca tactgtttct  85800
gatcgaaata aactgagaat aagaacgtca atgaatcgat ttcggacttg gttaggcgag  85860
atccgaaact aacgttttca aacacgtcat atttgttgaa acgcaagcaa taatcaatta  85920
gtgtagtgtc catttttgat taaaaacgaa ttttttattc acattaagcg accttataat  85980
```

-continued

```
attgttgaat atttattttt aagcgtacag taattttcca tattacaatg aaccaacaat  86040
atcgcgatgc gataagaata caaaatcgta taatcacata cagatttgtt ttgttgagaa  86100
ttttatatat acgtcgatta tatcccgagg aaaccggcaa aagtttagat cagattcgtg  86160
acagtttaac acatatcgta ccgcatttga aaaatctcca aacaaacatt gcagatttag  86220
ctattcaaga tgcgttacaa gagatcaatc gactgcacgg tttggccacg ggtaccgttg  86280
aacatttacc caatacgaca aaaacagcga cgactagttc ctatttactc gatacacaag  86340
aaactatcgt cgacatgccc cctgagtatc ctggccaacg taatgaaagc gaaacattgc  86400
cagcgtcgac ttcgattcga caaaacacca atcaacaaca cattactgac atggtaacga  86460
tcgttgaact tatcacgaaa ataaaacaac aaattcgaga cgaaaggacc atcgacagtt  86520
taaatcgtct agagacagca acaaaatcgt tgattgatga aaatgctcaa atcgaaacgg  86580
ttcgagaacg tttgtctaat gtgacgttat tgttcaatgg agataatttt ttagaacacg  86640
atcatttaca acaaattgcg acactctatc aaaaatatag caatcgggtc attgattatt  86700
ataacgccaa catttccaag tttgtagccg aactaaaaaa atatcccaat ttgatcatgt  86760
cgcagtcccc gtcggtgcgt aacgctttgt cacatatatt acagtatcca aaaaatgttg  86820
gcgttatcaa aatcagcaac gcacaatacg aagatataac taatgccctg gtcaaagcca  86880
caatcaacat ttatggaaca atgcacggag tacgatatac tcaaccgtcg ccgttcactt  86940
cgccagtaat cgaacccgat gtaacgacag acgatgagaa cgatacgttc gaggcaatgg  87000
aaatagacgt tcctcagcaa caacaaaaag tgcggcgcaa acgcaaagcc agaactcggt  87060
caccgacaac ttcgaacgaa aaacgacgag ccgaaataca gagtaacatc gtcgaaccgc  87120
cgacgattgc agatgttgtc acaacagatc aaaccgtaat cgcaccgaca ccgtcgtcga  87180
taccaagtta cacggccgct gaagcggtgg atcgtgcaaa ttttgtggat aaaacccgcc  87240
agcaatatac gtctgtggca tcgacgtcaa cgccgacttt gtttcgtttg gttttaaaca  87300
atgtaccaga tttacaggat caacatttaa tatacaaacc aattgatcta atgatacctc  87360
tggacgtcaa caactatgaa catctgtttg ctatgattaa acaaatgaat ctgtccgtgc  87420
tcgacaacaa tgttcatttt caggaaatac taatgcccat cgcatattat ggcgcaacaa  87480
acgaatccgt cgtgcactgt atttggtttg ttatactgtc atggcgttac tttgttcaat  87540
gtgcgcaaaa ttttacacaa atccgattgg cgctggctgg tcagaatttt cgcgatcctg  87600
accgagtcgc tttgtatttg ataaaataca actatttata tttctacagg caatttataa  87660
gtaacatact agctagtaag cgtaccccat ttcgtaacgc taaaattgaa aacgtcatac  87720
gcacacaaga tattgttgta caaaaaacct acaataaatt aatgtttaat ttcgagaaac  87780
cggcgccgaa ctccgaacgg cctatagagc cgttagtact tttaatggcc ggcaacaacg  87840
aatgatgctc gttctagccg tatttatttt gttgtcattc atatttgcct tgggtgcctt  87900
gtatttgctg agacagaata aacgcgattt gcgacgtcaa ctgtattatc aatacaaata  87960
tattcccgaa ccattagtaa gtctagtaac cgtacacaaa ttgaagactt tacaataaat  88020
tatttcaaca atatgacgtg tccttttaat attaaagtat gcatcagtga acgattcttt  88080
gcttttccct acgaatattg tattccacaa accgatctag gcaacgcacc agttcgtcaa  88140
ttggtcgtgt acgtgccaac cgacgacgac attcaatatg tcgacaagac acagttacaa  88200
gcgcaattcg attctatact tgtgtacaga cacgaaccga gcgacaaaat cgaaagtaga  88260
gcccctcgca agaacgctac agccactata gtttactgga atcccattgt gcccataaca  88320
gaagtgggcg ttggtgagac gcgcgttttt agcgtactgc tcacaaacag tctgttctat  88380
```

```
tgtaacacca tgattttaga tggccaagca cccatgtgtc caatagaatt cagacgcgac  88440
gtcaaatacg acaaactgat accgatcgct gcaaatacgc ctttgtttca cgcgcgagaa  88500
ctgctcgacg acaatattaa tgactttttg atatgcttca atttggagac ctcaacaatg  88560
gtcaaaatat tgaacgtcaa acgtgtactc agcatgatgg gttttagaaa tgtaccggca  88620
cgttacacta tcaatttgcc cgataacgaa gtcgacacca tctataataa attgacatgg  88680
gaacggactc gtcgtctaat gaaaggagac gtttccagtg ccggcggcgg atgtctctac  88740
gtaaatcgta acgcgctttc gttcattaga caagcgcagg aattgttggg tctgaaggat  88800
tattcgcaat ccattgttga ttttgtagta aaatttcaat cgctcatcat accgtacatg  88860
atagtgcccg acatattaat caaactgaac acactagaac gtttcaaaca tgtacgttta  88920
tattgtcaaa atgacagtta cgcgatcaca tcttttggtc ccgtacccaa caatttgccc  88980
gaagacaatt ctgtcgcgtt cgattacagc gacataaaca acagcaaaca tttgttcgat  89040
gtgcatcaga aaatatctag cgacagcaac attgacggac tacgagtgtc ggcaatgcgt  89100
tacaattact ttttctaagt gtcattacaa ctaataacat tggtttttttg tgatacgtta  89160
attatgcgac atagaaacgg aacagttgcc gtattcgccg ataataccgt gccggcctcg  89220
atactcgatt acgatcaaat caatcaagtg gttacgcgaa atcgcacatt tttgcgtgat  89280
ttcgttttgg tcatcgccag tttggtgata ttcgtcatga tcgtaacgtt catagcttta  89340
atatatagta tacaaaaatc gctagaactt caagtcgcac gcaaacaaaa attgaacgaa  89400
acattattgg ccaattacga ttaccgtact cgaaatcgaa taagataaca attttgtaca  89460
tatcaatata ataaaattca aaaagattat tttcaaagcg tttcattaat acaattatat  89520
tttaaattta aactgattag cgttgggatt gtcataataa aagtagttgt cttgtcgttt  89580
gatcacgttg gattgtagat tgcccactgt caacgataca tacgacagag gttgtatgag  89640
atcatcaatg ttcagccgat gattatagcg cgatctgttg gtggcgtcgt tgatggtcac  89700
ttcgttagtt tcataatcga caagtataat gtatggaaaa ttaataacac attttatgga  89760
cgaatcgttc gtttctatta ggaacgtgtc gggtgtcaaa cgaataatac tagtgtcatc  89820
gtattggtgt tgactttgaa cgagcaaact gaaacacgat gtgcccgtac cgttgttgat  89880
gctttcaaag ctaataatct gttcgacggt ttgcatgttt gccacatcga tggttcttat  89940
cacaaagttg gacatattgg gactgttcac tatgttgtga tgcttggcag tgacacgatt  90000
atacgatata atattagagg gcgcggtcca cgccggatcg ttgggcaaat tgacgttcaa  90060
gtctcgagcc aaaatgacac agcgggcatt cgatgacaac atctgcaaag cgcgaatctt  90120
gtcgtacact tgcgtcatgc ccagtcgatg gtacagtgta taactgaaga attcaatgtt  90180
caattctgca aaactacaat gctgagccat aacacccgca ttggtcgtag cgcatatacc  90240
agtgtaagca attttcggat gaaaactgct cgttgttggt ccggtcgtgg gcaccgacac  90300
tataccgttc aaattggtcg tgagtaacac tcctgattcg atgccgagca taccggaacg  90360
gtattgtatg atcgctccat cattggccca tattttgcga gtcatagccc acagaggcgc  90420
atgaaggttg ttgttctgat cagcttcgta ataagctatt tcgggcgatt gtcccaccac  90480
cgaaccaaag tacgtgttag tgcgtatgga caaaattttg ctataatcac cgctgacgac  90540
ttcgtttttg taatcgatga acgtaccaat aacgttagaa tagttgctac cctgtcgtgc  90600
tagaaccgcg ggattggcgt aacctctagg actgcccact aacgatatac acttttctaa  90660
attgtacatg ttggcaacgt cgtcgccaaa caaaaagttg taatagctga atgtgaaata  90720
```

```
actattgatg agataaccgt aggctctaac atcggtgtgg tcgaaataag catagtcgta  90780
atgtataccg ttgccttgat gaaccagcgg aaaacgaatc agatcgagca cgtaggccat  90840
ttcgcgttct tgcgcaattt gccggcatga atatccgcgc aacaattgtc cataagcgta  90900
cggtagaccc atgcgcattg cgttgccggc ggttcgacgc cagcccatcg acatggtcgg  90960
ttccggtagg taataacgaa gcacttcttc cacgggcgct gttaaattat agaatccccg  91020
caaaacaata caagtgtttt ggaaaaattc cggcatagta atactgaaat gataccaatc  91080
cactctttcg ccccaaggag ccgcgtttat cggcgccgga aaaggtaaac gatcgtgtat  91140
tagcattagt gccgttttca aatttgttgc caacgttgcg tcatgataca acgtatcgcc  91200
cactgtacta aagcgtacac cgtaaccgat tagtgtgtgc agagccgtgc caaaatctga  91260
agcagcctga aacggttgta ggccaacaaa aatgttacca tcattcgaga acagtcttgt  91320
tggatttacg attttctcgg ctttttgcat aaatttcggc accaacgtcg ccatatagtg  91380
ttgttcgaat atttttaaat catcttgtgg gggcgcaggc agcacaggtg gatttatttg  91440
aaaacatggc aatatattgc cgtttgttgt gcgcaaataa aacacaataa ttactacaat  91500
agctatcaat acagcaatta cggtcaacat cataatgtat tcgcgtataa tacttatttc  91560
atgtctcttt ccattagcat tctaaaatac ttccaaatga acagatccat gtacaatatt  91620
ttattatcgt ccacgatttg ccaaggttta acatcgccgt agtagttgat cacactgggt  91680
tcgagatttt tgctgagacg ttgatagttg ccagcattcc atacgtacat tagggacaat  91740
tgagtcacgc taatattgtt tttgatcaga gcttgcagaa atatttgttc atcaaaaccg  91800
ttgtgatagc gattcttcat tagacattta ttgtttttat tcagtaactg ttgaatggtg  91860
ctgagcaaat ctttatcggg attcaaaacg accgttcctg ttttgcccaa aattttgtta  91920
tacctaaaga acgctttcat attggtaggt gtaatcgtgg caccgtgtgc aaaactatca  91980
tagtatgtat aatattcgga acaaaaacac agtgccggcg ctgtcaaatc gaacaaatga  92040
tcaatgttac gaatgaccaa ctggtcggcg tccaagtaaa ttattttaga ataatcggac  92100
attgacaaac attgccattt ggtaaacgaa tagttaatcc atttgccgta caattgatcc  92160
tggcgccgag ttaacatttt cggacaagag tattcgataa aatcgacaag taccactcga  92220
gtatagtaac gaataagcga ttctctagcg tgatcgctga catcatttgt tatcatgcat  92280
attaaatcat gtttggtacc cgatagtaac aaactttttag ctaataccaa tgcgccttct  92340
acgtactcgt cgccgagcat gaccagtgtc acgtacgcat acattccgat atctccttaa  92400
caattgtacg cgaataccaa tcaccaaact ttgcccgcac ttttttgtaa tttatcaaat  92460
gttgcccgga ccttttcaaa caaatgatgt catgaagtta caatgttatc tcatataata  92520
taatttgggt gtggcatgaa ttaattatta gcaaaagatc acggctcgtt tcgaacgaaa  92580
agatccaaga ccagtttaaa aatacgttat ctttgggcgt ggcgagattc gtaaattacg  92640
tttgcgattg gacaactttt aaatcacgcc atatgacgtc atttgttttt tgggtcaagc  92700
cgtggaatgt tctagaacaa attttatcga tctttgccga cggtttcata tgaaagcgcg  92760
ggcgagtttc gaatttatag atgatgcaat attttaaacg aatgacgtaa tttgtttttt  92820
tgggtcacga agcgaaacaa aagatcacgg cccgtttcga acaaaaaaat ccaagactag  92880
tttgaacatg cgcgaaaatt tttattttgg tagatgatgt catttgtttt tttgggtcac  92940
gaagcgaaag atcacggccc gttttgaacg aaaagatcca agactagttt aaacgtgcgc  93000
gggaaatgtt atcttcggta ggtgacgtaa tttgtttttt tgggtcacga atcgaaacaa  93060
aagatcacgg cccgttttga acgaaaagat cacggccggt tttgaacatg cgcgataaat  93120
```

gttatctttg ggcgtggcgt gatttgtgaa attcgtatgt gattggacga ttccaaaatc 93180
acgccatatg acgcaatttg ttttttgagt agtgtcgtgt gcaaaatgtg tttgaatcat 93240
aaattgaagc aaaagatcat ggtccgtttc gaacaaaaag gttcaagaca agttgcaaca 93300
tgcgcggaaa ttttggtaga tgacgtaatt tgtttttagg tcgggccatc gaatgttcta 93360
gaacaaattt tatcaatctt cgccgacggt ttcgtatgaa agcgcgggcg agtttcgaat 93420
ttaaagatga tgcaatattt taaacgaatg acgtaatttg tttttttgga tcacgaatcg 93480
aaacaaaaga tcacggcccc tttcgaacga aaagatcacg gcccgttttg aacatgcgcg 93540
gtaaaatttc gtgtaaattt aaagtgtggc gtgatatgac gtcatttgtt ttttgggtcg 93600
agctatcgaa cgttctagaa caaattttat caatctttgc cgacggtttc gtatgaaagc 93660
gcgggctagt tttgaattta aagatgatgc aatattttaa acaatgatgt catttgtttt 93720
ttgggtcacg agtagaacga aaagattacg tcctgttttg aacgaaaaga tccaagacta 93780
gtttaaacat gcgcgggaaa tgttatctat atcgatgacg taatttgttt ttcaaataat 93840
gccgtgtgaa aatgacgtaa tttgtttttt tgggtcatag atcgaagcaa aagatcacgg 93900
ccagttttaa acgaaaagat ccaagactag tctaaacttg cgcgggaaat gctatctttg 93960
gtcgatgatg tcatttgttt ttttgggtca cgagtcgaaa caaaagatca cggccagttt 94020
tgaacgaaaa gatccaagac taaaaatacg ttaactgtgg gcgtaacgca attcgtacaa 94080
ctcgtttgtg attggacaac ttttaaatca cgccatatta cgtcatttgt ttttttgggt 94140
caagccgtaa aatgttctag aacaaatttt atcgatcttt gccgacggtt tcgtatgaaa 94200
gcgcgggcga gtttcgaatt taaagatgat gcaatattct aaacgaatga cgtaatttgt 94260
tttttgggt catgagttga agcaaatgat catgggcctt ttcaattttt gaatcatata 94320
gtttagcgat atgacataaa gccgttttaa acgaaaagtt tgttttatac gaatggtgtt 94380
catttgccgt ttcgaataca acgggtgtga acattgctgg gacatttttg atagatgatg 94440
tcatgctaaa attgtgaata ttacgcagac attttcgata tagatgatat catactatta 94500
aacatataaa aatatgatgc aataaaaaaa atgatgtcat ctagttgacg ttgctttggc 94560
gcaaattatt ttggtaattt tccatgcata tttcgttatg atatcatcgt taaatacgtg 94620
attgtctaaa atcgatcttt gcggacaatt ttatatcaaa atgccggcaa atatcgatta 94680
actgaataag caagcgtacc atcatgtatg ttcagttgac ggtgtttgtt ataatattat 94740
tagttttgtg cgttaacatt ttgtacgtag taacaaaatt aaactacaca gagaaaaaag 94800
cgacaagttt attaaacggc gacatggaat tgtcgtatca tcaaaacggt ctagtcaatt 94860
gcacacacac tcggctacct tgcattgtaa cccagcaatg tttagataat tgtgccagtt 94920
tcaatatgat aaataatatg gaatgtgatc agggattttg tactattcgt gaagcgcaaa 94980
gttcttcaaa taacgacaac gacattgaat gtgacgcaac caaaggattg attaaagttt 95040
ttactgccag cgaatttgtc atcaatcaat tgtgtataag cacgtatcgg gacgtgttcg 95100
acgacgacgg cgaactgcgt ccgtatatat gcgaaaacgg aacggtcgat attgatgtgt 95160
tgaatcgacc gtttagcgtg accgattgtg aatgtgctcc cggttataaa cgtatgattt 95220
ttcaacagac tgctttggca cgcacagtac ccgtttgtat accaaatact gcggtagctt 95280
tgtattcgaa aatttatcaa taaaatatgg tgttagtaat aaataaaaac tctgctgccg 95340
ttgccagcat cgattcgatt agcaacgatc gcaaagagaa acgattgtgc atatggaatt 95400
tggtagtgcg ttattatatt cgcaacccac gtattcaatt catgtttaaa cagcgtcccg 95460

-continued

```
gcgatgaaat aatacataat cgacattgga caaacatttt ggaaaattgc tatatgtgtg  95520
aaacagaaaa aagacgtttg ttgtcgtact tgtcaaaact atacaaacag tattgtgtgg  95580
atcagatgcg aaacgttgat gtcgacgaac tagataggat atggtgtact attgatgatt  95640
tgtgtaataa atgtcgtttt tgatataatt ttgttgtttt tatttatttt acacgtacgt  95700
atatgtatcg ttctactgaa taagcgcgct ataaaattta tacaatagaa acgacgacat  95760
ggccgttgaa caattaaaac agctcaatga cattcaaaaa tatttgctcg aggcagtcgt  95820
agaggcttgt aaatttattg gcaaaaatcc tgaagcgatg ccggcaagtc aattgttggt  95880
gcaattgatg aacactcgta gtagtctgaa cgaattgcga cagaacgccg tcaatattat  95940
cgattcagac attaacgagt ttgtgtttaa tacaatagct gaaatggcac tgatcaacga  96000
cgataccata acgatggtac agagtgtcgc cgactccttc gacgacgact tcgaacaaag  96060
acagaaccat gaggaaacgt tgccaccaac agaaacgata aacatcaata tggtgaattt  96120
acaatacgaa atgggccggc ttgccaccat tgtcaacatg gaaagtatag aagattttaa  96180
atatttcccc gagttgacgt acatagtcaa tcgcaaacac gtcaatgaaa tacaactaac  96240
agaacaaact ttgtcgcgtt tagattgcgc cacgcttatg gccaacgcat ttttcgccgg  96300
caacgtgcca aacttaaatt ttgacaccat caaatcaggc gcgacgggac tattgcgtca  96360
aaaattgatg tgcctactga attatttcaa aaatatttgt ttcctattga atatgaaaag  96420
tgattgggtc gaaacacgca taacgatcga acgttacgtg tgcgaaaatc gtatatcatt  96480
gtataattcg gagaagcctg ttaaaggtag cgacgtgacg gtggcgctgt acaatcacga  96540
aatcgactat aacgaacaaa acgtaccgga cgcgcacgat ttaattatag attatgtcga  96600
caagcgatta ggcagcgaca ccgtcttgac cgattcgatg acctatgaag atataatgtt  96660
tttgcgtttt ccagaattgt acgcggccat gtactttgat tctcgcgatt tgggcgattg  96720
cgattcattg tgtgtccgcg acgtggtaaa gtttaacaca gttttaggaa cggcgggggc  96780
gccaaaattt gtcgaatcca tattagacac ggccgggttc gtgtacatta atattttggc  96840
gttagaatcg tgtcatttga agaataatgt aggcagtgcc aacagcgatt tagcatactt  96900
agacatgtcc attaatcgtt tacaaactcc gttgatagcc aatcgtttgt ccattccgtc  96960
aacgggcaac ggcggcaaac ccacactata ttcgtcattt tggggatgtc cagaagaatc  97020
gagaccgttc agaatgctcg tagaattgat gacgtgcgcc gttgccgatt acaatatggt  97080
ttatattgct agcgattcgg aaactcaatt cgaaatggaa gataccattt tgatactaaa  97140
cgataatttc acagttcgtg aaatatataa tatgttgacc aattacaagt ttaacaattc  97200
aattcgctac aacgttttaa ctctaaacga aaaacaatcc aaatctaaac gaaacagaaa  97260
acaaactagt atcaatttag attaagttta catttgtgta ttttacaata aatataagcg  97320
ctacattcat gcggctattt gtcgttgtgc tcgtttacac ataatggagt cgattgatgt  97380
tgacgatttc gctaaacagc taatagcgga caaatgtagc gctttgatag aatcaaacaa  97440
gatgctttcg cccgacatga tggcgatggt gaaattggcc cgcgacgaat atttcaaaga  97500
cccatcttcg aaaaattacg aaatattaaa aaaactaatt ggtcacacaa aatacgtgga  97560
cgattccatc gactgcaaag atttcaatcg ccgcatgtta cttatcgcca tcaaagtgag  97620
cgcttcacgt gcgcgagact attttaacaa atacaaaact gtattcgaat tggctttgaa  97680
acgtttggac agcatcaatc ccgatatacg aagttcgcct agcgctctgc tacaacacta  97740
taaagaatgt ctcgacaatt tggacaatcc ccggaaggac gaacatcacc ttgtcacttt  97800
tgccaaagaa attgctacga aaatattcat cgatacaata gacgtgtaca gttacacgaa  97860
```

```
caaaagttct attcagatga cgactacatc gacacgtaac caatgcgcga cgtccttatc  97920
ggcaaactat ttatcaaatc gtaaagcaac aagtacggac agtctgctag cgaaaacatt  97980
acagttgaac gcgtctcgca agcgacaaca caagcggaaa aatagtgcaa ctttattaga  98040
cagcaaagtt aattctttcg tgtacaaggc acagatacac gatccgccca aatattacgt  98100
tgcaagagct ctgttcacat tgtagagcca gttgttatca tggaaaaaca ccaaatggac  98160
ttgtacaacg cgttgatgca gcacaaaact aaaatgacaa gtttaaaaca attgtcctta  98220
gaagcgttgg cggaacagca cattcgacac cgtttacaga tacccaaaca tactgtgaat  98280
gtttgtgtga acgacgaaac gacggtttca gtattgtgct atcctaattc tcaaacaaaa  98340
cacggtttgt tgattcggaa acctgttaaa gatctattct tcgacaacga tcacgattgt  98400
gtacagtgta taatacctag ttgtgtaaac aatgatgttt gtaataatat agttttaaat  98460
cattggcaat aaaacaatac ataaaaaatg caaaaatttt ttatttatct cattatttaa  98520
atacttttat ttaactgata aaaacctttg tcatatcgtc gattgatcta cgacacacaa  98580
cacatttttt tactttgaaa gcacattctt cacaacaggc caaatgatga cacggtaaaa  98640
acatgtaatt gcgttcgttc acgaagcaaa ctttacatgt acgtatgtca cattcagtag  98700
tttgattgtc ggaattactg ccttcttttt cgacacaggt ttcggtgatt accgtctgca  98760
cgaaatcttt gccttttcc gatactacaa aatcacaatt tctgtaccag cgtgcgtgtt  98820
ctcgccatgg ttcatgcgta agcgtccaat tgcttaattt tccgccgcaa tgaaaacata  98880
ttgtgatatc atctctaccc gtatataccc aaccagcttc tgctaattta ctcttcaaaa  98940
ttatcagtgt ttgcggccaa ttgtcaaacg attttaaacg attttcataa gttgaatagc  99000
ttgatagttt ggatttattt ttgtaagatt cttgatcagc aatgtaattc tgttctgaac  99060
atacgtttgc atcgctcata attgatttga cgtaagaaca ttgcggcgcc caacgtgcgt  99120
gttcttctag cggatcgtct tcgtgttgcc aattcatcat ttcgactttg caaaacgcac  99180
attttacatg gtcgtctttg ttcaaataat agaaaccggc ctgagccatt ttagcacaat  99240
ccataaaata atattgtaca ggccaatttg caaacgtaac atatcgatat gattcagttt  99300
ttaataattc caaatcggat tccatatagg acatcatcgc acaagcggcg aaggacaacg  99360
ctctactgaa ttctctatcg acaagacagg ctttttttata tctaacataa aagagcttac  99420
taaactattg cgtcgtattt tacgtaaatt ttgtttatta gatttgacaa gtaatgtttt  99480
tgtaaacatc aaagcctttg atgttacttt ggtaaacaca aaatgaataa aaaaaagggt  99540
taataaaaaa ccaacaaacc gtaaaggaaa tttattgctc acacaaataa cattacagat  99600
ttgttgacgt cgttgcttct gtagcagatg ttatatcttt ttgagtagtg acattttcaa  99660
tagccggcac attccctggt attatgtttg attcatcgta aaatcgaacg ttacatacat  99720
tcttgacaaa gtaattttga caattattca tggcgtgcac gacttgttgt gccgaataca  99780
cgtcgcctgc attggaatgt cgacgttgtg gcgtggaagg cacgagttct ttggccattt  99840
tttcgacaat attctccacg atagcattta tacgatcctt ggcatcgacg ctttgcgtca  99900
aacatttggc gacacaatcg tcttcgtcga tcaaatctaa cgctttaaac tcttcaatta  99960
gttttgtatt aacagttttg ttacgttgac acatttcgac atcggcgcga tatttggcac 100020
gtaattcagt ttcgtcgagc acctccattt ctgtgcacaa tttgttcgta tagcgcaaac 100080
cgtagaatac atgaggttcg tcggcccgta tcttacacca caccatcact gaattggaac 100140
atttgagttg taaaaatttg gtcgaatcgc acaaccacgc gtaacgaggc gacggcttaa 100200
```

atctttttgg agtacacaaa gtgtcacggt agcgttttgc cactttgtct tgcatttcta 100260
tcgcatacaa ttgactgcga cacatacgaa tacgacgttt gccattgact attcgttcgt 100320
aaccggttat gtattcttcc ttttcgggct gttttgtcag gaccggtacg acgcgattgc 100380
ttatcttttc gagcgtttga cgcagtcgat gattttcgtc aatgttatct ttggcgagga 100440
gtgcgttcgc tgcaaactga aacattgaca tgttagcttg atgtgccatg tccttcattt 100500
gtagttgcat tttgaactct cgctctttgt actcagacat ttgctgttcg taattgcgct 100560
tcatttccga catattcgtg ttccattccg cgatttttat attggcttcg gacagttgca 100620
attttaattg taacgcttcc atctgaacat tcgccaattt ttggtcgtaa ctcactactt 100680
cagtagaatt gtctgtggac gattgtcgcc tgttttctat actatatttt ccagttcgtc 100740
tcaattcggg caagacctct tcgaatagcc aactttgaaa ttcctcggct gcaggtagct 100800
tagaacgcat aattaaagcg taaataccgg cttcggtgat gaaaagcgta ttcggttgcc 100860
aatttaatgg catttctata gaatctgatg acgtcacaag ggagtgttga ttcaacaccc 100920
cctttatttc cgcccacgtt ttgcgccatt gcggtttcac gtgatcgtac agtgctcttc 100980
tgggacattt gtaacccaaa gcttcggcga caccgtgacc cgaacacaga aatcggtttt 101040
cttcgatttc agtaatccaa acttcaccca atttacattt gcgatttaca agatacatct 101100
ctaaaacagt gcgacaactt caaagtgtag acttaaaatg aacgaaatat taacacgtta 101160
caattgaaag ccatacatac atcgaaattg tcctatacat cgaaatcgtc ctatacatcg 101220
aaattgtcga tgtgactaac aacaaaaata agatcgaata tcataatgaa agctatttgt 101280
attttgagcg gtgacatcag cggcgaaatt tgtttcagtc aagaatcgcc tttacattta 101340
atcaaaatca ccggattcat acttaatttg ccgcgtggat tgcacggtat acacgttcac 101400
gagttcggcg acaccagcaa cggatgtacg tccgccgggg aacatttcaa tcctacgggc 101460
caaacgcacg gggcgccaaa cgcgaccgtg cgtcacgtcg gcgacttggg caacgtcgaa 101520
tctttcggta taaattcttt gacagaagtc aatatcgttg ataacgtcat gtctttgttt 101580
gggcctcata gtattttagg tcgcagtctt gtcgtgcaca cggaccgcga cgatctcggt 101640
ttgactgatc atccgttaag tcgtataacc ggtaattccg gcggccgtct cggatgcggt 101700
ataattggtg ttacgaacag ctataaagag gcttctgtaa aataatcggt catgtcttct 101760
gtacgatgtg tcatcgtaac gttattggcg ctcgcgacag tgggttacta tggcgcgttc 101820
aaaagtgcaa tagccattcc ggcgacggaa tctatgaagc agatcagttt gcgcgtccac 101880
aacaactatt ctaccgttga aacaaacgtg gaattgcttc aaacggcgat atcgctcgcg 101940
atcactatcg ttttgtcgat tgtatttcgt aattttgacg cagtatgtgt caacacaaga 102000
ctgctcggcc tatcggcgtt gggcatgttt ctcgatttga cattgcaaat atatttggcg 102060
atgaataccg ctacggtttc attgactttt gtgtatgtcg ccacgatgac tgtagcattg 102120
ttcggaggcg tttttctatt ggaactgtgt ttgctcgatt tggtaattgc tttaatgtac 102180
aacaacaata gtagcagcac tagcaaagcg acgcgttgcg attattttaa atggatcgta 102240
catatgcgtt gcgcaaaatt gctaggacaa agtttggttc aacttatacc gcccttgttt 102300
gagatagatg aaaatcaaat gttgcacggc gttgccgcgg gttctgttac aagttttgta 102360
ttggccatag tggcgttaaa tattatgact ccagcacata tgtttatgga tgattataat 102420
gttagcgact taattgaaac atatcgagct gttccgttcg acaacgatgt gaacatctac 102480
cgaccgacaa cattagtaca atcgtcgacc acattgacca acgtaaagtc gacacgaaat 102540
aatcgttttt atgtaaaata tttaatagca atactgattt atagtatgta cgagtcgcag 102600
caaagcgaac tcaaatttag ttattacttt cagaaggata cgataatgtt gcccactcgc 102660
gacataagaa tattgaacgg ttgtcagtac ataatgtttg cggtcatgtt atggcccttg 102720
gttactttgg ctagtcgtaa taattcaaca ttatatgtaa acatgttcta tatgtcgttg 102780
gcgtgcaata ttttggctcg tataattcaa tcttacgctt ggtactctca tgaaactctt 102840
gtgtggattg tgtcggttgt tgcgtcggcg ccaggtccaa ttgctggcgc tttaatgcaa 102900
actttagtgt acaaattatc tgacaacaat ggtcattatt ctaatttgat cgcaatcacc 102960
gctgatcggt gcttgttagt tatatttata ttgttgtatc aatgtactgt gtatgtcgaa 103020
catttttcac catttttgat tacattatgt tcattgatcg ctataataac aatcactatt 103080
gttaatacac caattaaaat gtggttaaaa gatatacact gctaaaattt gtcattggat 103140
aatgaataaa acactaaaac atatttttgt ggtattttta tttagacaat tcaaacgtac 103200
ataacagaga accgtaatcg tcgggcgaca atcgtattcg gttaggtttt accaatccta 103260
tatttctcca cggtggtaat attgccatgt ttttgcggat gcaatacggc ggaacgtttt 103320
gtatagttac attgatgtga tagtttattc ggttgtccac ttcaaagttg atcgtgccaa 103380
aattgatcaa cacatctcca ctccacatgt gttctacttt gccgattatc cagttgttat 103440
cgatgaactc tttgtaatac gatctgttgt cgcaatacat gccgtaccaa tcgtaattgt 103500
cccaacttag attttttca attaactttg tgctaccatt ttcgtagaca atttcaacgc 103560
acactttcca atggcaattg tacacgggac tttgtaaacg caaaattttt aattgacgca 103620
ttatcatgtt gcatgatttg gtatcgtgac tattgtacaa cgaaaacgat acattacgta 103680
aacgaacagt tataggagac tggctacca tacaatcgtt ttcaaaaaga aacacttgtg 103740
atcgccacga aatcatgatg aatgctaacg ttggtgcagc cgcgaccgaa cgttataaag 103800
ctggctaatg ttgttgttta tattatgata aaaccagata cggcaagtat ttaaattaga 103860
tgaccatata tatacattgc cattcgaatc acgttcgcac acacaaaacg aaataaaaaa 103920
taaaatggac gattacacgt acaacgatct atatgtaaaa gcgtcacaac ataatgtttt 103980
aaaacgcata gttaaccgcg aactagatag tcgcattgat aaattatcta gcgttttaaa 104040
tttgcaacgg ttgacgcaaa tagtacaaaa agcaccgtac accctaaact atgacaatcg 104100
aaagtgtccg tcgcagtacg aagcagaaag cgtggatcta gcgaagttta tgaagcgaaa 104160
atacgaaaca gttgtcagat gtaaattgtg tacgcgcagt ttgcacggga tgctggataa 104220
gaacaagagt gtgtgtactt tttgtctgaa tgctacaagc gctgaatcgt ctggcaaata 104280
actactctat tatgcaattg attgtgttcg tcatgcatat ctccaatgat gaacatttgc 104340
gtcaggacga aatttatgta aagtatttgc aacacatgga cgtttacgat gcggttatgg 104400
tttgcacggg agattgtttg gctgtgtgtg tatcgtcagc gcctattgtg ttgctgagta 104460
aaaatttgaa aattatcgac tatggagatt tgtcgtctat cgacagtttg tgtgataaaa 104520
tttatgatat tgccgaaatg tacgaacaaa atcaatgaat tattgtaaat aaatattttt 104580
tatattaaaa aattgtttta ttattcttct aagttgaata aagtaacatg tatgcgactt 104640
tggttattgt actgttgctt gtcgctataa ttttaataat aattaggtat acaatcctgt 104700
tgcaatatgc cgagccgcta ccaattcacg aagtgcacaa atttgataat ggacatgtac 104760
ctccgattga aatacccggc gaaatcaaca ttgacagtaa tccgatagca tgtcacaaac 104820
agttgaccaa atgtacaacg cacatggatt gcgacctatg tcgagaaggc ttggcaaatt 104880
gtcagtactt tgacgaacag accaaactga taatgcgcga cgaacacggc aacgaaactg 104940

-continued

```
aacatataat atatccaggc gaagcgtatt gtctagcgtt ggatcgcaat cgggcacgtt 105000
cttgtaacgc caacactggt acgtggattt tagctcagag cgaaactggg tttacattac 105060
tgtgcagctg tttgagtcca ggtgctgtaa ctcaactcaa cctgtacgaa gattgtaacg 105120
tgccagtagg ttgtcaaccg cacggcacca ttatcgacat caacgaacga ccgttacgtt 105180
gcgactgcga aaccggttac gtgcccgatt acaatgacga aaccgaaacg ccctattgcc 105240
ggccgttgtt agtgcgagac atgtacaacg atacgactgt gtttcctagg gcgccgtgtc 105300
caccaggtta cgtgcaaata acaaatccca atttgaatcc tgaatacgct cgtgaattcg 105360
ctttacatcg cgacatctgt gtcgtggatc cgtgttccgt tgattttgtg agcggactac 105420
gaaccaacgg cagattgtcg caagcaaatc gctaccacaa tcaaccctat tgcgattgtt 105480
caaacaacgg cagtaataat aacacgatgt tttcgattta cagcgtgact aatgccgtct 105540
tcttagcgcc aattaatcaa cacgcgcccg aactaaccaa cgcatgtatc gaaccgttca 105600
acgttaggtt caacaatgcc aattttataa tgtacaaaca tttttgggca cacgacgatg 105660
tacgtagcga cgacgaggtt gtttgtcata tcaatcctaa caatacactg ctgagacata 105720
atcgttatct atccctcacg tatcccagta tcgtttggtc cgacgtaatc aacggaatga 105780
actatttgat tttgaaattt tccattgcct ttgccgtcga caatatcgaa caagtatata 105840
gaagtttgtc tgccaataga accgtgccgt gtttcgcccc tggcgtgggt cgttgtattg 105900
ttgcaaatcc aaattattgc atcagacgac acgctaattt tcaagtgtgg actgcggaaa 105960
cgttttcaaa ctcctggtgt atatttagtc gtgaaaacaa ccacattcgc agttggcatc 106020
cgtcgcgcat atttcccgac ggcagatatc cgtctgtatt cagaattgca ctgaatcaaa 106080
tgtacaatgt tagaaataca aattcaacct gcgaactctt tgtaatatca ggccatagta 106140
tagtattaag agatcaattc gataatctga gatcgattct cggtacttat cccaattatt 106200
ccacgtacac atgagcgaca gcaatgaaaa ccttatagcc gaagcgcaat atctggcgca 106260
acgtttcgaa caggcgggac atttgtgtaa agccatacaa tgttatcgat taggaataca 106320
tttcgcacaa caagatcctt ccattgatag caatgtaata aatttgtttt tagaacaaat 106380
acaaagaatc aatacaatga aagaaaacaa aaaattatgt ttaaacaaat atgttttatt 106440
atattaatat atgtacgtta caacaacagt tagacattat tttttttga agttttcatt 106500
tttaaaggtg caggcacgca ttcatgaaaa tatacattag tgttatacac tgtcacagtc 106560
agaggtaaca tggatgatgt ctgtggatat gctcgttggg attcgctgtc ttcttttaat 106620
atctcctgaa tttggccttc caaatatgat ctctgtgaag tttttggcga atccggtagc 106680
aattgtatac tgaaatcgtt ttcgacacta tagaaattag tttggttcac tccctcggtg 106740
gcgttaacgt tgctatgttt taacgcaaca tagtcatttg ttgtttcaag tgttctaatg 106800
tccaagtcac atatttttct cggtttgtaa gcgagtttct cgttaatatt aggactgaca 106860
acacacttat gcgttataga cgcatgtttc caatccaacg tggtcaattt aacactggac 106920
ggttctaaag gacgatgtac accgctgcta ttgaccaaga cgtttcgtgg tttaccttca 106980
cgatttagag ctaagtacgc tcgggtatta ctgtcgaact gtttgtacat aacgtaggca 107040
gtttctttga tttcggtcga ccacagacat tctgaattag gcacgattgc cgtgtacaca 107100
tagccgcatt ggttaacgca aatataacgg cacgtttgtg ccgccttcaa caaatgattc 107160
atatagtgag gcacacgata aaatactgag tgcgagtcag tagaatttgt tataccccac 107220
acagtgccat ttcgagcgac cgacaaatag cgatgtctca tcacaatctg tatggggcga 107280
cttgcgtttt cgtgcgcgcc cggtcttgcc gatacactcc acatatacgt ggaacataat 107340
```

agaaatagca gcgttctcaa caataccgaa aacatgatcg tttagttctt cgatctaaaa 107400
acgtttgact gacctatttt agcgacccat tttatatagt atataatcaa ggacatattc 107460
catgcataca cacacacacg tacatttaca caatgtaatt atcattgttg ttgcattaat 107520
atagctctat attcgcaatt gtccgtgtgt gttatattga aattatctat tgataggccg 107580
caacagaatg ttttgtaacg tttggtgttt gtatcgtaaa acaatcccca tttggcgaat 107640
cttgaatctg ctccacgcgc cactagcgac ttcagtcgca tagaatgtgt tagaaattct 107700
ttatgtacgc atcgtatacc tctatcgatt ctgtcgtcgt cgtcgtcgtc atttttaaca 107760
aatgatgttt tgttatattt acaaatttta tgtttgtcga gaattgtgtc gacggattcg 107820
tcttcatcaa acgctgtatc gcaatacgcg catgctatat tgccgtacga ataatagaaa 107880
ccggccttgg cgagtttttc gacattgtca ttggtcaaag tcgtgttcgc aaacgattta 107940
atcctcacgg cacattgccg gaatctctca gcacttgtat ttttgttcac gaacattttg 108000
aacatcgttt gttcagtttt cgattctttg tcacaaaatt catcatcgcg ttttactatg 108060
ctagccacga aagagtcttt gaacctaacc aaatatatga ccaacgacga atctagtacg 108120
tgtagttgtc tttgcatttg acgataatgc gggtcggttt tttccacgac aaatctagcc 108180
ggtccgtttc tgttgacgct gaacgctgta tgtttgatgc ggtaccgttc tttgcgagcg 108240
ttcattgcac gtcggacttc gtctacagtc gtgtcgcgat atgtatgcgg gcattttatt 108300
tccataggca caatcgtgtc gtcgtctaga ataaagtagg cgtccggcga tgcggaatgt 108360
aatccgtatt tgctaaagaa cataccgcaa tcgagaacag tctctgtaat tttttttatta 108420 gtttcgcgtt cgacacattc acgaaccaga ttcaaaagcg attcattgtt tttcacgcaa 108480
gtttcctgtt ccaatccgta ggtgagcgcc ggaatcggtc gcagaccaat gccgctgctg 108540
ctgttcgtat tagatcccga agcagtttgt cgatcgagcc gcaacaaaaa ccatagcggg 108600
ttcgtcgatt gtccacgtgt tgctttttcg atttccatga tttcatgccg tgacaataat 108660
tgtgttatgc ttttcagttg actcacataa ttggtaaaac agtatttgtc aaatatgttc 108720
tgctgttcgg cggtgagcaa atcgcacggc gacactaatg atttggtcat ttttgtggtc 108780
gacatggtca cgcgcaataa tatattataa attatatttc gtgagaagcc aatcgagaag 108840
ttttacgtac acggccgact gtagcgtgtt atcggattca ctgtatttaa ctagaaattg 108900
cactaaaata tttaaaattc tgctctgatt gaacatcaat cgttccgttt caatagccat 108960
gtccatgaac gattgaacgg tgatcatcat accatgttgt tgaaaattaa ttttgcccaa 109020
tacgttttca actatactga tgaataccgt gtaaaatgtt tttcgagcaa tattctgatt 109080
acaattgaac ggatcgacga ccgtgtcgcg tagaaagtct atgacagatc taagtttaat 109140
cgatttgtca cgtattcgat cgttgcgttg caatcttttc acgtaaggtt tcatcgcaaa 109200
attacaatcg tgttggaaaa gttattccgt cacaaaaaaa gtcccttaaa ttaaaaaatt 109260
tctaccgtgt aatcgatctt cgccgacggt ttcatatgaa agcgcgggcg ggttttgaat 109320
ttaaagatga tgcaatatct taaatggatg acgtaatttg ttttttcctc aatcatgaat 109380
agaagcaaaa gatcacggcc cgtttcgaac gaaaagatcc aagaccggtt taaaagtacg 109440
ttatctttgg gagtggcgtg attcgtggaa tacgtttatg attggacaac ttttaaatca 109500
cgccatatga cgtcatttgt ttttttaggt cgagccatcg aacgttctag aacaaatttt 109560
atcgatcttt gccgacggtt tcatatgaaa gcgcgggcga gtttcgaatt taaagatgat 109620
gcaataattt aaacgaatga cgtaatttgt ttttttgggt cacgaagcga aacaaaagat 109680
cacggcccgt ttcgaacaaa aaaatccaag actagtttga acatgcgcga aaatttttat 109740
tttggtagat gatgtcattt gttttttttg ggtcacgaca aaaaatcacg gcccgtttca 109800
aacgaaaaga tccgagatca gtttaaacat tcgcgggaat ttttactttg ggcgatgatg 109860
tcatttgttt ttttgggtca taaatcgaaa caaaagatca cggtccgttt cgaacgaaaa 109920
gatccaagac tagtttaaac gtgcgcggga aacattatct ttggtagatg atgtcatttg 109980
tttttttggg tcatgaatcg aagcaaaaga tcacggcccg tttcgaacga acagatccaa 110040
gaccagttta aatttgcgcg ggaaatgtta tctgttgttg atgacgtaat ttgtttttcg 110100
aatagtgtcg tgtgcaaatt ttgggtcatg aaacaaaaga tcgcggcccg tttcaaacga 110160
aaagatccga gatcagttta aaaatgcgat gcgcgggaat ttttttaatt tggtcaatga 110220
cgtatttgtt tttcgagtag tgccgtgtgc aaaatgcttt gagtcataaa tcaaagcaaa 110280
agatcgcggc ccgtttcaaa cgaaaaggtt caagatcagt ttaaacctgc gcgggaaatg 110340
ttatctgttg ttgatgacgt aatttgtttt tcgagtagtg ccgagtgcaa aatgacttaa 110400
tctgtttttc taaatcacga atcgaagcaa gagatcacgg tccgtttcga acgaaaagat 110460
ccaagactag tttaaaaata cgttatgttt tgggtggggc aaaatttgta caatacgttt 110520
gtgattggac gatttaaaaa tcacgccata taacgtcatg agtcggccat cgaatgttct 110580
agaacaaatt ttatcgatct ttgccgacgg tttcatatga aagcgcgggc gggtttcgaa 110640
tttaaagatg atgcaatatt ttaaacgaat gacgtaattt gttattttgg gttattaatc 110700
aaagtaaacg atcacgatcc gtttcaaaca aaataatttt tgttatcgag cgtggcgtga 110760
tccgtaaaac tcgtatgatt ggacaattgt aaaatcacgc tatatgacgt catttgtttt 110820
tttggatcga gccgtgaaat atttttgaac aaattaatcg atttttgccg acggtttcat 110880
atgaaagcgc gggcaaattt cgaataaaat ttattagcga cattagtgca tacatcatta 110940
ggaaataaat cattaaaacg ttttttaaaa tattttatta caattttaca gattcgtaat 111000
aaacaatcat tttatcaata gcttgattta aaacagcgat aaaactcaac acatatttgt 111060
agtctttgta acgtttcatg taatattctt ccatggcttc aatacagttg gcatcgaaat 111120
gtgtaagata atctttgagg gcatttttaa aatcggtgtg tattttctcg acaatttcgt 111180
tcacatttcc aaccggttcc atgtctgtac ataagcaaat atgacaactc gtagccacaa 111240
tcaattcata ataaaagaga cgatatctgt agaaactttc tttgtcactc aatgtatagt 111300
cacaaatttt agacaaagaa ttatattgtg tgaatttttc ttttaacact ttgcatatag 111360
ttgccaattt ttgtattctc aatatacgac tgtcgtcatc gagcagtaat ggactgtggt 111420
cagctatgtc tttttgaag gtacatactt gcttcaaaca ccacaactcg ttcaccagta 111480
gtatatcttc gcgtaacata aattcgtacg tatcttttag tgcttcaatc agaaacgatt 111540
gaatctcttt atcgttgtat tgaaccgtat catacataaa ttcccaatga ctgatcaaat 111600
gaacaataaa catcatattt ttattgtatg ctgctataaa cagacactct ttgcgtatat 111660
cgcagatgtc ggcatgcaat tgtaactctt cgggcacttc aaacatggtg accaaacaat 111720
tcttgaacca ttcatatcga ttgaatttac acagcaaaac tattagacga ttaaatttta 111780
tgaaatcatc aaaatcaatt gttgccaatt ctctgaagta tgtcaccatt ccgtgattgg 111840
caaactcttc ataattgttg tttgcaatac aattataaag ttcgataatt gcgttttcaa 111900
acatgactga ctatgtagag ttactcaaca ctgaatatga tcccgtttgc aatacacgcc 111960
gtttatatac tcattttgtg acttcaagca gactgataac acctaatcta atgataataa 112020
ttgatagctt taactatata aattgaaaat gtgtgacaac tgaattatat attcgctgca 112080
gaagcttaga acgcattact aaaaatgcaa tcgaacaata acatcaacgg tttttataat 112140
gcttcacgag ttgccttgaa atcgaccacg ctacacgacg gtaacatgcc tgtacaacaa 112200
tatacatcag ttatacaaag tcgtaatgta cgcccagttt gctacaactc caaccctaca 112260
tcaagacaga agcgcttgaa attacacaaa aaatgtcaca acaaagaaaa tattcaataa 112320
tgcaataaaa atatatgttt taaaaaaaat ttttgtattt tatttttcaa tgcatagcat 112380
ttgtgattac aataaaacaa ataaaacatg ttatatttta tattttcttt attagtatca 112440
aaaattacaa ataggattgg aacctttaca cgacaacgat cgatgacata atttatcttt 112500
ttgtgccatt ttgtcacaat tgggaggttt gtatgttttt atattgaata tcgattgaaa 112560
ttcgcgtaca catttttcgt cgttctgata caaagcaatc atggctctct cgatacactg 112620
tttgttacat ttggtacaag tcaacaaatt gctaatgtaa caattaaata caaatcgttt 112680
gcgaaatcgt ccgttgcgag gtctcaccaa tatatccttc aaaatcaatt cgatacacgc 112740
cggcaatttg agtgctttgc gtaacgtatt tattatgtgc tgtcgtttgt attgagtatt 112800
aacgaaacat acgttacgca aacttttgtg catgccgttc tttgcaattg ccggttttcg 112860
gtcatataca gtcgtggcgt tgtttgtctt gttatccaac aaatgataaa gttgcgtacc 112920
gtaaacgcgc accaacaatc cgttttgttc aaattgcgtg taaggcgata ggtttaattc 112980
aaaatcttcg aatcgcacca aataaacagc ttttttgtca atttttgatt tacaaatcga 113040
agggttccac aacaactgcc gtggaactat tgtatcgttt gatggtgctg ttgttgttgt 113100
tgttgcgaac gacgtcggtg atgtcatggt tgttaacgcg atcgtcgagt ccatcgtaat 113160
atctagttgg tgggattacg acagttgttc gattggcaat gtgtggtaat gaatctatat 113220
ttgaattttt atacgtgctg ttatcgtaat ctgaattgat agagcgttga atgcgactac 113280
acagctcgct gtcgataccg cgcgtctggc gacacatatc gtacatgttg actttgaccg 113340
tgttcaattg agactgaatt tgctggtgtt ggcgatagag catattgttg tagcgcgccc 113400
ttgacgcgtt acccatattg tacatgacgg taaatttttg tttataattg tgtactgaag 113460
tttaattctt caaaaaataa gagaaactta ttgtgtacac gctcatttcg caactatgaa 113520
ctctaaccac acatacgaag gtacaactgg cacagttaac gacccaatcg tgaatacgaa 113580
tcaacaaact cagtttcaat acgacaatga tgtcatcgac gtttttatcg ttgaaaacaa 113640
cgaagatgac cgagacggtt ttgtcgagtt gaccgcggcc gtacgtttgc tggcgccagt 113700
ggtcgccatt cgggggttta ataaatccgt tctatgggcg aacgtgaaca attcgcacaa 113760
attaacgagg cacggcaaaa attacgtaca cgcttatgtt ttgtgcagat acttgtccct 113820
gtacaatagt tctaatcgcc aaagtcattc caacgaatat tacatgttga aacggttggt 113880
gtgcgattta cttgtgggcg ctcagagtca aattgtcgat ccgttgtccg acatcaaaaa 113940
tcaactctgt actttgcgcg aatgcataga aaacggtgtc gtgaccacca atcaacaaat 114000
gtaccaatct atgccgacca cagcccaaca cttgttcgaa aacaatacca acaatagtaa 114060
taataataat ttgcaacagc aaatagatat gattcgtgaa attttgcgca acgaacacaa 114120
tacattgtac ggtaatatta gttctcaact agactctatt aaatcgattc aaatcgatct 114180
gaccaacaaa attgccttta gtaacgacac catgttggac agttttaaat ccattaagga 114240
cgtcatcaac agaaaaaagt aatgatttta taagtagtga ccgtgtttaa tgattttcaa 114300
gtgaacgtcg catataagac aacatgtaca tcatcgccta caccaacatt gtgctgttaa 114360
tgttattggg ttactgtttg tacaccggtt cgttgggacg cgaaattgaa atcttaaaaa 114420

-continued acgtcatcga caaaatgtgt gaacaattgt gtcaacgttt cgatttattg cacgaactcg 114480
tgctgaacgg ttttgctcga atgcaaaacg acttgggcgt tttaagtacg accacattgg 114540
gcaatagcga caagctcgac gaaataaatc gcaagataga tagtttacta ctaaccaatg 114600
caaattaaat tttaccgaat aagtataaca caaaaacttt agttttcacc ttcaatataa 114660
tgacgtttaa cgtcattgta aaaaagattc aagacgtttc cgtgaccgtt ctgttcgaac 114720
cgtcatggac cgtttggttt agtttggacg aggtcgcgca tcttttgcga ctgcccgttt 114780
ctacggcggc cggtttggca ccgcgtcaca aacgatgttg gtcggacttc aaacatcaca 114840
atcatagatg tcgtctcaac gacaataaaa catttgtcga tcttttcggt ttggcgtttc 114900
tgtgcaatcg cgctaatccc tgccaactgt gcgactatct gttgactcaa ttaatcgcag 114960
aactctactg cgaattggca gaatcgagac gtcgaagtca gagtcgcagc tgttcacgca 115020
gccggagccg aagtcgatct cgtcgacgta gtctcagccg taaccgaaga cgcagtcgca 115080
gccgaagcaa cagtcgagga cgcagacgca gccgtagcaa cagtcgcgga cgcagacgca 115140
gccgaagccg cagccgtact tgtcaccgac gacgccgcac tagcgagtat ttagaaaaaa 115200
tttcgcgaca aaacgatttg ctggtcagtg cggtcaatca gatgacgctc acgaacacaa 115260
acaattttgc cgaaataaat aattcgttga gcacgatcag tttgcaaaac tccactttaa 115320
ctggccaagt ggcgcgtttg ttagaaagcg ttgatcgaca attgccactt ctgctcgatc 115380
gtttgaacct tttgtcgtcg gaagtacgac agcagctcaa tcaattcagt ggacaattgg 115440
ccgaatcgct taatcgtttt caagatgtac tgcgcaacga gctgaccggt attaattcgg 115500
cgctgaacaa tttaacgtcg agcgttacaa acatcaatgt cactctcaac aatctgctac 115560
aggctattgc gggtaccgat tttggcgaaa ttggcaatgt agtgcgttcg ctgatcgata 115620
aagtcgaaca gatattgaaa attttgacca cagtgacatt gactagcaag cgttgactag 115680
ataatgactg agtataaaag tcgcaatttg tacatcacgg tagtcagttg actttgtatc 115740
gtgactgctt cgccatgtac aaatactttt tgtatttttt acatttgtcc ggtttacacg 115800
aggaaatgtt acattttata aaccaatatg agaagttaca tttatttcaa gacgacaatg 115860
ttataaaatc aatagtaatc gagagtctac gacgcgtcaa cgcaaaggct caagaatgtc 115920
tacgtccaaa tgcacacgag aacgtgtacg aaatcattac tcttgaaact atatgcaaat 115980
gtttcttaaa tcgaaaattt cacaatccgt acgtgagggg ttgtcaaaaa gctgcgcaat 116040
tccttttgca agactgtgac atgaaaacaa ttgtcaaatt tatttgcgat aatcatttcg 116100
atttgcaggc aatggataat tatattaatg attgtctgat tttttttgac gagcgtgaca 116160
ttaacgacgc cgtcaatctt cttcgttgtg attgtgaaga cataatgtat attatctaat 116220
aaataatatt ttgtgaaata ttacatgact ttttattcgt acactctctg agtcaatata 116280
taaaacctca tttgatgaat aagtatattc agttgaaatt ctgaagcgaa ccgagctagc 116340
tcgtcagcaa tggaaacggt acgcacattc attctgccca tggacgtcga tgaagatttg 116400
agcgacaata actatcgtga cgatgactac gaagacgaaa tgttttcaat cgttagtgat 116460
accgagtctg aatcagaatt aaaacgagat ttggtcgatt ggatttatga cgattccgag 116520
gacacagtga agacaaatga gattcctcat aatccggcaa caattttaat atatcattca 116580
agcacacatg aaatcttaat ggaaaacatg tactatgatg aacaccacga cggacataaa 116640
atctatcttc gggtacgcaa cattgacaga aaccaactga tcgatcaaaa cacttgtaaa 116700
ataaatgaaa acgcgtacgc ttgtagtcta gccaaggaac aagttcgtgt aaaaatcggt 116760
gaccaagtgt ataatgttag tcgagtcgaa atttcctatt tgtggaatga tctgtatttg 116820

-continued tttttctaca aacaaaaacc aatatgtccc tctgaaaaag caaacgtgtt tgtctacttt 116880
aattacagtt attattgtaa caataaagtt gattggacaa ttccagaagc acaggaataa 116940
aatcacaaat aaaaccattt tgaacaatac acatatgttt tatttaaata gtttcattaa 117000
taaacgattt ggccgtgtcg atgttacact tgacgttgat caaacgtttg tttcgtttag 117060
tgtacgacaa atttttcatg tcgagctctt cgttgaaacg atgcacggcg acttgaggat 117120
tgggatgtac ggcgtcgtaa atcaaatcgc cagatttcaa ttttcgttta cgagtctgat 117180
aataattacg ctgaccggtc agaaactcta tttccgtatt gtgttgatcc actgaacgaa 117240
caagtacgcc cagatgcggg tgtttgctac tgtcacgcgg caatctaaat ccatttacga 117300
aattgtcttc ttcgctgtat agagctgtgt cgttacagtt gttggtttga agacgatgat 117360
aatttttcaa atgattgtat aacacatcga ttttttctat ggcagatatt ttgtgatcta 117420
actcgctcag tcgattttca atgtcgccca ctttgccgag gatacttttg tgcatgtttt 117480
cgttggcgct gtgatggtcc gcacgcaaat ccgaaatttt ttcatatatc atttgcaaac 117540
tttttctac acacaactgt gataatgatg acgacgacga tgacgacgaa gttttgggcg 117600
ctacggtcga cgacgacggc atatgcgaat acaatttgtc aaacgcatac gttaccaacc 117660
atgcgataaa ttcagacttg ttggcaaatt ctatatggtt aagtagttgt agacaaccat 117720
cacggttaat acacattgat cgctttacgt cgtcattttc gatttcgaca cgtttaccaa 117780
atatcagagt ctccaagcaa atttattat gatcggacac gtaattgtca acgacaaatt 117840
caggttcgtc gaatccgatt ccgctggcaa agtcggagcc tatcatccac atttgttgat 117900
ttcgggtcaa atggcgaacg gtaaacgaaa attggtcatc gaaatttatt cgttttcttt 117960
ccaatatata cgagaatgaa tcgattttgt tgtattcact atcgtttttg gcatggcgtt 118020
ctccatcagg atcaatgtta ttttctctgc tgttattgtc aacgtcgttg tcatcgtcgt 118080
cgggggcggc ggtggcggct gcagcaacgt tgttaccgat cagcgccgaa aatgtgcgat 118140
tgataatgtc tctgaacatg ttacaaaatt atttctttcg aatattttg tcctttataa 118200
ttgtagctga aaggcgctcg tatctgcgta aaattacaaa atatttgctg gtcgacttcg 118260
ggaaagaaac atttaatcaa ctcgactcgg tcggttttgt tggcgtataa cttgtctatt 118320
gtagatttaa tttcgggttc gtcgatgaca cttatcaacg caaacaagaa actgttggta 118380
cgcactcgtt ccaactgaat tgacttaggc acatcgaaca ctttatagta tttttcacga 118440
atctgcttgc tcgcgttcat gcgaaatcga caatgtttca accatacgtg tatgccacga 118500
ttgccggaat gtacgatacg gctaatgttg tcgccgaaaa attttgcaaa agtcaatgct 118560
gcgacacgcg ttttcaaatg caaacgatcc gggtcacttt cgtgaatatc cacatcgatc 118620
acccactcgc ggcccccgtt gtcaggcaag gctttcacgt gcacgtcgct gattcggttc 118680
tggattagaa atcgataaaa attatcaaaa tcgtcgaaac acttatcagg atgaagccaa 118740
cgttgagggc gtgcaaccat aaaagcccac ttgcgaaatg tattaaaagc gacagagtcc 118800
caaatgagac gcgcctgctc ttcactgtat ttacagtcag tggtttgcat agcgaatgac 118860
aatcgcagac tgttacacgt tagtgtagtt gaattcatgt atagttatcg tgttatcagc 118920
agcagcagca gtcgttgtgg tgggcgcatt gttagcgata cgacgattgc gtataaaggt 118980
tttacaggcg ctagttttaa acaacatgac acataacagc aatattatta tgaggacaga 119040
ttttaaaagt atgcggtcat tgttttctgt gtcttttatg ttgtctagtt cgtcgaacag 119100
cgcgtcgatt acgctatcta tgccatcgtg attcgacaga gttatattat ttattaatgt 119160

-continued gttgctgttg ttgcgtatga catcataggt attggtactg tcattgctaa atatagacat 119220
gaaataatta tcttcgttga ggttatcacg aacactagta gtcatcgtga cgatagatat 119280
ctgtaataca cacatcaaag taaacatgtt tacttaaaca gtagctgaat aataatttta 119340
acaaagcgac gccactataa gatgcagcat cccgtccgtt ggtcatcttt cgatagacgc 119400
tctgacccat aaacggacgt gcgctaattt ttttattgct aaattcaaaa tgtacaaaca 119460
gataataact attttattgt tggtgttgtt tctgtcggtt ctggatggag cgcgtatcct 119520
gtgcgttttt cctgttcctt cgtacagtca tcatgcagtg ttcgaagctt acaccaatgc 119580
tctagcgttg cgtggccata caatagtcag aatcacaccg tttcccacta agagaaacga 119640
ttcatccaac gtgacagatg tcgacgttag cttgtcgaaa gattatttta aaagtcttgt 119700
ggaccgatct agactgttca agaaacgagg cgttatttcg gaaacgtcca gcgtgaccgc 119760
tcgcaattac atcagtctag tacacatgtt gattgatcaa ttctctatgg agagtgtacg 119820
acaattgatc gaatccaaca atgttttcga tttgttggtg accgaagcct ttctagatta 119880
tcctctggtg ttttcgcatt tgtttggcga tgtgcctgtc atacaaattt cgtcgggtca 119940
cgctttggcc gaaaatttg agacaatggg agccgtgagc cgacatccca tttactatcc 120000
aaatttgtgg cgcaacaaat ttcaaaattt aaacgtttgg gagataataa cggaaatcta 120060
tacagaactg gtgctgtact tggaatttgc tcgtttagcc gacgaacaaa ctaaaatgct 120120
tcgccatcaa ttcggaccaa acacgcccag cgtggaagaa ctgcgacaac gcgttcaatt 120180
attgtttgtg aatacgcatc cgctgtttga taataacaga ccagtaccgc cgagtgtaca 120240
atatttggga agtctacatc ttgatcgaaa caatgatgtc gacgaacagc aaacgatgga 120300
ctataatttg atgcaatttt taaataattc tacaaacggt gtggtgtacg tgagcttcgg 120360
tacgtctata cgagtttcag acatggacga cgaatttctg tttgaattta taacagcttt 120420
caagcaatta ccctataata tattgtggaa gaccgatgga atgcccatgg aacacgtact 120480
gcccaaaaat gtgttgacac aaacttggct gccgcaacac catgtattga aacacagcaa 120540
tgtagttgct tttgttactc aaggcggaat gcagtcaacg gacgaagcca tcgacgcttg 120600
tgtaccacta atcggaatcc cgtttatggg cgaccaagca tacaatacca ataaatacga 120660
agaactcgga atcggacgca acctcgatcc cgtaacgctc acaagtcata ttttggtgtc 120720
tgccgtttta gatgtgaccg tcaacaacaa gagtcgttac acatctaata ttaaagcatt 120780
gaatcgttcc actaattatc gaacacggaa acctatggaa aaggccatct ggtacacaga 120840
acatgtaatt gataatggta aaaatcccat tttaaaaacg aaggccgcca acgtatcgta 120900
tagcaaatat tatatgagtg atatcatcgt tcctgttata acgtttttgg taatgactca 120960
tttgggtcag gctattcggc ggttggttgt tatttaatac tgtatgacaa tgtacacatg 121020
tgttaataaa aaaggcatta ctaatattta gattgtttca aattatttac gcatgactac 121080
ccgtctccta ttgcgcagct acgctagctt taaatacagc cgatggcgta gtaaagttca 121140
tttaaatatc taaattggtt agttcaacat cgcggtgcga gcgcacgact tataccatgc 121200
atcgttccaa tagtaacagc agcaaataca aacaatcgct gataaatcgc tttgaactgg 121260
aatacaaaag tgtgtctgtg cgcgatttgc aaaaattgtc agcggccatg tatcgtttgt 121320
tggctgtgaa cgataaactt atggaaaatt tacaaactct accgatgcat tatagagctc 121380
aaataaacat attaaaaaaa tctctgcgtc acaaacagca aataatcgac gaactcaaag 121440
acaaattgtc tcattgttcg ttgcgctatg tctatttagt tagacacgaa aatacgctgt 121500
ggctactgag cggcagtatg aagactatac gaaaaaaatt aaacggattg ccgatcgacc 121560
accgcatact attgaaaact atcaccaaac gtccgggcgc agactgtaag ttttgcttgc 121620
gtgtggccaa cacgaatttt ctcaatcact tgcgcagtat aaataagcaa aaaatcgtgt 121680
ttctcaacgg cgaccacgtc gaagaatatg tacaaaacat aaaacatgtc ttcgaacgaa 121740
acgacgacag tgctatcgcc acgattgagc attgaaccgc cgtttgcggt aaccgtttac 121800
gtggacgaca acgaagtgct agccgaagaa ataattttgt atcccaaatc aaattacatt 121860
gtgtacaagt atcgaatgaa tttcgacgac cgtgcaagca acgatgaaca aataatattt 121920
aaacgcgtca acgtgcgtat tgacagtggc aattgttacg tgcaaggtac atttaccgac 121980
ggcagacgac acgtggctgt cgtgaatgcc gccgacaaaa actcgcccat cacgtttgac 122040
gggtttcccg actacgataa tgacgattct caaactttgc catttgtgct aagacgtttg 122100
aatcaattga aaaatacaca caaattgacg catgccaagg acatagctcg ggcaatggaa 122160
caatcgtcta aacttagagt gtttgtcaac gaagtagcat tggatagcga tacacattca 122220
agcaagtggt attcgcggct atggttaaaa aactcgtcgt cgacaacgtc gaaaactgat 122280
catcagttgt acgaaacaca attgatagat gatgtcatgt cgtttagtga cctagttaaa 122340
agtgataaat tattagaggc tattgatgaa accgctgttc ctcatgttgt tgtaaaaaat 122400
aaacctattc atgtatgggc tcctgtcgaa tgtcgtacgg gtaaacggtt gtgttgtata 122460
gatcttgttt tcgagaacga aggaggtttg ttacttagca aaaataaaac tactaattct 122520
agttaaattt tattacacta acacttaatt tattttgtag cactaaggtt gtgtcgtgtc 122580
gtctattata taattaatta tatacattaa taaaacaata acttgtcatg ttcgtccctg 122640
taatagatgt ggttgtattt gttagtgtta tcataataat gcctattagt tttagtagca 122700
tatttatttt tttgttgatc tgaattgtga acaagtttac atttcgattg tttgtataca 122760
taaattattg ttaaagaaac actgtaaact aatagtacta ttgttgtaat taataatact 122820
attattacaa tatgtataat aaacgtgctt aagctatcat ggaaactaat gatcagactt 122880
ttattttcat tgtcagcctt tgatatagta ttagttgtaa tttcagtctt ttctgttacc 122940
gatatagttg ttttttctgg tttataagtt tgtacattaa tatagttagt gctagtggcc 123000
gtacaatact gatgaggtaa tttgttaaat tttctataat actgtcgatt cttgtgatag 123060
atcatttgtg gtgtttcatt gtcgctgttc aataacattt caacgacatt agtgtataaa 123120
cgtctgtaca cattataata cactaccggt ctgtacatgg ccagcaaatg tagtatagta 123180
ttgttacgca tatctatgcg aacagacacc aattgctctt gagacggcgt tacattactg 123240
gtcaagttgc gtgcgtaatg ttttaacgtc gtctccaaat tgggtaacgg caccacgggc 123300
ggtacgaatt catcacattc ctccaaaacc aatagtaaag atctaaaatg atctaatact 123360
tgttcgaatg tcagcctgcc cagtaccggt atctgtttcc acatacgcgt ttgcatcaca 123420
aactcgatca gcgcacgtgt tgtgtcgtaa gatagaacat cggagccgtt tgcgcacgtc 123480
aaatcgacat cgaaatcgta ttcggtgtac ggcaaatatt taatgtaaat ctcattgaaa 123540
tcaatagtat tttgccctgt ttcaccgcat attatgcgta acatatgtat aatggcaaac 123600
tttacgagac ttttttgaaa ccactcaaaa tcgtatgtcg acactgattc tttattgtgt 123660
tgtatttcgt gcagagcgtc tatactcgac gtgtatgacg atttactttt tcgtatacaa 123720
cgtgacggag tcagaataaa tgcgcaatct ttatagtcga attgtatgaa attaccacac 123780
tttccgaata gattagatgt tgcgttggaa ctttccagta tgccttgata ttcttgctca 123840
gtggaaaatt ttataatttt gtcgttacgt tgtctgatga cgtaatcaca gtaatctact 123900

-continued

```
aaattttgca aatacaatga aaactcatcg ttcatggttt cgtctacgtc gaatgtataa 123960
ttgctcgacc gaatcatatt cgctaacagt tcggaacgat gatcgctcaa aaatccagtt 124020
agcgcatatc ccatggcgta aagcatgtcg gagccgtgtt cggcagtaac gatctgttcg 124080
atgcgaacat tcagatgtga tttgataaaa tcgtggtcgc gttcgtaaca caattgatta 124140
ccgtagcgat cggcggagcc ttccacgtac caatcgggca tcgtgtccgt gtcgtctacc 124200
gcgtacatga gagcgtgatg tatttcgtgt ccgaaattca acggtaattc ggtgtgatga 124260
cgatcgaaat atacgtgcgc ttcgattctg accgtgtccg gattgatgtg cgtgtacccg 124320
ccgttgttcg tgctaatttt ccatagttcg ccttcgcgtt cgtatgtata acgatccggg 124380
tgcacgtaca cgtcgatgga cgttgagggt gtagcgctat aatcaatgtt caatttgtcg 124440
aaaaatgcca tgaacgtttg gtgaacataa gccacttcac gtgccatgtt cgatatgata 124500
gtttcattta ttacattatg atgtacgtta aatttaaact gttcaatttg ccatacggtc 124560
aggactggca aagcgttggt tcgattgaca acaacgaaca agttttcgaa tgatatcaaa 124620
cttggattcg ttcttttagt taaataatga acgtaaaaaa actttttaa atttaacaca 124680
tcgattcgat gtgccggata atttacggct aagtgggcta tgtcaaaaga cgcttcgtcg 124740
atttcgttaa ctatgtcaga gtttcttatt gcgaacttgg cgcgcaaact ggcatacgaa 124800
ttaacaatta gtccgaacag atactcgtgc ttcgaatccc acaacacaaa agtgttaaaa 124860
aaattccgta tgctcacgaa cttgtcgaga aaagttttgc ggtcgcgcgg atgatacagg 124920
ttccacgctt cggcgatcca acgaaacatt ttgtccgaac gtttttgcat gtctccggtg 124980
atgttgactc taatgtcggc gattttgtcg cactgtttaa tgatgttttc gataaattca 125040
tgtgtacgat attcatgata gtattgtaga ttcacaacaa gttttattaa ttttgtgaat 125100
ctatccagat cggcgacatc acgataattg aaaccgtaac gcatttgttt gtcaaattcg 125160
tacataaccg tcgctttgtc acacactgtt gcattaaatt tcgtagcgta gcataagctg 125220
tacacgtgtt ctaattcgtc agcggtcatc actctagctt gagacgattt tgcgtaaata 125280
ggcgccgacg cggccaaaat tgatgacaat atcgataaca actttaaagt aaccatatta 125340
tggaacactt gaccgcacac ccaaatagaa tgacaaagaa tgttttcatc gtttcgtcgc 125400
ccacacaatt caaacataac gttatcttta aagataacaa atgatgacat atattaaatt 125460
atggtgcaat atacatgaca caaacaactt acgtcatcgt aaccttaggt caaatcgtta 125520
attctaggaa attttgcaca aacaacttac gtcatcgtaa ccttaggtcg aatcgttaat 125580
tctaggaaat tttgcacaaa caacttacgt catcgtaacc ttaggtcgaa tcgttaattc 125640
taggaaattt tgcacaaaca acttacgtca tacatgttat taatcatttt tgttgcaatc 125700
gtcatcggat caaacgattt cgtttaaaat tttcgacact gctgttgtat tatctataat 125760
tatgttgcaa actatgtaca aattttagta ttgttcgagt gtgcgcctac acacacacac 125820
gttcgcaatg gaaacaaaaa ttcatcaaat tcaaactaaa gaaaataaag tgcgcgatca 125880
atacgaatta aaagttatgt cttttttgaa gcaaccagtg gaatcgcgca gccccgtttt 125940
gcaaaacgaa attgttcatc tgtctgcttt gttgcggggt tacgaagagc aactgtacgc 126000
gctgcgtcgg agctacgatg aaaagcgcca gttaaatttc attaacgata ttggcgagtt 126060
tgatttcagt tgcgaacaaa tcgaacagct catggaaagt gacaaaatac ttttagatcg 126120
ttacagagcc attgatttga acgagacatt gcgcaagtat ttcgacaaca acagtcagaa 126180
atttacaaaa attttaaaac aatttgtaca gaaacgcaac gcatatcgaa aatcgccaaa 126240
gttaacgttg ctgcaagaac tggtattttt gaaatcaaat ctaatttggc atttatgcgt 126300
```

actggaaact ttaactaagc ctctaatgtc ttgttgagtg tttgatataa ataaaactat 126360
ttttcacatt ttgtatgtat tttatttttg aatcacacaa atattatatt gacggaggtg 126420
gtaatggagg ggccgtcggt attgatacaa caggttttag ttgagcataa ttacattcgt 126480
cgctgggtat tgtcttgcaa aaagaaatcg gtcttgctgg atgcttagga acgcaataca 126540
ttgactcgac gtgatcgttt gtgtcgttgt tcttatggtt gacgaacgat ttgtgtctaa 126600
catatttgtt gagcaattgt attaaacaca aacagtgcca ggtgaagatc gtgccaagcg 126660
cgatgtacac agtgatacga tgatttttga aaaaagtcgc ttcgtacggt ttgtacacgt 126720
tgcgacatga agcgcaaaat atttgatatt ttatttcgta acaattcagc ggcatgtcca 126780
cgacaatact atttgagtcc acttgtttgt attcgacgat tcctttccaa caggttttgt 126840
cgatgtcgta gttgcgataa tgcacgtcga gcgctccaat gtgtccgtgt tgtacgaaca 126900
tttccagcat agttaacaaa cacattacta ttattgcaca taacaacgta aaatagaatg 126960
caaagactaa tggccatgtc gagttgactt ttgatgtaat aacagaaaat atacacgcta 127020
aacacaacat gaatccgtat gcgcataata aatttgaaca attatacgga gcgacactga 127080
cgaggccata atcgagttga accgcccagt ccgtgtcgaa tataccgtac atgccaaata 127140
acgtacaacc aatacctaaa acactaaaaa atattaattg taaatagaac atgttacaca 127200
tgtttgcaag accacataaa actgtactaa ttttattatg ctaattatat taaatacgaa 127260
aaaaaaacga ttattgccaa cattttgata tgaaagagtc ggcaagtatt atttattttt 127320
aaacatgaca tcattttgac gtatgacatc atctatttta tacggaccga gcaacaatcg 127380
aagtatatca ttgattttgc ctgcatgtag gaaaaaaacg ccggcaaaat tcgattgtta 127440
gtacaattgt taagtattaa acgatgttga tctggctgct attgtttgtg ttgctagtga 127500
tatttctgta tgtgctttac cggccaatgc atttggcatg gcgatttatg ctcaaagctc 127560
agcgcgaata taacgaaact atcgatgaca gaatagatta catgcaagaa gtattgcggc 127620
gacgacaata tgtgccgtta cattcgttgc cgaatatcaa tttcaataca aacttgggca 127680
caattaacga tggtgaactg aaatgtttat cggtgccggt gtttgtggga ccagtggaaa 127740
cgcccaattt tgattgtacc gaaacgtgcg acaatccgtc agctttttat ttttttgttg 127800
gtgaatacga taagttcgtt gtaaacggcg agttgttgga tcgcggcggt tattgtacaa 127860
ccaatagtat accgcgtaat tgtaatcgcg aaacaagcgt aattttacac ggtctaaatc 127920
aatggacatg catcgcggaa gatcctcgat attttgccgg tccgcaaaat atgagtcagg 127980
tagccggcag gcaacatgcc gatcgaatat ttccgggtca aattggtcgc aacatattgt 128040
ttgaccgttt gttgggaaca gaagtcgacg tgtccagaaa cacgtttcgt agtcattggg 128100
acgaactgtt gccggacggt actagacgat ttgaaatgcg ttgtaacgct ttagacgatc 128160
atgaaaaccg tatgtttctc aatccactca atccaataga atgtttgccc aatgtgtgca 128220
caaacgtgcg cagagtagcg cttagcgttc gtcctaattt ttctacaggc gaatgtgaat 128280
gcggtgatgt taacgaaacg cgcgtcactc atattgtgcc cggcgataaa acttcgatgt 128340
gtgccgctgt cgtggaccgt ttcaatcgtg atctaatgtc gcatcaactc agagtcgatt 128400
gtatcacaag ggacatgccc atgtcaaagt ggcacaaaga catgattctg tgtccgccag 128460
acgtgttcgt acaaaacagc gacaacgctt tttattttac tttgcctgga tcttttccca 128520
tatcggaaac gggtgtttac gaaccaacgt ataggtttta tatgcaaacc agaaatagag 128580
tcaactatgc tattcgtagg gatttgccgt cgtaacaaat taaacaaaaa aattttcata 128640

-continued aaaacatatt tatttttaca atttgtgttc atcatattga tcgaaagaat ctttagaacg 128700
atgattggct ttcaaataga cgagttgacg atcgttgcgc accaccgttc gtgtgggtct 128760
tcgtctcgat aatctatcgc acaagtccat acaacacgat acactacaaa aacatcgtaa 128820
aactacaaca gtcactaaca caacaacaat aacggataca ataattgtca aactactcag 128880
aaaattttgc catcccgtac ttaaattcca accgctaaac catccaacaa aaggtttatt 128940
gtcgttttcg atttgccaac ctttaaatat agtattgttg ttaatttctt tgcgcagctc 129000
cgtgaggcgg taagtcatgc ttttgagagt gtcgtgatca agatcgttgt tcgaacccag 129060
cgcttccaac tcgaattgca tgcgatctat gtcgcgtatc gctcggctga aattaaacgt 129120
actcgacatg tcgacgtact cggtgatgag taaattattt ttaacttcat gcaatgtgat 129180
cgtacttctt ttcgtagaca ctttgcagta tttgttacct ataccttcta gaagtccaac 129240
gcctgcgtcg agttgtaatg aacgttttac gtttttacac aaaaaattga gttccgttac 129300
ttcgtcgacc atatacagcc atctgttaaa atcggcaatg ggatgaaaaa tttctttgtc 129360
aaatctgccg atgcgtacgt cgcaatcgtt catcaagtcc atgtcgcgtg cctcgtttaa 129420
aaatatcttg atgtcgcata aagatgccaa attcgataac aaaatcgttt cgggtttgta 129480
gcacaattta gtgttggcac cggccgattt gcagctgtgt gtgtcgtcca agcgtacata 129540
gtttcttttg tcttgcgaca tgccaatata tttactagtc ggtatgatga cggcacaatt 129600
agttctgtta ttgttacaca taggcaccgg tacaatgttg tataaatcat aattttccgt 129660
attcactaat ggcacttcaa taatgaacaa caatgttctt tgtggtgtaa caaacacatg 129720
agtgttgacg acatgatcaa tcagagcgtg catgttgtta acattgagtt caataggcca 129780
agtgagcgaa tcgggcaatt ttcctgtaac attacgcatt tcgttgtaca atcgttgcgg 129840
agtcataatg gtaggactga gacgattgta tttggcgctg tctacggcac ggtctaaatt 129900
gatgtacaaa aatttcagtt cgttcaattg agtttgcatg agtttcattt tgtttgttac 129960
atagtcgcac gtttccgatt tcattttttc aatgcacgcc aaatgatctt catagttgac 130020
caaacgtatg agttcatcgt cgagttcttt cacttgttcg ttgagcgcgt tgttattttt 130080
ggctaaagcg tgcaattctt cggcatcgtc cgcgtccatc actccaaaca gaaacttgtc 130140
tacgcttcca acgaagttca atccaatgtt tcgtttgttg cgactcgaga atgttggttt 130200
atctgtgact aaaggtacgg gccattttcg gttagcatcg atttgtacta agtcgggatt 130260
cattgcaacc gcactgtgat caatggcgtt atttttttca atcaattcaa taatttgtct 130320
gtatatgtat gtttgcaaat cgtgaaatat agtttcgctg ttctcgcaac tggttaaatt 130380
tttattcttg atccattcaa ctagattatt gtacgaattg tgcaattgta ccagttcttc 130440
aaatataata ttgtgatcga cttcgatgac aaaatgccaa acgtcttcaa cgaatctcat 130500
ttgatagatt ttgtcaaagt acaaaccaat agtgcgcggc aaagagataa tttttagcaa 130560
atttgtagga tcgatggcaa aagactctgt cgtttcgacg actcgcgtca acgacataga 130620
aattaatata gtacacaata aaattttagt cagcttagag ctgaacagac tactttttat 130680
cgcaaccatt gttacaaaac tgacgttgaa cactttgaac ggtctacttt atatattttc 130740
gtaaccttat aactattacg gaaaggttta atataaaaat aactagatta ataaatgtat 130800
gtttttattg tataaagata acaaatacac atttatatta taaatccata aggattacac 130860
attttagagg ttattaattc gttaaaagta atataatttc tataagtatt tacgtctgtt 130920
acacaataat cggagttatt tgtagtattc atatctgtgt aaatgtcaca ataccaaggt 130980
tttctaaaag gtttgttttc gtcgtgacat ttaaatatat cggaaaagca aaaccacaaa 131040
aaatctttgt tcaaagccaa actaatatca gtaactagat tcaatttttc ttcatcaata 131100
ttttcaaaat tataaaatac ggtataggca ataccataat tgaaccactt gtcgttacgg 131160
caccattttt tccatctttt tatatattgt agcatctggt tccaattgat ttcttcgttt 131220
ttacacgcaa tttcgctttc gacagacgaa taataccatc cagacggtag agcaatacga 131280
atatgttcaa atatagccat atattctttt tcgatacgaa cattgtgata cacaacttgt 131340
aatagactca atgtacgcag actcgatggt gtacacattt tgttagattc ctaacgatgc 131400
gaatgctgaa tagcattatt gtttaaacga ttatatagta attattaatc taatcttgac 131460
attatcattt tattgataac aatagatatg ataaaattat actatataaa tcaaaacaga 131520
attcatttta attacagttt atacgattgt acaaacagtt tataaccaac catgtgtaac 131580
gtgtggccag tggttaaccg tgtgctttgc aaactagtca tgcaaaattt gtccaaaata 131640
tatggcaata tacaattttt atatttaatg ggcaacaagc caaaggaaat tcaagaggaa 131700
caagccaatt tcaacgaact atattacaag ttcaaagtgt ttagatcaca attgcccgac 131760
atgaattgtg aaacttttgc tcataaattg attgatcaga aaatattgta ttgcagagaa 131820
attcataatt tgtatttgaa ctttttatat tgtttctaca aacaatactt tgatacgctg 131880
aagattgact gcaatatttt taaggatttg atagatgacg atgtaccatt gcaagatttt 131940
gaagagttaa atgttgttct actcgacaat aacataccaa tgtatacggc tttgtgtgat 132000
gatgtgtttg aaaagaaaac cattatacaa gatatagaat atgtaatgaa caaaatatgc 132060
gttgaaggag cgtacgtgcc atttcaagaa gaaattttgc aatatcaaat ctttttgcaa 132120
gaatatgaag atttctgtcg tcgtgttgaa aatttgtaat aaaactaaat aaacctttaa 132180
tataaatatt aaacatacac ttttatttct aaaataagta ttttttttcct attgttcaag 132240 attgtgaaaa atcaaatatc ccata 132265

<210> SEQ ID NO 14
<211> LENGTH: 130992
<212> TYPE: DNA
<213> ORGANISM: Helicoverpa armigera SNPV
<220> FEATURE:
<221> NAME/KEY: misc_feature
<223> OTHER INFORMATION: country=Spain, Complete Genome HearLB6,
strain=HearSNPV-LB6

<400> SEQUENCE: 14
atgtatactc gttacagtta cagccctact ttgggcaaaa cctatgtgta cgacaacaaa 60
tactttaaga atttaggtgc tgttattaaa aatgccaaac gcaagaagca tttagaggag 120
cacgaacatg aagaacgcaa cttggattcg ctcgacaaat acttggtggc ggaagatcct 180
tttttgggac ccggcaaaaa tcaaaaacta actttgttta aagagattcg cagcgttaag 240
cccgacacaa tgaagcttgt agttaactgg agcggtcgcg aatttcttcg cgaaacttgg 300
actcgtttca tggaagacag ttttcccatt gtaaacgacc aagaaattat ggacgtgttt 360
ctgtctgtta atatgcgacc aaccaaaccg aaccgttgtt accgattctt agcgcaacac 420
gctctgcgtt gtgaccccga ctatattcct cacgaagtca ttcgtattgt agaaccttcc 480
tatgtaggca gtaacaacga gtacagaatt agtttagcca aaaaatacgg cggttgtccc 540
gttatgaact tgcacgctga atacactaat tcctttgaag atttcattac caacgtaatt 600
tgggagaact tctacaaacc aattgtttac gtaggcactg attctgccga agaagaggaa 660
atactcctag aggtttcttt gatatttaaa atcaaagaat ttgcacctga cgctccgcta 720

-continued

```
tacactggtc ctgcatatta aacttgcgat tcagttgaca tcgtcaattt gtaactcata    780
attttatcta aattcgatcg caattcttgt aatttttgat tggtcggttt ggttcctaat    840
gccgacacca cattagctaa cgctttatcg tactgttttt tgaatgtcaa atcttccacc    900
gccataatga attgttgtaa atttttatcg gacaattgaa gttcgacatc atcggatttg    960
tccaaaggat tatcatacgt tttttgtatc aagttatctt caataaatat ttgtagttta   1020
gcagaaattt gttgtgtttg tgcattcgaa agccgttgat ttaattgatt ttttattgat   1080
attaatgtgt cttgtgcttc agtagacaaa ggataatttt ttatccatga actgtccaat   1140
gttatattgt acaaagaacg tacatattgt ttcaattcgc tgctggctcg ctgctgttgt   1200
tcgtcgtcgg tccacccgtt ttccgattct gacgaaacta caggactcgg ttgaacggct   1260
atgcgtcgtt gtaaaatctt tgcagtagga ctggcggcgg cggtaacggt atttactatc   1320
gaaccgccat cggcgggttt tgatactttt tttaatttaa ttcctttctg tatttgttcc   1380
atcaattcgg tacgtggatc ttttaaaact tgccgagtcg acgttgtata atcgcgatct   1440
ttactggatg gtattactat atcttctatt aatggtaatg acggtggcgg aggaggcggc   1500
ggcggaggag gtatcgtcga agataagttt gtttgaggcg gcggcggtgg cggcggtatt   1560
ggtggtggta ttggtggcgg catatgtgtt tgcggcgagg aagattcaga atcgataatt   1620
attgttggcg aaattgtttt ttgcattata tccgatgtcg acacagttgt cggtttaggt   1680
attgttgttt taggtactgt tggtactgac attgtctgtg acaatgttgg tataataatt   1740
gatctatcac caatgtctat tagtacgtcg ttgttgtata tttcttgggc caatttcaat   1800
aactgaatac aatcgtacac gtttaattgt atccgatcag aattggactg agcgacagcg   1860
ctgaccgtac gtttcaaact gtgcggcgcc gagatcatgc gcagtagaaa gtcgacatta   1920
ttgatgtttg tgtagttttt ttcagccaaa tattgttgaa cactttgcag ttgaaccatt   1980
atcgcgaatc gcaatggacg accgtttcgt taaggaaata aaccaatttt tcgccgaaat   2040
aaaaatacaa aacaatgtgc gtttggtcga cggcaagttt ggcaaaatgt gtgttatcaa   2100
acacgagccc acgggcaaac tgttcgtaaa aaagagtgtc gcaattaaat atgtgaccga   2160
gatcgaacct atggtgcatc aactaatgaa ggacaaccga tattttatca aattatatta   2220
ctcgttgaca acgttaaaat ctcaaatact catattagat tacgttgctg gaggcgattt   2280
gtttgatttt ttaaaaaaac acaaaaaagt atctgaagcg gaaacacgtt caatagtggg   2340
tcaattaact gaagcactga acgcgcttca ctcttacaaa attatacata acgatctcaa   2400
actcgaaaac gtcctatacg tacgtcataa acaaatttat ttgtgtgatt atggactgtg   2460
taaaattgtc aacacgagtt cgtgtcgaga cggcacaaag gagtacatgt ctccggagaa   2520
gctcaaacga caaaactacg atgttcacgt cgattggtgg gctttgggca tcttgacgta   2580
tgaactttta attggacatc atccctacaa acatagcaac gacaacgatg aagatttcga   2640
tttggatgta ctacaacaga gacaacaaaa aaaacttcac aaatacaatt ttctaagtag   2700
tgacgctcaa aaatttttgg aagcaatgtt aatgtataac attaattaca ggttgtgtac   2760
atacgagact gtaataaaac acagtttttt atcataatat atatttaata aaaaaaaata   2820
atgttgtttc tttattacca ttacaactaa agtataaaat attacaaaag tttatttaca   2880
atctattaaa actaaaatat tatgatatta taaaagttac attaaatatt atctgctttg   2940
cgagcacgtg aagtgcgttg acgtttagct ggtggttctt cagtacgaag aactggtact   3000
ctaaccatac gaaaagtagc tatctgaggt ttcatgttat ctgcccattg cactatttca   3060
acctcatcgt cactatcgtc attgacgaac ctagcagggc ttaaaggtaa atttaaacat   3120
```

```
tcgacatcag acatatcgac aggttcttgt ttgggaacac attcttcatg atactcatta   3180
atataatcag gattttcaca ttcagtattg aaatcatctc caaacaattc tttttttatt   3240
gcaatgtcaa atggtgcagc gtcattatta ttagtgttag catcctttga tgttttttct   3300
gttttaacag tgatatgctc gaaatatttg ccatttttgt ctacattggt acttttagct   3360
aattctttat cgatactatc aagttcttca gtactcattg caactggtaa cactgtcgtt   3420
gatgatagtt ctttttcaag cagattgcgc acttcatttt caatttgact tatttcgttc   3480
aattgtgaca caattacttc tgaagctttc aattgctctg gactagtttt agacaatttt   3540
tgttttggtt gcaaagcaaa ttcattcata ttactattat tattactatt agaagaagga   3600
aacacgttat cggatgcgtt atcacaatga ttgtctataa cagtacgaga caaattagta   3660
atatttacaa taggaagaga taaattagaa atatcatcat catcgacgct gttcttgtca   3720
ttatcatttt ttgaattatt attaacttga ttactattga tattatcatg agaggtttga   3780
ctaacattat tactaacatt attatcgtta ttaacagtat gttgaacatt gtcattggct   3840
gctgaatttg ctacatcatc aacattagca ttagcattgg tatcaacatt agcattggta   3900
tcaacattag cattggtatt acaaacatta gcatcaacat tagtatcatt atcattagta   3960
gtattgttaa tttgattatc actattaaca ttagtattta catcattaac atcattaaca   4020
gtattatcat taacatcatc atcatcatca tcatcatcat cttgatcatc aacatcatca   4080
ttattttgat catcaacatt tgtattgtta ttaacactag catcgttgtt agtttcgata   4140
tcattattta cagtattagt attcaattcg gcagtatctt cattatgaat agttgcatcg   4200
tcacaattac tgttattgtc gtcatcacta tcattagtac tattattgtc gtcgttgtta   4260
tttgtattat taacattaac tatttcatcg taaacctcgc tatcactatt atcaccatca   4320
ctgttacggt ctgaagtttt acttcgttta catgtcatac aagtatttat ttgtatcgat   4380
cgcaatgaac attcagtgca caatctatgc atacattgcg gatataacgt atcagtggaa   4440
tgtatattac aataggaaca tttagttatt acattgtcga gtttgtgttg tttcaaataa   4500
tcagcatgtt tagttttggt tttttgtatt tcgattctga gacgatcatg ttcgttaaca   4560
aaagccggtc tacaatattc gtttaaaaga aataattgat gtcgtatgtc ttgcaaattt   4620
aaacttatcc cgttgtcgtc aactgaagca ctgtcgcacg ttttatacat gttgagacat   4680
tgaacgatag cttctttatt gttcatgtaa cgcattttgt taataaactt ttgagtcgca   4740
ctataaatac tgttgtcgtc cgacaaatta gcatttagat aggcagtcaa ttgtacagcg   4800
taatagttga tttttttccat ggccgctttt tttgtgagca aagtcacaaa attctccaaa   4860
ctcttgcgat aattgctgaa caccgacatc gttgatacgt gatcgtacaa atcaaacaat   4920
ttgttagagt aaacatgatg acacttggcc gtaacaccac tcatgcgaaa acgtttagta   4980
gtcttgcaca cataaccgag acgcttttta ttttgcgaca aatgcaaata cacatagatg   5040
cgttgttcac taatgttctc actaatttca agaattttgt gattatttaa ttgactaaca   5100
gccgtttcac taacagccgt ttcactgctc gaactcgagt cagagatgac tcgccgcttg   5160
ttgtttgaag gcatagtgct tgttccaaac tgaattccag tttggtttgc aactactata   5220
tataaatttg ttatcaggcg attacattta tcattgaggt cgaactacat tggtgtcacg   5280
agacgcgagc gtgtgcaaaa catttttatc tcgaatcgag gtcgaggcgt acgtgaccac   5340
tacagcgtag cttaccatgc aggcaaacga cgtaatacag ataacgtata tttttgttgt   5400
gcaaaaatgt acctattttt gtagtatatt gggagcatat cgtacagtgt agactattct   5460
```

-continued

```
ggttaaatag tcttcgattc gaaattttcc actgtatatt gatgacgtca ttaacacgaa   5520
tttttttgta gtgcaaaaaa attcaggtcg cttcgacaac actttatcaa tcatgtaaac   5580
caattggcag attagataaa atattcatta taaattgaaa ctgtccgagc aagaatcagt   5640
tcaacagcag aattgtcctg tgcaatactt gaacatacag tttgattttg tgtctcacca   5700
caatgttgcc atcatatttc tggagaatgt ctgctcattt taaaatgcat tgtattgtcg   5760
cgttaagatc gcgtccgaaa ataacgacca ggcaacaatg gcgtgataaa caattatcgg   5820
ccgttttgag atatcacaaa aaaatttatg ttttgaaaaa tttgttatac aaactaaaca   5880
acaatgtcac gccaactata gaagagtatc gtgaaaacgg cgaaagcagt atttgtaata   5940
ccgcgcacaa attgctgcat gccgtcaaac atcgtatcca attgaagatc aacaagttac   6000
gcaaaaaagc agtcttgcat aaacccattc aaaaaagatc tacattgaca cgttacgaac   6060
gtgatttgga gtgtttgatg ccgcgtcgtc gatcggtgcg ttctctggac tctgatcgca   6120
agtataaagt gttcgagaaa aatgtgtatc cgactgatgt gtcgcgtaaa gtgttaccca   6180
aaaagttaga tttcaaaacc aaccggtttt tgttcatgga cctcatgaat gttcgaaaaa   6240
agcattttga cgacaacgat agtgatgagg aaaacgatga taatgagaac atcagcgaac   6300
aagtgcgtga tattttatct catattcgtt atattcgttt tcagcaagcc aaagaccaaa   6360
ttacaagtgt aattaacttt aaattagaga acaacaaaag ttttttgttg gcaatgatat   6420
tggagccatt gattgaccaa tacaatagtg atttttttgtt tattaagata ttgcaaaaca   6480
gcaagtatta taatcatttt agtttagacg atatcgacga cggctcatat agagatcgtc   6540
ttgacgatta ttttatttaa aatatgttat aacctatata ataattataa tcaaaagtgt   6600
aactatataa tcattacaaa tgtttaccta tataattaat aaaaatgtta actagtatta   6660
ttgtaattag caattcactg ttctatgtat gtctatgtgt gtacaataaa aatattaaac   6720
aaaatatatg ccatgtttta ttcaaacaca attcaaatat aatttttttta tgtgtgcaaa   6780
tggcacatac atcctgtgac attgacaata tcctgccgaa tacactatat aagttgacaa   6840
attgataatg gaatttagtt ttgtcaatgg ttcacagcaa gctactagtg ttttaaaaaa   6900
tgtctggtac attgaaacgc atactgtacg acgatataag tgatgacagt gatcaagcca   6960
agttgttcag atataattct gaaatgcagc cgccggcgtc ccagcagatg aacactgctg   7020
tcgactacga aattgatgtt gaggtaataa aatgttttaa attaaaaaac atgtatagca   7080
gtgatgtaac tacgaatgct cgtgctcaat acaacgttaa attagcagct tttctaattg   7140
tactcgacga atacaaaaaa caatacaaaa acaatttaga caaacagtca gtgttgtatt   7200
acaaagaaac atccgaatct gtaataacgc tcgacgaaga tcagtgtcat cacactttgt   7260
tgcctatcat tcaacgattg ttaaaaaacca tatgctatct gatgaacttt tgcgatgacg   7320
aagtgaacta tgtcaaacaa aagtttattt ttctaccccta tttaaagtat ttaaataaaa   7380
tactcaaatt gtttcaatac gacaagtgtt gtgccaaact cacaaaacaa cttcaagctc   7440
aattgaatac attgctaaca caatcggcag attcgtgcaa acacattcac gccataaata   7500
gacaaagtca agtgttgact gtgtttctgg agaatccttt gtacgaatgt aacatatgtc   7560
gcgacacgtt caacgacgaa cgacacataa aacccaacga atgttgcggt tacaaaatat   7620
gcaatttgtg ctatgcaaat ctatggaaat atagcactgt atttccaacg tgtcccgttt   7680
gcaaaactag ttttaagtcg tcgtctgtgt catcgttcaa acaagtttac acggcggaca   7740
caacagacaa catttaagta agtccacaac aagatgaact tggacgaaaa caaagtcgct   7800
ttggagcgta acaattataa atatctgttt ttggcaagtt atttcaattt agcagacacc   7860
```

```
ggtttgcttt cgacatcatc aaaaccgttt attcgcgaat atttgtataa taattttaat   7920
aacattgacg atgccagttt attgggttat ctcgactatc tcgatcttat tggtttaaac   7980
aatgtattac tcgatcgtga cgttaacatg ttcaaataca taaaaccgca atttcgattc   8040
gtctgtacaa aaaagaatgt ggaaatactg aaattcgacc agcgcgtata cataaaacca   8100
gacacaccgg tttacgcaac aaactttttc gtcaaaaatc caagcgaatt taaatttttg   8160
ctatacaacg tattttcgag tgtgatcgat aaacgtaatt ttgttaacaa tgacaaaaac   8220
tattgtctca tacagggcaa tacgggctat gtgttcgacc aagcctacgt cgattggtgt   8280
ggcgtacgaa tgtgcgaagt gcctaaaata gaactcgaat catcgccttt tccctatcgt   8340
ctgtatttag tgggcgatgc tatggcgcgt cattttgcta cgaacaatat cagttttgac   8400
agtggcaatt ttatattgaa aaatttttat aaaggcttac ccatgtttcg aaccaattac   8460
aaaattatca atagtaaaaa atttacaact aagaaaccca atcatttgtt caacgaattc   8520
aaacaagaat ttgacacaaa atcagcttac gtaaagttta ttcagcgcga ttacatatat   8580
gatgcaaaag cctatcccga tgatttactc gatttgctaa acgaacacat gacatacacg   8640
tccgtatata aatttgtcac caaattcatg gaagacggcg aagaacctgg taattattat   8700
agcgaaatcg ttatcgatcg gtacgccgtg gacaaatatc aaaaattgag tataaaaatc   8760
gatgaaacaa ctatgtttcc cactttgcgt tacaacgacc cttcatatat ttttataaga   8820
cctgatttaa tacaaataaa aggtacactg aacgctttct acgtgcccaa acacaaactg   8880
tttgccatat tagccaacaa cagtttgttt ggatctacca ctttgttgga attcgatcga   8940
aaattgattc cttatcgtca gtatcaacca ccgtacaggc tgaacgacga aacttacgtt   9000
gtggataaaa aacaaaaatt gtatctaacc aagtacacat ttgccaacac aatccctgca   9060
tatcttttaa taagaggtga ttacgaaagt tcttcggaaa tcaaaacttt gcgcgatctc   9120
aaaccttggg ttcaaaacac tctgttgaaa ttactaatag cagcaccacc ttctaaataa   9180
tatatacaat atggacgatc tgcgcggaac aaccacaaca ggagctggtc gttttaaccc   9240
caacatgctc aacccgagca tgctaatgac catactcata gcattagtta ttataatttt   9300
gttgataatg cttttccaat ctagcagtcc gggcagcaaa ggagccgata caaatgcttt   9360
tgcgtttcaa aatccgttaa atgcaaccat gcgcaacaat ccgtttgtta atacgcccca   9420
aagaactatg atgtaaaata agaggcagcc atgaaaaagt ttaagtgtca aagtaataaa   9480
attcgcactg tcaccgaaat cataaatgcc gacgaaaaac tgcacaagga ctatgatttg   9540
gccgacttta atgccaaaaa tttgaacagc ctcgagagct atgataattt acagatcaaa   9600
atgattctag ccaagtacat ggcaatgttg aacatgctcg aattgacgca gccccttcta   9660
gccactttc gcgataaaaa cgctatcagg gaaattgtca gtatcgtttt tgcttcactg   9720
ggctttgttc acaaccgtgt caatccgatg atcaatcatt tcaattcaaa aatggaattt   9780
atcgtgaccg aaaatcgcaa tgccagtata cctggtgagc cgttgttttt ttgtcaacac   9840
gataatggtg atgttgtatg ctacattgat cgaccgtcca tattgcaaat gctcagcaaa   9900
gactttgatc tagacgtgga cgttaacaat atgcacaaag aacgcaataa atacatgata   9960
gcgaagactt ttcgatgtgc accgaaacgt cgacacagtc gtgaacgtga acctccaccg  10020
ctggaaatca atcttaccga aacggacgtt acacagtata tgacattgtt gtttattcac  10080
gaacatgcct atttgcatta ttatattttg aaaaactatg gcgtcgtcga ctacagtcga  10140
tcattgtccg atcatacttt gttttcgaac aagtcgcggc caactttaaa catgaagttt  10200
```

-continued

```
tcaaatttac ttttaagtaa atttaaattt tccattgaag attacgatag tatcaacacg  10260
aaaaatacta acaaaaactt gggcatattg acttatactg attaaattat tggttttttt  10320
gaaataaaat aaacgacgta agattaaata tgtggctttt attggcatta ttcattattg  10380
taaaattgtt agtataccat aaaatgcaaa atcttcaagt cgacatgcat caccataaac  10440
tttgccccgc cggttacaat ggtttaaatg cggatccatt cgattgcaac gcctactata  10500
tgtgtcctga aaaaattaaa ttttactgtc ctcgcaacta tcaattcaat ttggacgcgc  10560
aaggttgtca gcctgatagc ctcgaaactg gatgcatcgg ttataattat cggaatctac  10620
ttctttagaa tattttttg aaaattttcc atacttagtg agttataatt gtaacacgtg  10680
atgaattgat gataacgtgc ggatgagtaa tattgatcat gtcacaactt gttgtcgcgg  10740
ctttgttcaa tgacgcaata aaagcggcgg gtacgttgcc ttttaaaatg acgtgttctt  10800
ttttagagta tatttcgttg ccggcgctgt cggtcgtaaa tagagcgtcg acgcgttcgt  10860
aacatttggc catattagat cggcgtctca cacttagcac gtgccaaatt tccgtgctat  10920
tgttatagtc aactgccagt agtagcaccg gtctgctaaa acatttttcg tcttcgatca  10980
gtgaacgtgc cacaaaaggt aatctgaaca tagtaataat aaaaacgtcg ttcctgataa  11040
tgttttcacc ccatgattct gtcgtgctca tgttcatgct cacgtttcgg cctgattcgt  11100
gtccgctgac taatttagta ataacagtat ttggtccttc gttctgatcg ataacgttat  11160
ctttagcgtt gaacatgtaa actgtgaccg aaaaacgtgc atccactatc gtaaacacaa  11220
ttaaattatc gatatgcgat aacggttgat ataaattgat gttcattttt gtttcagaat  11280
ttattgaaat tgaactttac ggcaagtatg gcgaatcgaa ttaccacacc gctgcgcgat  11340
caagttggaa atcaagtcac aattaattat ccgtttcaaa gtcaagaatc gtgcaattat  11400
aacaacgaca gcgattctta catgaaccgc aacaatgatg tggatgtgaa aaagttgatt  11460
aaaacagtcg aaaatgcttc gaacaaaaca gtcgaaaatg cttctgcatt tttcgccagt  11520
tatataccgc caacatcatc gaacaagcca tcgccgaggc cgaatcattt acgttttggc  11580
gacgaaattg tgatgtcgcc aattgcgatg tcgccacaaa gaattacacc gagatccgaa  11640
aggtcagaaa acgttatcga atcattaccc gaatcgttgt cgtcgctcaa acaagttacc  11700
gtatcgctgc gtcgcggtag cggactttat ggtaaaaata tacaaaattt gaaggaaaac  11760
tacgaaaaaa ccatggatcc gtacgagtcg gatagtagca gtttggaatt aacaccaaag  11820
cctaaaaaac gtagcaatac tgagaaaaaa attgccgggg tgaacgaaaa aagaagtaaa  11880
aaagaaaagc cagcaacgcc actcaacgaa gtcggacctg tggccaacat gaacaaacaa  11940
ttattgatgg acgatgctcc caatcgtaga tacaaacaag tacatctaaa accgcaacat  12000
ccgcagccac gagacccgtc cgaacaagtg ttggccaatc cgagtttgaa cgaatacatg  12060
cgaacaaatg taatgccgct cgtacagaac atgcccacgt ttcgcgtcga caaatcacga  12120
cggtttgtag attttattca acaaaagaat tatcacatgt tcattgttaa ggaacaagaa  12180
aatgttaatt cttcatctat agaacatgta attttgtacg caaatacggt ggcgtcgatc  12240
aattacgaat attcttcata ttattacaat gtggacaaat tagtgcacgt ggtgacattc  12300
aatcgttaca gatttatgat atcgcatcgt ctcttgacca aattgaacgt gcacataccg  12360
gaatctgaac agtttccgat gcgtgtacac caggatgcat ctaccaagtg tcattttaat  12420
gaaatcaaag attatgtgtt tatgaacgaa ttgaatcaca tgtttaattt agacatggta  12480
atggtgcaaa ccgaattgta ctttttgatg tccgccatag gacctgacaa aggcaaagtg  12540
ctcataaaat ctgtaatgga acacattaat gacgatcatc ttttcgtgtt gcctatcaat  12600
```

-continued

```
ttgtcgcgtc aagagagcaa acttgaagac atacaaagaa cggtcgcctc tgtgtcgttg  12660
tacgtacaaa acatagtctc tctgagcaaa gacgtgcaat tcaaacaaac ggcggaaaat  12720
ttcatgaatc gtgacgatgt cataaattac gtgactgtag cactcaaatt ttggttgaga  12780
tcaaaaaatg aaaaaaatgt tgtaaaagaa caatccgatt ttttcaccta caaatacggc  12840
agtgtggttc gattgttatt caaagagagc attcacacga atgcgttgtt gaaaatcaaa  12900
agagaaaccg gtcatgccgg tttgattgac aactatttgg aagccaatca aaacgatacg  12960
acgtcaaaca gtttcatttt gatcaataca aaaatggacg aacgcataac cataattaaa  13020
aaaggtccag tatttttgtg gatcacgagc atcatcaaag acatcatagc aatggatttg  13080
attgaaaaat acaaaaagca cacacaccat gttttcaatt tgtcgaacac caatcgcaaa  13140
gaaatgaata acaaacataa cggcatgata aagttattaa gtttttacac ttcgaattta  13200
ttaatgttgg acgaattaaa aaagtttgct gtgaataatt ttaattgtag ttatgattgt  13260
aaacactatg cttaaacttg taataaattt tttattttta tattatctat gttgtttttt  13320
ttctttcatc tattatagtt aacaggcggc ggaggcggtt gcatcaacat acgtttaata  13380
acaatgtatc ctataaaaat tatcaatagt acaattccca aaacaacaat aataggcaaa  13440
agtttctgaa aagatgtgct cgatttatcg ctagatttat tcaaaagtcc ctcctcgcct  13500
aatagaccgt ccagaccgag atcgccaatt aaatcaccaa aatcgtacgg ttcaatgcaa  13560
gatattgtat gaccggtagc caaaggcgat atgtccacgt attgtaacga caagggatcc  13620
gcattcggat cgcttcgacg acacactgtt cgttcgactt cggcgttata gccgtgacat  13680
acactttgta acgcatttag attgtctatc aatggatcgg acggacatac gttaacatcg  13740
ttcaaattgt tcacgtccag aacgcatgtt ctgtaacgta acaaacaaga ttcaacttgt  13800
tcgccgccat tcagtccaat gtgatagtag ctaccaccgg tacgacgcaa agcttcaaca  13860
atatcgccaa taactgttgc cgttcgtgct actaatacga cacctactcc tactagaccc  13920
acgtaacctg cttgtttagc tgtttctaaa tagcggctga gtcgcggctg ttggttgaga  13980
acattggtga cgccttcggc tgtacgggta tttgttgatg gaaaattcgt ttttacactt  14040
tggcgtcgca aattgtttgc atgcaaacgg gcgtcgggca cgttgtccat gcgtcgcaat  14100
gtggacaacg aatccaattg attagtgttc gcgttgggaa atacctgacg caatcggggc  14160
acatcattgt tgcgcatgaa actattcatt tggggcgtac tgacaaaacc ggccggtgtt  14220
tgatatccgc ccaatacggt attgttttga agcggttgac tactgggtgt ctgaaataca  14280
ttgttaaaac cggaaggtgc gttgttcacg acagatgtgt tagcggtcac gaatgatgcg  14340
tgattcggaa acggtctgtt gacattacgc agatttctaa aaaacgacat gatgtcagct  14400
acttactttc tactaacaat tctcatgata tttacgtcag cacccattgg actgactagt  14460
aaacgaacga atatagctta gttctgactg gtggtcaagt ataaataaga gcttactagt  14520
cacggcaaag atcagtaaca attcgacatc atggcgtcaa catcgacggc agcgtcgcta  14580
gttaaccaac atcgtcaaga tttacgacac aagttcttga gtgtggaaag taaaaatcta  14640
ctatgcggca tggcaaagtt tgcggacgaa tatgttcgcg gcatccataa tgtgactcaa  14700
gtcaatttgc ataattgtga aaatttaaag agtccacacg atctcgccgt gcgcacaatg  14760
tgcgacaaat gtcagacagt gtttcgagga ccgccgttta cacgctggtt gttttgcgct  14820
gtgaactttc gaatttcgtt cgacaatacc aaacagaaac gtgaccaaaa gtttaagttg  14880
gtgtgcgaag attgcgctca aacttacata ttacatccag aatttcaagt ttacgaactc  14940
```

```
tatccgagga tacatttgaa acacgtcttg gagctgtgtc gtcatggatt tattcgaaaa  15000
tatttcctgc ccatcaatcc cgacctgtat tcggaacgtc gagtggacat tgttcgtaac  15060
gaaacttaca aagtcaacga catctacgct acgattcaag atatcatatc caacaagaat  15120
ccgcacgaac aaattactaa aatatcattt cgtaccattg gacgagtttt tttcgacgaa  15180
acattcgaag acatgtttgt agagaagcgc ggcacgatct ccgttgtacc tggaccgagc  15240
aaaatgctcg aatttttgtc gaaacctttt gattttacac caaattttac ctattactat  15300
catgtacatg ttgcggtcgg aagggaaaaa caacgctatg taatgtattt ggagatacca  15360
tgtttgcgct attgtaaatt gtgcactttg gaaaaacaac ataaaggtta tccggtggtt  15420
tggtgttcgg tgtgcggcta cacagacacc atgtattatg atgaagaatt tttgcatttt  15480
caaaatatgg aatatgagtc gtttcgtttg cgacccatgt acaacaaaaa gaaaactgaa  15540
tgcatcatat actacaaact gccgtttatg ccgccttcat ttctaaaaaa taagacacaa  15600
tcaactctgt tgtctgtcac caaacaatag ctatgaacaa aactaaaaat atgtgtaata  15660
tttatgtcat gagacaaacg gcagcgttgc aaactgattg tattcgcaat aaaacaacag  15720
accaaagtca taatcaatca tcacgatcat catcgtcttc acatgtacaa caaaataata  15780
aagaatacaa aaaaatataa aaatgtgttt tattgtaata atatgtacaa atatttcaca  15840
aacatataga atttaattta ttttcaattt acatttttgt ttgtctatct tcttcaaagt  15900
gttggcacga aatatgtaaa aagtagtgcc attatgacga ttaggcacag tatcgacgac  15960
gcgatattta agtcgacgct tccgttcttc gttgccggtc ataatactat ctagatcgac  16020
acatttgtat gcatagttaa acgtagagtc ggcattaata gccactatgt acacgtacgg  16080
cgaatgtttg tcaaaaactt ttttgttcaa ataatatatg atgttcttgt ccattttgtt  16140
tgatttctga tcaaatgtcc atgtcgaata tcatttatat acataacggc tatctcgaag  16200
agataagata cactagaatg agtcaaccta ctgtacctac gccaacattt gaagacgcgc  16260
tgaacgccgg caaattcgca ttcaacatta gtcggctaaa attcataccg aaatggcggg  16320
cgagatttcc gcacattttt atcgattaca aaatatggcc ggctaacaat gatgattttt  16380
acgttcccgc cgccctgttc aatcgagcta ttggtgttcg cgtcacgttt agtcgcaaag  16440
gctgcgaaag catgagttgt tatccgtttc acgaaacagg tccgataact ccgtacacac  16500
agttcgggta tacacaaaca tcggaaacgg cagtggcgta cgctcaaccc gcatgctaca  16560
atttggacag ggcggcggcg gtgcgcgacg gtgccgaaaa tgaaatacaa acgcccgaat  16620
tgcgttacac tgacggggga aaatgtatta tagtggacac tttgacaaaa atgtatttga  16680
atactcccta tttgcgtacc gatgaccatt tgatacaggg cgttgatgat gtgcccggat  16740
tcaatgtgac aaacgatacg gatcaacttt ttcccgaaag attcgaaggt tttttcaacg  16800
aagcctattg ccgtcgattc ggccgttcct tacaaccgaa cggcggttgt tcacttcaat  16860
ggtgggaaag tttaataggt ttcgttctag gcgatactgt acttgtcagt ttcaaattgt  16920
tagtgaataa tatttttagt gaactgcgag gattcgatta tacgcgaccg tcgccggtgt  16980
tgccaccgaa accggtagtg acatcgcccg cgctcgtggt ccaagaatgg cgtagccaac  17040
gcgatcgtga agcgcccatt gatctagaat tgtcgttttt agattacgaa caatattcgg  17100
acattggatt gactgcgaac actgttctcg aatatgtagc cgaaaacgga tttcgagtga  17160
atccttatcg cggaacaacg gatagatggc aacgcgaaac gacaactcta tacaacgacg  17220
ctaagcaaac gacgatcgac gaccaaactc taaaagatat aattactcaa tttttggagg  17280
acaacgcttt agtggctggt atagcggcaa gtttcggttt cgatttttttg tttgatgtgc  17340
```

-continued

```
tcaaagacat gttgaaacgt atcaatacac aattgttgcc gttactgaga cgagttctta  17400
tcagcggcag tcgtcagttc acaactcgtt tgttgggcga aacttacaaa gccgccgtca  17460
tccattcgat gaacaagatt gctatcaaaa ccgttacggc ggtcgccaaa gcgatgacta  17520
aaatagcaat taaagccgct tctgtcattg ggatcgtttt aatcatattg accattagcg  17580
atttggtatt agcgttgtgg gatccgttcg gttacagcaa catgtttccc cgcgaatttc  17640
cccgtgatct gtccaattct tttttgacag ccttttttca gagcatgggc gaaaataggg  17700
acatgatgga attgttgccc gaatattatg acgatttgtt ggcgcaaaac gaaaacgaca  17760
ccgaccaaac tatggccacc ttcgaagaca ttctaaatat tgccgaatac ctttccgcgt  17820
tgaccgtcaa ttccaacgga caaatgctgg atttaaacgc cggcgaacct attgacgatt  17880
ttgatgaaat gactctggta ggtgcggctt tagcttcgag cgccatgtat acgcatttgg  17940
aatttttaca atacaccgaa cggatgaaca aactgttcca acaaagtcag ccggaatcgt  18000
ttcgaaacga tacgctccta gccaaactgt ttggtcttag ctctttgata ttgatggcgt  18060
tagtgatgat tacaaacgat cacaacgcca catgtctgtt cgttattgtt ctgttgatta  18120
ttctgtttgt tatatgtcgc agttcgctga tgttttatat gggtttgcga aaacacgcgc  18180
aatacgcgac aatgccatgg taccacaatt tatacacata aaagtacaaa ttttttgat  18240
taataaaatt ttatttaaaa aaacgttgtt acattcattt tttattggac acttttcgat  18300
tgacgttggg aacaacttca tcggcaggag gtatcgtagg attgaggatt tctgtgatcg  18360
cttctacggc gtcttgaagc gtttccaaca cggcactttg accgtcgatc ttatcaacca  18420
gcaccgacac atcgggcaga ttacttttga cgtcggcaac ggcagcgctg agttcatcaa  18480
gttgagtttt aacggcggca atatcttgcc gtatgaccaa tagaatgttt tgtgacatga  18540
ttattttgtc gtacagaagg gtgcaatatt caagtacacg caactaacaa cttactataa  18600
tactaaattt tgtatcttta ttatttgtac aacaaaggcc catcgaatct gattctagaa  18660
atttcgaatt cgccttccga caaagttata actatttcat catcattata gaatatatga  18720
acgtttcgtg ttaggtttcg aaacgtggca cgattcgcga cactagttag ggcaaactct  18780
ttgatgccaa cagaacgttc gttcggcagg tacgacattt gacgacgacc gtacaccgat  18840
cgtccggtga gcaatcgttc cggtgttaca ccattgtttg aatcgaattg aatttgacca  18900
gaaactaaat tgcgcggacg tacacccgtc accgggaaca ttaccgcgtc gcgatcgcga  18960
tcgtcgtgac gatgcgtcac tacagacact agtttttttgt tacgaaaaat tggagcccct  19020
atgagtacca tgtcggcgac tgttcgatct tctagagcga aagttgccaa ttgactgtac  19080
acgagtcgat gtttgtgtac atgataatta gtgtagacga attctggaac cactcgtgcc  19140
atagcaccgt ttttcaaaag cacaaacaaa gcactagtca tgtcgatacg tggaaacatt  19200
acactcgtcg ctacaccggg aaaatgatgt agacgatcga gcgtgtcgct gttgttgctc  19260
tgatgcccga ttacatttat ggacactgta cggttatcca ctttgtgtat aaaaattctg  19320
tttagatcat tatcgatcgt atattcaaca ttgtatcgtt gcaatgattt agcagcgatt  19380
gccgaagcta aaatcgcaaa aaacaaacac gtttgtcgca acattatatc gtaaacacct  19440
taattatatt caaacggata acctatgact tttaattttg tatatatata tatggatccg  19500
agattcatct catatccatt aaatagaaat tattaaagat gtatacatct cacaagaaaa  19560
atttgaatat agctcaacaa ctgtacgata taacgcaagc taaacgccaa ttgaccataa  19620
aacaaactca ttatgagcgt ttgaaacgga tcaccaagga cgccagagaa cttcaagaaa  19680
```

-continued

```
tagaacaaca attgcatcag atacgaatgg attttctcaa atacagcaca accatgtttt  19740
aagtctaatg aagaatggga ataaataaaa tttaattttg ttttgcatta tatttattat  19800
tatcaaatac atatttatta atctttgaca ctcatacgtt taattttatt atacaaagtg  19860
ttatcttttg atcgttcatt attgccgtat ttgtcgtcgt tgtcgtcatt cggattcaaa  19920
aggcgttctt cgtcgacgtc tcgacaccag tctccgattt cagatatgcg atcggtactt  19980
ttaaaactca cactaccatc ggaggatcta cgacgatgac atttttgttt gcgtgtatag  20040
tcgctgtccg atgttaacgg tggcaggggc ggcggcgaaa acgaacgctt ctgtagatat  20100
tgttggtgtt tgtaatggcg gcgtttgcgt acaggcggcg atgtcatttg acgagtcgaa  20160
tacactcgac attcgaatcg ttcaccgctt ggccaaaaaa ctcgttgatt caattcggca  20220
aaacgatccg ccgcccagcg cgaagtaacc accaaacgtt ttcgagaaca ttcgctccaa  20280
atgacgcaat cgcgaatcgc cggtccgcac acgaacaaaa taaattcgcg cgaaaatcgt  20340
ttttcgattt gggctccgtt aatgtagacg acgtacgaca tgttggcagc tcggtcactg  20400
atcgactcct tcgatgcgaa agaacaccat aggttttatt gataaagaat atgatttttc  20460
aaacaatttc ttgcccgtga cagtttcaaa ttgtgtttcg ttcttgctta ttttgactcc  20520
ttctatgagc gctcccatca gcatttcaac ttcctcggaa ggttttggag gatcggtgtt  20580
ggattcaaac tgaaaaacgt cattaaacgt atccactgta aacggttcgc agcggacgct  20640
cttcactaaa tcgccggtgc tgaacacttt ttcgttttgg ctttgggtta tgttgaagaa  20700
cttgcgtaca aacatcattt tattggcgta gctcacattg tcctcgggca aattgaccaa  20760
tacactattt tgtagtttca aattttcctc ttgcaaatga ttcttcatga tgttgccgaa  20820
tatcttgttg tgaacgtgca tgttgggcca tgtgatcatg aaaaattcac cgtaaacact  20880
tttgtaacgt ttcattttga ccatgtcgaa aaagtaaaaa tgaaacatac cccctttaac  20940
gagaacgcca atcttgtatg tgagtttagg cggtttcaac ggttcgatca ccaccttgtc  21000
gttgacttgc ggatacaatt tgtctatcca agactccaat gaaatgcttt cattcagaaa  21060
gcccagcgac tcgaacagtt tgttaaaagg cgtatgacac cttagcaccg tcaaattttt  21120
cttttgcaga ttatgtgtaa atttgtccac ccatgttata gatcgtgttt cggtttgcgg  21180
tttaaagatg cacaacatct tgtcagattc gtcgtactct acaatttcgt cgctgtcgtc  21240
gttgtcattt tcattgcgat agacagccaa cgtcgtactc ggaacggaac tgtctagttt  21300
tgcacgtttg gactcggtgt ctccgttgtc ggcctcgcag tttatagatc gtttattatt  21360
cattatggtg acggtagtat tagcactccg actctatcag cacttgtgca atacactaca  21420
atcgcacttt gtgttttata ttaagtagcg tatcaggcaa cgattattat cactaatttt  21480
accagacgat atcatccaac tcgacgatgg aatacaattg taacaatcta ttaaaacaca  21540
cgccttattc caacaaactt aatttgtcat tcaaaagata catgatcaca ctgtctctgg  21600
ccaaaggtgt agtgccgtcg ctggccacgc tcgaatccgt taaggaatta caaaaattga  21660
aatttcaaat cgatcctgta accaattata tcagtaacgc gctcgattac gaaatgatag  21720
ttcaaaacga tgatttatcc gttatacatg tcctggaacg tgacaccaag cgctatgtag  21780
gccaaattaa gttaacgttc gaaatcgaca acaccatgca cattactact ttacccgtag  21840
ccacggatta ctcagaacaa aacaaacttg atcaggccgc cgtcgttgta gacgaccaat  21900
acaattcgcc attagtgttt catgacaatt ccacactcaa caactcttct gaactatgga  21960
atattccatc aacaaacaaa tgacatcatc gttcgaaatc tgctgtaggc aacgaattat  22020
cacacacgag attatattga aaaaaatgtc atcatcgttt taaaatattg catcatcttt  22080
```

```
agattcgaaa ctagcccgcg ctttcatatg aaaccgtcgg caaagatcga taaaatttat  22140
tctagaacat tccacggttt gacccaaaaa aacaaatgac gtcatatggc gtgatctaga  22200
aatggtccaa tcacaaacgt attccacgaa tcacgccacg cccaaagata acgtattttt  22260
aaactggcct tggatcatta cgttcgaaac gggccgtgat cttttgtttt gactcgtgat  22320
attttgcaca cggcactatt ccaacaaatt ttccgcgcat gttaaaatca atttaacaaa  22380
tcacgccacg cccaaagata acgtattttt aaactggtct tggatgtgtt cgttcgaaac  22440
gggccgtgat cttttcatga cccaaaaaaa aaacaaatta cgtcatccgt ttaggatatt  22500
gcatcatctt taaattcgaa actagcccgc gcttttatat gaaaccgtcg gcaaagattg  22560
ataaaatttg ttctagaacg ttccacggtt tgacccaaaa aaacaaatga cgtcatatag  22620
cgtgatctag aaaaagtcga atcacgagac gcccaaaaat aacgtacttt taaaccggtc  22680
ttatatcttt tcgttcgaaa cgggccgtga tttttgctt cgattcatga cccaaaaaaa  22740
caaatgacat catctaccaa agataatgtt tcccgcgcac gtttaaacta gtcttggatc  22800
ttttcgttcg aaacgggctg tgatcttttt gcttcgagtc atgaccagaa aaaaaaccga  22860
ttaagtcatt ttgcacacgg ctctctttga aaaacaaatt acgtcataaa acgtgattat  22920
agaatcgtcc aatcaaaaac gaacacgaat cgcgtcacgc gcacgaaatt tactattcga  22980
cttgacctaa aaaaacaaag aacgtattcc acgaatcacg ccacgcccaa acataacgta  23040
cttttaaact ggtcttggat tatttcgttc gaaacgggcc gtgatctttt gtttcgcttc  23100
gtgacttaaa aaaacaaatg acatcatcgc ccaaaaataa cgtactttta aactggtctt  23160
ggatcatttc gttcgaaacg ggccgtgatc ttttgtttcg cttcgtgacc caaaaaaaca  23220
aattacgtca tcgaccaaag caaaaattct tgcgcatgtt taaactagtc ttggatattt  23280
tcgttcgaaa cgggccgtga tcttttgttt cgcttcgtga cccaaaaaaa caaattacgt  23340
cattcgttta aaatattgca tcatctttaa attcgaaacc cgcccgcgct ttcatatgaa  23400
accgtcggca aagatcgata aaatttgttc tagaacattc gatggtttga cccaaaaaaa  23460
caaatgacgt catatagcgt gcgtccaatc acaacacgaa tcacgccttg tctaaagata  23520
acatttcccg cgccgggccg tgatcttttg tttcagttca tgatttagaa aaaaaaacga  23580
acataaaatt ttaccgcgca tttttaaact agtgttggat ttttttgttt gaaacgagcc  23640
gtgatctttt cgttcgaaac gggccgtgat cttttcgttc gaaacgggcc gtgatctttt  23700
gtttcgctga ctcgtgaccc aaaaaaacaa atcacgtcat tcgtttagaa tattgcatca  23760
tctttaaatt cgaaactcgc ccgcgctttc atacgaaacc gtcggcaaag atcgataaaa  23820
tttgttctag aacgttccac ggcttgaccc aaaaaaacaa atgacgtcat atggcgtgat  23880
tttaaatcta tttaatcgtc tctggcgtac aaaagtaaat tacacacgaa acgtgccatg  23940
ttaagtttgt ttacaataaa actgattgtg tcgattttaa tatgaacata agatttttgc  24000
aaaaaattcc attaatcgaa cgaaagcgac aataaacagt tcgtttgtta taccaaatcg  24060
aaatacgttt gtatattatt cacaatccat caattcaaaa catgcctcgt cgacgtcgtt  24120
cgcgtacgca taattataat gatcgaacaa ttgtttcaat gaagtgaaac cggttaaatc  24180
acgcagcaaa agtttagcag tcgtgttcca aaacggcaca cacaaatacg agtaatacaa  24240
ttcaacgaaa ctgataacgc ccatttcgct atttaaaaaa gatacgtatt cgtctggata  24300
ggttttcatg tctttgtcga atatgtattt tttgtgaaag tcacaacgaa gattggcatt  24360
tttgtgataa cacattcgac acgtatagaa cttttcgatt tgcaatgcgt ttaaataatc  24420
```

```
gcgagcttcg tccgatagtt cgttaatttc gtttatagca aaatcgttgt cttttttttc 24480
gcgcaataac aatttgtttc gtcccatata ttggagcaat gttcccaagc aaggtttttc 24540
gacaacgcca atgtttctgg cgacgatttg ttcgttaagg gttttagtca aatttttttag 24600
atctcgatga aattcggccg cgtccatcat tattgacgac gacaacaact tataagagtc 24660
ttgcgttaca aaagttatca tcatgcagat atttgttaaa accttaaccg gcaaaacgat 24720
aaccgtcgat gtcgaatcga gcgacagtgt agagactgta aaggaaaaaa ttgctgcaaa 24780
agaaggcgta ccggttgacc agcaacgtct aatatatgcg ggcaaacaac tggaagattc 24840
catgactatg aacgattaca gcatacagaa agaggccacg cttcatttag tgttacgatt 24900
gcgcggaggt caatcaattc gaactggttt ctgataacct aaatatgata gtataaatgt 24960
gtccatccgc agaatatttc tgcagtctaa gtttacaatg tccgaaatat cgcaccatac 25020
catgtatcaa gcgtatttgc aaagatcgtt tttgtcacaa aaagattggt tgtatttcga 25080
tataccatcg gaacaattac aaaaagattt tagtctcaat atgacgtcga acgatatgac 25140
tcgtatcatg caaaacgcca aaacctacaa tatggcacgg cgtatacttg atcgcctcct 25200
gccagtcgaa gccagattct atacaatgga actcttgtgg aacagcattc aaccatatgt 25260
aatttttgt ttcttattcg cgctgtgtat acacatggaa gattggaaca gtcacgaaac 25320
tgaccgttta ctggatgaat tgagcttgtt tttacgtcaa cccatcgatg aagattctca 25380
cagagacaaa atgtacgcca ctagttatcg cgatattaaa tttgaatatt tacattgttt 25440
cactgtaggt caattaaaga aattttcaaa agcattcaat aaaatcgtga tgagattcga 25500
ataaatgtac agcataagta aacatgtcgt attattcatt gtatccccag ttacctgctc 25560
atgtggtgta tcgaattcta gcttatgtgc cagttgacaa attattggaa ttgcaattgt 25620
ctgagtacga ctataaatgt attttacagt gtaaaaatgt aacttgtttt agtttgccaa 25680
aaatatgtta cagtacaaga ctactgttga acacattgat tgatattcat ggtatcgatc 25740
atgattttag acattcgtgt ttagttgatg gtcacaaatt ttatttgatc aataacaaaa 25800
cgttcgtttc gtataccggt ttgagacgtt actttacaaa acatagtatt cgtaaatgtt 25860
accaaagcaa tgcaaacgtt tcctttactt gtttgttcga tattattgct atacgatttc 25920
cggaacaatt tgaatggcac aaaaaatgtt gctttacatc gtgcggcggc ggcggcaaat 25980
tacgcaattt tgcgtgtgtc agtataaata tagttgatca gctaaaaaac gaaactgttt 26040
gcgaaccagc tttttttgttt ttcgattata tgtatcatat attacgatta gaataattaa 26100
aacaagacat ttataaaata ctataacaat ttattaaata tcaatgtaca aaattttaag 26160
cagacatttg actatcgtcg caagtgtcgc taaccattgc aggggacatg ggatgtattt 26220
gtaacggctg ctgctgctgc tgcggctgat gttgatattt tgcttttttc gatactggcg 26280
ctgaagacga tacggacgga gcttgatgtc ttttgggctc tttgcgtttg cgtaaacgtt 26340
tgcccacttc ttcgtttttg tcattgtcat tcgctgtggg aacgacagat tctttagtgg 26400
caattgtaac attgctcacg ctcgtattta atgcagtatg taggaatttt ttaaattgcg 26460
atacagcatt ttccaaaacg tttcgagtca atttcgaatc ataaattatg ctcgtagcgg 26520
gcgctttatt gtttgtgtac gtatatatga gaatattatt aaattccgtg taaacttttg 26580
aacgtttctc gttactctct ttgatttcgt ccagatttaa atcgcttttt ttaacgttca 26640
cagtgctcgt tttgttcgat ttggtgagaa ggttagtagt gttgttgttg ttgttggtgt 26700
cgtttgttgt tggcgtcggt gatatttgtt gtttcttgat gattattgct tttccgatct 26760
tttccatgta atcgaatatg tgtagaaaag catcgctttg gttgtgcact ttgacgagat 26820
```

```
tccacaagtg actgctgctc ggccatccgg attgtttaat tttcgatatg aatgtattga  26880
acagaatgta tttgttgttg ctggtaattt tcttgatttt tttcgataat tttttgtcgt  26940
ccgcaattgt tggcatcacg tgcacttgat aaccaatttt ttgtttctca aacagattga  27000
tcacattgac aagcgtttcg atgtgcgtct tgttgtacac gctattctcc aatttaatga  27060
tcaacgactc ggccgggatc gatgtcatat ttgctgaccg cttgagcgta ttcgtcttct  27120
agggtagttt ttaaattaaa taaattcgtt aaacgtttcg agtgatagct caacagtcgc  27180
ttcttctctg gacaatcgcc gacaactagt gaggcggtgt caagaatgct gtttatataa  27240
ttttgctgca cagcaaagcc gggatcggaa acgtgatcgc acacacgatc cacttgcata  27300
tgatgtttgc gccaattgat tacttctcgc agcagtgcgt acacttcgct acgcgtcaaa  27360
cagtcaccgt gattagtttc gaactgatcg caacgactgt tgattttagt attgccgctg  27420
catatttcgt tgaccatggc gctgctgtac gcgtaaaact gccgttttat cggcgccgtg  27480
gaagtgtaca cgtttttcag aatcaaaaat tgccggagtc ctgatcggaa cgttgcgtaa  27540
tgaaagagta aaaaatttat tcaattgtcc cgaatcgtaa tcgatcttga cttgttcgac  27600
gaaatcgaaa aaatccaagt agttgctgga atcgtacgtg accagttggc tttcgcgcat  27660
atattgaaag tagtctttaa tcggcactat gtacaaattg cgcggtatct cgtgattgtg  27720
acggcgaact tgtaaattga actggtactc gttactgtca cggttgttgc gctgcaattt  27780
gacgcaatac gtgttcggtt ttcgactgac ggtacgtaat gggcctttca aaatgcccac  27840
gtaaatggtg taacggtaaa ctacgccgtg atcttgccaa tgcaacaaga aaggtgaccg  27900
gtaaacgtaa gcgttttcga aaaatgtacc cgtttcttcg atgaactcgc gcacggcggt  27960
ctcgtaatcg aaaatatctc tactgtccca tttgccgcgc ggtatagaaa tcttttcaag  28020
gaaatgattg ccgttggcca cggacaagtt gtaggcgcga cgggcacaca gcaacaccgc  28080
cctgtccggt tccataataa tcagaagacc cgagcaccgc atgtcgcgct acacagtgct  28140
ggttatcgcg tgtcgaccaa actgaacgcg ttgactacaa gcgttagtga ggcagataaa  28200
gctttgtgcg caacagctaa taatagtttt atcattttat cgtgatatat tgtacactgt  28260
tacttattat ctggtgcggt gcgtatttgt agataacatt acagtataaa atatgcaact  28320
gaaactgtaa attatacagt ggtgcttcga tcatggcttc gaaaacgaca accgtatttc  28380
tcgtgatcga cgaactgttc gaatacaaat gttattacaa aattccaaac actggcggca  28440
acggttgtgc tcatgtctac acatacaaac cggtgcaact ggtaccggcc atgttcgata  28500
ccattactac gcatatacta actagcacag cggaatcatc atcatcgcct gaaaacatta  28560
aaaaaccgtt gagtgtggtt tatcctaaaa atgaacattt gttctcaaat tggtttaaat  28620
gtttaaagaa caatactgcg aaaataacag aatcgacgac ggagcaaaga gtttatttgt  28680
tgtgctcatt tgctaaatta aaatttgttt atgattttga catttacaaa ctggaacatt  28740
ttggattcgg agccagcggt tcgattgtgc atttggcgag acattgtaac gcccatccta  28800
cgtttggcaa actgattcta tcgtgcgtca tcatcgaatt gactgtgctg ttgcgcatgc  28860
tggccaaact cgaaaggatg ccgacgatac gagattgcaa cgacagcaat atggattgtc  28920
tggtggttca ttcgtttgct tcgtgcaaag tgctcgctca aatagcacta ggtataactc  28980
acaatattcg caagctcgcc gccgacgaca agatgatgac gagattgtct caatttttttg  29040
ttcaaatttt ggaagaacgt ttctgtccca gtttggatgc tctcgaaagc taccataact  29100
atttcaaatt ggccgtgcaa atgatcaagc tcaattacaa aagttgtgct caacgccagt  29160
```

-continued

```
ttagcgattt cgttgtgccg ggcgtgttcg atctgattct cgccgatcac agagttttga  29220
acaacatgtg tacgaattgt acaaacaaaa attccactgg ctacgtggac agcgtatatt  29280
acgactctag ttttgttcgt cacatgtatc agttgatagg actgagtaat ttgtacaaag  29340
aaaacagttg ttttatgaat attttggcaa tgttcagtca tgaacccatg cagactatgt  29400
gtttttctcg agtctataca tacaaaatgt aaactaaatg taatcaccaa ataatgtatt  29460
gaaataaaac caaatttata taaagaaaaa aaccattttt tatttgtatc attccaattg  29520
tacaatgcga tgtccatagt gagttcctgt cttgatccgt ttgccgtgta taaaatccat  29580
tttgatttcg ctatcgttgt gcacgatgcg cgattgcacg gcggcgcgtt tcaacgagtt  29640
gagtctacgt gttgacaatt ctaatggatt gtaaattaga gatttttcca aagtaaacga  29700
attgagatgg cccttgttgc accattctag actaatgatt agatttaata aaaatatcat  29760
ttcataatca cattcgtgaa acacaaattg attgcgcaaa cagtaataat ataattttaa  29820
cgaattgtac aaatagaaca tgtaatgtcc ctcctttaaa tagtactcga cgtcggtgac  29880
gaacagtacg ttgatatatt tgttgactag taattgttgc agtttcctac aatattgtaa  29940
agagtttttg tcatcgtcca attgcgtggc gcacaaattt ggcaaatggc aattttcaat  30000
tatacaaaac tcggcggcca acaggcgttt gagctcgaca ctgtgatgcg gttccaattc  30060
gaatacaata tatttagttg aaaatcggtg ccgtttaata acgtccgata tagatgtaaa  30120
acttgccaaa aacttttcga atgcaacgtc gttccagcca cgattgattg cggtcgcagt  30180
ggcgttttgc tgttggtgtt taaaatctaa gccgctttgg atcaattttg tagtgatgcg  30240
tatgctcaat tgttgcccta gagtatagtg gttttcgtag ccgcgttccc ataacacgtt  30300
acatgcaaaa ctaacgagat tatccacgtt tggttgagtt aacatctttt tcatgcgaac  30360
atgatcgcct ttataccacc gatcgcgcac caatagcttg aacaatcgaa tttgatgagc  30420
ggtcaaatta gcgccccgcg tcaggttcac gtacatgtcc aaatcgtcgg gcgtcgattg  30480
tgccacagcg ttgatatcga acagaacggt ccgtttttttg agttgaacga atccatgggc  30540
gtcgacgagg aacacttcgt caacggtgaa catgttggcg acatcgtcga cacttgctcc  30600
tttcagatgt aacaaataca tggtgatttc gtcggctaga tatttgcaac attgcggtaa  30660
cggttgagac tgtacgtcaa aatagcgagc aaacattgcg gtcgtatcgt ttttcttcac  30720
tgatggtgtt gaagcggcgg ttgtcataat atattaatta ttcgaaagtg ttgcacgcgt  30780
gtatttgcac attatttttg atcaataact aaagtgacaa tgtcgaaacc gagcacaacc  30840
attaatagcg ccagtactat taccgtgcta gataatgaag agtactcgac gcgtttgaaa  30900
agtattaaaa ctatagtcga tatcgccaag gaagccatcg aagacatggt taagtacaat  30960
gaacttgaac gtgacgacgc cgattcgctc agcgtggccg atgctaccgc tgcatgggtt  31020
tgcggtcgtg tggctaacaa taactatgta acgatgcgaa tccaatgtag caaagctaac  31080
ttcgacgggc atagcagagc gctcgatcga ttacatttcg atcagtcgta cgaacaactg  31140
ctattgtcca acagcgaatg gcaatatttt atctacacca agtatacgat acccatgttg  31200
aatctaatag tggtcaaacg aacggatgtc tctttgttgc tttcaaaccc gtgcttgcaa  31260
ttagcctatt tgatcaatgt acggactggc caaattgaga ctcgggattg tgattgtctg  31320
cgcgtaccaa acaatcgaca tggctatgtg gaaatgaaat tcgacgagga ctacgtgtgc  31380
gacgagcgcg atcaacactg tcgatctttg ctgttacaag aggatctgat cgaacagcct  31440
tacgatcacg gtatagtcaa agtggagtgt gaacacatta cacgattgta atcaataaaa  31500
ctctcaattg ttagcactgt cttttatttg tatagcataa catacaaact ggcgttgtgg  31560
```

taattaagat ataataatgt tcaaaaagag tataccacgc aacatatatg ctacatgttt 31620
cgtatgcgac gacaccatat atgtgtacag gaaatgttcc gcgctgaaaa atgatgcggc 31680
acgcgttgct caaaaatttt tctcttctca tcaaggcatc aaaaagaaca acactttctt 31740
ttgtcacaag tgttataacg acatgaatat gaaacccatg cctaagcaca aacatagtac 31800
tcttttgcaa ttctactagg acataattgt attattgcaa tgcatcaagc tagacatgac 31860
attgaattcg ccactcgatt cgggcaagtt tgaacgtccg cgaatacatt gcaaactctc 31920
cgcccagcgg ttaccggcga acgattgatt aatcgtccat tgatcgagac gagtgccttc 31980
gattttttcg tgacctgtat gatttatttt aataaactct ttgaaaatat tatcgggagt 32040
gttattaaag aacatgtatg gtatattaaa tattggatag cgaggcgctt gtttattgcc 32100
aaaatcaccg ttacgaacta catacttgcg ctcgatatta tcaaagttag actgtcgtga 32160
taaatacgaa atgggcgaca gacagatttg agcgcaagta ccgtcttcgg ccatccattc 32220
ggtgaggtct ttggcgtcgt tcatgacacc cttctggccg tgtatgccgc aaattttgac 32280
gcctctgaaa tcgttggtgc tcgtaattag cgataatttc aagtatgcag tatcgttgaa 32340
acacgtcagg gtcgcgtcaa ttttctccac gcgttgattg ttgatttgtc taaagtacac 32400
atagattttg tatacgtaaa agtttttatt gcggcacgtt tcgattttgt aacgtttgcc 32460
atcgtacacc caaccgattt tgacattgga cactaccacg cctacgatga gaagcacgtt 32520
gccgccttcg acggtcacgt aattgttgtc gttgctgttg ttgaatttca caacgggcgt 32580
ttcgtttttt gcgtacagca atttgccttt gagtttgttg attttgttgt tgtacagttt 32640
gataggtagt tttatgtccg gtatgtaggg atcttcggcg gtctgcaatc gatcgtcacg 32700
taccaacgtc caaagtttga acattttgtt gttgtgcaaa atgtgaggtg ccaccacaac 32760
cgaattgcca ttgggcaaca tattcaaaaa acgttcattg tcatcgcaca aatcctgata 32820
actcaaaacc ggcatggcgt ttttcaaatt ggtcaatgac acgatcagtt taggcaccgg 32880
gacggtgcag aacatttgcg tatacccttt ataatagtac tgcaccaatt tggacatcaa 32940
acaaacgact gtgtcctttt cgattattgt ggccacgtcg ttgtgcgtgc gcaaaatcga 33000
attggaatta tgatactcgt atgcggtgag cagcgctgta atgtgcacgt cgcgtatttt 33060
aagtttccgt ttgatgcaca ccatacccto gtgatggttg acaaacaaaa tgttgttggc 33120
taatttcagt tctactggac acatatttcg tttgaaataa tagaaaatcg tttgtaaatc 33180
agttcgtcga caattgaaca ctgtgggacg atcgttgaat gcgatcaaga gtaaatcgtc 33240
gttgttgtcg ccgtttgcgg atccaacatt gtttctgttg tcgcttctgt cacgatggtc 33300
caaatcgttg ctgcccaacc acgagcagtg aaatataaat ttcttgtcga tcaacatacg 33360
aaaacgttcg gcgaccatga tgtaatcgac gctcggcaaa cggacatcgc gacacaaaaa 33420
aaattttttt ccagccacag tcatttcgcc gtgaaaaaaa ctatccacaa acttgacaaa 33480
atcagattgt tgcatgagca tatcttgacg catagtgtcg ttagttatac gcaccacttc 33540
gttgcctatg cgatatttga gcgtgggcgg attgatttca atgttgttgt tgctggaatt 33600
gtcctggtaa ttgacaaaat ttttcttttg tttgctgaac gtcttcgata cgccatagat 33660
gagttttcca ttgactatag tgtctacgat ctttttttgat tctttgaaat ataatataga 33720
ctgaatcttt tttcgtttgt ttgcaccacc gttacaattg gagttttcat tttcgtctac 33780
ggcagttttt agcatgactt cgtaacattt caacacgggt ttataaatca ggctcagcaa 33840
atatacatgt ttgtagataa ttttattgga caaactgtcg atttgatagt ttatttgtgt 33900
gcgcatagtt tgtttgataa tgtccactag ttgaactact tgtttggcgg tgtattcgaa 33960
taggaaattt agcggttccc atttgccgct gcgactcaaa tatatttcca atatttgatt 34020
gagatcttcg gtgacgatat agtccttggc gtatacgtcg cgcgcgaaca gcacatcgtt 34080
ctgatgatcg tacaccaatt gaattgcacg attgatcttc ttctcctcgt ccagattgcc 34140
gtacagaaac attcgcttac aacttttaga gtagagtttg tcgtaaaaat tatgtatcag 34200
tatattgttg ttcatcatga cattgggaaa actcaaatgg cgaccgtcca acataaacgt 34260
accgttcaaa tcgggtctcg gcgcgtcgtt gcatcgcaac tgtttatcca gccacgtacc 34320
gaaaactacc aggacgcact tgtgtagaac acatcgacca acggtgtcgg cggcacagca 34380
aaagtaggat ttgcgctctt gcaaatattt tagcgtacat tcgttgacgg atctgtcgtt 34440
gcagtttaaa taaaaatcga gattatgttg gttgcggata ttgtcgtaca ttttgttgaa 34500
atcggcaatc acgtccgtca ttgttccaaa tcgttgcttg actaatcatg taagtgatta 34560
ttattatcgt acgataatgt cggaaacagc aacgacgccc acaaacagaa ctgatttaaa 34620
aaacacatta acgaaattgc gcgagcaatt gaaatgcgaa tcagacagat tactcggttt 34680
tgtcgatatt gtgtcgaact ttgaaacggc catcgaatca tcattgaacg cgtatgtcga 34740
aaatttgatc agtacaaatt tggccaatcg gatcatgtta cggtacacca cgctgaatcg 34800
tttgcgcatt tggtggaccg tattgcccga tcagacagaa accaacgccg gcattactga 34860
agaatatttg cgatcatatt tcgatcaata tggttacatt gttagtttaa tagtgtgttc 34920
tcaaatgtta ggttgcgccg tagttgaata cgaaactcaa cagagcgccg aagaagcgtt 34980
cgaaaccgaa aacgccaaga acaataaatt caaactgacc tggtacagtg acactcaaat 35040
gtatccccgt attcattacg tgcccaatat taatcccgac cattatgata gagttcaaaa 35100
tttaattcga aaacataaag ctgctcgcat cagtagtttg tcgttgcgag cctgatactt 35160
gttggaatta ataaaaatac ttttctgatg caatcaaatg actatattaa tcatctaaac 35220
caacgattat tgccgacatt ttgatatgaa aacgtcggca ataatcgtta ttacatttta 35280
agactactaa caatcatgta tccaaattta attgttgtta tcgaatataa tacgacgcga 35340
aaatttaaaa attattccaa ttacggtacg cgtcgacgac gttatatgaa acgacattgg 35400
ccaaaatcac taacgaatac gaatacatta aaaaaattcc tatactagta gtccattaca 35460
attcgttatg aatcaattta ctgtttgtac ctaggccgtt gcgatttgtt ttcatcaagc 35520
caacatgcat agcgttgagc aaatcgccgt tgtccgcatc gatttcccat gcgaataatc 35580
cgccgagtct acgcttaagc acgtattcgc ctttggccag taccgatctt tcgctgtcgt 35640
acgatattaa gtcgccagag gcgcggtcga atacgtacgc agccttggcc acgtcgtcga 35700
atgcgtattc gtaacgcgaa atgtttttag caatctgtct gtagtcgacc acgccgtttt 35760
cccatgtacc cgtgatcggt ccgacggcta cgccactgaa tggattgtca ctgtcgtagt 35820
tgtggacgcc cgtccaaccg cggccgtaca ttgctacgcc caacacgagt ttttttggat 35880
tcactcgttg cgcgagcaaa gcgtccacgg ccacgttggc ggtgtacggt tcgttaggtt 35940
tccacgcgga accgtacagt gccgtctgat gaccgagatc ggtattagac caagctcctt 36000
tgaaatcata actcatcacg aaaattttat ctaaatactg ttgtgctcgg tcgtaattaa 36060
tcgcggcgat cttgtctatg ccagcgctaa tcgctgtggt gagttctaaa gtacgattcg 36120
tttgtatttg aacttgatcg agcatggcgc gcaattcgcc caataaagcg atatacgtgt 36180
tattgtcgcg ttccacgtcg ccaacgtttg gattggcgcc tttgccgccc ggaaattccc 36240
aatcaatatc gatgccgtcg aaaaatttcc atgtcaacac aaattcacgc acggattcga 36300
caaaaatttg tcgcgttcgc gcatcgtgca tatgatagaa gggatcggac agtgtccaac 36360
cgccgattga tgccaacact tttagattgg gattggccaa ttttgctgcc attaattgac 36420
caaaattgcc tttgtagggt tcgttccatg cgctaacgcc tgtttgtggt ttttggagcg 36480
ccgcccacgg atcgtgtatg gaaactttaa aattgtccct gccagcgcac gatctttgca 36540
acgcttcaaa actccccgtg atagatttta aactgtcgtt tataccgtca ccgccgcaaa 36600
tcggtataaa tccgtataaa atgtgcgaaa ggttcggcgt gggcactttg tccacgggaa 36660
aagatcgacc gtaaacgccc cattcgacaa aataggccgc tacggtgtga tcagtgttgt 36720
acgtatacgg tttattgttt tcttgccacg tgtattgtaa cggttttaaa tgtttaccat 36780
cggtgtctgc gatcacgact tctacggttt gactagccga acagccgtcg gcattgcaca 36840
gttttacata catcgaataa cgaccgctcg tattgtaatc aaaagtagca aaacgatctt 36900
gcgtcggacc ggtccaaacg ttgattactt tgctgtctag tttattttct agatacactt 36960
gagcgatttc gccttgttcg cccgaccata cgctccatga tactttgata gttacaaacg 37020
gttgagagtt tactaatgat tcgtaagcgg tggcttgatg atttatttgc actaaagcgt 37080
aactgtgatc ggcccagtct aatgtgggaa cgccgggtgg agcagcgtag ctatgtaata 37140
ttaaaatact aaaagcaaac aaatacaaac aataattatt catatttatt ttgtgtaatt 37200
tatagtactt attataaaaa aaacatatta aaacaccaaa ataatcgtgt attatttaat 37260
tatttaaaag atataacagt gaataatgga aagaaacatc gatcacaaaa caaattatag 37320
tcaaattgat aataagtttc acctatattg ttacacgaca cagaacattg aacacatttg 37380
tcggcaatca ctttgtacaa cagtttctgg ttattatttc taatttgact agtaaattcc 37440
ccggtgctcc aagctagacg tatccgttcg cgccacacgc gttcgtctcc tggattttcc 37500
caatagcaag cgcttagcaa tgcgaacatt ctccaatccg tttcgaacga attcgaacag 37560
caatacaaag gaaaaaaaca ttgttcacaa aacagagcgt tatgtgtagt gttgtgaagg 37620
caaaattgac aaatgtttat agattcgttc ttctctgcta aatcttcgca aatgatttgt 37680
tcaacggcca gtgtttgtcc gttgacagct tgcagccaac tgtcgaagac agcctgacgt 37740
gtatgctcgt tgctgctgca tcgatacgct ttagaatatt tcacaaatat ctctacaaat 37800
tccattgtaa tgtagtaatt agtctgattt gatgtgctcc aataactgaa ttttttggt 37860
atcagtttgc cttttataag gctatgatag agttataaat tattgataag aaactacgac 37920
atgctgataa ctgtcgtggc aaacgataaa gctcaacaca tgtacaagag tttcaaacaa 37980
atctggtccg aatgtacagt cgaatgtcaa atttgtttcg atcgaattca cgacgagggc 38040
gtcgtcgccg ttacccaatg ttgtacgata aacattgaaa aaatgtttca tgctgaatgt 38100
ttaaagcggt ggcatcgcga aaacagccga gatcctttca acagaaacgt acgctattgg 38160
tatacgtttc cgcctcgttc actggacgaa tgtgcttcgt tgctagagaa aattaaaaac 38220
tttatcggtg accaggaggc ggacaaaaag tttcacgacg aatacaatcg attgcaaaac 38280
gccaaatatt tagatataga tttgaatttt gacagattgt tacgttatta agtatgttca 38340
atagcgcaaa cgagtttcga ctcgttgaac tctcaatggc acgtaaacga tggcaaattc 38400
cgctcgttgc ggtctaacgc ttcgatgaac gttgtcatcg ttgttttctg tatatttata 38460
gaatgttaca ttttgcaaat ctataatgcg actgttatat agattagtta atcggcgctg 38520
acgttcgtct aagagttcgt acacgtcccg tgtgtgtgtg cgagtttgta acggctgatt 38580
ttgaagcaat tgcaacagtg tgctgataac ataattagcg cacaaattta taaaatgaat 38640

```
tatcaattcc atgacattgg tttgatgttc tgtgtatttg acgttgactg taacatgtgt  38700
tagggtctcg actatatacg aatatgaaac gtagtagttg tacagcatgt ccatgacgcg  38760
agtaagattt tgcgtattaa cattgtattt cacaatctcg cgtatcaagt cgctgtagtc  38820
gattttacac tcctcgtttg aatccaatcg taaaaaagat gacaatgtat gagcagcgtt  38880
tgacggattg ttgaaggcta cttgcaaact ttgtatgtaa gcttgtaaac ggtctattgc  38940
ttgttgtatg tacggcacgc tgtcgggacg ctggggaatt tgatttattg cgggcggtat  39000
aatatacatt actctttggg attgcgggac gattgtcgtc gattcggaca cgttcatagg  39060
ggaaggcggt cgacgtggcg ttgttataat tgcattggcg ttgctttcgg cgacgttagt  39120
caccggtgtg ggcacttgaa acgtttgcgc taacgtttgc agttgagctt gcaattcgga  39180
atctggacgc gcagttatat cggcaatgat atcttccgcc gaaggcaatt tatcggcggg  39240
attttgtgat ggttttgctg acgtgatcat ttcgtctatg gaagacgaag gcggtggcgt  39300
tgttgttgaa atattttttt taccactacc gctggccata cctcccgacg ttttacttgt  39360
cgtcgccgtt tgggttttat cgacattttc gctggttttg cgtctgctca ttaaaccgag  39420
actcttggac gataacgatt tagatgaggc tgattgtttg ctgggattgc tcattttgtt  39480
actaatacac cagtaacaag taattgtcgt aatcgctcaa aactttttaat tgccggggaa  39540
acgattgctc cttattggta tagcggtcga tgtaataatg ttggccgtga ctcgtatgcg  39600
aatacgtgta ctgttgcaat tgatggtatt cgtcgtacct gagcacacgc acgcgtatta  39660
catcaaaaat gtccgagtcg ttggacaaac ctgacgtgct gtcgctcata ctgaaagaca  39720
atttgacgat cgtgcaagac acttatataa ttttaaatgt catcgacaaa cacggtgcgc  39780
ctaaatcaat gtgtatcggt gaaatcgata ccctacagac cgattcgatt tcaaaagaca  39840
cagtgtccga ttcatccgtt acgagcgaat tgtcgagtga ttgaacatat gtgtgaagac  39900
gaagatgacg acgacgacga gaacggctcg gaaacacgat ataccgatca tgtaacattt  39960
ttggaatcca catatcaaga ttggtgtagt aggccatatt ttactttgtt gctcgatgcg  40020
caacagcgaa attccgaaaa acgacacaaa tatttgaatg ctaccgatat ggcgtgcacg  40080
gtcaaattga aacgtgtcgc agacgatgaa aagtttttca ccatcgatca agccggcgaa  40140
cgtaacatgc acaccatacg tattgtaata aaatctttga tggactattt tcaaaatgcg  40200
gacaaatatt tcgttttaat gatcgacgaa caacacatcg atttgatata cacggagtat  40260
cgggcgttgt tgttgcccca aagattgcta tgtctactga aaagagattg gaatccgcaa  40320
acaatgtttt ctaattttat ttatttcgac gtgccctgca cagccgaagc gctagaatcg  40380
caactgattt acaaatcgtt tctattgtac aatactgtac tcaccatgat actgaaacaa  40440
acgaatccgt ttaatagtgt cggcggcaat aaaaatatat caattttatt tcgcaacttg  40500
ggcaaatgtc caaataacaa agaacgcatt aaatgttgcg atttacgtta cggtggcaat  40560
cctcctggtc atatcatgtg tccgccacgt gaaatggtta agcgcgtgtt tcattacgcc  40620
aaatgggctc gtacaccaaa caattaccgt cgttatttcg aattaattac gaaacccgtt  40680
gtgcgtgaac gatattacag aatggaccga accgtaacga cccccgttaa tctcacttcg  40740
gacattgccc tgctattgtt ggattggtac aattttatag atgatttcag aacatatttt  40800
ctttgataaa acaatgtagc cttgacacaa ttagtattta acaatggtcg tcggggacaa  40860
tattgcaatc tcaatcgcac tttggatgag ataacacatc agtgtgtatc ttcctcacaa  40920
cactcatgga tagagttaat tttaaattgg gcaacgttat cagtaacgct gtagattcta  40980
acatgaaatg ttacgaaaaa aaacagagtg tagcagaatt ctacgctaaa cataaagaag  41040
```

-continued

```
acactagcaa agtcggacgt acaaccacat acaacgtgac cggcgagcgc aattacaaat  41100
tgataagcga cgatcaacgt tacaaattct aaatggacgc cgtcagtcgt caatgttgtg  41160
aaaatagtgt cgtacgaata attgatacgg agaattcggt agtgcggtgt gtgaagtgtt  41220
tattcgtagc tcctatgtca attagttttg aagagtttct ctatttacac aaaatattta  41280
accaagcggt caacacacgc gtcgctcatg atcagcggtc aaagtaaata aagtatcatt  41340
agtttttgtt tattctatag atttgtgagc taaataaatc agttttgtat atacaggttg  41400
ttttgatttc tactcacttt cccgaagact gtcaaagtag aaagtaattt catttaaatt  41460
tgtttgtgtt tgaagggttt ctgtgtgact tcacttaata attgtattgg taaatagatt  41520
actacgcaga cagtaaagct ttgtataaaa gagaaatcct tgatagaaca gctttagttt  41580
atcttgattg tgagccctag taagtcatgc agagtgctcg atatattgag cgtgaccaat  41640
gcagcattga tatgcgacat gttcgcgtat cttgtgacca gaacaatcaa tcgaacaatg  41700
ctgattatat aatattttta atggtcaaac gagcttttta tcaaaatttt caattgacca  41760
cagatatgtc gatggaatcg ctgacgttgt atctgttcga taatttgata tattgccgca  41820
acggacacgt tcgacaatac aaacacgtcg attttgtcga atacattttc tttaacgagc  41880
aggataagaa ccaatcgatg atcatcgaac tcgaccacga tgcgcgtgtc atcgttgcta  41940
aacgattgca cgatcaagaa acttatcatc agcgagtcag cggttatatg gattttgaaa  42000
aaagacacaa tacaacaaca ccgatgcaga taataatgaa cagcgcggaa cgtgccgaat  42060
ttgatcgaac aatggaaatt acgttattaa atgattaaaa gtggtttttt ttataaataa  42120
caataattgt attgcaacaa aaatacatat caatagtttt gtaaaactaa tacatttaat  42180
tgctgtcata ttcatcgcta acgttatcgc cagatgtatt ttcttcatca tcatcatcat  42240
catcttcatc attacggtaa tctatattat tattgttagt tttatcgtag ttattgagtt  42300
gtccacgtcg tccattgtcg tctttgactc tgcgtgccgt ttggtctatg aagcgttgtt  42360
gattcatttc gtttttgttg ttgatgttat tgtcgtcgtc gtcgtcatcg tcttcgtcga  42420
cgatatcgtg tcgtacaatt tcagcggctg cggtttttgg tatccatctg ttgtttagtt  42480
taacataatg acgtgtgact gcttcatagg ccgttttaag tgcggcatct tcgtcgccag  42540
cgtgcaattt gtgatactga tgaaatgtac gacgaaataa ttgccgcgct tttgccggca  42600
tatattcgtt ttcgatcatt ttgtctagat aatacatatt atttaaaatc actccgtttc  42660
agattcggtc gtgtccgtgt tgtcggtttc gtcgtcgtct gttgtggtgt cgtgctcgtt  42720
ggcatctgcg cgcgctaccc aacgtgtacc catttttaca tattttcgtt tgaccgcgga  42780
ccaagccacg cgaaatgccg tcgattcgtc gcggtacgtt tcgattgcgc ggttaaaaac  42840
ttttaaaaat attcttttac catgataggg caaatgttga acggtactcg gtaaatctga  42900
tatactcgta tacatagtta taatcttgct atattcttac tttatagtaa cgttttaatt  42960
atattataat gtatggtgac ctataacgtt tacgataata atacaatttt tagtaaagta  43020
caattattta ttgagattca actgaacagt tccaacttta ttattaatca caacctaagt  43080
catagtatca caaccatatg acgggcaagg aagcggcgac ggctagtcaa atgagtcgcg  43140
tattaacgaa atccacttca tcgattccgc tgtcgatacc ggcaattgtt gacttgtcgt  43200
tttcatcgtc gaatttggta tataatttgt taaccaattc gtttatgtcc aattcatttt  43260
tcactatgaa cactttgctg cgatcgtttc gtcgcaccat tactccgcgt ttgcacagcg  43320
acacgtactt gtagaacggt aatagggcgt cacgggtttt tttcaataat tgtttgtgtt  43380
```

-continued

```
cagcagtggc cgcgacgaaa attttcacag gtccatcgta gtctatgtct agatcgtaat  43440
ttttaagtcg aacttcgcgc gatcgagttt gccactcttt ggccgttacg gcattggaca  43500
gtttcacgca aatgtgattt ttttcaaaat cagtttctgc cacgagtctg tagtcaagat  43560
cgaggagggt acaaattttt ctaacatagt tattacgaat ctttttgttg taaagttttc  43620
tatcgtgaat accgtaaatt tctaccgtgt cgtttaattt gtcgttttct aatttttttga  43680
tcttgccttt gattacgctc atattgtcgt taacgctacg gtcaatttcg tgtttgatga  43740
gacttttcag tataggtaca ttaattagat cagtttccat ttttaaattg tatttgtgta  43800
tatgtgtgcg tacgtgtgtg tacacaatac tgctcaatat gtaaattgta tttattaaat  43860
cccctcttat ttctttacat gcagtattat agctgagcta gttgtatatc tgacatctaa  43920
cgtgttgcta ctacacaatt attgtataaa aatgaatggc aaaaattcgt caaacacgtg  43980
gcgcactatc actttgaccg gtcaccaaat atggcctgta ctcattgagt ttatgcaaat  44040
gaccgacaac gaaaaagatt gtatcagaat aaagaagctc atccagtcgt atttgttaaa  44100
cgaacgtcct ttaaaattaa catattatgt aaaataatgt tattgtattg tacatacttt  44160
attgtctaca tgtgtatata tgtctgtgtg tgtgtgtgtg tttttaaatg aataaatatt  44220
gtaaaaattt ccatttagtt gtttcattgt aatcatgtcg gaaacacgtg gctcgattaa  44280
acgtaaattg ttatgtgatc atactgaaaa aacgtgcagc aaacgtgtga aaagcaaaat  44340
tcaatttgtt acaaaagaac cggtacaatt ttcattgctc accgatccca atcaaataaa  44400
caatgtcctc ttcataaaca tacacaattt caaagtgttt ctcaagaatt taattgccga  44460
tttaaaaaaa ataaaaatta atttttacaa cagtttgttg gagcagctga tctctgtgta  44520
ctcggactgc ggtcatagaa acgagcacac aaacttgctg agtcgaatct tggtagccac  44580
cagcgttgtc atcactgatc taccctcgaa cgtttttttg aaaaaactca aaactaaccg  44640
tttcaccgac aatatagact acttgatttt accgaacttt gtgctatggg atcacaattt  44700
cattatattc atgaacaaag catttaattc aaaacacgac aatggtctga tcgacatatc  44760
gggctcgctg caaaaaatca aattaaccca cggcgtaatt aaagatcaac tacagagcaa  44820
aaacggctat gccggtcagt ttttgtattc gacattcttg aatacggcct cgttctatgc  44880
caacgtgcaa tgtttaaacg gagcaaacga aattgtacca ccgaaggcca gtctgcgacg  44940
ctattatgga cgcgatgtga aaaatgtacg cgcctggaca acgcgtcatc cgaacatatc  45000
tcaattaagc acacagatat caagcgtgcg cgaaccggac aattacaccg attggaatgt  45060
taaagtcggc ttaggcacgt ttactggcgc taatcgcgac tgcgacggtg ataaagaagt  45120
tattactttt ttgcctcaac ccaattcatt gatagacttg gaatgtctca tgtacggaga  45180
tccgcgttac aatttcattt gtttcgacaa gaaccgttta tcgtttgtgt cgcagcaaat  45240
atattatctg cacaaaaaca aaaaacgtat cgaaaaacta ttgcacagta tgcctatttt  45300
atatacacta tggaagagct acaaacgtta cagctccatc aatttggcga caaaaattga  45360
ttggttgtta cgcgattgtg ctctattgct cagctccaat accagttttc tgctctacaa  45420
caaattggct acaattatag acaatgaaga aatgacttgc ggcgacgagg aaatatttaa  45480
tttggcagga caattcaacg acgtcatcga atgcggagcc aaaggcagcg ccgatttggt  45540
agcgagtact aaaaaatatc gcaacactca ttccgacgat atagatacaa tcgccaagcg  45600
tgccattacc ggtttgaaca gccatatcac gtcacacaat cgagtgaaaa tcggcggtgg  45660
tgatatctac cacaatacga cagtattgca aaatgtctat ctaaagaacg attacatttg  45720
ttataaaaat gacacgcgtc gtatttcaag cgtgtgcgcg ctgccgtcga aattcctatt  45780
```

-continued

```
tcctgaacat ttgctagaca tgtttttgat atgaacaaat aacaaatgat gatgtgtatt  45840
caaaatgtat tttatttaat aaaattacat agtatctaac tgtatggtgt atttttatta  45900
ttgaattacc gacgacgcgc cgaattcgtt gagtaatccg caggcgttga cgttgcgccg  45960
cactcgcaaa aagccgtttt cgccccaatc ttctccccat gaatttttta taatccaata  46020
gggtacattg ttttcgatac cccaaccgat aagcaaaacg gcatgattca aatcataaat  46080
gtgacattga ttcaatattc ctctgcgata attaataatg tccatggcgt cgactgctat  46140
cgccacaggt ccagtagtgt acaccaattc tttcaattta ttctcgtcac gtatgtcgta  46200
tttaaagcaa gagttcaatt tgacagctat tttgcgatta tctaaagtgc acatttgttc  46260
actgccctga tagggataat ctgcttccgt ttcaacaccg cccatcagca atagttcttg  46320
aaacgctaaa tgcatcaaac caccattaca acctaaatca acttcatcgc aatctaacag  46380
ttgctgttcg gacagatcta ttaatttgtt gtgccgtatg gcatattgac tttcaatatt  46440
gcctattgct acgaaagccc aacacgatcc gcaaactcct tgatctttta tgggagtcac  46500
tttattggtg tcgcgccaat cataataatc gggcaaacgt atgtcgggcg cgcctttaac  46560
tattctattt tcgcataatg tgtagtgttg gctaagattt aaaaaaaaac cagtgttcga  46620
gtgtaacact tcgtctgggg tcttgtcact aaatttgttc acaccaaatt gagccgatgt  46680
ggaaagcgag tcgttattgt tcttgttatt caacagattt tctcgatttt gagaattgat  46740
tttgttcaaa ttgtctttga acacattgta acggtattgg tattctttgg gatcgtcgta  46800
gcttttgttg tattgctgta ggaaatgttt gaaataaatt tcagattgat ctaaattata  46860
atacaggact ggcactggcg aagacaatgg cggtggcgac gacgacgtat gcaaagatat  46920
ttcatcacac acgacaaacg tccacaacaa ggacacaaat gtaataattt tatgcatgat  46980
atttgaatgg tacttgcgca taaaactaaa gtaccttaat tatgagcatg acaggcacga  47040
atcaacccaa aggtctaagt atattaaaaa tagtatttaa tttactcaaa agactatcga  47100
tattggtctt tgtgtctttt tgtagggaaa ctatttgcgc tgatagattt tcgttaatgg  47160
cctgtatttg agctgtcgta tcggttttaa tagtgtttaa ttgagtggcc aatgtgttga  47220
gttgtgtgtt taaagatttt acgtcggcac tgttgacgct cattgtttta gttaccgcgt  47280
caagtttggt agttatatct gaaacttgag attttacgtt atcaaaatta gctatcgcag  47340
cagtatttac gccagtgacc gctttttgaa tttcatttgt ttgcgtttta atattgtttt  47400
caattttatc ggctgtcgta ctaacattag taacaataga ttttacagta tcgtcaatag  47460
tgctgatttg atttaaaatt ttatctatcg gcatttgagt aattgtgttg ttcaatgttt  47520
ccatagacga cgtggacgcg ttcgtgtctg ttttgacggt ttttaaacgg tcgtcgacat  47580
ttttaatgtc ctgacgaatt atcagaaaaa tattattggg atccgccatt atttcaaatg  47640
catacaaaaa tacgacgcta taattttgaa taccttatac aactagtgat gaatattttt  47700
catccgaaac tattacggca ttgccaatta gactgttgct tagtaaaacg atggtttgcg  47760
gcgtgatcta atacgaaatc atcaaatacg acatctgcac aattgtagaa accttcgcca  47820
acggcatcgt gacgttgcca tcgcacatac aacatgaatt gggtctgtcg aaaaggaacg  47880
accactggta taacataaat cattgagttt gcgcatgacg aatcaatgtc gttgtttgca  47940
attagtttgc tgccgtttcc cccgatcagt tccagatcgt tccatgtcac ttgattgtta  48000
tgtgaccacg cacgctttgt aatatacact tcaaaatagc ttggttcgtg caccgttgtc  48060
gggcaaaagt acaaatttgt ggcgagtcca cgactataca acgaatcaac gggccagtac  48120
```

-continued

```
aaagtgtcgg gacgccaatc cggatacggt tcgtccatgc ccgatttatc gccgaaattt  48180
ttcaaacgat cgttggcgcc ggcagcgcat agattgtttt taacaacatt gtcgcgtacg  48240
tgttgtgcat cgttataatt tggacctgcc aatgccgcgt attcaaagta ttgttgaaac  48300
atgtattgag ctgcgtttgc ggccacgccc gatgattcac cggcggcgcg gtatttcgag  48360
tacacatgtt tgtatgctcg acggcacgca gcgtcgggta tttgatcgcc attttcgggc  48420
caccaaaaat tattgtcacg aaaacatttg tattgacgcg ccgccggttt tgacaaataa  48480
ccgtgtccgt ccacagaata tatgaaaata aatgtacata acacatataa tcgcagcatt  48540
gttctagcta taatatactc ttacataatt tacatattaa tctttgcttc cactttgata  48600
tcaaaacgcc ggcaagtttc gaatgaatga tgtcatttca tttaataatt atgtggtata  48660
gatcacgcaa tatgacgtaa tttgtttttt tgggacgaac aattatacaa aaaagatgat  48720
gcaatatttt aacggataac gtaatttgtt tttttctaaa tcatgaatcg aaacaaaaga  48780
tcacggcccg tttcgaacga aaagatccaa aactggttta aaaatacgtt atctttgggc  48840
atggcgtgat tcgtggaata cgtttatgat tggaccattt ctagatcacg ccatatgacg  48900
tcatttgttt ttttttgggt cgagccgtgg aatgttctag aacaaatttt atcaatcttt  48960
gccgacggtt tcgtatgaaa gcgcgggcgg gtttcgaatt taaagatgat gcaatatttt  49020
aaacgaatga cgtaatttgt ttttttgggt cataatcaaa acaaaaagat cacggcccgt  49080
ttcgaacgaa aagatccaag actactttaa acatgcgcgg gaatttttac tttggtcgat  49140
gatatcattt gttttttttgg atcatgactc gaagcaaaaa gatcacggcc cgtttcgaac  49200
aaaaagatct aagactagtt taaacatgcg cgggaaacat tatctttggt agatgatgtc  49260
atttgttttt ttgggtcacg agtcgaaaca aaagatcacg gcccgtttcg aacgaaatga  49320
tccaagacca gtttaaaagt acgttatgtt tgggcgtggc gtgattcgtg gaatatgcca  49380
tcgaatgttc tagaacattt ataatcgatc tttgccgacg gtttcatatg aaagcgcggg  49440
ctagtttcga atttaaagat gatgcaatat tttaaaagaa tgacgtaatt tgtttttttt  49500
tgggttatga atcaaaacaa aaagatcacg gcccgtttca aaaaaaaaga ttctgaacag  49560
tttaaatatg cgcgggaaat attatcgttg gtcgatgatg tcatttggtt tttaaatagt  49620
gccgtgtgca aaatgatgtc atttgttttt ttgggtcaag aatcgaagca aaagatcacg  49680
gcacgtttcg aactaaaaga ttcaagacta gtttaaactt gcgcggaaaa cattattttt  49740
agagatgatg taatttgttt ttgggtgatg aattgaagca taagatcacg gcttgtttcg  49800
aacgaaaaaa cttcagatta gtttaaacat ggattaacca caagccatat gtagttgatc  49860
atgccaattc aggctcataa taatttcgga tctcgttgta gtgagaccta tttgtaccta  49920
tttgaataac tttgttaaaa atgtctctga ctaaaattca attcggtgat aaggaggtcg  49980
agacttacac cgtggacctc gatggtgaaa aatggatggt tgccaatccc tttgccgaag  50040
ccttatctta ctctaatgtt aacagagcaa ttagagtaca cgtgagtgaa aaaaaccaac  50100
aaaattatga ggaatttaag tcagaccgta tcggtctgac cgactgcgtg acgtcactac  50160
cgcgcaacat ccaagcgaaa acgaagttca tcaaccgtgc gggcgtgttt gagttgatca  50220
acgcgagcga catgccgggt gcgaagcgtt tccaggcgtg gaacaacaac gacctgctgc  50280
ccacactgtg tcaggaggga gagtacaaaa tggcgaggga cgcgcccgcc aacatcgcgc  50340
atgggatgaa cgccgtgcac gtggcgacca acgagggggt cgcggctccg tggatgaagg  50400
atctggacca tctgaagact gctatcgttg agaaagatcg caagattgac gatctaacgc  50460
tggcacttaa gagctcgaac gatgaattgg tcaaggcgaa cgctcatttg tgcgacgcaa  50520
```

acaaagcgtt ggtatctttt gcgacggaaa tgatatctgc gcgtagagac tgcgagtccg 50580
ctcgtaagga ttgcgaggcg gctagaaaag aaacggcaga gctcgccaac cgaatggctg 50640
acatcgcgca agacgtcata gccaagccca gcgacccgca gctgctacac tcgttggcag 50700
tgtgctcgat gggcgaagat cagtacgctt tccttaggcc gcaaaaacgc agtttgaagc 50760
gcagcctcga tcggctgtcg gtcgacgaga aggacatcgt atttaagagc gattatgtgc 50820
ccaattcgat gaacgtgctg aacaaagtga aggagcgcct gccgaaagag aagtacaaag 50880
cgcgccacaa ccgcatcacg ctacacgaag atttgacgcg cgaagacctg ttgcaggcga 50940
tagaatcgac cgtttcttcg cgccaagtcg caataattgt gaacaaggcg acgagcaaca 51000
gcgtagttgg taacaagatg taggttggcg agtcgaagta tataaatttt gtgactaata 51060
aaaacgtatc atttacatga ttgattttta tttctcaatt ttacatcaaa tgtatcatta 51120
ggcactcgag agcgcccgag tgcagttgtg ttaaacaatt aattcttaaa atggccgtta 51180
ttaaagttca gttcgccaac tctgaattag aagtgatcag tattaaggac gataatggtg 51240
aattgtggat gcttgcaaat ccgtttgcga gaattttaga atattccaac gccaacagag 51300
ccgtaagagt tcatgtgcta gataaaaacc agtgtatttt agaaaaaata cgaccagacc 51360
actgcggtct ggatgacgtc acgctacatc cgttatcaaa gtttataaac cgcgccggcc 51420
tgttcgaact gattcaggcg tcgcgcatgc ccaaggccaa agaatttcgc gattggatca 51480
actcggacct actacctaag ctttgcgacg atggcaagta cgacatggca acggacgctc 51540
cggtgggaat cgccatgggt atgaacgccg tacacgccat tgcgaatgac ggcgccgacg 51600
caccgtggat gaaggacttg cacgaattga ggactgctgt ggtacagaaa gacaaaataa 51660
ttgaggccat atcgtacgaa aataaagaac tttcgttgtc gctgcgcact tcgaatgaaa 51720
agttgcaagg cgctaacgat aagttgatgt actttgccag cgccttggtg gaatctaaca 51780
acggactgat gaaagctaac gaacgtatcg aaaatctcgc caaccgcatg gcggacatcg 51840
ctcaggacgt gattgccaaa ccgtcggatc cgcagctgct gcactcgctg gcggtgtgtt 51900
cgatgggcgg cgatcagtac gcgttcctac ggccgcaaaa gcgtagtttg aagcgcagtc 51960
tcgatcgctt gagtgtggac gaaaaggaca tcgtattcaa gagcgattat gtgcccaatt 52020
cgatgaacgt gctgaacaaa gttaaggagc gcctgccgaa agagaagtac aaagcgcgcc 52080
acaatcgcat cacgctacac gaagacttga cgcgcgaaga cctgttgcag gcgatagaat 52140
cgaccgtttc ttcgcgccaa gtcgccataa ttgtgaacaa ggcgacgagc aatatcacta 52200
gtattggtaa taacactacg aataaataga gtcgtcgtac atggtcgttt tatttttacg 52260
ttcaatttat ccattaagac ccattgtact ccacgcagga catcgagtgt gagctatatc 52320
ggtacggtgt cgatgacgtc aatccgtacc gatacattac ttttagtatg actcacaact 52380
gctctcgtgg ccgaacgacg caatttgttt tttgagtagt gtcgtgtgca aaatgttttt 52440
gaatcataaa ttgaagcaaa agatcatagc cagtttcgaa ccaaaaaatt caaaacaagt 52500
tgcaacatgc gcggaaattt tttacttcaa acgtggcgtg atatgacgtc atttgttttt 52560
tgggtcgagc catcgaacgt tctagaacaa attttatcga tcttcgccga cggtttcata 52620
tgaaagcgcg ggcgagtttc aaattaaaga tgatgcaata ttttaaacgg atgacgaaat 52680
ttgttttttt tttcaactaa acatgttagg ttaatcttgt ttaggatttg gttcggtaat 52740
gtcattactt gacgcgtgat tatatgacgt aatttgtttg taactattta aatattgtgt 52800
aattatgtta ttttgtattg tcacgacatc gattctattt atattcatga cataaaacac 52860

-continued

```
aaatgtgcca ttattgaaaa gtttcatcat ttattcgtac tatagtccag tggagtatat  52920
ataaacagtg ctgttttatt gaaaacattt acagtcatgg agcctaccac actgtacaag  52980
atcgatcgcg gcagccgagc tatgggttat gacatacgat cgagcgacta tgattatatt  53040
gtgttttcca aatgtactcg tgaagagttt ttagaccatg tgtttgatag aaaaaagttt  53100
gtgaataaac attgcaaaat caaaaacgat gatgtcactc tgtccaattt gtttgtcgga  53160
ttgaagggga tctacaatgg caactacgcg cacttggcaa tattttctga accgcgacac  53220
tttggagttg acgattattt tttatacaag tttgtgaaaa ccgttgccaa actcagaatg  53280
ccgcttatac tgaaaaccat gctaaaatac aatctaaatt ctgaacatgt cacggccaaa  53340
caggctctgc aactactgta caatgtgtct tatgccgatt atgtactgag gcatggtatg  53400
ccagaaggga tcgttagaat gccagcagtt ttgtgcagta ctgttgccaa aaatgcgtac  53460
gctactttga tgtcgcagcg tttggaaaat gatacagaaa acatacgata caaactagaa  53520
gatgaagtaa aatttttgat caaatatcgt aacaacgtgc tggagagtgt caatgccatg  53580
ccgaatcctg aaaatcgtcc cgacatcgaa acgagcattt gtaattattt tctgtgcgaa  53640
aatgtaaatt taacgatacc tcaataaaaa tcaaataaaa atgttatatg ttttattttc  53700
aacatgagtt acatctgaca aaaaaaaatt attacaaaac accattactg taaatacact  53760
tcgaatcgtt cgactatttt tgctcgacac aaacagcatc gtttacatcg tgctgcgcaa  53820
attttgcaag tcattacatg acgacacggc ataaaacaaa cctgtcgtga ctggtcgaaa  53880
catattttgc acaaactatc atcttcgttg gtgttgtttt tgttggtaac gacaagatca  53940
ttacgatcgt ttccgtcttc ttcgctatag tttgatttgt ctatatcgat cagagtaggc  54000
gcggaaggaa tcgattggtc gtggtggttt acaaaaatac aatcaattga attgatacga  54060
tgaatatcgg caatattgtc gttgaaatta aacttgacga ttacaagcaa acaatatgca  54120
catctaactt cggttttgac tccgtagtaa taaaatccat tttgtgcgag caaatctaaa  54180
gaatttttaa aataggactt ggcctttttg tattgacgaa acgagtcgcg acgcagatat  54240
tcgctttgtc gcagcaaatg tagactgcgt ggacacagag agaatgaatg tgaccgaatc  54300
gagcgcatat caacttttaa catagtaaat gtgcaaaaat tacaacaata tgtgcttgtt  54360
ttgacattgt aatatattcc agccttggcc agtttttggc acaagtcacg gcttaaattc  54420
acatgataaa atgtaataag acgattgtct agaaaatgat acggcggcgc caagtctgct  54480
ttgattacac aatccattgc cctggcggtg acagctgagt gtgtcttata taaattacaa  54540
cactttattg agtattttct gatttggtca attctctgag tagcttattc aaagctctga  54600
tttgttttct agcgtattta gttgtttcca aatcgatgtg ctgagtgtca tggtcgattg  54660
ttaacaatct tggcgtggcc aatctattca aacacaccag atagcgttca gcgttagctg  54720
gtctcgacga tactggcttg aacacgtaaa attcactaaa gttactaatg aaactttcca  54780
gcacaacgaa tgtgttgcga gcaaaagtgt caaaaatttt cagcacacta ttaccaccga  54840
cgcgcaaaca atcaagtata atctcgcact gtttcgctat tagcggtaac atgatcaatt  54900
cttgatcgtt ttctttgccg taaacgtcta taccgccgtc ggccacgaca agatcacatc  54960
gatgtccgca cagcatgttt aatttgttct gaatgtcctc ttcgaaaatg tctccagtgt  55020
tggcgtctcc gtaaacggca cagaagttcg gcacagacac attatagtca agatggttgc  55080
gtaaagtgac gccgtacccc tgactgttta acgtactgtt gttggaaata tagtttgcaa  55140
attggcccgg tcctccgcac aaatccacat acaatcgtac atttcgacac agattgaaac  55200
gttcgtcgat ctctttcatt ttgtgccaac agcgtcggtg acgatgtgat ttacgtttgt  55260
```

ccaatcggtc gcgtgctact ttaatttgac tagttgtgaa ttcgtcgagt tgcgatttca 55320
gccggtccaa tttaatttta tatttcgatg taatcgtcga ggacgtcatt atctcgtaaa 55380
ctgttatcag atgggaacac gaacgctact acgagcgcga gcaggactgt gcaaataaaa 55440
gccaaaaata tttgtactga agttatattg agcggggata gcacagcgcg cggtctgttc 55500
agtgctcgat taaaaaactc actattaatc agcagagttt tatttgtgat ttcgtatacc 55560
aacggtcgat tgtagtcaaa gtttgatacg ttggctttat cgaaattagt tcggtaattg 55620
ttgtcacgcg gactcgtcaa caacaaatcg atcagcaaat ctttccaagc atattcgcga 55680
ctttccggcg atatttctac gcgatccgaa ttcaatatac gccaacgaat tcttgacatt 55740
gatatttaac tgatcgatat gtcgaatatg gatataagcc ctgtcaaaca actcattgat 55800
atcgaaaatg atgatgcaat gaatacgcca gagaaaggaa tgaaacgccc tttgatgcga 55860
actatgtcga gtgtggaaga accccaagcc aaaatggcaa aactgcgtac gctcagtgtg 55920
aaaggacaat tgcttaccaa aaccacaatg agtatcaaca atgaagatta ttacttattt 55980
aaatttttgg tcaacaacaa gagtatcgac tattacggaa cgcaaactca atttttctca 56040
ttgattaaca ataaaactta cgaattggtt ttgcaataca gccgcaaaaa gctactcatc 56100
aaatcgtatg agcaatgcga agacgaagac ctgttgatga ccgtatgcaa aagtgtgacc 56160
ctccaagagt tctgtgccaa cgagataaaa tcgctgctgg cgaaattcct atacggtttt 56220
aaagtctacg gcagttcaaa tgtttacaag ttagtttttg tgattttgct cgaagacaac 56280
aatggtacaa tcaacggtgt tcaagtagaa atgatgagcg acttcaaacg tttgagcgga 56340
gccttcaaga accatgttat tgaaaatgaa aacgatttgt ttgactgtat gtacaagtct 56400
gaagagaaat atttcaattt gtaccgtatc aaatgcaatc acaacgcaaa caattttaaa 56460
agtttgtcac tgtcgtcgaa cagtcaattg gagcgtctcg aaaccgacga cagtatgttt 56520
gaatatgaat ttcaatacga ttacactgtt aatattagtc gttcgaacaa gattatacag 56580
aaacaccgag ttaccggcaa ttttacttcg gagagaaata tctatcagaa ctccgatcgt 56640
tttgtgatca gttacgacac ggctaatgaa aaaatcaaga ccagcatcta caatcgtatg 56700
gaaaatgcag aatccaaaac tgattacgac acatcgataa cgttgaaaga cgtaactttg 56760
agtcaactca acagtttgat tgaatcgaat ctggtgcaag ttgacgtgta ccttgtgact 56820
gatccaaata atgttaaaaa caatgttatc gccggcatca ctaagattga aatcgacggc 56880
acttacgaac ctttgtaaat cttttgtgaa tatattttca taaatatatg tatatgtatc 56940
aataaatgtt attaaactaa tgtgtaaact ctttttatta caaaaaccct ttgaaattta 57000
tttcttataa tttttttgtt atttcttctt gttcgatggt ttcaaacgaa ggtaaagtat 57060
taagattttg agcgtattga gcaaagtcgc tatctattat tgcggtcatg tcaattggaa 57120
gaactcggtt gatattatat ttgtaattaa ttaaagtcaa ataatctctc aatccaatgg 57180
cacgaaccaa tcgagtgtaa ccttttggtg gtaaagtttt aggagacgcc tgtaattcta 57240
tgagagcatc gtctaacgct cgttgtgcaa taatcggatc gttaaatata tcgttgaaca 57300
atggattttg catccactgt tgcgaacgag tttctaaacc tttttctaaa caggcacgtt 57360
tactctcaac agcagcagtt tcgtcagccg gttctactga tcgtttattg actgttctat 57420
tagcaatagt tgtagcaaca atactggaag gagtcaatgt tgtaacatca ttaatttttt 57480
cggcattatc aacggtgcgc atgctaaccg atcttaacgg cggtctgacg tttggtttta 57540
ttgttggcgg cgcggccgac ggtcttgaat acggactagg acgcgtcgtt gtaatggttg 57600

-continued

```
acattttacc cgaaatttcc gcagagagat ttttgtctag aatattttca attctagtta  57660
tttgcactct tatcgattcg atgttgttcg ttgcggtttg tatatcgttg gttatggcgg  57720
tcagacgctg ttgttgttct gcggctactt ggtttttgta ttcggaaatt tgtactccga  57780
gagcttgacg caaagccgtt atgatactgt tgtcgtcggc ttctttattt ttcaaataac  57840
tgatttgatc atttagcaaa cgcacttcgt ctacggcggc tacgcttttt tgcgtcgtac  57900
tttcaagccg ttcgatttcg cgccgcatta cgtttacttc ggtttctagt tctttatatt  57960
gttcttcgag caaacggttt tgatatgtga cggtttcgtt agttgtttcc gttttaatat  58020
aattgtccga ttcgattttg catcggtttt ctaattgcgt gtaattcgtt tcgatagtta  58080
tcagacgttg tttcaattga tcacgttcag ttttgatttg ttcgtagtct tcaattttag  58140
cgttggcccg tagagtgtct atttcgtttt tttgttcgtt gatttgttcc cgtaaatctc  58200
tcaatgcggt ctgttcgttt tttactgata gagtctttcg gtcgacattg gacattagat  58260
cgatcaaacg ctcggtcaga ttagtgagaa acgtaggtga aacgtccaca attgtgctat  58320
aatttaaatt ttgtaattgt gccgtatttc tgtcgcgagc tatgattgcg tcggccaatt  58380
gattgtaact cgatttgtac aattgcagcg cttcgacacg atcgttgacc gacgtcaata  58440
tgtattgtaa attagtttcg tcggcgagac ccatgtccga tgaattggtt tccatttggg  58500
ctggtaattt ttctgtcttc acattagcca acaaccgatc gtgtatcaaa cgaagattgt  58560
cgtgcaattg cgatatcaca ttacaaacct gagacataga cctaaaagtg ctgcccgttc  58620
tgctgttgac gcaatcgagt aattcgttga tgtcgtttct ttcaatgaat ttttgatcta  58680
aacaatacaa acgacgcaaa gcggccacga aattgggtgt cacgacagaa tcatcgctaa  58740
atgcccgcat tactacatcg atcaaggtcg atgtaaattt gttcatattt tgcgatgtaa  58800
aatctacaca aacgttttca attgctcccg aaattaatga cacgtcatta ttagtgagtc  58860
gtgtcggcgg cgaagacggc gtgagacccg ccgatgttgt cgttgccggt tgtgcgttcg  58920
gtggttgaac tggatactga ttgatcactt gtacaggcgg cggtggcggc gcagatggtt  58980
gcgtcggctg cgccatattg ttttggaccg gtgttccgaa cgcgtcaaca ctgttcgcta  59040
acggaacgtt tgaattgtaa tcgtatttgt aattgtagtt gtgtgtaatc tgactgtgca  59100
tcggttggtc gtgatgacga ggcgaagcta gtgcttctat tatcaattcg ggcacttgta  59160
aatcgtgtcg atcgataaga tagggcctgt aaaggactat aattgagcgt atgcgttgca  59220
aaatatcttc agtagcgtcc aagcttttgc atcgttgact catcgagttt attgttcgca  59280
acaaactttg gaccgtgcct gaatttacat cggtgttttt atatttggct gcgtacgacg  59340
gaatacctct gtttcgatac atgttagtaa caacgacgac gacgacgacg acgacgacac  59400
aatggatatt gccttattga cttggaatga tttgatcggt caattgttgc ggttcggtaa  59460
tcgacaacat cgaaccgtca ttgagcctga agatgtgttt agaatcgtcc gtatgactta  59520
tcacgacaat tgcttgttga tattttttac tggctacgtg tcatcggatc ctacgaaaat  59580
ttttcaattt tacatggaga ccaaatgcga tttgtattcg tatcgtcgct gctacaatgt  59640
tcacactaac aacgagtgta gatacaaatg taaaagttat aaaacgttcg ttatgcccgg  59700
tttgcgcgga tcgtacaacg aacgtatcaa catagttcat tacaagagaa cacccggtga  59760
acatgacaga aacaacaaca aaaattgtct cgattctttt ttaaaagaca tcaacagagt  59820
acatatgcaa accgatctaa tggaaggcaa ttacgtacaa ttcaaacaga gacaatgcgt  59880
cactgatcac agattgtgct tgcaaagtaa caataacact ttcaaagaca tattcaccgt  59940
catcgatccg gacagtttga aacgcgaaat agttcctgtc attgcgtgtt acgacataga  60000
```

```
aacgcattcg gacggacaac gattttcatc ggctactgtg gataatatca tttcgatatc  60060
tattgtggtt cgtcgtgatg gtgtcgataa acgtatatgt ctatactata tggacgacac  60120
ggccaaagat ataaaatgga acacagacaa cgatgccata aacgcggccg aaatttgggc  60180
ggtacatttc aagaaagaaa gtgatatgtt gaaagcgttt ttttcgttgt ttccattgtt  60240
gaatatggat tttttgctgg attataatgg tgacagattc gatttaccat tcatactgga  60300
acgcgtaaaa cgtttgaaca gtggcaaaga aattgtgatt aaacgatacg atttgagtcc  60360
ggttgctata aaaactgaac aattgtgtga taaatttcaa aacaaaatca atacacatta  60420
ttttacatat tatgtacacg tggacttgta tcagtttctc agttcggact cggaacaaaa  60480
cgatgtggaa aattttcaat tgaacacggt tgccaaacat tatttgaata tgcaaaaagt  60540
tgatttaaaa attacggaca tgctgcgtcg gtacaatgaa aaattgatga aagacatcat  60600
cgtatataac gttcaagatt gtgtgctacc catcgatttg tttctgaaat tggaaattat  60660
ggactttatg tatacacaat gtatgctatt gtatttgtgt accgacgatg tgttacgcaa  60720
tatttctcat aaagtgaatg tggttctatt tcacaaggca ttgatcaata cgcgctacga  60780
cgaaaaaacgc aattgtaccg tacccgaacc gtattttttc aataaacacg atttgtcggt  60840
gacctcgggt cgcaaacgta acgccgccgg agattcggtg gacgatcagc aaatggtcga  60900
tttgagtctg ttacagcggc ggcccgtccc cgtagatatg ataccttcga atgctgtaaa  60960
attgtgcggt aaaagacaac gctgcgtgta caaaggcggt aaagtgctgg aacctcaacc  61020
tggtttcaag caatgggtgg tcaccttgga ttttaattct ttgtatttga gtataatgat  61080
gtatgaagga atatgtttgt ctaacgtttt tgtcgcccag gacgacaatg tttatttgca  61140
caaagatttg gacgctgtca atcctaaatt gttacgagaa ttgctcgatt tgcgcgccaa  61200
atacaagaat cgtcgcgaca aacacgaacc cggcacgttt caatacaatt tgaatgacaa  61260
aatacaaaat gccgtcaaac gcattgccaa cagtatttac ggatattttg gaattttttt  61320
taaaccgctc gccaattaca tcaccaagat cggtagagaa aaattgacgg aagctattgt  61380
acgcatacaa gcaatgagta atcgtgctga tattttgaaa gattttaatt tgtcaagaat  61440
caattttcga gtcatatatg gcgatactga ttcgtcgttt atacaagtcg attttgaaaa  61500
aacggacatt cccattaaag atcaacacaa cactataaaa accattgtca acgattatgt  61560
actaaagacg ttgaattcct cttggaacgg ttataaaatg gctttggaaa atgtaatgct  61620
gtcgttgatt ttgttaaaaa agaaaaaata ttgctattgg aatagcgaac aacgtatcaa  61680
atataaagga tggctagtca aaaaagacat gccgttgttt atgcgaaagt cgtttaggca  61740
agtggtggac tcgtacttgc acggacacag tttagcttgc ggactcgcat tgctgacaaa  61800
attgatgacc gaatattatg acaattttgg tgtcaacaac aactacaacg aatatggttt  61860
tagtatgaca tacaatgaga attcgactag tgccaaaaaa agaaaaacca ccaccgtttc  61920
aaccagtacg cgtcccaacg ttttgaccat tgccaaaaaa tgttacgaag atttgaaagg  61980
gagcggtact gattttttac ccacaaacgg tgatcgtatt ccgtatgtgc tcattgatgt  62040
tgagggcagc gttacgcaaa aggcttttcc tcttaaacta ttcgattcgt cgtacaatac  62100
catcaattgg atcaaacaca tgggtatttt gtgtacattt tttaacgagt tgatcgaagt  62160
gtttggcgat tcggaaactt tccaatatta tttcgaccaa atcacgtctg tttttatggc  62220
ccagcaacgg tacgatgtaa aatatccagt tttggtgacg ataaacccaa aaaagttaca  62280
aaccgctgac gatagcgacg acgatagcga tgacaaagaa tcaaatgtcg atgatgccaa  62340
```

```
tcaatgtaaa cccattccca atcatactac taaatttgca ttgcataaac gtcaaaaatc  62400
taaaatgact aaatcgatga ttatcgacaa tgaatgctct gtttgtaaga gtgctgtatg  62460
ttaaattgta ttctatgtgt gtatgtgtgt taattgatta aataaaatat aattaattga  62520
gtatcagttg ttttattgtg tatagtttgt ttcagtattt tcctcgtcga ctgtattgct  62580
aacaactgtc agtagttgtt ttaaaagagt cttgtaatca ttggtcacag atgtatcgtt  62640
gttttcgatt accactttag attctttatg tattttgtca cgaatttctt gcaatctgtt  62700
tacgattaat tgacaatcat tcttcacatt tgattgttgc aaagaccaaa aatgtacttt  62760
attaccgaca aaatcttgta tgatgtagtc taatagttca actacggtat gaacaaactc  62820
tttgtagtca tctgcagtta cattatcgtt tgatacgaat gcaacaatta gattaattaa  62880
ttttttattt tgttggtaat acgcaatgta gttggttttg aggatttgtg tgttgttcga  62940
catttgttcg tgttgtgtgc aactctcgtt ggaacaattg gttgaagtca tgataaataa  63000
taacaagcaa aatttttata tagtcttata ataatatttt taattacatc atcgtattag  63060
cgatatacaa gagcattatt aaattcttgc accataaatt cagcaatatc gtgtatttcc  63120
ggttcggtca aacgttcgtg ttcaatatag ttattgacta tacttaaaat gtagccgttg  63180
tcgtatattc tgcaatacaa atattcaatt tggtcttgtg acatattgac gtccacagcg  63240
ttcattatgt tggccatggc ttcgacgggc acctgttgtt cgacaaacat ttggagcaca  63300
gtgacgagtt tgtaacgcaa cgtgtcgtcg cgttccaagt ccttgagagc atgtttaatg  63360
tgtgttgttg caaaggccac ttttgtgact actggcatcg aagtggcaat ttgagtgaca  63420
aaatttttga tgaaatccat gcttctcaat caatagaact tgtgttctta tttattattg  63480
catcgaacgc tctttccaat tctcgtttct tttttatact cttagattta ccggtttgta  63540
agtccgccgg ggtcgaatcg ggtttgatat aatacacgtg cagcatcatt ataaaaataa  63600
aaaacagcaa caacaagaaa aacattaacg tgctgaaccc ttcgtttttg tcaaagatga  63660
acccgagagc tattaaaaaa agaaacgcaa aatatatttg cattttgctt caattgttgt  63720
cgaaacgtac ttattacaaa tacttaatta aaagataaca aatcggcatc gtcgccgcta  63780
ctgatattgt tgttaaaatc gttgccgctg gtgttattat tactgctgtt gccgctgctg  63840
ctgttgttaa tatcataatt tgaaatattt gcgccgcttg ggttttcatc aatgatacgg  63900
tcgtcgtttt cgtcgtcgtc gtcgtcgtcc tcgtcattgt cgtcgctttc gtcgacacca  63960
acatcgtatt tgttcaaata atgtcgcgtg ctggccgatg attcgtggtt catgagacgc  64020
gcaacttttt gcagtggcat accattattg tacaaattac tactcaaata atgacgtatc  64080
atgtttgaac gtggacggtc catttctaca ttggcttctt tgagtaggcg cttaaagtct  64140
ttgaatggag tcgaagtgtt cttggatata tttaaaatat tgggattttt tatatagatt  64200
tcgcgtgcca attccaatgg tttttgcttg atactattta gagaattgct tgtgcgatgt  64260
tttttccttt tcaagccaat agtgctgcgc agttttccgc gtttgatgag tgtgttgaga  64320
tcgtccacgg acaaatgacg ggcttcgttg atacgcatgc ccgtgccgag cattatacaa  64380
aacacgatag ctcctcgtat cagaccacga tcgtggacaa attcactgct caaatgtttg  64440
attttctttt ctatacaatc caatatggtg ttgatgattt ctcgcaaaac tatatttttt  64500
tcgttatttt ttatattttt aatttcttta tcgcgtggca acatcacctg ttttggaatt  64560
ttatattcgg gcaaattcat cgtattggta tagaaattta tagttaactg taaagtttct  64620
ttggttacag agcgcaattc aagcatgcgt ctacacaatt cttccggttt tatcaatggt  64680
tgttgctgaa cgatagaatt gaattctttg ttcaacgtgt gcgtgtcgta gttattcaaa  64740
```

tattcgtcat cgattaggca ataaattagt tttatgaaac gagacttgta actcttcaaa 64800
gtggtgggtg caaaaggttt gcaaaacatg tattgcgacc acaggctatt gtttttttact 64860
tcatctggag tacatctttg ccggtccgtg gtcaattcga aaatttcatc gaatttatcg 64920
tgattttgta ttcttgattt ccaatagttg aacgagctct cgttgcgtaa tgtagcggga 64980
tgattgttca taacgactcg attttaaacg taatagggtt gtcgaacaat tgatttccgt 65040
ctttctctta atataacaaa ataatacaat gcatacaaca gtaccatgac gcaaaacact 65100
gccagcaaac taatcaacaa tatattaccg atccatgtgg aattattgcg tttctgatag 65160
ttggatcgat acgatgtcaa atcgttgtgg ccgagtatag attttgtcga cgaatcgtca 65220
gtgttgttac ctaagtcggc cgcatctacg ttaaaatcgg atatagccaa ttttagcgga 65280
atatagtcca ctttgtcgtt aactccgaga cgatcgtagg gtatatctaa attcatattt 65340
ctgaacagtt atgcgtccaa tgtttttcaa caataaaaac caatgtataa tgccaaaatt 65400
tttttaata attttgtttg tagcttaact tttgaaaaat gtaacgacgt aacgcttcgt 65460
tttgaaacgc taactctgtt aaactctgct gacaagaagt acgattttgt tctacattag 65520
aaccgttgct agagggagcg ttgaggaacg tcgctccttg aaagaggctg ggtctcttgc 65580
cggcgcgtgt agccaaattg gcaatatatt gaaatatatc cgtggacgca gacaatggcg 65640
ctaaaaagcc tatgttctct ttgagcgtaa cgatgcgagc gcggttcttt tcattgagta 65700
cataataata ataatttcca tacacgcctg tgaacacgtc gtcaatcaca ttgttgatta 65760
gatcgttgat gatgttcaat gttgggtatt tgcgactgga cacagcgtct tgcacgttgg 65820
gcggaatgtt agctcgttgc aacagcaacg ttatatacgt gttgacgagc tgatggcgaa 65880
caggcaatgg aatcggagta ttactggcta cagcttcggc tatttgatat tgcaaagctt 65940
cgcccaattc atgcgccgct tccgacacgc tgtcgccgct cacgttttcc gcgcctttgt 66000
tgtaaaattt ttgggcataa ctcggcaaca cattatacac gaatgatggc tgaaatatat 66060
tttcggcaac ttcactaccg cccaattctt tgcgcaaacg tgaataatgt ttgattaaat 66120
tttcatcgct atcgaaccgt ttgaccacgt tcacgctaat cggatgcgat tccacgcaca 66180
aatcgcgtat ggtgttaatg agcataatca tttgcggtgt caaatgcgac atatcgtttg 66240
tcctataaaa tctaatgata cgttcgacgt aatcgacaca tttgttggtc caagcgtccg 66300
aactagattc ctgcagctgt ttttgatgct gctgatgctg taacgctgta gtgacggcgt 66360
gaggctgcga cattataatt tatcaatttg tgtggacagt aatttatcgt cggactactt 66420
atcatataat tgttgttcac atacaataat atcaaaatga atataatgaa aaatatatag 66480
aaccaagaaa attcgatcat attaaatatg agcacaacta tagtcatagt tattaggaca 66540
gtttgcatgc tacgtctttt gcacaatata gcttcacaat tgtgaaatgc caaattaaaa 66600
acgttttcgc cttcgacgaa agagcgcaat tcacgtttgc aacactcgtc gcacagtata 66660
cgtatgccga taagatgacc gtccgaatgg tcggtttgaa acgttttcgg ctgactacca 66720
gggtgaaatt cgaatgtata tccattggaa atttgtattt tagcataata gtgtgccaac 66780
aaagtaccac ccgccttttt tactcgcact ttacacactt taatgatgtt caaattttcg 66840
ctattattga gattgtcaaa caaataatgt atcaacagtt cagagtcata tttgatgcga 66900
ttaagagtgg tcaaattttt gtcgcttagc tgcaggttct tgaagggtcg atgcaacgtc 66960
tgccgatcca gtgttgtcgt atccgtcaat ggtgttgtcg acgtcggtat catcgtcgtc 67020
gtcatcatcg tttgaatgaa cttcgctcga gccgatgtcg gcaacaaatg tggatctgaa 67080
caattcgtcg gattcgttag ctatattggt gtcggtgtcg ttcgcaaggt tattatcaca 67140
caaaagtgta ggttccgtgt cgttcgacat cttattattc gttgaaatta aatgtgtttt 67200
gtcatcgttg tcatcgtaat aggatatttt aaaaagacat gaaccttttt tgagaatagt 67260
aggtcttgtg tttaacagaa tagcgtttat gccaccagtt tcgttttgat tgtaagttac 67320
cacgaaatat ccacaggcga ttgttgcaca ttgtttattg tgcaaattgg acagcaaacg 67380
agtgtccaat atattgacac aatacgcgcc gacggccagt ttttttaagt gatattcatc 67440
ttgaacaaca aaagagagcg tgattatatt tttttcaggc tctctatctt gtacaacgta 67500
cgttgcaatg tcaacggtcc cgttactgtt gatcgccatt attgtgcttg tagtttttac 67560
aataatatac ttatccatac tcgacgaagc ggcggagaat gcattcgaaa atcgtttagc 67620
cgtatataca gaatatttgc gtcgtaccaa tgcggaagtg ccgccaccac cgtttttggg 67680
ttacgtgtcc gatgtgtacg acaatttgtt caaagttacg tatttcgata ccgccaattt 67740
ggcagtgatc gacgccagcg tgcacgacga caactacgaa acgttcaatt tcataaatca 67800
aacattcgaa cagcaaaaat atactaaaaa cgaaccgcga atagcgccgc atagcacaga 67860
tcctgctaaa tttatggcac gcggcgacga cgacgactgg atggaaatcg attgtcccgc 67920
cgacaatcat tttaattcgc aaactaatag atgcgagccg gttccaccgt gctacaacaa 67980
gcagcccggt ttgtatccga tagacgaaaa actgttagat actttagtgt taaatcatcg 68040
agttccgaaa caacgggatg aaaatgtccc caacaaatat catccaacaa tgtatttgca 68100
atgtctaatg ggcggctcgc acgcagttca cgaatgtcca ccaaatcatt tgttcaacat 68160
tgattccgca gaatgtcaaa ttcgtaacga ctgcgaaaat cgcgccgacg gtttcattat 68220
tactcccgtg ccggaaaacc tcaatataaa cgaatatcta gaatgtcgca acggtgactt 68280
gaacgtcgct tcgtgtccgg ccggtgaaat tttcgacaga cgattgctaa tgtgtgtcag 68340
aggacatcca tgtaccatgt tcggcgacgg atacacgtac atcaccgacg aaattaacga 68400
caatcaattc tttagatgta catcacattc cgaatcacaa ttgatcacat gcatccgccg 68460
cgtgtttgcc aacgatcaat acgaatgtac gggcgacgat cggtgtttgg tattcgaaaa 68520
tggtagcggt ataatgccgt atgtacacaa tgacggcata cttgaatacg atacgggctc 68580
attgatttgc gacaattaca caataattaa tgacgtcatt tgcgacaatt ccaatttact 68640
acaaaacaaa ctgtattatg acaagtttgt cgcaaatata catttgccta aacaaatcta 68700
caatagcgca aataattctt gtgtaccgtt cgaaattgac cgtgtcaaaa ttgtaaatga 68760
tatttttccc atcaatatga tcgagaatga ttacaaaatt gacgcacaaa ctgctctagt 68820
gggaaaaaca aaaaatattt cgtctctaat gaacgatact aatacattgg ccgatgttgt 68880
cgtctacgct cgcgattcta actcgatcgg attgaatccg gtcgacggta gttctataga 68940
atgtttcggc gattatttgt atgatatctt cgacggcaaa caaataaatt tctgcaacga 69000
tccgatgtcg gccactccta gtttacgtca aacgctcgat ggaaaaaaat attttcaatc 69060
catcgttgtc aaagtgggca gcgattcaga ttatcaacag caatgtgttc ggtacttgga 69120
cgagatcgat caaaatttcg tagaattaga tcattttgcg gcatcgtata ttggcgatat 69180
actacacaat gacgaatgtt ctacactttt gacacaaatt catgattcat atactacact 69240
ttcccaaaaa tatactacac tcgactctaa atatacgtac gaaaacgtaa aaaacgaaaa 69300
attcgtcgaa caatacggga cgaatataca caaaaatgaa cactacgatt tacaaaacga 69360
aaaagatttg caacctcttt ttgatccatt tgttaaaatc gaaactgttc gaccgttatt 69420
taatccgttt gacatggatt cgccgccgat cattgatagt gaacccgaaa acaatcctga 69480

```
atttaatcct aatcccgtac ccgaacccga acaagaagaa ttgatattga aaaacaaaac  69540
tgtaaatttt gcatgtttct attctttacc tattttcaaa ttgtctgcgt gtcatttaaa  69600
caatgaatcg ttgataatta acatatataa tttacgaaaa aaagtggaca taagcgccga  69660
ttgtatcaac gccgccggtt tagttaacat cgttaattcc tacgcttatc tgggcaacga  69720
tattggttgt cgttgcaagt actcaacaga aaaaggcttg catattgaac gtgacgataa  69780
tccgattgtg tatactaatc tcgacacaca atcaaatgac ggaataaaat ataatatgta  69840
catacatcgc aatggaaaca attttatagc atgtccacca gaattgctta cggacacttt  69900
tgagtgtaac gtcgaaaacg acagaatgta tattatgcac aacattcaac ctgaatgaat  69960
tcaattaaca tgaaatttta attttagagc agttataatt gaaacacaaa attttttaaa  70020
ataatcattt attatataca tataattttt gttacataca acatttagaa ataaatatat  70080
atatatattt atgatttatt tctttttgcc tctggcgaca catcaatatt gggcaacgcc  70140
gatcgttttt tattgacact tttcttagtc tcttctagtg tatcaatttc acattgcaga  70200
gtgttacgat agcgcaacag ttccatgttc ttacgttgta tattgttctt gtctcttttc  70260
attttctcgt attctcgagt acattctgat ttggcgttca tcaaccgatc gacgtctgct  70320
cgatgattgt taatcttcgt ttccaattcg ttccatgtag attgtaattt ttctaatttt  70380
atttgttgac gtgtcacatt agtttcgatc gttttgagca aatcgttttt ttcacacaac  70440
aatttagttt gtttgtccaa aagcgattgt atagaagtgg ttttttcaat caactcttca  70500
atatgtttat tttgatctgc tataatactg tcataggcgg tattatcgtt cgtagtaacg  70560
ccactatctt ctgacgtgac actacttttg taaatatctt tggccaagct aactatatcg  70620
atagtttgta cagtatcatt tgcagatgtc gaactaatgt tcggacattt aacctcttca  70680
atatcagtgc tcgacattgt actaacaaca ttcactgtat tgccgctgat acagtaatac  70740
gaatatttaa tattgatcga tctgcacaga gggcacttga caattagtga ttttcgcata  70800
cgcttcagac acatggtaca caacgcatgc agacatgatt gcaatacaat caaaggcaat  70860
actaacaatt cttgttgatc gttattgtaa atagtggcgc ggcctaagca cacacaacaa  70920
ttcactgtaa tcgaattcat tgcagccaaa tagtagactg aatgtgaact gtaaatgttt  70980
tggtatttat agtgccgagc cagtgtgata aagtagatcg tcacagtctt atcgtcctgt  71040
gctgattatc tgtttgccta aaaacagcgg aatattaatc tgataaagtt cgtatcgtga  71100
taatttttgt tggagagcgt tggcgttgcc ttgaaactgt aacacgtttc tgatttgcag  71160
acggttttcg ttgaccccat acaaatattt gggttgtact gaattgtaca aacgcaccga  71220
ggccaataat ccttcgctgg ttatgcgaca agtgttacag ttacgcaact gtaaatcttc  71280
cgtaccaatg gtgagacttt caggagctac gcatttacgt atcaggtttt gtatgaacgt  71340
gggcagtacg ttgaacgcaa gatcgtcttc gacgcttaga ccaaaactgc gcgattcgtt  71400
ggtattagtt tgggcacagt aagcatcggg attggtgaga gcgagcactc tcaaagtgct  71460
attatataat tcttcgacca cttcgggtct gaatctttcg tacatgcgta gttgttggca  71520
aatttcgttt tgcttctctt tgttgtcgta aatcatgtag aacactaacc gttcggcggg  71580
accgagcagc gacaaattga gtaccgtttc gtagttgttc tgactcggta tcaaaatacg  71640
ttcaatgcct tcggctttgt cgtccaccag acttttgcct actgtacgat agtagttgtt  71700
gcccgtaccg tccggaatgg cgagagcgag tttttccatt ttaaagaatc gcgacgcatg  71760
atattcgcac acgaaccatc cgtcatcgac ggtggcgtcg gacgaacatg gactcgaata  71820
```

```
ttgatcgcaa aaatccaacg gtttcacgga actaaatacg caaaagttgc gcagtcgtgt  71880
agttgccgtc ggcacggtaa caagggccat ggcgttagaa aaagaaatct cttatacaat  71940
aaacttgagt caagatctat tgtatataat tttcaattct tatattgtaa aacacatgga  72000
ctaccgaaca caatactgcg accttatcga ctgcaacgat gtacgaacgc gattcgagag  72060
cggcactgtt cagagtgttc tcaaaaaaaa cgttgtcatg aaacgattcg ctcattacgt  72120
caacgacacg gcaacaattg ttggtctagt cgatcgccat agcatcgaag aagacatcgg  72180
tgacgtgaac aaattagatc ctcgattgag aagaatagtt cgatgtcaag tgtatcgcga  72240
tcgtcaatgt ccacagatcg aaataaaatt cgaacacatc tatttgaatc aacacatcat  72300
ggaccggttg gattcgctgt tggccgtcaa gcagatgaca cttctcaatt tgttaaatcg  72360
tactaacgat agtgttataa aaaattctca actcggatcc gatgaaatcc ttgccaatat  72420
tcgacttgaa tacgaatacg aaactgaaat tgccgatgtc gcggtgatcg atcgactatg  72480
tgttttggtc caagaaatgg acaaactttc gcattatcaa aacattcatc cgttgttagc  72540
gtacacgacc atacaaaaca atatcattta taggaaattt attgacgaac gtttattgtt  72600
tgatagtaac ggcgccagta acgaaattgt cgatttgaat atttataaat gggcactaaa  72660
attggacggc atacgtggca gaggcttctt tactcaacaa ttagtggtca tctttatgga  72720
cgacatgcaa ctgtttgccg gacacttgtc gtctccgttt gcggtcaaca atgttgtcgc  72780
gtttcaatgc gaactgttac ccaacaacag gttgtatatc acagatttgt tgcacgtttt  72840
caaatacgta tacaacaata agacccaata cgaatgttct ttggacgctt acgatctcga  72900
tccatatagc gccgtggcat gtttaaacca tatgcgtcac aatcgaatcg aattatcgtt  72960
caatacggac aataatgtta cgatgacgat ttgctttcaa caatttaacg agcccccgtt  73020
gaatgtggct ggttatcata gcgtgcccac ggacggtttt gttgtgctcg accacgaagg  73080
tcactacgtc aaatacaaac atatcaaaac tattgaagtc gagtatgatt ctgttaataa  73140
tagatttgtc actctcaacg gtccggttga aaataaaaaa atcattatgc aatcaaaact  73200
agaattgctt catggtcaga tatacgaagc aaacatggac gcagacaatt tgttcattat  73260
gaaaattcgt aaagacagat tagttccgaa ttgatctatt gttaaaattg atgaataaaa  73320
atccaatgta cagttttaca acaattttat tttaattgta atagattttt gtatgtagtc  73380
caatccatgc gctgggtgtt ctgctgtacg ggcggctgaa cgtttcgctg tatccaacga  73440
tagtcgttga cgtgattgtg aaacagcatg ctagcgtaaa gcatgccgtg gcgcatgagc  73500
acgttttcgg tagcgtcggt tgctcgcatc tcgtcgacca taacgatttt ttcaccgtat  73560
ttttcgcgat acaatgccac ttcgatacgc tcaacttgca ttatgagata gccttttata  73620
gtcaaataat gattacgaca catgggacaa tttagtttaa aaaatacatt ataaaaaacc  73680
ggtttcatta aacgtaaatg ttgacgaatc aattcgttgt cgtatttttc acgactctcc  73740
accatgtcgt ctatgagcaa acacaaaaaa tgaatcgaat cccatatggt tgtgaacgtg  73800
tacgcgtagt tttttggttg gggcgcacgt aaattgagtt gttccatttt attggaaaat  73860
tccgttttca tttgttctaa agtcatggtt tgcggcaacg acagtaacca ttcgcgcaac  73920
tgatcaattt cttgctcctg aatatctttg tacgttatta gacacgctat atgatataaa  73980
taagtcaatt ccttggacaa gatcagggcc agttccttcg agggcgacga acgtatcaag  74040
tccatatacc taaaagtgaa cagaaaataa ctgtcgcgat atcgtgaaaa gagaggtgtt  74100
aacggaatca ttatgacctc gtcacaggag caacaagacg aacgcacaat ctatttgtat  74160
ttgtgtgatc cgcccgaaaa tgtgcaaaac aataagcagg acgacgatag cgttatttat  74220
```

ttcgaaggta tcatagaatg tatgttggac gagacttgtg acaagtttag tttcttttcg 74280
gaactcaaaa aggaggaggc cttatttatg aaaaagacct ataacgattt gatagaacac 74340
aacaatggta catattttaa atatcacgtt ctattggacg cgctcataat gtataagaca 74400
ttcgtggaac tggtcgacga ctcggctttc ggtaaaagta tattgacata ttgcgaacaa 74460
ttcgtcgcgt acatatttaa attgtttcgt ttgcaaagtc gtattgttgt cgtgctgccg 74520
cccaacgtga attgggaaga ggataattta agtgcgcttt taaatcattt actgcaactg 74580
tctgtcatac aaattgtttg agagtcgtcg catatcaacc gtaatcttct acaataccag 74640
gacgtcatga tcggaactat cgtattgata ctgatagtgt tagccgtact gtattggctg 74700
tacacgaata ataaattgaa ttttgattcg ttgaacgatt cgtcaggcca aagcagcgaa 74760
tctattcgcg aaaacaacca aggacaattg actttaaaat ttaacagtcc gcgcataaaa 74820
actatgcgca ttttgcacgg cgacaataaa atcagtaaag tgtgcgtcgc cgaacgtcca 74880
ctgacgtaca gtgaaataat cgatgaaggc aatcgtaccg taggcgcaaa ttgcgtcttt 74940
atgggcacca taagcgaacc gtcgcaaacg tcaacattga atcagcaaca acaacaacaa 75000
caacagcaat cggcgggctc atctttgcct accaccgcaa atagggtcac agccaatttt 75060
gatattaaac aattcaaaaa cacatttatc gtgttcaaaa atgtcgaaat gataaagatt 75120
aaagagagcg ccaatatggt acggtatgaa tccgacggca tggtatattg cttgatcgat 75180
tcgcagtcta ccaccgtgcc cgacctaaga gaagtgtcat atcccatcgt agtgtacact 75240
accaatgcta atgtgcaatt gaaactcaag gaatggagct atgcccagat aaatgatgcc 75300
gggactatgt ttgtcaaaaa tgagacttca tttagaattc aataaataaa attgtattat 75360
ctttgaaatt gatgttttat tttataaatt tttcattatt attattgtca ttattacaca 75420
gacatttgtt atcgtttaat gtattgacac aatcgtctat ttctggatcg aaacaaaagg 75480
aatcagaaca tcgtaacatc attgctgtag gatgtaaaca caagataaac ttttgacaat 75540
catatttatg cggtaacctg ccccagtaat tatcgcattg tacggtacaa tcgcacgaag 75600
ttgaacactg ttgtgtttta ctgtcaaaac aagagggaca cacgtgcaac gttttttcag 75660
ggcattgtac ataagtgtcg caataagcat atagatatct gcctgtgaat ccggtcggac 75720
acagattgtc gtcatcatcg ggcggtgtta ctggtggcgg tggtggttga ggcggtaagg 75780
gatctggtgt tataggtttg gacataaaat gagacaacat ggccacaatt aggtatacaa 75840
gaaaaaccaa aagtattgca tattgaggac tcatatttat tatttgttac acttagcact 75900
taaaactagg tacatttaaa ttaaaatcat ttttattaaa tgacatatct aaatttacaa 75960
atactttatc gtagggtcta tagtgttttt caaaagcttt acgaaattca gcacacaaag 76020
ttgtttcgta aaatttttga taattttttt tgcgtaacaa tgcatgcaaa aacttatcca 76080
aaaatggaac agccaattcg atggctttat ctactttagt ttcgtcaatg ggtttggcgc 76140
ccggtcgcga ttttactttc aaaatataca cgatcgcttc caatggacta ttgttcaaat 76200
ccaaacattt tagattgtgt tcgtgtatcg aatccgattt taagatttcc ttgtagtaca 76260
cgtaaccgtc tttaggatta cgtttataca tgagaatgtg cgataaaaat aaacgaaccg 76320
gttttgtaag atcttcgaaa tacgcttttt cctgtgggta tttcttgttt ttggcatgaa 76380
agtatatcga accattgaat tgcatcgact ctaaaaattc atgatccgta tacactacac 76440
agaatctgtt gcgaacgccc ctgtcgtaat cgctaatgtg taatggtttg ttgttgacca 76500
ccaacaattt gtaattggct tcgtattttt gactaccctg atatttgcgg cagacactgt 76560

```
tgcttttgct tgaatcggcg gtgcttttga aaaaagaatc gttacattct ttgagttcgt  76620
taatgacgta caattgcgaa atcaatttgt tggcctccat ttcgtcagtt tctttttttgg  76680
acaaggtata tttgtccgcg tcgcgtttat gtactacaat aatggattct agcagatcga  76740
aaaagctaga tttgcccgag ccgggttcgc cgttcaaata tatacaacat ttttcgtagt  76800
cggtcggtat gcctaagcta gctccaaaat gcatcattaa caatgaattt tttacattaa  76860
aatttgtgaa caatctaaaa tacaaataac cacgtacaac ttgtttcaca aatagcggtg  76920
aatatgtttt gacatcgatg cgcgacatta ttacacgcat atagaaacga gtcaaccatt  76980
tggccaaatc gtccgacggt ctggctacaa ttaatttgtc ccaccacaca ctatatttgc  77040
gaagtatcac tattgtattg gcataatttt tgtaaaaatg atcaaaatac tgttcattac  77100
tattaccact aatataatca ctattgccat cgtcattgca attatttttt ggtgtctttg  77160
caaaatcatc atagtcataa ttgtcagcgg cggtgacgac gacattgcta tcgatggcag  77220
cgactgtact gtcttccatc gttagaattt ttaacaggat atttgcagac gaaaattcat  77280
atagtaacat gtcaatatcg atcgtgtcca atttgttgta caattgatcg attagctgta  77340
accgacgctc gtacacgata ggagcatatt tttcaattat aacgtcgttg gtttgagcgc  77400
ccaatatttt agtgtatgtt tcgggcgcat agtgcaaaca ccaaatcaat tctacaagtt  77460
gagcattgtc acaaaacaac tcaaagatta atgtcaattt gaaagctttt atgttgacat  77520
tcatttgagc gacgcacgaa caagaagtct gtgtcgtacc tgcttcttta cattcgacgc  77580
aacgtaaatt cttaatgagg tctgacattt tagtatcgtt caaataaata ccgtatatga  77640
ttaattcgtt tggtgaagag ttccagattt cgtgaaaata ctggttcaat ttggaatgtt  77700
ccgcgttttt gcattgacga caattgtcga acgaattaat tatcgacatg ttagttttga  77760
tgacttttat gtcgcgacac actttggcca cgtgataagt tttaaaaatt tccatttcat  77820
acttggcatt gttcagcatg taatcgatag tttccttggg taaaaattca ttttcatcga  77880
tatatctaaa cggattgact aagcaattgc caattatgaa cggacaacta ttgtgataat  77940
gattgatgaa cacattgaaa acaccctgtt cggcaaaaca caaatacttc caattattaa  78000
atttgattgt ggacaatttt acgcttggtc ctgtttcggt tactttgaac aattcatcgt  78060
ctttttcac gggaacatag tgtttgccgt tgaacacgta aaagctgcct tgagactcga  78120
gtttttcaa aaaacccaaa cacaacacat taggcggtaa tttacaagtc ataacccttt  78180
cgtatgtgta tgcccatcgt tcgttgaaac tcatgtcgtc attgagtgaa tttaaatata  78240
tacaatagtg tatggcataa taatagccga gtagcacgca aggattttcc attgaaaaaa  78300
aatgtaaact atcacaaaac ttcttgtaca ctcttgtcga caattgaaca tagggatcac  78360
atcgtgctct cactttcacc aatgattcgg catcgttctt gtagagcgct aaacataaca  78420
gttccaagta gagtttgatg tcggtctcac aaaactcgaa tcgttgtcga ctgaccattt  78480
tccagacaac aatgattaaa taatcaaaat tgaaatagtt actttcgctc aaataacgaa  78540
tcaaaacgtc accgtccaca ccttcttgat tttgcagccc ttcgatcatg cttgttttga  78600
ttttgtccaa actgatatcg atttcgtttt tgatgagttc atagttttca ctgctcgatg  78660
ttatgttttt gattatggtt ggtgagaatt tttgcacttt cacagtttca tagttactaa  78720
aagtcttgtc gtcaaacacg cgcatactac gcaaatcgat ctgaacgatg tcgctaaact  78780
ttggcgccgt aacacattct tgcagatgga tatcgtcacg aatatattca aacagatctt  78840
tgctcgaata caccagtttg ggtaggattt tgcatacacc cttgctgccg tccgacatgc  78900
gtatcgtgaa cagtgtatcg ttggaatcgt taaaaatcga atgtccgttg acaaagagcg  78960
```

```
tgtttcgatt gcacgtcatg cacaattcga cattcaaaaa atgttccgga taccaaacga  79020
atagattaac attgccgagg ctgcgattgt gcggcaacgg cacatactcg ccgatgtcga  79080
tgtcaaattt gagtttcaaa tacaaacgcc atccaaaata agaaatctca atattgggcc  79140
agtacacgta gtctcccgcc gattcagttt tgttggcata ttcttccgcg ttgctcatca  79200
caaattcact gaacgaaatc gagtcacgca cagcttcgta atatcgttgc aatataaacg  79260
gtctaatttt gatggcgaaa tagtttcctt gtacacacca atcgtgactg tctatacttt  79320
ttacatgatc tttcgaagac gacgcagccg ctccaccact atcggcatca acaacaccga  79380
atatttcgtt cacatgcacc aaattattgt tggcaatcgc gctattgttg ttgcatgatt  79440
tgtaattgca tcgcgtttgt ttagtagaaa ctgcgacaat aagtttttcc agaatttgat  79500
aggatttaat taaaaacttt tcctgcgtgg cactattttt gagcactata gtgtcaacac  79560
accccaaatt gacgacggtt tcattgtccg gttgttgaat acgattaaaa atgttctcaa  79620
atattgcgtc aacactaatt ggtgcggtgg ccattgtgtg tctattgatt ttttttatcg  79680
tgctcgccct tttaaatcct tatcgtaata acgttaaaaa attaatcgag gaccacaaaa  79740
ggacgttgca attcggcgcg tatatagacg tgttcgattt gagcacatcg tccgcgcacg  79800
ttgaacgtct gtttttgata cgtcccgaaa atgttgtgtt atacaatttc gacggcgctc  79860
tatggtatta tttggaatcg ggtagcgtgc tatgtccgcg cgaattcgcc atcgttaggt  79920
ttacgtttaa cgacatcaaa actgtcaacg aaagcggtct gttcaatatt gtctgtacaa  79980
atgtgaatgc gttgacttta atagaacatt ttatgactct aaagaacgga ctcgccgacg  80040
agagaatcat tttgaacttg caaaacatta atttcagtat cattgatgtc atcaatttgc  80100
ttatacacaa aggatacgtt tatctagaat gattgtacgg aaaattttgg atgacatcat  80160
ttgttatcgc gttagtgaca atattatgtt ctagaaaaaa acatttttat tatctatatt  80220
gttgaacatg ctttcgtatt cgattacatt gttaacgata atatcgtgat acagttgcca  80280
gtcgttgatc ggttcagggc atttgtttac gtgaacaaaa tagtcgtagc catgattgtt  80340
gacggccaaa tcgtcgacca gtgttatgct cttgatataa ttgatacctt gtttacgcaa  80400
ataccacaag actattcgtg gcgacttcgg taaacgttta ccatccggca aatccaaaaa  80460
aaacggtttg tccacaaaca ctcgtttgta atgattatcg acgaggactc gactcgtcga  80520
cggtgatgat gattttttcg ttttatgacc gccgcatatg actacgtcga aataattttg  80580
tagattacat cgatccatgg aataggcgac atgatcccga tcaccgtacg accacagcat  80640
caatatgaaa cctttcgttt tcaattcggc tagactgtcg taaacgaatt cgtcgcgaat  80700
gtttacgttc gtttcgtctg tgatcaatgt gctgtccaaa tcgaaaacga tcacgtgagg  80760
catttccaac acgtaaattt ccatgccgag ctggtaaatt tccatgtgac tttgaacata  80820
ccattcgttt aaacatgcgt acatgggaat tttttcattg acaacataca cgtgtcctaa  80880
agcagacgtt ttgtaggcgg ttttcaaatt caatctcaaa tctcgcatgt cgtcagcaca  80940
tcgaagcact tgcataaagt aacgtgacaa atcaattttc gtcgatgtaa tgtcatatcc  81000
gtcattgccg tggttatcaa tacgaaaaac gacgtactcg aacagttcgc gatgtttaaa  81060
accgaccata gccatgtctg cgtaactagt gaggaaaaga acgtgtcgtc gaatcagcgg  81120
atttcgcaat ctgagcgcga cccacaagca atgcattgct accagttgta tgtgattttt  81180
agtgagtttc gagagaagaa tcaacacaaa caattaatcg atttcctcgt cgaacactat  81240
ccgtcgaatg ttaaaaacaa aacgtttaat tttcaaaata ctggccactt atttcattcg  81300
```

-continued

```
ctgtatgcgt atgtgcccag tgtgactaat gcggaacgtg aacgcaaaca gattcgacta  81360
tccacagaat gtatacacaa actgttcgtg aacactataa atgattttaa aatgtacggt  81420
gaaatattcg atttaattca caccacgccc gagtacaaaa tgaaatacgt gtgtccgtgc  81480
caaattatgc tcgacaaacg tgacgctatt caatcgtacg tggacaaaat taaaaccaaa  81540
aaatttgaca gtaaaccgcc caagttaaaa aaagagccca tcgacaatat tatgtacaag  81600
tactctttga attggaaaaa tttactcatg aaaaaaaaat accacaacaa ttccaatacg  81660
ttacattcga acaatagtat cgctactagt tcgaattcga acgttacgtg tactcagaca  81720
tcgtcgtcta aaacaaccga tgtatattac cacaacagta tttacaagaa gaaaaggaga  81780
ctaaagaaaa gaaatatatt aactgacgaa ttgattttat ttaaacctat caacagttca  81840
ttaaaataca aattatattc cataaacgga atgtcattac gcgcgtgtca acacagtttt  81900
gtgacagtgg aaaaacagac gcgcgcaggt gacgagattg tgtccttcat aaagtattgt  81960
caaatttgca aaattatcgc caccgcagat gatcaataat tgcgtcggct gtacgaatag  82020
gggttcgaag atcgtctgcg accaccgctc gaacgtctgc gaccaccgcc cgaacgcctg  82080
cgacctccgc cgcctgatct tctacgtccg ccagaacttc ttcgtcgtct tccgccgccg  82140
ccaccaccag atctcctcct accgccgcct cgtctaccgc caccgctgga actgcgtcga  82200
cgaccgccgc tagaactacg tcgaccgccc gaacgtctac ggccgccgcc gccgcctgag  82260
cgtcgccttc caccaccgct gccgctgctg ctttgagtgc ttgatctacg tcttcggtac  82320
attttggaaa taaattattt ctatggcgga gattgttgtt tttttcgtat acaccttata  82380
aaataattat attcttctac gtttcgacga tgtcgacgtt aattgtacat taagcgaatc  82440
gctacgcagt tgttgtgctg tcaccgttgc gtcgctatac tctcgaatat tgtccattga  82500
tttgaatata ttattgtagt cgtcgggagc aaatttacaa ttggccacag cgtaattttc  82560
catagttgtg tagaacagag aatttgctgc attgtagaac atgcgttgca acgaaaaatc  82620
gtccatcaac ctgactaatt cctcgatgaa atctgaatct tgacaatagg gtattttcga  82680
ttcttgaccg ttggtacatt gtggttccag tttggaaatg acatcggccc tttccattat  82740
gagttcttca attgtacacc gtttgtcgcg agttaatttc gaactttgca tgagcataat  82800
tttaggaaat ctactaattg gatagttcat tactcgtccc aatgtaattt ttaacatttt  82860
tacatttgta aaatctataa ttgaagttgg tagttctagt agatttttga gaagcgccac  82920
aatattctgc atatcgattg gcgacatggc aggcatacat tcgtaatctt cagacatggt  82980
tgtttctaat agttgaaaca acggtttgta ttgaggtgtt ttattcaaat atatcatgca  83040
agccactatg tcttttacgt aaaattcgtt ggatgtggtg ctgtttaatg tgtaatgctg  83100
caacaatcgt tgacaacatg agcgtaacat tgttagattg ctgctcacat ggctttgctg  83160
ctccggtaac gtggtgcgaa acaagttgag taaatttcct ctcgacggtt gtcgttgcgc  83220
agatacttcg accgttggcg acgtttgtgt attattagta ttcgaagggg gatacgtata  83280
ttgactcgca agtgcagcgt tgttgtcggt gcggtctatt tcggcaatac gcgcggttgt  83340
aaccaaaaaa tccactagct catctaatgt caaatccaaa gtggcgttgg catccaccag  83400
cagcggaaaa aacttaggcc aaatcgacat gttcatgcgt ctgtcaattt tgtttttcat  83460
gttttcaatt tccaaaaaaa gcataacccc actcattttg gcaacgttta cttactttga  83520
aattttcaaa gtcactgtag tttacgcggc attgcctaca aacttattgt caaaaatatc  83580
actaaataat cgcaaagttt ctatggcttg catagagccg ttcaatttga tcttgtcgtt  83640
accgttttcg ataacgtcca acaatcgttt ggctacggcc gattgtttag ccaaaatact  83700
```

```
caaaacgtta cgtttatgcg gcgtcggatc ttttagtatc gtactcgcca aagtgtcgag  83760
ttcgttcaac gattgtacaa actcggcaat gggcacttcg ctgacatttt cttccccaat  83820
cgatgaatgt ctacgacgat tttgacgtcg cgaagattgt tgtcgacgtt gacgcgcttc  83880
cactgaatcg atggtttcta tcaggtccat tattgtaaag ataaactagt gctgttctgg  83940
ttgattagta cgcttatttc tttgtcaaga tcgtatttta cacacaaatt tcttatataa  84000
tgttcgggaa ctaagagatt ttccatcaaa gctacgcaca aatcgagttt tattgttttt  84060
aatttctcaa taaattgttc gaactcgtta ttgttgtaac ctttgaatag catacggcac  84120
acgttgcgta tttcgagttc cgaagctgac aaagtcttgt tgggtgccgc gtccaaatag  84180
tgacgcatat aaaatccagt gaacaccacc gaggctactt tattgatctt tttcaattta  84240
gtctgatgac caatctcgtc catgaaacgt ttgaacgggg cgaacaattt tatatgatac  84300
gaactcatgt tgagcgaaca caagagcatt tccagttcgt tgtcgactag accgacggtg  84360
acgcggcgac attcgttaac gaacggttga cacattttat gattgacaaa attagacgtg  84420
gacttgtcgc acaacagatt gtacaagaat tgtgcaaacg aattggtgat taaatcgtca  84480
gcgttgaaca cgttgttttc gtcaaactcg gttcgcaaca atatattcaa aaataacggc  84540
aagccgaaca tgggtcgcaa gaatatgtcc caaccgtctt gtatgcccac atcgaacgcc  84600
gacaccgacg ccgacaaata cctacaacga cactcgaaac aaagcaatcg attgtcgccg  84660
cacgaagaac ataatgcgct cagttcgttg atgttaggcg ttagaacggg tctataaatat  84720
ttgccaagat atttcataat aatctgaaaa ttaggcactt gtttcatgaa ctcatcgcgc  84780
aaaaacaaac taaatatacg ctttatttca ctggtgttct gtttactttc gaaattgttc  84840
tttatggttt cgacgcattg attgaactct gtaaaaaaag taagacctcg cactggtaca  84900
tactgtttct gatcgaaata aactgagaat aagaacgtca atgaatcgat ttcggacttg  84960
gttaggcgag atccgaaact aacgttttca aacacgtcat atttgttgaa acgcaagcaa  85020
taatcaatta gtgtagtgtc catttttgat taaaaacgaa ttttttattc acattaagcg  85080
accttataat attgttgaat atttattttt aagcgtacag taattttcca tattacaatg  85140
aaccaacaat atcgcgatgc gataagaata caaaatcgta taatcacata cagatttgtt  85200
ttgttgagaa ttttatatat acgtcgatta tatcccgagg aaaccggcaa aagtttagat  85260
cagattcgtg acagtttaac acatatcgta ccgcatttga aaaatctcca aacaaacatt  85320
gcagatttag ctattcaaga tgcgttacaa gagatcaatc gactgcacgg tttggccacg  85380
ggtaccgttg aacatttacc caatacgaca aaaacagcga cgactagttc ctatttactc  85440
gatacacaag aaactatcgt cgacatgccc cctgagtatc ctggccaacg taatgaaagc  85500
gaaacattgc cagcgtcgac ttcgattcga caaaacacca atcaacaaca cattactgac  85560
atggtaacga tcgttgaact tatcacgaaa ataaaacaac aaattcgaga cgaaaggacc  85620
atcgacagtt taaatcgtct agagacagca acaaaatcgt tgattgatga aaatgctcaa  85680
atcgaaacgg ttcgagaacg tttgtctaat gtgacgttat tgttcaatgg agataatttt  85740
ttagaacacg atcatttaca acaaattgcg acactctatc aaaaatatag caatcgggtc  85800
attgattatt ataacgccaa catttccaag tttgtagccg aactaaaaaa atatcccaat  85860
ttgatcatgt cgcagtcccc gtcggtgcgt aacgctttgt cacatatatt acagtatcca  85920
aaaaatgttg gcgttatcaa aatcagcaac gcacaatacg aagatataac taatgccctc  85980
gtcaaagcca caatcaacat ttatggaaca atgcacggag tacgatatac tcaaccgtcg  86040
```

```
ccgttcactt cgccagtaat cgaaaccgat gtaacgacag acgatgagaa cgatacgttc  86100
gaggcaatgg aaatagacgt tcctcagcaa caacaaaaag tgcggcgcaa acgcaaagcc  86160
agaactcggt caccgacaac ttcgaacgaa aaacgacgag ccgaaataca gagtaacatc  86220
gtcgaaccgc cgacgattgc agatgttgtc acaacagatc aaaccgtaat cgcaccgaca  86280
ccgtcgtcga taccaagtta cacggccgct gaagcggtgg atcgtgcaaa ttttgtggat  86340
aaaacccgcc agcaatatac gtctgtggca tcgacgtcaa cgccgacttt gtttcgtttg  86400
gttttaaaca atgtaccaga tttacaggat caacatttaa tatacaaacc aattgatcta  86460
atgatacctc tggacgtcaa caactatgaa catctgtttg ctatgattaa acaaatgaat  86520
ctgtccgtgc tcgacaacaa tgttcatttt caggaaatac taatgcccat cgcatattat  86580
ggcgcaacaa acgaatccgt cgtgcactgt atttggtttg ttatactgtc atggcgttac  86640
tttgttcaat gtgcgcaaaa ttttacacaa atccgattgg cgctggctgg tcagaatttt  86700
cgcgatcctg accgagtcgc tttgtatttg ataaaataca actatttata tttctacagg  86760
caatttataa gtaacatact agctagtaag cgtaccccat ttcgtaacgc taaaattgaa  86820
aacgtcatac gcacacaaga tattgttgta caaaaaacct acaataaatt aatgtttaat  86880
ttcgagaaac cggcgccgaa ctccgaacgg cctatagagc cgttagtact tttaatggcc  86940
ggcaacaacg aatgatgctc gttctagccg tatttatttt gttgtcattc atatttgcct  87000
tgggtgcctt gtatttgctg agacagaata aacgcgattt gcgacgtcaa ctgtattatc  87060
aatacaaata tattcccgaa ccattagtaa gtctagtaac cgtacacaaa ttgaagactt  87120
tacaataaat tatttcaaca atatgacgtg tccttttaat attaaagtat gcatcagtga  87180
acgattcttt gcttttccct acgaatattg tattccacaa accgatctag gcaacgcacc  87240
agttcgtcaa ttggtcgtgt acgtgccaac cgacgacgac attcaatatg tcgacaagac  87300
acagttacaa gcgcagttcg attctatact tgtgtacaga cacgaaccga gcgacaaaat  87360
cgaaagtaga gctcctcgca agaacgctac agccactata gtttactgga atcccattgt  87420
gcccataaca gaagtgggcg ttggtgagac gcgcgttttt agcgtactgc tcacaaacag  87480
tctgttctat tgtaacacca tgattttaga tggccaagca cccatgtgtc caatagaatt  87540
cagacgcgac gtcaaatacg acaaactgat accgatcgct gcaaatacgc ctttgtttca  87600
cgcgcgagaa ctgctcgacg acaatattaa tgacttttg atatgcttca atttggagac  87660
ctcaacaatg gtcaaaatat tgaacgttaa acgtgtactc agcatgatgg gttttagaaa  87720
tgtaccggca cgttacacta ttaatttgcc cgataacgaa gtcgacacca tctataataa  87780
attgacatgg gaacggactc gtcgtctaat gaaaggagac gtttccagtg ccggcggcgg  87840
atgtctctac gtaaatcgta acgcgctttc gttcattaga caagcgcagg aattgttggg  87900
tctgaaggat tattcgcaat ccattgttga ttttgtagta aaatttcaat cgctcatcat  87960
accgtacatg atagtgcccg acatattaat caaactgaac acactagaac gtttcaaaca  88020
tgtacgttta tattgtcaaa atgacagtta cgcgatcaca tcttttggtc ccgtacccaa  88080
caatttgccc gaagacaatt ctgtcgcgtt cgattacagc gacataaaca acagcaaaca  88140
tttgttcgat gtgcatcaga aaatatctag cgacagcaac attgacggac tacgagtgtc  88200
ggcaatgcgt tacaattact ttttctaagt gtcattacaa ctaataacat tggctttgtg  88260
atacgtaaat tatgcgacat agaaacggaa cagttgccgt attcgccgat aataccgtgc  88320
cggcctcgat actcgattac gatcaaatca atcaagtggt tacgcgaaat cgcacatttt  88380
tgcgtgattt cgttttggtc atcgccagtt tggtgatatt cgtcatgatc gtaacgttca  88440
```

tagctttaat atatagtata caaaaatcgc tagaacttca agtcgcacgc aaacaaaaat 88500
tgaacgaaac actattggcc aattacgatt accgtactcg aaatcgaata agataacaat 88560
tttgtacata tcaatataat aaaattcaaa aagattattt tcaaagcgtt tcatttatac 88620
aattatattt taaatttaaa ctgattagcg ttgggattgt cataataaaa gtagttgtct 88680
tgtcgtttga tcacgttgga ttgtagattg cccactgtca acgatacata cgacagaggt 88740
tgtatgagat catcaatgtt cagccgatga ttgtagcgcg atctgttggt ggcgtcgttg 88800
atggtcactt cgttagtttc ataatcgaca agtataatgt atggaaaatt aataacacat 88860
tttatggacg aatcgttcgt ttctattagg aacgtgtcgg gtgtcaaacg aataatacta 88920
gtgtcatcgt attggtgttg actttgaacg agcaaactga aacacgatgt gcccgtaccg 88980
ttgttgatgc tttcaaagct aataatctgt tcgacggttt gcatgtttgc cacatcgatg 89040
gttcttatca caaagttgga catattggga ctgttcacta tgttgtgatg cttggcagtg 89100
acacgattat acgatataat attagagggc gcggtccacg ccggatcgtt gggcaaattg 89160
acgttcaaat cacgagccaa aatgacacag cgggcattcg atgacaacat ctgcaaagcg 89220
cgaatcttgt cgtacacttg cgtcatgccc agtcgatggt acagtgtata actgaaaaat 89280
tcaatgttca attctgcaaa actacaatgc tgagccataa cacccgcatt ggtcgtagcg 89340
catataccag tgtaagcaat tttcggatga aaactgctcg ttgttggtcc ggtcgtgggc 89400
accgacacta taccgttcaa attggtcgtg agtaacactc ctgattcgat gccgagcata 89460
ccggaacggt attgtatgat cgctccatca ttggcccata ttttgcgagt catagcccac 89520
agaggcgcat gaaggttgtt gttctgatca gcttcgtaat aagctatttc gggcgattgt 89580
cccaccaccg aaccaaagta cgtgttagtg cgtatggaca aaattttgct ataatcaccg 89640
ctgacgactt cgtttttgta atcgatgaac gtaccaataa cgttagaata gttgctaccc 89700
tgtcgtgcta gaaccgcggg attggcgtaa cctctgggac tgcccactaa cgatatacac 89760
ttttctaaat tgtacatgtt ggcaacgtcg tcgccaaaca aaaagttgta atagctgaat 89820
gtgaaataac tattgatgag ataaccgtag gctctaacat cggtgtggtc gaaataagca 89880
tagtcgtaat gtataccgtt gccttgatga accagcggaa aacgaatcag atcgagcacg 89940
taggccattt cgcgttcttg cgcaatttgc cggcacgaat atccgcgcaa caattgtcca 90000
taagcgtacg gtagacccat gcgcattgcg ttgccggcgg ttcgacgcca gcccatcgac 90060
atggtcggtt ccggtaggta ataacgaagc acttcttcca cgggcgctgt taaattatag 90120
aatccccgca aaacaataca agtgttttgg aaaaattccg gcatagtaat actgaaatga 90180
taccaatcca ctctttcgcc ccaaggagcc gcgtttatcg gcgccggaaa aggtaaacga 90240
tcgtgtatta gcattagtgc cgttttcaaa tttgttgcca acgttgcgtc atggtacaac 90300
gtatcgccca ctgtactgaa gcgtacaccg taaccgatta gtgtgtgcag agccgtgcca 90360
aaatctgaag cagcctgaaa cggttgtagg ccaacaaaaa tgttaccatc attcgagaac 90420
agtcttgttg gatttacgat tttctcggct ttttgcataa atttcggcac caacgtcgcc 90480
atatagtgtt gttcgaatat ttttaaatca tcttgtgggg gcgcaggcag cacaggtgga 90540
tttatttgaa aacatggcaa tatattgtcg tttgttgtgc gcaaataaaa cacaataatt 90600
actacaatag ctatcaatac agcaattacg gtcaacatca taatgtattc gcgtataata 90660
cttatttcat gtctctttcc attagcattc taaaatactt ccaaatgaac agatccatgt 90720
acaatatttt attatcgtcc acgatttgcc aaggtttaac atcgccgtag tagttgatca 90780

-continued

```
cactgggttc gagattttg ctgagacgtt gatagttgcc agcattccat acgtacatta  90840
gggacaattg agtcacgcta atattgtttt tgatcagagc ttgcagaaat atttgttcat  90900
caaaaccgtt gtgatagcga ttcttcatta gacatttatt gtttttattc agtaactgtt  90960
gaatggtgct gagcaaatct ttatcgggat tcaaaactac cgttcctgtt ttgcccaaaa  91020
ttttgttata cctaaagaac gctttcatat tggtaggtgt aatcttggca ccgtgtgcaa  91080
aactatcata gtacgtataa tattcggaac aaaaacacag tgccggcgct gtcaaatcga  91140
acaaatgatc aatgttacga atgaccaact ggtcggcgtc caagtatatt attttagaat  91200
aatcggacat tgacaaacat tgccatttgg taaacgaata gttaatccat ttgccgtaca  91260
attgatcctg gcgccgagtt aacattttcg gacaagagta ttcgataaaa tcgacaagta  91320
ccactcgagt atagtaacga ataagcgatt ctctagcgtg atcgctgaca tcatttgtta  91380
tcatgcatat taaatcatgt ttggtacccg atagtaacaa acttttagct aataccaatg  91440
cgccttctac gtactcgtcg ccgagcatga ccagtgtcac gtacgcatac attccgatat  91500
ctccttaaca attgtacgcg aataccaatc aaactttgcc cgcacttttt tgtaatttat  91560
caaatgttgc ccggaccttt tcaaacaaat gatgtcatga agttacaatg ttatctcata  91620
taatataatt tgggtgtggc atgaattaat tattagcaaa agattacggc tcgtttcgaa  91680
cgaaaagatc caagaccagt ttaattatac gttatctttg ggcgtggcga gattcgtaaa  91740
atacgtttgc gattggacaa cttttaaatc acgccatatg acgtcatttg tttttttggg  91800
tcaatccatc gaatgttcta gaacaaattt tatcaatctt tgccgacggt ttcatatgaa  91860
agcgcgggtt agtttcgaat ttaaagatga tgcaatattt taaacaaatg acgtaatttg  91920
tttttttggg tcacgagtcg aaacaaaaga tcacggcccg tttcgaacga aaagatccaa  91980
gactagttta aacatgcgca aaaattttta ctttggtcga tgatgtcatt tgtttttttg  92040
ggtcacgaag cgaaagatca cggcccgttt tgaacgaaaa gatccaagac tagtttaaac  92100
gtgcgcggga aatgttatct tcggtaggtg acgtaatttg tttttttggg tcacgaatcg  92160
aaacaaaaga tcacggcccg ttttgaacga aaagatcacg gccggttttg aacatgcgcg  92220
gtaaaatttc gtgtaaattt aaagtgtggc gtgatatgac gtcatttgtt ttttgggtcg  92280
agctatcgaa cgttctagaa caaattttat caatctttgc cgacggtttc gtatgaaagc  92340
gcgggctagt ttcgaattta aagatgatgc aatattttaa acaatgatgt cttttgtttt  92400
ttgggtcacg agtagaacga aaagattacg tcctgttttg aacaaaagac tagtttaaac  92460
atgcgcggga aatgttatct atgtcgatga cgtaatttgt ttttcaaata gtgccgtgtg  92520
aaaatgacgt aatttgtttt tttgggtcat agatcgaagc aaaagatcac ggccagtttt  92580
aaacgaaaag atccaagact agtctaaact tgcgcgggaa atgctatctt tggtcgatga  92640
tgtcatttgt ttttttgggt cacgagtcga aacaaaagat cacggccagt tttgaacgaa  92700
aagatccaag actagtttaa aaatacgtta actgtgggcg taacgcaatt agtacaactc  92760
gtttgtgatt ggacaacttt taaatcacgc catatgacgt catttgtttt tttgggtcaa  92820
gccgtaaaat gttctagaac aaattttatc gatcttcgcc gacggtttca tatgaaagcg  92880
cgggcaagtt tcgaatttaa aaatgatgca ataatttaaa caaatgacgt aatttgtttt  92940
tttgggtcat gagttgaagc aaatgatcat gggccttttc aatttttgaa tcatatagtt  93000
tagcgatatg acataaagcc gttttaaacg aaaagtttgt tttatacgaa tggtgttcat  93060
ttgccgtttc gaatacaacg ggtgtgaaca ttgctgggac atttttgata gatgatgtca  93120
tgctaaaatt gtgaatatta cgcagacatt ttcgatatag atgatatcat actattaaac  93180
```

atatgatgca ataaaaaaaa tgatgtcatc tagttgacgt tgctttggcg caaattattt 93240
tggtaatttt ccatgcatat ttcgttatga tatcatcgtt aaatacgtga ttgtctaaaa 93300
tcgatctttg cggacaattt tatatcaaaa tgccggcaaa tatcgattaa ctgaataagc 93360
aagcgtacca tcatgtatgt tcagttgacg gtgtttgtta taatattatt agttttgtgc 93420
gttaacattt tgtacgtagt aacaaaatta aactacacag agaaaaaagc gacaagttta 93480
ttaaacggcg acatggaatt gtcgtatcat caaaacggtc tagtcaattg cacacacact 93540
cggctacctt gcattgtaac ccagcaatgt ttagataatt gtgccagttt caatatgata 93600
aataatatgg aatgtgatca gggattttgt actattcgtg aagcgcaaag ttcttcaaat 93660
aacgacaacg acattgaatg tgacgctacc aaaggattga ttaaagtttt tactgccagc 93720
gaatttgtca tcaatcaatt gtgtataagc acgtatcggg acgtgttcga cgacgacggc 93780
gaactgcgtc cgtatatatg cgaaaacgga acggtcgata ttgatgtgtt gaatcgaccg 93840
tttagcgtga ccgattgtga atgtgctccc ggttataaac gtatgatttt tcaacagact 93900
gctttggcac gcacagtacc cgtttgtata ccaaatactg cggtagcttt gtattcgaaa 93960
atttatcaat aaaatatggt gttagtaata aataaaaact ctgctgccgt tgccagcatc 94020
gattcgatta gcaacgatcg caaagagaaa cgattgtgca tatggaattt ggtagtgcgt 94080
tattatattc gcaacccacg tattcaattc atgtttaaac agcgtcccgg cgatgaaata 94140
atacataatc gacattggac aaacattttg gaaaattgct atatgtgtga aacagaaaaa 94200
agacgtttgt tgtcgtactt gtcaaaacta tacaaacagt attgtgtgga tcagatgcga 94260
aacgttgatg tcgacgaact agataggata tggtgtacta ttgatgattt gtgtaataaa 94320
tgtcgttttt gatataattt tgttgttttt atttatttta cacgtacgta tatgtatcgt 94380
tctactgaat aagcgcgcta taaaatttat acaatagaaa cgacgacatg gccgttgaac 94440
aattaaaaca gctcaatgac attcaaaaat atttgctcga ggcagtcgta gaggcttgta 94500
aatttattgg caaaaatcct gaagcgatgc cggcaagtca attgttggtg caattgatga 94560
acactcgtag tagtctgaac gaattgcgac agaacgccgt caatattatc gattcagaca 94620
ttaacgagtt tgtgtttaat acaatagctg aaatggcatt gatcaacgac gataccataa 94680
cgatggtaca gagtgtcgcc gactccttcg acgacgactt cgaacaaaga cagaaccatg 94740
aggaaacgtt gccaccaaca gaaacgataa acatcaatat ggtgaattta caatacgaaa 94800
tgggccggct tgccaccatt gtcaatatgg aaagtataga agattttaaa tatttccccg 94860
agttgacgta catagtcaat cgcaaacacg tcaatgaaat acaactaaca gaacaaactt 94920
tgtcgcgttt agattgcgcc acgcttatgg ccaacgcatt tttcgccggc aacgtgccaa 94980
acttaaattt tgacaccatc aaatcaggcg cgacgggact tttgcgtcaa aaattgatgt 95040
gcctactgaa ttatttcaaa aatatttgtt tcctattgaa tatgaaaagt gattgggtcg 95100
aaacacgcat aacgatcgaa cgttacgtgt gcgaaaatcg tatatcattg tataattcgg 95160
agaagcctgt taaaggtagc gacgtgacgg tggcgctgta caatcccgaa atcgactata 95220
acgaacaaaa cgtaccggac gcgcacgatt taattataga ttatgtcgac aagcgattag 95280
gcagcgacac cgtcttgacc gattcgatga cctatgaaga tataatgttt ttgcgttttc 95340
cagaattgta cgcggccatg tactttgatt ctcgcgattt gggcgattgc gattcattgt 95400
gtgtccgcga cgtggtaaag tttaacacag ttttaggaac ggcgggggcg ccaaaatttg 95460
tcgaatccat attagacacg gccgggttcg tgtacatcaa tattttggcg ttagaatcgt 95520

```
gtcatttgaa gaataatgta ggcagtgcca acagcgattt agcatactta gacatgtcca  95580
ttaatcgttt acaaactccg ttgatagcca atcgtttgtc cattccgtca acgggcaacg  95640
gcggcaaacc cacactatat tcgtcatttt ggggatgtcc agaagaatcg agaccgttca  95700
gaatgctagt agaattgatg acgtgcgccg ttgccgatta caatatggtt tatattgcta  95760
gcgattcgga aactcaattc gaaatggaag ataccatttt gatactaaac gataatttca  95820
cagttcgtga aatatataat atgttgacca attacaagtt taacaattca attcgctaca  95880
acgttttaac tctaaacgaa aaacaatcca aatctaaacg aaacagaaaa caaactagta  95940
tcaatttaga ttaagtttac atttgtgtat tttacaataa atataagcgc tacattcatg  96000
cggctatttg tcgttgtgct cgtttacaca taatggagtc gattgatgtt gacgatttcg  96060
ctaaacagct aatagcggac aaatgtagcg ctttgataga atcaaacaag atgctttcgc  96120
ccgacatgat ggcgatggtg aaattggccc gcgacgaata tttcaaagac ccatcgtcga  96180
aaaattacga aatattaaaa aaactgattg gtcacacaaa atacgtggac gattccatcg  96240
actgcaaaga tttcaatcgc cgcatgttac ttatcgccat caaagtgagc gcttcacgtg  96300
cgcgagacta ttttaacaaa tacaaaactg tatttgaatt ggctttgaaa cgtttggaca  96360
gcatcaatcc cgatatacga agttcgccta gcgctctgct acaacactat aaagaatgtc  96420
tcgacaattt ggacaatccc cggaaggacg aacatcacct tgtcactttt gccaaagaaa  96480
ttgctacgaa aatttttatc gatacaatag acgtgtacag ttacacgaac aaaagttcta  96540
ttcagatgac gactacatcg acacgtaacc aatgcgcgac gtccttatcg gcaaactatt  96600
tatcaaatcg taaagcaaca agtacggaca gtctgctagc gaaaacatta cagttgaacg  96660
cgtctcgcaa gcgacaacac aagcggaaaa atagtgcaac tttattagac agcaaagtta  96720
attctttcgt gtacaaggca cagatacacg atccgcccaa atattacgtt gcaagagctc  96780
tgttcacatt gtagagccag ttgttatcat ggaaaaacac caaatggact tgtacaacgc  96840
gttgatgcag cacaaaacta aaatgacaag tttaaaacaa ttgtccttag aagcgttggc  96900
ggaacagcac attcgacacc gtttacagat acccaaacat actgtgaatg tttgtgtgaa  96960
cgacgaaacg acggtttcag tactgtgcta tcctaattct caaacaaaac acggtttgtt  97020
gattcggaaa cctgttaaag atctattctt cgacaacgat cacgattgtg tacagtgtat  97080
aatacctagt tgtgtaaaca atgatgtttg taataatata attttaaatc attggcaata  97140
aaacaataca taaaaaatgc aaaaattttt tatttatctc attatttaaa tacatttttt  97200
taactgataa aaacctttgt catatcgtcg attgatctac gacacacaac acattttttt  97260
actttgaaag cacattcttc acaacaggcc aaatgatgac acggtaaaaa catgtaattg  97320
cgttcgttca cgaagcaaac tttacatgta cgtatgtcac attcagtagt ttgattgtcg  97380
gaattactgc cttctttttc gacacaggct tcggtgatta ccgtctgcac gaaatctttg  97440
cctttttccg atagtacaaa atcacaattt ctgtaccagc gtgcgtgttc tcgccatggt  97500
tcatgcgtaa gcgtccaatt gcttaatttt ccgccgcaat gaaaacatat tgtaatatca  97560
tctttacccg tatataccca accagcttct gctaatttac tcttcaagat tatcagtgtt  97620
tgcggccaat tgtcaaacga ttttaaacga ttttcataag ttatatagct tgatagcatg  97680
gatttatttt tgtaagattc ttgatcagca atgtaattct gttctgaaca tacgtttgca  97740
tcgctcataa ttgatttgac gtaagaacat tgcggtgccc aacgtgcgtg ttcttctagc  97800
ggatcgtctt cgtgttgcca attcatcatt tcgactttgc aaaacgcaca ttttacatgg  97860
tcgtctttgt tcaaataata gaaaccggcc tgagccattt tagcacaatc cataaaataa  97920
```

```
tattgtacag gccaatttgc aaacgtaaca tatcgatatg attcagtttt taataattcc  97980
aaatcggatt ccatatagga catcatcgca caagcggcga aagacaacgc tctactgaat  98040
tctctatcga caagacaggc tttttatat ctaacataaa agagcttact aaactattgc  98100
gtcgtatttt acgtaaattt tgtttattag atttgacaag taatgttttt gtaaacatca  98160
aagcctttga tgttactttg gtaaacacaa aatgaataaa aaaaagggtt aataaaaaac  98220
caacaaaccg taaaggaaat ttattgctca cacaaataac attacagatt tgttgacgtc  98280
gttgcttctg tagcagatgt tatatctttt tgagtagtga cattttcaat agccggcaca  98340
ttccctggta ttatgtttga ttcatcgtaa aatcgaacat tacatacatt cttgacaaag  98400
taattttgac aattattcat ggcgtgcacg acttgttgtg ccgaatacac gtcgcctgca  98460
ttggaatgac gacgttgtgg cgtggaaggc acgagttctt tggccatttt ttcgacaata  98520
ttctccacga tagcatttat acgatccttg gcatcgacgc tttgcgtcaa acatttggcg  98580
acacaatcgt cttcgtcgat caaatctaac gctttaaact cttcaattag ttttgtatta  98640
acagttttgt tacgttgaca catttcgaca tcggcgcgat atttggcacg taattcagtt  98700
tcgtcgagca cctccatttc tgtgcacaat ttattcgtat agcgcaaacc gtagaataca  98760
tgaggttcgt cggcccgtat cttacaccac accatcacag aattggaaca tttgagttgt  98820
aaaaatttgg tcgaatcgca caaccacgcg taacgaggcg acggcttaaa tctttttgga  98880
gtacacaaag tgtcacggta gcgttttgcc actttgtctt gcatttctat cgcatacaat  98940
tgactgcgac acatacgaat acgacgtttg ccattgacta ttcgttcgta accggttatg  99000
tattcttcct tttcgggctg ttttgtcagg accggtacga cgcgattgct tatcttttcg  99060
agcgtttgac gcagtcgatg attttcgtca atgttatctt tggcgagaag tgcgttcgct  99120
gcaaactgaa acattgacat gttagcttga tgtgccatgt ccttcatttg tagttgcatt  99180
ttgaactctc gctctttgta ctcagacatt tgctgttcgt aattgcgctt catttccgac  99240
atattcgtgt tccattccgc gatttttata ttggcttcgg acagttgcaa ttttaattgt  99300
aacgcttcca tctgaacatt cgccaatttt tggtcgtaac tcactacttc agtagaattg  99360
tctgtggacg attgtcgcct gttttctata ctatattttc cagttcgtct cagttcgggc  99420
aagacctctt cgaatagcca actttgaaat tcctcggctg caggtagctt agaacgcata  99480
attaaagcgt agataccggc ttcggtgatg aaaagcgtat tcggttgcca atttaatggc  99540
atttctatag aatctgatga cgtcacaagg gagtgttgat tcaacacccc ctttatttcc  99600
gcccacgttt tgcgccattg cggtttcacg tgatcgtaca gtgctcttct gggacatttg  99660
taacccaaag cttcggcgac accgtgaccc gaacacagaa atcggttttc ttcgatttca  99720
gtaatccaaa cttcacccaa tttacatttg cgatttacaa gatacatctc taaaacagtg  99780
cgacaacttc aaagtgtaga cttaaaatga acgaaatatt aacacgttac aattgaaagc  99840
catacataca tcgaaattgt cctatacatc gaaatcgtcc tatacatcga aattgtcgat  99900
gtgactaaca acaaaaataa gatcgaatat cataatgaaa gctatttgta ttttgagcgg  99960
tgacatcagc ggcgaaattt gtttcagtca agaatcgcct ttacatttaa tcaaaatcac 100020
cggattcata cttaatttgc cgcgtggatt gcacggtata cacgttcacg agttcggcga 100080
caccagcaac ggatgtacgt ccgccgggga acatttcaat cctacgggcc aaacgcacgg 100140
ggcgccaaac gcgaccgtgc gtcacgtcgg cgacttgggc aacgtcgaat ctttcggtat 100200
aaattctttg acagaagtca atatcgttga taacgtcatg tctttgtttg ggcctcatag 100260
```

```
tattttaggt cgcagtcttg tcgtgcacac ggaccgcgac gatctcggtt tgactgatca 100320
tccgttaagt cgtataaccg gtaattccgg cggccgtctc ggatgcggta taattggtgt 100380
tacgaacagc tataaagagg cttctgtaaa ataatcggtc atgtcttctg tacgatgtat 100440
catcgtaacg tttttggcgc tcgcgacagt gggttactat ggcgcgttca agagtgcaat 100500
agccattccg gcgaccgaat caatgaagca gatcagcctg cgcgtccaca acaactattc 100560
caccgttgaa acaaacgtgg aattgcttca aacggcgata tcgctcgcga tcactatcgt 100620
tttgtcgatt gtatttcgta attttgacgc tgtatgtgtc aacacaagac tgctcggcct 100680
atcggcgttg ggcatgtttc tcgatttgac attgcaaata tatttggcga tgaataccgc 100740
tacggtttca ttgacttttg tgtatgtcgc cacgatgact gtagcattgt tcggaggcgt 100800
ttttctattg gaactgtgtt tgctcgattt ggtaattgct ttaatgtaca acaacaatag 100860
tagcagcact agcaaagcga cgcgttgcga ttattttaaa tggatcgtac atatgcgttg 100920
cgcaaaattg ctaggacaaa gtttggttca acttataccg cccttgtttg agatagatga 100980
aaatcaaatg ttgcacggcg ttgccgcggg ttctgtgaca agttttgtat tggccatagt 101040
ggcgttaaat attatgactc cagcacatat gtttatggat gattataatg ttagcgacat 101100
aattgaaaca tatcgagccg ttccgttcga caacgatgtg aacatctacc gaccgacaac 101160
attagtacaa tcgtcgacca cattgaccaa cgtaaagtcg acacgaaata atcgttttta 101220
tgtaaaatat ctaatagcaa tactgatcta tagtatgtac gagtcgcagc aaagcgaact 101280
caaatttagt tattactttc agaaggatac gataatgttg cccactcgcg acataagaat 101340
attgaacggt tgtcagtaca taatgtttgc ggtcatgtta tggcccttgg ttactttggc 101400
tagtcgtaat aattcaacat tatatgtaaa catgttctat atgtcgttgg cgtgcaatat 101460
tttggctcgt ataattcaat cttacgcttg gtactctcat gaaactcttg tgtggattgt 101520
gtctgttgtt gcgtcggcgc caggtccaat tgctggcgct ttaatgcaaa ctttagtgta 101580
caaattatct gacaacaatg gtcattattc taatttgatc gcaatcaccg ctgatcggtg 101640
cttgtcagtt atatttatat tgttgtatca atgtactgtg tatgtcgaac atttttctcc 101700
atttttgatt acattatgtt cattgatcgc tataataaca atcactattg ttaatacacc 101760
aattaaaatg tggttaaaag atatacactg ctaaaatttg tcattggata atgaataaaa 101820
cactaaaaca tatttttgtg gtatttttat ttagacaatt caaacgtaca taacagagaa 101880
ccgtaatcgt cgggcgacaa tcgtattcgg ttaggtttta ccaatcctat atttctccac 101940
ggtggtaata ttgccatgtt tttacggatg caatacggcg gaacgttttg tatagttaca 102000
ttgatgtgat agtttattcg gttgtccact tcaaagttga tcgtgccaaa attgatcaac 102060
acatctccac tccacatgtg ttctactttg ccgattatcc agttgttatc gatgaactct 102120
ttgtaatacg atctgttgtc gcaatacatg ccgtaccaat cgtaattgtc ccaacttaga 102180
tttttttcaa ttgactttgt gctaccattt tcgtagacaa tttcaacgca cactttccaa 102240
tggcaattgt acacgggact ttgtaaacgc aaaatttttta attgacgcat tatcgtgttg 102300
catgatttgg tatcgtgact attgtacaac gaaaacgata cattacgtaa acgaacagtt 102360
ataggagact gggctaccat acaatcgttt tcaaaaagaa acacttgtga tcgccacgaa 102420
atcatgatga atgctaacgt tggtgcagcc gcgaccgaac gttataaagc tggctaatgt 102480
tgttgtttat gataaaacca gatacgacaa gtatttaaat tagatgacca tatatataca 102540
ttgccattcg aatcacgttc gcacacacaa aacgaaataa aaaataaaat ggacgattac 102600
acgtacaacg atctatatgt aaaagcgtca caacataatg ttttaaaacg catagttaac 102660
```

cgcgaactag atagtcgcat tgataaatta tctagcgttt taaatttgca acggttaacg 102720
caaatagtac aaaaagcacc gtacacccta aactatgaca atcgaaagtg tccgtcgcag 102780
tacgaagcag aaagcgtgga tctagcgaag tttatgaagc gaaaatacga aacagttgtc 102840
agatgtaaat tgtgtacgcg cagtttgcac gggatgctgg ataagaacaa gagtgtgtgt 102900
actttttgtc tgaatgctac aagcgctgaa gcgtctggca aataactact ctattatgca 102960
attgattgtg ttcgtcatgc atatctccaa tgatgaacat ttgcgtcagg acgaaattta 103020
tgtaaagtat ttgcaacaca tggacgttta cgatgcggtt atggtttgca cgggagattg 103080
tttggctgtg tgtgtatcgt cagcgcctat tgtgttgctg agtaaaaatt tgaaaattat 103140
cgattatgga gatttgtcgt ctatcgacag tttgtgtgat aaaatttatg atattgccga 103200
aatgtacgaa caaaatcaat gaaatattgt aaataaataa ttctatatta gaaaattgtt 103260
ttattattct tctaagttga ataaagtaac atgtatgcga ctttggttat tgtactgttg 103320
cttgtcgcta taattttaat aataattagg tatacaatcc tgttgcaata tgccgagccg 103380
ctaccaattc acgaagtgta caaatttgat aatggacatg tacctccgat tgaaataccc 103440
ggcgaaatca acattgacag taatccgata gcatgtcaca aacagttgac caaatgtaca 103500
acgcacatgg attgcgacct atgtcgagaa ggcttggcaa attgtcagta ctttgacgaa 103560
cagaccaaac tgataatgcg cgacgaacac ggcaacgaaa ctgaacatac aatatatcca 103620
ggcgaagcgt attgtctagc gttggatcgc aatcgggcac gttcttgtaa cgccaacact 103680
ggtacgtgga ttttagctca gagcgaaact gggtttacat tactgtgcag ctgtttgagt 103740
ccaggtgctg taactcaact caacctgtac gaagattgta acgtgccagt aggttgtcaa 103800
ccgcacggca ccattatcga catcaacgaa cgaccgctac gttgcgactg cgaaaccggt 103860
tacgtgcccg attacaatga cgaaaccgaa acgccttatt gccggccgtt gttagtgcga 103920
gacatgtaca acgatacgac tgtgtttcct agggcgccgt gtccaccagg ttacgtgcaa 103980
ataacaaatc ccaatttgaa tcctgaatac gctcgtgaat tcgctttaca tcgcgacatc 104040
tgtgtcgtgg atccgtgttc cgtggatttt gtgagcggac tacgaaccaa cggcagattg 104100
tcgcaagcaa atcgctacca caatcaaccc tattgcgatt gttcaaacaa cggcagtaat 104160
aataacacga tgttttcgat ttacagcgtg actaatgccg tcttcttagc gcccattaat 104220
caacacgcgc ccgaactaac caacgcatgt atcgaaccgt tcaatattag gttcaacaat 104280
gccaatttca taatgtacaa acatttttgg gcacacgacg atgtacgtag cgacgacgag 104340
gttgtatgtc atatcaatcc caacaataca ctgctgagac ataatcgtta tctatccctc 104400
acgtatccca gtatcgtttg gtccgacgta atcaacggaa tgaactattt gattttgaaa 104460
ttttccattg cctttgccgt cgacaatatc gaacaagtat atagaagttt gtctgccaat 104520
agaaccgtgc cgtgtttcgc ccctggcgtg ggtcgttgta ttgttgcaaa tccaaattat 104580
tgcatcagac gacacgctaa ttttcaagtg tggactgcgg aaacattttc aaactcctgg 104640
tgtatattta gtcgtgaaaa caaccacatt cgcagttggc atccgtcgcg catatttccc 104700
gacggcaggt atccgtctgt attcagaatt gcactgaatc aaatgtacaa tgttagaaat 104760
acaaattcaa cctgcgaact ctttgtaata tcaggccata gtatagtatt aagagatcaa 104820
ttcgataatc tgagatcgat tctcggtact tatcccaatt attccacgta cacatgagcg 104880
acagcaatga aaacctaata gccgaagcgc aatatctggc gcaacgtttc gaacaggcgg 104940
gacatttgtg taaagccata caatgttatc gattaggaat acatttcgca caacaagatt 105000

-continued cttccattga tagcaatgta ataaatttgt ttttagaaca aatacaaaga atcaatacaa 105060
tgaaagaaaa caaaaaatta tgtttaaaca aatatgtttt attatattaa tatatgtacg 105120
ttacaacaac agttagacat tatttttttt tgaagttttc atttttaaag gtgcaggcac 105180
gcattcatga aaatatacat tagtgttata cactgtcacg gtcagaggta acatggatga 105240
tgtctgtgga tatgctcgtt gggattcgct gtcttctttt aatatctcct gaatttggcc 105300
ttccaaatat gatctctgtg aagtttttgg cgaatccggt agcaattgta tactgaaatc 105360
gttttcgaca ctatagaaat tagtttggtt cactccctcg gtggcgttaa cgttgctatg 105420
ttttaacgca acatagtcat ttgttgtttc aagtgttcta atgtccaagt cacatatttt 105480
tctcggtttg taagcgagtt tctcgttaat attaggactg acaacacact tatgcgttat 105540
agacgcatgt ttccaatcca acgtggtcaa tttaacactg gacggttcta aaggacgatg 105600
tacaccgctg ctattgacca agacgtttcg tggtttacct tcacgattta gagctaagta 105660
cgctcgggta ttactgtcga actgtttgta cataacgtag gcagtttctt tgatttcggt 105720
cgaccacaga cattctgaat taggcacgat tgccgtgtac acatagccgc attggttaac 105780
gcaaatataa cggcacgttt gtgccgcctt caacaaatga ttcatatagt gaggcacacg 105840
ataaaatact gagtgcgagt cagtagaatt tgttataccc cacacagtgc catttcgagc 105900
gaccgacaaa tagcgatgtc tcatcacaat ctgtatgggg cgacttgcgt tttcgtgcgc 105960
gcccggtctt gccgatacac tccacatata cgtggaacat aatagaaata gcagcgttct 106020
caacaatacc gaaaacatga tcgtttagtt cttcgatcta aaaacgtttg actgacctat 106080
tttagcgacc cattttatat agtatataat caaggacata ttccatgcat acacacacac 106140
acacacacac aatgtaatta tcattgttgt tgcattaata tagctctata ttcgcaattg 106200
tccgtgtgtg ttatattaaa attatctatt gataggccgc aacagaatgt tttgtaacgt 106260
ttggtgtttg tatcgtaaaa caatccccat ttggcgaatc ttgaatctgc tccacgcgcc 106320
actagcgact tcagtcgcat agaatgtgtt agaaattctt tatgtacgca tcgtatacct 106380
ctatcgattc tgtcgtcgtc gtcgtcgtcg tcgtcgtcat ttttaacaaa tgatgttttg 106440
ttcgatttac aaattttatg tttgtcgaga attgtgtcga cggattcgtc ttcatcaaac 106500
gctgtatcgc aatacgcgca tgctatattg ccgtacgaat aatagaaacc ggccttggcg 106560
agtttttcga cattgtcatt ggtcaaagtc gtgttcgcaa acgatttaat cctcacggca 106620
cattgccgga atctctcagc acttgtattt ttgttcacga acattttgaa catcgtttgt 106680
tcagttttcg attctttgtc acaaaattca tcatcgcgtt ttactatgct agccacgaaa 106740
gagtctttga acctaaccaa atatatgacc aaagacgaat ccagtacgtg tagttgtctt 106800
tgcatttgac gataatgcgg gtcggttttt tccacgacaa atctagccgg tccgtttctg 106860
ttgacgctga acgctgtatg tttgatgcgg tagcgttctt tgcgagcgtt cattgcacgt 106920
cggacttcgt ctacagtcgt gtcgcgatat gtatgcgggc attttatttc cataggcaca 106980
atcgtgtcgt cgtctagaat aaagtaggcg tccggcgatg cggaatgtaa tccgtatttg 107040
ctaaagaaca taccgcaatc gagaacagtc tctgtaattt ttttattagt ttcgcgttcg 107100
acacattcac gaaccagatt caaaagcgat tcattgtttt tcacgcaagt ttcctgttcc 107160
aatccgtagg tgagcgccgg aatcggtcgc agaccaatgc cgctactgct gttcgtatta 107220
gatcccgaag cagtttgtcg atcgagccgc aacaaaaacc atagcgggtt cgtcgattgt 107280
ccacgtgttg ctttttcgat tttcatgatt tcatgccgtg acaataattg tgttatgctt 107340
ttcagttgac tcacataatt ggtaaaacag tatttgtcaa atatgttctg ctgttcggcg 107400

-continued gtgagcaaat cgcacggaga cactaatgat ttggtcattt ttgtggtcga catggtcacg 107460
cgcaataata tattataaat tatatttcgt gagaagccaa tcgagaagtt ttacgtacac 107520
ggccgactgt agcgtgttat cggattcact gtatttaact agaaattgca ctaaaatatt 107580
taaaattctg ctctgattga acatcaatcg ttccgtttca atagccatgt ccatgaacga 107640
ttgaacggtg atcatcatac catgttgttg aaaattaatt ttgcccaata cgttttcaac 107700
tatactgatg aataccgtgt aaaatgtttt tcgagcaata ttctgattac aattgaacgg 107760
atcgacgacc gtgtcgcgta gaaagtctat gacagatcta agtttaatcg atttgtcacg 107820
tattcgatcg ttgcgttgca atctttttcac gtaaggtttc atcgcaaaat tacaatcgtg 107880
ttggaaaagt tattccgtca caaaaaaagt cccttaaatt aaaaaatttc taccgtgtaa 107940
tcgatcctcg ccgacggttt catatgaaag cgcgggcggg tttcgaattt aaaaatgatg 108000
caatatctta aacggatgac gtaatttgtt ttttcctcaa tcatgaatag aagcaaaaga 108060
tcacggcccg tttcgaacga aaagatccaa gaccggttta aaagtacgtt atttttgggc 108120
gtggcgtgat tcgtagaata cgtttgtgat tggacaactt taaaaatcac gccatatgat 108180
gtcatttgtt ttttttaaat cgagccatcg aacgttctag aacaaatttt atcaatcttt 108240
gccgacggtt tcgtatgaaa gcgcgggcga gtttcgaatt taaagatgat gcaatatttt 108300
aaacaaatga cgtaatttgt ttttttgggt cacgaagcga aacaaaagat cacggcccgt 108360
ttcgaacata aaaaaaaatc caagactagt ttgaacatgc gcgagaattt ttattttgat 108420
agatgatgtc atttgttttt tttttgggtc acgacaaaaa atcacggccc gtttcaaacg 108480
aaaagatccg agatcagttt aaacattcgc gggaattttt actttggtcg atgatatcat 108540
ttgttttttt gggtcacgag tcgaaacaaa aaatcacggc ccgtttcgaa cgaaaagatc 108600
caagactagt ttaaacgtgc gcgggaaaca ttatctttgg tagatgatgt catttgtttt 108660
tttgggtcat gaatcgaagc aaaagatcac ggcccgtttc gaacgaacag atccaagacc 108720
agtttaaact tgcgcgggaa atgttatctg ttgttgatga cgtaaattgt ttttcgaata 108780
gtgtcgtgtg caaattttgg gtcatgaaac aaaagatcgc ggcccgtttc aaacgaaaag 108840
atccgagatc agtttaaaaa tgcgatgcgc gggaattttt tttaatttgg tcgatgacgt 108900
aatttgtttt tcgattagtg ccgtgtgcaa aatgctttga gtcatgaatc aaagcaaaag 108960
atcgcggccc gtttcaaacg aaaaggtcca agattagttt aaacatgcgc gggaaatgtt 109020
atctgttgtt gatgacataa tttgtttttc gagtagtgcc gagtgcaaaa tgacttaatc 109080
tgtttatcac gaatcgaagc aaaagatcac ggtccgtttc gaacgaaaag atccaagact 109140
agtttaaaaa tacgttatgt tttgggtggg gcaaaatttg tacaatacgt ttgtgattgg 109200
acgatttaaa aatcacgcca tataacgtca tgagtcatgc catcgaatgt tctagaataa 109260
attttttcga tctttgccga cggtttcgta tgaaagcgcg ggcgggtttc gaatttaaag 109320
atgatgcaat attttaaacg aatgacgtaa tttgttattt tgggttatta gtcaaagtaa 109380
acgatcacga tccgtttcaa acaaaataat ttttgttatc gagcgtggcg tgatccgtaa 109440
aactcgtatt attggacaat tgtaaaatca cgctatatga cgtcatttgt tttttggatc 109500
gagtcgtgaa atatccttga acaaattaat cgatttttgc cgacggtttc atatgaaagc 109560
gcgggcaaat ttcgaataaa gtttattagc gacattagtt catacatcat taggaaataa 109620
atcattaaaa cctttttttta aaatatttta ttacaatttt acagattcgt aataaacaat 109680
cattttatca atagcttgat ttaaaacagc gataaaactc aacacatatt tgtagtcttt 109740
gtaacgtttc atgtaatatt cttccatggc ttcaatacag ttggcatcga aatgtgtaag 109800
ataatctttg agggcatttt taaaatcggt gtgtattttc tcgacaattt cgttcacatt 109860
tccaaccggt tccatgtctg tacataagca aatatgacaa ctcgtagcca caatcaattc 109920
ataataaaag agacgatatc tgtagaaact ttctttgtca ctcaatgtat agtcacaaat 109980
tttagacaaa gaattatatt gtgtaaattt ttcttttaac actttgcata tagttgccaa 110040
tttttgtatt ctcaatatac gactgtcgtc atcgagtagt aatggactgt ggtcagctat 110100
gtctttttg aaggtacata cttgctttaa acaccacaac tcgttcacca gcagtatatc 110160
ttcgcgtaac ataaattcgt acgtatcttt tagtgcttca atcagaaacg attgaatatc 110220
tttatcgttg tattgaaccg tatcatacat aaattcccaa tgactgatca aatgaacaat 110280
aaacatcata tttttattgt atgctgctat aaacagacac tctttgcgta tatcgcagat 110340
gtcggcatgc aattgtaact cttcgggcac ttcaaacatg gtgaccaaac aattcttgaa 110400
ccattcatat cgattgaatt tacacagcaa aactattaga cgattaaatt ttatgaaatc 110460
atcaaaatca attgttgcca attctctgaa gtatgtcacc attctgtgat tggcaaactc 110520
ttcataattg ttgtttgcaa tacaattata aagttcgata attgcgtttt caaacatgac 110580
tgactatgta gagttactca acactgaata tgatcccgtt tgcaatacac gccgtttata 110640
tactcatttt gtgacttcaa gcagactgat aacacctaat ctaatgataa taattgatag 110700
ctttaactat ataaattgaa aatgtgtgac aactgaatta tatattcgct gcagaagctt 110760
agaacgcatt actaaaaatg caatcgaaca ataacatcaa cggtttttat aatgcttcac 110820
gagttgcctt gaaatcgacc acgctacacg acggtaacat gcctgtacaa caatatacat 110880
cagttataca aagtcgtaat gtacgcccag tttgctacga ctccaaccct acatcaagac 110940
agaagcgctt gaaattacac aaaaaatgtc acaacaagga aaatattcaa taatgcaata 111000
aaaatatatg ttttaaaaaa aatttttgta ttttattttt taatgcatag catttgtgat 111060
tacaataaaa caaataaaac atgttatatt ttatattttc tttattagta tcaaaaatta 111120
caaataggat tggaaccttt acacgacaac gatcgatgac ataatttatc tttttgtgcc 111180
attttgtcac aattgggagg tttgtatgtt tttatattga atatcgattg aaattcgcgt 111240
acacattttt cgtcgttctg atacaaagca atcatggctc tctcgataca ctgtttgtta 111300
catttggtac aagtcaacaa attgctaatg taacaattaa atacaaatcg tttgcgaaat 111360
cgtccgttgc gaggtctcac caatatatcc ttcaaaatca attcgataca cgccggcaat 111420
ttgagtgctt tgcgtaacgt atttattatg tgctgtcgtt tgtattgagt attaacgaaa 111480
catacgttac gcaaactttt gtgcatgccg ttctttgcaa ttgcctgttt tcggtcatat 111540
acagtcgtgg cgttgtttgt cttgttatcc aacaaatgat aaagttgcgt accgtaaacg 111600
cgcaccaaca atccgttttg ttcaaattgc gtgtaaggcg ataggtttaa ttcaaaatct 111660
tcgaatcgca ccaaataaac agctttttg tcaattttg atttacaaat cgaagggttc 111720
cacaacaact gccgtggaac tattgtatcg tttgatggtg ctgttgttgt tgttgttgcg 111780
aacgacgtcg gtgatgtcat ggttgttaac gcgatcgtcg agtccatcgt aatatctagt 111840
tggtgggatt acgacagttg ttcgattggc aatgtgtggt aatgaatcta tatttgaatt 111900
tttatacgtg ctgttatcgt aatctgaatt gatagagcgt tgaatgcgac tacacagctc 111960
gctgtcgata ccgcgcgtct ggcgacacat atcgtacatg ttgactttga ccgtgttcaa 112020
ttgagactga atttgctggt gttggcgata gagcatattg ttgtagcgcg cccttgacgc 112080
gttacccata ttgtacatga cggtaaattt ttgtttataa ttgtgtactg aagtttaatt 112140
cttcaaaaaa taagagaaac ttattgtgta cacgctcatt tcgcaactat gaactctaac 112200
cacacatacg aaggtacaac tggcacagtt aacgacccaa tcgtgaatac gaatcaacaa 112260
actcagtttc aatacgacaa tgatgtcatc gacgttttta tcgttgaaaa caacgaagat 112320
gaccgagacg gttttgtcga gttgaccgcg gccgtacgtt tgctggcgcc agtggtcgcc 112380
attcgggggt ttaataaatc cgttctatgg gcgaacgtga acaattcgca caaattaacg 112440
aggcacggca aaaattacgt acacgcttat gttttgtgca gatacttgtc cctgtacaat 112500
agttctaatc gccaaagtca ttccaacgaa tattacatgt tgaaacggtt ggtgtgcgat 112560
ttacttgtgg gcgctcagag tcaaattgtc gatccgttgt ccgacatcaa aaatcaactc 112620
tgtactttgc gcgaatgcat agaaaacggt gtcgtgacca ccaatcaaca aatgtaccaa 112680
tctatgccga ccacagccca gcacttgttc gaaaacaata ccaacaatag taataataat 112740
aatttgcaac agcaaataga tatgattcgt gaaattttgc gcaacgaaca caataccctg 112800
tacggtaata ttagttctca actagactct attaaatcga ttcaaatcga tctgaccaac 112860
aaaattgcct ttagtaacga caccatgttg gacagtttta aatccattaa ggacgtcatc 112920
aacagaaaaa agtaaagatt ttataagtag tgaccgtgtt taatgatttt caagtgaacg 112980
tcgcatataa gacaacatgt acatcatcgc ctatatcaac attgtgctgt taatgttatt 113040
gggttactgt ttgtacaccg gttcgttggg acgcgaaatt gaaatcttaa agaacgtcat 113100
cgacaaaatg tgtgaacaat tgtgtcaacg tttcgattta ttgcacgaac tcgtgctgaa 113160
cggttttgct cgaatgcaaa acgacttggg cgttttaagt acgaccacat tgggcaatag 113220
cgacaagctc gacgaaataa atcgcaagat agatagttta ctactaacca atgcaaatta 113280
aattttaccg aataagtata acacaaaaac tttagttttc accttcaata taatgacgtt 113340
taacgtcatt gtaaaaaaga ttcaagacgt ttccgtgacc gttctgttcg aaccgtcatg 113400
gaccgtttgg tttagtttgg acgaggtcgc gcatcttttg cgactgcccg tttctacggc 113460
ggccggtttg gcaccgcgtc acaaacgatg ttggtcggac ttcaaacatc acaatcatag 113520
atgtcgtctc aacgacaata aaacatttgt cgatcttttc ggtttggcgt ttctgtgcaa 113580
tcgcgctaat ccctgccaac tgtgcgacta tctgttgact caattaatcg cagaactcta 113640
ctgcgaattg gcagaatcga gacgtcgaag tcagagtcgc agctgttcac gcagccggag 113700
ccgaagtcga tctcgtcgac gtagtgtcag ccgtaaccga agacgcagtc gcagccgaag 113760
caacagtcga ggacgcagac gcagccgtag caacagtcgc ggacgcagac gcagccgaag 113820
ccgtagccgc agccgtactt gtcaccgacg acgccgcact agcgagtatt tagaaaaaat 113880
ttcgcgacaa aacgatttgc tggtcagtgc ggtcaatcag atgacgctca cgaacacaaa 113940
caattttgcc gacataaata attcgttgag cacgatcagt ttgcaaaact ccactttaac 114000
tggccaagtg gcgcgtttgt tagaaagcgt tgatcgacaa ttgccacttc tgctcgatcg 114060
tttgaacctt ttgtcgtcgg aagtacgaca gcagctcaat caattcagtg gacaattggc 114120
cgaatcgctt aatcgttttc aagatgtact gcgcaacgag ctgaccggta ttaattcggc 114180
gctgaacaat ttaacgtcca gcgttacaaa catcaatgtc actctcaaca atctgctaca 114240
ggctattgcg ggtaccgatt ttggtgaaat tggcaatgta gtgcgttcgc tgatcgataa 114300
agtcgaacag atattgaaaa ttttgaccac agtgacattg actagcaagc gttgactaga 114360
caatgactga gtataaaagt cgcaatttgt acatcacggt agtcagttga ctttgtatcg 114420
tgactgcttc gccatgtaca aatacttttt gtatttttta catttgtccg gtttacacga 114480
ggaaatgtta cattttataa accaatatga gaagttacat ttatttcaag acgacaatgt 114540
tataaaatca atagtaatcg agagtctacg acgcgtcaac gcaaaggctc aagaatgtct 114600
acgtccaaat gcacacgaga acgtgtacga aatcattact cttgaaacta tatgcaaatg 114660
tttcttaaat cgaaaatttc acaatccgta cgtgaggggt tgtcaaaaag ctgcgcaatt 114720
ccttctgcaa gactgtgaca tgaaaacaat tgtcaaattt atttgcgata atcatttcga 114780
tttgcaggca atggataatt atattaatga ttgtctgatt ttttttgacg agcgtgacat 114840
taacgacgcc gtcaatcttc ttcgttgtga ttgtgaagac ataatgtata ttatctaata 114900
aataatattt tgtgaaatat tacatgactt tttattcgta cactctctga gtcaatatat 114960
aaaacctcat ttgatgaata agtatattca gttgaaattc tgaagcgaac cgagctagct 115020
cgtcagcaat ggaaacggta cgcacattca ttctgcccat ggacgtcgat gaagatttga 115080
gcgacaataa ctatcgtgac gatgactacg aagacgaaat gttttcaatc gttagtgata 115140
ccgagtctga atcagaatta aaacgagatt tggtcgattg gatttatgac gattccgagg 115200
acacagtgaa gacaaatgag attcctcata atccggcaac aattttaata tatcattcaa 115260
gcacacatga aatcttaatg gaaaacatgt actatgatga acaccacgac ggacataaaa 115320
tctatcttcg ggtacgcaac attgacagaa accaactgat cgatcaaaac acttgtaaaa 115380
taaatgaaaa cgcgtacgct tgtagtctag ccaaggaaca agttcgtgta aaaatcggtg 115440
accaagtgta taatgttagt cgagtcgaaa tttcctattt gtggaatgat ctgtatttgt 115500
ttttctacaa acaaaaacca atatgtccct ctgaaaaagc aaacgtgttt gtctacttta 115560
attacagtta ttattgtaac aataaagttg attggacaat tccagaagca caggaataaa 115620
atcacaaata aaaccatttt gaacaataca catatgtttt atttaaatag tttcattaat 115680
aaaagatttg gccgtgtcaa tgttacactt gacgttgatc aaacgtttgt ttcgtttagt 115740
gtacgacaaa tttttcatgt cgagctcttc gttgaaacga tgcacggcga cttgaggatt 115800
gggatgtacg gcgtcgtaaa tcaaatcgcc agatttcaat tttcgtttac gagtctgata 115860
ataattacgc tgaccggtca gaaactctat ttccgtattg tgttgatcca ctgaacgaac 115920
aagtacgccc agatgcgggt gtttgctact gtcacgcggc aatctaaatc catttacgaa 115980
attgtcttct tcgctgtata aaactgtgtc gttactgttg ttggtttgaa gacgatgata 116040
atttttcaaa tgattgtata acacatcgat tttttctatg gcagatattt tgtgatctaa 116100
ctcgctcagt cgattttcaa tgtcgcccac tttgccgagg atacttttgt gcatgttttc 116160
gttggcgcta tgatggtccg cacgcaaatc cgtaattttc tcatatatca tttgcaaact 116220
tttttctaca cacaattgtg ataatgatga cgacgacgat gacgacgaag ttttgggcgc 116280
tacggtcgac gacgacggca tatgcgaata caatttgtca aacgcatacg ttaccaacca 116340
cgcgataaat tcagacttgt tggcaaattc tatatggtta agtagttgta gacaaccatc 116400
acggttaata cacattgatc gctttacgtc gtcattttcg atttcgacac gtttaccaaa 116460
tatcagagtc tccaagcaaa ttttattatg atcggacacg taattgtcaa cgacaaattc 116520
aggttcgtcg aatccgattc cgctggcaaa gtcggagcct atcatccaca tttgttgatt 116580
tcgggtcaaa tggcgaacgg taaacgaaaa ttggtcatcg aaatttattc gttttctttc 116640
caatatatac gagaatgaat cgattttgtt gtattcacta tcgtttttgg catggcgttc 116700
ttcatcagga tcaatgttat ttcctccgct gttattgtca acgtcgtagt catcgtcgtc 116760
gggggcggcg gcggctgctg cagcaacgtt gttaccgatc agcgccgaaa atgtgcgatt 116820
aataatgtct ctgaacatgt tacaaaatta tttcttgcga atatttttgt cctttataat 116880

-continued tgtagctgaa aggcgctcgt atctgcgtaa aattacaaaa tatttgctgg tcgacttcgg 116940
gaaaaaaaca tttaatcaac tcgactcggt cggttttgtt ggcgtataac ttgtctattg 117000
tagatttaat ttcgggttcg tcgatgacac ttatcaacgc gtacaagaaa ctgttggtac 117060
gcactcgttc caactgaatt gacttgggca catcgaacac tttatagtat ttttcacgaa 117120
tctgcttgct cgcgttcatg cgaaatcgac aatgtttcaa ccatacgtgt atgccacgat 117180
tgccggaatg tacgatacgg ctaatgttgt cgccgaaaaa ttttgcaaaa gtcaatgctg 117240
cgacacgcgt tttcaaatgc aaacgatccg ggtcactttc gtgaatatcc acatcgatca 117300
cccactcgcg gcccccgttg tcaggcaagg ctttcacgtg cacgtcgctg attcggttct 117360
ggattagaaa tcgataaaaa ttatcaaaat cgtcgaaaca cttatcagga tgaagccaac 117420
gttgagggcg tgcaaccata aaagcccact tgcgaaatgt attaaaagcg acagagtccc 117480
aaatgagacg cgcctgctct tcactgtatt tacagtcagt ggtttgcata gcgaatgaca 117540
atcgcagact gttacacgtt agtgtagttg aattcatgta tagttatcgt gttatcagca 117600
gcagcagcag tcgttgtggt gggcgcattg ttagcgatac gacgattgcg tataaaggtt 117660
ttacaggcgc tagttttaaa caacatgaca cataacagca atattattat gaggacagat 117720
tttaaaagta tgcggtcatt gttttctgtg tcttttatgt tgtctagttc gtcgaacagc 117780
gcgtcgatca cgctatctat gccatcgtga ttcgacagag ttatattatt tattaatgtg 117840
ttgctgttgt tgcgtatgac atcataggta ttggtactgt cattgctaaa tatagacatg 117900
aaataattat cttcgttgag gttatcacga acactagtag tcatcgtgac gatagatatc 117960
tgtaatacac acatcaaagt aaacatgttt acttaaacag tagctgaata ataattttaa 118020
catagcgacg ccactataag atgcagcatc ccgtctgttg gtcatctttc gataaacgct 118080
ctgacccata aacggacgtg cgctaatttt ttttattgct aaattcaaaa tgtacaaaca 118140
gataataact atgttattgt tggtgttgtt tctgtcggtt ctggatggag cgcgtatcct 118200
gtgcgttttt cctgttccct cgtacagtca tcatgcagtg ttcgaagctt acaccaatgc 118260
tctagcgttg cgtggccata caatagtcag aatcacaccg tttcccacta agagaaacga 118320
ttcatccaac gtgacagatg tcgacgttag cttgtcgaaa gattatttta aaagtcttgt 118380
ggaccgatct agactgttca agaaacgagg cgttatttcg gaaacgtcca gcgtgaccgc 118440
tcgcaattac atcagtcttg tacacatgtt gattgatcaa ttctctatgg agagtgtacg 118500
acaattgatc gaatccaaca atgttttcga tttgttggtg accgaagcct ttctagatta 118560
tcctctggtg ttttcgcatt tgtttggcga tgtgcctgtc atacaaattt cgtcgggtca 118620
cgctttggcc gaaaattttg agacaatggg agccgtgagc cgacatccca tttactatcc 118680
aaatttgtgg cgcaacaaat ttcaaaattt aaacgtttgg gagataataa cggaaatcta 118740
tacagaactg gtgctgtact tggaatttgc tcgtttagcc gacgaacaaa ctaaaatgct 118800
tcgccatcaa ttcggaccaa acacgcccag cgtggaagaa ctacgacaac gcgttcaatt 118860
attgtttgtg aatacgcatc cgctgtttga taataacaga ccagtaccgc cgagtgtaca 118920
atatttggga agtctacatc ttgatcgaaa caatgatgtc aacgaacagc aaacgatgga 118980
ctataatttg atgcaatttt taaataattc tacaaacggt gtggtgtacg tgagcttcgg 119040
tacgtctata cgagtttcag acatggacga cgaatttctg tttgaattta taacagcttt 119100
caagcaatta ccctataata tattgtggaa gaccgatgga atgcccatgg aacacgtact 119160
gcctaaaaat gtgttgacac aaacttggct gccgcaacac catgtattga aacacagcaa 119220
tgtagttgct tttgttactc aaggcggaat gcagtcaacg gacgaagcca tcgacgcttg 119280
tgtaccacta atcggaatcc cgtttatggg cgaccaagca tacaatacca ataaatacga 119340
agaactcgga attggacgca acctcgatcc cgtaacgctc acaagtcata ttttggtgtc 119400
tgccgtttta gatgtgaccg tcaacaacaa gagtcgttac acatctaata ttaaagcatt 119460
gaatcgttcc actaattatc gaacacggaa acctatggaa aaggccatct ggtacacaga 119520
acatgtaatt gataatggta aaaatcccat tttaaaaacg aaggccgcca acgtatcgta 119580
tagcaaatat tatatgagtg atatcatcgt tcctgttata acgtttttgg taatgactca 119640
tttgggtcag gctattcggc ggttggttgt tatttaatac tgtatgacaa tgtacacatg 119700
tgttaataaa aaaggcatta ctaatattta gattgtttca aattatttac gcatgactac 119760
ccgtctccta ttgcgcagct acgctagctt taaatacagc cgatggcgta gtaaagttca 119820
tttaaatatc taaattggtt agttcaacat cgcggtgcga gcgcacgact tataccatgc 119880
atcgttccaa tagtaacagc agcaaataca aacaatcgct gataaatcgc tttgaactgg 119940
aatacaaaag tgtgtctgtg cgcgatttgc aaaaattgtc agcggccatg tatcgtttgt 120000
tggctgtgaa cgataaactt atggaaaatt tacaaactct accgatgcat tatagagctc 120060
aaataaacat attaaaaaaa tctctgcgtc acaaacagca aataatcgac gaactcaaag 120120
acaaattgtc tcattgttcg ttgcgctatg tctatttagt tagacacgaa aacacgctgt 120180
ggctactgag cggcagtatg aagactatac gaaaaaaatt aaacggattg ccgatcgacc 120240
accgcatact attgaaaact atcaccaaac gtccgggcgc agactgtaag ttttgcttgc 120300
gtgtggccaa cacgaatttt ctcaatcact tgcgcagtat aaataagcaa aaaatcgtgt 120360
ttctcaacgg cgaccacgtc gaagaatatg tacaaaacat aaaacatgtc ttcgaacgaa 120420
acgacgacag tgctatcgcc acgatcgagc attgaaccgc cgtttgcgat aaccgtttac 120480
gtggacgaca acgaagtgct agccgaagaa ataattttgt atcccaaatc aaattacatt 120540
gtgtacaagt atcgaatgaa tttcgacgac cgtgcaagca acaatgaaca aataatattc 120600
aaacgcgtca acgtgcgtat tgacagtggc aattgttacg tgcaaggtac atttaccgac 120660
ggcagacgac acgtggctgt cgtgaatgcc gccgacaaaa actcgcccat cacgtttgac 120720
gggtttcccg actacgataa tgacgattct caaactctgc catttgtgct aagacgtttg 120780
aatcaattga aaaatacaca caaattgacg catgccaagg acatagctcg ggcaatggaa 120840
caatcgtcta aacttagagt gtttgtcaac gaagtagcat tggatagcga tacacattca 120900
agcaagtggt attcgcggct atggttaaaa aactcgtcgt cgacaacgtc gaaaactgat 120960
catcggttgt acgaaacaca attgatagat gatgtcatgt cgtttagtga cctagttaaa 121020
agtgataaat tattagaggc tattgatgaa accactgttc ctcatgttgt tgtaaaaaat 121080
aaacctattc atgtatgggc tcctgtcgaa tgtcgtacgg gtaaacggtt gtgttgtata 121140
gatcttgttt tcgagaacga aggaggtttg ttacttagca aaaataaaac tactaattct 121200
agttaaattt tattacacta acacttaatt tattttgtag cactaaggtt gtgtcgtgtc 121260
gtctattata taattaatta tatacattaa taaaacaata acttgtcatg ttcgtccctg 121320
taatagatgt ggttgtattt gttagtgtta tcataataat gcctattagt tttagtagca 121380
tatttatttt tttgttgatc tgaattgtga acaagtttac atttcgattg tttgtataca 121440
taaattattg ttaaagaaac actgtaaact aatagtacta ttgttgtaat taataatact 121500
attattacaa tatgtataat aaacgtgctt aagctatcat gcaaactaat gatcagactt 121560
ttattttcat tgtcagcctt tgatatagta ttagttgtaa tttcagtctt ttctgttacc 121620
gatattgttg ttttttctgg cctataagtt tgtacattaa tatagttagt gctagtggcc 121680
gtacaatact gatgaggtaa tttgttaaat tttctataat actgtcgatt cttgtgatag 121740
atcatttgtg gtgtttcatt gtcgctgttc aataacattt caacgacgtt agtgtataaa 121800
cgtctgtaca cattataata cactaccggt ctgtacatgg ccagcaaatg tagtatagta 121860
ttgttacgca tatctatgcg aacagacacc aattgctctt gagacggcgt tacattactg 121920
gtcaagttgc gtgcgtaatg ttttaacgtc gtctccaaat tgggtaacgg caccacgggc 121980
ggtacgaatt catcacattc ctccaaaacc aatagtaaaa atctaaaatg atccaatact 122040
tgttcgaatg tcagcctgcc cagtaccggt atctgtttcc acatacgcgt ttgcatcaca 122100
aactcgatca gcgcacgtgt tgtgtcgtaa gatagaactt cagagccgtt tgcgcacgtc 122160
aaatcgacat cgaaatcgta ttcggtgtac ggcaaatatt taatgtaaat ctcattgaaa 122220
tcaatagtat tttgccctgt ttcaccgcat attatgcgta atatatgtat aatggcaaac 122280
tttacgagac ttttttgaaa ccactcaaaa tcgtatgtcg acactgattc tttattgtgt 122340
tgtatttcgt gcagagcgtt tatactcgac gtgtatgacg atttactttt tcgtatacaa 122400
cgtgaagggg tcagaataaa tgcgcaatct ttatagtcga attgtatgaa attaccacac 122460
tttccgaata gattagatgt tgcgttggaa ctttccagta tgccttgata ttcttgctca 122520
gtggaaaatt ttataatttt gtcgttacgt tgtctgatga cgtaatcaca gtaatctact 122580
aaattttgca aatacaatga aaactcatcg ttcatggttt cgtctacgtc gaatgtataa 122640
ttgctcgacc gaatcatatt cgctaacagt tcggaacgat gatcgctcaa aaatccagtt 122700
agcgcatatc ccatggcgta aagcatgtcg gagccgtgtt cggcagtaac gatctgttcg 122760
atgcgaacat tcagatgtga tttgataaaa tcgtggtcgc gttcgtaaca caattgatta 122820
ccgtagcgat cggcggagcc ttccacgtac caatcgggca tcgtgtccgt gtcgtctacc 122880
gcgtacatga gagcgtgatg tatttcgtgt ccgaaattca acggtaattc ggtgtgatga 122940
cgatcgaaat atacgtgcgc ttcgattctg accgtgtccg gattgatgtg cgtgtacccg 123000
ccgttgttcg tgctaatttt ccatagttcg ccttcgcgtt cgtatgtata acgatccggg 123060
tgcacgtaca cgtcgatgga cgttgagggt gtagcgctat aatcaatgtt caatttgtcg 123120
aaaaatgcca tgaacgtttg gtgaacataa gccacttcac gtgccatgtt cgatatgata 123180
gtttcattta ttacattatg atgtacgtta aatttaaact gttcaatttg ccatacggtc 123240
aggactggca aagcgttggt tcgattgaca acaacgaaca agttttcgaa tgatatcaaa 123300
cttggattcg ttcttttagt taaataatga acgtaaaaaa actttttttaa atttaacaca 123360 tcgattcgat gtgccggata atttacggct aagtgggcta tgtcaaaagc cgcttcgtcg 123420
atttcgttaa ctatgtcaga gtttcttatt gcgaacttgg cgcgcaaact ggcatacgaa 123480
ttaacaatta gtccgaacag atactcgtgc ttcgaatccc acaacacaaa agtgttaaaa 123540
aaattccgta tgctcacgaa cttgtcgaga aaagttttgc ggtcgcgcgg atgatacagg 123600
ttccacgctt cggcgatcca acgaaacatt ttgtccgaac gtttttgcat gtctccggtg 123660
atgttgactc taatgtcggc gattttgtcg cactgtttaa tgatgttttc gataaattca 123720
tgtgtacgat attcatgata gtattgtaga ttcacaacaa gttttattaa ttttgtgaat 123780
ctatccagat cggcgacatc acgataattg aaaccgtaac gcatttgttt gtcaaattcg 123840
tacataaccg tcgctttgtc acacactgtt gcattaaatt tcgtagcgta gcataagctg 123900
tacacgtgtt ctaattcgtc agcggtcatc actctagctt gagacgattt tgcgtaaata 123960
ggcgccgacg cggccaaaat tgatgacaat atcgataaca actttaaagt aaccatatta 124020
tggaacactt gaccgcacac ccaaatagaa tgacaaagaa tgttttcatc gtttcgtcgc 124080
ccacacaatt caaacataac gttatcttta aagataacaa atgatgacat atattaaatt 124140
atggtgcaat atacatgaca caaacaactt acgtcatcgt aaccttgaat taaaatgtaa 124200
aaacaatttg tgatatcgtt aattctagga aattttgcac aaacaactta cgtcatcgta 124260
accttaggtc aaatcgttaa ttctaggaaa ttttgcacaa acaacttacg tcatcgtaac 124320
cttaggtcaa atcgttaatt ctaggaaatt ttgcacaaac aacttacgtc atacatgtta 124380
ttaatcattt tcgttgcaat cgtcatcgga tcaaacgatt tcgtttaaaa ttttcgacac 124440
tgctgttgta ttatctataa ttatgttgca aactatgtac aaattttagt attgttcgag 124500
tgtgcgccta cacacacaca cgttcgcaat ggaaacaaaa attcatcaaa ttcaaactaa 124560
agaaaataaa gtgcgcgatc aatacgaatt aaaagttatg tctttttttga agcaaccagt 124620 ggaatcgcgc agccccgttt tgcaaaacga aattgttcat ctgtctgctt tgttgcgggg 124680
ttacgaagag caactgtacg cgctgcgtcg gagctacgat gaaaagcgcc aattaaattt 124740
cattaacgat attggcgagt tcgatttcag ttgcgaacaa atcgaacagc tcatggaaag 124800
tgacaaaata cttttagatc gttacagagc catcgatttg aacgagacat tgcgcaagta 124860
tttcgacaac aacagtcaaa aatttacaaa aattttaaaa caatttgtac agaaacgcaa 124920
cgcatatcga aaatcgccaa agttaacgtt gctgcaagaa ctggtatttt tgaaatcaaa 124980
tctaatttgg catttatgcg tactggaaac tttaactaag cctctaatgt cttgttgagt 125040
gtttgatata aataaaacta tttttcacat tttgtatgta ttttattttt gaatcacaca 125100
aatattatat tgacggaggt ggtaatggag gggccgtcgg tattgataca acaggtttta 125160
gttgagcata attacattcg tcgctgggta ttgtcttgca aaaagaaatc ggtcttgctg 125220
gatgcttagg aacacaatac attgactcga cgtgatcgtt tgtgtcgttg ttcttatgat 125280
tgacgaacga tttgtgtcta acatatttgt tgagcaattg tattaaacac aaacagtgcc 125340
aggtgaagat cgtgccaagc gcgatgtaca cagtgatacg atgatttttg aaaaaagtcg 125400
cttcgtacgg tttgtacacg ttgcgacatg aagcgcaaaa tatttgatat tttatttcgt 125460
aacaattcag cggcatgtcc acgacaatac tatttgagtc cacttgtttg tattcgacga 125520
ttcctttcca acaggttttg tcgatgtcgt agttgcgata atgcacgtcg agcgctccaa 125580
tgtgtccgtg ttgtacgaac atttccagca tagttaacaa acacattact attattgcac 125640
ataacaacgt aaaataaaat gcaaagacta atggccatgt cgagttgact tttgatgtaa 125700
taacggaaaa tatacacgct aaacacaaca tgaatccgta tgcgcataat aaatttgaac 125760
aattatacgg agcgacactg acgaggccat aatcgagttg aaccgcccag tccgtgtcga 125820
atataccgta catgccaaat aacgtacaac caatacctaa aacactaaaa aatattaatt 125880
gtaaatataa catgttacac atgtttgcaa gaccacataa aactgtacta attttattat 125940
gctaattata ttaaatacga aaaaaaacga ttattgccga cattttgata tgaaagagtc 126000
ggcaagtatt atttattttt aaacatgaca tcattttgac gtatgacatc atttatttta 126060
tacggaccga gcaacaatcg aagtatataa ttgattttgc ctgcatgtag gaaaaaaacg 126120
ccggcaaaat tcgattgtta gtacaattgt taagtattaa acgatgttga tctggctgct 126180
attgtttgtg ttgctagtga tatttctgta tgttctttac cggccaatgc atttggcatg 126240
gcgatttatg ctcaaagctc agcgcgaata taacgaaact atcgatgaca gaatagatta 126300
catgcaagaa gtattgcggc gacgacaata tgtgccgtta cattcgttgc cgaatatcaa 126360

-continued

```
tttcaataca aacttgggca caattaacga tggtgaactg aaatgtttat cggtgccggt 126420
gtttgtggga ccagtggaaa cgcccaattt tgattgtacc gaaacgtgcg acaatccgtc 126480
agctttttat ttttttgttg gtgaatacga taagttcgtt gtaaacggcg agttgttgga 126540
tcgcggcggt tattgtacaa ccaatagtat accgcgtaat tgtaatcgcg aaacaagcgt 126600
aattttacac ggtctaaatc aatggacatg catcgcggaa gatcctcgat attttgccgg 126660
tccgcaaaat atgagtcagg tagccggcag gcaacatgcc gatcgaatat ttccgggtca 126720
aattggtcgc aacatattgt ttgaccgttt gttgggaaca gaagtcgacg tgtccagaaa 126780
cacgtttcgt agtcattggg acgaactgtt gccggacggt actagacgat ttgaaatgcg 126840
ctgtaacgct ttagacgatc atgaaaaccg tatgtttctc aatccactca atccaataga 126900
atgtttgccc aatgtgtgca caaacgtgcg cagagtagcg cttagcgttc gtcctaattt 126960
ttctacaggc gaatgtgaat gcggtgatgt taacgaaacg cgcgtcactc atattgtgcc 127020
cggcgataaa acttcgatgt gtgccgctgt cgtggaccgt ttcaatcgtg atctaatgtc 127080
gcatcaactc agagtcgatt gtatcacaag ggacatgccc atgtcaaagt ggcacaaaga 127140
catgattctg tgtccgccag acgtgttcgt acaaaacagc gacaacgctt tttattttac 127200
tttgcctgga tcttttccca tatcggaaac gggtgtttac gaaccaacgt ataggtttta 127260
tatgcaaacc agaaatagag tcaactatgc tattcgtagg gatttgccgt cgtaacaaat 127320
taaacaaaaa aattttcata aaaacaaatt tatttttaca atttgtgttc atcatattga 127380
tcgaaagaat ctttagaacg atgattggct ttcaaataga cgagttgacg atcgttgcgc 127440
accaccgttc gtgtgggtct tcgtctcgat aatctatcgc acaagtccat acaacaagat 127500
acactacaaa aacatcgtaa aactacaaca gtcactaaca caacaacaat aacggataca 127560
ataattgtca aactactcag aaaattttgc catcccgtac ttaaattcca accgctaaac 127620
catccaacaa aaggtttatt gtcgttttcg atttgccaac ctttaaatat cgtattgttg 127680
ttaatttctt tgcgcagctc cgtgaggcgg taagtcatgc ttttgagagt gtcgtgatca 127740
agatcgttgt tcgaacccag cgcttccaat tcgaattgca tgcgatctat gtcgcgtatc 127800
gctcggctga aattaaacgt actcgacatg tcgacgtact ccgtgatgag taaattattt 127860
ttgacttcat gcaatgtgat cgtacttctt ttcgtagaca ctttgcagta tttgttacct 127920
ataccttcta gaagtccaac gcctgcgtcg agttgtaatg aacgttttac gtttttacac 127980
aaaaaattga gttccgttac ttcgtcgacc atatacagcc atctgttaaa atcggcaatg 128040
ggatgaaaaa tttctttgtc aaatctgccg atgcgtacgt cgcaatcgtt catcaagtcc 128100
atgtcgcgtg cttcgtttaa aaatatcttg atgtcgcata aagatgccaa attcgataac 128160
agaatcgttt cgggtttgta gcacaattta gtgttggcac cggccgattt gcagctgtgt 128220
gtgtcgtcca agcgtacgta gtttcttttg tcttgcgaca tgccaatata tttactggtc 128280
ggtatgatga cggcacaatt agttctgtta ttgttacaca taggcaccgg tacgatgttg 128340
tataaatcat aattttccgt attcactaat ggcacttcaa taatgaacaa caatgttctt 128400
tgtggtgtaa caaacacatg agtgttgacg acatgatcaa tcagagcgtg catgttgttg 128460
acattgagtt caataggcca agtgagcgaa tcgggcaatt ttcctgtaac attacgcatt 128520
tcgttgtaca atcgttgcgg agtcataatg gtaggactga gacgattgta tttggcgctg 128580
tctacggcac ggtctaaatt gatgtacaaa aatttcagtt cgttcaattg agtttgcatg 128640
agtttcattt tgttagttac atagtcgcac gtttccgatt tcattttttc aatgcacgcc 128700
```

-continued

```
aaatgatctt catagttgac caaacgtata agttcatcgt cgagttcttt cacttgttcg 128760
ttgagcgcgt tgttattttt ggctaaagcg tgcaattctt cggcatcgtc cgcgtccatc 128820
actccaaaca gaaacttgtc tacgcttcca acgaagttta atccaatgtt tcgtttgttg 128880
cgactcgaaa atgttggttt atctgtgact aaaggtacgg gccattttcg gttagcatcg 128940
atttgtacta agtcgggatt cattgcaacc gcactgtgat caatggcgtt atttttttca 129000
atcaattcaa taatttgtct gtatatgtat gtttgcaaat cgtgaaatat agtttcgctg 129060
ttctcgcaac tggttaaatt tttattcttg atccattcaa ctagattatt gtacgaattg 129120
tgcaattgta ccagttcttc aaatataata ttgtgatcga cttcgatgac aaaatgccaa 129180
acgtcttcaa cgaatctcat ttgatagatt ttgtcaaagt acaaaccaat agtgcgcggc 129240
aaagagataa tttttagcaa atttgtagga tcgatggcaa aagactctgt cgtttcgacg 129300
actcgcgtca acgacataga aattaatata gtacacaata aaattttagt cagcttagag 129360
ctgaacagac tactttttat cgcaaccatt gttacaaaac tgacgttgaa cactttgaac 129420
ggtctacttt atatatttc gtaaccttat aactattacg gaaaggttta ataaaaataa 129480
ctagattaat aaatgtatgt ttttattgta taaagataac aaatacacat ttatattata 129540
aatccataag gattacacat ttatattata aatccataag gattacacat tttacaagtt 129600
cttaattcgt taaaagtaat ataatttcta taagtattta cgtctgttac acagtaatcg 129660
gagttatttg tagtattcat atctgtgtaa atgtcacaat accaaggttt tctaaaaggt 129720
ttgttttcgt cgtgacattt aaatatatcg gaaaagcaaa accacaaaaa atctttgttc 129780
aaagccaaac taatatcagt aactagattc aatttttctt cgtcaataat ttcaaaatta 129840
taaaatacgg tataggcaat accataattg aaccatttgt cgttacggca ccattttttc 129900
catcttttta tatattgtag catctggttc caattgattt cttcgttttt acacgcaatt 129960
tcgctttcga cagacgaata ataccatcca gacggtagag caatacgaat atgttccaat 130020
acagccatat attctttttc gatacgaaca ttgtgataca caacttgtaa tagactcaat 130080
gtacgcagac tcgatggtgt acacattttg ttagattcct aacgatgcga atgctgaata 130140
gcattattgt ttaaacgatt atatagtaat tattaatcta atcttgacat tatcatttta 130200
ttgataacaa tagatatgat aaaattatac tatataaatc aaaacagaat tcatttaatt 130260
acagttttta tgattgtaca aacagtctat aaccaaccat gtgtaacgtg tggccagtgg 130320
ttaaccgtgt gctttgcaaa ctagtcatgc aaaatttgtc caaaatatat ggcaatatac 130380
aatttttata tctgatgggc aacaagccaa aggaaattca agaggaacaa gccaatttca 130440
acgaactata ttacaagttc aaagtgttta gatcacaatt gcccgacatg aattgtgaaa 130500
cttttgctca taaattgatt gaccagaaaa tattgtattg cagagaaatt cataatttgt 130560
atttgaactt tttatattgt ttctacaaac aatactttga tacgctaaag attgactgca 130620
atatttttaa ggatttgata gatgacgatg taccattgca agattttgaa gagttaaatg 130680
ttgttctact cgacaataac ataccaatgt atacggcttt gtgtgatgat gtgtttgaaa 130740
agaaaaccat tatacaagat atagaatatg taatgaacaa aatatgcgtt gaaggagcgt 130800
acgtgccatt tcaagaagaa attttgcaat atcaaatctt tttgcaagaa tatgaagatt 130860
tctgtcgtcg tgttgaaaat ttgtaataaa actaaataaa cctttaatat aaatattaaa 130920
catacacttt tatttctaaa ataagtattt ttttcctatt gttcaagatt gtgaaaaatc 130980
aaatatccca ta                                                     130992
```